United States Patent
Pons et al.

(10) Patent No.: US 11,795,463 B2
(45) Date of Patent: *Oct. 24, 2023

(54) TRANSGLUTAMINASE-MEDIATED CONJUGATION

(71) Applicant: Tallac Therapeutics, Inc., Burlingame, CA (US)

(72) Inventors: Jaume Pons, San Francisco, CA (US); Hong I. Wan, Foster City, CA (US); Tracy Chia-Chien Kuo, San Mateo, CA (US); Curt W. Bradshaw, San Francisco, CA (US); Son Lam, San Francisco, CA (US); Bang Janet Sim, Brisbane, CA (US); Edward HyungSuk Ha, Cambridge, MA (US); Sukumar Sakamuri, San Diego, CA (US)

(73) Assignee: TALLAC THERAPEUTICS, INC., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/842,573

(22) Filed: Jun. 16, 2022

(65) Prior Publication Data
US 2023/0130194 A1    Apr. 27, 2023

Related U.S. Application Data

(63) Continuation of application No. 17/187,579, filed on Feb. 26, 2021.

(60) Provisional application No. 63/110,854, filed on Nov. 6, 2020, provisional application No. 62/983,463, filed on Feb. 28, 2020.

(51) Int. Cl.
*A61K 47/68* (2017.01)
*C07K 16/30* (2006.01)

(52) U.S. Cl.
CPC ...... *A61K 47/6811* (2017.08); *A61K 47/6849* (2017.08); *A61K 47/6851* (2017.08); *A61K 47/6889* (2017.08); *C07K 16/30* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,522,811 A | 6/1985 | Eppstein |
| 4,816,567 A | 3/1989 | Cabilly |
| 4,845,205 A | 7/1989 | Huynh et al. |
| 4,946,778 A | 8/1990 | Ladner |
| 5,033,252 A | 7/1991 | Carter |
| 5,052,558 A | 10/1991 | Carter |
| 5,130,302 A | 7/1992 | Spielvogel et al. |
| 5,134,066 A | 7/1992 | Rogers et al. |
| 5,175,273 A | 12/1992 | Bischofberger et al. |
| 5,260,203 A | 11/1993 | Ladner et al. |
| 5,323,907 A | 6/1994 | Kalvelage |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook |
| 5,476,786 A | 12/1995 | Huston et al. |
| 5,482,858 A | 1/1996 | Huston et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook |
| 5,594,121 A | 1/1997 | Froehler |
| 5,596,091 A | 1/1997 | Switzer |
| 5,614,617 A | 3/1997 | Cook et al. |
| 5,681,941 A | 10/1997 | Cook et al. |
| 5,837,242 A | 11/1998 | Holliger et al. |
| 6,054,297 A | 4/2000 | Carter |
| 6,054,438 A | 4/2000 | Taylor-papadimitriou et al. |
| 6,075,181 A | 6/2000 | Kucherlapati |
| 6,150,584 A | 11/2000 | Kucherlapati |
| 6,407,213 B1 | 6/2002 | Carter |
| 6,492,123 B1 | 12/2002 | Holliger et al. |
| 6,639,055 B1 | 10/2003 | Carter |
| 6,719,971 B1 | 4/2004 | Carter et al. |
| 6,800,738 B1 | 10/2004 | Carter et al. |
| 7,612,181 B2 | 11/2009 | Wu |
| 9,381,208 B2 | 7/2016 | Hartmann et al. |
| 9,650,427 B2 | 5/2017 | Kagan |
| 9,663,575 B2 | 5/2017 | Eckelman |

(Continued)

FOREIGN PATENT DOCUMENTS

| | | |
|---|---|---|
| WO | 199311161 A1 | 6/1993 |
| WO | 199804727 A1 | 2/1998 |

(Continued)

OTHER PUBLICATIONS

Al-Lazikani, B. et al. (1997). "Standard Conformations for the Canonical Structures of Immunoglobulins," J. Mol. Biol. 273:927-948.
Barbuto, S. et al. (Apr. 2013). "Induction of Innate and Adaptive Immunity By Delivery of PolydA: dT To Dendritic Cells," Nat. Chem. Biol. 9(4):250-256.
Berge, S. et al. (Jan. 1977). "Pharmaceutical Salts," Journal of Pharmaceutical Sciences, 66(1):1-19.
Boerner, P. et al. (Jul. 1, 1991). "Production of a Antigen-Specific Human Monoclonal Antibodies from In Vitro-Primed Human Splenocytes," J. Immunol. 147(1):86-95.

(Continued)

*Primary Examiner* — Phuong Huynh
(74) *Attorney, Agent, or Firm* — MORRISON & FOERSTER LLP

(57) ABSTRACT

The present disclosure provides for antibody-oligonucleotide conjugates, methods of preparation thereof, and methods of use thereof. Also provided are related compounds, compositions and kits.

16 Claims, 80 Drawing Sheets
Specification includes a Sequence Listing.

(56) References Cited

U.S. PATENT DOCUMENTS

| | | |
|---|---|---|
| 9,738,680 B2 | 8/2017 | Hartmann et al. |
| 9,803,016 B2 | 10/2017 | Grosveld et al. |
| 9,815,898 B2 | 11/2017 | Freeman et al. |
| 9,828,434 B2 | 11/2017 | Marasco et al. |
| 11,203,611 B2 | 12/2021 | Sakamuri et al. |
| 2006/0040887 A1 | 2/2006 | Karaolis |
| 2007/0189962 A1 | 8/2007 | Pastan |
| 2008/0031887 A1 | 2/2008 | Lustgarten |
| 2008/0286296 A1 | 11/2008 | Ebensen et al. |
| 2010/0098704 A1 | 4/2010 | Keler et al. |
| 2010/0261779 A1 | 10/2010 | Uhlmann et al. |
| 2012/0041057 A1 | 2/2012 | Jones et al. |
| 2014/0127197 A1 | 5/2014 | Ebens |
| 2014/0205653 A1 | 7/2014 | Dubensky, Jr. et al. |
| 2015/0056224 A1 | 2/2015 | Dubensky, Jr. et al. |
| 2016/0257961 A1 | 9/2016 | Bradshaw et al. |
| 2017/0057978 A1 | 3/2017 | Iadonato et al. |
| 2017/0258897 A1 | 9/2017 | Iadonato et al. |
| 2017/0267762 A1 | 9/2017 | Qiu et al. |
| 2017/0283498 A1 | 10/2017 | Frazier et al. |
| 2017/0298139 A1 | 10/2017 | Thompson et al. |
| 2017/0313774 A1 | 11/2017 | Wang et al. |
| 2017/0313776 A1 | 11/2017 | Zhou et al. |
| 2017/0319680 A1 | 11/2017 | Ishii et al. |
| 2017/0340734 A1 | 11/2017 | Robert et al. |
| 2017/0369572 A1 | 12/2017 | Sato et al. |
| 2018/0002423 A1 | 1/2018 | Wang et al. |
| 2018/0022809 A1 | 1/2018 | Kowanetz et al. |
| 2018/0028553 A1 | 2/2018 | Gajewski et al. |
| 2018/0030137 A1 | 2/2018 | Van Eenennaam et al. |
| 2018/0037652 A1 | 2/2018 | Liu et al. |
| 2018/0134802 A1 | 5/2018 | Mukherjee |
| 2018/0312536 A1 | 11/2018 | Sakamuri et al. |
| 2019/0127478 A1 | 5/2019 | Ekimova et al. |
| 2019/0194655 A1 | 6/2019 | Bradshaw et al. |
| 2022/0056069 A1 | 2/2022 | Sakamuri et al. |
| 2022/0096649 A1 | 3/2022 | Pons et al. |
| 2022/0380768 A1 | 12/2022 | Pons et al. |

FOREIGN PATENT DOCUMENTS

| | | | |
|---|---|---|---|
| WO | 199837095 A2 | 8/1998 | |
| WO | 199837095 A3 | 11/1998 | |
| WO | 2012092616 A1 | 7/2012 | |
| WO | 2014011521 A1 | 1/2014 | |
| WO | 2014179335 A1 | 11/2014 | |
| WO | 2014179760 A1 | 11/2014 | |
| WO | 2015069932 A1 | 5/2015 | |
| WO | 2015188197 A2 | 12/2015 | |
| WO | 2015188197 A3 | 2/2016 | |
| WO | 2016096174 A1 | 6/2016 | |
| WO | 2016205042 A1 | 12/2016 | |
| WO | 2017011444 A1 | 1/2017 | |
| WO | 2017011622 A1 | 1/2017 | |
| WO | 2017019846 A1 | 2/2017 | |
| WO | 2017027645 A1 | 2/2017 | |
| WO | 2017027646 A1 | 2/2017 | |
| WO | 2017049251 A2 | 3/2017 | |
| WO | 2017049251 A3 | 4/2017 | |
| WO | 2017143171 A1 | 8/2017 | |
| WO | 2017173427 A1 | 10/2017 | |
| WO | 2017178653 A2 | 10/2017 | |
| WO | 2017196793 A1 | 11/2017 | |
| WO | 2017196867 A1 | 11/2017 | |
| WO | 2017215585 A1 | 12/2017 | |
| WO | 2017215590 A1 | 12/2017 | |
| WO | 2017218435 A1 | 12/2017 | |
| WO | 2017220990 A1 | 12/2017 | |
| WO | 2018013017 A1 | 1/2018 | |
| WO | 2018057669 A1 | 3/2018 | |
| WO | 2018107058 A1 | 6/2018 | |
| WO | 2017178653 A3 | 7/2018 | |
| WO | 2018189382 A1 | 10/2018 | |
| WO | WO-2018189382 A1 * | 10/2018 | ......... A61K 31/7125 |
| WO | 2019241430 A2 | 12/2019 | |
| WO | 2019241430 A3 | 1/2020 | |
| WO | 2020081744 A1 | 4/2020 | |
| WO | 2022040173 A1 | 2/2022 | |

OTHER PUBLICATIONS

Borrebaeck, C.A.K. (1995). "Strategies for Humanizing Antibodies," in Antibody Engineering 2nd Ed. pp. 179-181.

Brüggemann, M. et al. (Aug. 1997) "Production of Human Antibody Repertoires in Transgenic Mice," Curr Opin Biotechnol 8(4):455-458. Abstract Only.

Carter, P. et al. (May 1992). "Humanization of an Anti-p185HER2 Antibody For Human Cancer Therapy," Proc. Natl. Acad. Sci. USA 89:4285-4289.

Chao, G. et al. (2006). "Isolating and Engineering Human Antibodies Using Yeast Surface Display," Nature Protocols 1(2):755-769.

Chothia, C. et al. (Aug. 20, 1987). "Canonical Structures for the Hypervariable Regions of Immunoglobulins," J. Mol. Biol. 196(4):901-917.

Clackson, T. et al. (Aug. 15, 1991). "Making Antibody Fragments Using Phage Display Libraries," Nature 352:624-628.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Delmar, J.A. et al. (Dec. 2019). "Machine Learning Enables Accurate Prediction of Asparagine Deamidation Probability and Rate," Molecular Therapy: Methods & Clinical Development 15:264-274.

Edelman, G.M. et al. (1969). "The Covalent Structure of an Entire γG Immunoglobulin Molecule," Proc. Natl. Acad. Sci. USA 63:78-85.

Harlow, E. et al. (1988). Antibodies: A Laboratory Manual, Cold Spring Harbor Press, 89 pages.

Holliger, P. et al. (Jul. 1993). "Diabodies: Small Bivalent And Bispecific Antibody Fragments," Proc. Natl. Acad. Sci. USA 90:6444-6448.

Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.

Hudson, P.J. et al. (Jan. 2003). "Engineered Antibodies," Nat. Med. 9(1):129-134.

Huston, J.S. et al. (1993). "Antigen Recognition and Targeted Delivery by the Single-Chain Fv," Cell Biophysics 22:189-224.

International Preliminary Report on Patentability, dated Aug. 30, 2022, for PCT Application No. PCT/US2021/020039, filed Feb. 26, 2021, 10 pages.

International Preliminary Report on Patentability, dated Oct. 15, 2019, for PCT Application No. PCT/EP2018/059554, filed Apr. 13, 2018, 16 pages.

International Search Report and Written Opinion, dated May 24, 2021, for PCT Application No. PCT/US2021/020039, filed Feb. 26, 2021, 17 pages.

International Search Report and Written Opinion, dated Sep. 6, 2018, for PCT Application No. PCT/EP2018/059554, filed Apr. 13, 2018, 16 pages.

Jain, H.V. et al. (2013, e-pub. May 7, 2013). "Assessment of The Cellular Internalization of Thermolytic Phosphorothioate DNA Oligonucleotide Prodrugs," Bioor. &. Med. Chem. 21:6224-6232.

Jakobovits, A. (1995). "Production of Fully Human Antibodies by Transgenic Mice," Current Opinion in Biotechnology 6:561-566.

Jones, P.T. et al. (May 29, 1986). "Replacing the Complementarity-Determing Regions in a Human Antibody With Those From a Mouse," Nature 321:522-525.

Kabat, E. A. et al., "Sequences of Proteins of Immunological Interest," Fifth Edition, U.S. Department of Health and Human Services, NIH Publication No. 91-3242 (1991), 83 pages.

Kabat, E.A. et al. (1991). Sequences of Proteins of Immunological Interest, 5th ed., Public Health Service, National Institutes of Health, Bethesda, MD. TOC, 21 pages.

Kabat, E.A. et al. (Oct. 10, 1977). "Unusual Distributions Of Amino Acids In Complementarity-Determining (Hypervariable) Segments

(56) References Cited

OTHER PUBLICATIONS

Of Heavy And Light Chains Of Immunoglobulins And Their Possible Roles In Specificity Of Antibody-Combining Sites," J. Biol. Chem. 252(19):6609-6616.

Kreutz, M. et al. (Jul. 10, 2012). "Antibody-Antigen-Adjuvant Conjugates Enable Co-Delivery of Antigen and Adjuvant to Dendritic Cells in Cis But Only Have Partial Targeting Specificity," PLoS ONE 7(7):e40208, 12 pages.

Köhler, G. et al. (Aug. 7, 1975). "Continuous Cultures of Fused Cells Secreting Antibody of Predefined Specificity," Nature 256:495-497.

Li, J. et al. (Mar. 7, 2006). Human Antibodies for Immunotherapy Development Generated Via a Human B Cell Hybridoma Technology, Proc. Natl. Acad. Sci. USA 103(10):3557-3562.

Liu, Y. et al. (Jan. 3, 2017). "Host and Viral Modulation of RIG-I-Mediated Antiviral Immunity," Front. Immunol. 7:662, 12 pages.

Lu, D. et al. (May 20, 2005). "A Fully Human Recombinant IgG-Like Bispecific Antibody to Both the Epidermal growth Factor Receptor and the Insulin-Like Growth Factor Receptor for Enhanced Antitumor Activity," The Journal of Biological Chemistry 280(20):19665-19672.

Marks, J.D. et al. (1991). "By-Passing Immunization. Human Antibodies From V-Gene Libraries Displayed on Phage," J. Mol. Biol. 222:581-597.

Martinez-Campos, C. et al. (2016). "Role of TLR9 in Oncogenic Virus-Produced Cancer," Viral Immunol. 30(2):98-105.

Mongis, A. et al. (Mar. 15, 2017). "Coupling of Immunostimulants to Live Cells Through Metabolic Glycoengineering and Bioorthogonal Click Chemistry," Bioconjugate Chem. 28:1151-1165.

Notley, C.A. et al. (Feb. 7, 2017). "DNA Methylation Governs the Dynamic Regulation of Inflammation by Apoptotic Cells During Efferocytosis," Sci. Rep. 7:42204, 10 pages.

Puig, M. et al. (2006, e-pub. Nov. 27, 2006). "Use of Thermolytic Protective Groups To Prevent G-Tetrad Formation in CpG ODN Type D: Structural Studies and Immunomodulatory Activity In Primates," Nucl. Acids Res. 34(22):6488-6495.

Riechmann, L. et al. (Mar. 24, 1988). "Reshaping Human Antibodies for Therapy," Nature 332:323-329.

Sharma, S. et al. (Sep. 15, 2008). "Systemic Targeting of CpG-ODN to the Tumor Microenvironment With Anti-neuCpG Hybrid Molecule and T Regulatory Cell Depletion Induces Memory Responses in BALB-neu T Tolerant Mice," Cancer Research 68(18):7530-7540.

Streltsov, V.A. et al. (Aug. 24, 2004). "Structural Evidence For Evolution of Shark LG New Antigen Receptor Variable Domain Antibodies From a Cell-Surface Receptor," Proc. Natl. Acad. Sci. U.S.A. 101(34):12444-12449.

U.S. Appl. No. 17/461,826, filed Aug. 30, 2021, by Sakamuri et al.

Van Dijk, M.A. et al. (Aug. 2001). "Human Antibodies as Next Generation Therapeutics," Curr. Opin. Che. Biology 5(4):368-374.

Wu, T.Y.-H. (2016). "Strategies For Designing Synthetic Immune Agonists," Immunology 148:315-325.

Akira, S. et al. (Jul. 2004). "Toll-Like Receptor Signalling," Nat. Rev. Immunol. 4:499-511.

Alizadeh, D. et al. (Jan. 1, 2014). "Doxorubicin Eliminates Myeloid-Derived Suppressor Cells and Enhances the Efficacy of Adoptive T Cell Transfer in Breast Cancer," Cancer Res. 74(1):104-118, 24 pages.

Barclay, A.N. et al. (Jun. 2006). "The SIRP Family of Receptors and Immune Regulation," Nat. Rev. Immunol. 6(6):457-464.

Benaduce, A.P. et al. (Jul. 1, 2018). "Abstract 4702: Upgrading Cancer Immunotherapy: Checkpoint Blockade mAb-ODN Conjugate," Cancer Research 78(13):4702, with Supplement, 5 pages.

Berrien-Elliot, M.M. et al. (Dec. 2015). "Improving Natural Killer Cell Cancer Immunotherapy," Curr. Opin. Organ Transplant. 20(6):671-680, 19 pages.

Betting, D.J. et al. (Nov. 20, 2009). "In Vivo Eradication of a Rituzimab-Resistant Human CD20+ B Cell Lymphoma by Rituximab-CpG Oligodeoxynuceotide Conjugate Is Mediated by Natural Killer Cells and Complement," Abstract 723, Blood 114(22):723, 2 pages.

Bravman, T. et al. (Nov. 15, 2006, e-pub. Aug. 18, 2006). "Exploring "One-Shot" Kinetics and Small Molecule Analysis Using The ProteOn XPR36 Array Biosensor," Anal. Biochem. 358(2):281-288.

Chan, K. S. et al. (Aug. 18, 2009). "Identification, Molecular Characterization, Clinical Prognosis, and Therapeutic Targeting of Human Bladder Tumor-Initiating Cells," Proc. Natl. Acad. Sci. USA 106(33):14016-14021.

D'Arpa, P. et al. (2017). "Toll-Like Receptor Signaling in Burn Wound Healing and Scarring," Adv. Wound Care 6(10):330-343.

Du, X. et al. (Sep. 2000). "Three Novel Mammalian Toll-Like Receptors: Gene Structure, Expression, and Evolution," Eur. Cytokine Netw. 11(3):362-371.

Englisch, U. et al. (Jun. 1991). "Chemically Modified Oligonucleotides as Probes and Inhibitors," Angewandte Chemie, International Edition 30(6): 613-629.

Extended European Search Report, dated Sep. 27, 2022, for European Patent Application No. 19874575.4, 15 pages.

Gay, N.J. et al. (2007, e-pub. Mar. 15, 2007). "Structure and Function of Toll Receptors and Their Ligands," Annu. Rev. Biochem. 76:141-165.

Hashimoto, G. et al. (Nov. 1983). "Antibody-Dependent Cell-Mediated Cytotoxicity Against Influenza Virus-Infected Cells," J. Infect. Dis. 148(5):785-794.

Honegger, A. et al. (Jun. 8, 2001). "Yet Another Numbering Scheme For Immunoglobulin Variable Domains: An Automatic Modeling And Analysis Tool," J. Mol. Biol. 309:657-670.

Hoogenboom, H.R. et al. (Sep. 2005), "Selecting and Screening Recombinant Antibody Libraries," Nat Biotechnol. 23(9):1105-1116.

Imai, K. et al. (Nov. 25, 2000). "Natural Cytotoxic Activity of Peripheral-Blood Lymphocytes and Cancer Incidence: An 11-Year Follow-Up Study of a General Population," Lancet 356(9244):1795-1799.

International Preliminary Report on Patentability, dated Apr. 14, 2021, for PCT Application No. PCT/US2019/056619, filed Oct. 16, 2019, 6 pages.

International Search Report and Written Opinion, dated Jan. 10, 2022, for PCT Application No. PCT/US2019/056619, filed Oct. 16, 2019, 12 pages.

Jang, J.K. et al. (May 2016). "Systemic Delivery of chTNT-3/CpG Immunoconjugates for Immunotherapy in Murine Solid Tumor Models," Cancer Immunology Immunotherapy 65(5):511-523, 21 pages.

Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.

Li, Z. et al. (2013, e-pub. Dec. 29, 2012). "Generation of Tumor-Targeted Antibody-CpG Conjugates," Journal of Immunological Methods 389(1):45-51.

Oka, N. et al. (Nov. 26, 2008). "Solid-Phase Synthesis of Stereoregular Oligodeoxyribonucleoside Phosphorothioates Using Bicyclic Oxazaphospholidine Derivatives As Monomer Units," J. Am. Chem. Soc. 130(47):16031-16037.

Paust, S. et al. (Jun. 2011). "Natural Killer Cell Memory," Nat. Immunol. 12(6):500-508.

Quiroz, F.G. et al. (2010). "Engineering Antibody Fragments: Replicating The Immune System and Beyond," Revista Ingenieria Biomedica 4:39-51.

Sanghvi, Y.S. (1993). "Heterocyclic Base Modification in Nucleic Acids and Their Applications in Antisense Oligonucleotides," Chapter 15 in Antisense Research and Applications, CRC Press, Crooke, S.T. et al. eds., pp. 274-301.

Schettini, J. et al. (Nov. 2012). "Intratumoral Delivery of CpG-Conjugated Anti-MUC1 Antibody Enhances NK Cell Anti-Tumor Activity," Cancer Immunol. Immunother. 61(11):1-19.

Schraml, B.U. et al. (2015, e-pub. Dec. 3, 2014). "Defining Dendritic Cells," Curr. Opin. immunol. 32:13-20.

Sheng, J. et al. (2011, e-pub. Jan. 17, 2011). "Synthesis, Structure and Imaging of Oligodeoxyribonucleotides With Tellurium-Nucleobase Derivatization," Nucleic Acids Research 39(9):3962-3971.

(56) References Cited

OTHER PUBLICATIONS

Shi, M. et al. (Jan. 15, 2016). "MAP1S Protein Regulates the Phagocytosis of Bacteria and Toll-like Receptor (TLR) Signaling," J. Biol. Chem. 291(3):1243-1250.

Takeda, K. et al. (2004). "TLR Signaling Pathways," Semin. Immunol. 16:3-9.

Van Acker, H.H. et al. (Jul. 24, 2017). "CD56 in the Immune System: More Than a Marker for Cytotoxicity?," Front. Immunol. 8(892):1-9.

Waight, J.D. et al. (Oct. 2013). "Myeloid-Derived Suppressor Cell Development Is Regulated By a STAT/IRF-8 Axis," J. Clin. Investig. 123(10):4464-4478.

Wang, W. et al. (Jul. 27, 2015). "NK Cell-Mediated Antibodydependent Cellular Cytotoxicity In Cancer Immunotherapy," Front. Immunol. 6(368):1-15.

Willingham, S.B. et al. (Apr. 24, 2012, e-pub. Mar. 26, 2012). "The CD47-Signal Regulatory Protein Alpha (SIRPa) Interaction is a Therapeutic Target for Human Solid Tumors," Proc. Natl. Acad. Sci. USA 109(17):6662-6667.

Yanagita, T. et al. (Jan. 12, 2017). "Anti-SIRPα Antibodies as a Potential New Tool for Cancer Immunotherapy," JCI Insight 2(1):1-15.

Yang, L. et al. (2017). "Tumor-Associated Macrophages: From Basic Research To Clinical Application," J. Hematol. Oncol. 10:58, 12 pages.

Zahavi, D. et al. (2018, e-pub. Jul. 24, 2018). "Enhancing Antibody-Dependent Cell-Mediated Cytotoxicity: A Strategy For Improving Antibody-Based Immunotherapy," Antibody Therapeut. 1(1):7-12.

Zhang, D. et al. (Mar. 5, 2004). "A Toll-like Receptor That Prevents Infection by Uropathogenic Bacteria," Science 303:1522-1526.

Zhang, J.-Y. et al. (2009). "Identification of Tumor-Associated Antigens (TAAs) as Diagnostic and Predictive Biomarkers In Cancer," Methods Mol. Biol. 520:1-10, 9 pages.

Zhao, X. et al. (Jul. 2, 2014). "Targeting CD47-SIRP Interaction for Potentiating Therapeutic Antibody-Mediated Tumor Cell Destruction by Phagocytes," PhD Thesis 1-151.

Bork, P. (2000). "Powers and Pitfalls in Sequence Analysis: The 70% Hurdle," Genome Research 10:398-400.

Bowie, J.U. et al. (Mar. 1990). "Deciphering The Message In Protein Sequences; Tolerance To Amino Acid Substitutions," Science 247(4948):1306-1310.

Burgess, W.H. et al. (1990). "Possible Dissociation Of The Heparin-Binding And Mitogenic Activities Of Heparin- Binding (Acidic Fibroblast) Growth Factor-1 From Its Receptor-Binding Activities By Site-Directed Mutagenesis Of A Single Lysine Residue," J. Cell Biol. 111:2129-2138.

Casset, F. et al. (2003) "A Peptide Mimetic Of An Anti-CD4 Monoclonal Antibody By Rational Design," BBRC 307:198-205, 8 pages.

Greenspan, N.S. et al. (Oct. 1999). "Structural Analysis: Defining Epitopes: It's Not As Easy As It Seems," Nature Biotechnology 17:936-937.

Lazar, E. et al. (Mar. 1998). "Transforming Growth Factor α: Mutation Of Aspartic Acid 47 and Leucine 48 Results In Different Biological Activities," Molecular and Cellular Biology 8(3):1247-1252.

Liu, H. et al. (Jul. 2008). "Heterogeneity of Monoclonal Antibodies," Journal of Pharmaceutical Sciences 97 (7):2426-2447.

MacCallum, R.M. et al. (1996). "Antibody-Antigen Interactions: Contact Analysis and Binding Site Topography," J. Mol. Biol. 262:732-745.

Paul (2003). Fundamental Immunology 5th Edition. Raven Press, New York Chapter 3, pp. 109-147, 2990 pages.

Sela-Culang, I. et al. (Oct. 8, 2013). "The Structural Basis of Antibody-Antigen Recognition," Frontiers in Immunology 4(Article 302):1-13.

Vajdos, F.F. et al. (2002) "Comprehensive Functional Maps of the Antigen Binding Site of an Anti-ErbB2 Antibody Obtained with Shotgun Scanning Mutagenesis," J. Mol. Biol. 320:415-428.

\* cited by examiner

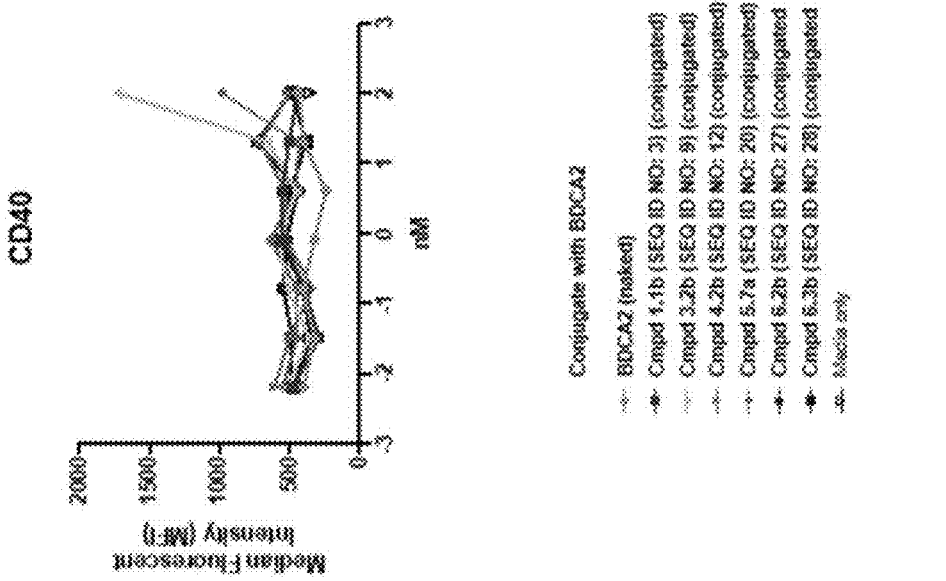
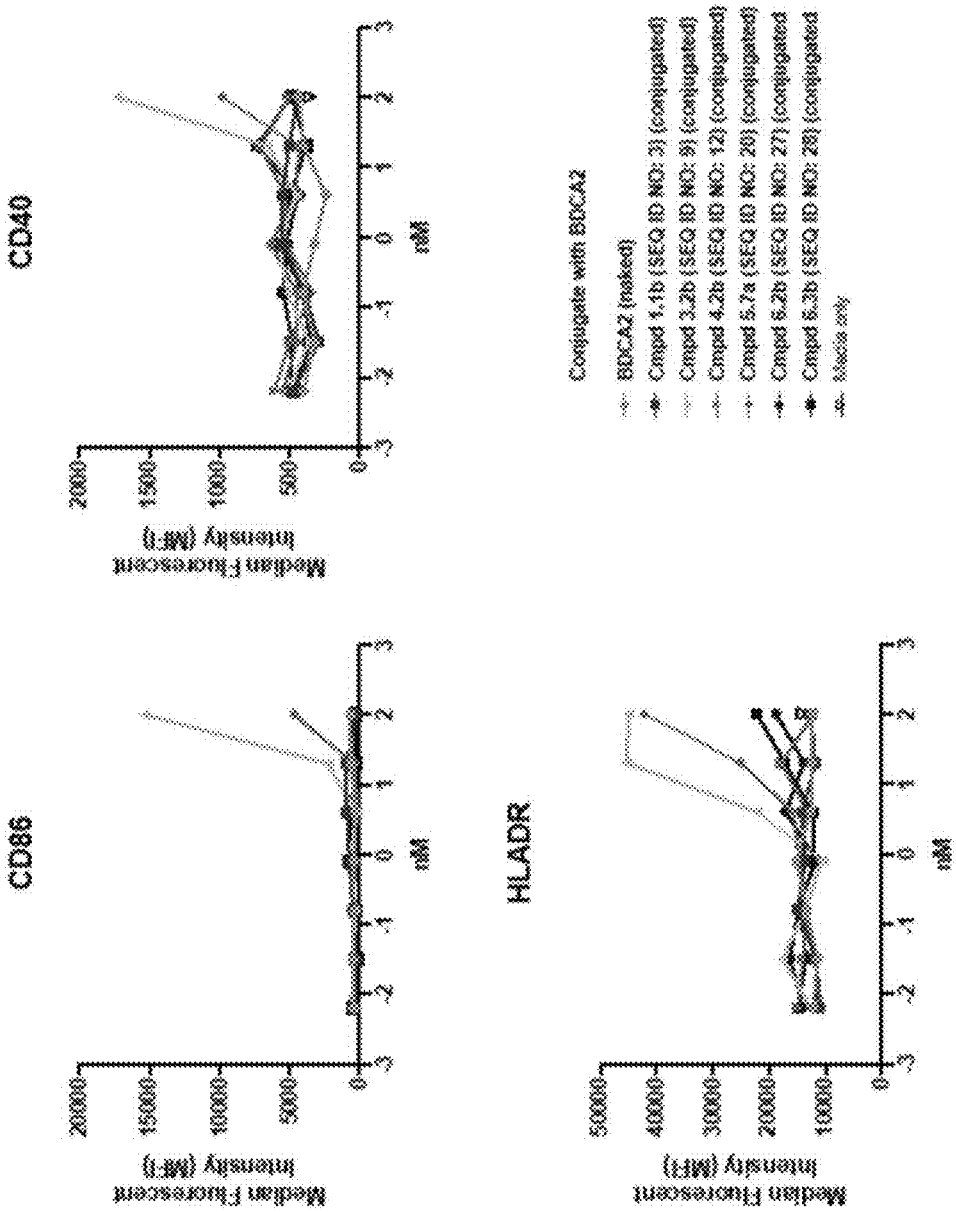
FIG. 6A, FIG. 6B, FIG. 6C

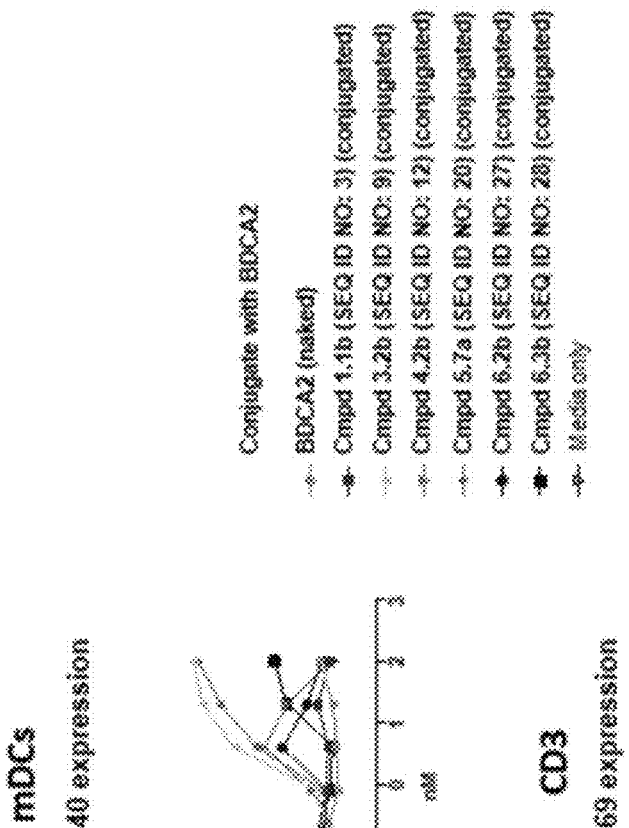
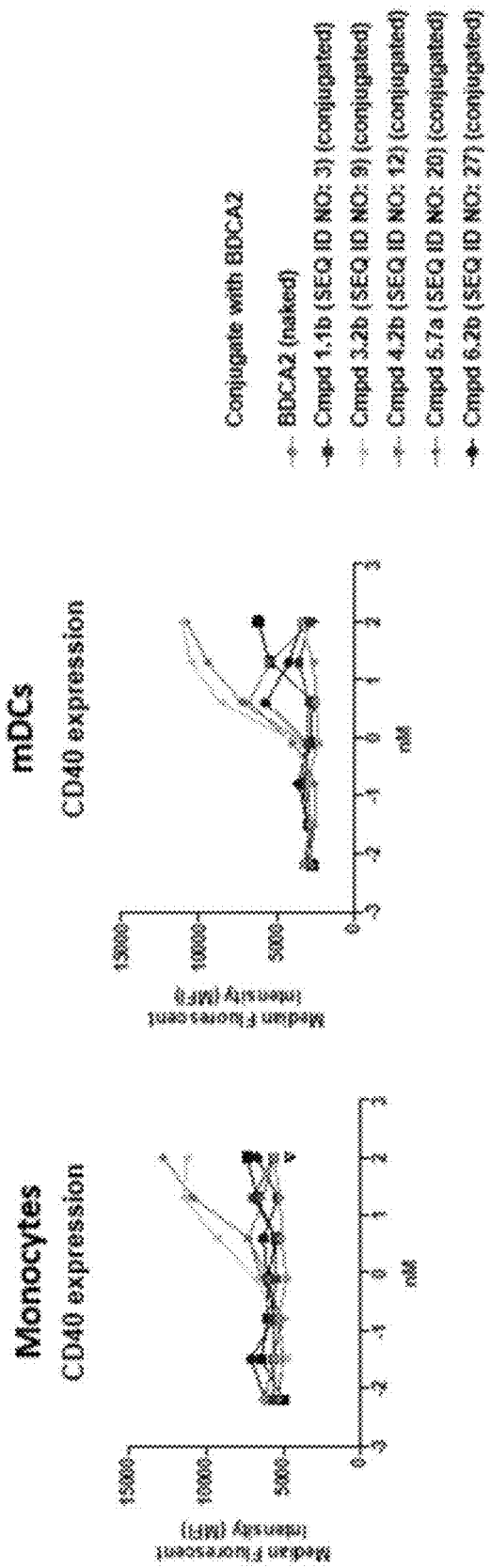
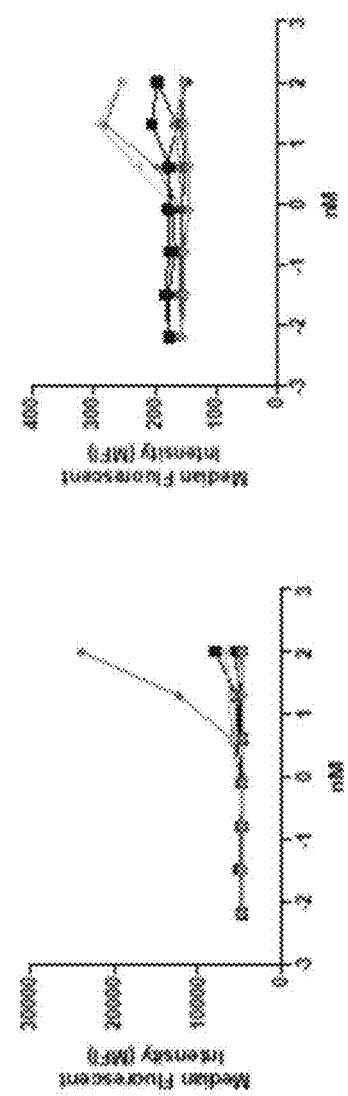
FIG. 7A  FIG. 7B  FIG. 7C  FIG. 7D

```
                         1                                                    50
mRFB4_HC   (1)  EVQLVESGGGLVKPGGSLKLSCAASGFAFSIYDMSWVRQTPEKRLEWVAY
RH1        (1)  EVQLVESGGGLVQPGGSLRLSCAASGFAFSIYDMSWVRQAPGKGLEWVAY
RH2        (1)  QVQLLESGGGVVQPGGSLRLSCAASGFAFSIYDMNWVRQAPGKGLEWVSA
RH3        (1)  EVQLVESGGGLVQPGGSLRLSCAASGFTFSSYEMNWVRQAPGKGLEWVSY
RH4        (1)  QVQLQESGPGLVKPSDTLSLTCTVSGFAFSIYDMSWIRQPPGKGLEWIAY
                              H1
                         51                                                   100
mRFB4_HC  (51)  ISSGGGTTYYPDTVKGRFTISRDNAKNTLYLQMSSLKSEDTAMYYCARHS
RH1       (51)  ISSGGGTTYYPDTVKGRFTISRDNSKNTLYLQMNSLRAEDTAVYYCARHS
RH2       (51)  ISSGGGTTYYADSVKGRFTISRDNAKNSLYLQMNSLRAEDTAVYYCARHS
RH3       (51)  ISSTIYYADSVKGRFTISRDNAKNSLYLQMNSLRAEDTAVYYCARHS
RH4       (51)  ISSGGGTTYYNPSLKSRVTISVDTSKNQFSLKLSSVTAADTAVYYCARHS
                    H2                                          H3
                         101                          123
mRFB4_HC (101)  GYGSSYGVLFAYNGQGTLVTVSS
RH1      (101)  GYGTHNGVLFAYNGRGTLVTVSS
RH2      (101)  GYGTHNGVLFAYNGRGTLVTVSS
RH3      (101)  GYGTHNGVLFAYNGRGTLVTVSS
RH4      (101)  GYGTHNGVLFAYNGRGTLVTVSS
```

FIG. 8A

```
                                                                    50
mRFB4_LC  (1)  DIQMTQTTSSLSASLGDRVTITCRAS QDISNYL NWYQQKPDGTVKLLIY Y
RL1       (1)  DIQMTQSPSSLSASVGDRVTITCRAS QDIHGYL NWYQQKPGKAPKLLIY A
RL2       (1)  DIQMTQSPSSVSASVGDRVTITCRAS QDIHGYL AWYQQKPGKAPKLLIY A
RL3       (1)  DIQMTQSPSSLSASVGDRVTITCRAS QSISSYL NWYQQKPGKAPKLLIY Y
RL4       (1)  EIVLTQSPATLSLSPGERATLSCRAS QDIHGYL NWYQQKPGQAPRLLIY Y
RL5       (1)  DIVMTQTPLSLSVTPGQPASISCRAS QDIHGYL NWYQQKPGQSPQLLIY Y
                              L1

100
mRFB4_LC  (51) TS LHSGVPSRFSGSGSGTDYSLTISNLEQEDFATYFC QGNTLPWTFGG
RL1       (51) TS LHSGVPSRFSGSGSGTDFTLTISSLQPEDFATYFC QGNTLPWTFGQ
RL2       (51) TS LQSGVPSRFSGSGSGTDFTLTISSLQPEDFATYYC QGNTLPWTFGQ
RL3       (51) AS LQSGVPSRFSGSGSGTDFTLTISSLQPEDFATYYC QGNTLPWTFGQ
RL4       (51) TS LHSGIPARFSGSGSGTDFTLTISSLEPEDFAVYYC QGNTLPWTFGQ
RL5       (51) TS LHSGVPDRFSGSGSGTDFTLKISRVEAEDVGVYFC QGNTLPWTFGG
                 L2                                     L3

101
mRFB4_LC (101) GTKLEIK
RL1      (101) GTKLEIK
RL2      (101) GTKLEIK
RL3      (101) GTKLEIK
RL4      (101) GTKLEIK
RL5      (101) GTKLEIK
```

FIG. 8B

| Sample | HC | LC | Expression (Expi293) | Expression (CHO) | % HMW | % Monomer | VH/VL Pairings | CD22 KD (nM) | Cyno binding |
|---|---|---|---|---|---|---|---|---|---|
| TNT69 | RH1 | RL1 | | | ND | Double peak | HV3/KV1 | 0.6 | High |
| TNT73 | RH1 | RL2 | | | ND | Broad peak | HV3/KV1 | 14 | Med |
| TNT77 | RH1 | RL3 | | | ND | Broad peak | HV3/KV1 | 10 | Med |
| TNT81 | RH1 | RL4 | | | ND | Broad peak | HV3/KV3 | 0.7 | High |
| TNT85 | RH1 | RL5 | | | ND | Broad peak | HV3/KV2 | 1.3 | High |
| TNT70 | RH2 | RL1 | | | 3.3 | 96.7 | HV3/KV1 | 0.4 | High |
| TNT74 | RH2 | RL2 | | | 5.0 | 95.0 | HV3/KV1 | 16 | Low |
| TNT78 | RH2 | RL3 | | | 2.4 | 97.7 | HV3/KV1 | 25 | Low |
| TNT82 | RH2 | RL4 | | | 2.6 | 97.4 | HV3/KV3 | 0.9 | High |
| TNT86 | RH2 | RL5 | | | 1.6 | 98.4 | HV3/KV2 | 1.1 | High |
| TNT71 | RH3 | RL1 | | | 12.5 | 87.5 | HV3/KV1 | 0.3 | High |
| TNT75 | RH3 | RL2 | | | 10.2 | 89.8 | HV3/KV1 | 30 | High |
| TNT79 | RH3 | RL3 | | | 4.3 | 95.7 | HV3/KV1 | 23 | Med |
| TNT83 | RH3 | RL4 | | | 4.8 | 95.2 | HV3/KV3 | 6 | High |
| TNT87 | RH3 | RL5 | | | 15.1 | 84.9 | HV3/KV2 | 0.7 | High |
| TNT72 | RH4 | RL1 | | | 0.9 | 99.1 | HV4/KV1 | 0.7 | High |
| TNT76 | RH4 | RL2 | | | 1.0 | 99.0 | HV4/KV1 | 30 | Low |
| TNT80 | RH4 | RL3 | | | 1.1 | 98.9 | HV4/KV1 | 23 | Low |
| TNT84 | RH4 | RL4 | | | 0.0 | 100.0 | HV4/KV3 | 2.5 | Med |
| TNT88 | RH4 | RL5 | | | 4.6 | 95.4 | HV4/KV2 | 1.3 | High |

FIG. 13A

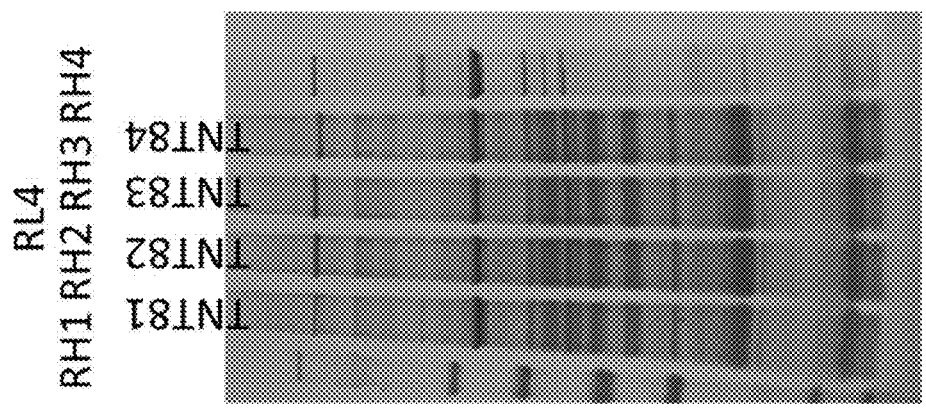
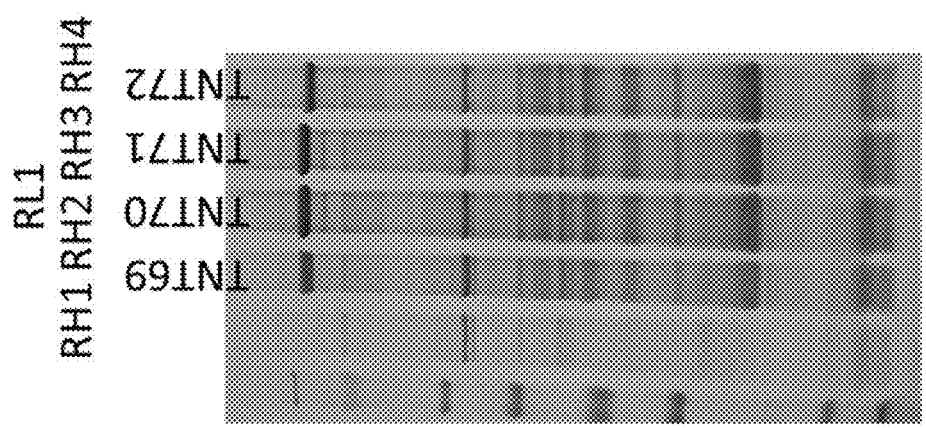
FIG. 13B

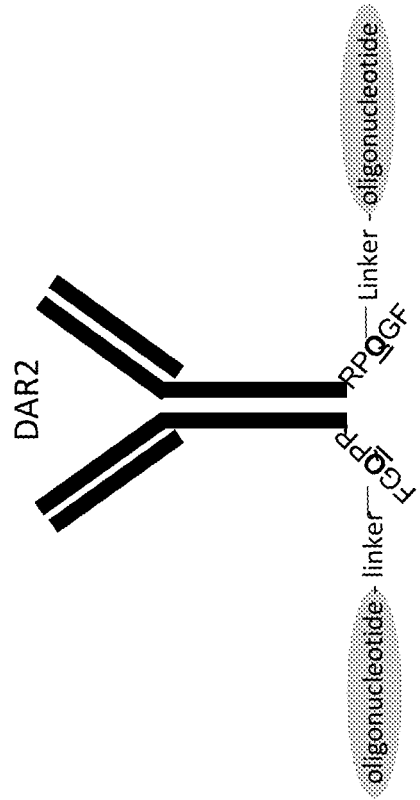
FIG. 16A. Engineered Q-tag (RPQGF)
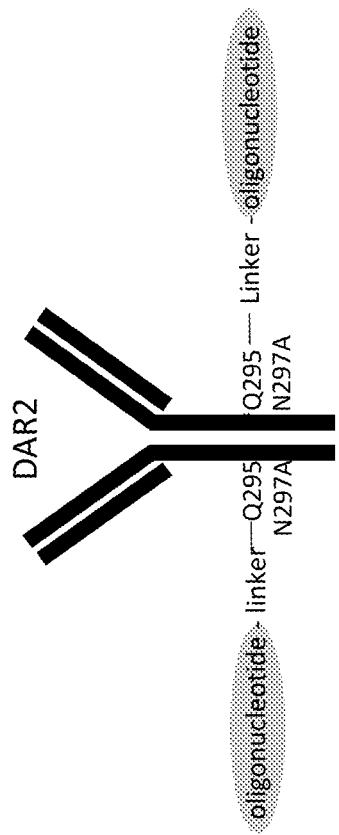
FIG. 16C. Naturally occurring Q-tag
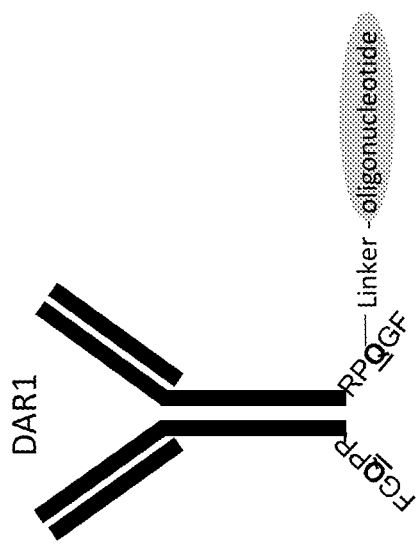
FIG. 16B. Engineered Q-tag (RPQGF)
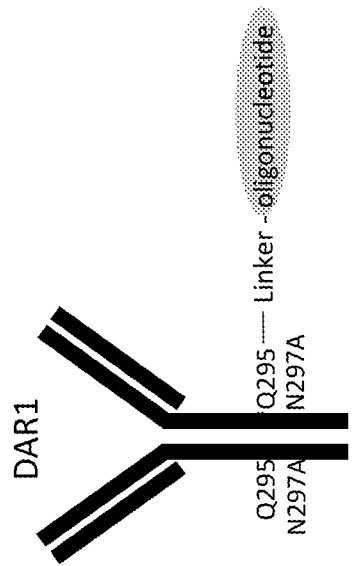
FIG. 16D. Naturally occurring Q-tag

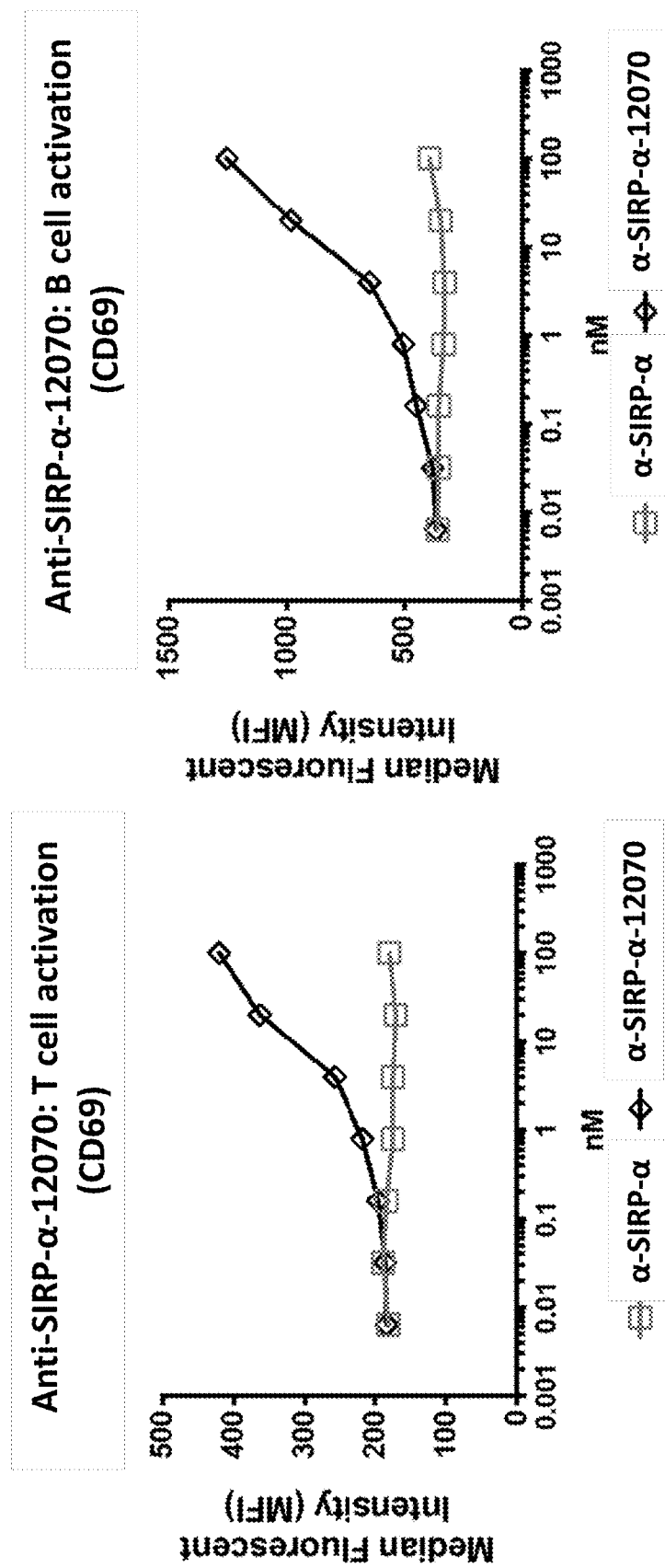

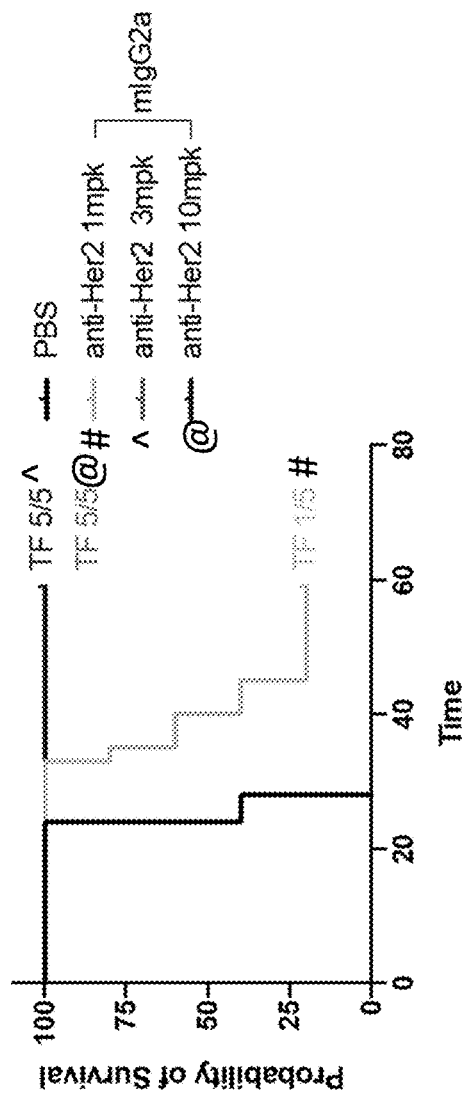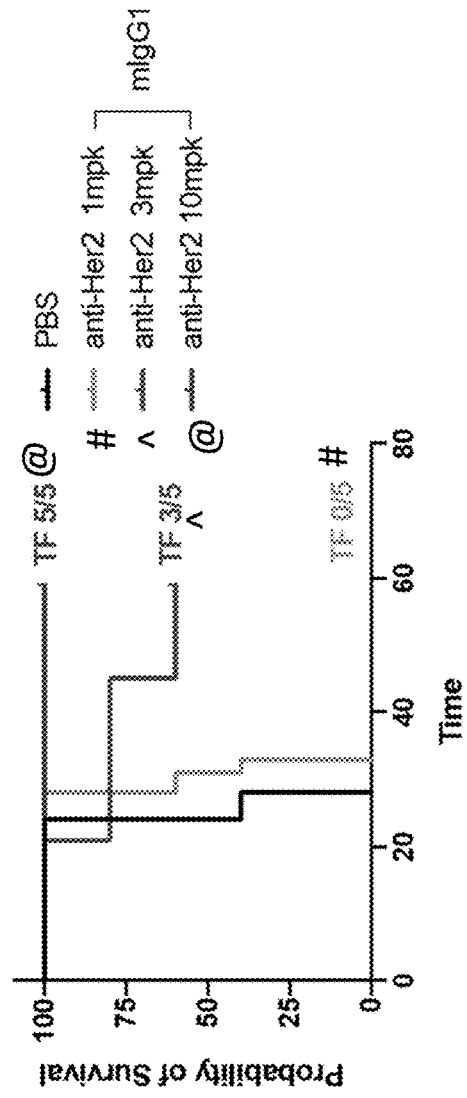

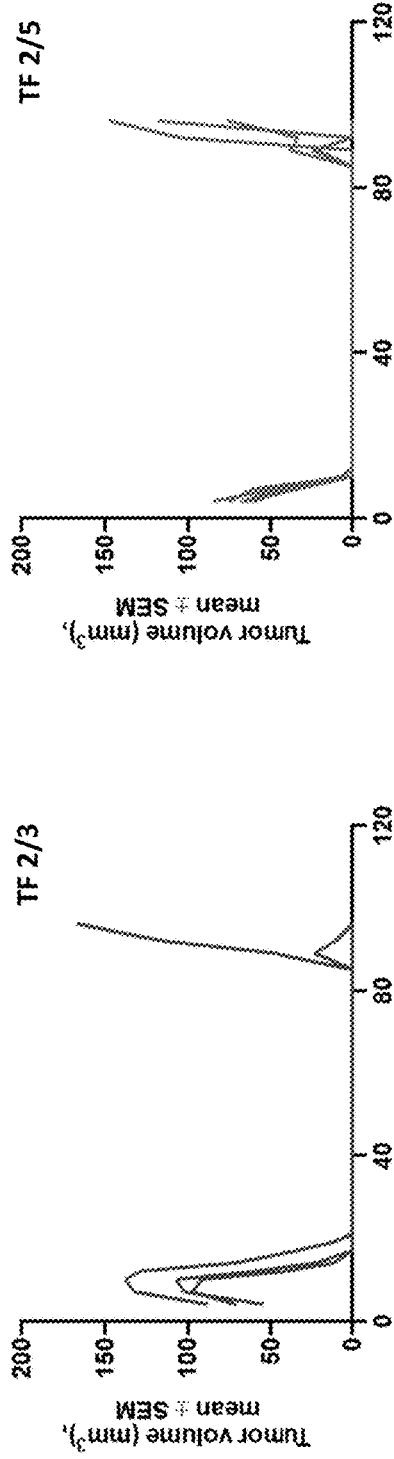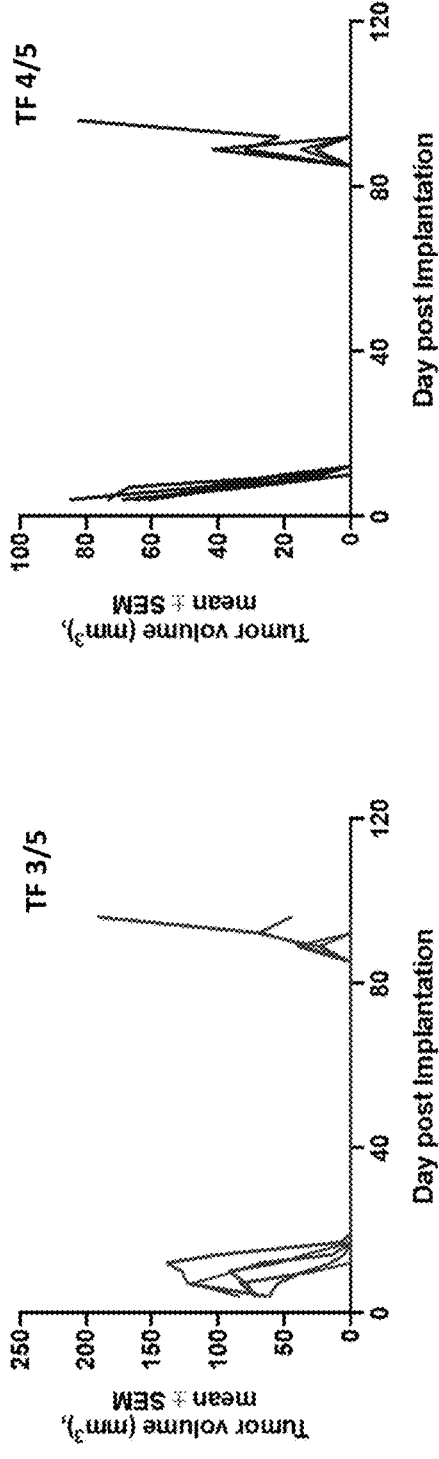
FIG. 23H

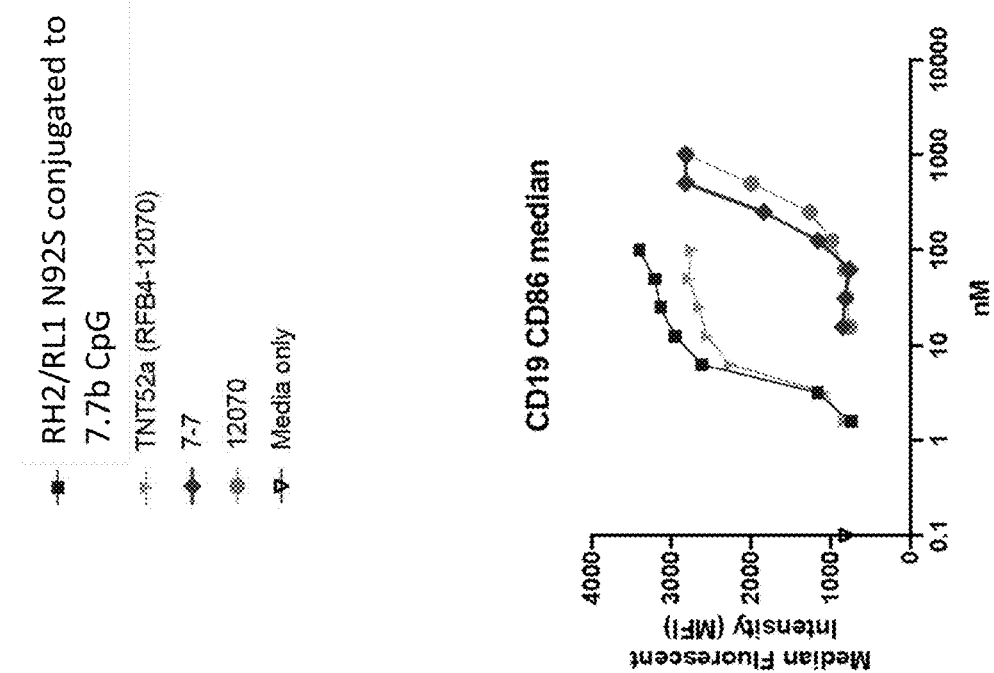
FIG. 26A
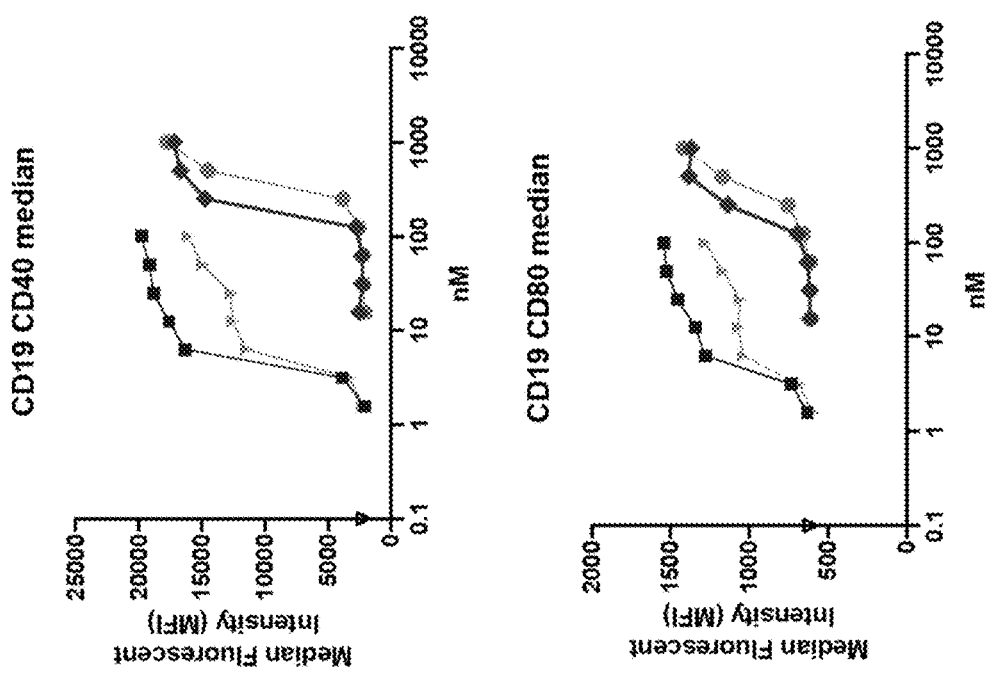
FIG. 26B
FIG. 26C

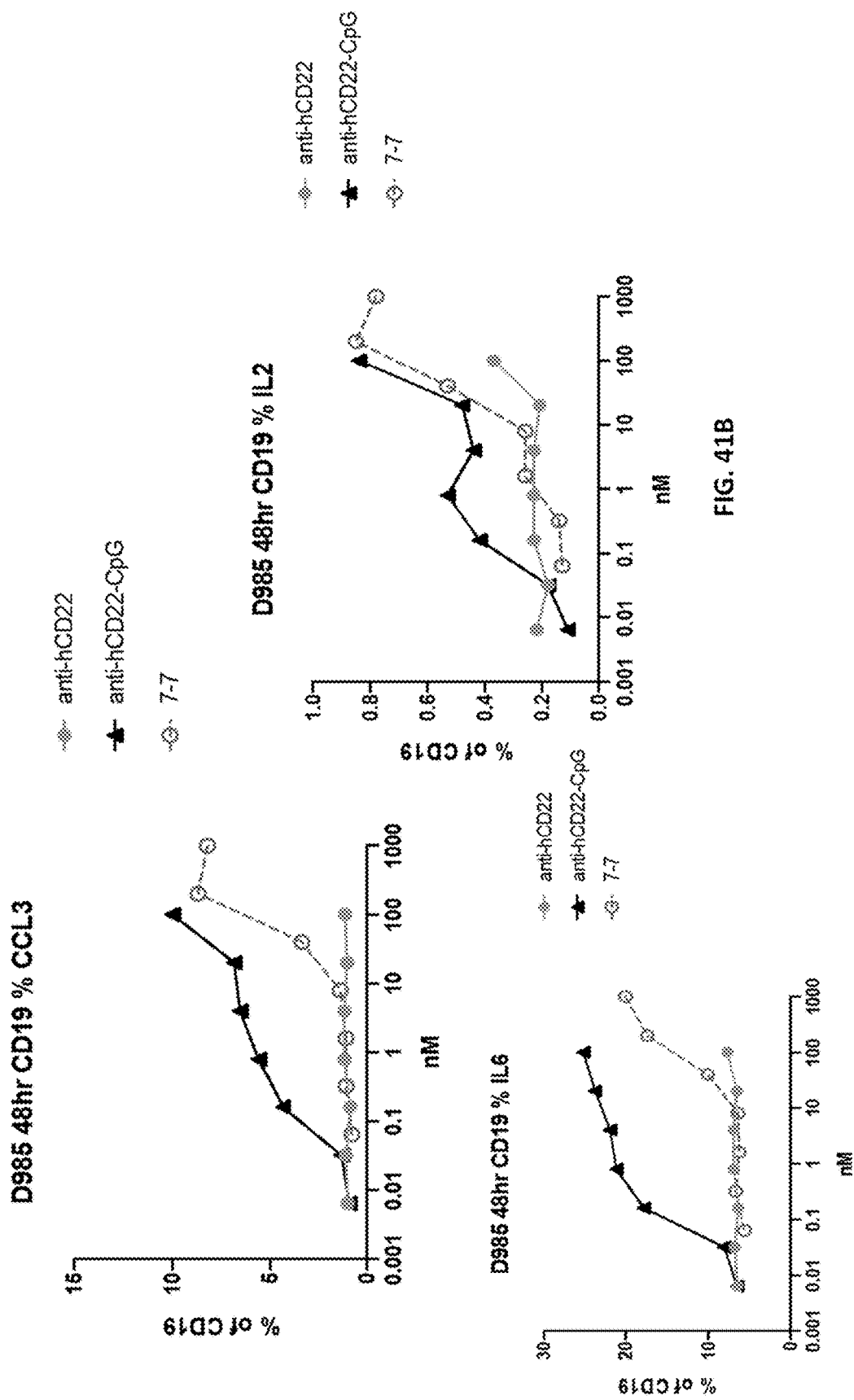

TRANSGLUTAMINASE-MEDIATED CONJUGATION

CROSS-REFERENCE TO RELATED APPLICATIONS

This application is a continuation of U.S. patent application Ser. No. 17/187,579, filed on Feb. 26, 2021, which claims priority to and benefit of U.S. Provisional Patent Application No. 62/983,463, filed on Feb. 28, 2020, and U.S. Provisional Patent Application 63/110,854, filed on Nov. 6, 2020, the disclosure of each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 186492000201SEQLIST.TXT, date recorded: Jun. 15, 2022, size: 174,071 bytes).

FIELD OF INVENTION

The present disclosure relates generally to methods for conjugating an oligonucleotide and a polypeptide and related compounds, compositions and kits.

BACKGROUND

Pathogen-associated molecular patterns (PAMPs) are molecules associated with various pathogens and are recognized by toll-like receptors (TLRs) and other pattern recognition receptors (PRRs) activating innate immune responses. The ability of PAMPs to recruit immune system in the absence of pathogens provides a strategy for treating a variety of diseases involving cell destruction (e.g., anticancer therapy) through the use of innate immune system response. One class of PAMPs that has been investigated for a variety of therapeutic applications is immunostimulating polynucleotides, such as unmethylated cytosine-guanine dinucleotide (CpG)-containing oligodeoxynucleotides (CpG ODNs) (e.g., agatolimod). It is thought that CpG ODNs mediate TLR9 dimerization in immune cells (e.g., B cells, monocytes and plasmacytoid dendritic cells (pDCs)) to upregulate cytokines (e.g., type I interferon and interleukins), thereby activating natural killer cells.

Toll-like receptor 9 (TLR9), also designated as CD289, is an important receptor expressed in immune system cells including dendritic cells (DCs), B lymphocytes, macrophages, natural killer cells, and other antigen presenting cells. TLR9 activation triggers intracellular signaling cascades, leading to activation, maturation, proliferation and cytokine productions in these immune cells, thus bridges the innate and adaptive immunity. Martinez-Campos et al., *Viral Immunol.* 2016, 30, 98-105; Notley et al., *Sci. Rep.* 2017, 7, 42204. Natural TLR-9 agonists include unmethylated cytosine-guanine dinucleotide (CpG)-containing oligodeoxynucleotides (CpG ODNs).

CpG ODNs may include, for example, oligodeoxynucleotides having poly-G tails with phosphorothioate backbones at 3'- and 5'-termini and a central palindromic sequence including a phosphate backbone and a CpG within its central palindrome sequence, or oligodeoxynucleotides having a fully phosphorothioate backbone, and a sequence at the 5' end for TLR9 activation, or oligodeoxynucleotides having a fully phosphorothioate backbone with a 3'-end sequence enabling formation of a duplex. However, CpG ODNs are often susceptible to degradation in serum and thus pharmacokinetics of CpG ODNs may be one of the limiting factors in their development as therapeutics. Also CpG ODNs often exhibit uneven tissue distribution in vivo, with primary sites of accumulation being in liver, kidney, and spleen. Such distribution can elicit off-target activity and local toxicity associated with PAMPs.

One solution is to conjugate the immunomodulating polynucleotides (e.g., CpG ODNs) with a targeting moiety for specifically targeted tissues or cells to overcome the uneven distribution of the polynucleotide. See US 2018/0312536. Particularly, transglutaminase-mediated reaction can be used to conjugate a polypeptide targeting moiety containing a glutamine residue with a CpG ODN containing a primary amine group. Microbial transglutaminase (mTG) is from the species *Streptomyces mobaraensis*. The mTG catalyzes under pH-controlled aqueous conditions (including physiological conditions) a transamidation reaction between a 'reactive' glutamine of a protein and a 'reactive' lysine residue whereas the latter can also be a simple, low molecular weight primary amine such as a 5-aminopentyl group. For an endogenous glutamine on a protein to be recognized as an mTG-substrate two criteria seem important: 1) the presence of hydrophobic amino acids in the peptide sequence adjacent to the glutamine residue and 2) the positioning of the glutamine on a loop with local chain flexibility enhancing reactivity toward mTG.

Although conjugation of these immunomodulating polynucleotides may lead to improved stability and distribution, there remains a need for immunomodulating polynucleotides with improved stability and selectivity with or without conjugation to targeting moieties, and methods for preparing them.

BRIEF SUMMARY

In one aspect, provided herein is a conjugate comprising an antibody or antigen-binding fragment thereof and one or more immunomodulating oligonucleotides (P), wherein each immunomodulating oligonucleotide is linked via an amide bond to a glutamine residue (Q) of the antibody or fragment and a linker (L) as shown in Formula (A):

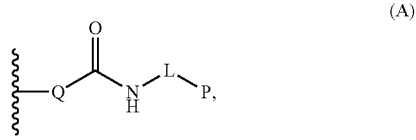

wherein ⁓ indicates the point of attachment of each Q to the antibody or antigen-binding fragment thereof (Ab). In some embodiments, the glutamine residue is part of a Q-tag peptide linked to the antibody, e.g., to the C-terminus of the antibody Fc region. In some embodiments, the glutamine residue is part of the antibody (e.g., part of the Fc region, such as residue Q295). In some embodiments, the antibody further comprises an N297A mutation. Exemplary Q-tag peptide sequences are provided, e.g., in Table 3. Exemplary immunomodulating oligonucleotides are described herein and provided, e.g., in Tables 2 & 9-12. In some embodiments, 1-4 immunomodulating oligonucleotides are conjugated to the antibody. Exemplary linkers (L) are described herein. In some embodiments, the linker comprises a polyethylene glycol moiety.

In one aspect, provided herein is a conjugate comprising an antibody or antigen-binding fragment thereof and one or more immunomodulating oligonucleotides (P), wherein the antibody or antigen-binding fragment is linked to one or more Q-tag peptides (Q) that comprise the amino acid sequence RPQGF (SEQ ID NO:47), wherein each immunomodulating oligonucleotide is linked to a Q-tag peptide via an amide bond with the glutamine residue of the Q-tag peptide and a linker (L) as shown in Formula (A):

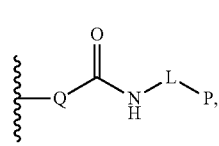

(A)

wherein ～ indicates the point of attachment of each Q to the antibody or antigen-binding fragment thereof (Ab).

In some embodiments, the antibody is linked to 2 Q-tag peptides, and one of the Q-tag peptides is linked to an immunomodulating oligonucleotide. In some embodiments, the antibody is linked to 2 Q-tag peptides, and each of the 2 Q-tag peptides is linked to an immunomodulating oligonucleotide. In some embodiments, the antibody or fragment thereof is a monoclonal antibody or fragment thereof. In an additional embodiment of the present aspect, the antibody or fragment thereof is a Fab, F(ab')2, Fab'-SH, Fv, scFv, single domain, single heavy chain, or single light chain antibody or antibody fragment. In yet another embodiment of this aspect which may be combined with any of the preceding embodiments, the antibody or fragment thereof is a humanized, human, or chimeric antibody or fragment thereof. In still further embodiments of the present aspect, the antibody or fragment thereof specifically binds a tumor associated antigen.

In still further embodiments of the present aspect, the antibody or fragment thereof specifically binds human CD22. In still yet another embodiment of the present aspect, the antibody comprises a heavy chain variable (VH) domain and a light chain variable (VL) domain, wherein the VH domain comprises CDR-H1, CDR-H2, and CDR-H3 sequences from a VH domain sequence selected from the group consisting of:

```
                                         (SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GYGTHWGVLFAYWGRGTLVTVSS,
                                         (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS,
                                         (SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GGYGTHWGVLFAYWGRTLVTVSS,
``` and

```
                                         (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.
```

In still et another embodiment of the present aspect, the antibody comprises a heavy chain variable (VH) domain and a light chain variable (VL) domain, wherein the VH domain comprises CDR-H1, CDR-H2, and CDR-H3 sequences from a VH domain shown in Table 8. In still yet another embodiment of the present aspect, the antibody comprises a heavy chain variable (VH) domain and a light chain variable (VL) domain, wherein the VH domain comprises a CDR-H1 comprising the sequence of SEQ ID NO:113, a CDR-H2 comprising the sequence of SEQ ID NO:115, and a CDR-H3 comprising the sequence of SEQ ID NO:116; or a CDR-H1 comprising the sequence of SEQ ID NO:114, a CDR-H2 comprising the sequence of SEQ ID NO:189, and a CDR-H3 comprising the sequence of SEQ ID NO: 116. In still yet another embodiment of the present aspect, the antibody comprises a heavy chain variable (VH) domain and a light chain variable (VL) domain, wherein the VH domain comprises a CDR-H1 comprising the sequence of SEQ ID NO:113, a CDR-H2 comprising the sequence of SEQ ID NO: 115, and a CDR-H3 comprising the sequence of SEQ ID NO: 116, and the VL domain comprises a CDR-L1 comprising the sequence of SEQ ID NO:117, a CDR-L2 comprising the sequence of SEQ ID NO:119, and a CDR-L3 comprising the sequence of SEQ ID NO:120. In yet another embodiment of the present aspect, the antibody comprises a heavy chain variable (VH) domain and a light chain variable (VL) domain, and wherein the VH domain comprises an amino acid sequence selected from the group consisting of

```
                                         (SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GGYGTHWGVLFAYWGRTLVTVSS,
                                         (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS,
                                         (SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GYGTHWGVLFAYWGRGTLVTVSS,
``` and

```
                                         (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.
```

In et another embodiment of the present aspect, the antibody comprises a heavy chain variable (VH) domain and a light chain variable (VL) domain, wherein the VH domain comprises the sequence of SEQ ID NO:65, and the VL domain comprises the sequence of SEQ ID NO:87. In still yet another embodiment of the present aspect, the antibody comprises a heavy chain variable (VH) domain and a light chain variable (VL) domain, wherein the VL domain comprises CDR-L1, CDR-L2, and CDR-L3 sequences from a VL domain sequence selected from the group consisting of:

(SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

TSILHSGIPARFSGSGPGTDFTLTISSLEPEDFAVYYCQQGNTLPWTFGG

GTKLEIK,
and (SEQ ID NO: 72)
DIVMTQTPLSLSVTPGQPASISCRASQDIHGYLNWYQQKPGQSPQLLIYY

TSILHSGVPDRFSGSGSGTDFTLKISRVEAEDVGVYFCQQGNTLPWTFGG

GTKLEIK.

In still yet another embodiment of the present aspect, the antibody comprises a heavy chain variable (VH) domain and a light chain variable (VL) domain, wherein the VL domain comprises CDR-L1, CDR-L2, and CDR-L3 sequences from a VL domain sequence selected from the group consisting of SEQ ID Nos: 68-91. In still yet another embodiment of the present aspect, the antibody comprises a heavy chain variable (VH) domain and a light chain variable (VL) domain, wherein the VL domain comprises CDR-L1, CDR-L2, and CDR-L3 sequences from a VL domain shown in Table 8. In still yet another embodiment of the present aspect, the antibody comprises a heavy chain variable (VH) domain and a light chain variable (VL) domain, wherein the VL domain comprises a CDR-L1 comprising the sequence of SEQ ID NO:117, a CDR-L2 comprising the sequence of SEQ ID NO:119, and a CDR-L3 comprising the sequence of SEQ ID NO:120; or a CDR-L1 comprising the sequence of SEQ ID NO:118, a CDR-L2 comprising the sequence of SEQ ID NO:177, and a CDR-L3 comprising the sequence of SEQ ID NO:120. In still further embodiments of the present aspect, the VL domain further comprises an amino acid substitution at residue N92. In certain embodiments wherein the VL domain comprises an amino acid substitution at residue N92, the amino acid substitution at residue N92 is selected from the group consisting of N92A, N92L and N92S. In still further embodiments of the present aspect, the antibody comprises a heavy chain variable (VH) domain and a light chain variable (VL) domain, wherein the VL domain an amino acid sequence selected from the group consisting of (SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

TSILHSGIPARFSGSGPGTDFTLTISSLEPEDFAVYYCQQGNTLPWTFGG

GTKLEIK,
and (SEQ ID NO: 72)
DIVMTQTPLSLSVTPGQPASISCRASQDIHGYLNWYQQKPGQSPQLLIYY

TSILHSGVPDRFSGSGSGTDFTLKISRVEAEDVGVYFCQQGNTLPWTFGG

GTKLEIK.

In still further embodiments of the present aspect, the antibody comprises a heavy chain variable (VH) domain and a light chain variable (VL) domain, wherein the VH domain comprises the amino acid sequence (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS, and wherein the VL domain comprises an amino acid sequence selected from the group consisting of (SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 73)
DIQMTQSPSSLSASVGDRVTITCRASQDIHGYLNWYQQKPGKAPKLLIYY

TSILHSGVPSRFSGSGSGTDFTLTISSLQPEDFATYFCQQGATLPWTFGQ

GTKLEIK, (SEQ ID NO: 82)
DIQMTQSPSSLSASVGDRVTITCRASQDIHGYLNWYQQKPGKAPKLLIYY

TSILHSGVPSRFSGSGSGTDFTLTISSLQPEDFATYFCQQGLTLPWTFGQ

GTKLEIK,
and (SEQ ID NO: 87)
DIQMTQSPSSLSASVGDRVTITCRASQDIHGYLNWYQQKPGKAPKLLIYY

TSILHSGVPSRFSGSGSGTDFTLTISSLQPEDFATYFCQQGSTLPWTFGQ

GTKLEIK.

In still further embodiments, the antibody or fragment thereof specifically binds human Her2. In still yet another embodiment of the present aspect, the antibody comprises a heavy chain variable (VH) domain and a light chain variable (VL) domain, wherein the VH domain comprises CDR-H1, CDR-H2, and CDR-H3 sequences from the VH domain sequence (SEQ ID NO: 168)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS and/or wherein the VL domain comprises CDR-L1, CDR-L2, and CDR-L3 sequences from the VL domain sequence (SEQ ID NO: 169)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK.

In still yet another embodiment of the present aspect, the antibody comprises a heavy chain variable (VH) domain and a light chain variable (VL) domain, wherein the VH domain comprises the sequence (SEQ ID NO: 168)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS and/or wherein the VL domain comprises the sequence (SEQ ID NO: 169)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK.

In still yet another embodiment of the present aspect, the antibody comprises a heavy chain variable (VH) domain and a light chain variable (VL) domain, wherein the VH domain comprises CDR-H1, CDR-H2, and CDR-H3 sequences from the VH domain sequence (SEQ ID NO: 170)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSS and/or wherein the VL domain comprises CDR-L1, CDR-L2, and CDR-L3 sequences from the VL domain sequence (SEQ ID NO: 171)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK.

In still yet another embodiment of the present aspect, the antibody comprises a heavy chain variable (VH) domain and a light chain variable (VL) domain, wherein the VH domain comprises the sequence (SEQ ID NO: 170)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSS and/or wherein the VL domain comprises the sequence (SEQ ID NO: 171)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK.

In some embodiments, the anti-Her2 antibody is trastuzumab or pertuzumab

In still yet another embodiments of the present aspect that can be combined with any of the preceding aspects, the antibody comprises an Fc region. In certain embodiments, the Fc region is a human Fc region selected from the group consisting of an IgG1 Fc region, an IgG2 Fc region, and an IgG4 Fc region. In some embodiments, the Fc region is a wild-type human IgG1, IgG2, or IgG4 Fc region. In some embodiments, the Fc region is a human Fc region comprising one or more amino acid substitutions that reduce one or more effector functions, as compared with the effector function(s) of a human Fc region that lacks the amino acid substitution(s). In still further embodiments, the Fc region is: (a) a human IgG1 Fc region comprising L234A, L235A, and/or G237A substitutions, amino acid position numbering according to EU index; (b) a human IgG2 Fc region comprising A330S and/or P331S substitutions, amino acid position numbering according to EU index; or (c) a human IgG4 Fc region comprising S228P and/or L235E substitutions, amino acid position numbering according to EU index. In still yet another embodiment, the Fc region further comprises an N297A substitution, amino acid position numbering according to EU index. In some embodiments, the antibody comprises an antibody heavy chain constant domain comprising an amino acid sequence selected from the group consisting of SEQ ID Nos:92-107 and 178. In certain embodiments wherein the Fc region comprises an N297A substitution, the conjugate further comprises an immunomodulating oligonucleotide P attached to the Q295 residue of the Fc region as shown in the following formula

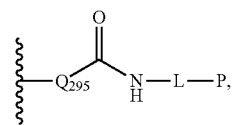

wherein L is a linker moiety connected to Q295 via an amide bond. In yet other embodiments, the Fc region further comprises a D265A substitution, amino acid position numbering according to EU index. In some embodiments, the conjugate binds to human CD22 expressed on the surface of a B cell. In some embodiments, the conjugate induces activation of TLR9.

In some embodiments of the present aspect, the antibody comprises a human lambda light chain. In other embodiments of the present aspect, the antibody comprises a human kappa light chain. In some embodiments, the antibody comprises an antibody light chain constant domain comprising an amino acid sequence selected from the group consisting of SEQ ID Nos:108-110. In still further embodiments which may be combined with any preceding embodiments of the present aspect, at least one Q-tag is attached to the heavy chain of the antibody. In certain embodiments, at least one Q-tag is fused to the C-terminus of the heavy chain of the antibody. In other embodiments, at least one Q-tag is attached to the light chain of the antibody. In still yet other embodiments, 1 or 2 Q-tags is/are linked to the antibody or antigen-binding fragment. In still further embodiments, the conjugate has a DAR of 1. In still further embodiments, the conjugate has a DAR of 2.

In still further embodiments of the present aspect, each immunomodulating oligonucleotide P is independently $$X^{5'}-(Y^N-X^N)_b-Y^{PTE}-(X^N-Y^N)_c-X^{3'}-Y^{3'},$$
$$*$$

wherein b and c are each independently an integer from 1 to 25; with the proviso that the sum of b and c is at least 5;

~~~* indicates the point of attachment of the immunomodulating oligonucleotide P to the rest of the conjugate;

$X^5$ is a 5' terminal nucleoside having the structure

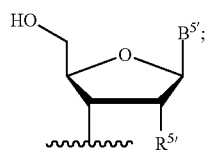

$X^3$ is a 3' terminal nucleoside having the structure

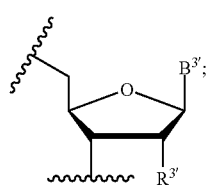

$Y^{PTE}$ is an internucleoside phosphotriester having the structure

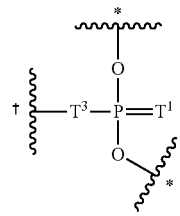

wherein * indicates the points of attachment to the rest of the oligonucleotide and ~~~† indicates the point of attachment to the linker L, or, if L is absent, ~~~† indicates the point of attachment to the Q tag peptide Q at the glutamine residue via an amide bond;

$Y^3$ is a terminal phosphotriester having the structure

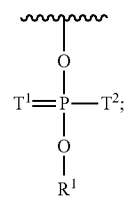

each $X^N$ is independently a nucleoside having the structure

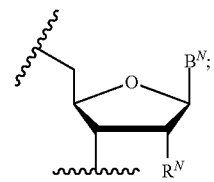

each $Y^N$ is independently an internucleoside linker having the structure

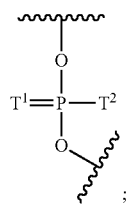

wherein each $B^N$ is independently a modified or unmodified nucleobase;
each $R^N$ is independently —H or —O—$C_{1-4}$-alkyl, wherein the $C_{1-4}$-alkyl of the —O—$C_{1-4}$-alkyl is further optionally substituted by —O—$C_1$-$C_4$-alkyl;
$B^{5'}$ and $B^{3'}$ are independently a modified or unmodified nucleobase;
$R^{5'}$ and $R^{3'}$ are independently —H or —O—$C_1$-$C_4$-alkyl, wherein the $C_{1-4}$-alkyl of the —O—$C_{1-4}$-alkyl is further optionally substituted by —O—$C_1$-$C_4$-alkyl;
each $T_1$ is independently O or S;
each $T_2$ is independently O⁻ or S⁻; and
$T_3$ is a group comprising an oligoethylene glycol moiety; and
$R^1$ is $C_{1-4}$-alkylene-hydroxy.

In certain embodiments of the present aspect, b is 3. In additional embodiments of the present aspect, (i) P comprises at least one modified nucleoside $X^N$; (ii) P has at least one modified internucleoside linker $Y^N$, wherein at least one of $T^1$ or $T^2$ is S; or (iii) both (i) and (ii). In some embodiments, P has at least one phosphorodithioate or phosphorothioate internucleoside linker. In certain embodiments, P comprises 0, 1, 2 or 3 phosphorodithioate internucleoside linkers. In still further embodiments, P comprises a modified nucleoside selected from the group consisting of 2'-O-alkyl nucleoside, 2'-O-alkoxyalkyl nucleoside, 2'-deoxynucleoside and ribonucleoside. In certain embodiments, the modified nucleoside is selected from the group consisting of 5-bromo-2'-O-methyluridine, 5-bromo-2'-deoxyuridine, 2'-O-methyluridine, 2'-deoxyuridine, 2'-O-methylthymidine, 2'-O-methylcytidine, 2'-O-(2-methoxyethyl)thymidine and 8-oxo-7,8-dihydro-2'-deoxyguanosine. In yet other embodiments, $Y^{3'}$ or the $Y^N$ at the 3' position of $X^{5'}$ comprises an unsubstituted or substituted phosphorothioate.

In yet other embodiments of the present aspect, $Y^{PTE}$ is:

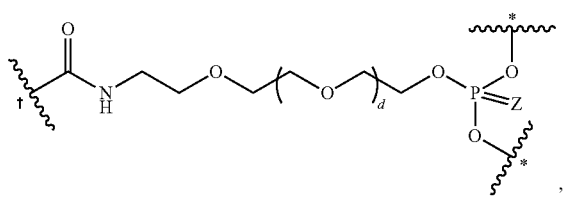

wherein Z is O or S; d is an integer from 0 to 95; the two ⁓* on the right side of the structure indicate the points of attachment to the adjacent nucleosides $X^N$ in the oligonucleotide P, and the ⁓† t on the left side of the structure indicates the point of attachment to the linker L. In other embodiments, $Y^{PTE}$ is:

ments, Z is S. In still further embodiments, d is an integer from 1 to 25. In additional embodiments which may be combined with any of the preceding embodiments, the linker L comprises a polyethylene glycol moiety. In yet further embodiments, the linker L is

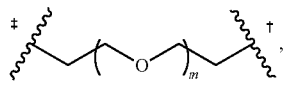

wherein m is an integer ranging from about 0 to about 50, and wherein ⁓† indicates the point of attachment to $Y^{PTE}$, and ⁓‡ indicates the point of attachment to the rest of the conjugate. In still further embodiments, P comprises one or more CpG sites. In still another embodiment, P comprises at least 3 CpG sites. In yet other embodiments, each P independently comprises an oligonucleotide sequence selected from the group consisting of the oligonucleotides of Table 9 and Table 10.

In some embodiments, the conjugate comprises one or more, two or more, three or more, four or more, five or more, or ten or more Q-tag peptides. In some embodiments, the conjugate comprises two Q-tag peptides. In some embodiments, the conjugate comprises one or more, two or more, three or more, four or more, five or more, or ten or more immunomodulating oligonucleotides. In some embodiments, the conjugate comprises one immunomodulating oligonucleotide. In certain embodiments, the antibody is linked to 2 Q-tag peptides, and wherein one of the Q-tag peptides is linked to an immunomodulating oligonucleotide. In some embodiments, the antibody comprises two antibody light chains, two antibody heavy chains, and two Q-tag peptides; wherein each of the Q-tag peptides is linked to the C-terminus of one of the antibody heavy chains; and wherein one of the Q-tag peptides is linked to an immuno-

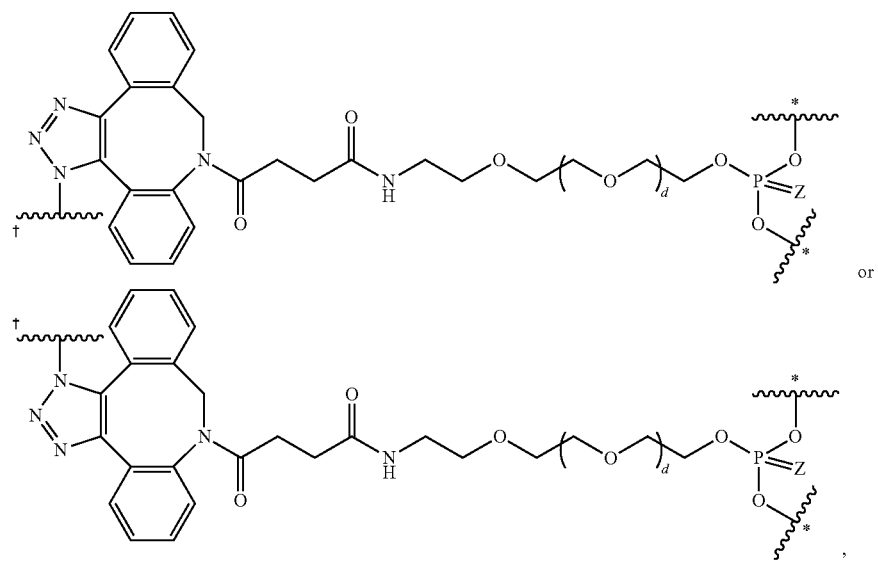

wherein Z is O or S; d is an integer from 0 to 95; the two ⁓* on the right side of the structure indicate the points of attachment to the adjacent nucleosides $X^N$ in the oligonucleotide P, and the one t on the left side of the structure indicates the point of attachment to the linker L. In certain embodimodulating oligonucleotide (P) via an amide bond with the glutamine residue of the Q-tag peptide and linker (L), e.g., as shown in FIG. 16.

In yet another aspect, the present disclosure provides a conjugate that comprises an antibody or antigen-binding fragment thereof (Ab) and one or more immunomodulating oligonucleotides (P), wherein the antibody or antigen-binding fragment is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in Formula (A),

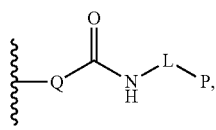

(A)

wherein:
- ∼ indicates the point of attachment of each Q to the antibody or antigen-binding fragment thereof (Ab);
- each Q is independently a Q-tag peptide sequence having at least one glutamine residue;
- each L is independently a bond or a linker moiety connected to Q via an amide bond with the glutamine residue; and
- each P is independently an immunomodulating oligonucleotide of having the structure

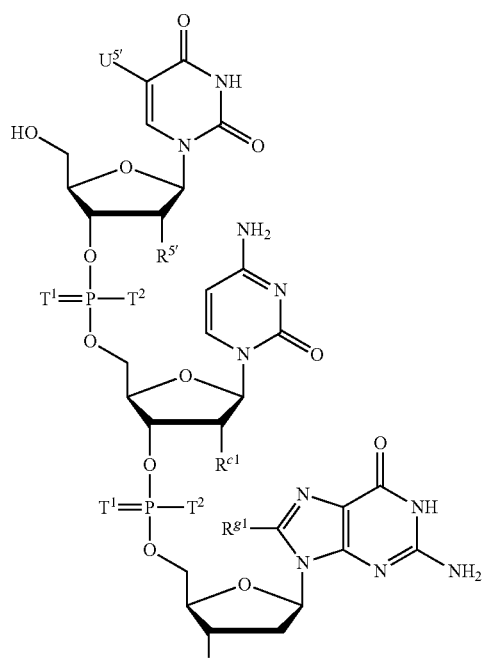

-continued

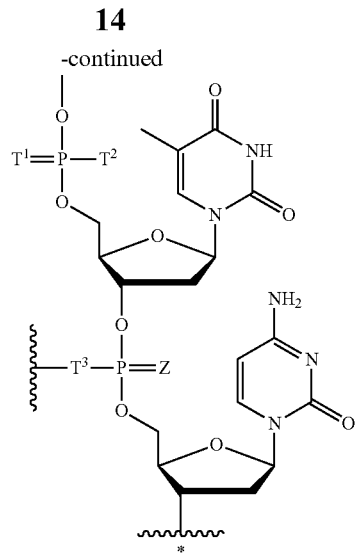

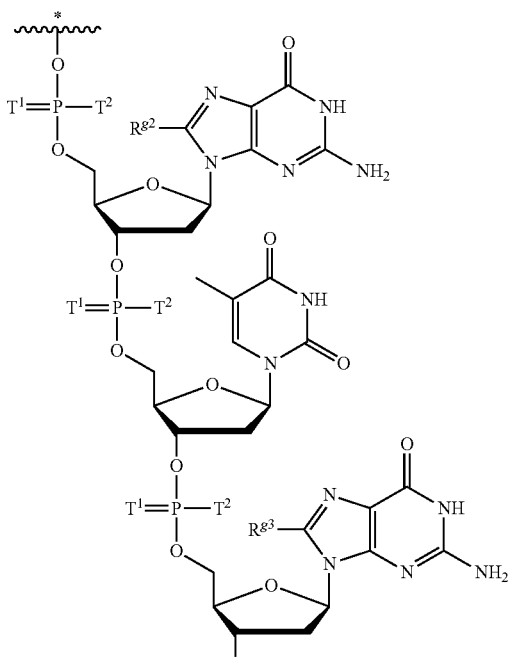

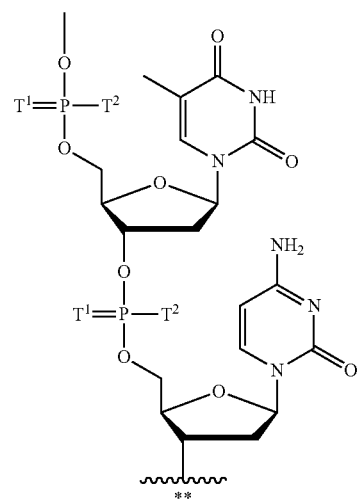

-continued

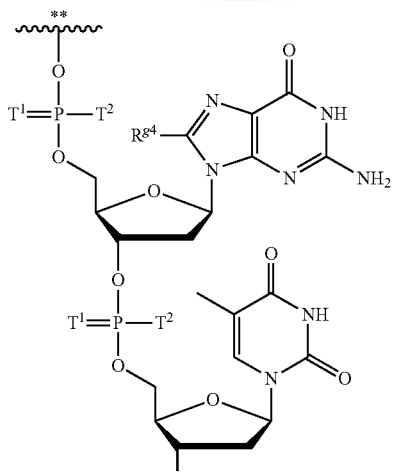

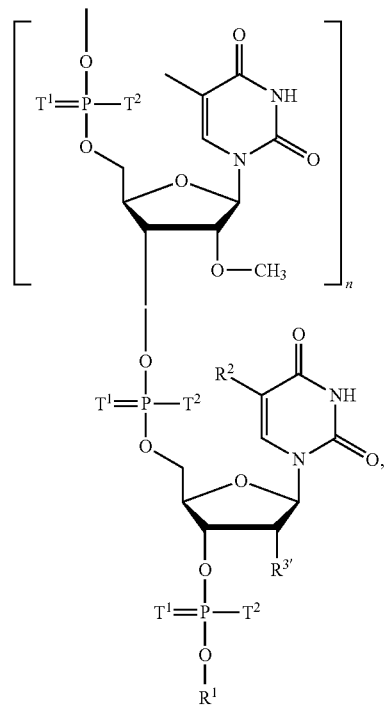

wherein
  $\sim\!\!\sim\!\!*$ and $\sim\!\!\sim\!\!**$ indicate the points of attachment within the oligonucleotide;
  each $T^1$ is independently O or S;
  each $T^2$ is $S^-$;
  $T^3$ is a group

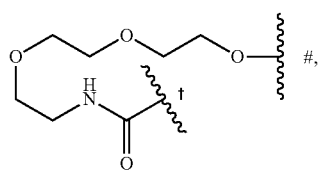 [SMILES: *OCCOCCOCCNC(*)=O]

wherein $\sim\!\!\sim\!$† indicated the point of attachment to L and wherein $\sim\!\!\sim\!$# indicated the point of attachment to the rest of the oligonucleotide;

Z is O or S;
$U^{5'}$ is —H or halogen;
$R^{5'}$ is —H or methoxy;
$R^{c1}$ is —H or methoxy;
$R^{g1}$, $R^{g2}$, $R^{g3}$, and $R^{g4}$ are H;
$R^{3'}$ is methoxy;
$R^1$ is —(CH$_2$)$_3$—OH;
$R^2$ is —H or methyl; and
n is an integer from 0 to 2.

In still further embodiments of the present aspect, the antibody or fragment thereof specifically binds a tumor associated antigen.

In yet another aspect, the present disclosure provides a conjugate that comprises an antibody or antigen-binding fragment thereof (Ab) and one or more immunomodulating oligonucleotides (P), wherein the antibody or antigen-binding fragment is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in Formula (A),

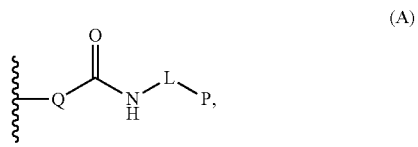

(A)

wherein:
  $\sim\!\!\sim\!$ indicates the point of attachment of each Q to the antibody or antigen-binding fragment thereof (Ab);
  each Q is independently a Q-tag peptide sequence having at least one glutamine residue;
  each L is independently a bond or a linker moiety connected to Q via an amide bond with the glutamine residue; and
  each P is independently an immunomodulating oligonucleotide of having the structure

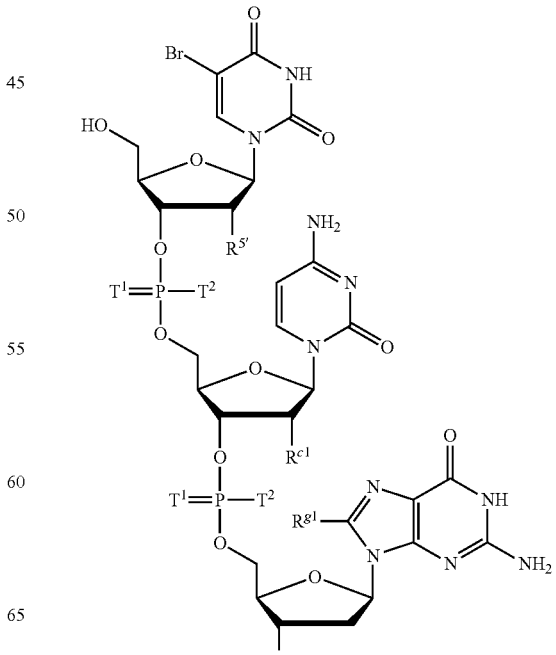

-continued
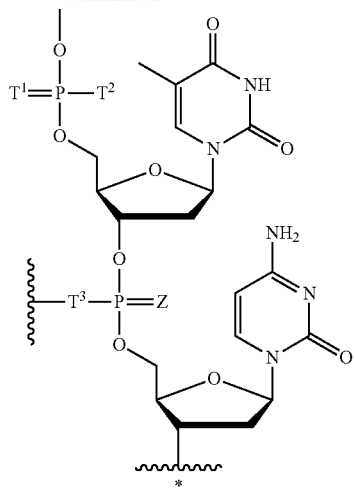
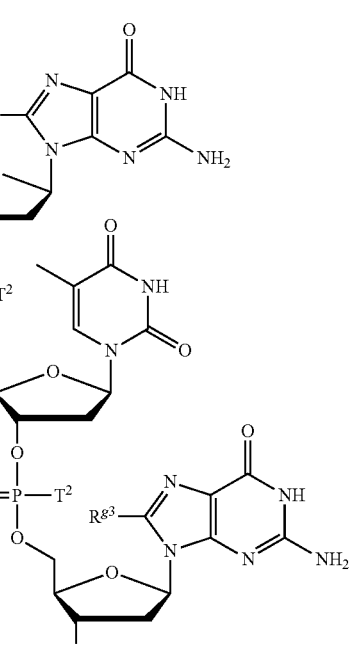
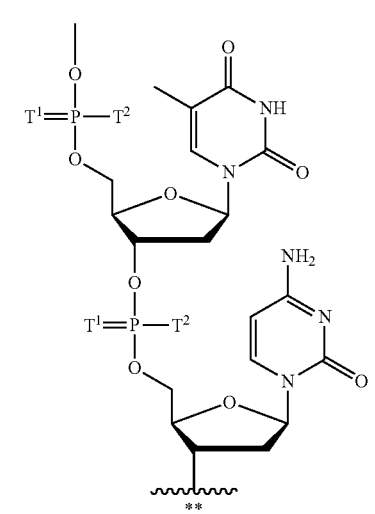
-continued
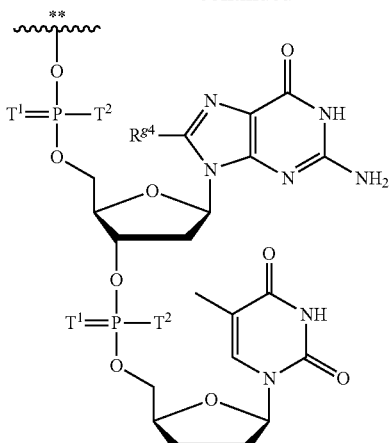
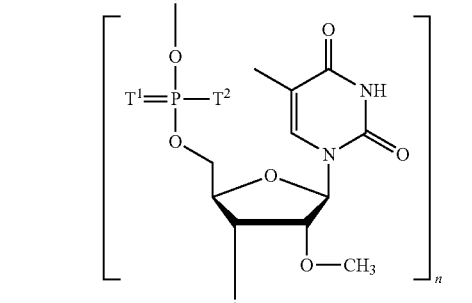
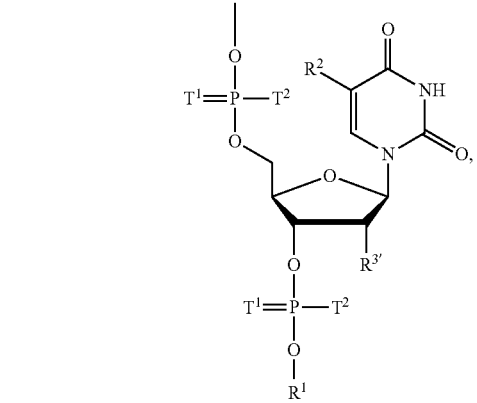
wherein
~~* and ~~** indicate the points of attachment within the oligonucleotide;
each T is independently O or S;
each $T^2$ is $S^-$;
$T^3$ is a group
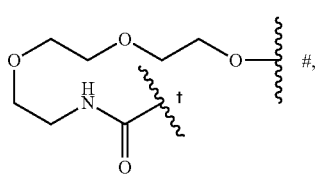 [SMILES: *OCCOCCOCCNC(*)=O]
wherein ~~† indicates the point of attachment to L and wherein ~~# indicates the point of attachment to the rest of the oligonucleotide;
Z is O or S;
$R^{5'}$ is —H or methoxy;

$R^{c1}$ is —H or methoxy;

$R^{g1}$, $R^{g2}$, $R^{g3}$, and $R^{g4}$ are H;

$R^{3'}$ is methoxy;

$R^1$ is —(CH$_2$)$_3$—OH;

$R^2$ is —H or methyl; and n is an integer from 0 to 2.

In still further embodiments of the present aspect, the antibody or fragment thereof specifically binds a tumor associated antigen.

In another aspect, provided herein is a conjugate comprising an antibody or antigen-binding fragment thereof (Ab) and one or more immunomodulating oligonucleotides (P), wherein the antibody or antigen-binding fragment is linked to one or more Q-tag peptides (Q) comprising a Q-tag peptide sequence RPQGF (SEQ ID NO:47), and wherein each immunomodulating oligonucleotide is linked to a Q-tag peptide via an amide bond with the glutamine residue of the Q-tag peptide and a linker (L) as shown in Formula (A)

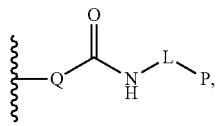

(A)

wherein:

⁓ indicates the point of attachment of each Q to the antibody or antigen-binding fragment thereof (Ab)

each Q independently comprises a Q-tag peptide sequence RPQGF (SEQ ID NO:47)

each L is independently a bond or a linker moiety

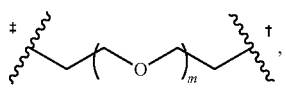

wherein m is an integer ranging from about 0 to about 50, and wherein ⁓† indicates the point of attachment to P, and ⁓‡ indicates the point of attachment to the rest of the conjugate connected to Q via an amide bond with the glutamine residue; and each P is independently an immunomodulating oligonucleotide having the structure

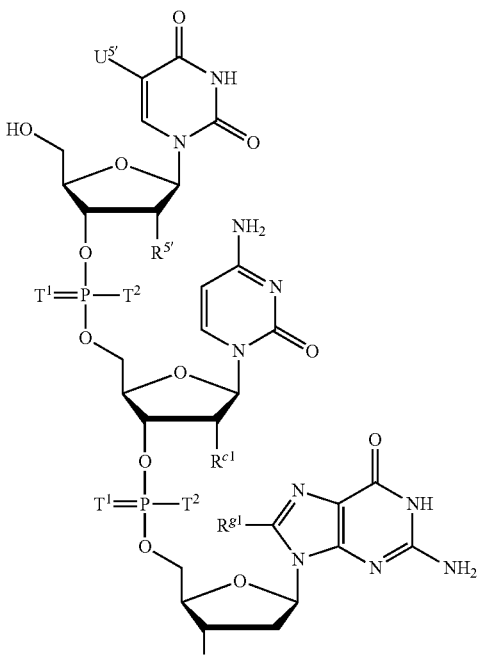

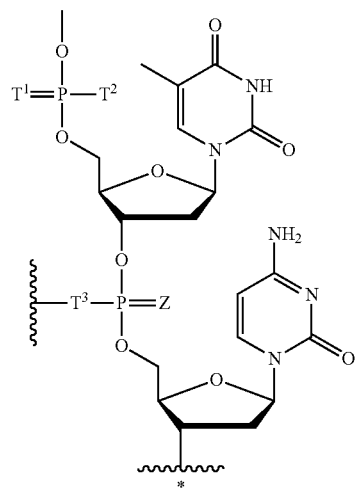

21
-continued

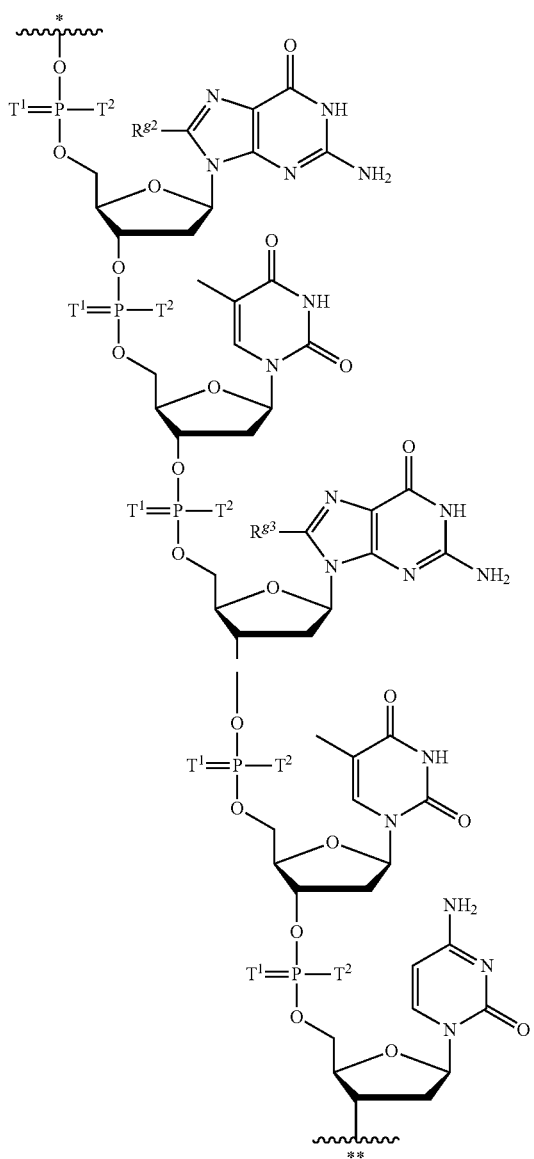

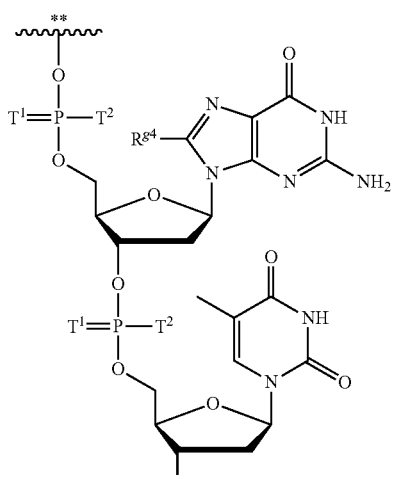

22
-continued

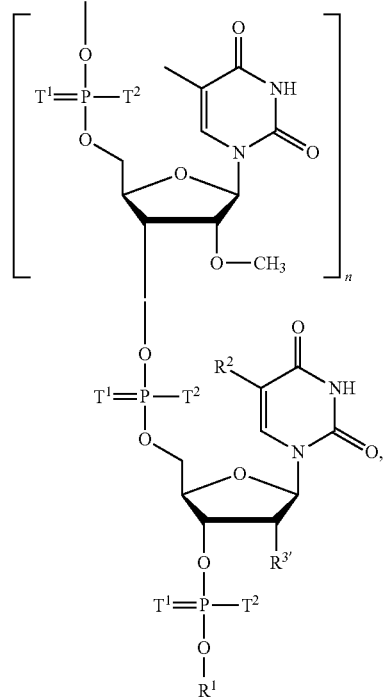

wherein ⁓* and ⁓** indicates the point of attachment within oligonucleotide; each $T^1$ is independently O or S; each $T^2$ is $S^-$;

$T^3$ is a group

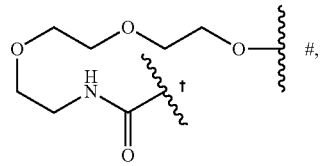 [SMILES: *OCCOCCOCCNC(*)=O]

wherein ⁓† indicates the point of attachment to L and wherein ⁓# indicated the point of attachment to the rest of the oligonucleotide;

Z is O or S;
$U^{5'}$ is —H or halogen;
$R^{5'}$ is —H or methoxy;
$R^{c1}$ is —H or methoxy;
$R^{g1}$, $R^{g2}$, $R^{g3}$, and $R^{g4}$ are H;
$R^{3'}$ is methoxy;
$R^1$ is —(CH$_2$)$_3$—OH;
$R^2$ is —H or methyl; and
n is an integer from 0 to 2,
wherein Ab is an antibody or antigen-binding fragment thereof that binds a tumor associated antigen.

In yet another aspect, the present disclosure provides a conjugate comprising an antibody or antigen-binding fragment thereof (Ab) and one or more immunomodulating oligonucleotides (P), wherein the antibody or antigen-binding fragment is linked to one or more Q-tag peptides (Q) comprising a Q-tag peptide sequence RPQGF (SEQ ID NO:47), and wherein each immunomodulating oligonucleotide is linked to a Q-tag peptide via an amide bond with the glutamine residue of the Q-tag peptide and a linker (L) as shown in Formula (A)

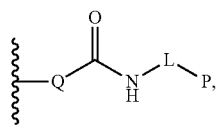 (A)

wherein:
  ⌇ indicates the point of attachment of each Q to the antibody or antigen-binding fragment thereof (Ab)
  each Q independently comprises a Q-tag peptide sequence RPQGF SEQ ID NO:47);
  each L is independently a bond or a linker moiety

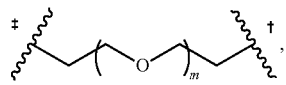, wherein m is an integer ranging from about 0 to about 50, and wherein ⌇† indicates the point of attachment to P, and ⌇‡ indicates the point of attachment to the rest of the conjugate connected to Q via an amide bond with the glutamine residue; and each P is independently an immunomodulating oligonucleotide having the structure

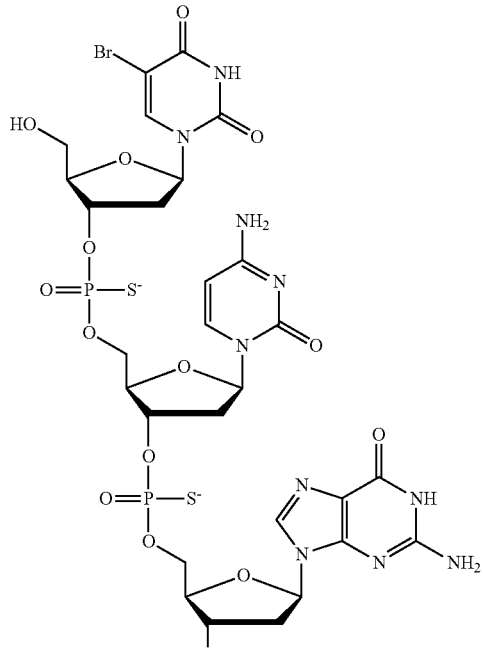

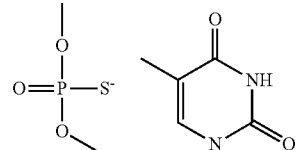

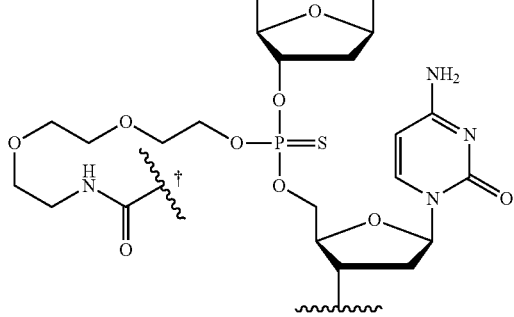

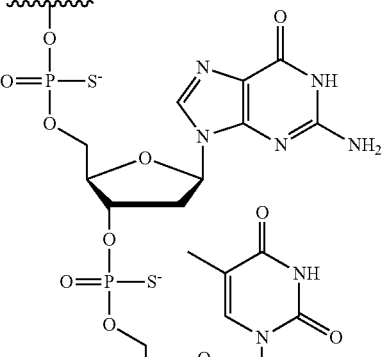

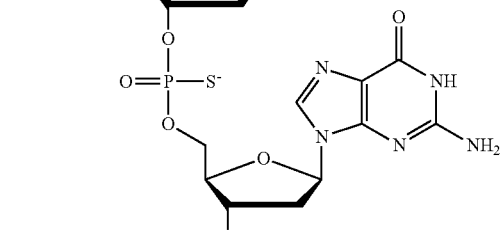

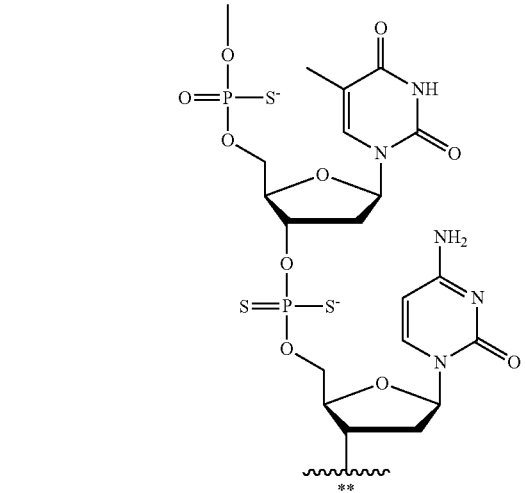

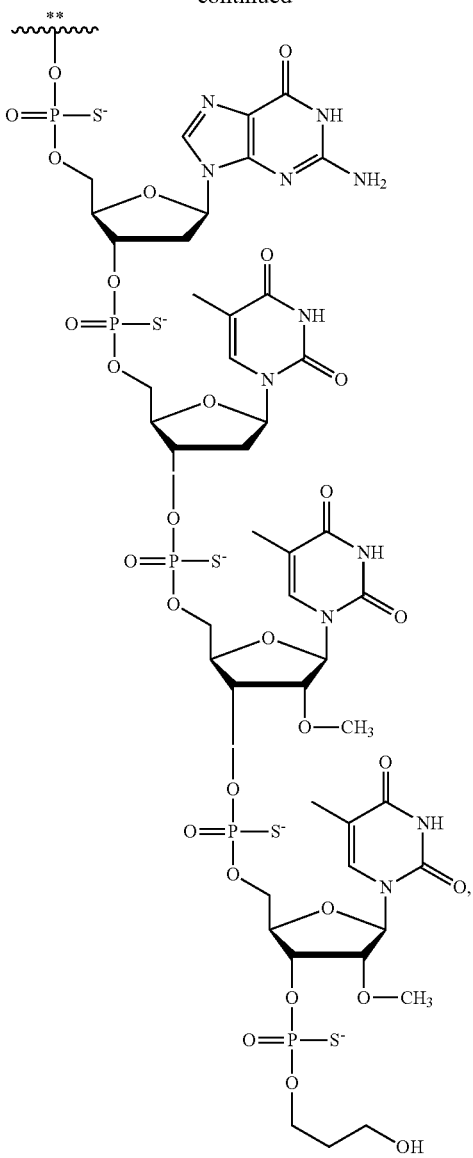

wherein ~* and ~** indicate the points of attachment within the oligonucleotide; wherein Ab is an antibody or antigen-binding fragment thereof that binds a tumor associated antigen.

In some embodiments, the tumor associated antigen is expressed by a cancer cell. In some embodiments, the tumor associated antigen is expressed by a cancer-associated stromal cell. In some embodiments, the tumor associated antigen is selected from the group consisting of CD19, CD20, CD22, CD25, CD30, CD33, CD38, CD40, CD44, CD45R (B220), CD49, CD52, CD56, CD70, CD74, CD79a, CD79b, CD93, CD123, CD138, CD163, CD205, CD206, CD274, CD303, and CD304, folate receptor alpha, folate receptor beta, mesothelin, PSMA, Her-2, EGFR, CLDN18.2, 5T4, CD47, nectin 4, transferrin receptor, integrin, cripto, EphA2, AGS-5, AGS-16, CanAg, EpCAM, IL4 receptor, IL2 receptor, Lewis Y, GPNMB, DLL3, GCC, GPA33, tissue factor (TF), and Trop2. In some embodiments, the cancer is breast cancer, colorectal cancer, lung cancer, head and neck cancer, melanoma, lymphoma, or leukemia.

In some embodiments of the present aspect, the antibody or fragment thereof is a monoclonal antibody or fragment thereof. In some embodiments, the antibody is linked to 2 Q-tag peptides, and wherein one of the Q-tag peptides is linked to an immunomodulating oligonucleotide. In additional embodiments of the present aspect, the antibody or fragment thereof is a Fab, F(ab')2, Fab'-SH, Fv, scFv, single domain, single heavy chain, or single light chain antibody or antibody fragment. In yet other embodiments of the present aspect, the antibody or fragment thereof is a humanized, human, or chimeric antibody or fragment thereof.

In still further embodiments, the antibody or fragment thereof specifically binds human CD22. In still yet another embodiment of the present aspect, the antibody comprises a heavy chain variable (VH) domain and a light chain variable (VL) domain, wherein the VH domain comprises CDR-H1, CDR-H2, and CDR-H3 sequences from a VH domain sequence selected from the group consisting of:

```
                                              (SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GYGTHWGVLFAYWGRGTLVTVSS, (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS, (SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GYGTHWGVLFAYWGRGTLVTVSS,
and
                                              (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.
```

In still yet another embodiment of the present aspect, the antibody comprises a heavy chain variable (VH) domain and a light chain variable (VL) domain, wherein the VH domain comprises CDR-H1, CDR-H2, and CDR-H3 sequences from a VH domain shown in Table 8. In yet another embodiment of the present aspect, the antibody comprises a heavy chain variable (VH) domain and a light chain variable (VL) domain, and wherein the VH domain comprises an amino acid sequence selected from the group consisting of

```
                                              (SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GYGTHWGVLFAYWGRGTLVTVSS, (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS,
```

(SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GGYGTHWGVLFAYWGRTLVTVSS,
and (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.

In still yet other embodiment of the present aspect, the antibody comprises a heavy chain variable (VH) domain and a light chain variable (VL) domain, wherein the VL domain comprises CDR-L1, CDR-L2, and CDR-L3 sequences from a VL domain sequence selected from the group consisting of:

(SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

FTSILHSGIPARSGSGPGTDFTLTISSLEPEDFAVYYCQQGNTLPWTFGG

GTKLEIK,
and (SEQ ID NO: 72)
DIVMTQTPLSLSVTPGQPASISCRASQDIHGYLNWYQQKPGQSPQLLIYY

TSILHSGVPDRFSGSGSGTDFTLKISRVEAEDVGVYFCQQGNTLPWTFGG

GTKLEIK.

In still yet another embodiment of the present aspect, the antibody comprises a heavy chain variable (VH) domain and a light chain variable (VL) domain, wherein the VL domain comprises CDR-L1, CDR-L2, and CDR-L3 sequences from a VL domain shown in Table 8. In still further embodiments of the present aspect, the VL domain further comprises an amino acid substitution at residue N92. In certain embodiments wherein the VL domain comprises an amino acid substitution at residue N92, the amino acid substitution at residue N92 is selected from the group consisting of N92A, N92L and N92S. In still further embodiments of the present aspect, the antibody comprises a heavy chain variable (VH) domain and a light chain variable (VL) domain, wherein the VL domain an amino acid sequence selected from the group consisting of (SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

FTSILHSGIPARSGSGPGTDFTLTISSLEPEDFAVYYCQQGNTLPWTFGG

GTKLEIK, (SEQ ID NO: 72)
DIVMTQTPLSLSVTPGQPASISCRASQDIHGYLNWYQQKPGQSPQLLIYY

TSILHSGVPDRFSGSGSGTDFTLKISRVEAEDVGVYFCQQGNTLPWTFGG

GTKLEIK, (SEQ ID NO: 73)
DIQMTQSPSSLSASVGDRVTITCRASQDIHGYLNWYQQKPGKAPKLLIYY

TSILHSGVPSRFSGSGSGTDFTLTISSLQPEDFATYFCQQGATLPWTFGQ

GTKLEIK,
and (SEQ ID NO: 82)
DIQMTQSPSSLSASVGDRVTITCRASQDIHGYLNWYQQKPGKAPKLLIYY

TSILHSGVPSRFSGSGSGTDFTLTISSLQPEDFATYFCQQGLTLPWTFGQ

GTKLEIK.

In still further embodiments of the present aspect, the antibody comprises a heavy chain variable (VH) domain and a light chain variable (VL) domain, wherein the VH domain comprises the amino acid sequence (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS, and wherein the VL domain comprises an amino acid sequence selected from the group consisting of (SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 73)
DIQMTQSPSSLSASVGDRVTITCRASQDIHGYLNWYQQKPGKAPKLLIYY

-continued

TSILHSGVPSRFSGSGSGTDFTLTISSLQPEDFATYFCQQGATLPWTFGQ

GTKLEIK, (SEQ ID NO: 82)
DIQMTQSPSSLSASVGDRVTITCRASQDIHGYLNWYQQKPGKAPKLLIYY

TSILHSGVPSRFSGSGSGTDFTLTISSLQPEDFATYFCQQGLTLPWTFGQ

GTKLEIK,
and (SEQ ID NO: 87)
DIQMTQSPSSLSASVGDRVTITCRASQDIHGYLNWYQQKPGKAPKLLIYY

TSILHSGVPSRFSGSGSGTDFTLTISSLQPEDFATYFCQQGSTLPWTFGQ

GTKLEIK.

In still further embodiments, the antibody or fragment thereof specifically binds human Her2. In still yet another embodiment of the present aspect, the antibody comprises a heavy chain variable (VH) domain and a light chain variable (VL) domain, wherein the VH domain comprises CDR-H1, CDR-H2, and CDR-H3 sequences from the VH domain sequence (SEQ ID NO: 168)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS and/or wherein the VL domain comprises CDR-L1, CDR-L2, and CDR-L3 sequences from the VL domain sequence (SEQ ID NO: 169)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK.

In still yet another embodiment of the present aspect, the antibody comprises a heavy chain variable (VH) domain and a light chain variable (VL) domain, wherein the VH domain comprises the sequence (SEQ ID NO: 168)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS and/or wherein the VL domain comprises the sequence (SEQ ID NO: 169)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK.

In still yet another embodiment of the present aspect, the antibody comprises a heavy chain variable (VH) domain and a light chain variable (VL) domain, wherein the VH domain comprises CDR-H1, CDR-H2, and CDR-H3 sequences from the VH domain sequence (SEQ ID NO:170)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSS and/or wherein the VL domain comprises CDR-L1, CDR-L2, and CDR-L3 sequences from the VL domain sequence (SEQ ID NO: 171)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK.

In still yet another embodiment of the present aspect, the antibody comprises a heavy chain variable (VH) domain and a light chain variable (VL) domain, wherein the VH domain comprises the sequence (SEQ ID NO: 170)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSS and/or wherein the VL domain comprises the sequence (SEQ ID NO: 171)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK.

In some embodiments, the anti-Her2 antibody is trastuzumab or pertuzumab.

In still yet another embodiments of the present aspect that can be combined with any of the preceding aspects, the antibody comprises an Fc region. In certain embodiments, wherein the Fc region is a human Fc region selected from the group consisting of an IgG1 Fc region, an IgG2 Fc region, and an IgG4 Fc region. In some embodiments, the Fc region is a wild-type human IgG1, IgG2, or IgG4 Fc region. In some embodiments, the Fc region is a human Fc region comprising one or more amino acid substitutions that reduce one or more effector functions, as compared with the effector function(s) of a human Fc region that lacks the amino acid substitution(s). In still further embodiments, the Fc region is: (a) a human IgG1 Fc region comprising L234A, L235A, and/or G237A substitutions, amino acid position numbering according to EU index; (b) a human IgG2 Fc region comprising A330S and/or P331S substitutions, amino acid position numbering according to EU index; or (c) a human IgG4 Fc region comprising S228P and/or L235E substitutions, amino acid position numbering according to EU index. In still yet another embodiment, the Fc region further comprises an N297A substitution, amino acid position numbering according to EU index. In certain embodiments the Fc region further comprises an N297A substitution. In some embodiments, the antibody comprises an antibody heavy chain constant domain comprising an amino acid sequence selected from the group consisting of SEQ ID Nos:92-107 and 178. In some embodiments, the conjugate further comprises an immunomodulating oligonucleotide P attached to the Q295 residue of the Fc region as shown in the following formula

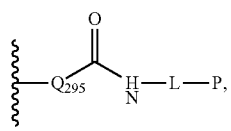

wherein L is a linker moiety connected to Q295 via an amide bond. In yet other embodiments, the Fc region further comprises a D265A substitution, amino acid position numbering according to EU index. In some embodiments, the conjugate binds to human CD22 expressed on the surface of a B cell. In some embodiments, the conjugate induces activation of TLR9.

In some embodiments of the present aspect, the antibody comprises a human lambda light chain. In other embodiments of the present aspect, the antibody comprises a human kappa light chain. In some embodiments, the antibody comprises an antibody light chain constant domain comprising an amino acid sequence selected from the group consisting of SEQ ID Nos:108-110. In still further embodiments which may be combined with any preceding embodiments of the present aspect, at least one Q-tag is attached to the heavy chain of the antibody. In certain embodiments, at least one Q-tag is fused to the C-terminus of the heavy chain of the antibody. In other embodiments, at least one Q-tag is attached to the light chain of the antibody. In certain embodiments, the antibody comprises two heavy chains and two light chains, and at least one Q-tag is fused to the C-terminus of each heavy chain.

In still further embodiments, at least one Q-tag is within the Fc domain. In additional embodiments, each Q-tag independently comprises a peptide sequence having between 5 and 15 amino acid residues. In certain embodiments of the present aspect, the Q-tag is naturally occurring. In still further embodiments, the peptide sequence of each Q-tag is independently selected from the group consisting of SEQ ID NOs: 39-55. In certain embodiments, wherein the Q-tag comprises the peptide sequence RPQGF (SEQ ID NO:47). In still yet other embodiments, 1 or 2 Q-tags is/are linked to the antibody or antigen-binding fragment. In yet other embodiments, the conjugate has a DAR of 1. In yet other embodiments, the conjugate has a DAR of 2. In additional embodiments which may be combined with any of the preceding embodiments, the linker L comprises a polyethylene glycol moiety. In yet further embodiments, the linker L is

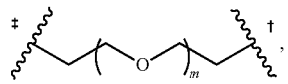

wherein m is an integer ranging from about 0 to about 50, and wherein ⁓† indicates the point of attachment to $Y^{PTE}$, and ⁓‡ indicates the point of attachment to the rest of the conjugate.

In some embodiments, Z is S. In still further embodiments, the oligonucleotide comprises at least one pair of geminal $T^1$ and $T^2$ wherein $T^1$ is S and $T^2$ is S⁻. In certain embodiments, the oligonucleotide comprises at least two pairs of geminal $T^1$ and $T^2$ wherein $T^1$ is S and $T^2$ is S⁻. In still further embodiments, which may be combined with any of the preceding embodiments, $R^{5'}$ is H. In other embodiments, $R^{5'}$ is methoxy. In some embodiments, $R^{c1}$ is H. In yet other embodiments, $R^{c1}$ is methoxy. In still further embodiments, $R^2$ is methyl. In still other embodiments, $R^2$ is H. In additional embodiments, m is an integer from 20 to 25. In some embodiments of the present aspect, each P independently comprises an oligonucleotide sequence selected from the group consisting of the oligonucleotides of Table 10.

In some embodiments, the conjugate comprises one or more, two or more, three or more, four or more, five or more, or ten or more Q-tag peptides. In some embodiments, the conjugate comprises two Q-tag peptides. In some embodiments, the conjugate comprises one or more, two or more, three or more, four or more, five or more, or ten or more immunomodulating oligonucleotides. In some embodiments, the conjugate comprises one immunomodulating oligonucleotide. In other embodiments, the antibody is linked to 2 Q-tag peptides, and wherein one of the Q-tag peptides is linked to an immunomodulating oligonucleotide. In some embodiments, the antibody comprises two antibody light chains, two antibody heavy chains, and two Q-tag peptides; wherein each of the Q-tag peptides is linked to the C-terminus of one of the antibody heavy chains; and wherein at least one of the Q-tag peptides is linked to an immunomodulating oligonucleotide (P) via an amide bond with the glutamine residue of the Q-tag peptide and linker (L), e.g., as shown in FIGS. 16A-16D. In certain embodiments, the two Q-tag peptides comprise the peptide sequence RPQGF (SEQ ID NO:47). In other embodiments, the two Q-tag peptides comprise a Q295 residue exposed by N297A mutation (of the Fc region). In still other embodiments, the conjugate has a DAR of 1 or 2.

In yet another aspect, provided herein is a conjugate that comprises an antibody or antigen-binding fragment thereof (Ab) and one or more immunomodulating oligonucleotides (P), wherein the antibody or antigen-binding fragment is linked to one or more Q-tag peptides (Q) comprising the amino acid sequence RPQGF (SEQ ID NO:47), wherein each immunomodulating oligonucleotide is linked to a Q-tag peptide via an amide bond with the glutamine residue of the Q-tag peptide and a linker (L) as shown in formula (A),

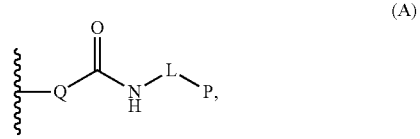

wherein:
⁓ indicates the point of attachment of each Q to the antibody or antigen-binding fragment thereof (Ab);
each Q comprises a Q-tag peptide sequence RPQGF (SEQ ID NO:47);
each L is independently a bond or a linker moiety

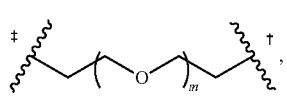

wherein m is an integer ranging from about 0 to about 50, and wherein ⁓† indicates the point of attachment to P, and ⁓‡ indicates the point of attachment to the rest of the conjugate connected to Q via an amide bond with the glutamine residue;

and each P is an immunomodulating oligonucleotide having the structure
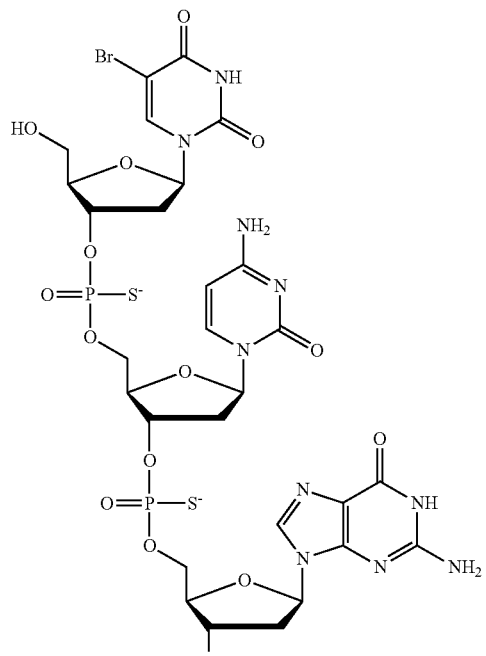
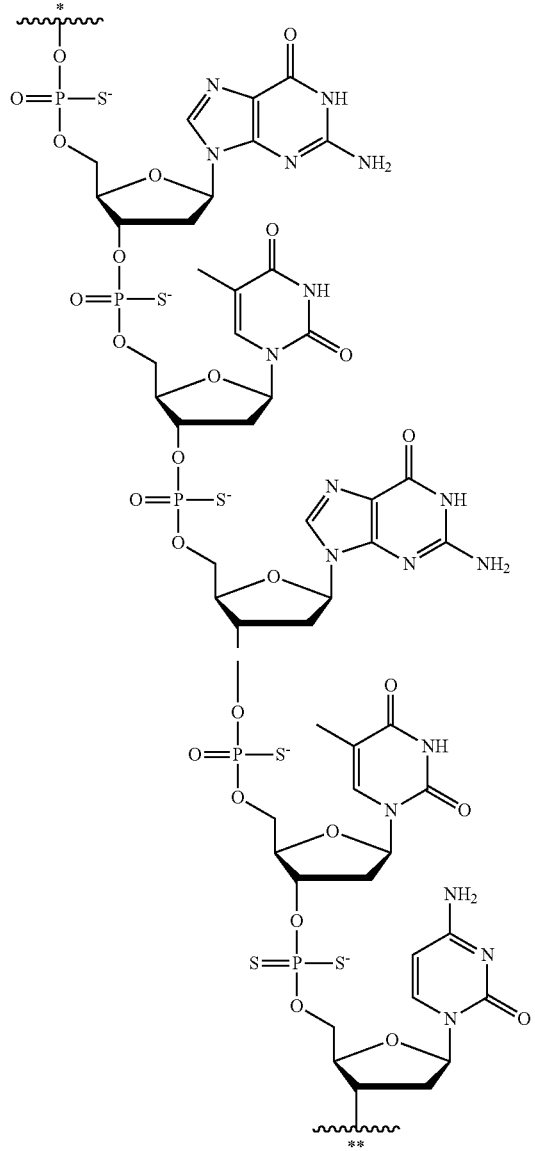 [SMILES: *OP(=O)([S-])OC[C@H]1O[C@@H](n2cnc3c(=O)[nH]c(N)nc32)C[C@H]1OP(=O)([S-])OC[C@H]1O[C@@H](n2cc(C)c(=O)[nH]c2=O)C[C@H]1OP(=O)([S-])OC[C@H]1O[C@@H](n2cnc3c(=O)[nH]c(N)nc32)C[C@H]1OP(=O)([S-])OC[C@H]1O[C@@H](n2cc(C)c(=O)[nH]c2=O)C[C@H]1OP(=S)([S-])OC[C@H]1O[C@@H](n2ccc(N)nc2=O)C[C@H]1*]

-continued

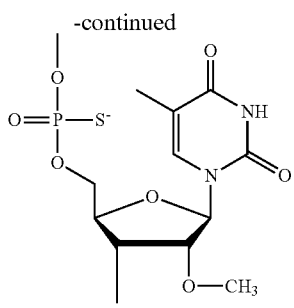

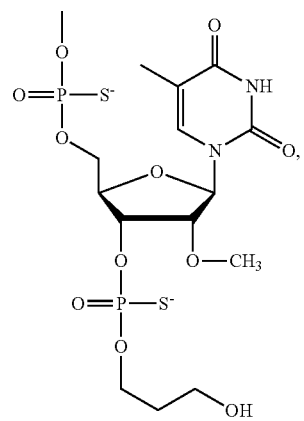

wherein ⁓* and ⁓** indicate the points of attachment within the oligonucleotide;

wherein Ab comprises a heavy chain variable (VH) domain and a light chain variable (VL) domain, wherein the VH domain comprises CDR-H1, CDR-H2, and CDR-H3 sequences from a VH domain sequence (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS or a VH domain shown in Table 8;
wherein the VL domain comprises CDR-L1, CDR-L2, and CDR-L3 sequences from a VL domain sequence:

(SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK or a VL domain shown in Table 8.
In some embodiments of the present aspect, the VL domain further comprises an amino acid substitution N92A.

In other embodiments, the VL domain further comprises an amino acid substitution N92L. In still other embodiments, the VL domain further comprises an amino acid substitution N92S.

In other embodiments of the present aspect, each Q tag is independently selected from the group consisting of RPQGF (SEQ ID NO:47), RPQGFPP (SEQ ID NO:48), and RPQGFGPP (SEQ ID NO:49). In certain embodiments, each Q tag is RPQGFGPP (SEQ ID NO:49). In some embodiments, 1 or 2 Q-tags are linked to the antibody or antigen-binding fragment. In other embodiments, the Q-tag is linked to the C-terminus of the heavy chain of the antibody. In still further embodiments, the antibody comprises a human IgG1 Fc region comprising L234A, L235A, and/or G237A substitutions, amino acid position numbering according to EU index. In yet other embodiments, m is an integer from about 20 to about 25. In certain embodiments, m is 24. In yet further embodiments, the conjugate has a DAR of 1. In yet further embodiments, the conjugate has a DAR of 2. In still other embodiments, the conjugate binds to human CD22 expressed on the surface of a B cell.

In another aspect, provided herein is a conjugate that comprises an antibody or antigen-binding fragment thereof (Ab) and one or more immunomodulating oligonucleotides (P), wherein the antibody or antigen-binding fragment is linked to one or more Q-tag peptides (Q) comprising the amino acid sequence RPQGF (SEQ ID NO:47), wherein each immunomodulating oligonucleotide is linked to a Q-tag peptide via an amide bond with the glutamine residue of the Q-tag peptide and a linker (L) as shown in formula (A),

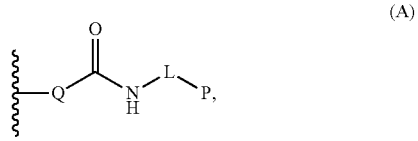

(A)

wherein:
⁓ indicates the point of attachment of each Q to the antibody or antigen-binding fragment thereof (Ab);
each Q comprises a Q-tag peptide sequence RPQGF (SEQ ID NO:47);

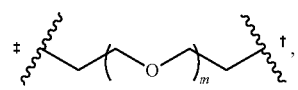

each L is independently a bond or a linker moiety wherein m is an integer ranging from about 0 to about 50, and wherein ⁓† indicates the point of attachment to P, and ⁓‡ indicates the point of attachment to the rest of the conjugate connected to Q via an amide bond with the glutamine residue;

and each P is an immunomodulating oligonucleotide having the structure

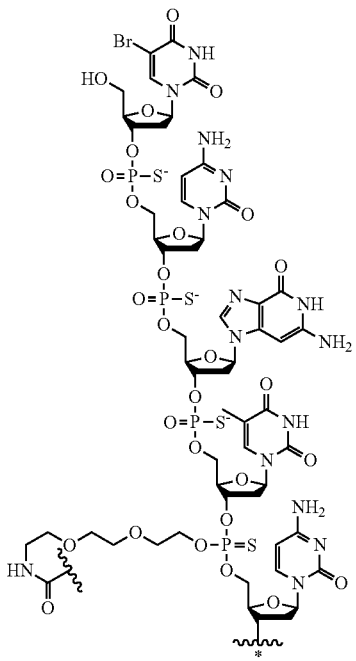

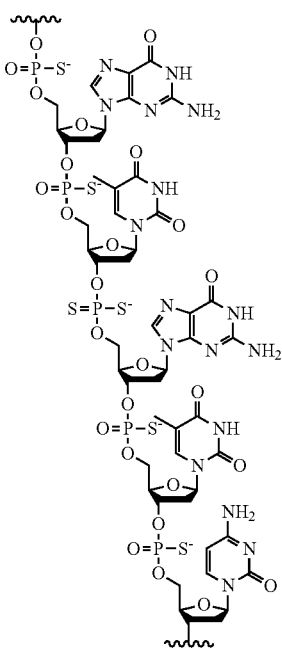

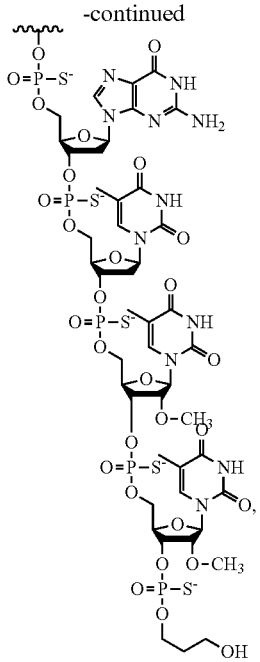

wherein ∼∼* and ∼∼** indicate the points of attachment within the oligonucleotide;

wherein Ab comprises a heavy chain variable (VH) domain and a light chain variable (VL) domain, wherein the VH domain comprises CDR-H1, CDR-H2, and CDR-H3 sequences from a VH domain sequence

```
                                        (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS;
``` wherein the VL domain comprises CDR-L1, CDR-L2, and CDR-L3 sequences from a VL domain sequence:

```
                                        (SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK.
```

In some embodiments of the present aspect, the VL domain further comprises an amino acid substitution N92A. In other embodiments, the VL domain further comprises an amino acid substitution N92L. In still other embodiments, the VL domain further comprises an amino acid substitution N92 S.

In other embodiments of the present aspect, each Q tag is independently selected from the group consisting of RPQGF (SEQ ID NO:47), RPQGFPP (SEQ ID NO:48), and RPQGFGPP. In certain embodiments, each Q tag is RPQGFGPP (SEQ ID NO:49). In some embodiments, 1 or 2 Q-tags are linked to the antibody or antigen-binding fragment. In other embodiments, the Q-tag is linked to the C-terminus of the heavy chain of the antibody. In still further embodiments, the antibody comprises a human IgG1 Fc region comprising L234A, L235A, and/or G237A substitutions, amino acid position numbering according to EU index. In yet other embodiments, m is an integer from about 20 to about 25. In certain embodiments, m is 24. In yet further embodiments, the conjugate has a DAR of 1. In yet further embodiments, the conjugate has a DAR of 2. In still other embodiments, the conjugate binds to human CD22 expressed on the surface of a B cell.

In still yet another aspect, the present disclosure also provides an immunomodulating oligonucleotide of Formula (C):

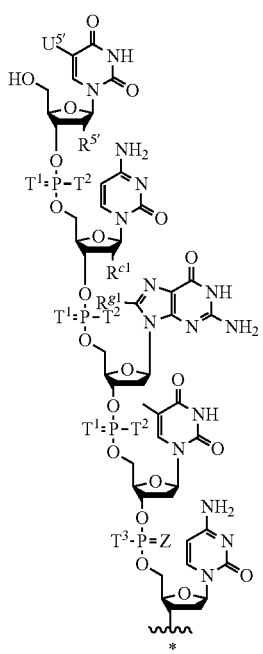

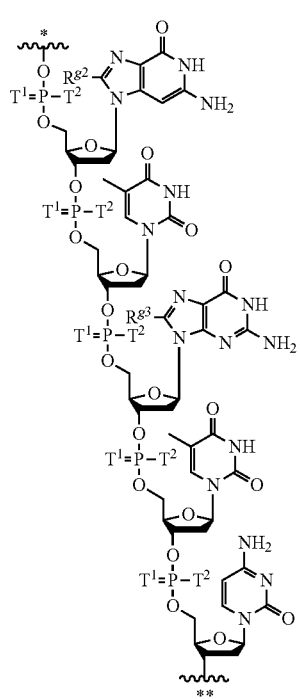

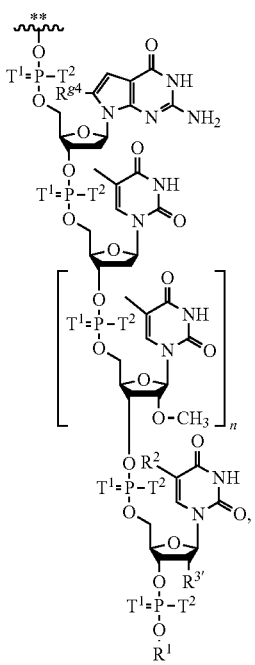

wherein

~~~* and ~~~** indicate the points of attachment within the oligonucleotide;

each $T^1$ is independently O or S;

each $T^2$ is $S^-$;

$T^3$ is a group

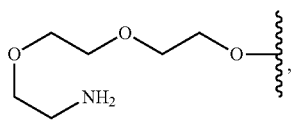

wherein m is an integer from 0 to 50 and wherein ~~~ indicates the point of attachment to the rest of the oligonucleotide;

Z is O or S;

$U^{5'}$ is —H or halogen;

$R^{5'}$ is —H or methoxy;

$R^{c1}$ is —H or methoxy;

$R^{g1}$, $R^{g2}$, $R^{g3}$, and V are H;

$R^{3'}$ is methoxy;

$R^1$ is —(CH$_2$)$_3$—OH;

$R^2$ is —H or methyl; and n is an integer from 0 to 2, or a pharmaceutically acceptable salt thereof.

In some embodiments, the present disclosure also provides an immunomodulating oligonucleotide of Formula (C'):

wherein

~* and ~** indicate the points of attachment within the oligonucleotide;

each $T^1$ is independently O or S;

each $T^2$ is $S^-$;

$T^3$ is a group wherein m is an integer from 0 to 50 and wherein ~ indicates the point of attachment to the rest of the oligonucleotide;

Z is O or S;

$R^{5'}$ is —H or methoxy;

$R^{c1}$ is —H or methoxy;

$R^{g1}$, $R^{g2}$, $R^{g3}$, and $R^{g4}$ are H;

$R^{3'}$ is methoxy;

$R^1$ is —(CH$_2$)$_3$—OH;

$R^2$ is —H or methyl; and n is an integer from 0 to 2.

In some embodiments of the present aspect, Z is S. In additional embodiments, the oligonucleotide comprises at least one pair of geminal $T^1$ and $T^2$ wherein $T^1$ is S and $T^2$ is $S^-$. In certain embodiments, the oligonucleotide comprises at least two pairs of geminal $T^1$ and $T^2$ wherein $T^1$ is S and $T^2$ is $S^-$.

In some embodiments, $R^{5'}$ is H. In other embodiments, $R^{5'}$ is methoxy. In some embodiments, $R^{c1}$ is H. In yet other embodiments, $R^{c1}$ is methoxy. In still other embodiments, $R^2$ is methyl. In still other embodiments, $R^2$ is H. In yet other additional embodiments, which may be combined with any of the preceding embodiments, $T^3$ is

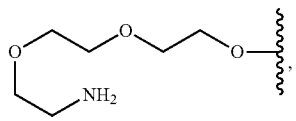

In still other embodiments, T³ is

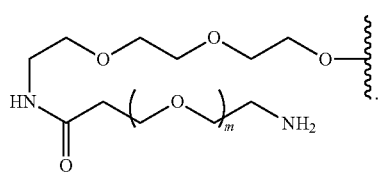

In certain embodiments, m is an integer from 20 to 25.

In still further embodiments of the present aspect, the oligonucleotide is selected from the group consisting of the oligonucleotides of Table 10.

In still yet another aspect, provided herein is an immunomodulating oligonucleotide of formula (D):

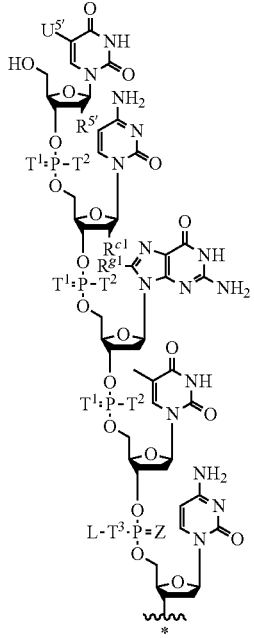

(D)

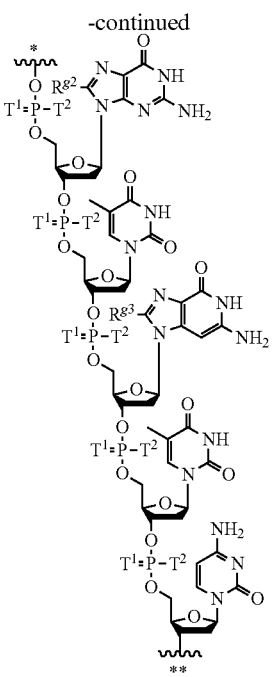

-continued

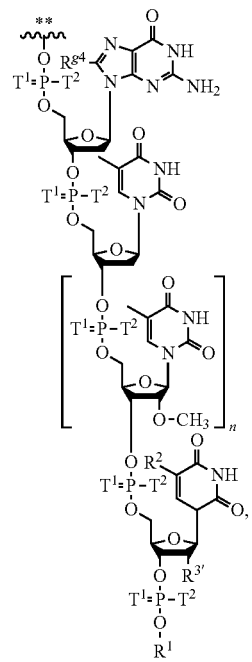

wherein
  ⁓* and ⁓** indicate the points of attachment within the oligonucleotide;
  each T¹ is independently O or S;
  each T² is S⁻;

$T^3$ is a group

[structure: HOCH2CH2-O-CH2CH2-O-CH2CH2-O-# with NH-C(=O)- branch marked †]

wherein ∼∼ indicates the point of attachment to L and wherein ∼∼# indicates the point of attachment to the rest of the oligonucleotide;

L is a group

[structure: †∼∼-(CH2-O)m-CH2CH2-NH2]

wherein m is an integer from 0 to 50 and wherein ∼∼† indicates the point of attachment to the rest of the oligonucleotide via $T^3$;

Z is O or S;
$U^{5'}$ is —H or halogen;
$R^{5'}$ is —H or methoxy;
$R^{c1}$ is —H or methoxy;
$R^{g1}$, $R^{g2}$, $R^{g3}$, and V are H;
$R^{3'}$ is methoxy;
$R^1$ is —(CH$_2$)$_3$—OH;
$R^2$ is —H or methyl; and
n is an integer from 0 to 2.

In some embodiments, provided herein is an immunomodulating oligonucleotide of formula (D'):

(D')

[Chemical structure diagram of oligonucleotide formula D' showing nucleotide chain with Br-substituted uracil at 5' end, and L-T3-P(=Z)-O- group, with intermediate residues containing $R^{5'}$, $R^{c1}$, $R^{g1}$, labeled with * at bottom]

[Continued chemical structure diagram showing additional nucleotide residues with $R^{g2}$, $R^{g3}$ substituents, with ** at bottom, and * marking continuation point at top]

[Further continued chemical structure diagram showing additional nucleotide residues with $R^{g2}$, $R^{g3}$ labeled, ending with ** at bottom]

47

-continued

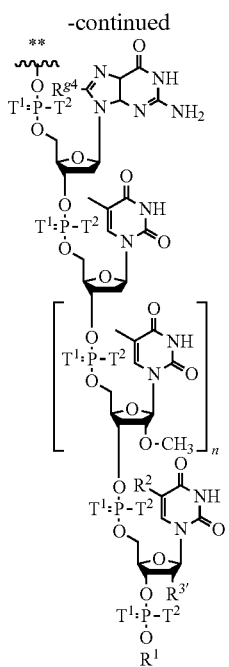

wherein

∼* and ∼** indicate the points of attachment within the oligonucleotide;

each $T^1$ is independently O or S;

each $T^2$ is $S^-$;

$T^3$ is a group

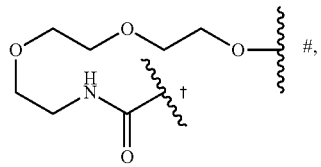 [SMILES: *OCCOCCOCCNC(*)=O]

wherein ∼† indicates the point of attachment to L and wherein ∼# indicates the point of attachment to the rest of the oligonucleotide;

L is a group

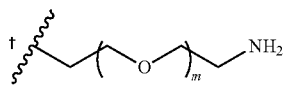

wherein m is an integer from 0 to 50 and wherein ∼⏌ indicates the point of attachment to the rest of the oligonucleotide via $T^3$;

Z is O or S;

$R^{5'}$ is —H or methoxy;

$R^{c1}$ is —H or methoxy;

$R^{g1}$, $R^{g2}$, $R^{g3}$, and V are H;

$R^{3'}$ is methoxy;

$R^1$ is —(CH$_2$)$_3$—OH;

$R^2$ is —H or methyl; and n is an integer from 0 to 2.

In some embodiments of the present aspect, Z is S. In additional embodiments, the oligonucleotide comprises at least one pair of geminal $T^1$ and $T^2$ wherein $T^1$ is S and $T^2$

48 is $S^-$. In certain embodiments, the oligonucleotide comprises at least two pairs of geminal $T^1$ and $T^2$ wherein $T^1$ is S and $T^2$ is $S^-$.

In some embodiments, $R^{5'}$ is H. In other embodiments, $R^{5'}$ is methoxy. In some embodiments, $R^{c1}$ is H. In yet other embodiments, $R^{c1}$ is methoxy. In still further embodiments, $R^2$ is methyl. In still other embodiments, $R^2$ is H. In certain embodiments, m is an integer from 20 to 25.

In still further embodiments of the present aspect, the oligonucleotide is selected from the group consisting of the oligonucleotides of Table 12.

In yet another aspect, provided herein is an immunomodulating oligonucleotide selected from the group consisting of the oligonucleotides of Table 10 and Table 12.

In still yet another aspect, the present disclosure provides a conjugate comprising a protein, at least one Q tag peptide sequence comprising a glutamine residue, and at least one immunomodulatory oligonucleotide, wherein the Q-tag peptide sequence is naturally occurring or synthetic, and wherein the immunomodulatory oligonucleotide is linked to the Q-tag via an amide bond with the glutamine residue, wherein the Q-tag peptide sequence is selected from the group consisting of SEQ ID NOs: 39-55. In some embodiments of the present aspect, immunomodulatory oligonucleotide has a sequence selected from the group consisting of the oligonucleotides of Table 10 and Table 12. In further embodiments, the antibody comprises a light chain variable domain (VL) and a heavy chain variable domain (VH), and wherein VH comprises the sequence SEQ ID NO: 56; and VL comprises the sequence SEQ ID NO: 57.

In still yet another aspect, the present disclosure provides a conjugate comprising an antibody linked to two Q-tag peptides (Q) and an immunomodulating oligonucleotide (P); wherein the antibody comprises two antibody light chains, two antibody heavy chains, and two Q-tag peptides; wherein each of the Q-tag peptides is linked to the C-terminus of one of the antibody heavy chains; and wherein one of the Q-tag peptides is linked to the immunomodulating oligonucleotide via an amide bond with the glutamine residue of the Q-tag peptide and a linker (L) as shown in Formula (A):

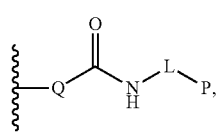

(A)

wherein ∼ indicates the point of attachment of each Q to the antibody.

In some embodiments, each Q-tag peptide comprises the amino acid sequence RPQGF (SEQ ID NO:47). In some embodiments, each L is a linker as described herein. In some embodiments, each (P) is an immunomodulating oligonucleotide as described herein. In some embodiments, the antibody is an antibody as described herein. In some embodiments, the antibody binds to CD22 (e.g., human CD22).

In yet another aspect, provided herein is a conjugate comprising an antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence RPQGF (SEQ ID NO:47); wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L) as shown in Formula (A):

$$\text{\{-Q-C(=O)-N(H)-L-P,}\tag{A}$$

wherein ~~~ indicates the point of attachment of each Q to the antibody (Ab).

In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:65 and a constant region comprising the sequence of SEQ ID NO:92, wherein the two antibody light chains comprise a VL domain comprising the sequence of SEQ ID NO:87 and a constant region comprising the sequence of SEQ ID NO:108, and wherein the immunomodulating oligonucleotide comprises the sequence of SEQ ID NO:35. In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:65 and a constant region comprising the sequence of SEQ ID NO:94, wherein the two antibody light chains comprise a VL domain comprising the sequence of SEQ ID NO:87 and a constant region comprising the sequence of SEQ ID NO:108, and wherein the immunomodulating oligonucleotide comprises the sequence of SEQ ID NO:35. In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:65 and a constant region comprising the sequence of SEQ ID NO:94, wherein the two antibody light chains comprise a VL domain comprising the sequence of SEQ ID NO:73 and a constant region comprising the sequence of SEQ ID NO:108, and wherein the immunomodulating oligonucleotide comprises the sequence of SEQ ID NO:34. In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:65 and a constant region comprising the sequence of SEQ ID NO:92, wherein the two antibody light chains comprise a VL domain comprising the sequence of SEQ ID NO:73 and a constant region comprising the sequence of SEQ ID NO:108, and wherein the immunomodulating oligonucleotide comprises the sequence of SEQ ID NO:34. In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:65 and a constant region comprising the sequence of SEQ ID NO:92, wherein the two antibody light chains comprise a VL domain comprising the sequence of SEQ ID NO:73 and a constant region comprising the sequence of SEQ ID NO:108, and wherein the immunomodulating oligonucleotide comprises the sequence of SEQ ID NO:163. In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:65 and a constant region comprising the sequence of SEQ ID NO:92, wherein the two antibody light chains comprise a VL domain comprising the sequence of SEQ ID NO:87 and a constant region comprising the sequence of SEQ ID NO:108, and wherein the immunomodulating oligonucleotide comprises the sequence of SEQ ID NO:163. In some embodiments, the linker comprises the linker moiety $$\ddagger\text{-}\{\text{-CH}_2\text{-CH}_2\text{-O-}\}_m\text{-CH}_2\text{-CH}_2\text{-}\dagger,$$

wherein m is an integer 24, and wherein ⁓† indicates the point of attachment to P, and ⁓‡ indicates the point of attachment to the rest of the conjugate connected to Q via an amide bond with the glutamine residue.

In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:168 and a constant region comprising the sequence of SEQ ID NO:92, wherein the two antibody light chains comprise a VL domain comprising the sequence of SEQ ID NO:169 and a constant region comprising the sequence of SEQ ID NO:108, and wherein the immunomodulating oligonucleotide comprises the sequence of SEQ ID NO:35. In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:168 and a constant region comprising the sequence of SEQ ID NO:104, wherein the two antibody light chains comprise a VL domain comprising the sequence of SEQ ID NO:169 and a constant region comprising the sequence of SEQ ID NO:108, and wherein the immunomodulating oligonucleotide comprises the sequence of SEQ ID NO:35. In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:168 and a constant region comprising the sequence of SEQ ID NO:92, wherein the two antibody light chains comprise a VL domain comprising the sequence of SEQ ID NO:169 and a constant region comprising the sequence of SEQ ID NO:108, and wherein the immunomodulating oligonucleotide comprises the sequence of SEQ ID NO:163. In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:170 and a constant region comprising the sequence of SEQ ID NO:92, wherein the two antibody light chains comprise a VL domain comprising the sequence of SEQ ID NO:171 and a constant region comprising the sequence of SEQ ID NO:108, and wherein the immunomodulating oligonucleotide comprises the sequence of SEQ ID NO:35. In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:170 and a constant region comprising the sequence of SEQ ID NO:104, wherein the two antibody light chains comprise a VL domain comprising the sequence of SEQ ID NO:171 and a constant region comprising the sequence of SEQ ID NO:108, and wherein the immunomodulating oligonucleotide comprises the sequence of SEQ ID NO:35. In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the Q-tag peptides (Q) comprises the amino acid sequence of SEQ ID NO:49; wherein each of the Q-tag peptides is linked to the C-terminus of one of the antibody heavy chains; wherein one of the two Q-tag peptides is linked to the immunomodulating oligonucleotide via an amide bond with the glutamine residue of the Q-tag peptide and a linker (L), wherein the two antibody heavy chains comprise a VH domain comprising the sequence of SEQ ID NO:170 and a constant region comprising the sequence of SEQ ID NO:92, wherein the two antibody light chains comprise a VL domain comprising the sequence of SEQ ID NO:171 and a constant region comprising the sequence of SEQ ID NO:108, and wherein the immunomodulating oligonucleotide comprises the sequence of SEQ ID NO:163. In some embodiments, the linker comprises the linker moiety $$\ce{\underset{\ddagger}{\wedge}\!\!\!\sim\!\!\!\overset{}{\diagup}\!\!\!\diagdown\!\!\!\underset{m}{O}\!\!\!\diagup\!\!\!\diagdown\!\!\!\sim\!\!\!\underset{\dagger}{\wedge}}$$

wherein m is an integer 24, and wherein ⁓† indicates the point of attachment to P, and ⁓‡ indicates the point of attachment to the rest of the conjugate connected to Q via an amide bond with the glutamine residue.

In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:182; wherein each of the antibody heavy chains comprises the amino acid sequence of SEQ ID NO:179; wherein the immunomodulating oligonucleotide comprises the sequence of SEQ ID NO:35; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:182; wherein each of the antibody heavy chains comprises the amino acid sequence of SEQ ID NO:180; wherein the immunomodulating oligonucleotide comprises the sequence of SEQ ID NO:35; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:181; wherein each of the antibody heavy chains comprises the amino acid sequence of SEQ ID NO:180; wherein the immunomodulating oligonucleotide comprises the sequence of SEQ ID NO:34; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:181; wherein each of the antibody heavy chains comprises the amino acid sequence of SEQ ID NO:179; wherein the immunomodulating oligonucleotide comprises the sequence of SEQ ID NO:34; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:181; wherein each of the antibody heavy chains comprises the amino acid sequence of SEQ ID NO:179; wherein the immunomodulating oligonucleotide comprises the sequence of SEQ ID NO:163; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-CD22 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:182; wherein each of the antibody heavy chains comprises the amino acid sequence of SEQ ID NO:179; wherein the immunomodulating oligonucleotide comprises the sequence of SEQ ID NO:163; and wherein at least one of the two Q-tag peptides is linked to the immunomodulating oligonucleotide via an amide bond with the glutamine residue of the Q-tag peptide and a linker (L). In some embodiments, one of the two Q-tag peptides is linked to the immunomodulating oligonucleotide. In some embodiments, the conjugate comprises two immunomodulating oligonucleotides, wherein each of the two Q-tag peptides is linked to one of the two immunomodulating oligonucleotides. In some embodiments, the conjugate has a DAR of 1. In some embodiments, the conjugate has a DAR of 2. In some embodiments, the linker comprises the linker moiety

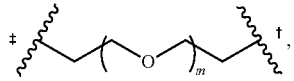

wherein m is an integer 24, and wherein ∼∼∼ † indicates the point of attachment to P, and ∼∼∼ ‡ indicates the point of attachment to the rest of the conjugate connected to Q via an amide bond with the glutamine residue.

In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:185; wherein each of the antibody heavy chains comprises the amino acid sequence of SEQ ID NO:184; wherein the immunomodulating oligonucleotide comprises the sequence of SEQ ID NO:35; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:185; wherein each of the antibody heavy chains comprises the amino acid sequence of SEQ ID NO:183; wherein the immunomodulating oligonucleotide comprises the sequence of SEQ ID NO:35; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:185; wherein each of the antibody heavy chains comprises the amino acid sequence of SEQ ID NO:184; wherein the immunomodulating oligonucleotide comprises the sequence of SEQ ID NO:163; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:188; wherein each of the antibody heavy chains comprises the amino acid sequence of SEQ ID NO:187; wherein the immunomodulating oligonucleotide comprises the sequence of SEQ ID NO:35; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:188; wherein each of the antibody heavy chains comprises the amino acid sequence of SEQ ID NO:186; wherein the immunomodulating oligonucleotide comprises the sequence of SEQ ID NO:35; and wherein at least one of the two Q-tag peptides is linked to the immunomodulating oligonucleotide via an amide bond with the glutamine residue of the Q-tag peptide and a linker (L). In yet another aspect, provided herein is a conjugate comprising an anti-Her2 antibody (Ab) and an immunomodulating oligonucleotide (P), wherein the antibody comprises two antibody light chains, two antibody heavy chains, and two Q-tag peptides; wherein each of the antibody light chains comprises the amino acid sequence of SEQ ID NO:188; wherein each of the antibody heavy chains comprises the amino acid sequence of SEQ ID NO:187; wherein the immunomodulating oligonucleotide comprises the sequence of SEQ ID NO:163; and wherein at least one of the two Q-tag peptides is linked to the immunomodulating oligonucleotide via an amide bond with the glutamine residue of the Q-tag peptide and a linker (L). In some embodiments, one of the two Q-tag peptides is linked to the immunomodulating oligonucleotide. In some embodiments, the conjugate comprises two immunomodulating oligonucleotides, wherein each of the two Q-tag peptides is linked to one of the two immunomodulating oligonucleotides. In some embodiments, the conjugate has a DAR of 1. In some embodiments, the conjugate has a DAR of 2. In some embodiments, the linker comprises the linker moiety

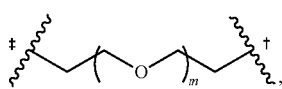

wherein m is an integer 24, and wherein ⌇ † indicates the point of attachment to P, and ⌇ ‡ indicates the point of attachment to the rest of the conjugate connected to Q via an amide bond with the glutamine residue.

In yet another aspect, provided herein is a conjugate that comprises an antibody (Ab) and one or more immunomodulating oligonucleotides (P), wherein the antibody is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in formula (A),

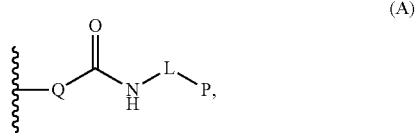

wherein:

wherein ⌇ indicates the point of attachment of Q to the antibody (Ab);

the antibody comprises two antibody light chains, two antibody heavy chains, and two Q-tag peptides;

each of the Q-tag peptides is linked to the C-terminus of one of the antibody heavy chains;

one of the two Q-tag peptides is linked to the immunomodulating oligonucleotide via an amide bond with the glutamine residue of the Q-tag peptide;

each Q is independently a Q-tag peptide sequence having at least one glutamine residue;

each L is independently a bond or a linker moiety connected to Q via an amide bond with the glutamine residue; and each P is independently an immunomodulating oligonucleotide having the structure

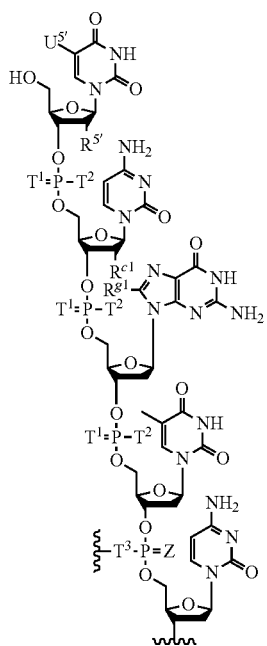

-continued

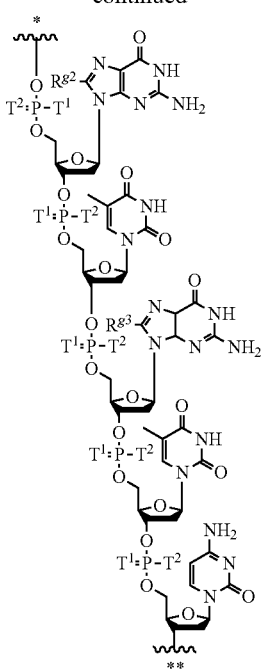

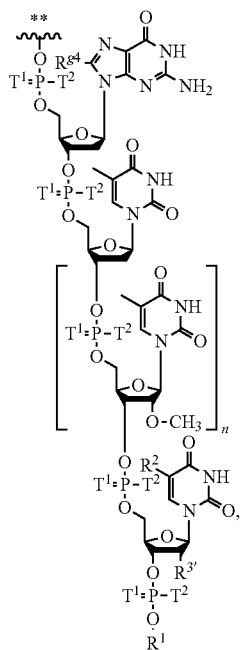

wherein

∼ and ∼** indicate the points of attachment within the oligonucleotide;

each $T^1$ is independently O or S;

each $T^2$ is $S^-$;

$T^3$ is a group

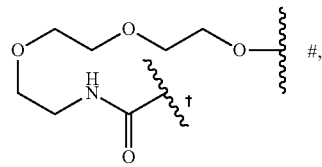

wherein ∼† indicates the point of attachment to L and wherein ∼# indicates the point of attachment to the rest of the oligonucleotide;

Z is O or S;

$U^{5'}$ is —H or halogen;

$R^{5'}$ is —H or methoxy;

$R^{c1}$ is —H or methoxy;

$R^{g1}$, $R^{g2}$, $R^{g3}$, and V are H;

$R^{3'}$ is methoxy;

$R^1$ is —(CH$_2$)$_3$—OH;

$R^2$ is —H or methyl; and n is an integer from 0 to 2.

In yet another aspect, provided herein is a conjugate that comprises an antibody (Ab) and one or more immunomodulating oligonucleotides (P), wherein the antibody is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in formula (A),

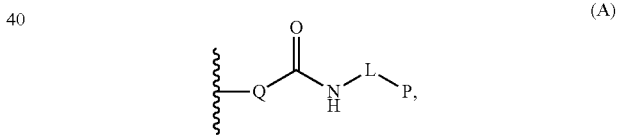

(A)

wherein:

wherein ∼ indicates the point of attachment of Q to the antibody (Ab);

the antibody comprises two antibody light chains, two antibody heavy chains, and two Q-tag peptides;

each of the Q-tag peptides is linked to the C-terminus of one of the antibody heavy chains;

one of the two Q-tag peptides is linked to the immunomodulating oligonucleotide via an amide bond with the glutamine residue of the Q-tag peptide;

each Q is independently a Q-tag peptide sequence having at least one glutamine residue;

each L is independently a bond or a linker moiety connected to Q via an amide bond with the glutamine residue; and each P is independently an immunomodulating oligonucleotide having the structure

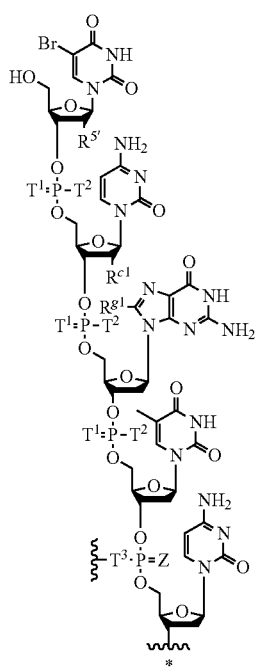

wherein ∿* and ∿** indicate the points of attachment within the oligonucleotide;

each $T^1$ is independently O or S;

each $T^2$ is $S^-$;

$T^3$ is a group wherein ∿† indicates the point of attachment to L and wherein ∿# indicates the point of attachment to the rest of the oligonucleotide;

Z is O or S;

$R^{5'}$ is —H or methoxy;

$R^{c1}$ is —H or methoxy;

$R^{g1}$, $R^{g2}$, $R^{g3}$, and V are H;

$R^{3'}$ is methoxy;

$R^1$ is —$(CH_2)_3$—OH;

$R^2$ is —H or methyl; and n is an integer from 0 to 2.

In still another aspect, provided herein is a conjugate comprising an antibody or antigen-binding fragment thereof (Ab) and one or more immunomodulating oligonucleotides (P), wherein the antibody or antigen-binding fragment is linked to one or more Q-tag peptides (Q) comprising a Q-tag peptide sequence RPQGF (SEQ ID NO:47), and wherein each immunomodulating oligonucleotide is linked to a Q-tag peptide via an amide bond with the glutamine residue of the Q-tag peptide and a linker (L) as shown in Formula (A)

(A)

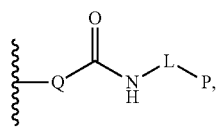

wherein:
 ⌇ indicates the point of attachment of each Q to the antibody or antigen-binding fragment thereof (Ab)
 each Q independently comprises a Q-tag peptide sequence RPQGF (SEQ ID NO:47);
 each L is independently a bond or a linker moiety wherein m is an integer ranging from about 0 to about 50, and wherein ⌇† indicates the point of attachment to P, and ⌇‡ indicates the point of attachment to the rest of the conjugate connected to Q via an amide bond with the glutamine residue; and each P is independently an immunomodulating oligonucleotide having the structure

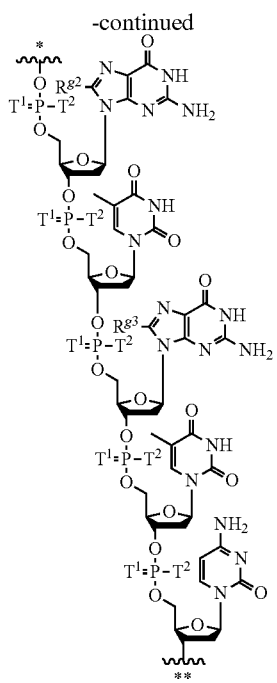

wherein ⌇* and ⌇** indicate the points of attachment within the oligonucleotide;
 each $T^1$ is independently O or S;
 each $T^2$ is $S^-$;
 provided that each P comprises at least one pair of geminal $T^1$ and $T^2$ wherein $T^1$ is S and $T^3$ is a group

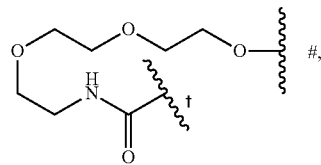 [SMILES: *OCCOCCOCCNC(*)=O]

wherein ⁓† indicates the point of attachment to L and wherein ⁓# indicates the point of attachment to the rest of the oligonucleotide;
Z is O or S;
$U^{5'}$ is —H or halogen;
$R^{5'}$ is —H;
$R^{c1}$ is —H;
$R^{g1}$, $R^{g2}$, $R^{g3}$, and V are H;
$R^{3'}$ is methoxy;
$R^1$ is —$(CH_2)_3$—OH;
$R^2$ is -methyl; and
n is 1,
wherein Ab is an antibody or antigen-binding fragment thereof that binds a tumor associated antigen.

In some embodiments, the antibody or conjugate specifically binds an antigen expressed by the cancer or cancer-associated stroma.

In another aspect, also provided herein is a pharmaceutical composition comprising a conjugate as described herein. In still another aspect, provided herein is a pharmaceutical composition comprising an immunomodulating oligonucleotide as described herein. In still yet a further aspect, provided herein is a kit comprising a conjugate as described herein, and instructions for use of the conjugate.

In still further aspects, provided herein are methods for preparing the conjugates as described herein. In one aspect, provided herein is a method for preparing a conjugate that comprises an antibody or antigen-binding fragment thereof (Ab) and one or more immunomodulating oligonucleotides (P), wherein the antibody or antigen-binding fragment is linked to one or more Q-tag peptides (Q) comprising the amino acid sequence RPQGF (SEQ ID NO:47), wherein each immunomodulating oligonucleotide is linked to a Q-tag peptide via an amide bond with the glutamine residue of the Q-tag peptide and a linker (L) as shown in formula (A),

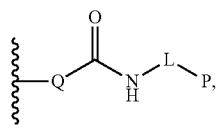 (A)

wherein:
⁓ indicates the point of attachment of each Q to the antibody or antigen-binding fragment thereof (Ab);
each Q independently comprises a Q-tag peptide sequence RPQGF (SEQ ID NO:47);
each L is independently a bond or a linker moiety connected to Q via an amide bond with the glutamine residue; and
each P is independently an immunomodulating oligonucleotide;
comprising contacting a compound of formula (B)

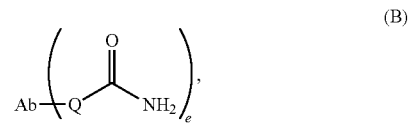 (B)

wherein Ab and Q are as defined for formula (A) above, and e is an integer from 1 to 20, with one or more immunomodulating oligonucleotides P, wherein each P independently has the following formula:

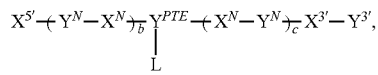

wherein
$X^{5'}$ is a 5' terminal nucleoside;
$X^{3'}$ is a 3' terminal nucleoside;
$Y^{PTE}$ is an internucleoside phosphotriester;
$Y^{3'}$ is a terminal phosphotriester;
each $X^N$ is independently a nucleoside;
each $Y^N$ is independently an internucleoside linker;
b and c are each independently an integer from 1 to 25; with the proviso that the sum of b and c is at least 5; and
L is a linker moiety having a terminal amine,
in the presence of a transglutaminase.

In another aspect, provided herein is a method for preparing a conjugate that comprises an antibody or antigen-binding fragment thereof (Ab) and one or more immunomodulating oligonucleotides (P), wherein the antibody or antigen-binding fragment is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in formula (A),

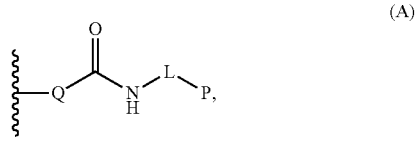 (A)

wherein:
⁓ indicates the point of attachment of each Q to the antibody or antigen-binding fragment thereof (Ab);
each Q is independently a Q-tag peptide having at least one glutamine residue;
each L is independently a bond or a linker moiety connected to Q via an amide bond with the glutamine residue; and
each P is independently an immunomodulating oligonucleotide;
comprising contacting a compound of formula (B)

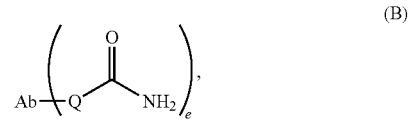 (B)

wherein Ab and Q are as defined for formula (A) above, and e is an integer from 1 to 20, with one or more immunomodulating oligonucleotides P, wherein each immunomodulating oligonucleotide P is independently an oligonucleotide of formula (C) as described herein or an oligonucleotide of formula (D) according to as described herein, in the presence of a transglutaminase. In some embodiments of the present aspects of methods of preparing conjugates, each immunomodulating oligonucleotide is independently an oligonucleotide of formula (C) or formula (D) is selected from the group consisting of the oligonucleotides of Table 10 and Table 12.

In still other aspects, provided herein is an antibody or antigen binding fragment thereof that binds to CD22, wherein the antibody or fragment comprises a heavy chain variable (VH) domain and a light chain variable (VL) domain, wherein the VH domain comprises a VH domain sequence selected from the group consisting of SEQ ID Nos:64-67; and wherein the VL domain comprises a VL domain sequence selected from the group consisting of SEQ ID Nos:68-91. In still other aspects, provided herein is an antibody or antigen binding fragment thereof that binds to CD22, wherein the antibody or fragment comprises a heavy chain variable (VH) domain and a light chain variable (VL) domain, wherein the VH domain comprises a CDR-H1, CDR-H2, and CDR-H3 from a VH domain shown in Table 8, and wherein the VL domain comprises a CDR-L1, CDR-L2, and CDR-L3 from a VL domain shown in Table 8. In some embodiments, the antibody is a Fab, F(ab')2, Fab'-SH, Fv, scFv, single domain, single heavy chain, or single light chain antibody or antibody fragment. In some embodiments, the antibody comprises an Fc region. In some embodiments, the Fc region is a human Fc region selected from the group consisting of an IgG1 Fc region, an IgG2 Fc region, and an IgG4 Fc region. In some embodiments, the Fc region is a wild-type human IgG1, IgG2, or IgG4 Fc region. In some embodiments, the Fc region is a human Fc region comprising one or more amino acid substitutions that reduce binding to C1q. In some embodiments, the Fc region is a human Fc region comprising one or more amino acid substitutions that reduce effector function, as compared with a human Fc region that lacks the amino acid substitution(s). In some embodiments, the Fc region is: (a) a human IgG1 Fc region comprising L234A, L235A, and/or G237A substitutions, amino acid position numbering according to EU index; (b) a human IgG2 Fc region comprising A330S and/or P331S substitutions, amino acid position numbering according to EU index; or (c) a human IgG4 Fc region comprising S228P and/or L235E substitutions, amino acid position numbering according to EU index. In some embodiments, the Fc region further comprises an N297A substitution, amino acid position numbering according to EU index. In some embodiments, the antibody further comprises an amino acid sequence selected from the group consisting of SEQ ID Nos:92-110.

In still other aspects, provided herein is an antibody that binds to human CD22, wherein the antibody comprises an antibody heavy chain and an antibody light chain, wherein the antibody heavy chain comprises the sequence of SEQ ID NO:179 or 180, and the antibody light chain comprises the sequence of SEQ ID NO:181 or 182. In some embodiments, the antibody heavy chain comprises the sequence of SEQ ID NO:179, and the antibody light chain comprises the sequence of SEQ ID NO:181. In some embodiments, the antibody heavy chain comprises the sequence of SEQ ID NO:179, and the antibody light chain comprises the sequence of SEQ ID NO:182. In some embodiments, the antibody heavy chain comprises the sequence of SEQ ID NO:180, and the antibody light chain comprises the sequence of SEQ ID NO:181. In some embodiments, the antibody heavy chain comprises the sequence of SEQ ID NO:180, and the antibody light chain comprises the sequence of SEQ ID NO:182.

In still other aspects, provided herein is an antibody that binds to human Her2, wherein the antibody comprises an antibody heavy chain and an antibody light chain, wherein the antibody heavy chain comprises the sequence of SEQ ID NO:183, 184, 186, or 187, and the antibody light chain comprises the sequence of SEQ ID NO:185 or 188. In some embodiments, the antibody heavy chain comprises the sequence of SEQ ID NO:183, and the antibody light chain comprises the sequence of SEQ ID NO:185. In some embodiments, the antibody heavy chain comprises the sequence of SEQ ID NO:184, and the antibody light chain comprises the sequence of SEQ ID NO:185. In some embodiments, the antibody heavy chain comprises the sequence of SEQ ID NO:186, and the antibody light chain comprises the sequence of SEQ ID NO:185. In some embodiments, the antibody heavy chain comprises the sequence of SEQ ID NO:187, and the antibody light chain comprises the sequence of SEQ ID NO:185. In some embodiments, the antibody heavy chain comprises the sequence of SEQ ID NO:183, and the antibody light chain comprises the sequence of SEQ ID NO:188. In some embodiments, the antibody heavy chain comprises the sequence of SEQ ID NO:184, and the antibody light chain comprises the sequence of SEQ ID NO:188. In some embodiments, the antibody heavy chain comprises the sequence of SEQ ID NO:186, and the antibody light chain comprises the sequence of SEQ ID NO:188. In some embodiments, the antibody heavy chain comprises the sequence of SEQ ID NO:187, and the antibody light chain comprises the sequence of SEQ ID NO:188.

In still other aspects, provided herein is a pharmaceutical composition comprising the conjugate or antibody according to any one of the embodiments herein and a pharmaceutically acceptable carrier. In still other aspect, provided herein is a pharmaceutical composition comprising the immunomodulating oligonucleotide according to any one of the embodiments herein and a pharmaceutically acceptable carrier. In still other aspect, provided herein are methods for treatment of a disease or disorder. In one aspect, provided herein is a method of treating cancer, comprising administering to an individual an effective amount of the conjugate, immunomodulating oligonucleotide, antibody, or pharmaceutical composition according to any one of the embodiments herein. In one aspect, provided herein is a method for treating cancer, comprising administering to an individual an effective amount of: (a) an immune checkpoint inhibitor and (b) the conjugate according to any one of the embodiments herein, or the pharmaceutical composition according to any one of the embodiments herein; wherein the cancer is refractory or resistant to the immune checkpoint inhibitor when administered in the absence of the conjugate; and wherein the antibody or antigen-binding fragment thereof binds to human CD22. In some embodiments, the immune checkpoint inhibitor is a PD-1 inhibitor or a PD-L1 inhibitor. In some embodiments, the immune checkpoint inhibitor is an anti-PD-1 antibody or an anti-PD-L1 antibody. In some embodiments, the administration results in reduced growth, size, and/or volume of the cancer. In one aspect, provided herein is a method for treating cancer, comprising administering to an individual an effective amount of the conjugate according to any one of the embodiments herein, or the pharmaceutical composition according to any one of the embodiments herein; wherein the administration results in B cell activation in the individual. In one aspect, provided herein is a method for treating cancer, comprising administering to an individual an effective amount of the conjugate according to any one of the embodiments herein, or the pharmaceutical composition according to any one of the embodiments herein; wherein the cancer is selected from the group consisting of head and neck squamous cell carcinoma (HNSCC), non-small-cell lung carcinoma (NSCLC), renal cell carcinoma (RCC), gastric cancer, hepatocellular carcinoma (HCC), esophageal cancer, cervical cancer, cervical squamous cell carcinoma, Merkle cell carcinoma, endometrial cancer, ovarian cancer, pancreatic cancer, melanoma, cutaneous melanoma, sarcoma, colorectal cancer, breast cancer, small cell lung cancer (SCLC), cutaneous squamous cell carcinoma, and urothelial carcinoma. In one aspect, provided herein is a method for treating cancer, comprising administering to an individual an effective amount of the conjugate according to any one of the embodiments herein, or the pharmaceutical composition according to any one of the embodiments herein; wherein the cancer is selected from the group consisting of acute lymphoblastic leukemia (ALL), hairy cell leukemia, and diffuse large B cell lymphoma (DLBCL). In one aspect, provided herein is a method for treating cancer, comprising administering to an individual an effective amount of the conjugate according to any one of the embodiments herein, or the pharmaceutical composition according to any one of the embodiments herein; wherein the cancer is selected from the group consisting of breast cancer, urothelial cancer, and gastric cancer. In some embodiments, the administration results in reduced growth, size, and/or volume of the cancer. In another aspect, provided herein is the conjugate, immunomodulating oligonucleotide, antibody, or pharmaceutical composition according to any one of the embodiments herein for use in a method of treating cancer, wherein the method comprises administering an effective amount of the conjugate, immunomodulating oligonucleotide, antibody, or pharmaceutical composition to an individual. In some embodiments, the cancer is a solid tumor. In some embodiments, the cancer is a liquid tumor. In some embodiments, the cancer is a B cell cancer. In some embodiments, the cancer is a lymphoma or leukemia. In some embodiments, the cancer is breast cancer, colorectal cancer, lung cancer, head and neck cancer, melanoma, lymphoma, or leukemia. In still other aspect, provided herein is a method for delivering the immunomodulating oligonucleotide according to any of the embodiments herein, comprising contacting the immunomodulating oligonucleotide with a cell. In some embodiments, the immunomodulating oligonucleotide is pegylated. In some embodiments, the immunomodulating oligonucleotide is formulated in a nanoparticle. In some embodiments, the immunomodulating oligonucleotide is conjugated to a polypeptide. In some embodiments, the antibody or conjugate specifically binds an antigen expressed by the cancer or cancer-associated stroma.

DESCRIPTION OF THE FIGURES

The present application can be understood by reference to the following description taken in conjunction with the accompanying figures.

FIG. 2A depicts the observed effect on B cell numbers by the various immunomodulating polypeptides alone. FIGS. 2B-2C depict the observed activation of B cells (via detection of CD40 expression) produced by the immunomodulating polynucleotides alone. FIG. 2D depicts the observed activity of antibody-oligonucleotide conjugates with RFB4 (anti-CD22) (DAR1).

FIGS. 6A-6D depict activity of BDCA2 conjugates with various oligonucleotides as shown by their pDC activation, as assessed by expression of (a) CD86, (b) CD40, (c) HLADR, or (d) IFNα.

FIGS. 7A-7D show the activity of BDCA2 conjugates with various oligonucleotides as shown by their activation of (a) monocytes; (b) mDCs; (c) CD19$^+$ B cells; or (d) CD3$^+$ T cells.

FIG. 8A shows an alignment of mouse and humanized anti-CD22 variable heavy (VH) domain sequences. CDR-H1, -H2, and —H3 are depicted in boxes. Sequences correspond to SEQ ID Nos:56 and 64-67 (top to bottom).

FIG. 8B shows an alignment of mouse and humanized anti-CD22 variable light (VL) domain sequences. CDR-L1, -L2, and -L3 are depicted in boxes. Sequences correspond to SEQ ID Nos:57 and 68-72 (top to bottom).

FIG. 10E shows analysis of starting material and CpG conjugates in reduced (r) or non-reduced (n.r.) form, as indicated.

FIG. 13A summarizes selected properties of the indicated CpG:anti-CD22 conjugates, including expression level in Expi293 or CHO cells, % high molecular weight (HMW) or monomer species by SEC-HPLC, VH/VL pairing, binding affinity to human CD22, and binding to cynomolgus CD22. FIG. 13B shows expression level of the indicated CpG:anti-CD22 conjugates from CHO cells.

FIGS. 16A-16E show a schematic diagram of exemplary conjugates, in accordance with some embodiments. Exemplary antibody:CpG conjugates with an engineered Q-tag (RPQGF; SEQ ID NO:47) fused to the C-terminus of the heavy chain are shown in FIGS. 16A & 16E (with a DAR 1) and in FIG. 16B (with DAR 2). Exemplary antibody:CpG conjugates with an naturally occurring Q-tag (Q295) exposed for conjugation by an N297A mutation are shown in FIG. 16C (with a DAR 1) and in FIG. 16D (with DAR 2).

FIG. 17A shows the half-life of CpG-antibody conjugates of Cmpd 1.1b (SEQ ID NO:3), Cmpd 3.2b (SEQ ID NO:9), Cmpd 4.2b (SEQ ID NO:12), Cmpd 4.3b (SEQ ID NO:13), Cmpd 5.2a (SEQ ID NO:15) or Cmpd 5.7a (SEQ ID NO:20) with RFB4 (SEQ ID NOS: 56 and 57) as compared to naked RFB4. FIG. 17B shows the half-life of RFB4 conjugates as evaluated by capturing the 5' region of the CpG using anti-BrdU antibody; conjugates of RFB4 with Cmpd 3.2b (SEQ ID NO:9), Cmpd 4.2b (SEQ ID NO:12), Cmpd 4.3b (SEQ ID NO:13), Cmpd 5.2a (SEQ ID NO:15) and Cmpd 5.7a (SEQ ID NO:20) have increased half-life compared to the RFB4 conjugate with Cmpd 1.1b (SEQ ID NO:3).

FIGS. 20A & 20B show non-targeted activation of T cells (FIG. 20A) and B cells (FIG. 20B) by anti-SIRP-α conjugated to compound 1.1b (12070), as compared to treatment with unconjugated anti-SIRP-α.

FIGS. 22A-22D show that an active Fc region (FIGS. 22A & 22C) is superior for targeting tumors with anti-Her2:CpG oligonucleotide conjugates, as compared to less active Fc region (FIGS. 22B & 22D). m/h Her2 expressing MC38 cells was generated by lentiviral transduction and sorted to obtain cells that express m/h Her2. m/h Her2-MC38 cells were injected into the right flank of C57BL/6 female mice, at a concentration of 2×10⁶ cells per mouse in DMEM. Tumors were monitored until the average size of tumors reached 70 mm³. Mice were randomized into PBS control, TNT149a blocking (anti-Her2 mIgG2a), and TNT150a (anti-Her2 mIgG1) with 5 mice per cohort. Anti-Her2-CpG nucleotide conjugate-treated mice were dosed with 1, 3 and 10 mg/kg three times in total, three days apart (FIGS. 22A & 22B). Both drugs were administered intraperitoneally. Arrows indicate administration. By day 60, 1, 3 and 10 mg/kg TNT149a treated mice dosed three times, three days apart showed tumor eradication (1/5, 5/5 and 5/5 mice, respectively; FIG. 22C) while mice treated with 1, 3 and 10 mg/kg TNT150a showed lower number of mice with eradicated tumors (0/5, 3/5 and 5/5, respectively; FIG. 22D). Mice treated with PBS control reached endpoint by day 24 and all groups treated with TNT149a or TNT150a showed delayed tumor growth as compared to PBS control.

FIGS. 23A-23I show the results of an MC38 m/h Her2 mouse immune re-challenge assay. FIG. 23A shows a diagram of the assay. On day 81, mice with eradicated tumors were rechallenged with m/h Her2 MC38 (lower right flank), parent MC38 (lower left flank), m/h Her2 B16F10 (upper right flank) and parent B16F10 (upper left flank) at 2×10⁶ cells (m/h Her2 MC38 and MC38 cells) and 1×10⁶ cells (m/h Her2 B16F10 and B16F10 cells) per mouse in DMEM. On day 81, there were 5 mice with eradicated tumors for groups treated with 10 mg/kg TNT150a, 3 and 10 mg/kg TNT149a and 3 mice with eradicated tumors for group treated with 3 mg/kg TNT150a. Naïve mice showed growth for all implanted cells. m/h Her2 B16F10, MC38 and m/h Her2 MC38 showed eradicated tumors or significant delayed tumor growth as compared to naïve. In all groups, the parent B16F10 tumors grew with one mouse that showed no growth in the 10 mg/kg mIgG2a group. By day 99, all mice showed complete eradication with m/h Her2 MC38 cells. Both MC38 parent and m/h Her2 B16F10 cells showed tumor eradication with the exception of one mouse for both 3 and 10 mg/kg mice previously treated with TNT149a for MC38 parent cells and 1-3 mice for all previously 3 and 10 mg/kg treated groups. These data show that m/h Her2 MC38 tumor bearing mice with eradicated tumors after treatment with anti-Her2 mIgG1 and mIgG2a have potent and durable anti-tumor response to m/h Her2 MC38, parent MC38 and m/h B16F10 but not parent B16F10 tumors. FIGS. 23B-23I show the results of the individual mice in the re-challenge groups, B16F10, MC38, m/h Her2 B6F10 and m/h Her2 MC38 tumors respectively.

FIGS. 26A-26C show induction of B cell activation in human PBMCs by anti-CD22:CpG oligonucleotide conjugates, as compared to naked CpGs. Shown are expression of CD40 (FIG. 26A), CD80 (FIG. 26B), and CD86 (FIG. 26C) following treatment of human PBMCs with anti-CD22 antibody with RH2 VH domain and RL1 N92S VL domain (SEQ ID Nos:65 and 87, respectively) conjugated to compound 7.7b (7-7) CpG, TNT52a (RFB4 conjugated to 12070), compound 7.7b (7-7) CpG, 12070 CpG, or media only.

FIG. 35A shows co-culture of splenocytes from Balbc syngeneic mouse (full immune system) in the presence of human breast tumor cell line SKBR3 (Her2+++), gating on monocytes/macrophages (Lin-CD11b+, F480+, GR1mid), and assaying CD40 expression. FIG. 35B shows co-culture of splenocytes from Balbc syngeneic mouse (full immune system) in the presence of human breast tumor cell line SKBR3 (Her2+++), gating on dendritic cells (lin–, F480–, CD11c+, MHCII+), and assaying CD40 expression.

FIGS. 41A-41C show robust induction of cytokines and chemokines upon CD22-mediated TLR9 engagement in human B cells.

DETAILED DESCRIPTION

Figure 1A:
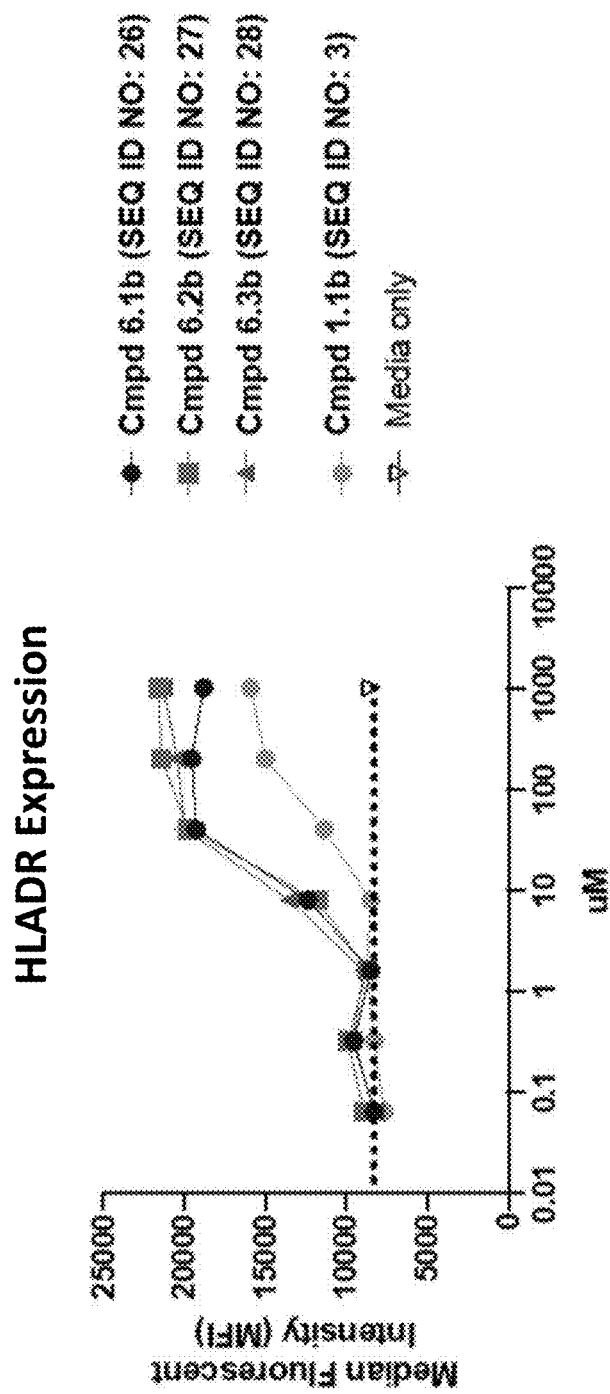
FIGS. 1A and 1B depict the activity of immunomodulating oligonucleotides alone in human PBMCs based upon observed increased expression of (a) HLADR and (b) CD40.

The following description sets forth exemplary methods, parameters and the like. It should be recognized, however, that such description is not intended as a limitation on the scope of the present disclosure but is instead provided as a description of exemplary embodiments.

The present description is based on the discovery that certain polypeptide-oligonucleotide conjugates provide enhanced stability and delivery selectivity. The description also provides the methods for preparing these conjugates. Particularly, the conjugation can be performed by a transglutaminase (Tgase)-mediated reaction. The description also provides intermediate compounds that can be used to prepare these conjugates as well as compositions and kits that contain these polypeptide-oligonucleotide conjugates.

I. Definitions

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to particular method steps, reagents, or conditions are specifically embraced by the present disclosure and are disclosed herein just as if each and every combination was individually and explicitly disclosed.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Throughout this application, unless the context indicates otherwise, references to a compound of Formula (A)-(D) include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (A)-(D) include polymorphs, solvates, co-crystals, isomers, tautomers and/or oxides thereof. In some embodiments, references to a compound of Formula (A)-(D) include polymorphs, solvates, and/or co-crystals thereof. In some embodiments, references to a compound of Formula (A)-(D) include isomers, tautomers and/or oxides thereof. In some embodiments, references to a compound of Formula (A)-(D) include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

The term "amino," as used herein, represents $-N(R^{N1})_2$, where, if amino is unsubstituted, both $R^{N1}$ are H; or, if amino is substituted, each $R^{N1}$ is independently H, $-OH$, $-NO_2$, $-N(R^{N2})_2$, $-SO_2OR^{N2}$, $-SO_2R^{N2}$, $-SOR^{N2}$, $-COOR^{N2}$, an N-protecting group, alkyl, alkenyl, alkynyl, alkoxy, aryl, arylalkyl, aryloxy, cycloalkyl, cycloalkenyl, heteroalkyl, or heterocyclyl, provided that at least one $R^{N1}$ is not H, and where each $R^{N2}$ is independently H, alkyl, or aryl. Each of the substituents may itself be unsubstituted or substituted with unsubstituted substituent(s) defined herein for each respective group. In some embodiments, amino is unsubstituted amino (i.e., $-NH_2$) or substituted amino (e.g., $-NHR^{N1}$), where $R^{N1}$ is independently $-OH$, $-SO_2OR^{N2}$, $-SO_2R^{N2}$, $-SOR^{N2}$, $-COOR^{N2}$, optionally substituted alkyl, or optionally substituted aryl, and each $R^{N2}$ can be optionally substituted alkyl or optionally substituted aryl. In some embodiments, substituted amino may be alkylamino, in which the alkyl groups are optionally substituted as described herein for alkyl. In certain embodiments, an amino group is $-NHR^{N1}$, in which $R^{N1}$ is optionally substituted alkyl. Non-limiting examples of $-NHR^{N1}$, in which $R^{N1}$ is optionally substituted alkyl, include: optionally substituted alkylamino, a proteinogenic amino acid, a non-proteinogenic amino acid, a $C_{1-6}$ alkyl ester of a proteinogenic amino acid, and a $C_{1-6}$ alkyl ester of a non-proteinogenic amino acid. The amino acid employed is optionally in the L-form.

The term "immunomodulating polynucleotide" as used herein, represents a polynucleotide construct containing a total of from 6 to 50 contiguous nucleosides covalently bound together by internucleoside bridging groups independently selected from the group consisting of internucleoside phosphoesters and optionally internucleoside abasic spacers. The immunomodulating polynucleotides are capped at 5'- and 3'-termini with 5'- and 3'-capping groups, respectively. The immunomodulating polynucleotides are capable of modulating an innate immune response, as determined by, e.g., a change in the activation of intracellular signaling pathway(s) including but not limited to NFκB, a change in the expression of an activation marker or a change in the secretion of at least one inflammatory cytokine or at least one type I interferon in an immune cell (e.g., antigen-presenting cell) to which an immunomodulating polynucleotide was delivered (e.g., in comparison to another immune cell (e.g., antigen-presenting cell) to which an immunomodulating polynucleotide was not delivered) or in an immune cell that interacts with an immune cell (e.g., antigen-presenting cell) to which an immunomodulating polynucleotide was delivered (including direct cell-to-cell interactions as well as indirect stimulation, e.g., from one or more cytokines secreted by the cell to which an immunomodulating polynucleotide was delivered). The immunomodulating polynucleotide may contain a conjugating group or, if the immunomodulating polynucleotide is part of a conjugate, a linker bonded to a targeting moiety and optionally to one or more (e.g., 1 to 6) auxiliary moieties (e.g., polyethylene glycols). The conjugating group or the linker may be part of the phosphotriester or the terminal capping group.

The term "immunostimulating polynucleotide" as used herein, represents an immunomodulating polynucleotide capable of activating an immune response, as determined by, e.g., an increase in the activation of intracellular signaling pathway(s) such as NFκB or an increase in levels of cell surface marker(s) of activation or function or an increase in the secretion of at least one inflammatory cytokine or at least one type I interferon in an immune cell (e.g., antigen-presenting cell) to which an immunostimulating polynucleotide was delivered (e.g., in comparison to another immune cell (e.g., antigen-presenting cell) to which an immunostimulating polynucleotide was not delivered) or in an immune cell that interacts with an immune cell (e.g., antigen-presenting cell) to which an immunomodulating polynucleotide was delivered (including direct cell-to-cell interactions as well as indirect stimulation, e.g., from one or more cytokines secreted by the cell to which an immunomodulating polynucleotide was delivered). In some embodiments, the immunostimulating polynucleotide contains at least one cytidine-p-guanosine (CpG) sequence, in which p is an internucleoside phosphodiester (e.g., phosphate or phosphorothioate) or an internucleoside phosphotriester or phosphothiotriester. As used herein, the CpG-containing immunostimulating polynucleotide can be naturally existing, such as CpG ODNs of bacterial or viral origins, or synthetic. For example, in some embodiments, the CpG sequence in the immunostimulating polynucleotide contains 2'-deoxyribose. In some embodiments, the CpG sequence in the immunostimulating polynucleotide is unmethylated. In some embodiments, the immunostimulating polynucleotide is a polynucleotide of Formula (C) as provided herein. In some embodiments, the immunostimulating polynucleotide is compound of Formula (D) as provided herein.

The term "immunosuppressive polynucleotide" as used herein, represents an immunomodulating polynucleotide capable of antagonizing an immune response, as determined by e.g., a reduction in the activation or lack of activation of NFκB or lack on increase in the levels of cell surface marker(s) of activation of function or a reduction or lack of increase in the secretion of at least one inflammatory cytokine or at least one type I interferon in an immune cell (e.g., antigen-presenting cell) to which an immunosuppressive polynucleotide was delivered (e.g., in comparison to another immune cell (e.g., antigen-presenting cell) to which an immunosuppressive polynucleotide was not delivered) or in an immune cell that interacts with an immune cell (e.g., antigen-presenting cell) to which an immunomodulating polynucleotide was delivered (including direct cell-to-cell interactions as well as indirect stimulation, e.g., from one or more cytokines secreted by the cell to which an immunomodulating polynucleotide was delivered).

It is to be understood that the terms "polynucleotide" and "oligonucleotide" may be used interchangeably herein. It is further to be understood that the terms "immunomodulating polynucleotide," "immunostimulating polynucleotide," "immunosuppressive polynucleotide," and "conjugate" encompass salts of the immunomodulating polynucleotide, immunostimulating polynucleotide, immunosuppressive polynucleotide and conjugate, respectively. For example, the terms "immunomodulating polynucleotide," "immunostimulating polynucleotide," "immunosuppressive polynucleotide," and "conjugate" encompasses both the protonated, neutral form (P-XH moiety, where X is O or S) of a phosphate, phosphorothioate, or phosphorodithioate and the deprotonated, ionic form (P-X⁻ moiety, where X is O or S) of a phosphate, phosphorothioate, or phosphorodithioate. Accordingly, it is to be understood that the phosphoesters and phosphodiesters described as having one or more of $R^{E1}$, $R^{E2}$, and $R^{E3}$ as hydrogen encompass salts, in which the phosphate, phosphorothioate, or phosphorodithioate is present in a deprotonated, ionic form. In addition, the terms "free," "naked," and "unconjugated" referring to immuno-modulating polynucleotides, immunostimulating polynucleotides, immunosuppressive polynucleotides, and/or oligonucleotides (e.g., CpG oligonucleotides) may be used interchangeably herein.

The term "phosphotriester," as used herein, refers to a phosphoester, in which all three valences are substituted with non-hydrogen substituents. The phosphotriester consists of phosphate, phosphorothioate, or phosphorodithioate; one or two bonds to nucleoside(s), or abasic spacer(s), and/or phosphoryl group(s); and one or two groups independently selected from the group consisting of a bioreversible group; a non-bioreversible group; an auxiliary moiety; a conjugating group; and a linker bonded to a targeting moiety and optionally to one or more (e.g., 1 to 6) auxiliary moieties. A terminal phosphotriester includes one bond to a group containing a nucleoside and two groups independently selected from the group consisting of a bioreversible group; a non-bioreversible group; an auxiliary moiety; a conjugating group; a phosphoryl group; and a linker bonded to a targeting moiety and optionally to one or more (e.g., 1 to 6) auxiliary moieties. In some embodiments, a terminal phosphotriester contains 1 or 0 linkers bonded to a targeting moiety and optionally to one or more (e.g., 1 to 6) auxiliary moieties. An internucleoside phosphotriester includes two bonds to nucleoside-containing groups. A phosphotriester may be a group of the following structure:

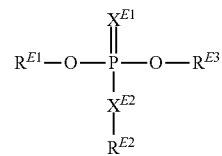

wherein:
each of $X^{E1}$ and $X^{E2}$ is independently O or S;
each or $R^{E1}$ and $R^{E3}$ is independently a bond to a nucleoside; a sugar analogue of an abasic spacer; a bioreversible group; a non-bioreversible group; an auxiliary moiety; a conjugating group; a linker bonded to a targeting moiety; a linker bonded to a targeting moiety and one or more (e.g., 1 to 6) auxiliary moieties; or the phosphorus atom in a group of formula —P(—$X^{E1}$)($X^{E2}$—$R^{E2}$A)-O—,
where $R^{E2}$ A is hydrogen; a bioreversible group; a non-bioreversible group; an auxiliary moiety; a conjugating group; a linker bonded to a targeting moiety; or a linker bonded to a targeting moiety and one or more (e.g., 1 to 6) auxiliary moieties; and
$R^{E2}$ is a bioreversible group; a non-bioreversible group; an auxiliary moiety; a conjugating group; a linker bonded to a targeting moiety; or a linker bonded to a targeting moiety and one or more (e.g., 1 to 6) auxiliary moieties;
provided that at least one of $R^{E1}$ and $R^{E3}$ is a bond to a group containing at least one nucleoside.
If both $R^{E1}$ and $R^{E3}$ are bonds to groups containing at least one nucleoside, the phosphotriester is an internucleoside phosphotriester. If one and only one of $R^{E1}$ and $R^{E3}$ is a bond to a group containing a nucleoside, the phosphotriester is a terminal phosphotriester.

As used herein, the term "amino acid" refers to any amino acid (both standard and non-standard amino acids), including, but not limited to, α-amino acids, (β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "antibody," "immunoglobulin," and "Ig" are used interchangeably herein, and are used in the broadest sense and specifically cover, for example, individual monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments of antibodies. An antibody can be human, humanized, chimeric and/or affinity matured as well as an antibody from other species, for example, mouse and rabbit.

The term "antibody" is intended to include a polypeptide product of B cells within the immunoglobulin class of polypeptides that is able to bind to a specific antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxyl-terminal portion of each chain includes a constant region. See Borrebaeck (ed.) (1995) Antibody Engineering, Second Ed., Oxford University Press.; Kuby (1997) Immunology, Third Ed., W.H. Freeman and Company, New York. Antibodies also include, but are not limited to, synthetic antibodies, monoclonal antibodies, recombinant antibodies, multispecific antibodies (including bispecific antibodies), human antibodies, humanized antibodies, camelized antibodies, chimeric antibodies, intrabodies, anti-idiotypic (anti-Id) antibodies, and functional fragments thereof, which refers a portion of an antibody heavy or light chain polypeptide that retains some or all of the binding activity of the antibody from which the fragment is derived. Non-limiting examples of functional fragments of an antibody include single-chain Fvs (scFv) (e.g., including monospecific or bispecific), Fab fragments, F(ab') fragments, F(ab)$_2$ fragments, F(ab')$_2$ fragments, disulfide-linked Fvs (sdFv), Fd fragments, Fv fragments, scRv-Fc, nanobody, diabody, triabody, tetrabody, and minibody. In some embodiments, the antibody comprises an Fc variant that has reduced or ablated effector function. In particular, antibodies provided herein include immunoglobulin molecules and immunologically active portions of immunoglobulin molecules, for example, antigen-binding domains or molecules that contain an antigen-binding site that binds to the antigen (e.g., one or more complementarity determining regions (CDRs) of an anti-CD56 antibody or an anti-SIRPα antibody). Such antibody fragments are described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., *Cell Biophysics* 1993, 22, 189-224; Plückthun and Skerra, *Meth. Enzymol.* 1989, 178, 497-515; and Day, Advanced Immunochemistry, Second Ed., Wiley-Liss, Inc., New York, NY (1990). The antibodies provided herein can be of any type (e.g., IgG, IgE, IgM, IgD, IgA, and IgY), any class (e.g., IgG1, IgG2, IgG3, IgG4, IgA1, and IgA2), or any subclass (e.g., IgG2a and IgG2b) of an immunoglobulin molecule.

The term "antigen" refers to a predetermined target to which an antibody can selectively bind. A target antigen can be a polypeptide, carbohydrate, nucleic acid, lipid, hapten, or fragment thereof, or other naturally occurring or synthetic compound. In one embodiment, the target antigen is a polypeptide.

The terms "antigen-binding fragment," "antigen-binding domain," and "antigen-binding region" refer to a portion of an antibody that comprises the amino acid residues that interact with an antigen (e.g., a polypeptide, carbohydrate, nucleic acid, lipid, hapten, or fragment thereof, or other naturally occurring or synthetic compound) and confer on the binding agent its specificity and affinity for the antigen (e.g., complementarity determining regions (CDRs)).

The term "specific binding," "specifically binds to," or "specific for" a particular polypeptide or an epitope on a particular polypeptide target can be exhibited, for example, by a molecule (e.g., an antibody) having a dissociation constant ($K_d$) for the target of at least about $10^{-4}$ M, at least about $10^{-5}$ M, at least about $10^{-6}$ M, at least about $10^{-7}$ M, at least about $10^{-8}$ M, at least about $10^{-9}$ M, at least about $10^{-10}$ at least about $10^{-11}$ M, or at least about $10^{-12}$ M. In one embodiment, the term "specific binding" refers to binding where a molecule binds to a particular polypeptide or epitope on a particular polypeptide without substantially binding to any other polypeptide or polypeptide epitope.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Stites et al. (eds.), Appleton & Lange, Norwalk, C T, 1994, page 71 and Chapter 6.

The term "variable region" or "variable domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, M D, 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. The variability in sequence is concentrated in the CDRs while the less variable portions in the variable region are referred to as framework regions (FR). The CDRs of the light and heavy chains are primarily responsible for the interaction of the antibody with antigen. In specific embodiments, the variable region is a human variable region.

The term "variable region residue numbering as in Kabat" or "amino acid position numbering as in Kabat", and variations thereof, refers to the numbering system used for heavy chain variable regions or light chain variable regions of the compilation of antibodies in Kabat et al., Sequences of Proteins of Immunological Interest, 5th Ed. Public Health Service, National Institutes of Health, Bethesda, MD. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, including, for example, by AbM, Chothia, Contact, IMGT and AHon.

An "intact" antibody is one comprising an antigen-binding site as well as a CL and at least heavy chain constant regions, CH1, CH2 and CH3. The constant regions may include human constant regions or amino acid sequence variants thereof. Preferably, an intact antibody has one or more effector functions.

The term "antibody fragment" refers to a portion of an intact antibody, preferably the antigen-binding or variable region of the intact antibody. Examples of antibody fragments include, without limitation, Fab, Fab', F(ab')2, and Fv fragments; diabodies and di-diabodies (see, e.g., Holliger et al., Proc. Natl. Acad. Sci. U.S.A. 1993, 90, 6444-8; Lu et al., J. Biol. Chem. 2005, 280, 19665-72; Hudson et al., Nat. Med. 2003, 9, 129-134; WO 93/11161; and U.S. Pat. Nos. 5,837,242 and 6,492,123); single-chain antibody molecules (see, e.g., U.S. Pat. Nos. 4,946,778; 5,260,203; 5,482,858 and 5,476,786); dual variable domain antibodies (see, e.g., U.S. Pat. No. 7,612,181); single variable domain antibodies (SdAbs) (see, e.g., Woolven et al., Immunogenetics 1999, 50, 98-101 Streltsov et al., Proc. Natl. Acad. Sci. U.S.A. 2004, 101, 12444-12449); and multispecific antibodies formed from antibody fragments.

The term "functional fragment," "binding fragment," or "antigen-binding fragment" of an antibody refers to a molecule that exhibits at least one of the biological functions attributed to the intact antibody, the function comprising at least binding to the target antigen.

The term "heavy chain" when used in reference to an antibody refers to a polypeptide chain of about 50-70 kDa, wherein the amino-terminal portion includes a variable region of about 120 to 130 or more amino acids and a carboxyl-terminal portion that includes a constant region. The constant region can be one of five distinct types, (e.g., isotypes) referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG and IgM, respectively, including four subclasses of IgG, namely IgG1, IgG2, IgG3, and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxyl-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a beta klotho epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., Nature 1975, 256, 495; or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature 1991, 352, 624-628 and Marks et al., J. Mol. Biol. 1991, 222, 581-597, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Exemplary methods of producing monoclonal antibodies are provided in the Examples herein.

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., *Nature* 1986, 321, 522-525; Riechmann et al., *Nature* 1988, 332, 323-329; Presta, *Curr. Opin. Biotechnol.* 1992, 3, 394-398; Carter et al., *Proc. Natl. Acad. Sci. U.S.A.* 1992, 89, 4285-4289; and U.S. Pat. Nos. 6,800,738, 6,719,971, 6,639,055, 6,407,213, and 6,054,297.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, *J. Mol. Biol.* 1991, 227, 381; Marks et al., *J. Mol. Biol.* 1991, 222, 581) and yeast display libraries (Chao et al., *Nature Protocols* 2006, 1, 755-768). Also available for the preparation of human monoclonal antibodies are methods described in Cole et al., *Monoclonal Antibodies and Cancer Therapy*, Alan R. Liss, p. 77 (1985); Boerner et al., *J. Immunol.* 1991, 147, 86-95. See also van Dijk and van de Winkel, *Curr. Opin. Pharmacol.* 2001, 5, 368-374. Human antibodies can be prepared by administering the antigen to a transgenic animal that has been modified to produce such antibodies in response to antigenic challenge, but whose endogenous loci have been disabled, e.g., mice (see, e.g., Jakobovits, *Curr. Opin. Biotechnol.* 1995, 6, 561-566; Bruggemann and Taussing, *Curr. Opin. Biotechnol.* 1997, 8, 455-458; and U.S. Pat. Nos. 6,075,181 and 6,150,584 regarding XENOMOUSE™ technology). See also, for example, Li et al., *Proc. Natl. Acad. Sci. U.S.A.* 2006, 103, 3557-3562 regarding human antibodies generated via a human B-cell hybridoma technology.

A "CDR" refers to one of three hypervariable regions (H1, H2, or H3) within the non-framework region of the immunoglobulin (Ig or antibody) VH β-sheet framework, or one of three hypervariable regions (L1, L2, or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains. Kabat et al., *J. Biol. Chem.* 1977, 252, 6609-6616; Kabat, *Adv. Protein Chem.* 1978, 32, 1-75. CDR region sequences also have been defined structurally by Chothia as those residues that are not part of the conserved β-sheet framework, and thus are able to adapt different conformations. Chothia and Lesk, *J. Mol. Biol.* 1987, 196, 901-917. Both terminologies are well recognized in the art. CDR region sequences have also been defined by AbM, Contact and IMGT. The positions of CDRs within a canonical antibody variable region have been determined by comparison of numerous structures. Al-Lazikani et al., *J. Mol. Biol.* 1997, 273, 927-948; Morea et al., *Methods.* 2000, 20, 267-279. Because the number of residues within a hypervariable region varies in different antibodies, additional residues relative to the canonical positions are conventionally numbered with a, b, c and so forth next to the residue number in the canonical variable region numbering scheme. Al-Lazikani et al., supra (1997). Such nomenclature is similarly well known to those skilled in the art.

The term "hypervariable region", "HVR", or "HV", when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., Sequences of Proteins of Immunological Interest, 5th Ed. Public Health Service, National Institutes of Health, Bethesda, MD. (1991)). Chothia refers instead to the location of the structural loops. See, e.g., Chothia and Lesk, *J. Mol. Biol.* 1987, 196, 901-917. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Cycloalkynyl" refers to an unsaturated hydrocarbon group within a cycloalkyl having at least one site of acetylenic unsaturation (i.e., having at least one moiety of the formula C≡C). Cycloalkynyl can consist of one ring, such as cyclooctyne, or multiple rings. One cycloalkynyl moiety is an unsaturated cyclic hydrocarbon having from 5 to 10 annular carbon atoms (a "$C_5$-$C_{10}$ cycloalkynyl"). Examples include cyclopentyne, cyclohexyne, cycloheptyne, cyclooctyne, cyclononyne, and the like.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

The term "DAR" refers to a drug-antibody ratio of an oligonucleotide-antibody conjugate, more specifically an immunomodulating polynucleotide-antibody ratio. In some instances, for example, an oligonucleotide-antibody conjugate may be described herein as having a DAR of 1 or as a DAR1 conjugate, wherein the oligonucleotide-antibody ratio is 1-to-1. In other instances, an an oligonucleotide-antibody conjugate may be described herein as having a DAR of 2 or as a DAR2 conjugate, wherein the oligonucleotide-antibody ratio is 2-to-1.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

As used herein, the terms "including," "containing," and "comprising" are used in their open, non-limiting sense. It is also understood that aspects and embodiments of the invention described herein may include "consisting" and/or "consisting essentially of" aspects and embodiments.

It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

As used herein, a "carrier" includes pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "effective amount" or "therapeutically effective amount" of a substance is at least the minimum concentration required to bring about a measurable improvement or prevention of a particular disorder. An effective amount herein may vary according to factors such as the disease state, age, sex, and weight of the patient, and the ability of the substance to elicit a desired response in the individual. An effective amount is also one in which any toxic or detrimental effects of the treatment are outweighed by the therapeutically beneficial effects. In reference to cancer, an effective amount comprises an amount sufficient to cause a tumor to shrink and/or to decrease the growth rate of the tumor (such as to suppress tumor growth) or to prevent or delay other unwanted cell proliferation in cancer. In some embodiments, an effective amount is an amount sufficient to delay development of cancer. In some embodiments, an effective amount is an amount sufficient to prevent or delay recurrence. In some embodiments, an effective amount is an amount sufficient to reduce recurrence rate in the individual. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) reduce recurrence rate of tumor, and/or (viii) relieve to some extent one or more of the symptoms associated with the cancer. An effective amount can be administered in one or more administrations. For purposes of this disclosure, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

The terms "protein," "polypeptide" and "peptide" are used herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Typically, a protein for use herein will have a molecular weight of at least about 5-20 kDa, alternatively at least about 20-100 kDa, or at least about 100 kDa. Also included within the definition are, for example, proteins containing one or more analogs of an amino acid (including, for example, unnatural amino acids, etc.), as well as other modifications known in the art.

A "pharmaceutically acceptable salt" is a salt form that is non-toxic, biologically tolerable, or otherwise biologically suitable for administration to the subject. See generally Berge et al. (1977) *J. Pharm. Sci.* 66, 1. Particular pharmaceutically acceptable salts are those that are pharmacologically effective and suitable for contact with the tissues of subjects without undue toxicity, irritation, or allergic response. Pharmaceutically acceptable salts include, without limitation, acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. These salts may be derived from inorganic or organic acids.

Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, 7-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include, without limitation, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimethamine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include, without limitation, aluminum hydroxide, calcium hydroxide, potassium hydroxide, sodium carbonate, sodium hydroxide, and the like. Lists of other suitable pharmaceutically acceptable salts are found in *Remington's Pharmaceutical Sciences*, 17th Edition, Mack Publishing Company, Easton, Pa., 1985.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

A "subject," "patient" or "individual" includes a mammal, such as a human or other animal, and typically is human. In some embodiments, the subject, e.g., patient, to whom the therapeutic agents and compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent, a dog, a cat, a farm animal, such as a cow or a horse, etc.

The term "cancer" or "tumor" refers to the presence of cells possessing characteristics typical of cancer-causing cells, such as uncontrolled proliferation, immortality, metastatic potential, rapid growth and proliferation rate, and certain characteristic morphological features. Cancer cells are often in the form of a solid tumor, which is detectable on the basis of tumor mass, e.g., by procedures such as CAT scan, MR imaging, X-ray, ultrasound or palpation, and/or which is detectable because of the expression of one or more cancer-specific antigens in a sample obtainable from a patient. In some embodiments, a solid tumor does not need to have measurable dimensions. Cancer cells may also in the form of a liquid tumor, which cancer cells may exist alone or disseminated within an animal. As used herein, the terms "disseminated tumor" and "liquid tumor" are used interchangeably, and include, without limitation, leukemia and lymphoma and other blood cell cancers.

The term "leukemia" refers to a type of cancer of the blood or bone marrow characterized by an abnormal increase of immature white blood cells called "blasts." Leukemia is a broad term covering a spectrum of diseases. In turn, it is part of the even broader group of diseases affecting the blood, bone marrow, and lymphoid system, which are all known as hematological neoplasms. Leukemias can be divided into four major classifications, acute lymphocytic (or lymphoblastic) leukemia (ALL), acute myelogenous (or myeloid or non-lymphatic) leukemia (AML), chronic lymphocytic leukemia (CLL), and chronic myelogenous leukemia (CML). Further types of leukemia include Hairy cell leukemia (HCL), T-cell prolymphocytic leukemia (T-PLL), large granular lymphocytic leukemia, and adult T-cell leukemia.

The term "lymphoma" refers to a group of blood cell tumors that develop from lymphatic cells. The two main categories of lymphomas are Hodgkin lymphomas (HL) and non-Hodgkin lymphomas (NHL) Lymphomas include any neoplasms of the lymphatic tissues. The main classes are cancers of the lymphocytes, a type of white blood cell that belongs to both the lymph and the blood and pervades both.

As used herein, the term "cancer" includes premalignant as well as malignant cancers, and also includes primary tumors (e.g., those whose cells have not migrated to sites in the subject's body other than the site of the original tumor) and secondary tumors (e.g., those arising from metastasis, the migration of tumor cells to secondary sites that are different from the site of the original tumor), recurrent cancer and refractory cancer.

The terms "cancer recurrence" and "cancer relapse" are used interchangeably and refer to the return of a sign, symptom or disease after a remission. The recurrent cancer cells may re-appear in the same site of the primary tumor or in another location, such as in secondary cancer. The cancer cells may re-appear in the same diseased form as the primary cancer or a different diseased form. For example, in some embodiments, a primary cancer is a solid tumor, and the recurrent cancer is a liquid tumor. In other embodiments, a primary cancer is a liquid tumor, and the recurrent cancer is a solid tumor. In yet other embodiments, the primary cancer and the recurrent cancer are both solid tumors, or both liquid tumors. In some embodiments, the recurrent tumor expresses at least one tumor-associated antigen that is also expressed by the primary tumor.

The term "refractory cancer" as used herein refers to a cancer that does not respond to a treatment, for example, a cancer that is resistant at the beginning of treatment (e.g., treatment with an immunotherapy) or a cancer that may become resistant during treatment. The terms "respond," "response" or "responsiveness" refer to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

As used herein, cancers include, but are not limited to, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, B cell cancer, e.g., multiple myeloma, Waldenström's macroglobulinemia, the heavy chain diseases, such as, for example, alpha chain disease, gamma chain disease, and mu chain disease, benign monoclonal qammopathy, and immunocytic amyloidosis, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, sominoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "cancer therapy" or "cancer therapeutic agent" as used herein, refers to those therapies or agents that can exert anti-tumor effect or have an anti-tumor activity. Such anti-tumor effect or anti-tumor activity can be exhibited as a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The terms "treat," "treating," and "treatment" are meant to include alleviating or abrogating a condition, disorder, or disease, or one or more of the symptoms associated with the condition, disorder, or disease; or alleviating or eradicating the cause(s) of the condition, disorder, or disease itself.

The terms "prevent," "preventing," and "prevention" are meant to include a method of delaying and/or precluding the onset of a condition, disorder, or disease, and/or its attendant symptoms; barring a subject from acquiring a condition, disorder, or disease; or reducing a subject's risk of acquiring a condition, disorder, or disease.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocyclyl, aralkyl, aminosulfonyl, sulfonylamino, sulfonyl, oxo, and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The term "Q-tag," as used herein, refers to a portion of a polypeptide containing glutamine residue that, upon transglutaminase-mediated reaction with a compound containing —NH₂ amine, provides a conjugate containing the portion of polypeptide, in which the glutamine residue includes a side chain modified to include the amide bonded to the compound. Q-tags are known in the art. Non-limiting examples of Q-tags are LLQGG (SEQ ID NO:172) and GGGLLQGG (SEQ ID NO:173). In some embodiments, the Q tag is attached to the C terminal of the heavy chain of the antibody. In some embodiments, the Q tag is attached to the light chain of the antibody. In some embodiments, the Q tag is naturally occurring. For example, mutation of N297 to N297A exposes Q295 of the antibody, where the conjugation could occur (numbering according to EU index, e.g., as listed in Edelman, G. M. et al., Proc. Natl. Acad. USA, 63, 78-85 (1969) and Kabat, E. A. et al., Sequences of proteins of immunological interest. 5th Edition—US Department of Health and Human Services, NIH publication no 91-3242, pp 662,680,689 (1991)). In some embodiments, the Q tag is within the Fc domain of the antibody.

II. Conjugates

Immunostimulating polynucleotides have been used in a variety of therapeutic applications. To improve targeting specificity and in vivo distribution, the immunomodulating polynucleotides (e.g., CpG ODNs) can be conjugated to a targeting moiety (e.g., polypeptides). Particularly, transglutaminase-mediated reaction can be used to conduct such a conjugation reaction due to its high reaction rates and suitable site specificity. The present disclosure provides oligonucleotide-polypeptide conjugates exhibiting favorable activity. In some embodiments, the polypeptide is an antibody, such as an antibody heavy or light chain.

Provided herein is an oligonucleotide-antibody conjugate wherein the oligonucleotide and antibody are attached together via a linking moiety. In some embodiments, one antibody can be conjugated to one or more oligonucleotides. In some embodiments, the oligonucleotide-antibody conjugate is a conjugate comprising an antibody or antigen-binding fragment thereof and one or more immunomodulating oligonucleotides (P), wherein the antibody or antigen-binding fragment is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in Formula (A):

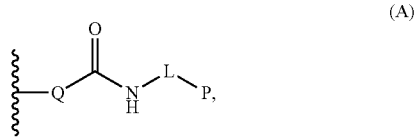

(A)

or a stereoisomer, a mixture of two or more diastereomers, a tautomer, or a mixture of two or more tautomers thereof, or a pharmaceutically acceptable salt, solvate, or hydrate thereof;
wherein:
    〜 indicates the point of attachment of each Q to the antibody or antigen-binding fragment thereof (Ab);
    each Q is independently a Q-tag peptide sequence comprising at least one glutamine residue;
    each L is independently a bond or a linker moiety connected to Q via an amide bond with the glutamine residue; and
    each P is independently an immunomodulating oligonucleotide.

In some embodiments, the conjugate is a conjugate comprising an antibody or antigen-binding fragment thereof and one or more immunomodulating oligonucleotides (P), wherein the antibody or antigen-binding fragment is linked to one or more Q-tag peptides (Q) that comprise the amino acid sequence RPQGF (SEQ ID NO:47), wherein each immunomodulating oligonucleotide is linked to a Q-tag peptide via an amide bond with the glutamine residue of the Q-tag peptide and a linker (L) as shown in Formula (A),

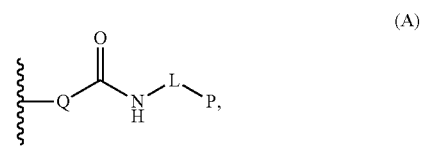

(A)

or a stereoisomer, a mixture of two or more diastereomers, a tautomer, or a mixture of two or more tautomers thereof, or a pharmaceutically acceptable salt, solvate, or hydrate thereof;
wherein:
    〜 indicates the point of attachment of each Q to the antibody or antigen-binding fragment thereof (Ab);
    each Q independently comprises a Q-tag peptide comprising a peptide sequence RPQGF (SEQ ID NO:47);
    each L is independently a bond or a linker moiety connected to Q via an amide bond with the glutamine residue; and
    each P is independently an immunomodulating oligonucleotide.

In other embodiments, the conjugate is a conjugate comprising an antibody or antigen-binding fragment thereof and one or more immunomodulating oligonucleotides (P), wherein the antibody or antigen-binding fragment is linked to one or more Q-tag peptides (Q) comprising at least one glutamine residue, wherein each immunomodulating oligonucleotide is linked to a Q-tag peptide via an amide bond with the glutamine residue of the Q-tag peptide and a linker (L) as shown in formula (A),

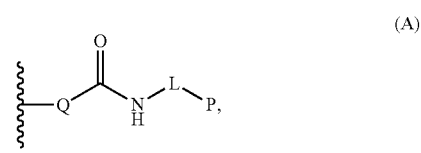

(A)

or a stereoisomer, a mixture of two or more diastereomers, a tautomer, or a mixture of two or more tautomers thereof, or a pharmaceutically acceptable salt, solvate, or hydrate thereof;
wherein:
    〜 indicates the point of attachment of each Q to the antibody or antigen-binding fragment thereof (Ab);
    each Q is independently a Q-tag peptide comprising at least one glutamine residue;
    each L is independently a bond or a linker moiety connected to Q via an amide bond with the glutamine residue; and
    each P is independently an immunomodulating oligonucleotide selected from the group consisting of the oligonucleotides of Table 10.

In one embodiment, the oligonucleotide-antibody conjugate has a DAR ranging from about 1 to about 20, from about 1 to about 10, from about 1 to about 8, from about 1 to about 4, or from about 1 to about 2. In another embodiment, the oligonucleotide-antibody conjugate has a DAR of about 1, about 2, about 3, about 4, about 5, about 6, about 7, or about 8.

In some embodiments, the conjugate comprises one or more, two or more, three or more, four or more, five or more, six or more, seven or more, eight or more, nine or more, ten or more, or twenty or more Q-tag peptides. In some embodiments, the conjugate comprises one, two, three, four, five, six, seven, eight, nine, ten, or twenty Q-tag peptides. In some embodiments, the conjugate has 2 Q-tag peptides. In some embodiments, the conjugate comprises one or more, two or more, three or more, four or more, five or more, six or more, seven or more, eight or more, nine or more, ten or more, or twenty or more immunomodulating oligonucleotides. In some embodiments, the conjugate comprises one, two, three, four, five, six, seven, eight, nine, ten, or twenty immunomodulating oligonucleotides. In some embodiments, the conjugate has one immunomodulating oligonucleotide. An exemplary conjugate is shown in FIGS. 16A-16D.

In one aspect, the oligonucleotide in the oligonucleotide-antibody conjugate is an immunomodulating (e.g., immunostimulating) polynucleotide. In certain embodiments, the immunomodulating polynucleotide comprises a 5-modified uridine or 5-modified cytidine. In certain embodiments, the inclusion of 5-modified uridine (e.g., 5-ethynyl-uridine) at the 5'-terminus of the immunomodulating polynucleotide (e.g., among the two 5'-terminal nucleosides) enhances the immunomodulating properties of the polynucleotide. In certain embodiments, the immunomodulating polynucleotide is shorter (e.g., comprising a total of from about 6 to about 16 nucleotides or from about 12 to about 14 nucleotides) than a typical CpG ODN, which is from 18 to 28 nucleotides in length. In certain embodiments, the shorter immunomodulating polynucleotide (e.g., those comprising a total of from about 6 to about 16 nucleotides or from about 12 to about 14 nucleotides) retains the immunomodulating activity of a longer, typical CpG ODN; or exhibits higher immunomodulating activity (e.g., as measured by NFκB activation or by the changes in the expression levels of cell surface markers of activation or function such as CD40, HLADR, CD69 or CD80 or by the changes in the levels of at least one cytokine (e.g., IL-6 or IL-10), as compared to the longer CpG ODN. In certain embodiments, the immunomodulating polynucleotide comprises an abasic spacer. In certain embodiments, the immunomodulating polynucleotide comprises an internucleoside phosphotriester.

In certain embodiments, the immunomodulating polynucleotide provided herein exhibits stability (e.g., stability against nucleases) that is superior to that of a CpG ODN containing mostly internucleoside phosphate (e.g., more than 50% of internucleoside phosphates) without substantially sacrificing its immunostimulating activity. This effect can be achieved, e.g., by incorporating at least 50% (e.g., at least 70%) internucleoside phosphorothioates or phosphorodithioates or through the inclusion of internucleoside phosphotriesters and/or internucleoside abasic spacers. Phosphotriesters and abasic spacers are also convenient for conjugation to a targeting moiety. Phosphate-based phosphotriesters and abasic spacers can also be used for reduction of off-target activity, relative to polynucleotides with fully phosphorothioate backbones. Without wishing to be bound by theory, this effect may be achieved by reducing self-delivery without disrupting targeting moiety-mediated delivery to target cells. Accordingly, a polynucleotide provided herein can include about 15 or fewer, about 14 or fewer, about 13 or fewer, about 12 or fewer, about 11 or fewer, or about 10 or fewer contiguous internucleoside phosphorothioates. For example, an immunostimulating polynucleotide comprising a total of from about 12 to about 16 nucleosides can contain about 10 or fewer contiguous internucleoside phosphorothioates.

The immunostimulating polynucleotide provided herein can contain a total of about 50 or fewer, about 30 or fewer, about 28 or fewer, or about 16 or fewer nucleosides. The immunostimulating polynucleotide can contain a total of at least 6, about 10 or more, or about 12 or more nucleosides. For example, the immunostimulating polynucleotide can contain a total of from about 6 to about 30, from about 6 to about 28, from about 6 to about 20, from about 6 to about 16, from about 10 to about 20, from about 10 to about 16, from about 12 to about 28, from about 12 to about 20, or from about 12 to about 16 nucleosides.

In certain embodiments, the immunostimulating polynucleotide comprises one or more phosphotriesters (e.g., internucleoside phosphotriesters) and/or phosphorothioates (e.g., from about 1 to about 6 or from about 1 to about 4), e.g., at one or both termini (e.g., within the six 5'-terminal nucleosides or the six 3'-terminal nucleosides). The inclusion of one or more internucleoside phosphotriesters and/or phosphorothioates can enhance the stability of the polynucleotide by reducing the rate of exonuclease-mediated degradation.

In certain embodiments, the immunostimulating polynucleotide comprises a phosphotriester or a terminal phosphodiester, where the phosphotriester or the terminal phosphodiester comprises a linker bonded to a targeting moiety or a conjugating group and optionally to one or more (e.g., from about 1 to about 6) auxiliary moieties. In certain embodiments, the immunostimulating polynucleotide comprises only one linker. In certain embodiments, the immunostimulating polynucleotide comprises only one conjugating group.

The polynucleotide provided herein can be a hybridized polynucleotide including a strand and its partial or whole complement. The hybridized polynucleotides can have at least 6 complementary base pairings (e.g., about 6, about 7, about 8, about 9, about 10, about 11, about 12, about 13, about 14, about 15, about 16, about 17, about 18, about 19, about 20, about 21, about 22, or about 23), up to the total number of the nucleotides present in the included shorter strand. For example, the hybridized portion of the hybridized polynucleotide can contain about 6, about 7, about 8, about 9, about 10, about 11, about 12, about 13, about 14, about 15, about 16, about 17, about 18, about 19, about 20, about 21, about 22, or about 23 base pairs.

In one aspect, the oligonucleotide in the oligonucleotide-antibody conjugate comprises one or more CpG sites. In some embodiments, the oligonucleotide comprises at least 1, at least 2, or at least 3 CpG sites. In some embodiments, the oligonucleotide is an antisense oligonucleotide As used herein, a "modified nucleotide" is a nucleotide other than a ribonucleotide (2'-hydroxyl nucleotide). In some embodiments, at least 50%, at least 55%, at least 60%, at least 65%, at least 70%, at least 75%, at least 80%, at least 85%, at least 90%, at least 95%, at least 97%, at least 98%, at least 99%, or 100% of the nucleotides are modified nucleotides. As used herein, modified nucleotides include, but are not limited to, deoxyribonucleotides, nucleotide mimics, abasic nucleotides, 2'-modified nucleotides, 3' to 3' linkages (inverted) nucleotides, non-natural base-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides (cPrpN). The 2'-modified nucleotides (i.e. a nucleotide with a group other than a hydroxyl group at the 2' position of the five-membered sugar ring) include, but are not limited to, 2'-O-alkyl nucleotides, 2'-deoxy-2'-halo nucleotides, 2'-deoxy nucleotides, 2'-methoxyethyl (2'-O-2-methoxylethyl) nucleotides, 2'-amino nucleotides, 2'aminoalkyl nucleotides, and 2'-alkyl nucleotides. In some embodiments, modified nucleotide is selected from the group consisting of 5-bromo-2'-O-methyluridine, 5-bromo-2'-deoxyuridine, 2'-O-methyluridine, 2'-deoxyuridine, 2'-O-methylthymidine, 2'-O-methylcytidine, 2'-O-(2-methoxyethyl)thymidine and 8-oxo-7,8-dihydro-2'-deoxyguanosine. It is not necessary for all positions in a given compound to be uniformly modified. Conversely, more than one modification may be incorporated in a single oligonucleotide or even in a single nucleotide thereof. The oligonucleotides may be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-Me-C), 5-hydroxymethyl cytosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil (e.g., 5-bromouracil and 5-iodouracil), cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl, 8-oxo and other 8-substituted adenines and guanines, 5-halo (e.g., 5-bromo and 5-iodo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, one or more nucleotides of the oligonucleotide are linked by non-standard linkages or backbones (e.g., modified internucleoside linkages or modified backbones). In some embodiments, a modified internucleoside linkage is a non-phosphate-containing covalent internucleoside linkage. Modified internucleoside linkages or backbones include, but are not limited to, 5'-phosphorothioate groups, chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, the oligonucleotide comprises at least 2, at least 3, at least 4, at least 5, at least 6, at least 7, at least 8, at least 9, at least 10, at least 11, at least 12, at least 13, at least 14, or at least 15 phosphorothioate linkages. In some embodiments, the oligonucleotide comprises at least 2, at least 3, at least 4, at least 5, at least 6, at least 7, at least 8, at least 9, at least 10, at least 11, at least 12, at least 13, at least 14, or at least 15 phosphorodithioate linkages. In some embodiments, the oligonucleotide comprises 1, 2, 3, 4, 5, 6, 7, 8, 9, 10, 11, 12, 13, 14, or 15 phosphorothioate linkages. In some embodiments, the oligonucleotide comprises 1, 2, 3, 4, 5, 6, 7, 8, 9, 10, 11, 12, 13, 14, or 15 phosphorodithioate linkages. In some embodiments, the phosphorothioate internucleoside linkages or phosphorodithioate internucleoside linkages are between the nucleotides at positions 1-3, 2-4, 3-5, 4-6, 4-5, 6-8, 7-9, 8-10, 9-11, 10-12, 11-13, 12-14, 13-15, 14-16, 15-17, 16-18, 17-19, 18-20 or 19-21 from the 5' end of the oligonucleotide. In some embodiments, the oligonucleotide comprises one or more modified nucleotides and one or more modified internucleoside linkages.

In some embodiments, the oligonucleotide comprises a terminal cap. In some embodiments, the terminal cap is at the 3' end of the oligonucleotide. In some embodiments, the terminal cap is at the 5' end of the oligonucleotide. In some embodiments, the terminal cap is at the 5' end and 3' end of the oligonucleotide. The term "terminal cap" can also be referred to as "cap," and has meaning generally accepted in the art. For example, the term refers to a moiety, which can be a chemically modified nucleotide or non-nucleotide that can be incorporated at one or more termini of one or more nucleic acid molecules of the invention. These terminal modifications can protect the nucleic acid molecule from exonuclease degradation, and can help in delivery and/or localization within a cell. In non-limiting examples, the cap includes, but is not limited to a polymer; a ligand; locked nucleic acid (LNA); glyceryl; an abasic ribose residue; inverted deoxy abasic residue; an inverted nucleotide; 4',5'-methylene nucleotide; 1-(beta-D-erythrofuranosyl) nucleotide; 5'-mercapto moieties; 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide; 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; 5'-5'-inverted nucleotide moiety; 5'-5'-inverted abasic moiety; 5'-phosphoramidate; 5'-phosphorothioate; 1,4-butanediol phosphate; 5'-amino; bridging and/or nonbridging 5'-phosphoramidate; phosphorothioate and/or phosphorodithioate; or bridging or non-bridging methylphosphonate moiety. In some embodiments, the oligonucleotide comprises one or more terminal cap molecules. In some embodiments, [N] is a 3' terminal cap. In some embodiments, the 3' terminal cap is O-(3-hydroxypropyl)phosphorothioate.

In some embodiments, the oligonucleotide is about 10-30, about 10-15, about 15-20, about 20-25, about 25-30, about 15-25 nucleotides in length. In some embodiments, the oligonucleotide is about 18, 19, 20, 21, 22, 23, 24 or 25 nucleotides in length.

In another aspect, the oligonucleotide of the conjugate is:

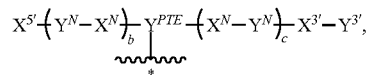

wherein b and c are each independently an integer from 1 to 25; with the proviso that the sum of b and c is at least 5;

~~* indicates the point of attachment of the immunomodulating oligonucleotide P to the rest of the conjugate;

$X^{5'}$ is a 5' terminal nucleoside having the structure

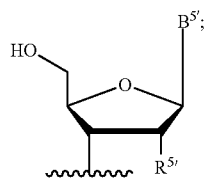

$X^{3'}$ is a 3' terminal nucleoside having the structure

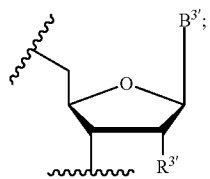

$Y^{PTE}$ is an internucleoside phosphotriester having the structure

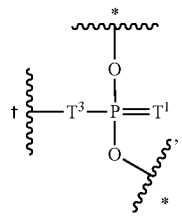

wherein * indicates the points of attachment to the rest of the oligonucleotide and ~~† indicates the point of attachment to the linker L, or, if L is absent, ~~† indicates the point of attachment to the Q tag peptide Q at the glutamine residue via an amide bond;

$Y^{3'}$ is a terminal phosphotriester having the structure

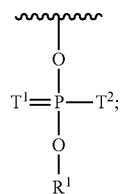

each $X^N$ is independently a nucleoside having the structure

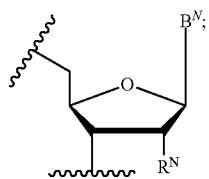

each $Y^N$ is independently an internucleoside linker having the structure

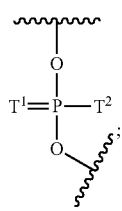

wherein each $B^N$ is independently a modified or unmodified nucleobase;
each $R^N$ is independently —H or —O—$C_{1-4}$-alkyl, wherein the $C_{1-4}$-alkyl of the —O—$C_{1-4}$-alkyl is optionally further substituted by —O—$C_{1-4}$-alkyl;
$B^{5'}$ and $B^{3'}$ are independently a modified or unmodified nucleobase;
$R^{5'}$ and $R^{3'}$ are independently —H or —O—$C_1$-C4-alkyl, wherein the $C_{1-4}$-alkyl of the —O—$C_{1-4}$-alkyl is optionally further substituted by —O—$C_{1-4}$-alkyl;
each $T_1$ is independently O or S;
each $T_2$ is independently O⁻ or S⁻; and
$T_3$ is a group comprising an oligoethylene glycol moiety; and
$R^1$ is $C_{1-4}$-alkylene-hydroxy.

In certain embodiments, the oligonucleotide comprises a nucleotide with a modified nucleobase. In some embodiments, $B^{5'}$ is a modified nucleobase. In other embodiments, $B^{3'}$ is a modified nucleobase. In some embodiments, $B^{5'}$ is an unmodified nucleobase. In other embodiments, $B^{3'}$ is an unmodified nucleobase. In still other embodiments, at least one $B^N$ is a modified nucleobase.

In certain embodiments, b is an integer ranging from about 1 to about 15. In certain embodiments, b is an integer of about 1, about 2, about 3, about 4, about 5, about 6, about 7, about 8, about 9, about 10, about 11, about 12, about 13, about 14, or about 15. In certain embodiments, b is an integer of about 3, about 4, about 11, or about 14. In certain embodiments, b is an integer of about 3. In certain embodiments, b is an integer of about 4. In certain embodiments, b is an integer of about 11. In certain embodiments, b is an integer of about 14.

In certain embodiments, c is an integer ranging from about 0 to about 10. In certain embodiments, c is an integer of about 0, about 1, about 2, about 3, about 4, about 5, about 6, about 7, about 8, about 9, or about 10. In certain embodiments, c is an integer of about 0 or about 8. In certain embodiments, c is an integer of about 0. In certain embodiments, c is an integer of about 8.

In certain embodiments, b is an integer of about 3 and c is an integer of about 8. In certain embodiments, b is an integer of about 4 and c is an integer of about 8. In certain embodiments, b is an integer of about 11 and c is an integer of about 0. In certain embodiments, b is an integer of about 14 and c is an integer of about 0.

In certain embodiments, b and c together in total are ranging from about 5 to about 20. In certain embodiments, b and c together in total are ranging from about 5 to about 15. In certain embodiments, b and c together in total are about 5, about 6, about 7, about 8, about 9, about 10, about 11, about 12, about 13, about 14, or about 15. In certain embodiments, b and c together in total are about 8, about 9, about 10, about 11, about 12, about 13, or about 14. In certain embodiments, b and c together in total are about 11. In certain embodiments, b and c together in total are about 12. In certain embodiments, b and c together in total are about 14.

In certain embodiments, each $X^N$ is independently a 2'-deoxyribonucleoside or a 2'-modified ribonucleoside. In certain embodiments, each $X^N$ is independently 2'-deoxyadenosine (A), 2'-deoxyguanosine (G), 2'-deoxycytidine (C), a 5-halo-2'-deoxycytidine, 2'-deoxythymidine (T), 2'-deoxyuridine (U), a 5-halo-2'-deoxyuridine, a 2'-fluororibonucleoside, a 2'-methoxyribonucleoside, or a 2'-(2-methoxyethoxy)ribonucleoside. In certain embodiments, each $X^N$ is independently a 2'-deoxyribonucleoside. In certain embodiments, each $X^N$ is independently 2'-deoxyadenosine, 2'-deoxyguanosine, 2'-deoxycytidine, a 5-halo-2'-deoxycytidine, 2'-deoxythymidine, 2'-deoxyuridine, or a 5-halo-2'-deoxyuridine. In certain embodiments, each $X^N$ is independently 2'-deoxyadenosine, 2'-deoxyguanosine, 2'-deoxycytidine, 2'-deoxythymidine, 5-bromo-2'-deoxyuridine, or 5-iodo-2'-deoxyuridine.

In certain embodiments, $X^{3'}$ is a 2'-deoxyribonucleoside or a 2'-modified ribonucleoside. In certain embodiments, $X^{3'}$ is a 2'-deoxyribonucleoside. In certain embodiments, $X^{3'}$ is 2'-deoxyadenosine, 2'-deoxyguanosine, 2'-deoxycytidine, a 5-halo-2'-deoxycytidine, 2'-deoxythymidine, 2'-deoxyuridine, a 5-halo-2'-deoxyuridine, a 2'-fluororibonucleoside, a 2'-methoxyribonucleoside, or a 2'-(2-methoxyethoxy)ribonucleoside. In certain embodiments, $X^{3'}$ is 2'-deoxyadenosine, 2'-deoxyguanosine, 2'-deoxycytidine, a 5-halo-2'-deoxycytidine, 2'-deoxythymidine, 2'-deoxyuridine, or a 5-halo-2'-deoxyuridine. In certain embodiments, $X^{3'}$ is 2'-deoxythymidine. In certain embodiments, $X^{3'}$ is a 2'-deoxyribonucleoside with a substituted pyrimidine base. In certain embodiments, $X^{3'}$ is a 2'-deoxyribonucleoside with a 5-substituted pyrimidine base. In certain embodiments, $X^{3'}$ is 2'-deoxythymidine, a 5-halo-2'-deoxycytidine, or a 5-halo-2'-deoxyuridine. In certain embodiments, $X^{3'}$ is 2'-deoxythymidine, 5-bromo-2'-deoxycytidine, 5-iodo-2'-deoxycytidine, 5-bromo-2'-deoxyuridine, or 5-iodo-2'-deoxyuridine. In certain embodiments, $X^{3'}$ is 2'-deoxythymidine, 5-bromo-2'-deoxyuridine, or 5-iodo-2'-deoxyuridine. In certain embodiments, $X^{3'}$ is a terminal nucleotide comprising a 3' capping group. In certain embodiments, the 3' capping group is a terminal phosphoester. In certain embodiments, the 3' capping group is 3-hydroxyl-propylphosphoryl (i.e., —P(O$_2$)—OCH$_2$CH$_2$CH$_2$OH).

In certain embodiments, $X^{5'}$ is a 2'-deoxyribonucleoside or a 2'-modified ribonucleoside. In certain embodiments, $X^{5'}$ is a 2'-deoxyribonucleoside. In certain embodiments, $X^{5'}$ is 2'-deoxyadenosine, 2'-deoxyguanosine, 2'-deoxycytidine, a 5-halo-2'-deoxycytidine, 2'-deoxythymidine, 2'-deoxyuridine, a 5-halo-2'-deoxyuridine, a 2'-fluororibonucleoside, a 2'-methoxyribonucleoside, or a 2'-(2-methoxyethoxy)ribonucleoside. In certain embodiments, $X^{5'}$ is 2'-deoxyadenosine, 2'-deoxyguanosine, 2'-deoxycytidine, a 5-halo-2'-deoxycytidine, 2'-deoxythymidine, 2'-deoxyuridine, or a 5-halo-2'-deoxyuridine. In certain embodiments, $X^{5'}$ is a 2'-deoxyribonucleoside with a substituted pyrimidine base. In certain embodiments, $X^{5'}$ is a 2'-deoxyribonucleoside with a 5-substituted pyrimidine base. In certain embodiments, $X^{5'}$ is 2'-deoxythymidine, a 5-halo-2'-deoxycytidine, or a 5-halo-2'-deoxyuridine. In certain embodiments, $X^{5'}$ is a 5-halo-2'-deoxycytidine. In some embodiments, $X^{5'}$ is a 2'-deoxyuridine, a 5-halo-2'-deoxyuridine, 2'-methoxyuridine, or a 5-halo-2'-methoxyuridine. In certain embodiments, $X^{5'}$ is a 5-halo-2'-deoxyuridine. In certain other embodiments, $X^{5'}$ is a 2'-deoxyuridine. In certain embodiments, $X^{5'}$ is a 5-halo-2'-methoxyuridine. In certain other embodiments, $X^{5'}$ is a 2'-methoxyuridine. In certain embodiments, $X^{5'}$ is 2'-deoxythymidine, 5-bromo-2'-deoxycytidine, 5-iodo-2'-deoxycytidine, 5-bromo-2'-deoxyuridine, or 5-iodo-2'-deoxyuridine. In certain embodiments, $X^{5'}$ is 2'-deoxythymidine, 5-bromo-2'-deoxyuridine, or 5-iodo-2'-deoxyuridine. In certain embodiments, $X^{5'}$ is 5-bromo-2'-deoxyuridine. In certain embodiments, $X^{5'}$ is 5-iodo-2'-deoxyuridine. In certain embodiments, $X^{5'}$ has a 3'-phosphorothioate group. In certain embodiments, $X^{5'}$ has a 3'-phosphorothioate group with a chirality of Rp. In certain embodiments, $X^{5'}$ has a 3'-phosphorothioate group with a chirality of Sp.

In certain embodiments, $Y^{PTE}$ is an internucleoside phosphothiotriester.

In some embodiments, $Y^{PTE}$ is

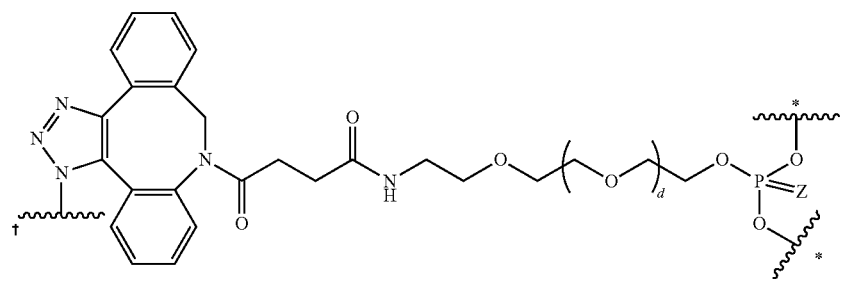

or

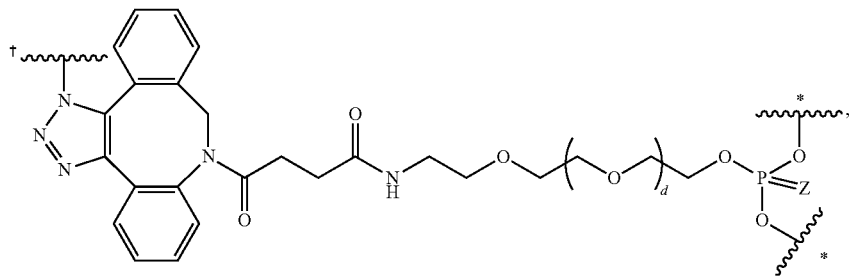

wherein Z is O or S; d is an integer ranging from about 0 to about 50; the two ⁓* on the right side of the structure indicate the points of attachment to the oligonucleotide P; and the ⁓† on the left side of the structure indicates the point of attachment to the rest of the conjugate. In certain embodiments, Z is O. In certain embodiments, Z is S. In certain embodiments, d is an integer ranging from about 0 to about 10. In certain embodiments, d is an integer ranging from about 0 to about 5. In certain embodiments, d is an integer of about 0, about 1, about 2, about 3, about 4, or about 5. In certain embodiments, d is an integer of about 0, about 1, or about 3.

In some embodiments, $Y^{PTE}$ is

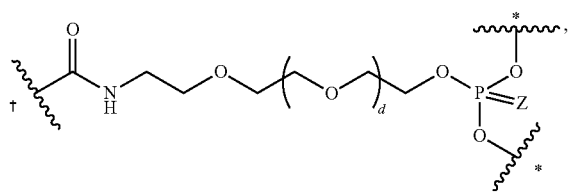

wherein Z is O or S; d is an integer ranging from about 0 to about 50; the two ⁓* on the right side of the structure indicate the points of attachment to the oligonucleotide P; and the ⁓† on the left side of the structure indicates the point of attachment to the rest of the conjugate. In certain embodiments, Z is O. In certain embodiments, Z is S. In certain embodiments, d is an integer ranging from about 0 to about 10. In certain embodiments, d is an integer ranging from about 0 to about 5. In certain embodiments, d is an integer of about 0, about 1, about 2, about 3, about 4, or about 5. In certain embodiments, d is an integer of about 0, about 1, or about 3.

In certain embodiments, the oligonucleotide comprises one additional internucleoside phosphotriester. In one embodiment, the additional internucleoside phosphotriester is a $C_{1-6}$ alkylphosphotriester. In another embodiment, the additional internucleoside phosphotriester is ethylphosphotriester.

In certain embodiments, the oligonucleotide comprises one 5-halo-2'-deoxyuridine. In one embodiment, the 5-halo-2'-deoxyuridine is 5-fluoro-2'-deoxyuridine, 5-bromo-2'-deoxyuridine, or 5-iodo-2'-deoxyuridine. In another embodiment, the 5-halo-2'-deoxyuridine is 5-bromo-2'-deoxyuridine or 5-iodo-2'-deoxyuridine. In yet another embodiment, the 5-halo-2'-deoxyuridine is 5-fluoro-2'-deoxyuridine. In yet another embodiment, the 5-halo-2'-deoxyuridine is 5-bromo-2'-deoxyuridine. In still another embodiment, the 5-halo-2'-deoxyuridine is 5-iodo-2'-deoxyuridine.

In certain embodiments, the oligonucleotide comprises three or more 2'-deoxycytidines. In certain embodiments, the oligonucleotide comprises three 2'-deoxycytidines.

In certain embodiments, the oligonucleotide comprises four or more 2'-deoxyguanosines. In certain embodiments, the oligonucleotide comprises four 2'-deoxyguanosines.

In certain embodiments, the oligonucleotide comprises three 2'-deoxycytidines and four 2'-deoxyguanosines. In certain embodiments, the oligonucleotide comprises one, two, or three CG dinucleotides. In certain embodiments, the oligonucleotide comprises three CG dinucleotides.

In certain embodiments, the oligonucleotide comprises three or more 2'-deoxythymidines. In certain embodiments, the oligonucleotide comprises three, four, five, six, seven, or eight 2'-deoxythymidines. In certain embodiments, the oligonucleotide comprises three, four, five, or eight 2'-deoxythymidines.

In certain embodiments, the oligonucleotide does not comprise a 2'-deoxyadenosine. In certain embodiments, the oligonucleotide comprises one or two 2'-deoxyadenosines.

In certain embodiments, the oligonucleotide has a length ranging from about 5 to about 20 or from about 6 to about 15. In certain embodiments, the oligonucleotide has a length of about 6, about 7, about 8, about 9, about 10, about 11, about 12, about 13, about 14, or about 15. In certain embodiments, the oligonucleotide has a length of about 10, about 11, about 12, about 13, about 14, or about 15.

In certain embodiments, the oligonucleotide comprises one or more internucleoside phosphorothioates. In certain embodiments, all the internucleoside phosphoesters in the oligonucleotide are internucleoside phosphorothioates. In certain embodiments, the oligonucleotide comprises one or more chiral internucleoside phosphorothioates.

In certain embodiments, the oligonucleotides comprising a sequence of $N^1N^2CGN^3CG(T)_xGN^4CGN^5T$ (SEQ ID NO:174), or a stereoisomer, a mixture of two or more diastereomers, a tautomer, or a mixture of two or more tautomers thereof; or a pharmaceutically acceptable salt, solvate, or hydrate thereof are as described in, for example, WO2018/189382 A1.

In one embodiment, the oligonucleotide comprises a sequence of $N^1N^2CGN^3CG(T)_xGN^4CGN^5T$ (SEQ ID NO:174), or a stereoisomer, a mixture of two or more diastereomers, a tautomer, or a mixture of two or more tautomers thereof; or a pharmaceutically acceptable salt, solvate, or hydrate thereof; wherein:

x is an integer ranging from about 1 to about 4;
$N^1$ is absent or 2'-deoxythymidine;
$N^2$ is a 2'-deoxyribonucleotide with a modified nucleobase;

N³ is 2'-deoxyadenosine or 2'-deoxythymidine, each optionally comprising a 3'-phosphotriester;
N⁴ is 2'-deoxyadenosine or 2'-deoxythymidine;
N⁵ is 2'-deoxythymidine optionally comprising a 3'-phosphotriester; and
C is 2'-deoxycytidine and G is 2'-deoxyguanosine.

In certain embodiments, in $N^1N^2CGN^3CG(T)_xGN^4CGN^5T$ (SEQ ID NO:174), x is an integer of about 1, about 2, about 3, or about 4. In certain embodiments, in $N^1N^2CGN^3CG(T)_xGN^4CGN^5T$ (SEQ ID NO:174), x is an integer of about 1. In certain embodiments, in $N^1N^2CGN^3CG(T)_xGN^4CGN^5T$ (SEQ ID NO:174), x is an integer of about 4.

In certain embodiments, in $N^1N^2CGN^3CG(T)_xGN^4CGN^5T$ (SEQ ID NO:174), $N^1$ is absent. In certain embodiments, in $N^1N^2CGN^3CG(T)_xGN^4CGN^5T$ (SEQ ID NO:174), $N^1$ is 2'-deoxythymidine.

In certain embodiments, in $N^1N^2CGN^3CG(T)_xGN^4CGN^5T$ (SEQ ID NO:174), $N^2$ is a 2'-deoxyribonucleotide with a substituted pyrimidine base. In certain embodiments, in $N^1N^2CGN^3CG(T)_xGN^4CGN^5T$ (SEQ ID NO:174), $N^2$ is a 2'-deoxyribonucleotide with a 5-substituted pyrimidine base. In certain embodiments, in $N^1N^2CGN^3CG(T)_xGN^4CGN^5T$ (SEQ ID NO:174), $N^2$ is a 5-halo-2'-deoxycytidine or a 5-halo-2'-deoxyuridine. In certain embodiments, in $N^1N^2CGN^3CG(T)_xGN^4CGN^5T$ (SEQ ID NO:174), $N^2$ is 5-bromo-2'-deoxyuridine or 5-iodo-2'-deoxyuridine.

In certain embodiments, in $N^1N^2CGN^3CG(T)_xGN^4CGN^5T$ (SEQ ID NO:174), $N^3$ is 2'-deoxyadenosine comprising a 3'-phosphotriester. In certain embodiments, in $N^1N^2CGN^3CG(T)_xGN^4CGN^5T$ (SEQ ID NO:174), $N^3$ is 2'-deoxythymidine. In certain embodiments, in $N^1N^2CGN^3CG(T)_xGN^4CGN^5T$ (SEQ ID NO:174), $N^3$ is 2'-deoxythymidine comprising a 3'-phosphotriester.

In certain embodiments, in $N^1N^2CGN^3CG(T)_xGN^4CGN^5T$ (SEQ ID NO:174), $N^4$ is 2'-deoxyadenosine. In certain embodiments, in $N^1N^2CGN^3CG(T)_xGN^4CGN^5T$ (SEQ ID NO:174), $N^4$ is 2'-deoxythymidine.

In certain embodiments, in $N^1N^2CGN^3CG(T)_xGN^4CGN^5T$ (SEQ ID NO:174), $N^5$ is 2'-deoxythymidine. In certain embodiments, in $N^1N^2CGN^3CG(T)_xGN^4CGN^5T$ (SEQ ID NO:174), $N^5$ is 2'-deoxythymidine comprising a 3'-phosphotriester.

In certain embodiments, the oligonucleotide of $N^1N^2CGN^3CG(T)_xGN^4CGN^5T$ (SEQ ID NO:174) comprises one or more internucleoside phosphorothioates or phosphorotdithioates. In certain embodiments, the oligonucleotide of $N^1N^2CGN^3CG(T)_xGN^4CGN^5T$ (SEQ ID NO:174) comprises at least one chiral internucleoside phosphorothioate or phosphorotdithioates. In certain embodiments, the oligonucleotide of $N^1N^2CGN^3CG(T)_xGN^4CGN^5T$ (SEQ ID NO:174) comprises at least one chiral phosphorotdithioates. In certain embodiments, the oligonucleotide of $N^1N^2CGN^3CG(T)_xGN^4CGN^5T$ (SEQ ID NO:174) is an oligonucleotide sequence as described in, for example, WO2018/189382 A1.

In certain embodiments, the oligonucleotide provided herein is an immunostimulating polynucleotide. In certain embodiments, the oligonucleotide provided herein functions as a PAMS. In certain embodiments, the oligonucleotide provided herein activates innate immune response or stimulates the adaptive immune response by triggering TLR9 signaling. In certain embodiments, the oligonucleotide provided herein is a TLR9 agonist.

In certain embodiments, the oligonucleotide provided herein is CpG oligonucleotide, comprising a modification including 5-halouridine or 5-alkynyluridine, or a truncated version thereof (e.g., those comprising a total of about 6 to about 16 nucleosides). In certain embodiments, the truncated oligonucleotide provided herein comprises a truncated oligonucleotide sequence, from which one or more 3'-terminal nucleotides are eliminated or one or more of the intrasequence nucleotides excised).

In certain embodiments, the oligonucleotide provided herein comprises at least one immunostimulating sequence (ISS). In certain embodiments, the oligonucleotide provided herein comprises about 1, about 2, about 3, or about 4 ISS. The ISS in immunostimulating polynucleotides is dependent on the targeted organism. The common feature of the ISS used in the oligonucleotide provided herein is the cytidine-p-guanosine sequence, in which p is an internucleoside phosphodiester (e.g., phosphate or phosphorothioate) or an internucleoside phosphotriester. In certain embodiments, cytidine and guanosine in the ISS each independently comprises 2'-deoxyribose. In certain embodiments, the oligonucleotide provided herein comprises about 1, about 2, or about 3 human ISSs. In certain embodiments, the human ISS is CG or NCG, where N is uridine, cytidine, or thymidine, or a modified uridine or cytidine; and G is guanosine or a modified guanosine. In certain embodiments, the modified uridine or cytidine is a 5-halouridine (e.g., 5-iodouridine or 5-bromouridine), a 5-alkynyluridine (e.g., 5-ethynyluridine or 5-propynyluridine), 5-heteroaryluridine, or 5-halocytidine. In certain embodiments, the modified guanosine is 7-deazaguanosine. In certain embodiments, the human ISS is NCG, in one embodiment, N is 5-halouridine. In certain embodiments, the human ISS is UCG, in one embodiment, U is 5-alkynyluridine, and in another embodiment, U is 5-ethynyluridine. In certain embodiments, the oligonucleotide provided herein targeting humans comprises an ISS within four contiguous nucleotides that include a 5'-terminal nucleotide. In certain embodiments, the oligonucleotide provided herein targeting humans comprises a 5'-terminal ISS. In certain embodiments, the oligonucleotide provided herein comprises a murine ISS. In certain embodiments, the murine ISS is a hexameric nucleotide sequence: Pu-Pu-CG-Py-Py, where each Pu is independently a purine nucleotide, and each Py is independently a pyrimidine nucleotide.

In certain embodiments, the 5'-flanking nucleotides relative to CpG in the oligonucleotide provided herein does not contain 2'-alkoxyriboses. In certain embodiments, the 5'-flanking nucleotides relative to CpG in the oligonucleotide provided herein comprises only 2'-deoxyriboses as sugars.

In certain embodiments, the oligonucleotide provided herein has (1) a high content of phosphorothioates or phosphorodithioates (e.g., at least 50%, at least 60%, at least 70%, or at least 80% of nucleosides may be linked by phosphorothioates or phosphorodithioates); (2) absence of poly-G tails; (3) nucleosides in the oligonucleotide comprises 2'-deoxyriboses or 2'-modified riboses (e.g., 2'-halo (e.g., 2'-fluoro, 2'-bromo, or 2'-iodo) or optionally substituted 2'-alkoxy (e.g., 2'-methoxy)); and/or (4) the inclusion of 5'-terminal ISS that is NCG, in which N is uridine, cytidine, or thymidine, or a modified uridine or cytidine, and G is guanosine or a modified guanosine.

In certain embodiments, the oligonucleotide provided herein suppresses the adaptive immune response by reducing activation of TLR9 signaling (e.g., through TLR9 antagonism). In certain embodiments, the immunosuppressive polynucleotide provided herein comprises at least two 2'-alkoxynucleotides that are 5'-flanking relative to CpG as described by the formula of N'-12-CG, where N' and 12 are each independently a nucleotide containing 2'-alkoxyribose (e.g., 2'-methoxyribose).

In some embodiments, the oligonucleotide has the structure

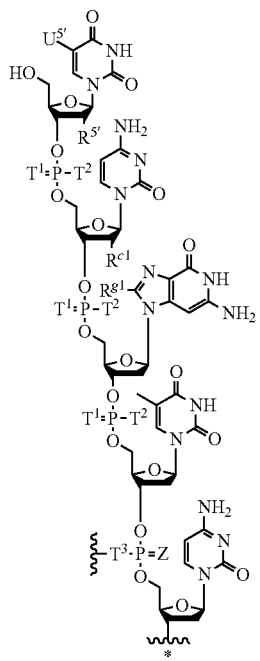

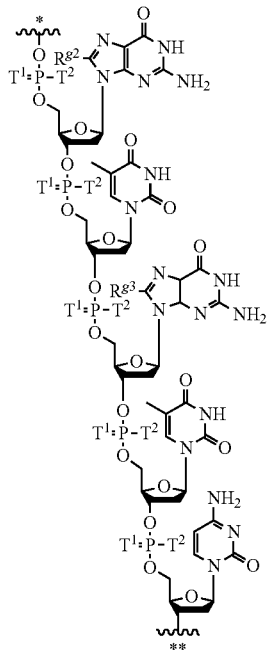

-continued

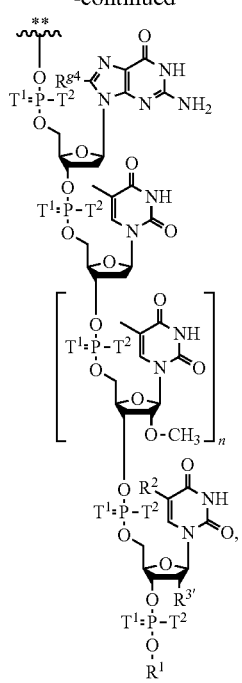

wherein

~~* and ~~** indicate the points of attachment within the oligonucleotide;

each $T^1$ is independently O or S;

each $T^2$ is $O^-$ or $S^-$;

$T^3$ is a group

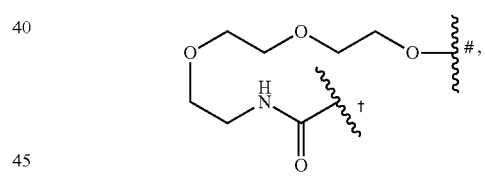

wherein ~~ † indicates the point of attachment to L and wherein ~~ # indicates the point of attachment to the rest of the oligonucleotide;

Z is O or S;

$U^{5'}$ is —H or halogen;

$R^{5'}$ is —H or methoxy;

$R^{c1}$ is —H or methoxy;

$R^{g1}$, $R^{g2}$, $R^{g3}$, and $R^{g4}$ are H or oxo, wherein $R^{3'}$ is methoxy;

$R^1$ is $C_{1-4}$-alkylene-hydroxy;

$R^2$ is —H or methyl; and n is an integer from 0 to 2.

In other embodiments, the oligonucleotide has the structure

107

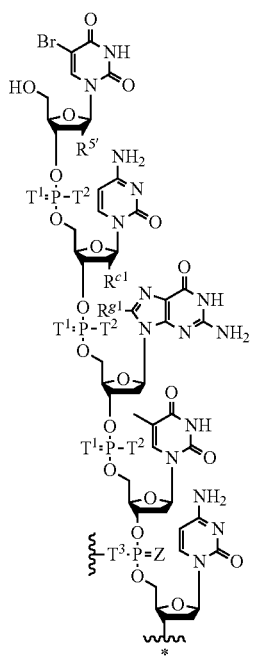

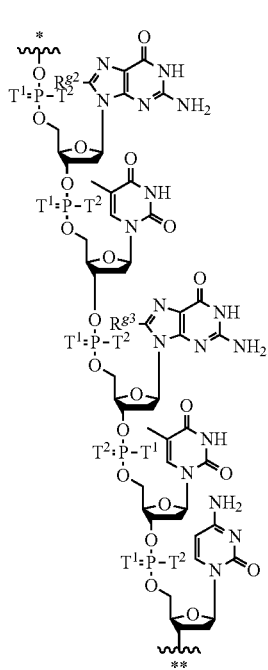

108

-continued

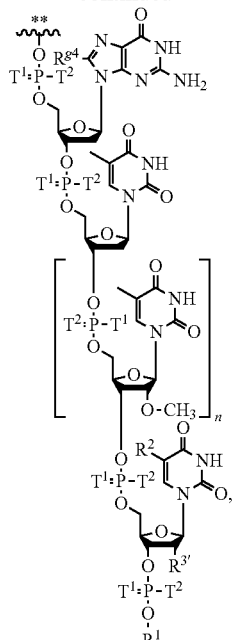

wherein

~~* and ~~** indicate the points of attachment within the oligonucleotide;

each $T^1$ is independently O or S;

each $T^2$ is $O^-$ or $S^-$;

$T^3$ is a group

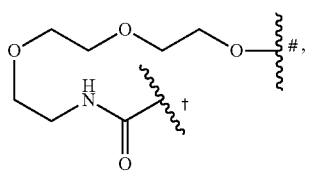 [SMILES: *OCCOCCOCCNC(*)=O]

wherein ~~† indicates the point of attachment to L and wherein ~~# indicates the point of attachment to the rest of the oligonucleotide;

Z is O or S;

$R^{5'}$ is —H or methoxy;

$R^{c1}$ is —H or methoxy;

$R^{g1}$, $R^{g2}$, $R^{g3}$, and $R^{g4}$ are H or oxo, wherein $R^{3'}$ is methoxy;

$R^1$ is $C_{1-4}$-alkylene-hydroxy;

$R^2$ is —H or methyl; and n is an integer from 0 to 2.

In still other embodiments, the oligonucleotide has the structure

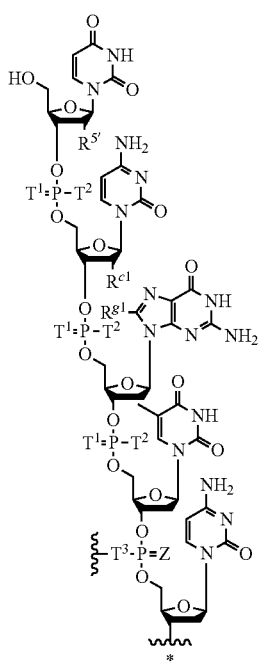

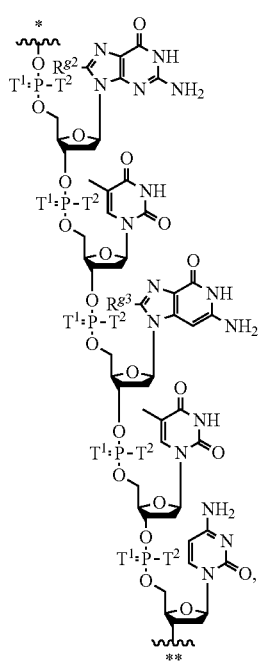

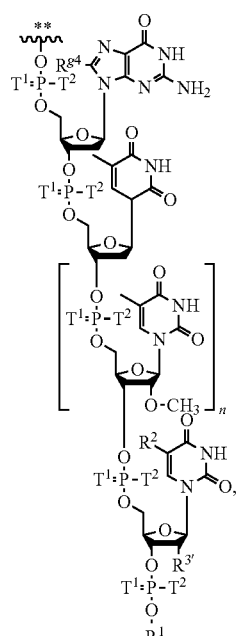

wherein

~~* and ~~** indicate the points of attachment within the oligonucleotide;

each T¹ is independently O or S;

each T² is O⁻ or S⁻;

T³ is a group

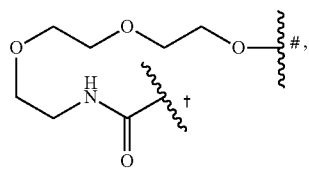 [SMILES: *OCCOCCOCCNC(*)=O]

wherein ~~† indicates the point of attachment to L and wherein ~~# indicates the point of attachment to the rest of the oligonucleotide;

Z is O or S;

$R^{5'}$ is —H or methoxy;

$R^{c1}$ is —H or methoxy;

$R^{g1}$, $R^{g2}$, $R^{g3}$, and $R^{g4}$ are H or oxo, wherein $R^{3'}$ is methoxy;

$R^1$ is $C_{1-4}$-alkylene-hydroxy;

$R^2$ is —H or methyl; and n is an integer from 0 to 2.

In some embodiments, the oligonucleotide comprises one or more of unmodified sequences differing by 0, 1, 2 or 3 nucleobases from the sequences shown in Table 1. In some embodiments, the oligonucleotide comprises one or more of modified sequences differing by 0, 1, 2 or 3 nucleobases from the sequences shown in Table 2.

TABLE 1

Unmodified Oligonucleotides

| SEQ ID NO. | Unmodified Oligonucleotide Sequence (5'—>3') |
|---|---|
| 1 | tucgtcgtgacgtt |
| 2 | ucgtcgtgtcgtt |
| 129 | tcgtcgttttgtcgttttgtcgtt |

TABLE 2

Modified Oligonucleotides

| SEQ ID NO. | Modified Oligonucleotide Sequence (5'—>3') | Cmpd # |
|---|---|---|
| 3 | uscsgstscsgstsgstscsgstsT-c3 | 1.1b |
| 4 | uscsgstscsgstsgstscsgsts t -c3 | 2.1b |
| 5 | uscsgstscsgstsgstscsgsts t -c3 | 2.2b |
| 6 | uscsgstscsgstsgstscsgsts t -c3 | 2.3b |
| 7 | uscsgstscsgstsgscsgsts t -c3 | 2.4b |
| 8 | uscsgstscsgstsgstscsgsts t -c3 | 3.1b |
| 9 | uscsgstscsgstsgstscsgsts t s t -c3 | 3.2b |
| 10 | uscsgstscsgstsgstscsgsts t s t s t -c3 | 3.3b |
| 11 | uscsgstscsgstsgstscsgsts t -c3 | 4.1b |
| 12 | uscsgstscsgstsgstscsgsts t s t -c3 | 4.2b |
| 13 | uscsgstscsgstsgstscsgsts t s t -c3 | 4.3b |
| 14 | uscs2gstscsgstsgstscsgsts t -c3 | 5.1a |
| 15 | uscsgs2tscsgstsgstscsgsts t -c3 | 5.2a |
| 16 | uscsgstscs2gstsgstscsgsts t -c3 | 5.3a |
| 17 | uscsgstscsgs2tstscsgsts t -c3 | 5.4a |
| 18 | uscsgstscsgsts2gstscsgsts t -c3 | 5.5a |
| 19 | uscsgstscsgstsgs2tscsgsts t -c3 | 5.6a |
| 20 | uscsgstscsgstsgstscs2gsts t -c3 | 5.7a |
| 21 | uscsgstscsgstsgstscsgs2ts t -c3 | 5.8a |
| 22 | uscsgstscsgstsgstscsgs2ts t -c3 | 5.9a |
| 23 | uscsgstscsgstsgstscsgsts2 t -c3 | 5.10a |
| 24 | uscsgstscsgstsgstscsgsts u s2-c3 | 5.11a |
| 25 | uscs2gstscsgstsgstscsgsts u s2-c3 | 5.12a |
| 26 | uscsgs2tscsgstsgstscsgsts t s t -c3 | 6.1b |
| 27 | uscsgs2tscsgstsgsts2csgsts t s t -c3 | 6.2b |
| 28 | uscsgs2tscsgstsgsts2csgsts t s t -c3 | 6.3b |
| 29 | uscs2gstscsgstsgstscsgsts t s t -c3 | 7.1b |
| 30 | uscsgstscsgstsgs2tscsgsts t s t -c3 | 7.2b |
| 31 | uscs2gstscsgstsgs2tscsgsts t s t -c3 | 7.3b |
| 32 | uscsgstscs2gstsgstscsgsts t s t -c3 | 7.4b |
| 33 | uscsgstscsgs2tsgstscsgsts t s t -c3 | 7.5b |
| 34 | uscsgstscsgstsgs2tscsgsts t s t -c3 | 7.6b |
| 35 | uscsgstscsgstsgsts2csgsts t s t -c3 | 7.7b |
| 36 | uscs2gstscsgstsgsts2csgsts t s t -c3 | 7.8b |
| 37 | uscsgs2tscsgstsgstscsgsts t s t -c3 | 7.9b |
| 38 | uscsgstscsgstsgstscs2gsts t s t -c3 | 7.10b |
| 130 | uscsgstscsgstsgstscsgstsT-c3 | 8.1b |
| 131 | uscsgstscsgstsgstscsgsts t -c3 | 9.1b |
| 132 | uscsgstscsgstsgstscsgsts t -c3 | 9.2b |
| 133 | uscsgstscsgstsgstscsgsts t -c3 | 9.3b |
| 134 | uscsgstscsgstsgstscsgsts t -c3 | 9.4b |
| 135 | uscsgstscsgstsgstscsgsts t -c3 | 10.1b |
| 136 | uscsgstscsgstsgstscsgsts t s t -c3 | 10.2b |
| 137 | uscsgstscsgstsgstscsgsts t s t s t -c3 | 10.3b |
| 138 | u scsgstscsgstsgstscsgsts t -c3 | 12.1b |
| 139 | u scsgstscsgstsgstscsgsts t s t -c3 | 12.2b |
| 140 | u scsgstscsgstsgstscsgsts t s t -c3 | 12.3b |
| 141 | uscs2gstscsgstsgstscsgsts t -c3 | 13.1a |
| 142 | uscsgs2tscsgstsgstscsgsts t -c3 | 13.2a |
| 143 | uscsgstscs2gstsgstscsgsts t -c3 | 13.3a |
| 144 | uscsgstscsgs2tsgstscsgsts t -c3 | 13.4a |
| 145 | uscsgstscsgsts2gstscsgsts t -c3 | 13.5a |
| 146 | uscsgstscsgstsgs2tscsgsts t -c3 | 13.6a |
| 147 | uscsgstscsgstsgstscs2gsts t -c3 | 13.7a |
| 148 | uscsgstscsgstsgstscsgs2ts t -c3 | 13.8a |
| 149 | uscsgstscsgstsgstscsgs2ts t -c3 | 13.9a |
| 150 | uscsgstscsgstsgstscsgsts2 t -c3 | 13.10a |
| 151 | uscsgstscsgstsgstscsgsts u s2-c3 | 13.11a |
| 152 | uscs2gstscsgstsgstscsgsts u s2-c3 | 13.12a |
| 153 | u scsgs2tscsgstsgstscsgsts t s t -c3 | 14.1b |
| 154 | u scsgstscsgstsgsts2csgsts t s t -c3 | 14.2b |

TABLE 2-continued

Modified Oligonucleotides

| SEQ ID NO. | Modified Oligonucleotide Sequence (5'—>3') | Cmpd # |
|---|---|---|
| 155 | u scsgs2tscsgstsgsts2csgsts t s t -c3 | 14.3b |
| 156 | uscs2gstscsgstsgstscsgsts t s t -c3 | 15.1b |
| 157 | uscsgstscsgstsgs2tscsgsts t s t -c3 | 15.2b |
| 158 | uscs2gstscsgstsgs2tscsgsts t s t -c3 | 15.3b |
| 159 | uscsgstscs2gstsgstscsgsts t s t -c3 | 15.4b |
| 160 | uscsgstscsgs2tsgstscsgsts t s t -c3 | 15.5b |
| 161 | uscsgstscsgsts2gstscsgsts t s t -c3 | 15.6b |
| 162 | uscsgstscsgstsgsts2csgsts t s t -c3 | 15.7a |
| 163 | uscsgstscsgstsgsts2csgsts t s t -c3 | 15.7b |
| 164 | uscs2gstscsgstsgsts2csgsts t s t -c3 | 15.8b |
| 165 | uscsgs2tscsgstsgstscsgsts t s t -c3 | 15.9b |
| 166 | uscsgstscsgstsgstscs2gsts t s t -c3 | 15.10b |

* u: 5-Bromo-2'-deoxyuridine
  g: 8-oxo-7,8-dihydro-2'-deoxyguanosine
  *u*: 5-Bromo 2'-OMe uridine
  *c* : 2'-OMe- Cytidine
  *t*: 2'-OMe- Thymidine
  u : 2'-OMe- Uridine
  u: 2'-deoxyuridine T: 2'-OMOE thymidine ts: phosphotriester linker-PEG$_{24}$-NH$_2$

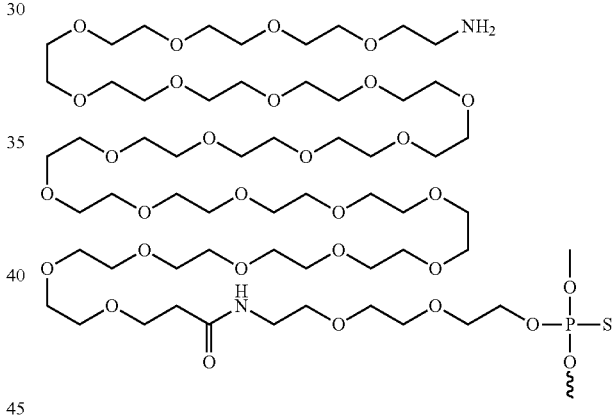

following thymidine;

ts: phosphotriester linker following thymidine;

Lower case: 2'-deoxy nucleotide s: phosphorothioate linkage s2: phosphorodithioate linkage c3:

s2-c3:

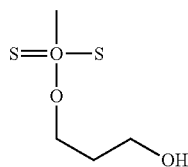

In some embodiments, the oligonucleotide is functionalized with a chemical tag for attachment to the linking moiety. In some embodiments, the chemical tag is attached to an inter-nucleoside linkage of the oligonucleotide. In some embodiments, the chemical tag is attached to a 5' inter-nucleoside linkage. In some embodiments, the chemical tag is attached to a 3' inter-nucleoside linkage. In some embodiments, the inter-nucleoside linkage is a phosphorothioate linkage. In some embodiments, the inter-nucleoside linkage is a phosphorodithioate linkage. In some embodiments, the chemical tag is closer to the 5' end than the 3' end of the oligonucleotide. In some embodiments, the chemical tag is attached to a nucleobase.

Linking Moieties

In another aspect, the oligonucleotide is conjugated to the polypeptide via a linking moiety. The length, rigidity and chemical composition of the linking moiety impact the conjugation reaction rates and the stability of the resulting conjugates. In some embodiments, the linking moiety comprises polyethylene glycol (PEG). In some embodiments, the PEG contains about 10-50 ethylene glycol units. In some embodiments, the linking moiety is an aliphatic chain.

For Formula (A), the linking moiety is represented by L. In some embodiments, the linker L comprises an oligoethylene glycol or polyethylene glycol moiety. In certain embodiments, the linker L is a group having the structure

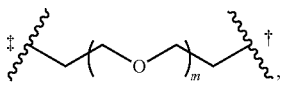

wherein ⁓† indicates the point of attachment to $Y^{PTE}$, and ⁓‡ indicates the point of attachment to the rest of the conjugate.

In other embodiments, the linker L is a group having the structure

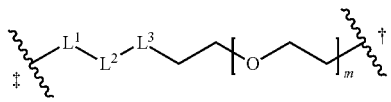

wherein ⁓† indicates the point of attachment to $Y^{PTE}$, and ⁓‡ indicates the point of attachment to the rest of the conjugate. In some embodiments, $L^1$ is absent. In some embodiments, $L^1$ is unsubstituted alkyl. In some embodiments, $L^1$ is independently an unsubstituted $C_{1-6}$ alkyl. In some embodiments, each $L^1$ is methyl or ethyl. In some embodiments, $L^1$ is independently a substituted alkyl. In some embodiments, $L^1$ is independently a substituted $C_{1-6}$ alkyl. In some embodiments, $L^1$ is $C_{1-6}$ alkyl substituted with one or more substituents selected from the group consisting of alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, cyano, azido, halo, hydroxyl, nitro, carboxyl, thiol, thioalkyl, alkyl, alkenyl, alkynyl, heterocyclyl, aminosulfonyl, sulfonylamino, sulfonyl and oxo. In some embodiments, $L^2$ is absent. In some embodiments, $L^2$ is unsubstituted or substituted alkyl.

In some embodiments, $L^3$ is absent. In some embodiments, $L^3$ is a linker moiety. In some embodiments, the linker moiety is an unsubstituted or substituted alkyl. In some embodiments, the linker moiety is independently an unsubstituted $C_{1-6}$ alkyl. In some embodiments, the linker moiety is methyl or ethyl. In some embodiments, the linker moiety is independently a substituted alkyl. In some embodiments, the linker moiety is independently a substituted $C_{1-6}$ alkyl. In some embodiments, the linker moiety is $C_{1-6}$ alkyl substituted with one or more substituents selected from the group consisting of alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, cyano, azido, halo, hydroxyl, nitro, carboxyl, thiol, thioalkyl, alkyl, alkenyl, alkynyl, heterocyclyl, aminosulfonyl, sulfonylamino, sulfonyl and oxo. In some embodiments, the linker moiety is an amino acid residue. In some embodiments, the amino acid is selected from the group consisting of glycine, alanine, glutamic acid and proline. In some embodiments, the linker is methyl. In some embodiments, the linker moiety is —$R^5C(O)R^6NHR^7$—, wherein $R^5$, and $R^7$ are independently absent or unsubstituted or substituted alkyl and $R^6$ is an amino acid residue. In some embodiments, the amino acid is selected from the group consisting of glycine, alanine, glutamic acid and proline. In some embodiments, the linker moiety is —$R^3C(O)NHR^4$—, wherein $R^3$ and $R^4$ are independently absent or unsubstituted or substituted alkyl. In some embodiments, $R^3$ is methylene and $R^4$ is —$(CH_2)_4$—. In some embodiments, $R^3$ is methylene and $R^4$ is absent. When more than one oligonucleotide (i.e., p=2), the two $L^1$ can be different or same, the two $L^2$ can be different or same and the two $L^3$ can be different or same.

In some embodiments, m is about 3-10, about 10-15, about 15-20, about 20-25, about 25-30, about 5-16, about 15-30, about 15-25 or about 20-30. In some embodiments, m is 20, 21, 22, 23, 24 or 25.

Protein

In some embodiments, an oligonucleotide of the present disclosure is conjugated to a polypeptide or protein, e.g., an antibody. In some embodiments, the oligonucleotide is conjugated to an antibody via one or more Q tags. In some embodiments, the Q tag comprises a glutamine residue which is linked to the rest of the conjugate. In still further embodiments of the present aspect, which may be combined with any of the preceding embodiments, each Q tag independently comprises or is a peptide sequence selected from the group consisting of SEQ ID NOs: 39-55. In some embodiments, each Q tag independently comprises or is a peptide sequence selected from the group consisting of the peptide sequences of Table 3. In other embodiments of the present aspect, each Q tag independently comprises or is a peptide sequence selected from the group consisting of SEQ ID NOs: 40-55. In yet other embodiments, each Q tag independently comprises or is a peptide sequence selected from the group consisting of SEQ ID NOs: 47-49. In some embodiments, the Q-tag comprises LLQGG (SEQ ID NO:172), GGGLLQGG (SEQ ID NO:173), RPQGF (SEQ ID NO:47), or RPQGFGPP (SEQ ID NO:49). In some embodiments, the Q-tag comprises a peptide sequence RPQGF (SEQ ID NO:47). In certain embodiments, the Q-tag comprising a peptide sequence RPQGF (SEQ ID NO:47) is selected from the group consisting of RPQGF (SEQ ID NO:47), RPQGFPP (SEQ ID NO:48), and RPQGFGPP (SEQ ID NO:49).

In some embodiments, the protein is a protein fragment, a peptide or a Fc-fusion protein. In some embodiments, the protein is an antibody selected from a group consisting of a polyclonal antibody, a monoclonal antibody, a humanized antibody, a human antibody, a chimeric antibody, and an antibody fragment. In some embodiments, the antibody fragment is selected from the group consisting of Fab, Fab', Fab'-SH, F(ab')2, Fv fragments, scFv, single domain antibody, single heavy chain antibody and single light chain antibody. In some embodiments, the antibody is a human anti-IgG antibody. In some embodiments, the antibody is an anti-IgG1, anti-IgG2 or anti-IgG4 antibody. In some embodiments, the antibody is an anti-CD22 antibody (e.g., RFB4, EPRA, 10F4, m971). In some embodiments, the antibody comprises a light chain variable domain (VL) and a heavy chain variable domain (VH). In some embodiments, VH comprises the sequence SEQ ID NO: 56 and VL comprises the sequence SEQ ID NO: 57. In some embodiments, VH comprises the sequence SEQ ID NO: 58 and VL comprises the sequence SEQ ID NO: 59. In some embodiments, VH comprises the sequence SEQ ID NO: 60 and VL comprises the sequence SEQ ID NO: 61. In some embodiments, VH comprises the sequence SEQ ID NO: 62 and VL comprises the sequence SEQ ID NO: 63.

In some embodiments, the antibody comprises a heavy chain variable (VH) domain and a light chain variable (VL) domain, wherein the VH domain comprises CDR-H1, CDR-H2, and CDR-H3 sequences from a VH domain sequence selected from the group consisting of:

(SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GYGTHWGVLFAYWGRGTLVTVSS, (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS, (SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GYGTHWGVLFAYWGRGTLVTVSS,
and (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.

In some embodiments, the antibody comprises a heavy chain variable (VH) domain and a light chain variable (VL) domain, and wherein the VH domain comprises an amino acid sequence selected from the group consisting of:

(SEQ ID NO: 64)
EVQLVESGGGLVQPGGSLRLSCAASGFAFSIYDMS

WVRQAPGKGLEWVAYISSGGGTTYYPDTVKGRFTI

SRDNSKNTLYLQMNSLRAEDTAVYYCARHSGYGTH

WGVLFAYWGRGTLVTVSS, (SEQ ID NO: 65)
QVQLLESGGGVVQPGGSLRLSCAASGFAFSIYDMN

WVRQAPGKGLEWVSAISSGGGTTYYADSVKGRFTI

SRDNAKNSLYLQMNSLRAEDTAVYYCARHSGYGTH

WGVLFAYWGRGTLVTVSS, (SEQ ID NO: 66)
EVQLVESGGGLVQPGGSLRLSCAASGFTFSSYEMN

WVRQAPGKGLEWVSYISSSGSTIYYADSVKGRFTI

SRDNAKNSLYLQMNSLRAEDTAVYYCARHSGYGTH

WGVLFAYWGRGTLVTVSS,
and (SEQ ID NO: 67)
QVQLQESGPGLVKPSDTLSLTCTVSGFAFSIYDMS

WIRQPPGKGLEWIAYISSGGGTTYYNPSLKSRVTI

SVDTSKNQFSLKLSSVTAADTAVYYCARIISGYGT

IIWGVLFAYWGRGTLVTVSS.

In other embodiments, which may be combined with any of the foregoing embodiments, the antibody comprises a heavy chain variable (VH) domain and a light chain variable (VL) domain, wherein the VL domain comprises CDR-L1, CDR-L2, and CDR-L3 sequences from a VL domain sequence selected from the group consisting of:

(SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

TSILHSGIPARFSGSGPGTDFTLTISSLEPEDFAVYYCQQGNTLPWTFGG

GTKLEIK,
and (SEQ ID NO: 72)
DIVMTQTPLSLSVTPGQPASISCRASQDIFIGYLNWYQQKPGQSPQLLIY

YTSILHSGVPDRFSGSGSGTDFTLKISRVEAEDVGVYFCQQGNTLPWTFG

GGTKLEIK.

In some embodiments, which may be combined with any of the foregoing embodiments, the antibody comprises an Fc region. In certain embodiments, the Fc region is a human Fc region selected from the group consisting of an IgG1 Fc region, an IgG2 Fc region, and an IgG4 Fc region. In some embodiments, the Fc region is a wild-type human IgG1, IgG2, or IgG4 Fc region. In some embodiments, the Fc region is a human Fc region comprising one or more amino acid substitutions that reduce or eliminate one or more effector functions, as compared with the effector function(s) of a human Fc region that lacks the amino acid substitution(s). In still yet further embodiments, the Fc region is: (a) a human IgG1 Fc region comprising L234A, L235A, and/or G237A substitutions, amino acid position numbering according to EU index; (b) a human IgG2 Fc region comprising A330S and/or P331S substitutions, amino acid position numbering according to EU index; or (c) a human IgG4 Fc region comprising S228P and/or L235E substitutions, amino acid position numbering according to EU index. In some embodiments, the Fc region is a human Fc region comprising one or more amino acid substitutions that reduce or eliminate binding to human C1q, as compared with the binding of a human Fc region that lacks the amino acid substitution(s). In some embodiments, the Fc region is a human Fc region comprising one or more amino acid substitutions that reduce or eliminate antibody-dependent cellular cytotoxicity (ADCC), as compared with the ADCC of a human Fc region that lacks the amino acid substitution(s).

Antibodies that target cell surface antigens can trigger immunostimulatory and effector functions that are associated with Fc receptor (FcR) engagement on immune cells. There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, an Fc domain can refer to a dimer of two Fc domain monomers. In a wild-type Fc domain, two Fc domain monomers dimerize by the interaction between the two $CH_3$ antibody constant domains, as well as one or more disulfide bonds that form between the hinge domains of the two dimerized Fc domain monomers. In some embodiments, an Fc domain is mutated to lack effector functions, for example a "dead Fc domain." In some embodiments, each of the Fc domain monomers in an Fc domain includes amino acid substitutions in the $CH_2$ antibody constant domain to reduce the interaction or binding between the Fc domain and an Fc receptor, such as an Fcγ receptor (FcγR), an Fcα receptor (FcαR), or an FCC (FcεR).

The Fc domain is not involved directly in binding an antibody to its target, but can be involved in various effector functions, such as participation of the antibody in antibody-dependent cellular toxicity. In some embodiments, the Fc domain in an antibody or conjugate of the disclosure comprises one or more amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. In some embodiments, the antibodies or conjugates of the disclosure are characterized by decreased binding (e.g., minimal binding or absence of binding) to a human Fc receptor and decreased binding (e.g., minimal binding or absence of binding) to complement protein C1q. In some embodiments, the antibodies or conjugates of the disclosure are characterized by decreased binding (e.g., minimal binding or absence of binding) to human FcγRI, FcγRIIA, FcγRIIB, FcγRIIIB, FcγRIIIB, or any combinations thereof, and C1q. To alter or reduce an antibody-dependent effector function, such as ADCC, CDC, ADCP, or any combinations thereof, in some embodiments, the Fc domains in antibodies or conjugates of the disclosure are of the IgG class and comprise one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda, MD. (1991))).

In some embodiments, antibodies or conjugates comprising a non-native Fc region described herein exhibit reduced or ablated binding to at least one of Fcγ receptors CD16a, CD32a, CD32b, CD32c, and CD64 as compared to a polypeptide construct comprising a native Fc region. In some cases, the antibodies or conjugates described herein exhibit reduced or ablated binding to CD16a, CD32a, CD32b, CD32c, and CD64 Fcγ receptors.

CDC refers to a form of cytotoxicity in which the complement cascade is activated by the complement component C1q binding to antibody Fc. In some embodiments, antibodies or conjugates comprising a non-native Fc region described herein exhibit at least a 5%, 10%, 15%, 20%, 30%, 40%, 50%, 60%, 70%, 80%, 90% or greater reduction in C1q binding compared to an antibody or conjugate comprising a wild-type Fc region. In some cases, antibodies or conjugates comprising a non-native Fc region as described herein exhibit reduced CDC as compared to antibodies or conjugates comprising a wild-type Fc region. In some embodiments, antibodies or conjugates comprising a non-native Fc region as described herein exhibit at least a 5%, 10%, 15%, 20%, 30%, 40%, 50%, 60%, 70%, 80%, 90% or greater reduction in CDC compared to antibodies or conjugates comprising a wild-type Fc region. In some cases, antibodies or conjugates comprising a non-natural Fc variant as described herein exhibit negligible CDC as compared to antibodies or conjugates comprising a wild-type Fc region.

In some embodiments, the Fc variants herein are minimally glycosylated or have reduced glycosylation relative to a wild-type sequence. In some embodiments, deglycosylation is accomplished with a mutation of N297A, or by mutating N297 to any amino acid which is not N. In some embodiments, deglycosylation is accomplished by disrupting the motif N-Xaa1-Xaa2-Xaa3 (SEQ ID NO:175), wherein N=asparagine; Xaa1=any amino acid except P (proline); Xaa2=T (threonine), S (serine) or C (cysteine);

and Xaa3=any amino acid except P (proline). In one embodiment, the N-Xaa1-Xaa2-Xaa3 (SEQ ID NO:175) motif refers to residues 297-300 as designated according to Kabat et al., 1991. In some embodiments, a mutation to any one or more of N, Xaa1, Xaa2, or Xaa3 results in deglycosylation of the Fc variant.

In some embodiments, variants of antibody IgG constant regions (e.g., Fc variants) possess a reduced capacity to specifically bind Fcγ receptors or have a reduced capacity to induce phagocytosis. In some embodiments, variants of antibody IgG constant regions (e.g., Fc variants) possess a reduced capacity to specifically bind Fcγ receptors and have a reduced capacity to induce phagocytosis. For example, in some embodiments, an Fc domain is mutated to lack effector functions, typical of a "dead" Fc domain. For example, in some embodiments, an Fc domain includes specific amino acid substitutions that are known to minimize the interaction between the Fc domain and an Fcγ receptor. In some embodiments, an Fc domain monomer is from an IgG1 antibody and includes one or more of amino acid substitutions L234A, L235A, G237A, and N297A (as designated according to the EU numbering system per Kabat et al., 1991). In some embodiments, one or more additional mutations are included in such IgG1 Fc variant. Non-limiting examples of such additional mutations for human IgG1 Fc variants include E318A and K322A. In some instances, a human IgG1 Fc variant has up to 12, 11, 10, 9, 8, 7, 6, 5 or 4 or fewer mutations in total as compared to wild-type human IgG1 sequence. In some embodiments, one or more additional deletions are included in such IgG1 Fc variant. For example, in some embodiments, the C-terminal lysine of the Fc IgG1 heavy chain constant region is deleted, for example to increase the homogeneity of the polypeptide when the polypeptide is produced in bacterial or mammalian cells. In some instances, a human IgG1 Fc variant has up to 12, 11, 10, 9, 8, 7, 6, 5 or 4 or fewer deletions in total as compared to wild-type human IgG1 sequence.

In some embodiments, an Fc domain monomer is from an IgG2 or IgG4 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc variant comprises a human IgG2 Fc sequence comprising one or more of A330S, P331S and N297A amino acid substitutions (as designated according to the EU numbering system per Kabat, et al. (1991). In some embodiments, one or more additional mutations are included in such IgG2 Fc variants. Non-limiting examples of such additional mutations for human IgG2 Fc variant include V234A, G237A, P238S, V309L and H268A (as designated according to the EU numbering system per Kabat et al. (1991)). In some instances, a human IgG2 Fc variant has up to 12, 11, 10, 9, 8, 7, 6, 5, 4, 3 or fewer mutations in total as compared to wild-type human IgG2 sequence. In some embodiments, one or more additional deletions are included in such IgG2 Fc variant. For example, in some embodiments, the C-terminal lysine of the Fc IgG2 heavy chain constant region is deleted, for example to increase the homogeneity of the polypeptide when the polypeptide is produced in bacterial or mammalian cells. In some instances, a human IgG2 Fc variant has up to 12, 11, 10, 9, 8, 7, 6, 5 or 4 or fewer deletions in total as compared to wild-type human IgG2 sequence.

When the Fc variant is an IgG4 Fc variant, in some embodiments, such Fc variant comprises a S228P mutation (as designated according to Kabat, et al. (1991)), e.g., as represented in SEQ ID NO:104 in Table 7. In some instances, a human IgG4 Fc variant has up to 12, 11, 10, 9, 8, 7, 6, 5, 4, 3, 2 or 1 mutation(s) in total as compared to wild-type human IgG4 sequence.

In some embodiments, the Fc variant includes at least one of the mutations L234A, L235A, G237A or N297A of an IgG1 Fc region or at least one of the mutations A330S, P331S or N297A of an IgG2 Fc region. In some embodiments, the Fc variant includes at least two of the mutations L234A, L235A, G237A or N297A of an IgG1 Fc region or at least two of the mutations A330S, P331S or N297A of an IgG2 Fc region. In some embodiments, the Fc variant includes at least three of the mutations L234A, L235A, G237A or N297A of an IgG1 Fc region or consists of the mutations A330S, P331S and N297A of an IgG2 Fc region. In some embodiments, the Fc variant consists of the mutations L234A, L235A, G237A and N297A.

In some embodiments, the Fc variant exhibits reduced binding to an Fc receptor of the subject compared to the wild-type human IgG Fc region. In some embodiments, the Fc variant exhibits ablated binding to an Fc receptor of the subject compared to the wild-type human IgG Fc region. In some embodiments, the Fc variant exhibits a reduction of phagocytosis compared to the wild-type human IgG Fc region. In some embodiments, the Fc variant exhibits ablated phagocytosis compared to the wild-type human IgG Fc region.

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, antibodies or conjugates comprising an Fc variant as described herein exhibit reduced ADCC or ADCP as compared to antibodies or conjugates comprising a wild-type Fc region. In some embodiments, antibodies or conjugates comprising an Fc variant as described herein exhibit at least a 5%, 10%, 15%, 20%, 30%, 40%, 50%, 60%, 70%, 80%, 90% or greater reduction in ADCC or ADCP compared to antibodies or conjugates comprising a wild-type Fc region. In some embodiments, antibodies or conjugates comprising an Fc variant as described herein exhibit ablated ADCC or ADCP as compared to antibodies or conjugates comprising a wild-type Fc region.

Complement-directed cytotoxicity, which is also referred to herein as CDC, refers to a form of cytotoxicity in which the complement cascade is activated by the complement component C1q binding to antibody Fc. In some embodiments, antibodies or conjugates comprising an Fc variant as described herein exhibit at least a 5%, 10%, 15%, 20%, 30%, 40%, 50%, 60%, 70%, 80%, 90% or greater reduction in C1q binding compared to antibodies or conjugates comprising a wild-type Fc region. In some cases, antibodies or conjugates comprising an Fc variant as described herein exhibit reduced CDC as compared to antibodies or conjugates comprising a wild-type Fc region. In some embodiments, antibodies or conjugates comprising an Fc variant as described herein exhibit at least a 5%, 10%, 15%, 20%, 30%, 40%, 50%, 60%, 70%, 80%, 90% or greater reduction in CDC compared to antibodies or conjugates comprising a wild-type Fc region. In some cases, antibodies or conjugates comprising an Fc variant as described herein exhibit negligible CDC as compared to antibodies or conjugates comprising a wild-type Fc region.

Fc variants herein include those that exhibit reduced binding to an Fcγ receptor compared to the wild-type human IgG Fc region. For example, in some embodiments, an Fc variant exhibits binding to an Fcγ receptor that is less than the binding exhibited by a wild-type human IgG Fc region to an Fcγ receptor, as described in the Examples. In some instances, an Fc variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptor, e.g., CD16a, CD32a, CD32b, CD32c, or CD64.

In some instances, the Fc variants disclosed herein exhibit a reduction of phagocytosis compared to its wild-type human IgG Fc region. Such Fc variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc variant exhibits ablated phagocytosis compared to its wild-type human IgG Fc region.

In some embodiments, a Q-tag of the present disclosure is attached to an antibody, polypeptide, small molecule (e.g., a small molecule agonist or antagonist), natural product, DNA molecule, RNA molecule (e.g., RNA, siRNA, antisense oligonucleotide, CRISPR guide RNA, etc.), other nucleic acid, CRISPR complex, or carbohydrate.

In some embodiments, the Q-tag is attached to the heavy chain of the antibody. In some embodiments, the Q-tag is attached to the heavy chain of the antibody via a linker (e.g., an amino acid or other chemical linker). In some embodiments, the Q-tag is attached to the heavy chain of the antibody (e.g., fused in frame with the heavy chain). In some embodiments, the Q-tag is attached at the C-terminus of the heavy chain of the antibody. In some embodiments, the Q-tag is fused to the C-terminus of the heavy chain of the antibody (e.g., in frame and contiguous with the amino acid sequence of the C-terminus). In some embodiments, the Q-tag is within the Fc domain of the antibody. In some embodiments, the Q tag is naturally occurring. For example, mutation of N297 to N297A exposes Q295 of the antibody, where the conjugation could occur. In certain embodiments wherein the Fc region comprises an N297A substitution, the conjugate further comprises an immunomodulating oligonucleotide P attached to the Q295 residue as shown in the following formula

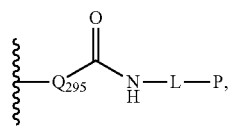

wherein L is a linker moiety connected to Q295 via an amide bond.

In some embodiments, the Q-tag comprises one or more sequences shown in Table 3.

TABLE 3

| Q-tag Peptide Sequences | |
|---|---|
| SEQ ID NO. | Peptide Sequences |
| 39 | LSLSPGLLQGG-OH |
| 40 | WPAQGPT |
| 41 | WPQGPT |
| 42 | WAPQGPT |
| 43 | WAQGPT |
| 44 | TPGQAPW |
| 45 | PNPQLPF |
| 46 | RPQQF |
| 47 | RPQGF |
| 48 | RPQGFPP |
| 49 | RPQGFGPP |
| 50 | RPRPQQF |
| 51 | LSQSKVLG |
| 52 | WGGQLL |
| 53 | WALQRPHYSYPD |
| 54 | WALQRPYTLTES |
| 55 | WALQGPYTLTES |

In some embodiments, the conjugate provided herein is to a target specific cell and tissue in a body for targeted delivery of a conjugated payload polynucleotide. In certain embodiments, the cell targeted by the conjugate provided herein is a natural killer cell. In certain embodiments, the cell targeted by the conjugate provided herein is myeloid cell. In certain embodiments, the cell targeted by the conjugate provided herein is B cell or T cell. In certain embodiments, the cell targeted by the conjugate provided herein is a neutrophil. In certain embodiments, the cell targeted by the conjugate provided herein is a monocyte. In certain embodiments, the cell targeted by the conjugate provided herein is a macrophage. In certain embodiments, the cell targeted by the conjugate provided herein is a dendritic cell (DC). In certain embodiments, the cell targeted by the conjugate provided herein is a mast cell. In certain embodiments, the cell targeted by the conjugate provided herein is a tumor-associated macrophage (TAM). In certain embodiments, the cell targeted by the conjugate provided herein is a myeloid-derived suppressor cell (MDSC).

In some embodiments, an antibody or conjugate of the present disclosure can be delivered as a naked protein-drug conjugate, or as a protein-drug conjugate formulated with a carrier and delivered, e.g., as encapsulated or as part of a nanocarrier, nanoparticle, liposome, polymer vesicle, or viral envelope. In some embodiments, an antibody or conjugate of the present disclosure can be delivered intracellularly, e.g., by conjugation to a protein-transduction domain or mimic. In some embodiments, an antibody or conjugate of the present disclosure can be delivered by electroporation or microinjection.

In some embodiments, a conjugate of the present disclosure targets more than one population or type of cell, e.g., from those described supra. In some embodiments, a conjugate of the present disclosure targets both B-cells and monocytes. In some embodiments, a conjugate of the present disclosure targets both B-cells, monocytes and/or DCs. In some embodiments, a conjugate of the present disclosure targets both NKs and DCs.

In certain embodiments, the antigen-binding moiety in the conjugate provided herein is an antibody or an antigen-binding fragment thereof (e.g., F(ab)₂ or Fab) or an engineered derivative thereof (e.g., Fcab or a fusion protein (e.g., scFv)). In certain embodiments, the antigen-binding moiety in the conjugate provided herein is a human or chimeric (e.g., humanized) antibody.

In some embodiments, the antibodies or conjugates target one or more type(s) of normal cell selected from T cells, B cells, natural killer cells, neutrophils, mast cells, macrophages, antigen-presenting cells (APC), basophils, and eosinophils. In some embodiments, the antibodies or conjugates target a normal APC. In some embodiments, the antibodies or conjugates target one or more type(s) of normal APC selected from B cells, monocytes, dendritic cells, Langerhans cells, keratinocytes, endothelial cells, astrocytes, fibroblasts, and oligodendrocytes. In some embodiments, the antibodies or conjugates target a normal B cell. In some embodiments, the antibodies or conjugates target a normal dendritic cell. In some embodiments, the antibodies or conjugates target a normal macrophage. In some embodiments the antibodies or conjugates targeting one or more type(s) of normal cells do not target an abnormal cell, such as a cancer cell.

In some embodiments, an antibody or conjugate of the present disclosure can comprise a multispecific (e.g., bispecific) antibody. For example, in some embodiments, an antibody of the present disclosure is a bispecific antibody comprising 2 antigen binding domains that bind different targets expressed on B cells. In some embodiments, an antibody of the present disclosure is a bispecific antibody comprising an antigen binding site that binds a target expressed on a B cell and an antigen binding site that binds a target expressed on another cell (e.g., a monocyte). In some embodiments, an antibody of the present disclosure is a bispecific antibody comprising an antigen binding site that binds a target expressed on an immune cell and an antigen binding site that binds a target expressed on the surface of a cancer cell.

In certain embodiments, the antibody binds to an antigen expressed by a B cell. Exemplary antigens expressed by B cells that can be targeted by the conjugates provided herein include, but are not limited to, B220/CD45R, B7-1/CD80, B7-2/CD86, BCMA/TNFRSF17, BLIMP1/PRDM1, C1q R¹/CD93, CD117/c-kit, CD11b/Integrin alpha M, CD19, CD1c/BDCA-1, CD1d, CD20, CD21, CD23/Fc epsilon RII, CD24, CD25/IL-2 R alpha, CD27/TNFRSF7, CD34, CD37, CD38, CD40/TNFRSF5, CD43, CD5, CD69, CD72, CD83, CXCR4, CXCR5, DEP-1/CD148, EMMPRIN/CD147, FCRL3/FcRH3, Flt-3/Flk-2, HLA-DR, IgM, IL-10, IL-12 R beta 2, IL-12/IL-35 p35, IL-21, IL-21 R, IL-27 R alpha/WSX-1/TCCR, IL-27/IL-35 EBI3 Subunit, IL-3 R alpha/CD123, IL-4 R alpha, IL-6 receptor, IL-7 R alpha/CD127, IRF4, MHC class II (I-A/I-E), Neprilysin/CD10, Pax5/BSAP, Sca-1/Ly6, Siglec-2/CD22, STAT1, STAT3, Syndecan-1/CD138, TACI/TNFRSF13B, TGF-beta, TIM-1/KIM-1/HAVCR, TLR4. In particular embodiments, B cell specific antigens are selected from CD1, CD2, CD5, CD9, CD11, CD17, CD18, CD19, CD20, CD21/CD35, CD22, CD23, CD24, CD25, CD27, CD30, CD38, CD40, CD45R/B220, CD69, CD70, CD78, CD79a (Iga), CD79b (Ig(3), CD80, CD86, CD93 (C1Rqp), CD137/4-1BB, CD138, CD180, CD252/OX40L, CD267, CD268/BAFF-R, CD279/PD1, CD319, PDL-2, Pax-5, IgD, IgM, Notch 2, and TLR4.

In certain embodiments, the antibody binds to an antigen expressed by a T cell (e.g., on the surface of a T cell). Exemplary antigens expressed by a T-cell that can be targeted by the conjugates provided herein include, but are not limited to, T-cell costimulatory molecules, OX40, CD2, CD27, CD S, ICAM-1, LFA-1/CD11a/CD18, ICOS/CD278, 4-1BB/CD137, GITR, CD30, CD40, BAFFR, HVEM, CD7, LIGHT, NKG2C, SLAMF7, NKp80, CD160, B7-H3, CD83, BLIMP1/PRDNM1, SIRPγ, TNFR2, B7-H4, A2AR, STING and TIGIT.

In certain embodiments, the antibody binds to an antigen expressed by a dendritic cell. Exemplary antigens expressed by a dendritic cell that can be targeted by the conjugates provided herein include, but are not limited to, B220/CD45R, BATF3, BST-2/Tetherin, CD11b/Integrin alpha M, CD11c, CD14, CD163, CD19, CD1c/BDCA-1, CD1d1, CD20, CD3, CD4, CD8, CLEC9a, CX3CR1, DC-SIGN/CD209, DEC-205/CD205, DLEC/CLEC4C/BDCA-2, E-Cadherin, EpCAM/TROP1, F4/80, Fc epsilon RI alpha, Fc gamma RI/CD64, Fc gamma RIA/CD64, Fc gamma RIB/CD64, Fc gamma RIII (CD16), Fc gamma RIIIA/CD16a, Fc gamma RIIIB/CD16b, FLT3, GFI-1, HLA-DR, IFN-alpha, IFN-beta, IFN-gamma, IGSF4A/SynCAM1, A2AR, Ikaros, IL-1 beta/IL-1F2, IL-10, IL-12, IL-2, IL-23, IL-3 R alpha/CD123, IL-6, iNOS, Integrin alpha E/CD103, IRF4, IRF8, Langerin/CD207, Ly-6G (Gr-1), Ly-6G/Ly-6C (Gr-1), MHC class II (I-A/I-E), MMR/CD206, NCAM-1/CD56, Neuropilin-1, NFIL3/E4BP4, Nitric Oxide, PU.1/Spi-1, SIRP alpha/CD172a, Spi-B, Thrombomodulin/BDCA-3, TLR7, TLR9, TNF-alpha, TREM2, and XCR1. In particular embodiments, dendritic cell specific antigens are selected from CD1a, CD1b/c, CD4, CD8, CD11b, CD11c, CD40, CD45R/B220, CD49d, CD80, CD83, CD85a, CD85f, CD85g/ILT7, CD85i, CD85j, CD86, CD123, CD180, CD197/CCR7, CD205, CD206, CD207, CD208, CD209, CD273/B7-DC/PD-L2, CD303/BDCA-2, CD304/neuropilin-1, DC marker/33D1, F4/80, MHC class I, fascin, HLA-DR, STING, and Siglec H. In particular embodiments, dendritic cell specific antigens are plasmacytoid dendritic cell antigens selected from CD1a, CD1b, CD1c, CD4, CD8, CD11b, CD11c, CD40, CD45R/B220, CD49d, CD80, CD83, CD85g/ILT7, CD86, CD123, CD197 (CCR7), CD273 (B7-DC, PD-L2), CD303 (BDCA-2), CD304 (Neuropilin-1), DC Marker (33D1), F4/80, HLA-DR, MHC Class II, and Siglec H.

In certain embodiments, the antibody binds to an antigen expressed by a macrophage. Exemplary antigens expressed by a macrophage that can be targeted by the conjugates provided herein include, but are not limited to, Activin A, AIF-1/Iba1, Arginase 1/ARG1, A2AR, B7-1/CD80, B7-2/CD86, Calcitonin R, CCL1/I-309/TCA-3, CCL11/Eotaxin, CCL14/HCC-1/HCC-3, CCL15/MIP-1 delta, CCL16/HCC-4, CCL17/TARC, CCL18/PARC, CCL19/MIP-3 beta, CCL2/JE/MCP-1, CCL20/MIP-3 alpha, CCL22/MDC, CCL23/Ck beta 8-1, CCL23/MPIF-1, CCL24/Eotaxin-2/MPIF-2, CCL26/Eotaxin-3, CCL3/CCL4, CCL3/MIP-1 alpha, CCL4/MIP-1 beta, CCL5/RANTES, CCL8/MCP-2, CCR2, CCR5, CD11b/Integrin alpha M, CD11c, CD15/Lewis X, CD163, CD200 R1, CD200R1L, CD36/SR-B3, CD43, CD45, CD68/SR-D1, CLEC10A/CD301, COX-2, CX3CL1/Fractalkine, CX3CR1, CXCL1/GRO alpha/KC/CINC-1, CXCL10/IP-10/CRG-2, CXCL11/I-TAC, CXCL13/BLC/BCA-1, CXCL16, CXCL2/GRO beta/MIP-2/CINC-3, CXCL3/GRO gamma/CINC-2/DCIP-1, CXCL5/ENA-70, CXCL5/ENA-74, CXCL5/ENA-78, CXCL9/MIG, CXCR1/IL-8 RA, CXCR2/IL-8 RB, DC-SIGN/CD209, DEC-205/CD205, Dectin-1/CLEC7A, Dectin-2/CLEC6A, EMR1, F4/80, Fc epsilon RI alpha, Fc gamma RI/CD64, Fc gamma RIA/CD64, Fc gamma RIB/CD64, Fc gamma RII/CD32, Fc gamma RIII (CD16), FIZZ1/RELM alpha, Galectin-3, GATA-6, G-CSF, GITR Ligand/TNFSF18, GM-CSF, HLA-DR, ID2, IFN-gamma, IFN-gamma R1/CD119, IL-1 beta/IL-1F2, IL-1 RII, IL-10, IL-15, IL-17/IL-17A, IL-18/IL-1F4, IL-1ra/IL-1F3, IL-23, IL-4 R alpha, IL-6, IL-8/CXCL8, iNOS, Integrin alpha L/CD11a, IRF4, IRF5, LAMP-2/CD107b, Langerin/CD207, LILRB4/CD85k/ILT3, L-Selectin/CD62L, LXR alpha/NR1H3, Ly-6G (Gr-1), Ly-6G/Ly-6C (Gr-1), MARCO, M-CSF R/CD115, Mer, MERTK, MFG-E8, MHC class II (I-A/I-E), MMR/CD206, NFATC1, NGFI-B alpha/Nur77/NR4A1, PPAR delta/NR1C2, PPAR gamma/NR1C3, RANK/TNFRSF11A, RUNX3/CBFA3, Siglec-1/CD169, Siglec-3/CD33, Siglec-F, SIGNR1/CD209b, SIRP alpha/CD172a, SLAM/CD150, SOCS-3, Sphingosine Kinase 1/SPHK1, Sphingosine Kinase 2/SPHK2, SR-AI/MSR, SR-BI, STAT1, STATE, STING, TGF-beta, TIM-4, TLR1, TLR2, TLR4, TLR8, TNF-alpha, TRACP/PAP/ACP5, TREM1, VCAM-1/CD106, VEGF, and YM1/Chitinase 3-like 3. In particular embodiments, macrophage specific antigens are selected from CD11a, CD11b, CD11c, CD14, CD15 (SSEA-1), CD16/32, CD33, CD64, CD68, CD80, CD85k (ILT3), CD86, CD105 (Endoglin), CD107b, CD115, CD163, CD195 (CCR5), CD282 (TLR2), CD284 (TLR4), F4/80, GITRL, HLA-DR, Mac-2 (Galectin-3), and MHC Class II.

In certain embodiments, the antibody binds to an antigen expressed by an NK cell. Exemplary antigens expressed by a NK cell that can be targeted by the conjugates provided herein include, but are not limited to, CD11b, CD11c, CD16/32, CD49b, CD56 (NCAM), CD57, CD69, CD94, CD122, CD158 (Kir), CD161 (NK-1.1), CD180, CD244 (2B4), CD314 (NKG2D), CD319 (CRACC), CD328 (Siglec-7), CD335 (NKp46), A2AR, Ly49, Ly108, Va24-Ja18 TCR (iNKT), granulysin, granzyme, perforin, SIRP-α, LAIR1, SIGLEC-3 (CD33), SIGLEC-7, SIGLEC-9, LIR1 (ILT2, LILRB1), NKR-P1A (KLRB1), CD94-NKG2A, KLRG1, KIR2DL5A, KIR2DL5B, KIR2DL1, KIR2DL2, KIR2DL3, KIR2DS2, KIR2DS3, KIR2DS4, KIR2DS5, KIR3DS1, KIR2DS1, CD94-NKG2C/E, NKG2D, CD160 (BY55), CD16 (FcγRIIIA), NKp46 (NCR1), NKp30 (NCR3), NKp44 (NCR2), DNAM1(CD226), CRTAM, CD2, CD7, CD11a, CD18, CD25, CD27, CD28, NTB-A (SLAMF6), PSGL1, CD96 (Tactile), CD100 (SEMA4D), NKp80 (KLRF1, CLECSC), SLAMF7 (CRACC, CS1, CD319), STING, and CD244 (2B4, SLAMF4).

In certain embodiments, the antibody binds to an antigen expressed by a myeloid cell. Exemplary antigens expressed by a myeloid cell and can be targeted by the conjugated provided herein include, but are not limited to, siglec-3, siglec 7, siglec 9, siglec 10, siglec 15, CD200, CD200R, LILRB1, LILRB2, LILRB3, LILRB4, LILRB5, M-CSF, CSF-1R, GM-CSF R, IL4 R, arginase, IDO, TDO, MPO, EP2, COX-2, CCR2, CCR-7, CXCR1, CX3CR1, CXCR2, CXCR3, CXCR4, CXCR7, c-Kit, CD244, L-selectin/CD62L, CD11b, CD11c, CD68, CD163, CD180, CD204, DEC205, IL-1R, CD31, SIRPα, SIRPβ, PD-L1, CEACAM-8/CD66b, CD103, BDCA-1, BDCA2. BDCA-4, CD123, STING, and ILT-7.

In certain embodiments, the antibody binds to an antigen expressed by an MDSC. Exemplary antigens expressed by an MDSC and can be targeted by the conjugated provided herein include, but are not limited to, siglec-3, Siglec 7, siglec 9, siglec 10, siglec 15, CD200, CD200R, LILRB1, LILRB2, LILRB3, LILRB4, LILRB5, M-CSF, CSF-1R, GM-CSF R, IL4 R, arginase, IDO, TDO, MPO, EP2, COX-2, CCR2, CCR-7, CXCR1, CX3CR1, CXCR2, CXCR3, CXCR4, CXCR7, c-Kit, CD244, L-selectin/CD62L, CD11b, CD11c, CD68, CD163, CD180, CD204, DEC205, IL-1R, CD31, SIRPα, SIRPβ, PD-L1, CEACAM-8/CD66b, CD103, BDCA-1, BDCA2. BDCA-4, CD123, and ILT-7.

In certain embodiments, the antibody binds to an antigen expressed by a TAM. Exemplary antigens expressed by a TAM and can be targeted by the conjugated provided herein include, but are not limited to, siglec-3, Siglec 7, siglec 9, siglec 10, siglec 15, CD200, CD200R, nerophilin 2 (NRP2), B7-H3, B7-H4, LILRB1, LILRB2, LILRB3, LILRB4, LILRB5, M-CSF, CSF-1R, GM-CSF R, IL4 R, arginase, IDO, TDO, MPO, EP2, COX-2, CCR2, CCR-7, CXCR1, CX3CR1, CXCR2, CXCR3, CXCR4, CXCR7, c-Kit, CD244, L-selectin/CD62L, CD11b, CD11c, CD68, CD163, CD204, DEC205, IL-1R, CD31, MARCO, TREM2, CD81, APOE, SIRPα, SIRPβ, PD-L1, CEACAM-8/CD66b, CD103, BDCA-1, BDCA2. BDCA-4, CD123, and ILT-7.

In certain embodiments, the antibody binds to an antigen specific to a NK cell. In certain embodiments, an NK cell is targeted by an anti-CD56 antibody. In certain embodiments, the antibody is an anti-CD56 antibody. In certain embodiments, the antibody is a monoclonal anti-CD56 antibody. In certain embodiments, the antibody is a murine anti-CD56 antibody. In certain embodiments, the murine anti-CD56 antibody is clone 5.1H11 (BioLegend, Cat No: 362502). In certain embodiments, the murine anti-CD56 antibody is clone MEM-188 (BioLegend, 304601). In certain embodiments, the murine anti-CD56 antibody is clone QA17A16 (BioLegend, Cat No: 392402). In certain embodiments, the antibody is a humanized anti-CD56 antibody. In certain embodiments, the antibody is a human anti-CD56 antibody. In certain embodiments, the antibody is a humanized anti-CD56 antibody B cells can be targeted by anti-CD38, anti-CD79b, anti-CD30, anti-CD22, or anti-CD20, anti-CD19 antibodies or antigen-binding fragments thereof or engineered derivatives thereof. Plasmacytoid dendritic cells (pDCs) can be targeted by anti-DEC205, anti-CD304 (BDCA4), anti-CD303 (BDCA2), anti-CD40, anti-CD74, or anti-CD123 antibodies or antigen-binding fragments thereof or engineered derivatives thereof. Macrophages can be targeted by anti-CD163, anti-CD40, anti-CD74, anti-CD206, or anti-CD123 antibodies or antigen-binding fragments thereof or engineered derivatives thereof. In some embodiments, a conjugate of the present disclosure comprises an immunomodulating oligonucleotide as described herein conjugated to a polypeptide, carbohydrate, or other compound that associates with or binds a target antigen described herein (e.g., CD22, a B cell antigen, a macrophage antigen, and so forth).

Non-limiting examples of anti-CD38 antibodies are daratumumab, SAR650984, MOR202, or any one of antibodies Ab79, Ab19, Ab43, Ab72, and Ab110 disclosed in WO 2012/092616, the disclosure of these antibodies is incorporated herein by reference. A non-limiting example of an anti-CD79b antibody is huMA79b v28 disclosed in WO 2014/011521. A non-limiting example of an anti-CD22 antibody is 10F4 disclosed in US 2014/0127197. A non-limiting example of an anti-CD20 antibody is rituximab. A non-limiting example of an anti-DEC205 antibody is provided in US 2010/0098704, the antibodies of which are incorporated herein by reference. Non-limiting examples of anti-CD40 antibodies are lucatumumab and dacetuzumab. A non-limiting example of an anti-CD304 antibody is vesencumab.

In some embodiments, the antibody is selected from the group consisting of an anti-CD20 antibody, anti-CD22 antibody, anti-CD30 antibody, anti CD37 antibody, anti-CD38 antibody, anti-CD40 antibody, anti-CD74 antibody, anti-CD79b antibody, anti-CD205 antibody, anti-CD274 antibody, anti-CD303 antibody, anti-CD304 antibody, anti-CD19 antibody, anti-CD1 antibody, anti-CD2 antibody, anti- CD3 antibody, anti-CD5 antibody, anti-CD6 antibody, anti-CD9 antibody, anti-CD11 antibody, anti-CD18 antibody, anti-CD21 antibody, anti-CD23 antibody, anti-CD24 antibody, anti-CD25 antibody, anti-CD26 antibody, anti-CD44 antibody, anti-CD45R antibody, anti-CD49 antibody, anti-CD66 (Carcinoembrionic antigen, CEA) antibody, anti-CD93 antibody, anti-CD52 antibody, anti-CD56 antibody, anti-CD123 antibody, anti-CD138 antibody, anti-CD163 antibody, anti-SLAMF7 antibody, anti-CD180 antibody, anti-DEC205 antibody, and anti-CD206 antibody. In some embodiments, the antibody is an anti-CD20 antibody. In some embodiments, the antibody is an anti-CD22 antibody.

In some embodiments, the CpG-Ab immunoconjugate specifically binds to a tumor associated antigen of the cancer being treated by the present method. Examples of tumor associated antigens (TAAs) that can be targeted by the CpG-Ab immunoconjugate of the present disclosure include, but are not limited to, sequences comprising all or part of the sequences of DLL3, GCC, GPA33, tissue factor (TF), TEM8, FOLR1, CEACAM5, LRRC15, Claudin18.2, AXL, CA9, CD155, AMHR2, NT5E, FLT1, nectin 4, 5T4 MT-1/MMP-14, DKK1, myostatin, sema4D, Trop-2, HER3, Her2, Her2/neu, HER1, VWF, IGF-1, GRP78, CXCR4, cMET, vitmentin, VEGFR2, VEGFR1, VEGF, VEGF-A, TYRP1 (glycoprotein 75), TWEAK receptor, tumor antigen CTAA16.88, TRAIL-R2, TRAIL-R1, TNF-alpha, TGF-beta, TGF beta 2, TGF beta 1, TFPI, tenascin C, TEM1, TAG-72, STEAP1, sphingosine-1-phosphate, SOST, SLAMF7, BCL-2, selectin P, SDC1, sclerostin, RTN4, RON, Rhesus factor, RHD, respiratory syncytial virus, RANKL, rabies virus glycoprotein, PDGF-R beta, phosphatidylserine, phosphate-sodium co-transporter, PDGF-R alpha, PDCD1, PD-1, PD-L1, PCSK9, oxLDL, OX-40, NRP1, Notch receptor 4, Notch receptor 3, Notch receptor 2, Notch receptor 1, NOGO-A, NGF, neural apoptosis-regulated proteinase 1, NCA-90 (granulocyte antigen), NARP-1, N-glycolylneuraminic acid, myostatin, myelin-associated glycoprotein, mucin CanAg, MSLN, MS4A1, MIF, MCP-1, LTA, LOXL2, lipoteichoic acid, LINGO-1, LFA-1 (CD11a), Lewis-Y antigen, L-selectin (CD62L), KIR, KIR ligand, ITGB2 (CD18), ITGA2, interferon receptor, interferon gamma-induced protein, integrin αvβ3, integrin αIIβ3, integrin α7β7, integrin α5β1, integrin α4β7, integrin α4, insulin-like growth factor I receptor, Influenza A hemagglutinin, ILGF2, IL9, IL6, IL4, IL3 IRA, IL23, IL-I 7A, IL-6 receptor, IL-6, IL-S, IL-4, IL-23, IL-22, IL-I, IL-I 7A, IL-I 7, IL-13, IL-I 2, IL-I, IL 20, IGHE, IGF-I, IGF-I receptor, IgE Fc region, IFN-gamma, IFN-alpha, ICAM-1 (CD54), human TNF, human scatter factor receptor kinase, Hsp90, HNGF, HLA-DR, HIV-1, histone complex, HHGFR, HGF, hepatitis B surface antigen, GUCY2C, GPNMB, GMCSF receptor alpha-chain, glypican 3, GD3 ganglioside, GD2, ganglioside GD2, Frizzled receptor, folate receptor 1, folate hydrolase, fibronectin extra domain-B, fibrin II, beta chain, FAP, F protein of respiratory syncytial virus, ERBB3, episialin, EpCAM, endotoxin, EGFR, EGFL7, *E. coli* shiga toxin type-2, *E. coli* shiga toxin type-I, DRS, DPP4, DLL4, dabigatran, cytomegalovirus glycoprotein B, CTLA-4, CSF2, CSF1R, clumping factor A, CLDN6, CLDN18.1, CLDN18.2, ch4DS, CFD, CEA-related antigen, CEA, CD80, CD79B, CD74, CD73, CD70, CD6, CD56, CD52, CD51, CD5, CD44 v6, CD41, CD40 ligand, CD40, CD47, CD4, CD39, CD38, CD37, CD33, CD30 (TNFRSF8), CD123, CD138, CD3 epsilon, CD3, CD28, CD274, CD27, CD2S (a chain of IL-2 receptor), CD23 (IgE receptor), CD221, CD22, CD200, CD20, CD2, CD19, CD137, CD142, CD154, CD152, CD15, CD147 (basigin), CD140a, CD125, CD11, CD-18, CCR5, CCR4, CCL11 (eotaxin-I), cardiac myosin, carbonic anhydrase 9 (CA-IX), *Canis lupus familiaris* IL31, CA-125, C5, C242 antigen, C—X—C chemokine receptor type 4, beta-amyloid, BAFF, B7-H3, B-lymphoma cell, AOC3 (VAP-I), anthrax toxin, protective antigen, angiopoietin 3, angiopoietin 2, alpha-fetoprotein, AGS-22M6, adenocarcinoma antigen, ACVR2B, activin receptor-like kinase I, 5T4, SAC, 4-IBB, 1-40-beta-amyloid, EGFR, EGFRvIII, gp100 or Pme117, CEA, MART-1/Melan-A, MAGE-A1, MAGE-A2, MAGE-A3, MAGE-A4, MUC-1, GPNMB, HMW-MAA, TIM1, ROR1, CD19, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family (e.g. MUC1, MUC16, etc; see e.g. U.S. Pat. No. 6,054,438; WO98/04727; or WO98/37095), p21ras, RCAS1, alpha-fetoprotein, E-cadherin, alpha-catenin, beta-catenin and gamma-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, Smad family of tumor antigens brain glycogen phosphorylase, SSX-1, SSX-2 (HOM-MEL-40), SSX-1, SSX-4, SSX-5, SCP-1 and CT-7, and c-erbB-2 and viral antigens such as the HPV-16 and HPV-18 E6 and E7 antigens and the EBV-encoded nuclear antigen (EBNA)-1, βhCG, WT1, TRP-2, NY-BR-1, NY-CO-58, MN (gp250), Telomerase, and germ cell derived tumor antigens. Tumor associated antigens also include the blood group antigens, for example, Lea, Leb, LeX, LeY, H-2, B-1, B-2 antigens. Tumor associated antigen can be identified using methods known in the art, such as disclosed in Zhang et al. Supra.

Particularly, in some embodiments, the CpG-Ab immunoconjugate specifically binds to a tumor associated antigen selected from CD19, CD20, CD22, CD25, CD30, CD33, CD38, CD40, CD44, CD45R (B220), CD49, CD52, CD56, CD70, CD74, CD79a, CD79b, CD93, CD123, CD138, CD163, CD205, CD206, CD274, CD303, and CD304, folate receptor alpha, folate receptor beta, mesothelin, PSMA, Her-2, EGFR, CLDN18.2, 5T4, CD47, nectin 4, transferrin receptor, integrin, cripto, EphA2, AGS-5, AGS-16, CanAg, EpCAM, IL4 receptor, IL2 receptor, Lewis Y, GPNMB, DLL3, GCC, GPA33, tissue factor (TF), and Trop2. In some embodiments, the tumor associated antigen is expressed by tumor cells. In some embodiments, the tumor associated antigen is expressed by stromal cells, e.g., part of the tumor stroma.

Certain aspects of the present disclosure relate to CD22 and anti-CD22 antibodies. In some embodiments, CD22 refers to human CD22, and the antibodies bind human CD22. CD22 is also known as Siglec-2, and CD22 gene and polypeptide sequences (e.g., human gene and polypeptide sequences) are known in the art. See, e.g., NCBI Gene ID No. 933 and NCBI Ref. Seq. Accession No. NP_001172028. In certain embodiments, the anti-CD22 antibody is an antibody comprising a VH and VL as shown below in Table 4. Anti-CD22 Antibody Sequences.

TABLE 4

Anti-CD22 Antibody Sequences

| Name | Domain | SEQ ID NO: | Sequence |
|---|---|---|---|
| RFB4 | VH | 56 | EVQLVESGGGLVKPGGSLKLSCAASGFAFSIYDMSWVRQTPEKRLEWVAYISSGGGTTYYPDTVKGRFTISRDNAKNTLYLQMSSLKSEDTAMYYCARHSGYGSSYGVLFAYWGQGTLVTVSS |
| RFB4 | VL | 57 | DIQMTQTTSSLSASLGDRVTISCRASQDISNYLNWYQQKPDGTVKLLIYYTSILHSGVPSRFSGSGSGTDYSLTISNLEQEDFATYFCQQGNTLPWTFGGGTKLEIK |
| epratuzumab | VH | 58 | QVQLVQSGAEVKKPGSSVKVSCKASGYTFTSYWLHWVRQAPGQGLEWIGYINPRNDYTEYNQNFKDKATITADESTNTAYMELSSLRSEDTAFYFCARRDITTFYWGQGTTVTVSS |
| epratuzumab | VL | 59 | DIQLTQSPSSLSASVGDRVTMSCKSSQSVLYSANHKNYLAWYQQKPGKAPKLLIYWASTRESGVPSRFSGSGSGTDFTLTISSLQPEDIATYYCHQYLSSWTFGGGTKLEIK |
| m971 | VH | 60 | QVQLQQSGPGLVKPSQTLSLTCAISGDSVSSNSAAWNWIRQSPSRGLEWLGRTYYRSKWYNDYAVSVKSRITINPDTSKNQFSLQLNSVTPEDTAVYYCAREVTGDLEDAFDIWGQGTMVTVSS |
| m971 | VL | 61 | DIQMTQSPSSLSASVGDRVTITCRASQTIWSYLNWYQQRPGKAPNLLIYAASSLQSGVPSRFSGRGSGTDFTLTISSLQAEDFATYYCQQSYSIPQTFGQGTKLEIK |
| 10F4 | VH | 62 | EVQLVESGGGLVQPGGSLRLSCAASGYEFSRSWMNWVRQAPGKGLEWVGRIYPGDGDTNYSGKFKGRFTISADTSKNTAYLQMNSLRAEDTAVYYCARDGSSWDWYFDVWGQGTLVTVSS |
| 10F4 | VL | 63 | MDIQMTQSPSSLSASVGDRVTITCRSSQSIVHSVGNTFLEWYQQKPGKAPKLLIYKVSNRFSGVPSRFSGSGSGTDFTLTISSLQPEDFATYYCFQGSQFPYTFGQGTKVEIK |
| RH1 | VH | 64 | EVQLVESGGGLVQPGGSLRLSCAASGFAFSIYDMSWVRQAPGKGLEWVAYISSGGGTTYYPDTVKGRFTISRDNSKNTLYLQMNSLRAEDTAVYYCARHSGYGTHWGVLFAYWGRGTLVTVSS |
| RH2 | VH | 65 | QVQLLESGGGVVQPGGSLRLSCAASGFAFSIYDMNWVRQAPGKGLEWVSAISSGGGTTYYADSVKGRFTISRDNAKNSLYLQMNSLRAEDTAVYYCARHSGYGTHWGVLFAYWGRGTLVTVSS |
| RH3 | VH | 66 | EVQLVESGGGLVQPGGSLRLSCAASGFTFSSYEMNWVRQAPGKGLEWVSYISSSGSTIYYADSVKGRFTISRDNAKNSLYLQMNSLRAEDTAVYYCARHSGYGTHWGVLFAYWGRGTLVTVSS |
| RH4 | VH | 67 | QVQLQESGPGLVKPSDTLSLTCTVSGFAFSIYDMSWIRQPPGKGLEWIAYISSGGGTTYYNPSLKSRVTISVDTSKNQFSLKLSSVTAADTAVYYCARHSGYGTHWGVLFAYWGRGTLVTVSS |
| RL1 | VL | 68 | DIQMTQSPSSLSASVGDRVTITCRASQDIHGYLNWYQQKPGKAPKLLIYYTSILHSGVPSRFSGSGSGTDFTLTISSLQPEDFATYFCQQGNTLPWTFGQGTKLEIK |
| RL2 | VL | 69 | DIQMTQSPSSVSASVGDRVTITCRASQDIHGYLAWYQQKPGKAPKLLIYYTSSLQSGVPSRFSGSGSGTDFTLTISSLQPEDFATYYCQQGNTLPWTFGQGTKLEIK |
| RL3 | VL | 70 | DIQMTQSPSSLSASVGDRVTITCRASQSISSYLNWYQQKPGKAPKLLIYAASSLQSGVPSRFSGSGSGTDFTLTISSLQPEDFATYYCQQGNTLPWTFGQGTKLEIK |
| RL4 | VL | 71 | EIVLTQSPATLSLSPGERATLSCRASQDIHGYLNWYQQKPGQAPRLLIYYTSILHSGIPARFSGSGPGTDFTLTISSLEPEDFAVYYCQQGNTLPWTFGGGTKLEIK |
| RL5 | VL | 72 | DIVMTQTPLSLSVTPGQPASISCRASQDIHGYLNWYQQKPGQSPQLLIYYTSILHSGVPDRFSGSGSGTDFTLKISRVEAEDVGVYFCQQGNTLPWTFGQGTKLEIK |

TABLE 5

Anti-CD22 Antibody VH Sequences.

| Name | Sequence | SEQ ID NO |
|---|---|---|
| RH1 | EVQLVESGGGLVQPGGSLRLSCAASGFAFSIYDMSWVRQAPGKGLEWVAYISSGGGTTYYPDTVKGRFTISRDNSKNTLYLQMNSLRAEDTAVYYCARHSGYGTHWGVLFAYWGRGTLVTVSS | 64 |
| RH2 | QVQLLESGGGVVQPGGSLRLSCAASGFAFSIYDMNWVRQAPGKGLEWVSAISSGGGTTYYADSVKGRFTISRDNAKNSLYLQMNSLRAEDTAVYYCARHSGYGTHWGVLFAYWGRGTLVTVSS | 65 |
| RH3 | EVQLVESGGGLVQPGGSLRLSCAASGFTFSSYEIVINWVRQAPGKGLEWVSYISSSGSTIYYADSVKGRFTISRDNAKNSLYLQMNSLRAEDTAVYYCARHSGYGTHWGVLFAYWGRGTLVTVSS | 66 |
| RH4 | QVQLQESGPGLVKPSDTLSLTCTVSGFAFSIYDIVISWIRQPPGKGLEWIAYISSGGGTTYYNPSLKSRVTISVDTSKNQFSLKLSSVTAADTAVYYCARHSGYGTHWGVLFAYWGRGTLVTVSS | 67 |

TABLE 6

Anti-CD22 Antibody VL Sequences.

| Name | Sequence | SEQ ID NO |
|---|---|---|
| RL1 | DIQMTQSPSSLSASVGDRVTITCRASQDIHGYLNWYQQKPGKAPKLLIYYTSILHSGVPSRFSGSGSGTDFTLTISSLQPEDFATYFCQQGNTLPWTFGQGTKLEIK | 68 |
| RL2 | DIQMTQSPSSVSASVGDRVTITCRASQDIHGYLAWYQQKPGKAPKLLIYYTSSLQSGVPSRFSGSGSGTDFTLTISSLQPEDFATYYCQQGNTLPWTFGQGTKLEIK | 69 |
| RL3 | DIQMTQSPSSLSASVGDRVTITCRASQSISSYLNWYQQKPGKAPKLLIYAASSLQSGVPSRFSGSGSGTDFTLTISSLQPEDFATYYCQQGNTLPWTFGQGTKLEIK | 70 |
| RL4 | EIVLTQSPATLSLSPGERATLSCRASQDIHGYLNWYQQKPGQAPRLLIYYTSILHSGIPARFSGSGPGTDFTLTISSLEPEDFAVYYCQQGNTLPWTFGGGTKLEIK | 71 |
| RL5 | DIVMTQTPLSLSVTPGQPASISCRASQDIHGYLNWYQQKPGQSPQLLIYYTSILHSGVPDRFSGSGSGTDFTLKISRVEAEDVGVYFCQQGNTLPWTFGGGTKLEIK | 72 |
| RL1 N92A | DIQMTQSPSSLSASVGDRVTITCRASQDIHGYLNWYQQKPGKAPKLLIYYTSILHSGVPSRFSGSGSGTDFTLTISSLQPEDFATYFCQQGATLPWTFGQGTKLEIK | 73 |
| RL1 N92C | DIQMTQSPSSLSASVGDRVTITCRASQDIHGYLNWYQQKPGKAPKLLIYYTSILHSGVPSRFSGSGSGTDFTLTISSLQPEDFATYFCQQGCTLPWTFGQGTKLEIK | 74 |
| RL1 N92D | DIQMTQSPSSLSASVGDRVTITCRASQDIHGYLNWYQQKPGKAPKLLIYYTSILHSGVPSRFSGSGSGTDFTLTISSLQPEDFATYFCQQGDTLPWTFGQGTKLEIK | 75 |
| RL1 N92E | DIQMTQSPSSLSASVGDRVTITCRASQDIHGYLNWYQQKPGKAPKLLIYYTSILHSGVPSRFSGSGSGTDFTLTISSLQPEDFATYFCQQGETLPWTFGQGTKLEIK | 76 |
| RL1 N92F | DIQMTQSPSSLSASVGDRVTITCRASQDIHGYLNWYQQKPGKAPKLLIYYTSILHSGVPSRFSGSGSGTDFTLTISSLQPEDFATYFCQQGFTLPWTFGQGTKLEIK | 77 |
| RL1 N92G | DIQMTQSPSSLSASVGDRVTITCRASQDIHGYLNWYQQKPGKAPKLLIYYTSILHSGVPSRFSGSGSGTDFTLTISSLQPEDFATYFCQQGGTLPWTFGQGTKLEIK | 78 |
| RL1 N92H | DIQMTQSPSSLSASVGDRVTITCRASQDIHGYLNWYQQKPGKAPKLLIYYTSILHSGVPSRFSGSGSGTDFTLTISSLQPEDFATYFCQQGHTLPWTFGQGTKLEIK | 79 |
| RL1 N92I | DIQMTQSPSSLSASVGDRVTITCRASQDIHGYLNWYQQKPGKAPKLLIYYTSILHSGVPSRFSGSGSGTDFTLTISSLQPEDFATYFCQQGITLPWTFGQGTKLEIK | 80 |
| RL1 N92K | DIQMTQSPSSLSASVGDRVTITCRASQDIHGYLNWYQQKPGKAPKLLIYYTSILHSGVPSRFSGSGSGTDFTLTISSLQPEDFATYFCQQGKTLPWTFGQGTKLEIK | 81 |
| RL1 N92L | DIQMTQSPSSLSASVGDRVTITCRASQDIHGYLNWYQQKPGKAPKLLIYYTSILHSGVPSRFSGSGSGTDFTLTISSLQPEDFATYFCQQGLTLPWTFGQGTKLEIK | 82 |
| RL1 N92M | DIQMTQSPSSLSASVGDRVTITCRASQDIHGYLNWYQQKPGKAPKLLIYYTSILHSGVPSRFSGSGSGTDFTLTISSLQPEDFATYFCQQGMTLPWTFGQGTKLEIK | 83 |
| RL1 N92P | DIQMTQSPSSLSASVGDRVTITCRASQDIHGYLNWYQQKPGKAPKLLIYYTSILHSGVPSRFSGSGSGTDFTLTISSLQPEDFATYFCQQGPTLPWTFGQGTKLEIK | 84 |
| RL1 N92Q | DIQMTQSPSSLSASVGDRVTITCRASQDIHGYLNWYQQKPGKAPKLLIYYTSILHSGVPSRFSGSGSGTDFTLTISSLQPEDFATYFCQQGQTLPWTFGQGTKLEIK | 85 |
| RL1 N92R | DIQMTQSPSSLSASVGDRVTITCRASQDIHGYLNWYQQKPGKAPKLLIYYTSILHSGVPSRFSGSGSGTDFTLTISSLQPEDFATYFCQQGRTLPWTFGQGTKLEIK | 86 |
| RL1 N92S | DIQMTQSPSSLSASVGDRVTITCRASQDIHGYLNWYQQKPGKAPKLLIYYTSILHSGVPSRFSGSGSGTDFTLTISSLQPEDFATYFCQQGSTLPWTFGQGTKLEIK | 87 |
| RL1 N92T | DIQMTQSPSSLSASVGDRVTITCRASQDIHGYLNWYQQKPGKAPKLLIYYTSILHSGVPSRFSGSGSGTDFTLTISSLQPEDFATYFCQQGTTLPWTFGQGTKLEIK | 88 |
| RL1 N92V | DIQMTQSPSSLSASVGDRVTITCRASQDIHGYLNWYQQKPGKAPKLLIYYTSILHSGVPSRFSGSGSGTDFTLTISSLQPEDFATYFCQQGVTLPWTFGQGTKLEIK | 89 |
| RL1 N92W | DIQMTQSPSSLSASVGDRVTITCRASQDIHGYLNWYQQKPGKAPKLLIYYTSILHSGVPSRFSGSGSGTDFTLTISSLQPEDFATYFCQQGWTLPWTFGQGTKLEIK | 90 |
| RL1 N92Y | DIQMTQSPSSLSASVGDRVTITCRASQDIHGYLNWYQQKPGKAPKLLIYYTSILHSGVPSRFSGSGSGTDFTLTISSLQPEDFATYFCQQGYTLPWTFGQGTKLEIK | 91 |

TABLE 13

Anti-CD22 antibody sequences

| Heavy chain | Light chain |
|---|---|
| QVQLLESGGGVVQPGGSLRLSCAASGFAFSIYDMNWVRQAPGKGLEWVSAISSGGGTTYYADSVKGRFTISRDNAKNSLYLQMNSLRAEDTAVYYCARHSGYGTHWGVLFAYWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGRPQGFGPP (SEQ ID NO: 179) | DIQMTQSPSSLSASVGDRVTITCRASQDIHGYLNWYQQKPGKAPKLLIYYTSILHSGVPSRFSGSGSGTDFTLTISSLQPEDFATYFCQQGATLPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 181) |
| QVQLLESGGGVVQPGGSLRLSCAASGFAFSIYDMNWVRQAPGKGLEWVSAISSGGGTTYYADSVKGRFTISRDNAKNSLYLQMNSLRAEDTAVYYCARHSGYGTHWGVLFAYWGRGTLVTVSSASTKGPSVFPLAPSSKSTSGGTAALGCLVKDYFPEPVTVSWNSGALTSGVHTFPAVLQSSGLYSLSSVVTVPSSSLGT | DIQMTQSPSSLSASVGDRVTITCRASQDIHGYLNWYQQKPGKAPKLLIYYTSILHSGVPSRFSGSGSGTDFTLTISSLQPEDFATYFCQQGSTLPWTFGQGTKLEIKRTVAAPSVFIFPPSDEQLKSGTASVVCLLNNFYPREAKVQWKVDNALQSGNSQESVTEQDSKDSTY |

TABLE 13-continued

Anti-CD22 antibody sequences

Heavy chain

QTYICNVNHKPSNTKVDKKVEPKSCDKTHTCPPCPAPEAA
GAPSVFLFPPKPKDTLMISRTPEVTCVVVDVSHEDPEVKFN
WYVDGVEVHNAKTKPREEQYNSTYRVVSVLTVLHQDWL
NGKEYKCKVSNKALPAPIEKTISKAKGQPREPQVYTLPPSRE
EMTKNQVSLTCLVKGFYPSDIAVEWESNGQPENNYKTTPP
VLDSDGSFFLYSKLTVDKSRWQQGNVFSCSVMHEALHNH
YTQKSLSLSPGRPQGFGPP (SEQ ID NO: 180)

Light chain

SLSSTLTLSKADYEKHKVYACEVTHQGLSSPVTKSF
NRGEC (SEQ ID NO: 182)

In some embodiments, the anti-CD22 antibody or conjugate comprises a heavy chain comprising the sequence of SEQ ID NO:179 or 180, and a light chain comprising the sequence of SEQ ID NO:181 or 182.

Certain aspects of the present disclosure relate to Her2 and anti-Her2 antibodies. In some embodiments, Her2 refers to human Her2, and the antibodies bind human Her2. Her2 is also known as erb-b2 receptor tyrosine kinase 2 (ERBB2), Neu, NGL, TKR1, CD340, and MLN19. Her2 gene and polypeptide sequences (e.g., human gene and polypeptide sequences) are known in the art. See, e.g., NCBI Gene ID No. 2064 and NCBI Ref. Seq. Accession No. NP_001005862. In some embodiments, the CpG-Ab immunoconjugate specifically binds to a Her2 polypeptide, e.g., a human Her2 polypeptide. In some embodiments, the CpG-Ab immunoconjugate specifically binds to an extracellular domain of a Her2 polypeptide, e.g., a human Her2 polypeptide. In some embodiments, the CpG-Ab immunoconjugate specifically binds to a cell (e.g., a tumor cell) that expresses a Her2 polypeptide, e.g., a human Her2 polypeptide, on its cell surface. Antibodies that bind a Her2 polypeptide, e.g., a human Her2 polypeptide, are known in the art. In some embodiments, the antibody comprises a VH domain comprising 1, 2, or 3 CDR sequences from the VH domain of the anti-Her2 antibody trastuzumab and/or a VL domain comprising 1, 2, or 3 CDR sequences from the VL domain of the anti-Her2 antibody trastuzumab. In some embodiments, the antibody comprises a VH domain comprising 1, 2, or 3 CDR sequences from a VH domain comprising the amino acid sequence of (SEQ ID NO: 168)
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSS and/or a VL domain comprising 1, 2, or 3 CDR sequences from a VL domain comprising the amino acid sequence of (SEQ ID NO: 169)
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIK.

In some embodiments, the antibody comprises the VH domain of the anti-Her2 antibody trastuzumab and/or the VL domain of the anti-Her2 antibody trastuzumab. In some embodiments, the antibody comprises a VH domain comprising the amino acid sequence of (SEQ ID NO: 168)
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSS and/or a VL domain comprising the amino acid sequence of (SEQ ID NO: 169)
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIK.

In some embodiments, the antibody comprises a VH domain comprising 1, 2, or 3 CDR sequences from the VH domain of the anti-Her2 antibody pertuzumab and/or a VL domain comprising 1, 2, or 3 CDR sequences from the VL domain of the anti-Her2 antibody pertuzumab. In some embodiments, the antibody comprises a VH domain comprising 1, 2, or 3 CDR sequences from a VH domain comprising the amino acid sequence of (SEQ ID NO: 170)
EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSS and/or a VL domain comprising 1, 2, or 3 CDR sequences from a VL domain comprising the amino acid sequence of (SEQ ID NO: 171)
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GQGTKVEIK

In some embodiments, the antibody comprises the VH domain of the anti-Her2 antibody pertuzumab and/or the VL domain of the anti-Her2 antibody pertuzumab. In some embodiments, the antibody comprises a VH domain comprising the amino acid sequence of (SEQ ID NO:170)
EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSS and/or a VL domain comprising the amino acid sequence of

```
                                      (SEQ ID NO: 171)
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GQGTKVEIK
```

In some embodiments, the anti-Her2 antibody is trastuzumab. In some embodiments, the anti-Her2 antibody is pertuzumab. In some embodiments, the anti-Her2 antibody has one or more effector functions, including without limitation ADCC and/or ADCP. In some embodiments, the anti-Her2 antibody comprises a human Fc region, e.g., a human IgG Fc region. In some embodiments, the anti-Her2 antibody comprises a wild-type human IgG1, IgG2, or IgG4 Fc region. In some embodiments, the anti-Her2 antibody comprises the antibody constant domain sequence of SEQ ID NO:178.

In some embodiments, the anti-Her2 antibody or conjugate comprises a heavy chain comprising the sequence of SEQ ID NO:183, 184, 186, or 187; and a light chain comprising the sequence of SEQ ID NO:185 or 188.

In some embodiments, an antibody of the present disclosure (e.g., an anti-CD22 antibody or anti-Her2 antibody) comprises an antibody constant domain. In some embodiments, an antibody of the present disclosure (e.g., an anti-CD22 antibody or anti-Her2 antibody) comprises an antibody heavy chain constant domain and/or antibody light chain constant domain listed in Table 7. In some embodiments, an antibody of the present disclosure (e.g., an anti-CD22 antibody or anti-Her2 antibody) comprises an antibody heavy chain constant domain selected from the group consisting of SEQ ID Nos:92-107 and 178. In some embodiments, an antibody of the present disclosure (e.g., an anti-CD22 antibody or anti-Her2 antibody) comprises an antibody heavy chain constant domain with a Q-tag at the C-terminus of the Fc region, e.g., as shown in SEQ ID No:

TABLE 14

Anti-Her2 antibody sequences

| Heavy chain | Light chain |
| --- | --- |
| EVQLVESGGGLVQPGGSLRLSCAASGFNIKDTYIHWVRQA PGKGLEWVARIYPTNGYTRYADSVKGRFTISADTSKNTAYL QMNSLRAEDTAVYYCSRWGGDGFYAMDYWGQGTLVTV SSASTKGPSVFPLAPCSRSTSESTAALGCLVKDYFPEPVTVS WNSGALTSGVHTFPAVLQSSGLYSLSSVVTVPSSSLGTKTY TCNVDHKPSNTKVDKRVESKYGPPCPPCPAPEFLGGPSVFL FPPKPKDTLMISRTPEVTCVVVDVSQEDPEVQFNWYVDG VEVHNAKTKPREEQFNSTYRVVSVLTVLHQDWLNGKEYKC KVSNKGLPSSIEKTISKAKGQPREPQVYTLPPSQEEMTKNQ VSLTCLVKGFYPSDIAVEWESNGQPENNYKTTPPVLDSDGS FFLYSRLTVDKSRWQEGNVFSCSVMHEALHNHYTQKSLSL SLGRPQGFGPP (SEQ ID NO: 183) | DIQMTQSPSSLSASVGDRVTITCRASQDVNTAVA WYQQKPGKAPKLLIYSASFLYSGVPSRFSGSRSGT DFTLTISSLQPEDFATYYCQQHYTTPPTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKSF NRGEC (SEQ ID NO: 185) |
| EVQLVESGGGLVQPGGSLRLSCAASGFNIKDTYIHWVRQA PGKGLEWVARIYPTNGYTRYADSVKGRFTISADTSKNTAYL QMNSLRAEDTAVYYCSRWGGDGFYAMDYWGQGTLVTV SSASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDKTHTCPPCPAPELLGGPS VFLFPPKPKDTLMISRTPEVTCVVVDVSHEDPEVKFNWYV DGVEVHNAKTKPREEQYNSTYRVVSVLTVLHQDWLNGKE YKCKVSNKALPAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQK SLSLSPGRPQGFGPP (SEQ ID NO: 184) | DIQMTQSPSSLSASVGDRVTITCKASQDVSIGVA WYQQKPGKAPKLLIYSASYRYTGVPSRFSGSGSGT DFTLTISSLQPEDFATYYCQQYYIYPYTFGQGTKVE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKSFN RGEC (SEQ ID NO: 188) |
| EVQLVESGGGLVQPGGSLRLSCAASGFTFTDYTMDWVRQ APGKGLEWVADVNPNSGGSIYNQRFKGRFTLSVDRSKNTL YLQMNSLRAEDTAVYYCARNLGPSFYFDYWGQGTLVTVSS ASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFP PKPKDTLMISRTPEVTCVVVDVSQEDPEVQFNWYVDGVE VHNAKTKPREEQFNSTYRVVSVLTVLHQDWLNGKEYKCK VSNKGLPSSIEKTISKAKGQPREPQVYTLPPSQEEMTKNQV SLTCLVKGFYPSDIAVEWESNGQPENNYKTTPPVLDSDGSF FLYSRLTVDKSRWQEGNVFSCSVMHEALHNHYTQKSLSLS LGRPQGFGPP (SEQ ID NO: 186) | |
| EVQLVESGGGLVQPGGSLRLSCAASGFTFTDYTMDWVRQ APGKGLEWVADVNPNSGGSIYNQRFKGRFTLSVDRSKNTL YLQMNSLRAEDTAVYYCARNLGPSFYFDYWGQGTLVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSV FLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQK SLSLSPGRPQGFGPP (SEQ ID NO: 187) | |

95 or 178. In some embodiments, an antibody of the present disclosure (e.g., an anti-CD22 antibody or anti-Her2 antibody) comprises two antibody heavy chains, each with a constant domain, wherein each of the two antibody heavy chains comprises a Q-tag at the C-terminus of the Fc region, e.g., as shown in SEQ ID No: 95 or 178. In some embodiments, an antibody of the present disclosure (e.g., an anti-CD22 antibody or anti-Her2 antibody) comprises two antibody heavy chains, each with a constant domain, wherein only one of the two antibody heavy chains comprises a Q-tag at the C-terminus of the Fc region, e.g., as shown in SEQ ID No: 95 or 178. In some embodiments, an antibody of the present disclosure (e.g., an anti-CD22 antibody or anti-Her2 antibody) comprises an antibody light chain constant domain selected from the group consisting of SEQ ID Nos:108-110.

TABLE 7

Antibody constant domain sequences

| Name | SEQ ID NO: | Sequence |
|---|---|---|
| IgG1 wildtype | 92 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYSKLTVDKSRW QQGNVFSCSVMHEALHNHYTQKSLSLSPG |
| IgG1_AAA_N297A | 93 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| IgG1_AAA | 94 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| IgG1_AAA + S-tag | 95 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG*RPQGFGPP* |
| IgG1_N297A | 96 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYSKLTVDKSRW QQGNVFSCSVMHEALHNHYTQKSLSLSPG |
| IgG1_D265A | 97 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYSKLTVDKSRW QQGNVFSCSVMHEALHNHYTQKSLSLSPG |
| IgG1_N297A/D265A | 98 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVAVSHEDPEVKFNWYVDGVEVHNAKTKPREEQYASTYRVVSVLTVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYSKLTVDKSRW QQGNVFSCSVMHEALHNHYTQKSLSLSPG |
| IgG2 | 99 | ASTKGPSVFPLAPCSRSTSESTAALGCLVKDYFPEPVTVSWNSGALTSGVHTFPAVLQSSG LYSLSSVVTVPSSNFGTQTYTCNVDHKPSNTKVDKTVERKCCVECPPCPAPPVAGPSVFL |

TABLE 7-continued

Antibody constant domain sequences

| Name | SEQ ID NO: | Sequence |
|---|---|---|
| | | FPPKPKDTLMISRTPEVTCVVVDVSHEDPEVQFNWYVDGVEVHN AKTKPREEQFNSTFRV VSVLTVVHQDWLNGKEYKCKVSNKGLPAPIEKTISKTKGQPREPQ VYTLPPSREEMTKNQ VSLTCLVKGFYPSDIAVEWESNGQPENNYKTTPPMLDSDGSFFLY SKLTVDKSRWQQGNV FSCSVMHEALHNHYTQKSLSLSPG |
| IgG2Da | 100 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPE VTCVVVDVSHEDPEVQFNWYVDGVEVHNAKTKPREEQFNSTFR VVSVLTVVHQDWLNGKEYKCKVSNKGLPSSIEKTISKTKGQPREP QVYTLPPSREEMTKNQVSLTCLVKGFYPSDIAVEWESNGQPENN YKTTPPMLDSDGSFFLYSKLTVDKSRWQQGNVFSCSVMHEALHN HYTQKSLSLSPG |
| IgG2Da_N297A | 101 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPE VTCVVVDVSHEDPEVQFNWYVDGVEVHNAKTKPREEQFASTFR VVSVLTVVHQDWLNGKEYKCKVSNKGLPSSIEKTISKTKGQPREP QVYTLPPSREEMTKNQVSLTCLVKGFYPSDIAVEWESNGQPENN YKTTPPMLDSDGSFFLYSKLTVDKSRWQQGNVFSCSVMHEALHN HYTQKSLSLSPG |
| IgG2_N297A | 102 | ASTKGPSVFPLAPCSRSTSESTAALGCLVKDYFPEPVTVSWNSGAL TSGVHTFPAVLQSSG LYSLSSVVTVPSSNFGTQTYTCNVDHKPSNTKVDKTVERKCCVEC PPCPAPPVAGPSVFL FPPKPKDTLMISRTPEVTCVVVDVSHEDPEVQFNWYVDGVEVHN AKTKPREEQFASTFRV VSVLTVVHQDWLNGKEYKCKVSNKGLPAPIEKTISKTKGQPREPQ VYTLPPSREEMTKNQ VSLTCLVKGFYPSDIAVEWESNGQPENNYKTTPPMLDSDGSFFLY SKLTVDKSRWQQGNV FSCSVMHEALHNHYTQKSLSLSPG |
| IgG2Da_D265A | 103 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPE VTCVVVAVSHEDPEVQFNWYVDGVEVHNAKTKPREEQFNSTFR VVSVLTVVHQDWLNGKEYKCKVSNKGLPSSIEKTISKTKGQPREP QVYTLPPSREEMTKNQVSLTCLVKGFYPSDIAVEWESNGQPENN YKTTPPMLDSDGSFFLYSKLTVDKSRWQQGNVFSCSVMHEALHN HYTQKSLSLSPG |
| IgG4_S228P | 104 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| IgG4_S228P_D265A | 105 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVAVSQEDPEVQFNWYVDGVEVHNAKTKPREEQFNSTYR VVSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| IgG4_S228P, L235E | 106 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFEGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| IgG4_S228P,N297A | 107 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFASTYR VVSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |

TABLE 7-continued

Antibody constant domain sequences

| Name | SEQ ID NO: | Sequence |
| --- | --- | --- |
| IgG1_wt + S-tag | 178 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMI SRTPEVTCVVVDVSHEDPEVKFNWYVDGVEVHNAKTKPREEQY NSTYRVVSVLTVLHQDWLNGKEYKCKVSNKALPAPIEKTISKAKG QPREPQVYTLPPSREE MTKNQVSLTCLVKGFYPSDIAVEWESNGQPENNYKTTPPVLDSD GSFFLYSKLTVDKSRW QQGNVFSCSVMHEALHNHYTQKSLSLSPGRPQGFGPP |
| Human Kappa | 108 | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC |
| Human Lambda IGLC1 | 109 | GQPKANPTVTLFPPSSEELQANKATLVCLISDFYPGAVTVAWKAD GSPVKAGVETTKPSKQSNNKYAASSYLSLTPEQWKSHRSYSCQVT HEGSTVEKTVAPTECS |
| Human Lambda IGLC2 | 110 | GQPKAAPSVTLFPPSSEELQANKATLVCLISDFYPGAVTVAWKAD SSPVKAGVETTTPSKQSNNKYAASSYLSLTPEQWKSHRSYSCQVT HEGSTVEKTVAPTECS |

In some embodiments, an antibody or conjugate of the present disclosure comprises a VH domain comprising 1, 2, or 3 CDRs of a single antibody shown in Table 8. In some embodiments, an antibody or conjugate of the present disclosure comprises a VH domain comprising the 3 CDRs of a single antibody shown in Table 8. In some embodiments, an antibody or conjugate of the present disclosure comprises a VL domain comprising 1, 2, or 3 CDRs of a single antibody shown in Table 8. In some embodiments, an antibody or conjugate of the present disclosure comprises a VL domain comprising the 3 CDRs of a single antibody shown in Table 8. In some embodiments, an antibody or conjugate of the present disclosure comprises a VH domain comprising 1, 2, or 3 CDRs of a single antibody shown in Table 8 and a VL domain comprising 1, 2, or 3 CDRs of a single antibody shown in Table 8. In some embodiments, an antibody or conjugate of the present disclosure comprises a VH domain comprising the 3 CDRs of a single antibody shown in Table 8 and a VL domain comprising the 3 CDRs of a single antibody shown in Table 8. In some embodiments, an antibody or conjugate of the present disclosure comprises a VH domain comprising a CDR-H1 comprising the sequence of SEQ ID NO:113, a CDR-H2 comprising the sequence of SEQ ID NO:115, and a CDR-H3 comprising the sequence of SEQ ID NO:116. In some embodiments, an antibody or conjugate of the present disclosure comprises a VH domain comprising a CDR-H1 comprising the sequence of SEQ ID NO:114, a CDR-H2 comprising the sequence of SEQ ID NO:189, and a CDR-H3 comprising the sequence of SEQ ID NO:116. In some embodiments, an antibody or conjugate of the present disclosure comprises a VL domain comprising a CDR-L1 comprising the sequence of SEQ ID NO:117, a CDR-L2 comprising the sequence of SEQ ID NO:119, and a CDR-L3 comprising the sequence of SEQ ID NO:120. In some embodiments, an antibody or conjugate of the present disclosure comprises a VL domain comprising a CDR-L1 comprising the sequence of SEQ ID NO:118, a CDR-L2 comprising the sequence of SEQ ID NO:177, and a CDR-L3 comprising the sequence of SEQ ID NO:120.

TABLE 8

Anti-CD22 antibody CDR sequences

| Antibody | CDR-H1 | CDR-H2 | CDR-H3 | CDR-L1 | CDR-L2 | CDR-L3 |
| --- | --- | --- | --- | --- | --- | --- |
| RH1 | GFAFSIYD (SEQ ID NO: 113) | ISSGGGTT (SEQ ID NO: 115) | ARHSGYGTHWGVLFAY (SEQ ID NO: 116) | — | — | — |
| RH2 | GFAFSIYD (SEQ ID NO: 113) | ISSGGGTT (SEQ ID NO: 115) | ARHSGYGTHWGVLFAY (SEQ ID NO: 116) | — | — | — |
| RH3 | GFTFSSYE (SEQ ID NO: 114) | ISSSGSTI (SEQ ID NO: 189) | ARHSGYGTHWGVLFAY (SEQ ID NO: 116) | — | — | — |
| RH4 | GFAFSIYD (SEQ ID NO: 113) | ISSGGGTT (SEQ ID NO: 115) | ARHSGYGTHWGVLFAY (SEQ ID NO: 116) | — | — | — |
| RL1 | — | — | — | QDIHGY (SEQ ID NO: 117) | YTS (SEQ ID NO: 119) | QQGNTLPWT (SEQ ID NO: 120) |
| RL2 | — | — | — | QDIHGY (SEQ ID NO: 117) | YTS (SEQ ID NO: 119) | QQGNTLPWT (SEQ ID NO: 120) |
| RL3 | — | — | — | QSISSY (SEQ ID NO: 118) | AAS (SEQ ID NO: 177) | QQGNTLPWT (SEQ ID NO: 120) |

TABLE 8-continued

Anti-CD22 antibody CDR sequences

| Antibody | CDR-H1 | CDR-H2 | CDR-H3 | CDR-L1 | CDR-L2 | CDR-L3 |
|---|---|---|---|---|---|---|
| RL4 | — | — | — | QDIHGY (SEQ ID NO: 117) | YTS (SEQ ID NO: 119) | QQGNTLPWT (SEQ ID NO: 120) |
| RL5 | — | — | — | QDIHGY (SEQ ID NO: 117) | YTS (SEQ ID NO: 119) | QQGNTLPWT (SEQ ID NO: 120) |

In still yet another aspect of the present disclosure, provided herein is a conjugate comprising an antibody or antigen-binding fragment thereof and one or more immunomodulating oligonucleotides (P), wherein the antibody or antigen-binding fragment is linked to one or more Q-tag peptides (Q) comprising the amino acid sequence RPQGF (SEQ ID NO:47), wherein each immunomodulating oligonucleotide is linked to a Q-tag peptide via an amide bond with the glutamine residue of the Q-tag peptide and a linker (L) as shown in formula (A),

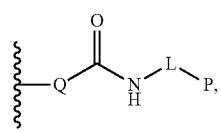

(A)

wherein:
  each Q independently comprises a Q-tag peptide sequence RPQGF (SEQ ID NO:47);
  each L is independently a bond or a linker moiety

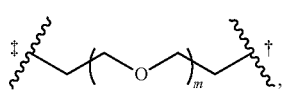

wherein m is an integer ranging from about 0 to about 50, and wherein ⁓† indicates the point of attachment to P, and ⁓‡ indicates the point of attachment to the rest of the conjugate connected to Q via an amide bond with the glutamine residue;
  and each P is independently an immunomodulating oligonucleotide having the structure

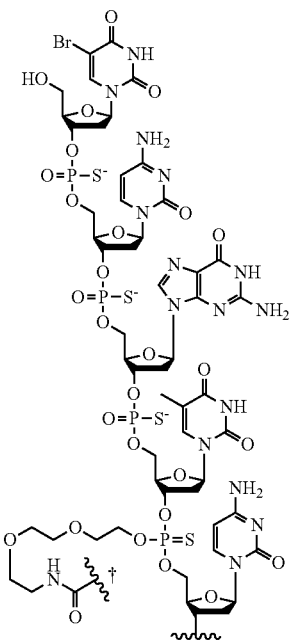

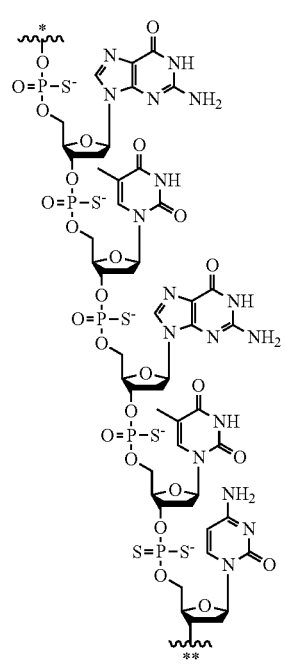

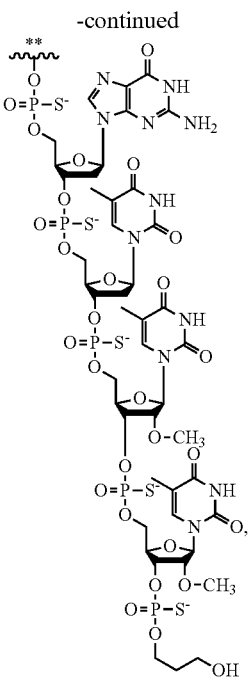

wherein ~* and ~** indicate the points of attachment within the oligonucleotide, and wherein ~† indicates the point of attachment to L;

wherein Ab comprises a heavy chain variable (VH) domain and a light chain variable (VL) domain, wherein the VH domain comprises CDR-H1, CDR-H2, and CDR-H3 sequences from a VH domain sequence (SEQ ID NO: 65)
QVQLLESGGGVVQPGGSLRLSCAASGFAFSIYDMNWVRQAPGKGLEWVS

AISSGGGTTYYADSVKGRFTISRDNAKNSLYLQMNSLRAEDTAVYYCAR

HSGYGTHWGVLFAYWGRGTLVTVSS;

wherein the VL domain comprises CDR-L1, CDR-L2, and CDR-L3 sequences from a VL domain sequence:

(SEQ ID NO: 68)
DIQMTQSPSSLSASVGDRVTITCRASQDIHGYLNWYQQKPGKAPKLLIY

YTSILHSGVPSRFSGSGSGTDFTLTISSLQPEDFATYFCQQGNTLPWTF

GQGTKLEIK.

In some embodiments of the foregoing, the VL domain further comprises an amino acid substitution at the N92 residue (numbering starting at the N-terminus of the VL domain sequence). In certain embodiments wherein the VL domain comprises an amino acid substitution at N92, the VL domain comprises an amino acid substitution N92A. In certain other embodiments wherein the VL domain comprises an amino acid substitution at N92, the VL domain comprises an amino acid substitution N92L. In still certain other embodiments wherein the VL domain comprises an amino acid substitution at N92, the VL domain comprises an amino acid substitution N92S. In some embodiments of the foregoing, the VL domain comprises a VL domain sequence shown in Table 6, e.g., SEQ ID Nos: 73-91.

In still other aspects, provided herein is a conjugate comprising a protein, at least one Q tag peptide sequence comprising a glutamine residue, and at least one immunomodulatory oligonucleotide, wherein the Q-tag peptide sequence is naturally occurring or synthetic, and wherein the immunomodulatory oligonucleotide is linked to the Q-tag via an amide bond with the glutamine residue, wherein at least one Q-tag peptide sequence is selected from the group consisting of SEQ ID NOs: 39-55.

In some embodiments, the immunomodulatory oligonucleotide has a sequence selected from the group consisting of the oligonucleotides of Table 10 and Table 12.

In some embodiments, the preferred immunomodulatory agent in the anti-CD22 conjugate is a toll-like receptor agonist selected from TLR1 agonist, TLR2 agonist, TLR3 agonist, TLR4 agonist, TLR5 agonist, TLR6 agonist, TLR7 agonist, TLR8 agonist, and TLR10 agonist. In some embodiments, the immunomodulatory agent is a toll-like receptor agonist selected from TLR7 agonist, TLR8 agonist, TLR7/TLR8 agonist.

In some embodiments, the immunomodulatory agent in the anti-CD22 conjugate is a STING pathway agonist or modulator of upstream enzymes that modulate STING (e.g., inhibitors of ENPP1, a phosphodiesterase that negatively regulates the STING pathway). STING (stimulator of interferon genes, also known as TMEM173, MITA, EMS, and MPYS) is a transmembrane protein localized to the ER that undergoes a conformational change in response to direct binding of cyclic dinucleotides (CDNs), resulting in a downstream signaling cascade involving TBK1 activation, IRF-3 phosphorylation, and production of IFN-β and other cytokines. The STING pathway in tumor-resident host antigen presenting cells is involved in the induction of a spontaneous CD8+ T cell response against tumor associated antigens. Activation of this pathway and the subsequent production of IFN-β also contributes to the anti-tumor effect. In some embodiments, the STING pathway agonist is ADU-S100. Additional STING agonists and their uses are described in, for example, US20180028553, US20170319680, US20170298139, US20060040887, US20080286296, US20120041057, US20140205653, WO2014179335, WO 2014179760, US20150056224, WO 2016096174, WO 2017011444, WO 2017027645, and WO 2017027646.

In some embodiments, the immunomodulatory agent in the anti-CD22 conjugate is a RIG-I pathway agonist. RIG-I (retinoic acid-inducible gene-I) is a member of pattern-recognition receptors that initiates a host's innate immune system to defend against pathogenic microbes in early phases of infection. There are three members of the (RIG-I)-like receptors family: RIG-I, MDA5 (melanoma differentiation factor 5), and LGP2 (laboratory of genetics and physiology 2), which are expressed in most cell and tissue types. RIG-I functions as a cytoplasmic sensor for the recognition of a variety of RNA viruses and subsequent activation of downstream signaling to drive type I IFN production and antiviral gene expressions. Activated RIG-I recruits its downstream adaptor molecule MAVS (also known as IPS-1, CARDIF, and VISA) through CARD-CARD-mediated interactions. The oligomeric RIG-I CARD assembly and the polymeric formation of MAVS, together serve as a signaling platform for protein complexes that mediate the bifurcation of signaling into two branches. One branch recruits tumor necrosis factor receptor-associated factors (TRAF)-2/6 and the receptor-interacting protein 1 to subsequently activate the IKK complex, resulting in NF-κB activation. The other branch signals through TRAF3 and activates the TANK/IKKγ/IKKε/TBK1 complex, leading to the phosphorylation and dimerization of interferon regulator factors (IRF)-3 and -7. Liu et al., *Front Immunol.* 2017, 7:662. Activation of this pathway contributes to the antitumor effect. In some embodiments, the RIG-I pathway agonist is RGT100. RIG-I agonists and their uses are described in, for example, US20170057978, US20170258897, U.S. Pat. Nos. 9,381,208, 9,738,680, 9,650,427, WO2017173427, and WO2017011622.

III. Proteins with Q-Tag

In one aspect, provided herein is a protein comprising at least one Q tag peptide sequence comprising a glutamine residue. In some embodiments, the Q tag peptide sequence is naturally occurring or synthetic. In certain embodiments, the Q tag peptide sequence is an internal reactive glutamine exposed by an amino acid substitution. In further embodiments, the Q tag is fused to the C-terminus of the heavy chain of the protein. In still further embodiments, at least one of the at least one Q tag peptide sequences is elected from the group consisting of SEQ ID NOs: 39-55.

In some embodiments the protein is an antibody or an antigen-binding fragment thereof. In certain embodiments, the antibody comprises a light chain variable domain (VL) and a heavy chain variable domain (VH), and wherein VH comprises the sequence SEQ ID NO: 56; and VL comprises the sequence SEQ ID NO: 57.

In another aspect of the present disclosure, provided herein are antibodies of formula (B)

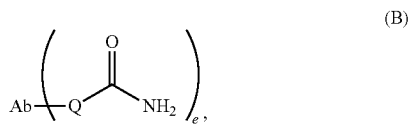

(B)

wherein:
 each Q is independently a Q-tag comprising a peptide sequence with at least one glutamine residue;
 Ab is an antibody or antigen-binding fragment thereof; and
 e is an integer from 1 to 20.

The antibodies of formula (B) may be precursors to the antibody-oligonucleotide conjugates of formula (A) as described above. Accordingly, the properties and embodiments of the antibodies as described in the previous aspect of formula (A) may be the same or different from the properties and/or embodiments of the antibodies of formula (B).

In some embodiments of the present aspect, the antibody or fragment thereof is a monoclonal antibody or fragment thereof. In certain embodiments, the antibody or fragment thereof is a Fab, F(ab')2, Fab'-SH, Fv, scFv, single domain, single heavy chain, or single light chain antibody or antibody fragment. In other embodiments, the antibody or fragment thereof is a humanized, human, or chimeric antibody or fragment thereof. In certain embodiments, which may be combined with any of the preceding embodiments, the antibody or fragment thereof specifically binds human CD22.

In some embodiments, wherein the antibody comprises a heavy chain variable (VH) domain and a light chain variable (VL) domain, wherein the VH domain comprises CDR-H1, CDR-H2, and CDR-H3 sequences from a VH domain sequence selected from the group consisting of:

(SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GYGTHWGVLFAYWGRGTLVTVSS, (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS, (SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GYGTHWGVLFAYWGRGTLVTVSS,
and (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.

The antibody of any one of embodiments 87 to 90, wherein the antibody comprises a heavy chain variable (VH) domain and a light chain variable (VL) domain, and wherein the VH domain comprises an amino acid sequence selected from the group consisting of:

(SEQ ID NO: 64)
EVQLVESGGGLVQPGGSLRLSCAASGFAFSIYDMSWVRQAPGKGLEWVAY

ISSGGGTTYYPDTVKGRFTISRDNSKNTLYLQMNSLRAEDTAVYYCARHS

GYGTHWGVLFAYWGRGTLVTVSS, (SEQ ID NO: 65)
QVQLLESGGGVVQPGGSLRLSCAASGFAFSIYDMNWVRQAPGKGLEWVSA

ISSGGGTTYYADSVKGRFTISRDNAKNSLYLQMNSLRAEDTAVYYCARHS

GYGTHWGVLFAYWGRGTLVTVSS, (SEQ ID NO: 66)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCARHS

GYGTHWGVLFAYWGRGTLVTVSS,
and (SEQ ID NO: 67)
QVQLQESGPGLVKPSDTLSLTCTVSGFAFSIYDMSWIRQPPGKGLEWIAY

ISSGGGTTYYNPSLKSRVTISVDTSKNQFSLKLSSVTAADTAVYYCARHS

GYGTHWGVLFAYWGRGTLVTVSS.

The antibody of any one of embodiments 87 to 93, wherein the antibody comprises a heavy chain variable (VH) domain and a light chain variable (VL) domain, wherein the VL domain comprises CDR-L1, CDR-L2, and CDR-L3 sequences from a VL domain sequence selected from the group consisting of:

(SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK,

```
                                          (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

TSILHSGIPARFSGSGPGTDFTLTISSLEPEDFAVYYCQQGNTLPWTFGG

GTKLEIK,
and (SEQ ID NO: 72)
DIVMTQTPLSLSVTPGQPASISCRASQDIFIGYLNWYQQKPGQSPQLLIY

YTSILHSGVPDRFSGSGSGTDFTLKISRVEAEDVGVYFCQQGNTLPWTFG

GGTKLEIK.
```

In some embodiments of the foregoing, the VL domain further comprises an amino acid substitution at residue N92. In certain embodiments of the foregoing, the VL domain comprises an amino acid substitution at residue N92 selected from the group consisting of N92A, N92L and N92S.

In some embodiments, the antibody comprises a heavy chain variable (VH) domain and a light chain variable (VL) domain, wherein the VL domain an amino acid sequence selected from the group consisting of:

```
                                          (SEQ ID NO: 68)
DIQMTQSPSSLSASVGDRVTITCRASQDIHGYLNWYQQKPGKAPKLLIYY

TSILHSGVPSRFSGSGSGTDFTLTISSLQPEDFATYFCQQGNTLPWTFGQ

GTKLEIK, (SEQ ID NO: 69)
DIQMTQSPSSVSASVGDRVTITCRASQDIHGYLAWYQQKPGKAPKLLIYY

TSSLQSGVPSRFSGSGSGTDFTLTISSLQPEDFATYYCQQGNTLPWTFGQ

GTKLEIK, (SEQ ID NO: 70)
DIQMTQSPSSLSASVGDRVTITCRASQSISSYLNWYQQKPGKAPKLLIYA

ASSLQSGVPSRFSGSGSGTDFTLTISSLQPEDFATYYCQQGNTLPWTFGQ

GTKLEIK, (SEQ ID NO: 71)
EIVLTQSPATLSLSPGERATLSCRASQDIHGYLNWYQQKPGQAPRLLIYY

TSILHSGIPARFSGSGPGTDFTLTISSLEPEDFAVYYCQQGNTLPWTFGG

GTKLEIK,
and (SEQ ID NO: 72)
DIVMTQTPLSLSVTPGQPASISCRASQDIFIGYLNWYQQKPGQSPQLLIY

YTSILHSGVPDRFSGSGSGTDFTLKISRVEAEDVGVYFCQQGNTLPWTFG

GGTKLEIK.
```

In some embodiments, the antibody comprises an Fc region. In certain embodiments wherein the antibody comprises an Fc region, the Fc region is a human Fc region selected from the group consisting of an IgG1 Fc region, an IgG2 Fc region, and an IgG4 Fc region.

In certain embodiments of the present aspect, the Fc region is:
(a) a human IgG1 Fc region comprising L234A, L235A, and/or G237A substitutions, amino acid position numbering according to EU index;
(b) a human IgG2 Fc region comprising A330S and/or P331S substitutions, amino acid position numbering according to EU index; or
(c) a human IgG4 Fc region comprising S228P and/or L235E substitutions, amino acid position numbering according to EU index.

In some embodiments, the Fc region further comprises an N297A substitution, amino acid position numbering according to EU index. In other embodiments, the Fc region further comprises a D265A substitution, amino acid position numbering according to EU index. In yet further embodiments, the antibody comprises a human lambda light chain. In other embodiments, the antibody comprises a human kappa light chain.

In some embodiments, at least one Q-tag is attached to the heavy chain of the antibody. In certain embodiments, at least one Q-tag is fused to the C-terminus of the heavy chain of the antibody. In other embodiments, at least one Q-tag is attached to the light chain of the antibody. In still further embodiments, at least one Q-tag is within the Fc domain.

In some embodiments of the present aspect, the antibody is linked to from 1 to 20 Q-tags Q. In certain embodiments, the number of Q-tags linked to the antibody/conjugate is an integer of about 1, about 2, about 3, about 4, about 5, about 6, about 7 about 8, about 9, about 10, about 11 about 12, about 13, about 14, about 15, about 16, about 17, about 18, about 19, or about 20. In certain other embodiments, 1 or 2 Q-tags is/are linked to the antibody or antigen-binding fragment. In yet other embodiments, the number of Q-tags linked to the antibody/conjugate is an integer from 1 to 10, from 10 to 20, from 5 to 10, from 10 to 15, from 15 to 20, or from 1 to 5.

In still further embodiments of the present aspect, which may be combined with any of the preceding embodiments, each Q tag independently comprises or is a peptide sequence selected from the group consisting of SEQ ID NOs: 39-55. In some embodiments, each Q tag independently comprises or is a peptide sequence selected from the group consisting of the peptide sequences of Table 3. In other embodiments of the present aspect, each Q tag independently comprises or is a peptide sequence selected from the group consisting of SEQ ID NOs: 40-55. In yet other embodiments, each Q tag independently comprises or is a peptide sequence selected from the group consisting of SEQ ID NOs: 47-49. In some embodiments, the Q-tag comprises LLQGG (SEQ ID NO:172), GGGLLQGG (SEQ ID NO:173), RPQGF (SEQ ID NO:47), or RPQGFGPP (SEQ ID NO:49). In some embodiments of the present aspect, each Q is independently a Q-tag comprising a peptide sequence RPQGF (SEQ ID NO:47). In certain embodiments, each Q-tag comprising a peptide sequence RPQGF (SEQ ID NO:47) is selected from the group consisting of RPQGF (SEQ ID NO:47), RPQGFPP (SEQ ID NO:48), and RPQGFGPP (SEQ ID NO:49). In certain embodiments, each Q tag independently comprises or is a peptide sequence RPQGFGPP (SEQ ID NO:49).

IV. Immunomodulating Polynucleotides

In yet another aspect, provided herein is an immunomodulating polynucleotide of formula (C), (C)

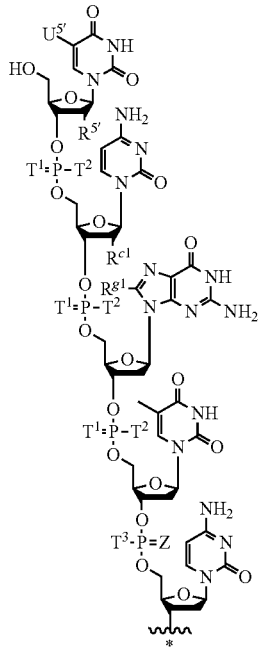

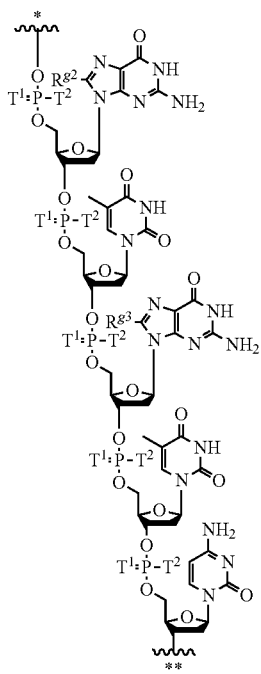

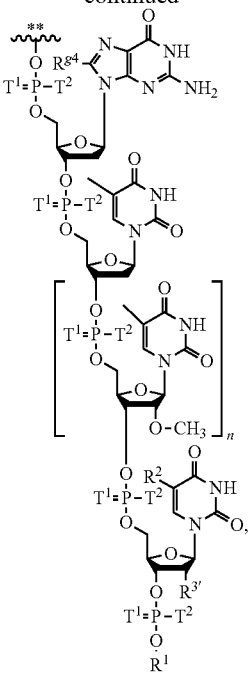

wherein
~* and ~** indicate the points of attachment within the oligonucleotide;
each $T^1$ is independently O or S;
each $T^2$ is $S^-$;
$T^3$ is a group $$\text{[group with OCH}_2\text{CH}_2\text{OCH}_2\text{CH}_2\text{OCH}_2\text{CH}_2\text{NH}_2\text{]}$$

wherein ~ indicates the point of attachment to the rest of the oligonucleotide;
Z is O or S;
$U^{5'}$ is —H or halogen;
$R^{5'}$ is —H or methoxy;
$R^{c1}$ is —H or methoxy;
$R^{g1}$, $R^{g2}$, $R^{g3}$, and $R^{g4}$ are H or oxo, provided that at least one of $R^{g1}$, $R^{g2}$, $R^{g3}$, and $R^{g4}$ is oxo and wherein the carbon to which the oxo is attached has a single bond to the ring nitrogen at the 7-position);
$R^{3'}$ is methoxy or 2-methoxyethoxy;
$R^1$ is —(CH$_2$)$_3$—OH;
$R^2$ is —H or methyl; and
n is an integer from 0 to 2,
or a pharmaceutically acceptable salt thereof.

In some embodiments of the present aspect, $U^{5'}$ is —H In other embodiments, $U^{5'}$ is halogen. In certain embodiments, $U^{5'}$ is iodo or bromo. In some embodiments of the present aspect, the immunomodulatory oligonucleotide of formula (C) is an immunomodulatory oligonucleotide of formula (C'). In other embodiments of the present aspect, the immunomodulatory oligonucleotide of formula (C) is an immunomodulatory oligonucleotide of formula (C").

In some embodiments of the present aspect, provided herein is an immunomodulatory oligonucleotide of formula (C')

(C')

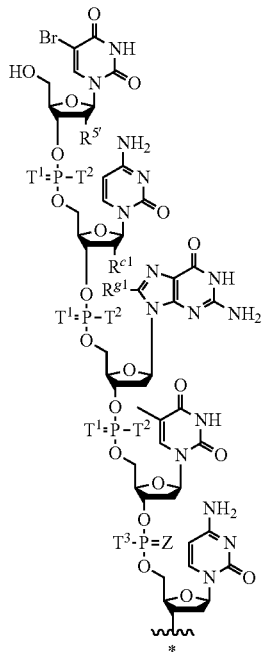

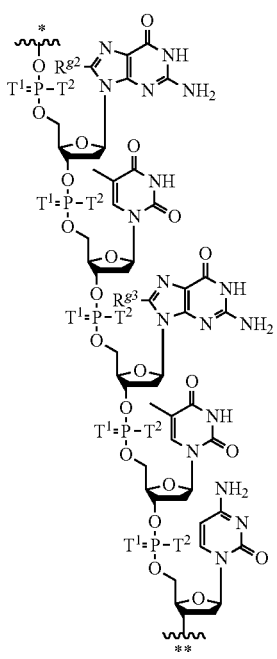

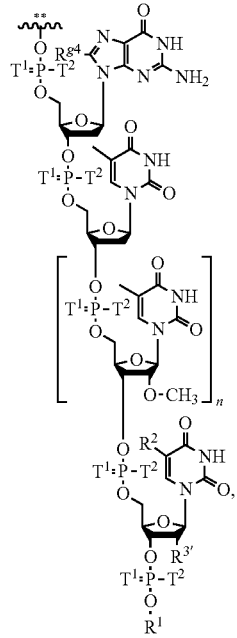

wherein

~* and ~** indicate the points of attachment within the oligonucleotide;

each $T^1$ is independently O or S;

each $T^2$ is $S^-$;

$T^3$ is a group wherein ~ indicates the point of attachment to the rest of the oligonucleotide;

Z is O or S;

$R^{5'}$ is —H or methoxy;

$R^{c1}$ is —H or methoxy;

$R^{g1}$, $R^{g2}$, $R^{g3}$, and $R^{g4}$ are H or oxo, provided that at least one of $R^{g1}$, $R^{g2}$, $R^{g3}$, and $R^{g4}$ is oxo and wherein the carbon to which the oxo is attached has a single bond to the ring nitrogen at the 7-position);

$R^{3'}$ is methoxy or 2-methoxyethoxy;

$R^1$ is —(CH$_2$)$_3$—OH;

$R^2$ is —H or methyl; and n is an integer from 0 to 2, or a pharmaceutically acceptable salt thereof.

In other embodiments of the present aspect, provided herein is an immunomodulatory oligonucleotide of formula (C'')

(C'')

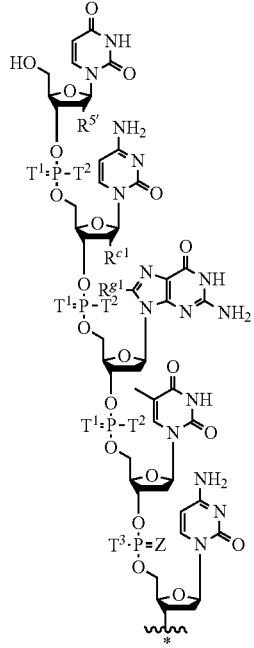

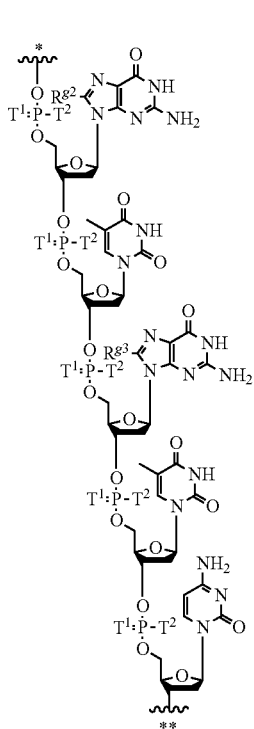

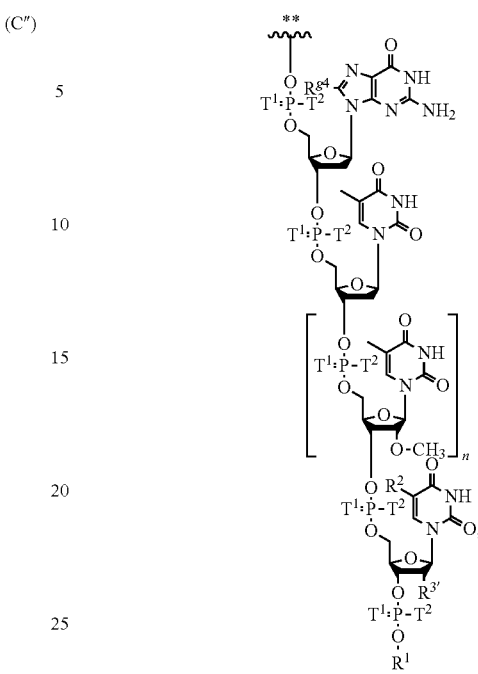

wherein

~* and ~** indicate the points of attachment within the oligonucleotide;

each $T^1$ is independently O or S;

each $T^2$ is $S^-$;

$T^3$ is a group

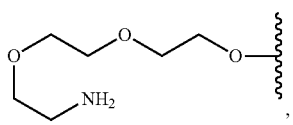 [SMILES: *OCCOCCOCCN]

wherein ~ indicates the point of attachment to the rest of the oligonucleotide;

Z is O or S;

$R^{5'}$ is —H or methoxy;

$R^{c1}$ is —H or methoxy;

$R^{g1}$, $R^{g2}$, $R^{g3}$, and $R^{g4}$ are H or oxo, provided that at least one of $R^{g1}$, $R^{g2}$, $R^{g3}$, and $R^{g4}$ is oxo and wherein the carbon to which the oxo is attached has a single bond to the ring nitrogen at the 7-position);

$R^{3'}$ is methoxy or 2-methoxyethoxy;

$R^1$ is —$(CH_2)_3$—OH;

$R^2$ is —H or methyl; and n is an integer from 0 to 2, or a pharmaceutically acceptable salt thereof.

In some embodiments of the present aspect, provided herein is an immunomodulatory oligonucleotide of formula (C')

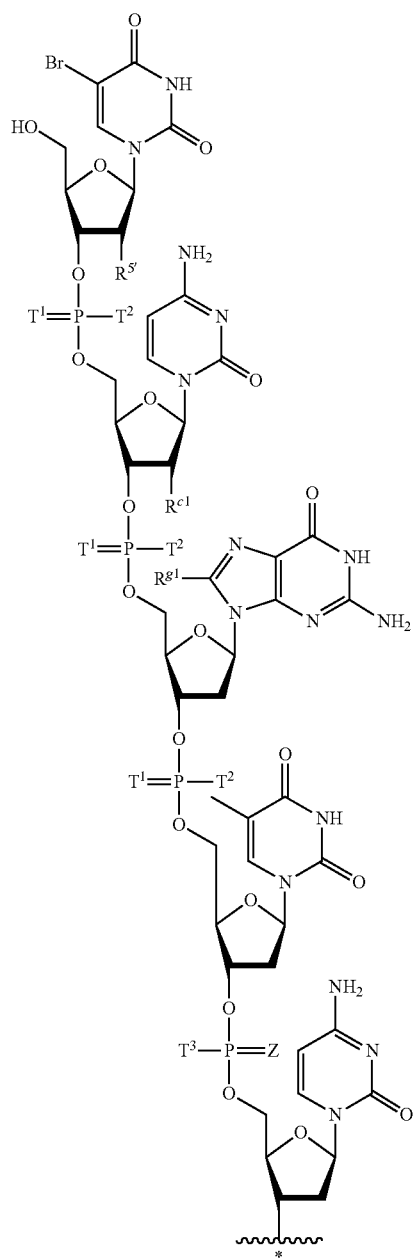
(C')
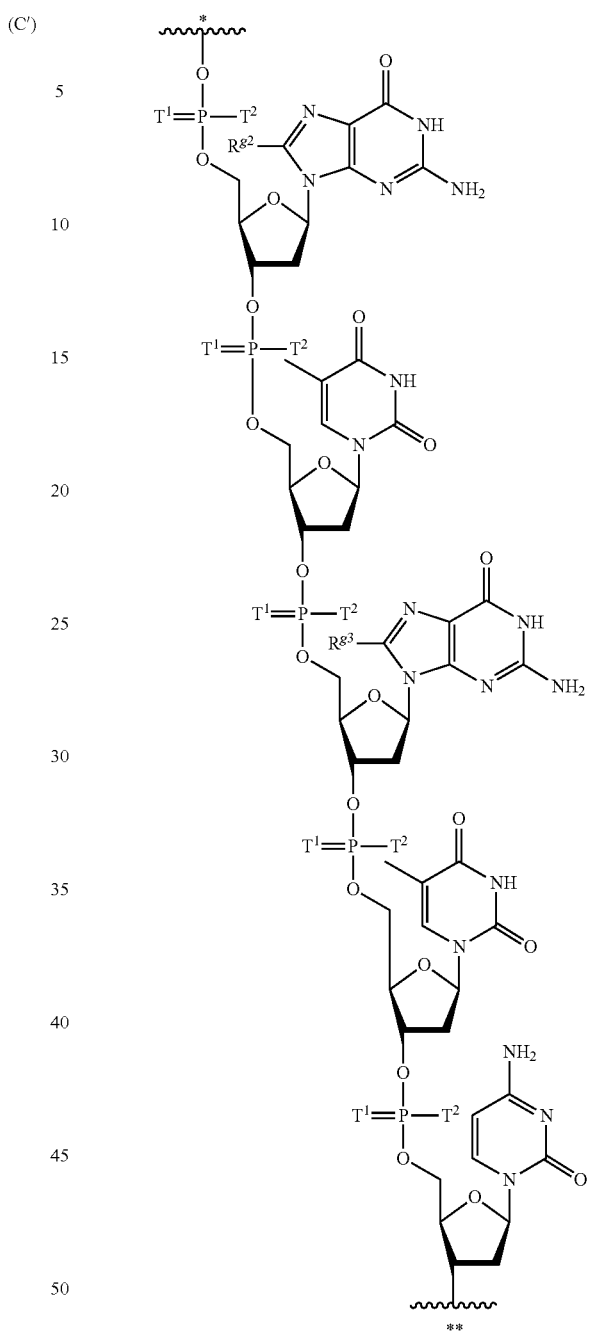

-continued

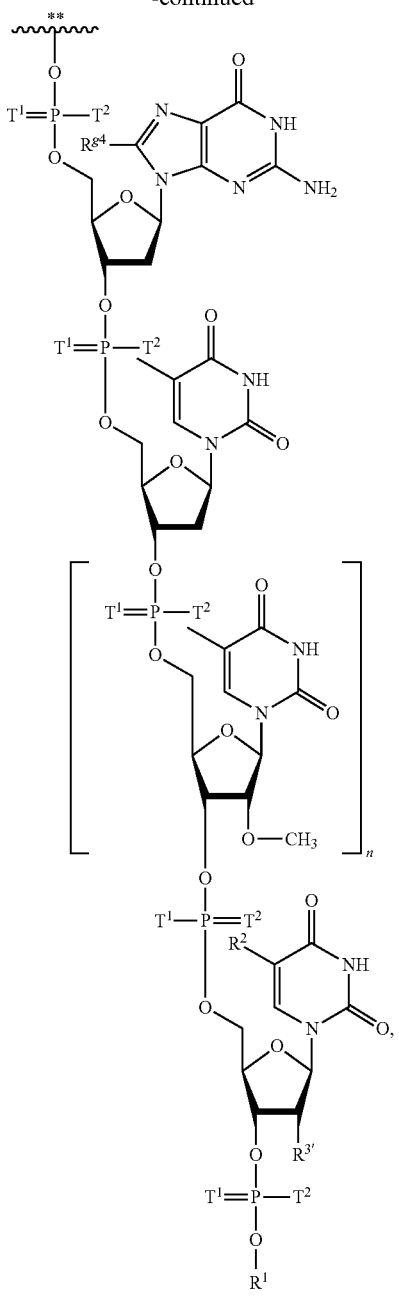

wherein:
  ~* and ~** indicate the points of attachment within the oligonucleotide;
  each $T^1$ is independently O or S;
  each $T^2$ is $S^-$;
  $T^3$ is a group

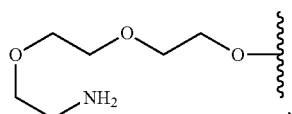

wherein ~ indicates the point of attachment to the rest of the oligonucleotide;

Z is O or S;
$R^{5'}$ is —H or methoxy;
$R^{c1}$ is —H or methoxy;
$R^{g1}$, $R^{g2}$, $R^{g3}$, and $R^{g4}$ are H;
$R^{3'}$ is methoxy;
$R^1$ is —(CH$_2$)$_3$—OH;
$R^2$ is —H or methyl; and
n is an integer from 0 to 2,
or a pharmaceutically acceptable salt thereof.

In other embodiments of the present aspect, provided herein is an immunomodulatory oligonucleotide of formula (C″)

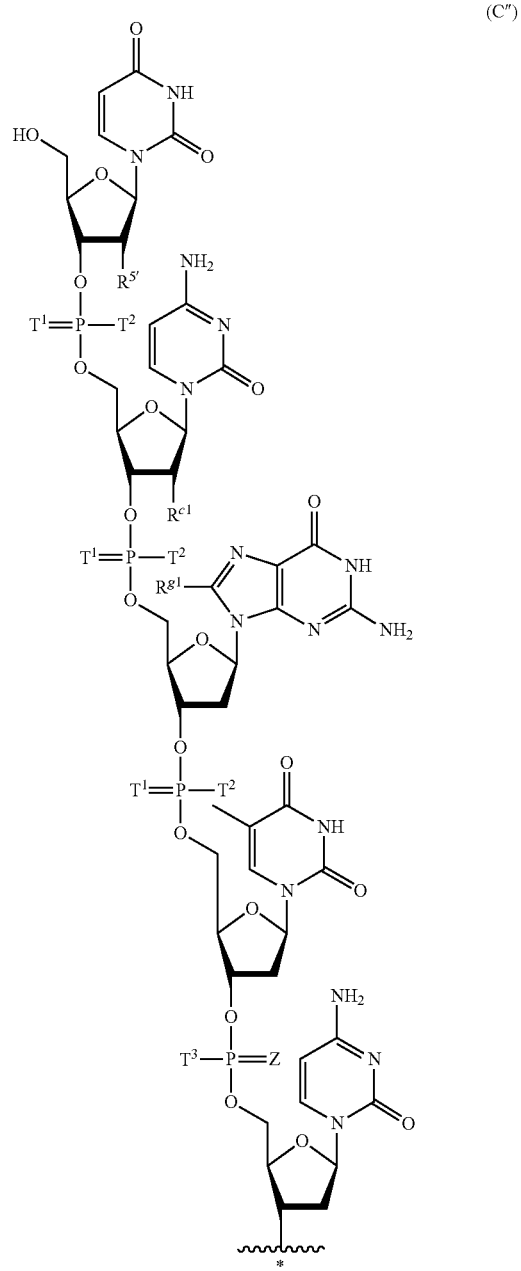

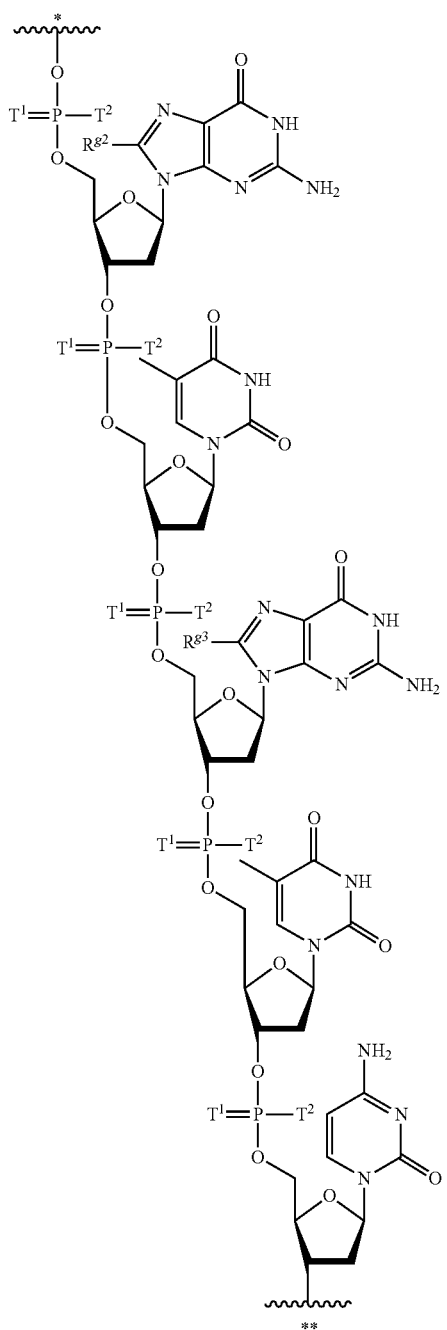
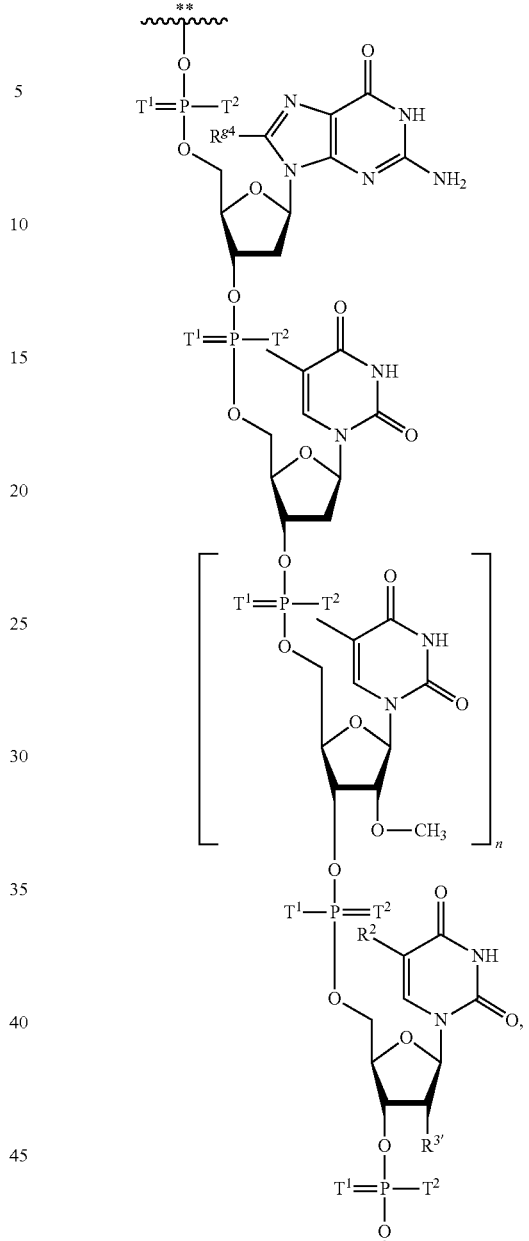
wherein:
⁓* and ⁓** indicate the points of attachment within the oligonucleotide;
each $T^1$ is independently O or S;
each $T^2$ is $S^-$;
$T^3$ is a group
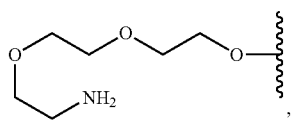 [SMILES: *OCCOCCOCCN]
wherein ⁓ indicates the point of attachment to the rest of the oligonucleotide;

Z is O or S;
R$^{5'}$ is —H or methoxy;
R$^{c1}$ is —H or methoxy;
R$^{g1}$, R$^{g2}$, R$^{g3}$, and R$^{g4}$ are H;
R$^{3'}$ is methoxy;
R$^1$ is —(CH$_2$)$_3$—OH;
R$^2$ is —H or methyl; and
n is an integer from 0 to 2,
or a pharmaceutically acceptable salt thereof.

In some embodiments of the present aspect, Z is S. In additional embodiments, the oligonucleotide comprises at least one pair of geminal T$^1$ and T$^2$ wherein T$^1$ is S and T$^2$ is S$^-$. In certain embodiments, the oligonucleotide comprises at least two pairs of geminal T$^1$ and T$^2$ wherein T$^1$ is S and T$^2$ is S$^-$. The pair(s) of geminal T$^1$ and T$^2$ wherein T$^1$ is S and T$^2$ is S$^-$ may also be described as phosphorodithioate linkages.

It should be recognized that in some instances wherein the oligonucleotide has at least one pair of geminal T$^1$ and T$^2$ wherein T$^1$ is S and T$^2$ is S$^-$, the phosphorodithioate linkage(s) may be further described in terms of the position within the oligonucleotide at which the linkage is located. The position of the linkage may be characterized, for example, as being between two nucleoside residues, e.g., between the first and second nucleoside residues (or between nucleoside residues 1 and 2) as counted from the 5' end of the oligonucleotide. Alternatively, the position of the linkage may be described as being located at the 3'-position of a given nucleoside residue, e.g., on the internucleoside linker immediately following the specified nucleoside residue or the 3'-position of the '3-terminal residue.

In some embodiments wherein the oligonucleotide comprises at least one pair of geminal T$^1$ and T$^2$ wherein T$^1$ is S and T$^2$ is S$^-$, and wherein n is 0, the at least one phosphorodithioate linkage is between nucleoside residues 1 and 2, between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, between nucleoside residues 10 and 11, or between nucleoside residues 11 and 12. In some embodiments wherein the oligonucleotide comprises at least one pair of geminal T$^1$ and T$^2$ wherein T$^1$ is S and T$^2$ is S$^-$, and wherein n is 0, the at least one phosphorodithioate linkage is located at the 3'-position of nucleoside residue 1, nucleoside residue 2, nucleoside residue 3, nucleoside residue 5, nucleoside residue 6, nucleoside residue 7, nucleoside residue 8, nucleoside residue 9, nucleoside residue 10, nucleoside residue 11, nucleoside residue 12, or nucleoside residue 13.

In some embodiments wherein the oligonucleotide comprises at least one pair of geminal T$^1$ and T$^2$ wherein T$^1$ is S and T$^2$ is S$^-$, and wherein n is 1, the at least one phosphorodithioate linkage is between nucleoside residues 1 and 2, between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, between nucleoside residues 10 and 11, between nucleoside residues 11 and 12, or between nucleoside residues 12 and 13. In some embodiments wherein the oligonucleotide comprises at least one pair of geminal T$^1$ and T$^2$ wherein T$^1$ is S and T$^2$ is S$^-$, and wherein n is 0, the at least one phosphorodithioate linkage is located at the 3'-position of nucleoside residue 1, nucleoside residue 2, nucleoside residue 3, nucleoside residue 5, nucleoside residue 6, nucleoside residue 7, nucleoside residue 8, nucleoside residue 9, nucleoside residue 10, nucleoside residue 11, nucleoside residue 12, nucleoside residue 13, or nucleoside residue 14.

In some embodiments wherein the oligonucleotide comprises at least one pair of geminal T$^1$ and T$^2$ wherein T$^1$ is S and T$^2$ is S$^-$, and wherein n is 1, the at least one phosphorodithioate linkage is between nucleoside residues 1 and 2, between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, between nucleoside residues 10 and 11, between nucleoside residues 11 and 12, or between nucleoside residues 12 and 13. In some embodiments wherein the oligonucleotide comprises at least one pair of geminal T$^1$ and T$^2$ wherein T$^1$ is S and T$^2$ is S$^-$, and wherein n is 1, the at least one phosphorodithioate linkage is located at the 3'-position of nucleoside residue 1, nucleoside residue 2, nucleoside residue 3, nucleoside residue 5, nucleoside residue 6, nucleoside residue 7, nucleoside residue 8, nucleoside residue 9, nucleoside residue 10, nucleoside residue 11, nucleoside residue 12, nucleoside residue 13, or nucleoside residue 14.

In some embodiments wherein the oligonucleotide comprises at least one pair of geminal T$^1$ and T$^2$ wherein T$^1$ is S and T$^2$ is S$^-$, and wherein n is 2, the at least one phosphorodithioate linkage is between nucleoside residues 1 and 2, between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, between nucleoside residues 10 and 11, between nucleoside residues 11 and 12, between nucleoside residues 12 and 13, or between residues 13 and 14. In some embodiments wherein the oligonucleotide comprises at least one pair of geminal T$^1$ and T$^2$ wherein T$^1$ is S and T$^2$ is S$^-$, and wherein n is 2, the at least one phosphorodithioate linkage is located at the 3'-position of nucleoside residue 1, nucleoside residue 2, nucleoside residue 3, nucleoside residue 5, nucleoside residue 6, nucleoside residue 7, nucleoside residue 8, nucleoside residue 9, nucleoside residue 10, nucleoside residue 11, nucleoside residue 12, nucleoside residue 13, nucleoside residue 14, or residue 15.

In still other embodiments wherein the oligonucleotide has at least two phosphorodithioate linkages or comprises at least two pairs of geminal T$^1$ and T$^2$ wherein T$^1$ is S and T$^2$ is S$^-$, the positions of one or both phosphorodithioate linkages or pairs of T$^1$ and T$^2$ may be specified. It should be recognized that the positions of one or both phosphorodithioate linkages may be independently varied.

In some embodiments of the present aspect, provided herein is an immunomodulatory oligonucleotide of formula (C')

165
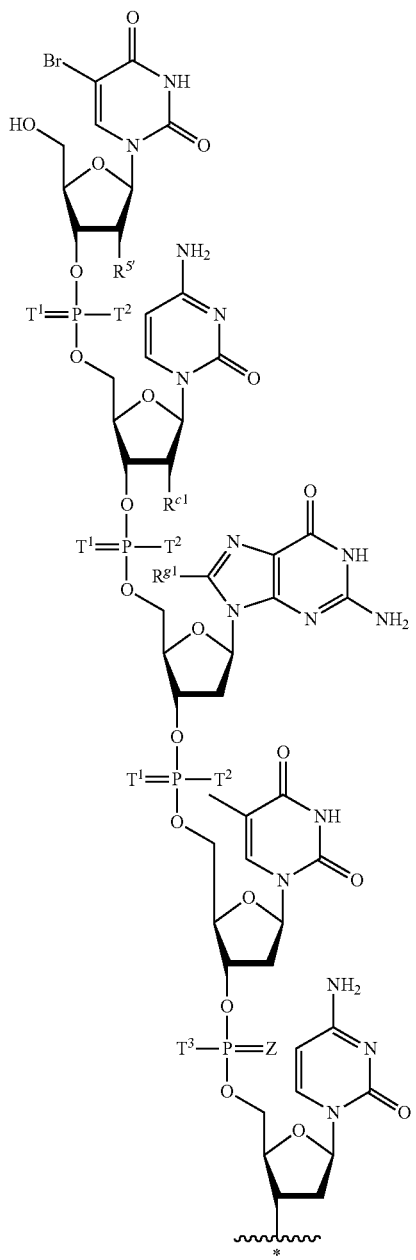
(C')
166
-continued
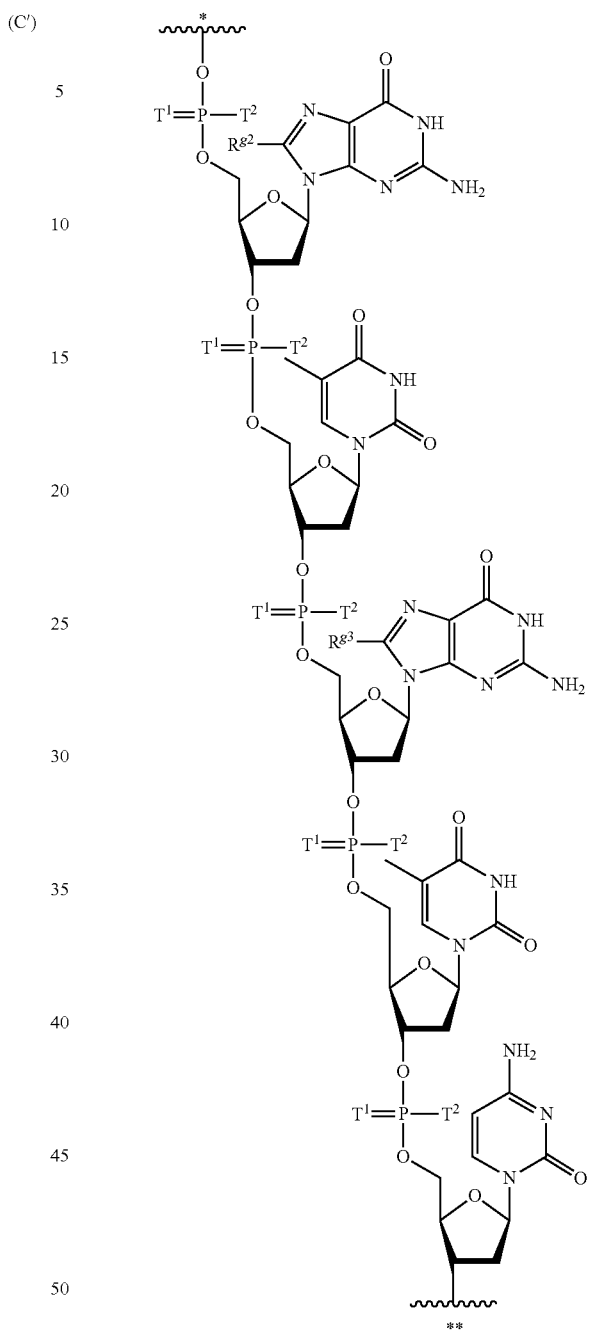

-continued

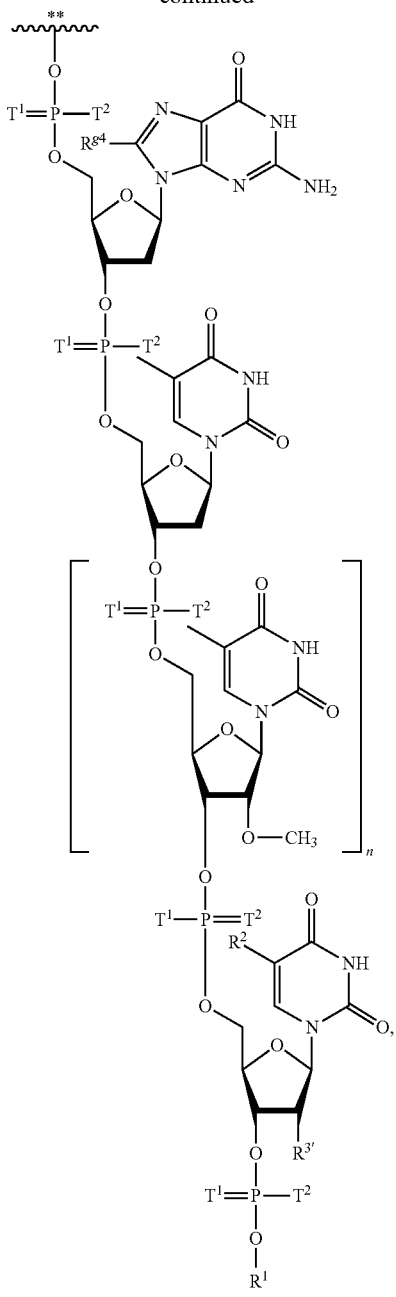

wherein:
⁓* and ⁓** indicate the points of attachment within the oligonucleotide;
each T¹ is independently O or S;
each T² is S⁻;
T³ is a group

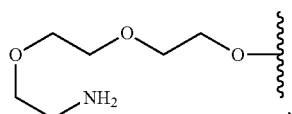

wherein ⁓ indicates the point of attachment to the rest of the oligonucleotide;

Z is O or S;
R⁵' is —H or methoxy;
R^{c1} is —H or methoxy;
R^{g1}, R^{g2}, R^{g3}, and R^{g4} are H;
R³' is methoxy;
R¹ is —(CH₂)₃—OH;
R² is —H or methyl; and
n is an integer from 0 to 2,
or a pharmaceutically acceptable salt thereof.

In other embodiments of the present aspect, provided herein is an immunomodulatory oligonucleotide of formula (C″)

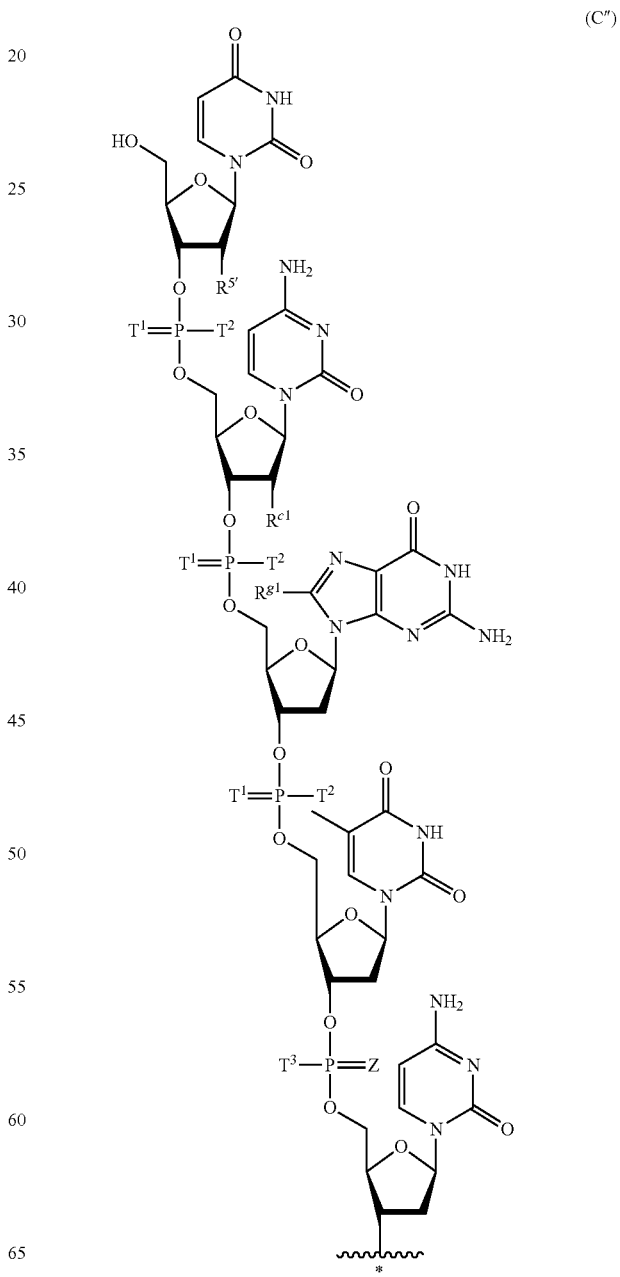

169
-continued
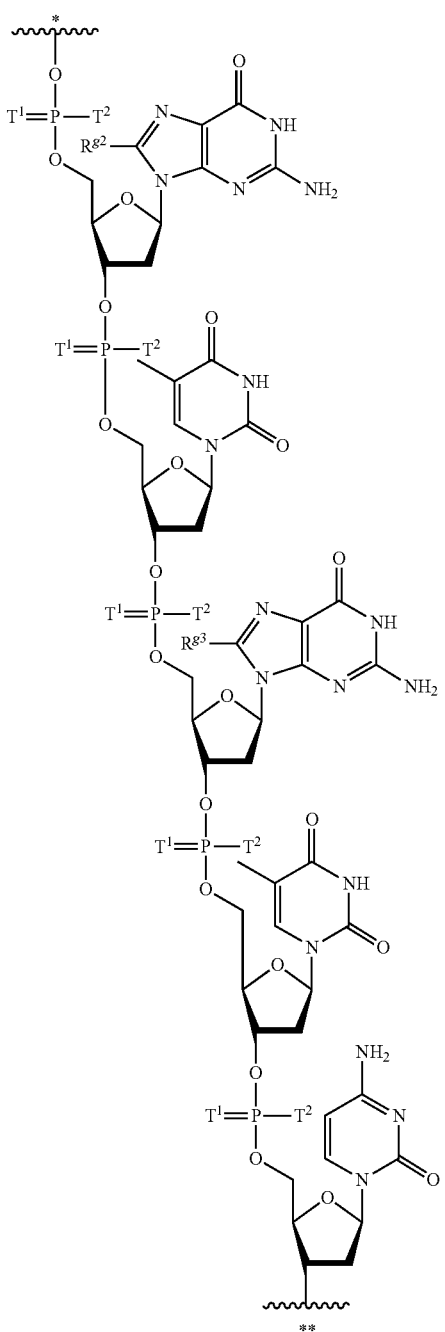
170
-continued
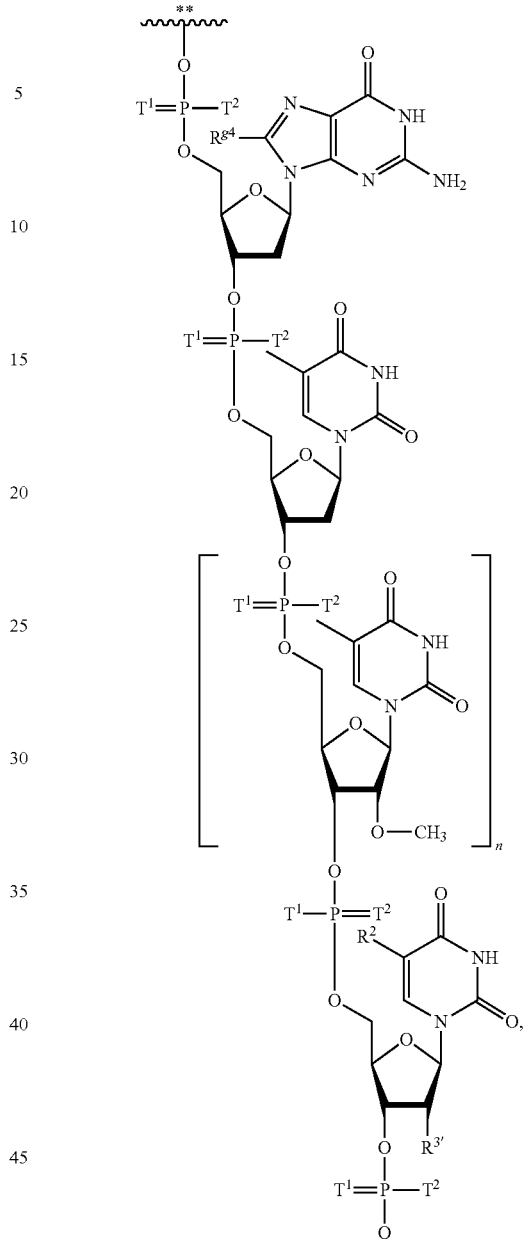
wherein:
⌇* and ⌇** indicate the points of attachment within the oligonucleotide;
each $T^1$ is independently O or S;
each $T^2$ is $S^-$;
$T^3$ is a group
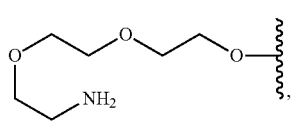 [SMILES: *OCCOCCOCCN]
wherein ⌇ indicates the point of attachment to the rest of the oligonucleotide;

Z is O or S;
$R^{5'}$ is —H or methoxy;
$R^{c1}$ is —H or methoxy;
$R^{g1}$, $R^{g2}$, $R^{g3}$, and $R^{g4}$ are H;
$R^{3'}$ is methoxy;
$R^1$ is —(CH$_2$)$_3$—OH;
$R^2$ is —H or methyl; and
n is an integer from 0 to 2,
or a pharmaceutically acceptable salt thereof.

In some embodiments of the present aspect, Z is S. In additional embodiments, the oligonucleotide comprises at least one pair of geminal $T^1$ and $T^2$ wherein $T^1$ is S and $T^2$ is $S^-$. In certain embodiments, the oligonucleotide comprises at least two pairs of geminal $T^1$ and $T^2$ wherein $T^1$ is S and $T^2$ is $S^-$.

In still yet another embodiment of the present aspect, provided herein is an oligonucleotide of formula (C)

(C′)

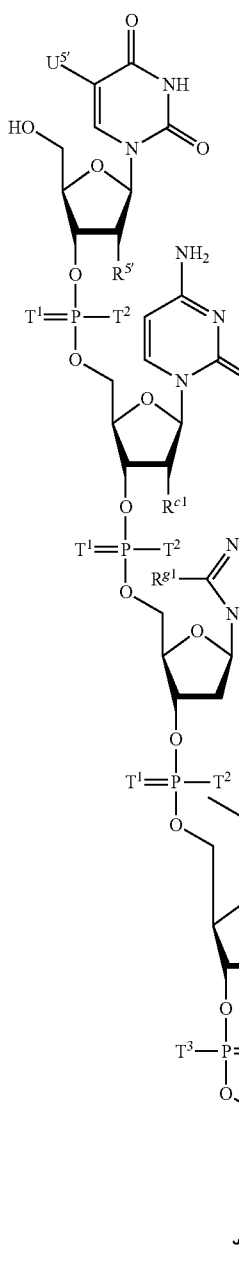

-continued

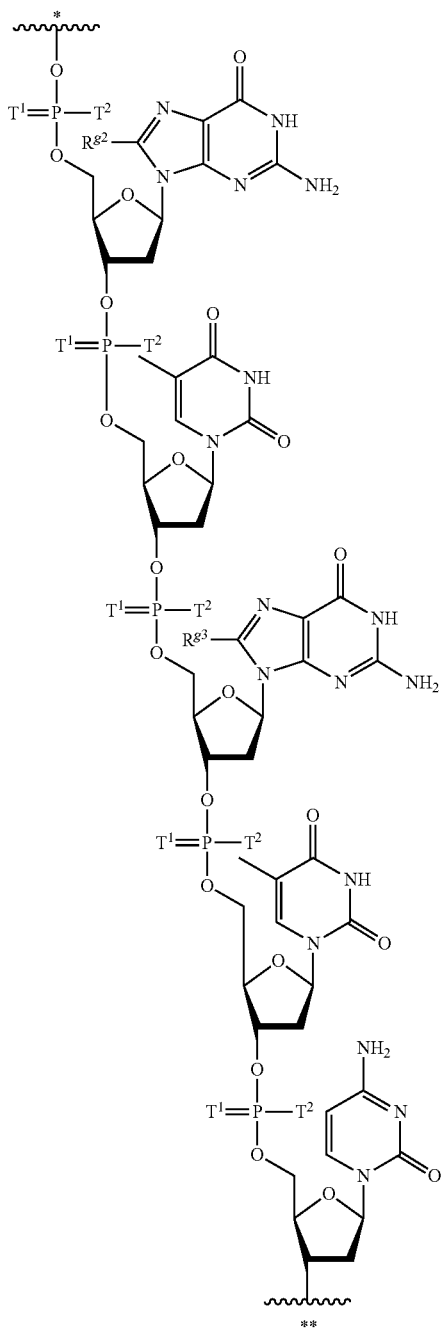

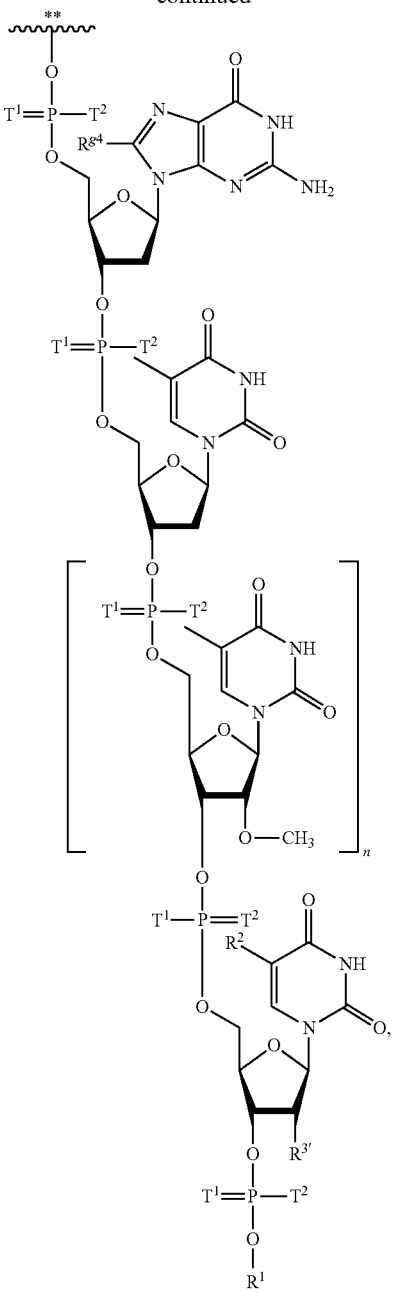

wherein ∼* and ∼** indicate the points of attachment within the oligonucleotide;
each $T^1$ is independently O or S;
each $T^2$ is $S^-$;
provided that the oligonucleotide comprises at least one pair of geminal $T^1$ and $T^2$ wherein $T^1$ is S and $T^2$ is S, $T^3$ is a group

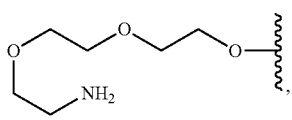 [SMILES: *OCCOCCOCCN]

wherein ∼ indicates the point of attachment to the rest of the oligonucleotide;

Z is O or S;
$U^{5'}$ is —H or halogen;
$R^{5'}$ is —H;
$R^{c1}$ is —H;
$R^{g1}$, $R^{g2}$, $R^{g3}$, and V are H;
$R^{3'}$ is methoxy;
$R^1$ is —$(CH_2)_3$—OH;
$R^2$ is -methyl; and
n is 1,
or a pharmaceutically acceptable salt thereof.

In some embodiments of any of the foregoing, the at least one pair of geminal $T^1$ and $T^2$ wherein $T^1$ is S and $T^2$ is S is between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11. In still other embodiments of the foregoing, the oligonucleotide comprises at least two pairs of of geminal $T^1$ and $T^2$ wherein $T^1$ is S and $T^2$ is S, and wherein the at least two pairs of of geminal $T^1$ and $T^2$ wherein $T^1$ is S and $T^2$ is S are between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11.

In some embodiments, the oligonucleotide comprises one or two pairs of geminal $T^1$ and $T^2$ wherein $T^1$ is S and $T^2$ is S, and wherein the one or two pairs of geminal $T^1$ and $T^2$ are between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11. In certain embodiments, the oligonucleotide comprises one pair of geminal $T^1$ and $T^2$ wherein $T^1$ is S and $T^2$ is S, and wherein the pair of geminal $T^1$ and $T^2$ is between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11. In certain other embodiments, the oligonucleotide comprises two pairs of geminal $T^1$ and $T^2$ wherein $T^1$ is S and $T^2$ is S, and wherein the two pairs of geminal $T^1$ and $T^2$ wherein $T^1$ is S and $T^2$ is S are between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11.

In some embodiments, $R^{5'}$ is H. In other embodiments, $R^{5'}$ is methoxy. In some embodiments, $R^{c1}$ is H. In yet other embodiments, $R^{c1}$ is methoxy. In still further embodiments, $R^2$ is methyl. In still other embodiments, $R^2$ is H. In yet other additional embodiments, which may be combined with any of the preceding embodiments, $T^3$ is

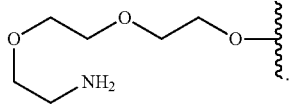 [SMILES: *OCCOCCOCCN]

In still other embodiments, $T^3$ is

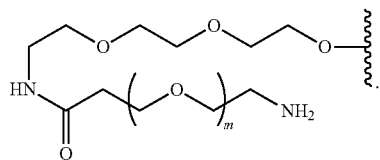

In certain embodiments, m is an integer from 20 to 25.

In another aspect, the immunomodulating oligonucleotide of formula (C) is an oligonucleotide selected from the group consisting of the oligonucleotides of Table 9 and Table 10, or a pharmaceutically acceptable salt thereof. In still other embodiments, the immunomodulating oligonucleotide of formula (C) is an oligonucleotide selected from the group consisting of the oligonucleotides of Table 10, or a pharmaceutically acceptable salt thereof.

TABLE 9-continued

Modified Oligonucleotide Structures (with PEG₃NH₂)

| Cmpd # | Structure |
|---|---|
| 2.1a | (structure) |
| 2.2a | (structure) |

TABLE 9-continued

Modified Oligonucleotide Structures (with PEG₃NH₂)

| Cmpd # | Structure |
|---|---|

TABLE 9-continued

Modified Oligonucleotide Structures (with PEG₃NH₂)

| Cmpd # | Structure |
|---|---|
| 2.3a | 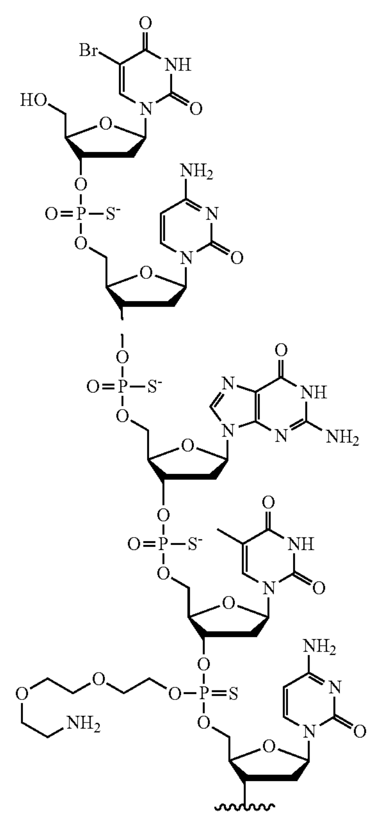 |

TABLE 9-continued

Modified Oligonucleotide Structures (with PEG₃NH₂)

| Cmpd # | Structure |
|---|---|
| 2.4a | (structure) |

183
TABLE 9-continued
Modified Oligonucleotide Structures (with PEG3NH2)
| Cmpd # | Structure |
|---|---|
| | 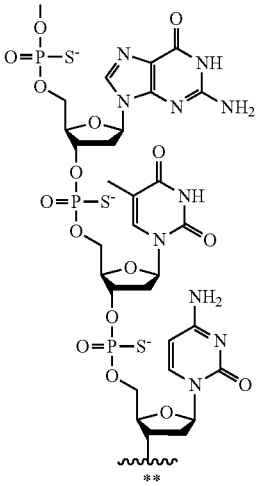 |
| | 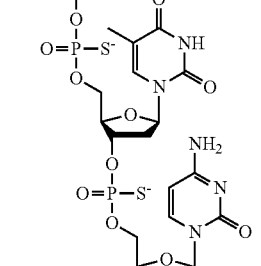 |
184
TABLE 10
Modified Oligonucleotide Structures (with -PEG3NH2)
| Cmpd # | Structure |
|---|---|
| 3.1a | 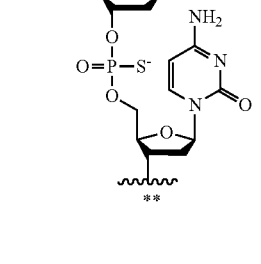 |
| | 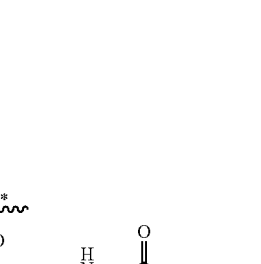 |

TABLE 10-continued

Modified Oligonucleotide Structures (with -PEG₃NH₂)

| Cmpd # | Structure |
|---|---|
| 3.2a | (chemical structure) |

TABLE 10-continued
Modified Oligonucleotide Structures (with -PEG₃NH₂)
| Cmpd # | Structure |
|---|---|
187
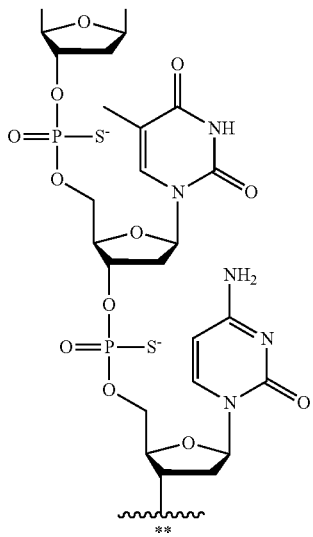
188
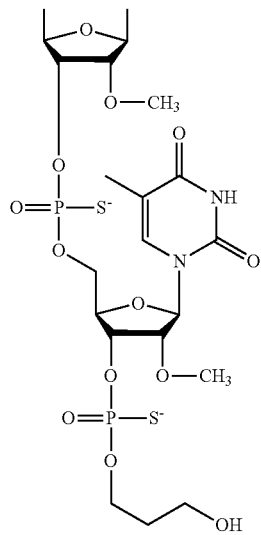

TABLE 10-continued

Modified Oligonucleotide Structures (with -PEG₃NH₂)

| Cmpd # | Structure |
|---|---|

3.3a

TABLE 10-continued

Modified Oligonucleotide Structures (with -PEG₃NH₂)

| Cmpd # | Structure |
|---|---|
| | (structure) |
| 4.1a | (structure) |

TABLE 10-continued

Modified Oligonucleotide Structures (with -PEG₃NH₂)

| Cmpd # | Structure |
|---|---|

TABLE 10-continued

Modified Oligonucleotide Structures (with -PEG₃NH₂)

| Cmpd # | Structure |
|---|---|
| 4.2a | (structure image) |

TABLE 10-continued

Modified Oligonucleotide Structures (with -PEG₃NH₂)

| Cmpd # | Structure |
|---|---|

4.3a (chemical structure)

TABLE 10-continued
Modified Oligonucleotide Structures (with -PEG₃NH₂)
| Cmpd # | Structure |
|---|---|
| 199 | 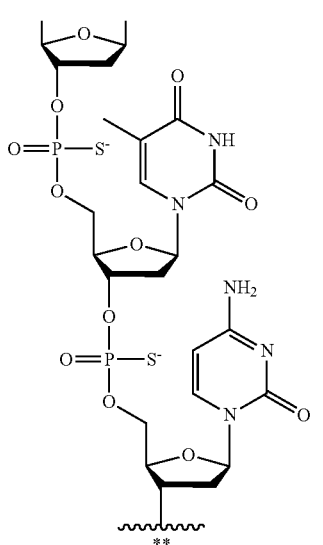 |
| 200 | |

TABLE 10-continued

Modified Oligonucleotide Structures (with -PEG₃NH₂)

| Cmpd # | Structure |
|---|---|
| 5.1a | (structure) |

TABLE 10-continued

Modified Oligonucleotide Structures (with -PEG₃NH₂)

| Cmpd # | Structure |
|---|---|

| Cmpd # | Structure |
|---|---|
| 5.2a | 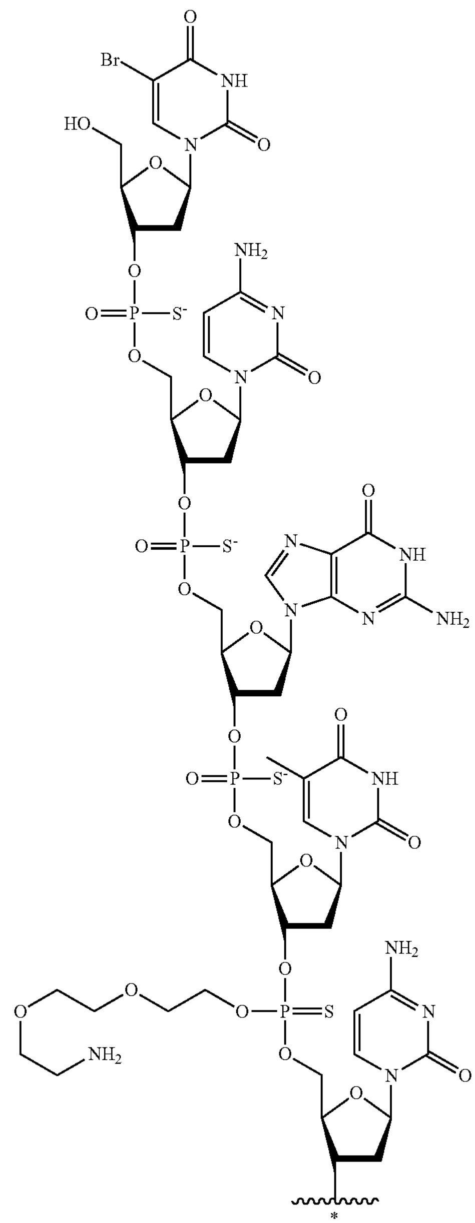 [SMILES: *[C@@H]1C[C@H](n2ccc(N)nc2=O)O[C@@H]1COP(=S)(OCCOCCOCCN)O[C@@H]1C[C@H](n2cc(C)c(=O)[nH]c2=O)O[C@@H]1COP(=O)([S-])O[C@@H]1C[C@H](n2cnc3c(=O)[nH]c(N)nc32)O[C@@H]1COP(=O)([S-])O[C@@H]1C[C@H](n2ccc(N)nc2=O)O[C@@H]1COP(=O)([S-])O[C@@H]1C[C@H](n2cc(Br)c(=O)[nH]c2=O)O[C@@H]1CO] |

TABLE 10-continued
Modified Oligonucleotide Structures (with -PEG3NH2)
| Cmpd # | Structure |
|---|---|
| 205 | 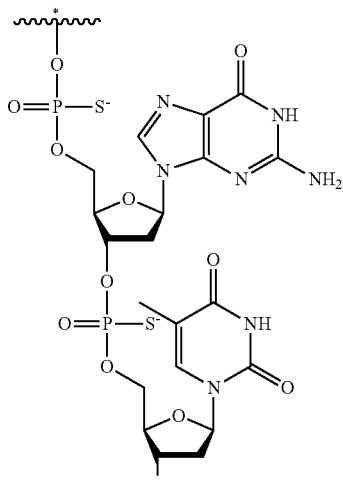 |
| | 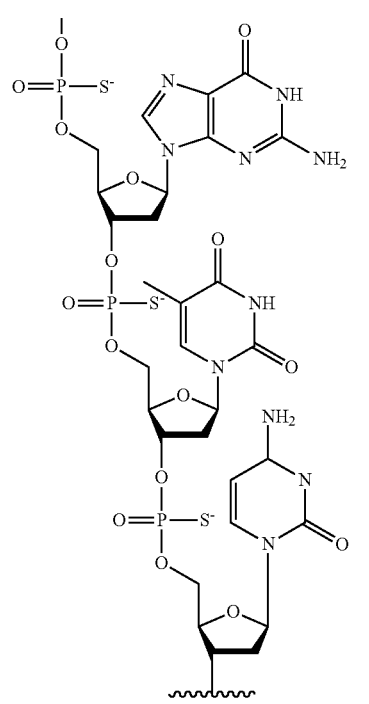 |
| 206 | 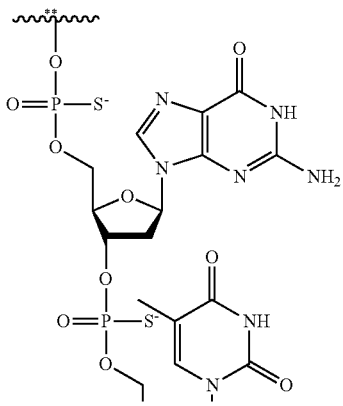 |
| | 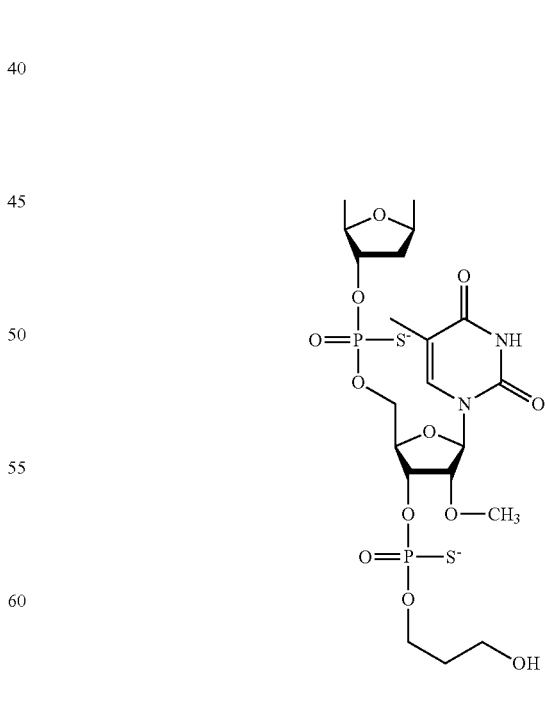 |

TABLE 10-continued
Modified Oligonucleotide Structures (with -PEG3NH2)
| Cmpd # | Structure |
|---|---|
| 5.3a | 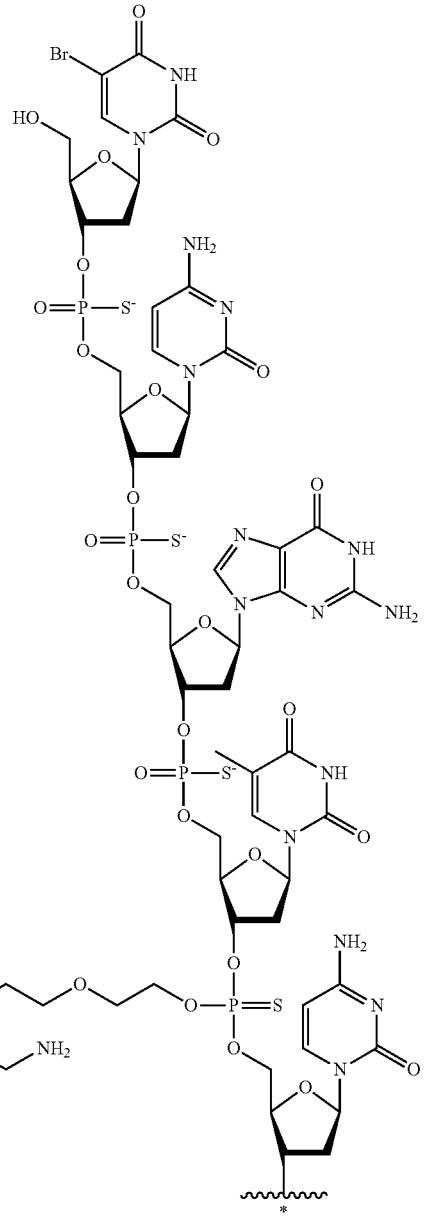 |
|  | 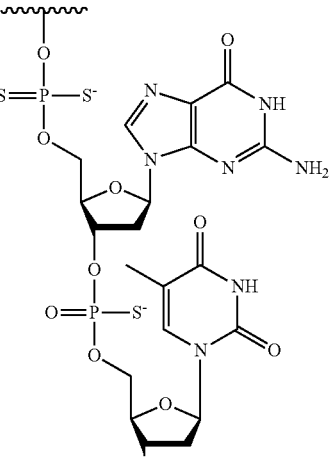 |

TABLE 10-continued

Modified Oligonucleotide Structures (with -PEG₃NH₂)

| Cmpd # | Structure |
|---|---|

5.4a

TABLE 10-continued
Modified Oligonucleotide Structures (with -PEG₃NH₂)
| Cmpd # | Structure |
|---|---|
| 211 | 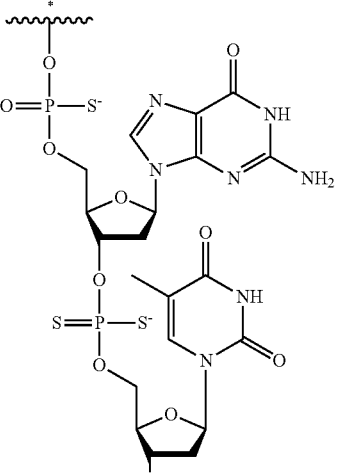 |
| 212 | 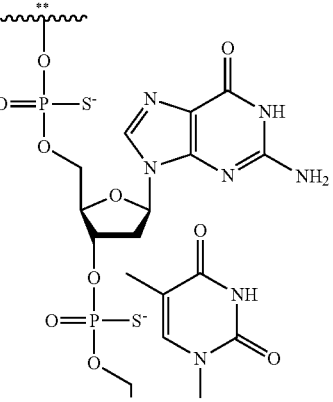 |

TABLE 10-continued

Modified Oligonucleotide Structures (with -PEG₃NH₂)

| Cmpd # | Structure |
|---|---|
| 5.5a | (structure) |

TABLE 10-continued

Modified Oligonucleotide Structures (with -PEG₃NH₂)

| Cmpd # | Structure |
| --- | --- |
| 5.6a | 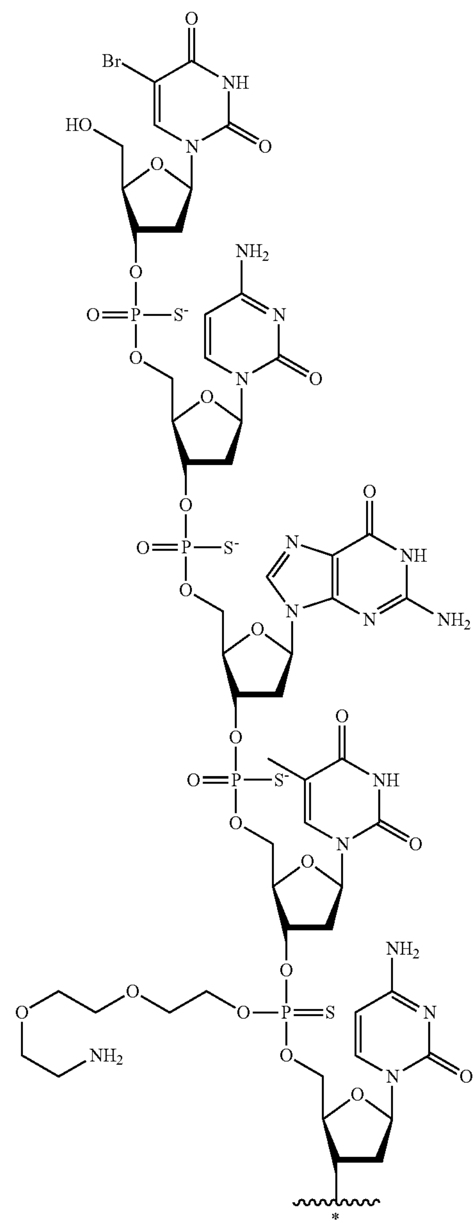 [SMILES: *[C@@H]1C[C@H](n2ccc(N)nc2=O)O[C@@H]1COP(=S)(OCCOCCOCCN)O[C@@H]1C[C@H](n2cc(C)c(=O)[nH]c2=O)O[C@@H]1COP(=O)([S-])O[C@@H]1C[C@H](n2cnc3c(=O)[nH]c(N)nc32)O[C@@H]1COP(=O)([S-])O[C@@H]1C[C@H](n2ccc(N)nc2=O)O[C@@H]1COP(=O)([S-])O[C@@H]1C[C@H](n2cc(Br)c(=O)[nH]c2=O)O[C@@H]1CO] |

TABLE 10-continued
Modified Oligonucleotide Structures (with -PEG3NH2)
Cmpd # | Structure
217
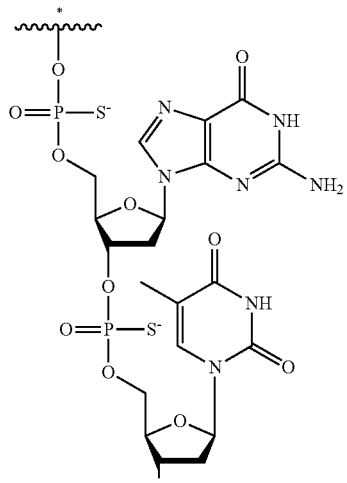
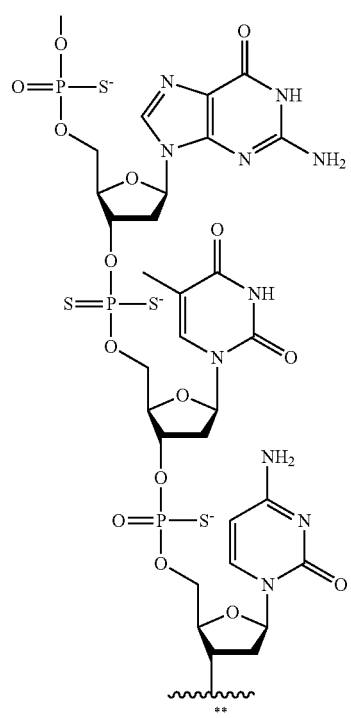
TABLE 10-continued
Modified Oligonucleotide Structures (with -PEG3NH2)
Cmpd # | Structure
218
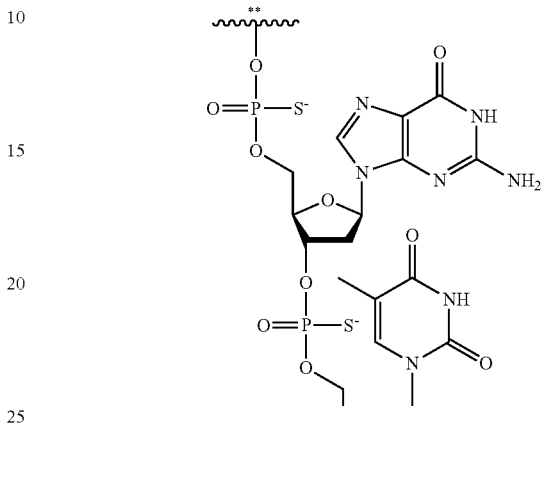
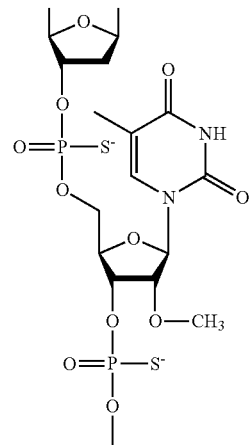

TABLE 10-continued

Modified Oligonucleotide Structures (with -PEG₃NH₂)

| Cmpd # | Structure |
|---|---|
| 5.7a | (structure) |

TABLE 10-continued

Modified Oligonucleotide Structures (with -PEG₃NH₂)

| Cmpd # | Structure |
|---|---|

TABLE 10-continued

Modified Oligonucleotide Structures (with -PEG₃NH₂)

| Cmpd # | Structure |
|---|---|
| 5.8a | 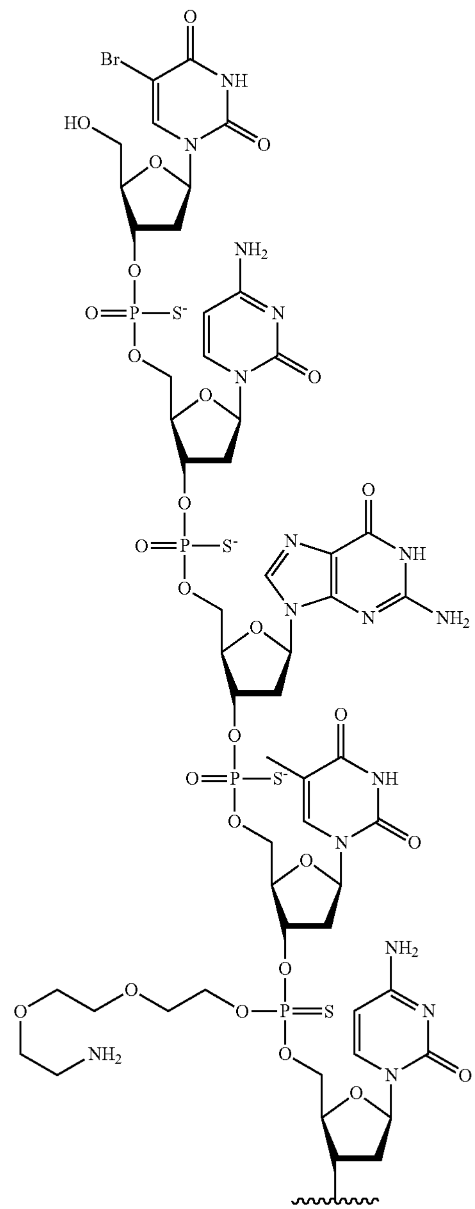 |

TABLE 10-continued
Modified Oligonucleotide Structures (with -PEG3NH2)
| Cmpd # | Structure |
|---|---|
| 223 | 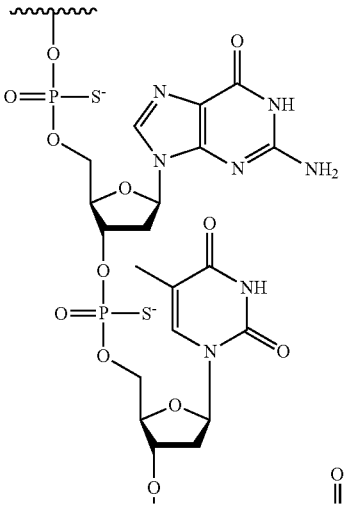 |
| 224 | 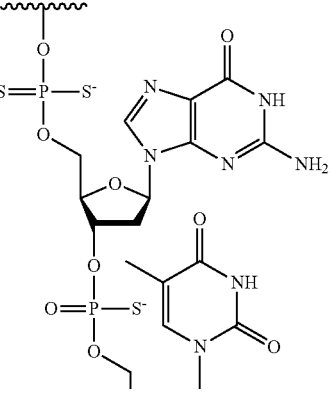 |
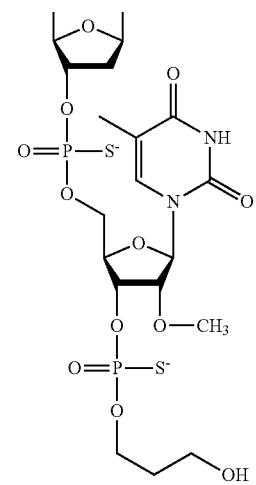

TABLE 10-continued

Modified Oligonucleotide Structures (with -PEG₃NH₂)

| Cmpd # | Structure |
|---|---|

5.9a

TABLE 10-continued
Modified Oligonucleotide Structures (with -PEG3NH2)
| Cmpd # | Structure |
|---|---|
| | 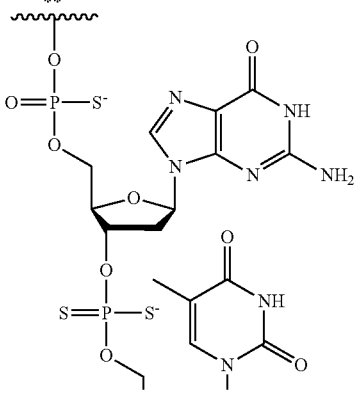 |
| 5.10a | 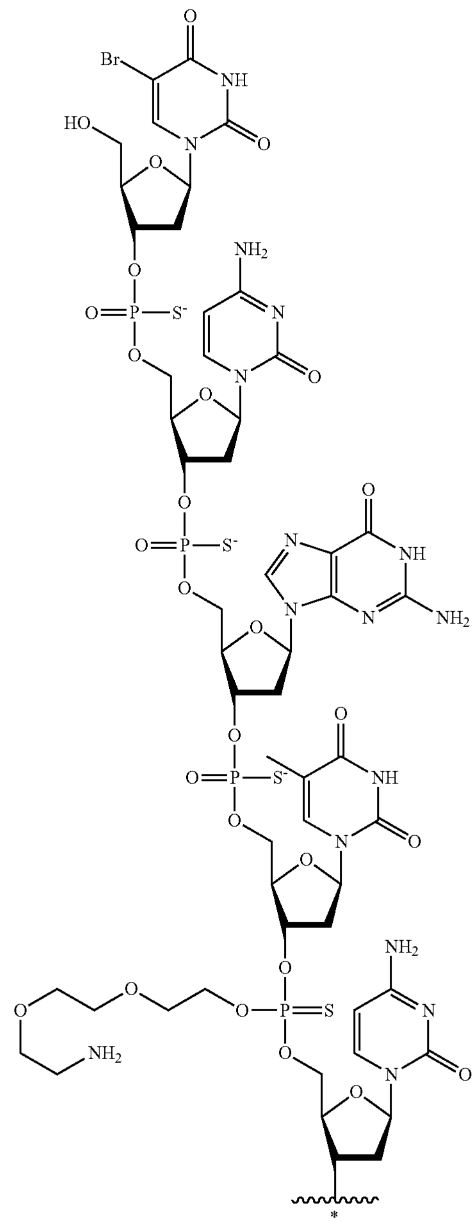 [SMILES: *[C@@H]1C[C@H](n2ccc(N)nc2=O)O[C@@H]1COP(=S)(OCCOCCOCCN)O[C@@H]1C[C@H](n2cc(C)c(=O)[nH]c2=O)O[C@@H]1COP(=O)([S-])O[C@@H]1C[C@H](n2cnc3c(=O)[nH]c(N)nc32)O[C@@H]1COP(=O)([S-])O[C@@H]1C[C@H](n2ccc(N)nc2=O)O[C@@H]1COP(=O)([S-])O[C@@H]1C[C@H](n2cc(Br)c(=O)[nH]c2=O)O[C@@H]1CO] |

TABLE 10-continued

Modified Oligonucleotide Structures (with -PEG₃NH₂)

| Cmpd # | Structure |
|---|---|

TABLE 10-continued
Modified Oligonucleotide Structures (with -PEG₃NH₂)
Cmpd # | Structure
--- | ---
5.11a | 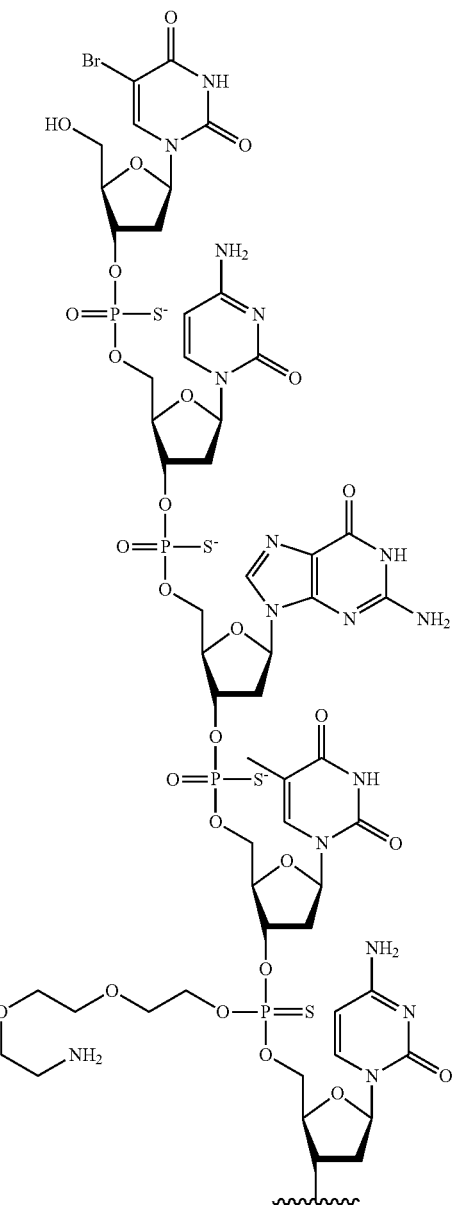
 | 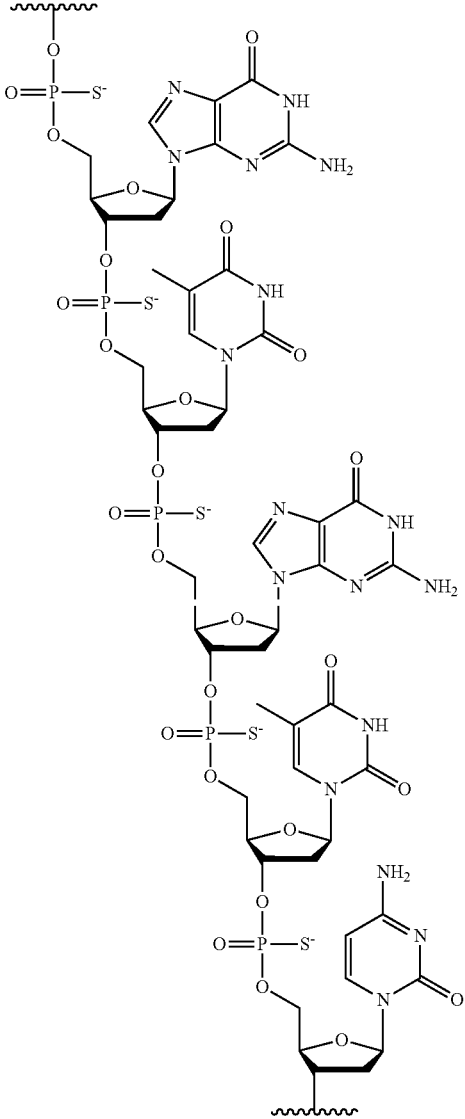

TABLE 10-continued

Modified Oligonucleotide Structures (with -PEG₃NH₂)

Cmpd # | Structure
--- | ---
5.12a | (chemical structure)
234 | (chemical structure)

TABLE 10-continued
Modified Oligonucleotide Structures (with -PEG$_3$NH$_2$)
| Cmpd # | Structure |
|---|---|
| | 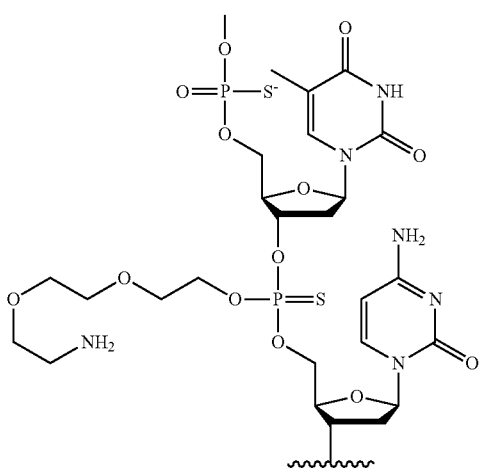 |
| 6.1a | 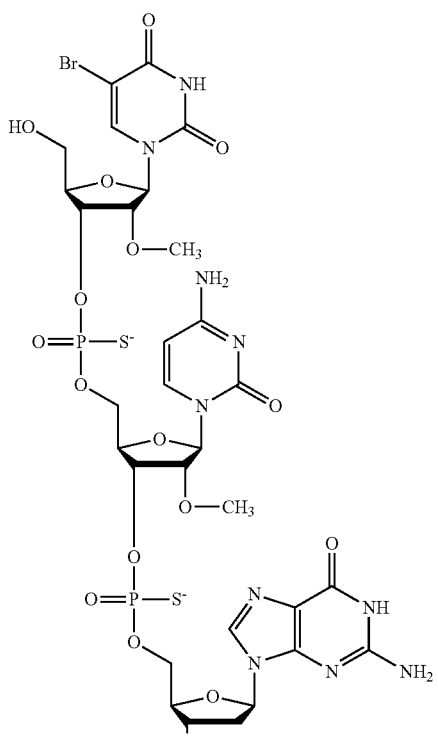 |
| | 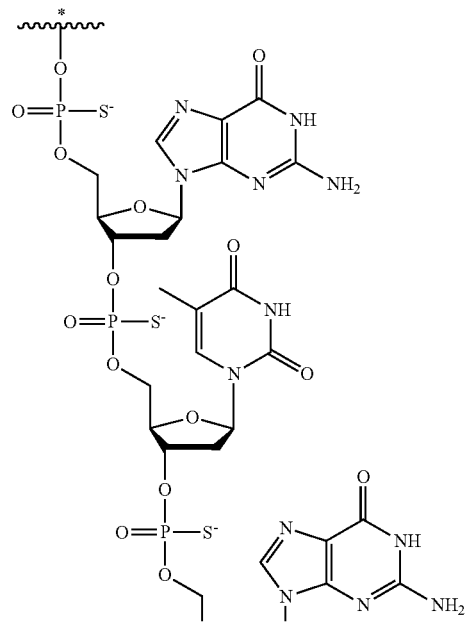 |

TABLE 10-continued
Modified Oligonucleotide Structures (with -PEG₃NH₂)
| Cmpd # | Structure |
|---|---|
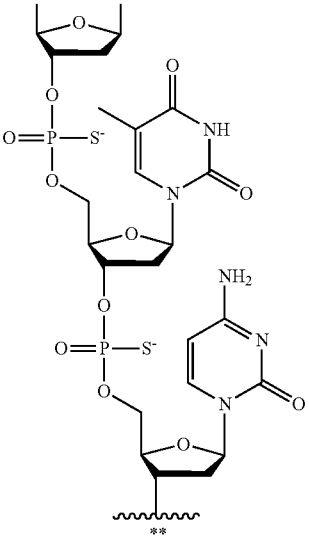
6.2a TABLE 10-continued
Modified Oligonucleotide Structures (with -PEG₃NH₂)
| Cmpd # | Structure |
|---|---|
| 239 | 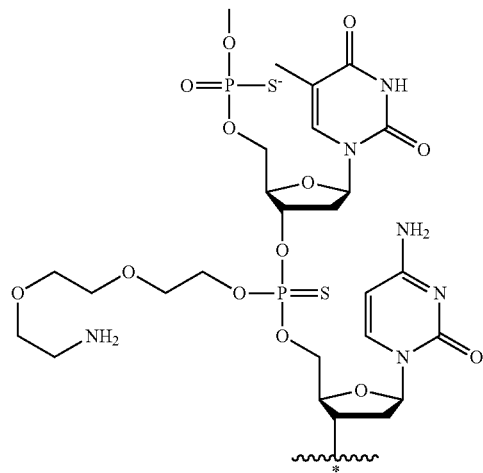 |
| 240 | 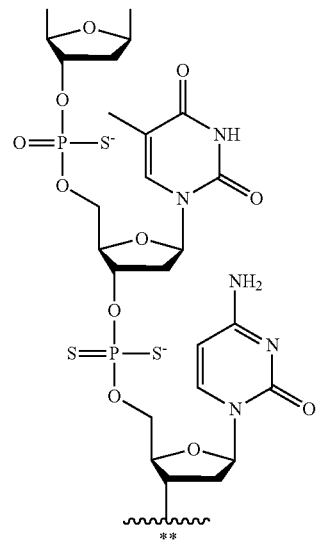 |

TABLE 10-continued

Modified Oligonucleotide Structures (with -PEG$_3$NH$_2$)

| Cmpd # | Structure |
|---|---|
| | (structure) |
| 6.3a | (structure) |
| 242 | (structure) |

TABLE 10-continued
Modified Oligonucleotide Structures (with -PEG₃NH₂)
| Cmpd # | Structure |
|---|---|
| | (structure 243) |
| | (structure 244) |
| 7.1a | 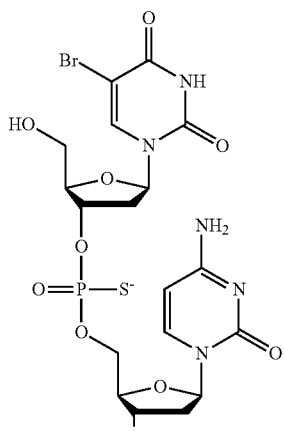 |

TABLE 10-continued
Modified Oligonucleotide Structures (with -PEG₃NH₂)
Cmpd # | Structure
245
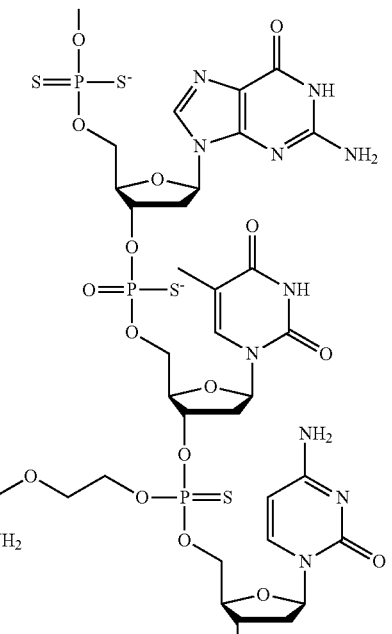
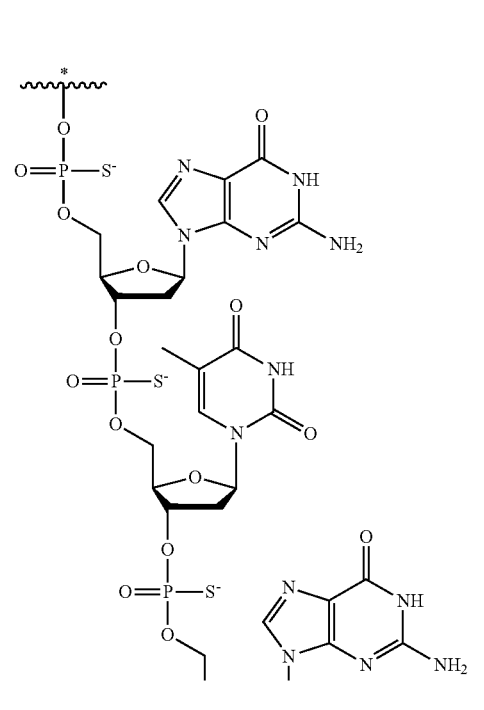
246
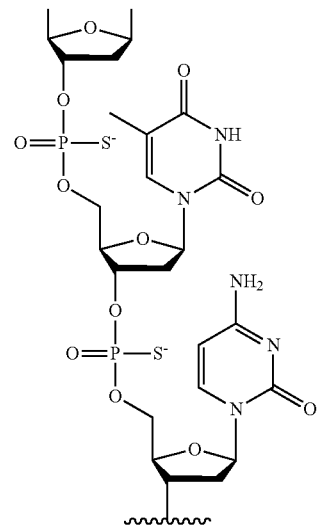
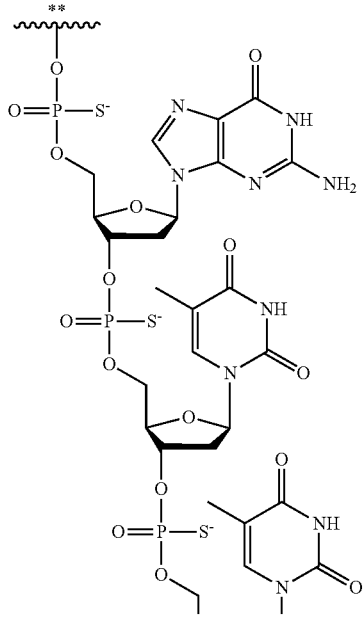

TABLE 10-continued
Modified Oligonucleotide Structures (with -PEG₃NH₂)
| Cmpd # | Structure |
|---|---|
| | 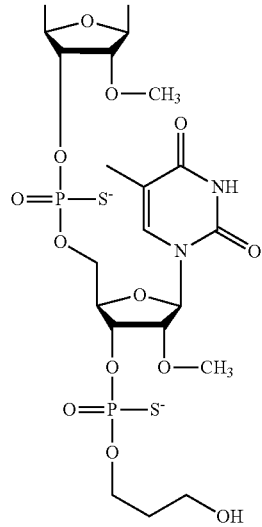 |
| 7.2a | 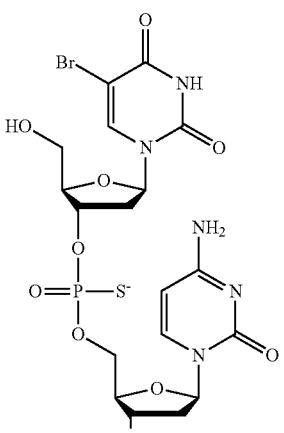 |
TABLE 10-continued
Modified Oligonucleotide Structures (with -PEG₃NH₂)
| Cmpd # | Structure |
|---|---|
| | 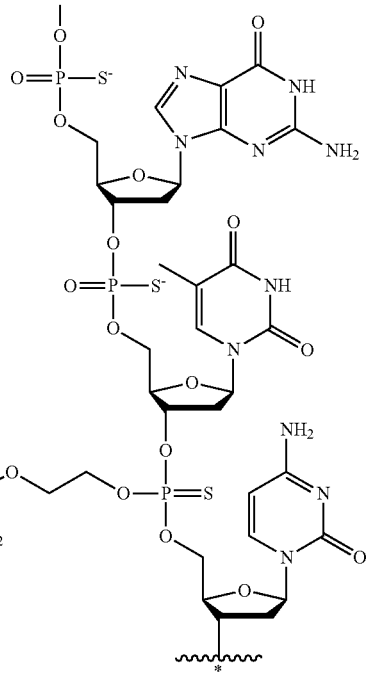 |
| | 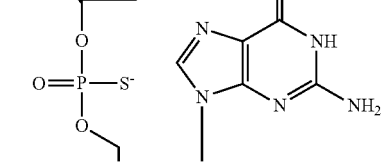 |

TABLE 10-continued

Modified Oligonucleotide Structures (with -PEG₃NH₂)

| Cmpd # | Structure |
|---|---|
| 249 | (structure) |
| 250 | (structure) |
| 7.3a | (structure) |

TABLE 10-continued

Modified Oligonucleotide Structures (with -PEG₃NH₂)

| Cmpd # | Structure |
|---|---|
| 251 | (structure) |
| 252 | (structure) |

TABLE 10-continued

Modified Oligonucleotide Structures (with -PEG₃NH₂)

| Cmpd # | Structure |
|---|---|
| 7.4a | (structure image) |

TABLE 10-continued

Modified Oligonucleotide Structures (with -PEG₃NH₂)

| Cmpd # | Structure |
|---|---|

TABLE 10-continued
Modified Oligonucleotide Structures (with -PEG3NH2)
| Cmpd # | Structure |
|---|---|
| | 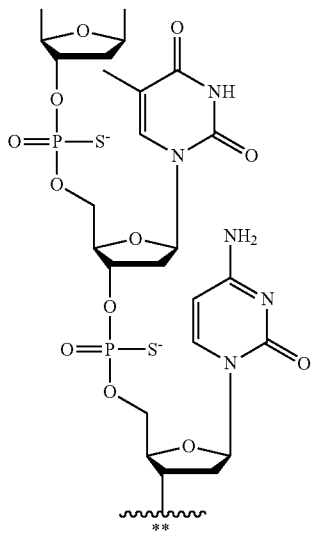 |
| | 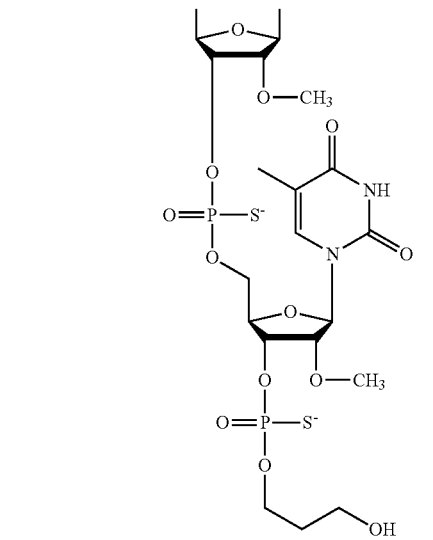 |
| 7.5a | 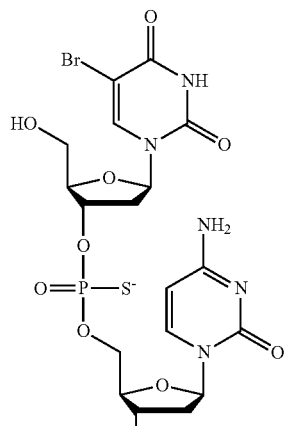 |

TABLE 10-continued

Modified Oligonucleotide Structures (with -PEG₃NH₂)

Cmpd # | Structure

TABLE 10-continued

Modified Oligonucleotide Structures (with -PEG₃NH₂)

| Cmpd # | Structure |
|---|---|
| 7.6a | 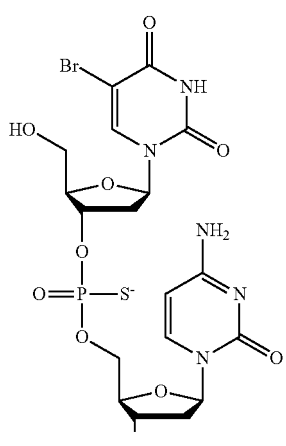 |
| 260 | |

TABLE 10-continued

Modified Oligonucleotide Structures (with -PEG₃NH₂)

| Cmpd # | Structure |
|---|---|
| 261 | |
| | |
| 262 | |
| 7.7a | |

TABLE 10-continued
Modified Oligonucleotide Structures (with -PEG3NH2)
| Cmpd # | Structure |
|---|---|
263
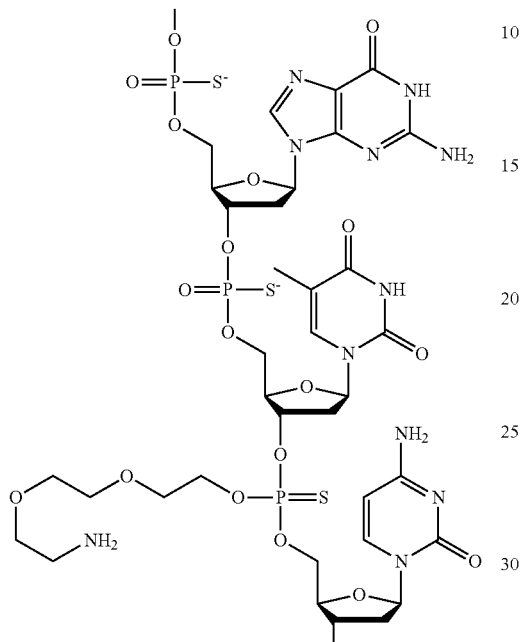
264
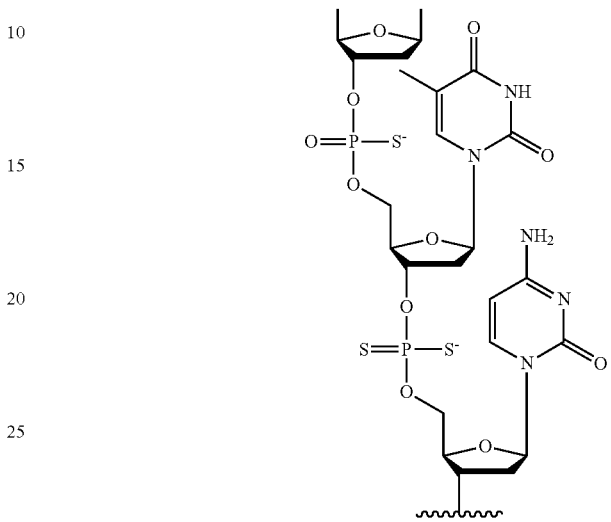
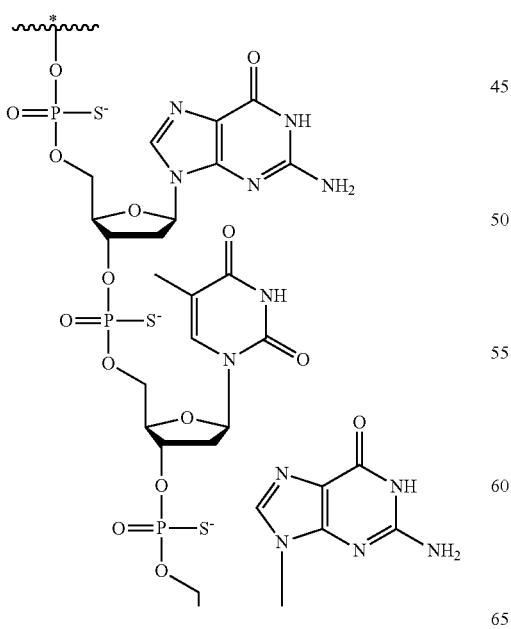
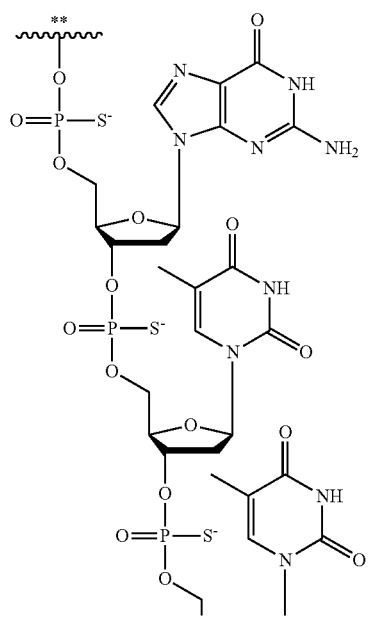

TABLE 10-continued

Modified Oligonucleotide Structures (with -PEG₃NH₂)

| Cmpd # | Structure |
|---|---|
| | (structure for compound 265 continued) |
| 7.8a | (structure) |
| | (structure for compound 266 continued) |

TABLE 10-continued

Modified Oligonucleotide Structures (with -PEG₃NH₂)

| Cmpd # | Structure |
|---|---|
| 267 | |
| 7.9a | 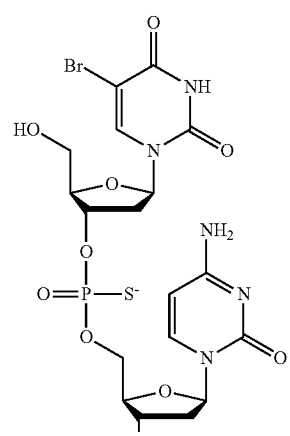 |

TABLE 10-continued

Modified Oligonucleotide Structures (with -PEG₃NH₂)

| Cmpd # | Structure |
|---|---|
| 269 | |
| 270 | |

TABLE 10-continued

Modified Oligonucleotide Structures (with -PEG₃NH₂)

| Cmpd # | Structure |
|---|---|
| 7.10a | 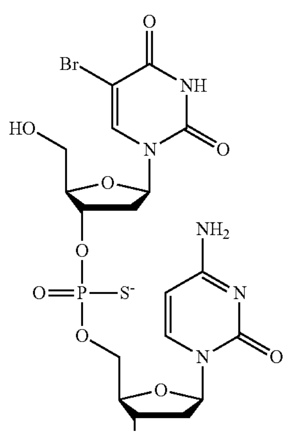 |

TABLE 10-continued

Modified Oligonucleotide Structures (with -PEG₃NH₂)

| Cmpd # | Structure |
|---|---|
| | (chemical structure) |
| 15.7a | (chemical structure) |

TABLE 10-continued
Modified Oligonucleotide Structures (with -PEG3NH2)
Cmpd # | Structure
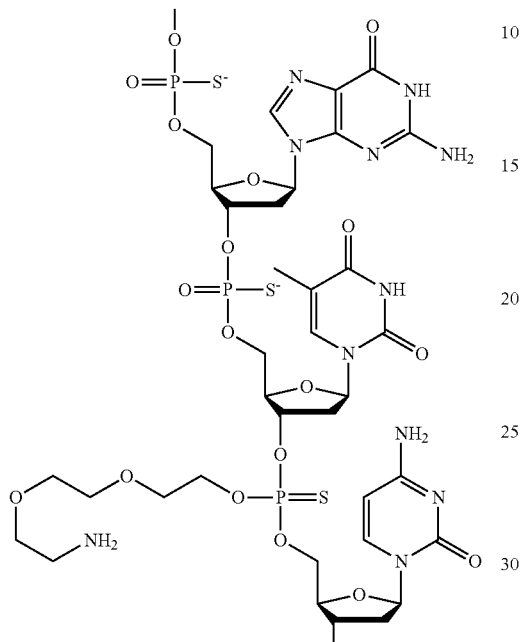
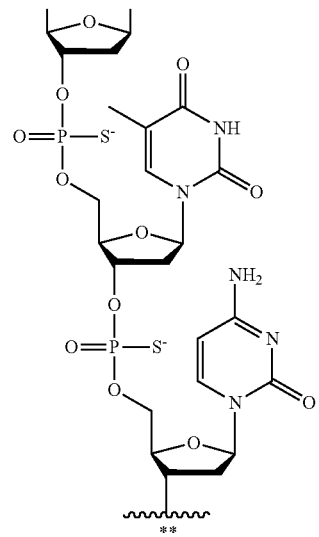
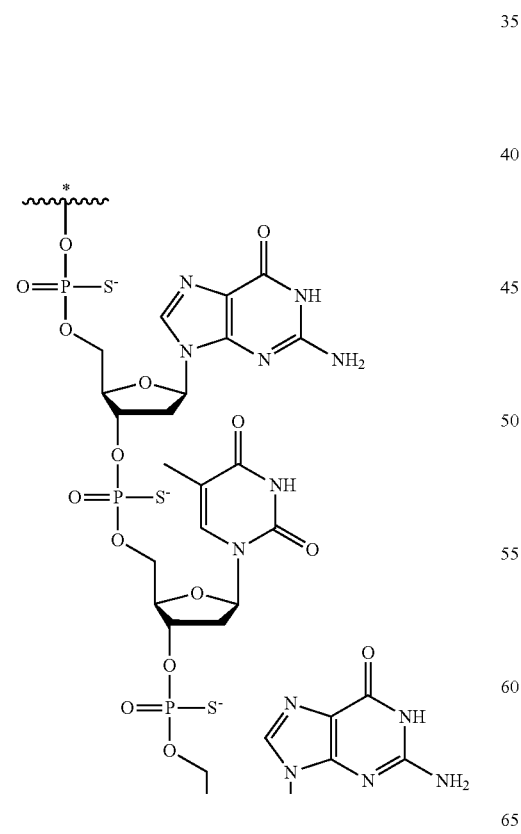
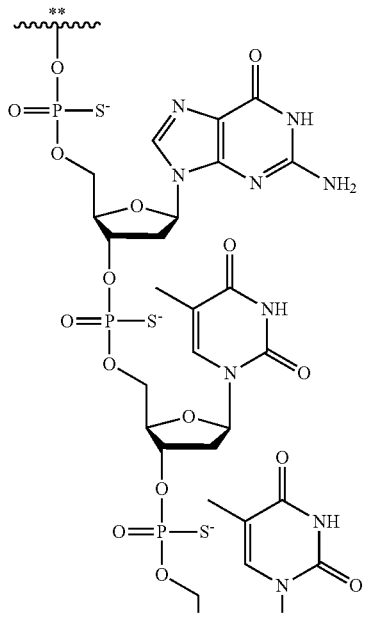

TABLE 10-continued

Modified Oligonucleotide Structures (with -PEG₃NH₂)

| Cmpd # | Structure |
|---|---|
|  | 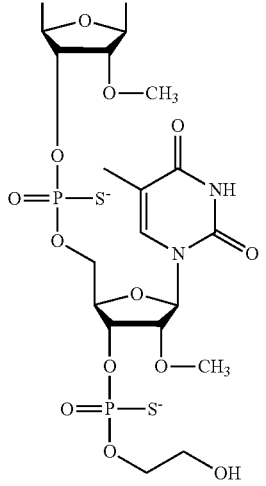 |

In some embodiments, the immunomodulating oligonucleotides of formula (C) may be utilized without conjugation to an antibody or antigen-binding fragment thereof or may be used as precursors to prepare conjugates comprising an antibody or antigen-binding fragment thereof and one or more immunomodulating oligonucleotides of formula (C) linked via Q-tag as shown in the structures of formula (A) as described herein.

In one aspect, provided herein is an immunomodulating oligonucleotide of formula (C), wherein the oligonucleotide is not conjugated to any delivery modality (such as a nanoparticle or protein) or targeting moiety (such as an antibody or antigen-fragment thereof). Such oligonucleotides may be further referred to as "naked" oligonucleotides or "naked" CpGs.

In another aspect, provided herein are immunomodulating oligonucleotides of formula (C), wherein the immunomodulating oligonucleotide is pegylated. In a further aspect, provided herein are immunomodulating oligonucleotides of formula (C), wherein the immunomodulating oligonucleotide is immobilized on a bead. In yet another aspect, provided herein are immunomodulating oligonucleotides of formula (C), wherein the immunomodulating oligonucleotide is formulated in a nanoparticle. In still a further aspect, provided herein are immunomodulating oligonucleotides of formula (C), wherein the immunomodulating oligonucleotide is encapsulated in a liposome. In yet a further aspect, provided herein are immunomodulating oligonucleotides of formula (C), wherein the immunomodulating oligonucleotide is conjugated to a polypeptide.

In still other aspect, provided herein is a method for delivering the immunomodulating oligonucleotide according to any of the embodiments herein, comprising contacting the immunomodulating oligonucleotide with a cell. In some embodiments, the immunomodulating oligonucleotide is pegylated. In other embodiments, the immunomodulating oligonucleotide is immobilized on a bead. In some embodiments, the immunomodulating oligonucleotide is formulated in a nanoparticle. In still other embodiments, the immunomodulating oligonucleotide is encapsulated in a liposome. In some embodiments, the immunomodulating oligonucleotide is conjugated to a polypeptide.

In still further embodiments, the immunomodulating oligonucleotides of formula (C) may be modified to attach a linker moiety L to the terminal group $T^3$ in formula (C) to provide immunomodulating oligonucleotides of formula (D). In still another aspect, provided herein are immunomodulating oligonucleotides of formula (D)

(D)

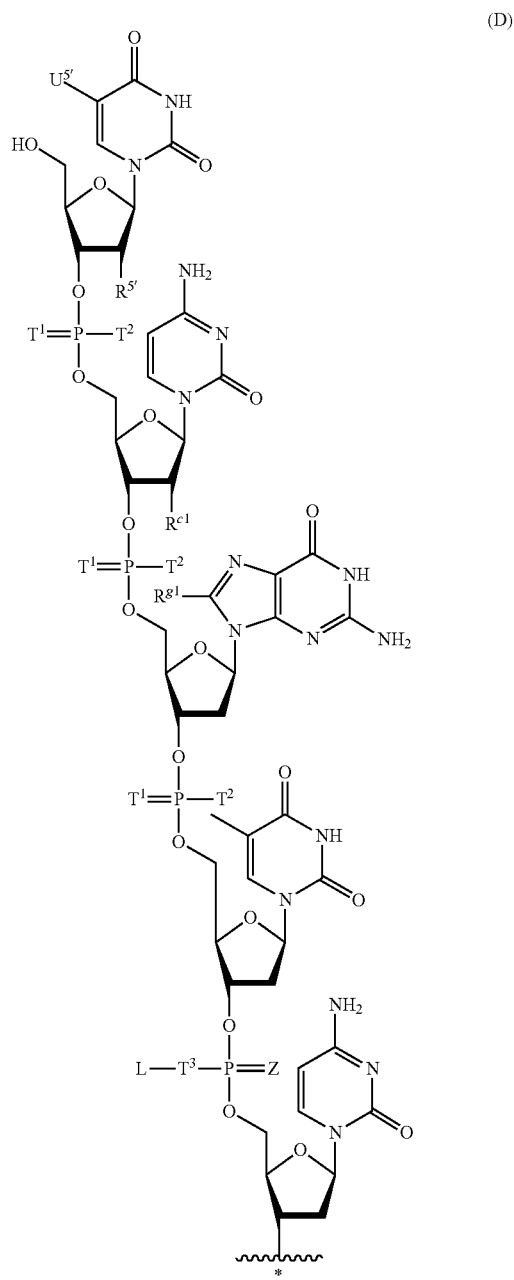

279
-continued
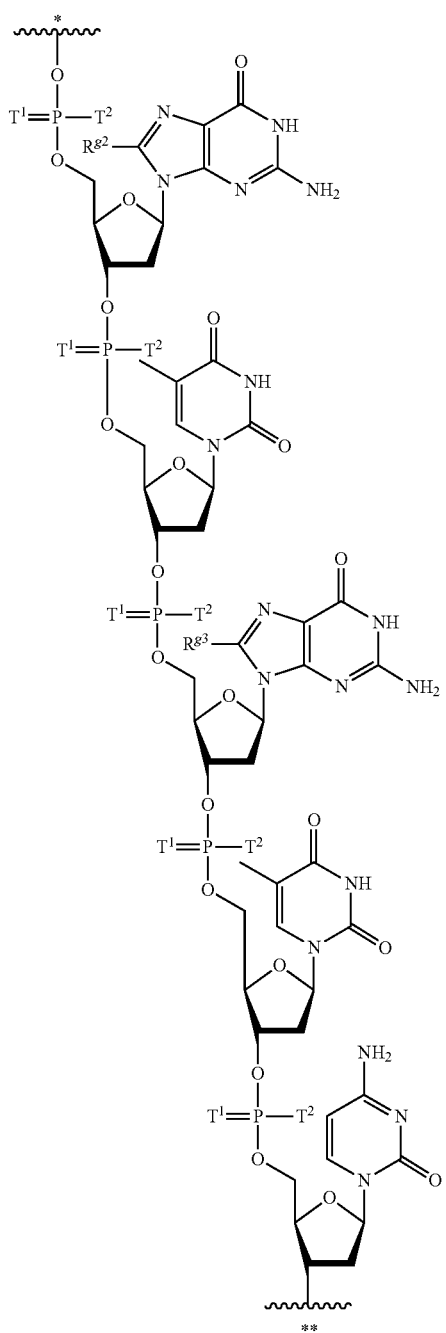
280
-continued
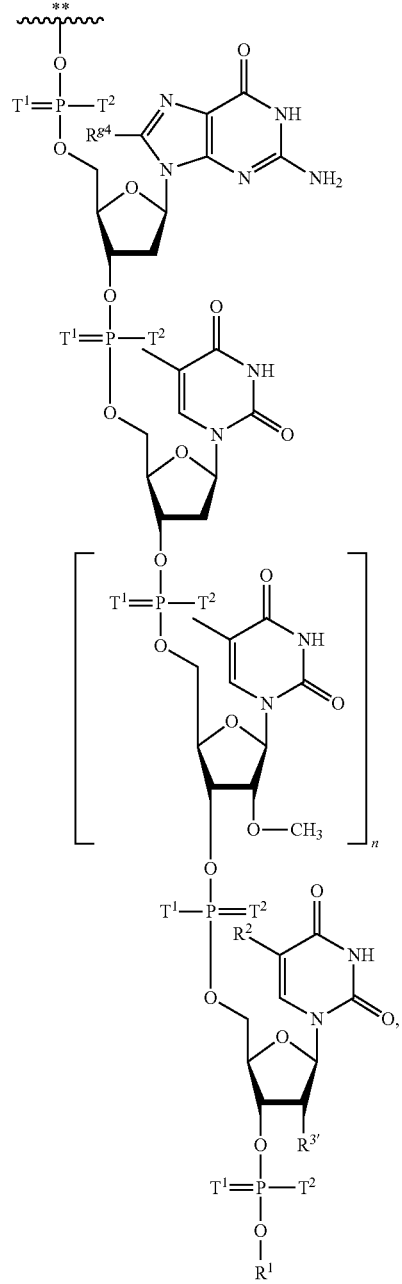
wherein
~* and ~** indicate the points of attachment within the oligonucleotide;
each $T^1$ is independently O or S;
each $T^2$ is $S^-$;
$T^3$ is a group
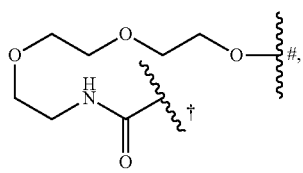 [SMILES: *OCCOCCOCCNC(*)=O]

wherein ∿† indicates the point of attachment to L and wherein ∿# indicates the point of attachment to the rest of the oligonucleotide;

L is a group

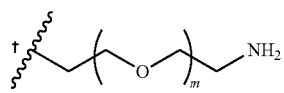

wherein m is an integer from 0 to 50 and wherein ∿† indicates the point of attachment to the rest of the oligonucleotide via $T^3$;

Z is O or S;

$U^{5'}$ is —H or halogen;

$R^{5'}$ is —H or methoxy;

$R^{c1}$ is —H or methoxy;

$R^{g1}$, $R^{g2}$, $R^{g3}$, and $R^{g4}$ are H or oxo, provided that at least one of $R^{g1}$, $R^{g2}$, $R^{g3}$, and $R^{g4}$ is oxo and wherein the carbon to which the oxo is attached has a single bond to the ring nitrogen at the 7-position;

$R^{3'}$ is methoxy or 2-methoxyethoxy;

$R^1$ is —(CH$_2$)$_3$—OH;

$R^2$ is —H or methyl; and n is an integer from 0 to 2, or a pharmaceutically acceptable salt thereof.

In some embodiments of the present aspect, $U^{5'}$ is —H In other embodiments, $U^{5'}$ is halogen. In certain embodiments, $U^{5'}$ is iodo or bromo. In some embodiments of the present aspect, the immunomodulatory oligonucleotide of formula (D) is an immunomodulatory oligonucleotide of formula (D'). In other embodiments of the present aspect, the immunomodulatory oligonucleotide of formula (D) is an immunomodulatory oligonucleotide of formula (D").

In some embodiments of the present aspect, provided herein is an immunomodulatory oligonucleotide of formula (D')

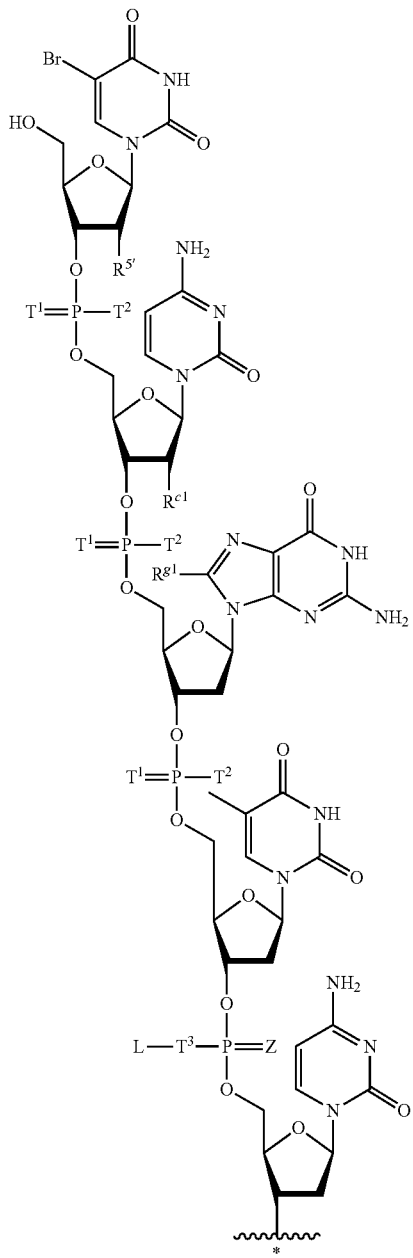

(D')

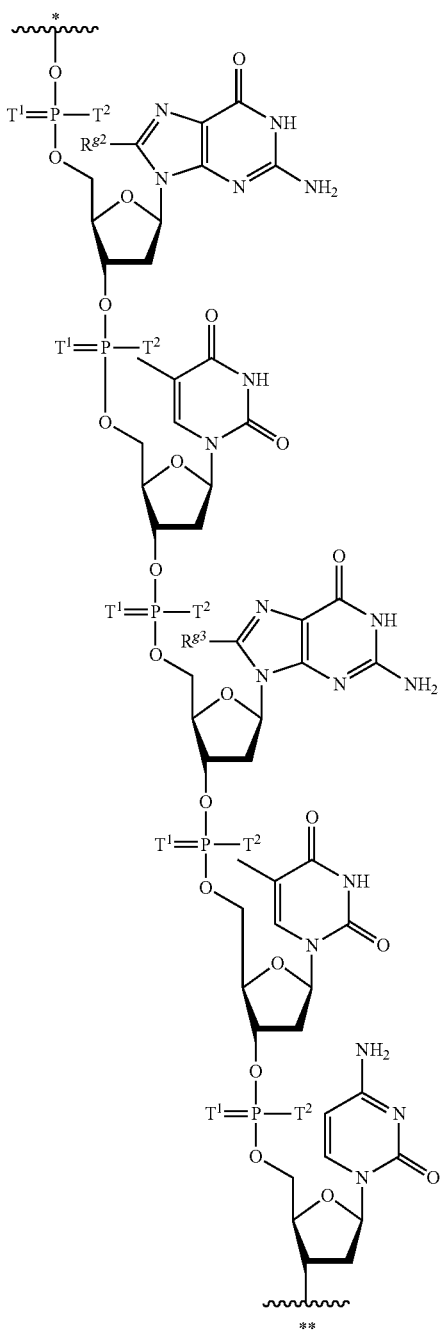
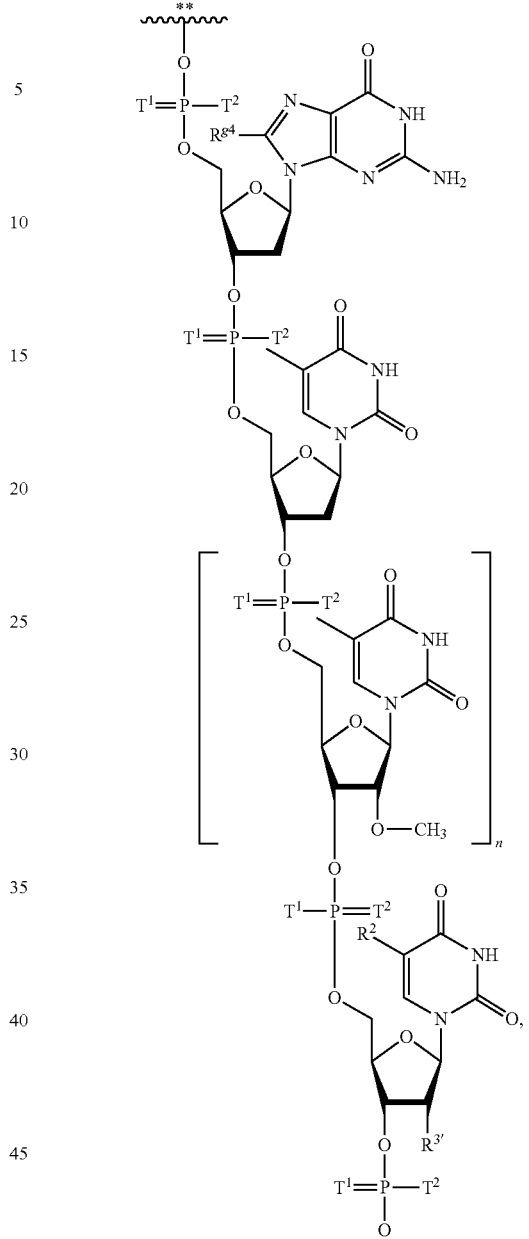
wherein
∼* and ∼** indicate the points of attachment within the oligonucleotide;
each $T^1$ is independently O or S;
each $T^2$ is $S^-$;
$T^3$ is a group
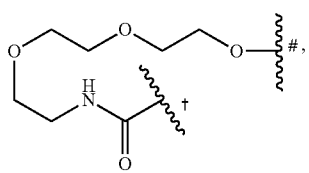

wherein ⁓† indicates the point of attachment to L and wherein ⁓# indicates the point of attachment to the rest of the oligonucleotide;

L is a group

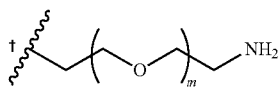

wherein m is an integer from 0 to 50 and wherein ⁓† indicates the point of attachment to the rest of the oligonucleotide via $T^3$;

Z is O or S;

$R^{5'}$ is —H or methoxy;

$R^{c1}$ is —H or methoxy;

$R^{g1}$, $R^{g2}$, $R^{g3}$, and $R^{g4}$ are H or oxo, provided that at least one of $R^{g1}$, $R^{g2}$, $R^{g3}$, and $R^{g4}$ is oxo and wherein the carbon to which the oxo is attached has a single bond to the ring nitrogen at the 7-position;

$R^{3'}$ is methoxy or 2-methoxyethoxy;

$R^1$ is —(CH$_2$)$_3$—OH;

$R^2$ is —H or methyl; and n is an integer from 0 to 2, or a pharmaceutically acceptable salt thereof.

In other embodiments of the present aspect, provided herein is an immunomodulatory oligonucleotide of formula (D″)

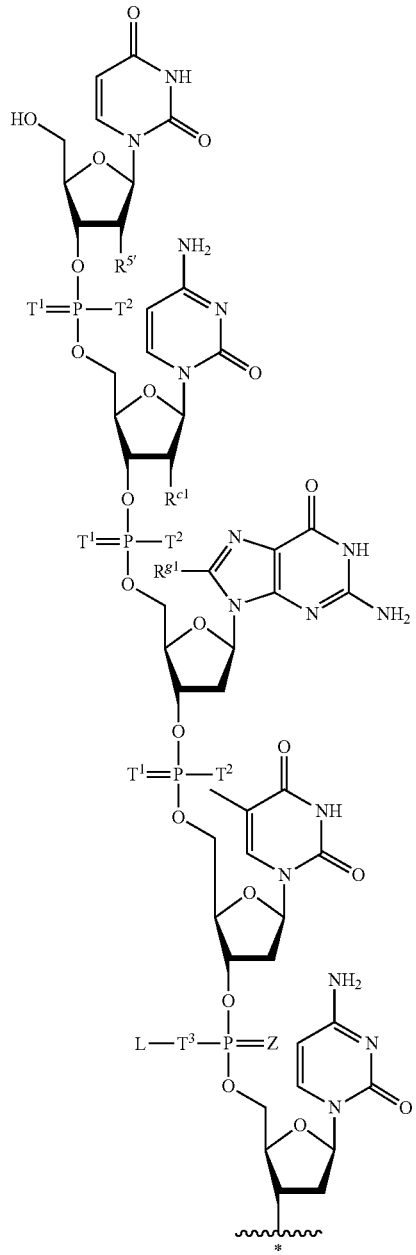

287
-continued
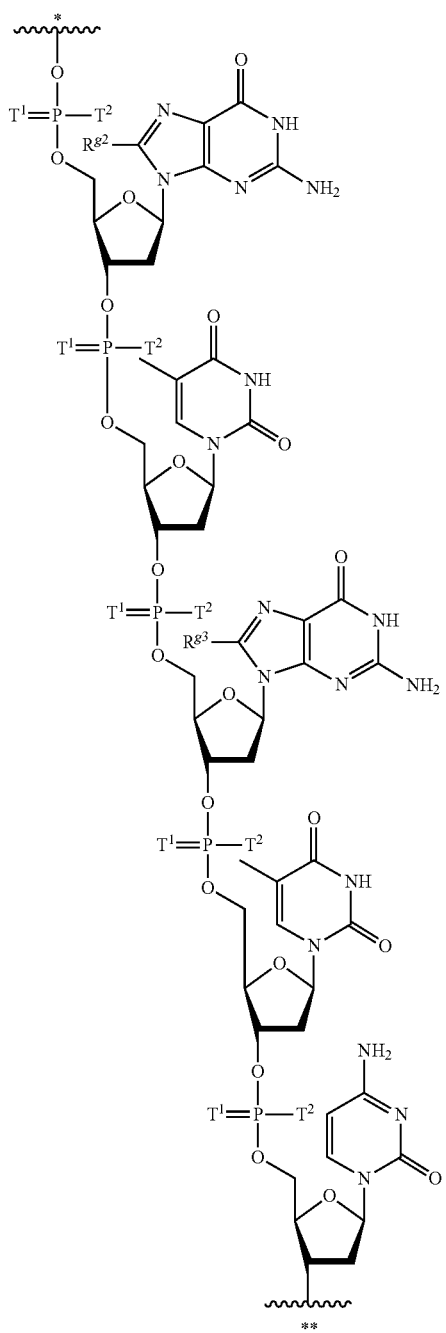
288
-continued
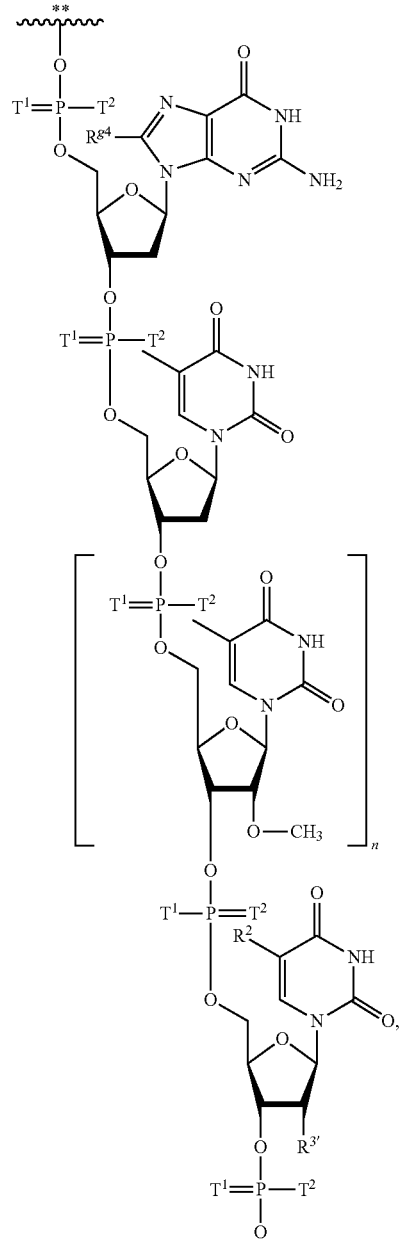
wherein
  $\sim$* and $\sim$** indicate the points of attachment within the oligonucleotide;
  each $T^1$ is independently O or S;
  each $T^2$ is $S^-$;
  $T^3$ is a group
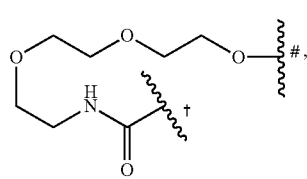 [SMILES: *OCCOCCOCCNC(*)=O]

wherein ∼† indicates the point of attachment to L and wherein ∼# indicates the point of attachment to the rest of the oligonucleotide;

L is a group

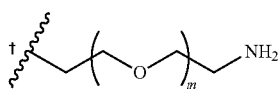

wherein m is an integer from 0 to 50 and wherein ∼† indicates the point of attachment to the rest of the oligonucleotide via $T^3$;

Z is O or S;

$R^{5'}$ is —H or methoxy;

$R^{c1}$ is —H or methoxy;

$R^{g1}$, $R^{g2}$, $R^{g3}$, and $R^{g4}$ are H or oxo, provided that at least one of $R^{g1}$, $R^{g2}$, $R^{g3}$, and $R^{g4}$ is oxo and wherein the carbon to which the oxo is attached has a single bond to the ring nitrogen at the 7-position;

$R^{3'}$ is methoxy or 2-methoxyethoxy;

$R^1$ is —(CH$_2$)$_3$—OH;

$R^2$ is —H or methyl; and n is an integer from 0 to 2, or a pharmaceutically acceptable salt thereof.

In some embodiments of the present aspect, the present disclosure also provides immunomodulating oligonucleotides of formula (D')

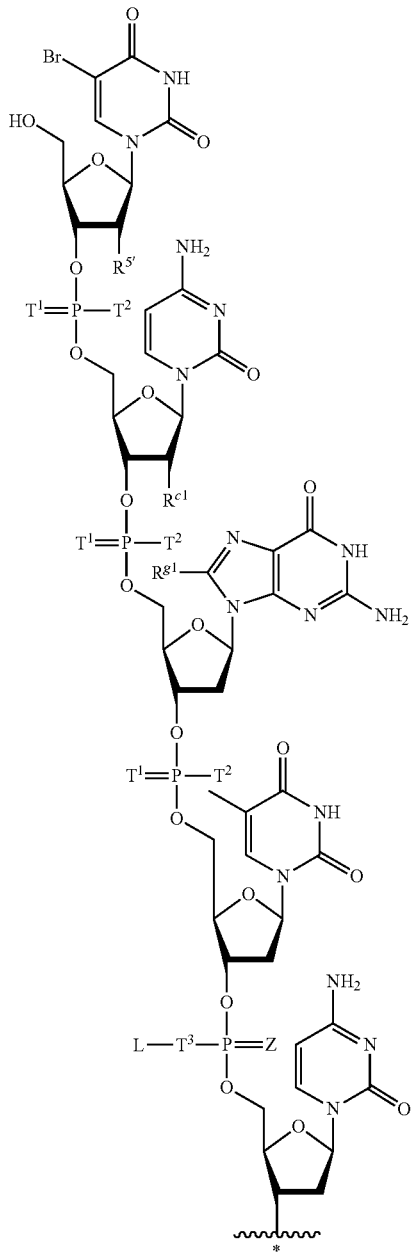

(D')

291
-continued
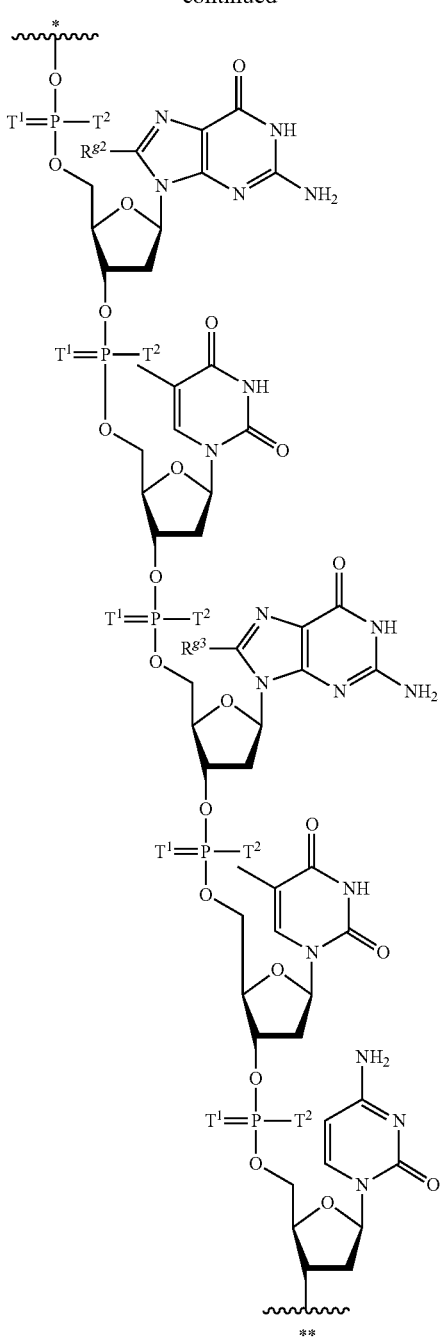
292
-continued
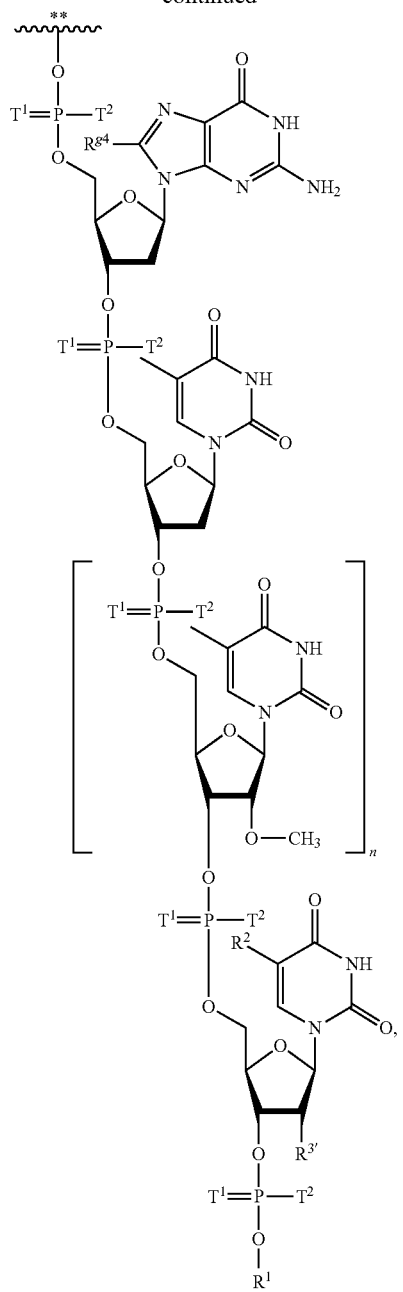
wherein
~~* and ~~** indicate the points of attachment within the oligonucleotide;
each $T^1$ is independently O or S;
each $T^2$ is $S^-$;
$T^3$ is a group
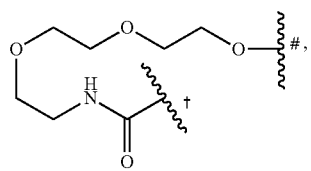 [SMILES: *OCCOCCOCCNC(*)=O]

wherein ⌇† indicates the point of attachment to L and wherein ⌇# indicates the point of attachment to the rest of the oligonucleotide;

L is a group

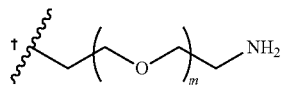

wherein m is an integer from 0 to 50 and wherein ⌇† indicates the point of attachment to the rest of the oligonucleotide via T³;

Z is O or S;

R⁵' is —H or methoxy;

R^{c1} is —H or methoxy;

R^{g1}, R^{g2}, R^{g3}, and V are H;

R³' is methoxy;

R¹ is —(CH₂)₃—OH;

R² is —H or methyl; and n is an integer from 0 to 2, or a pharmaceutically acceptable salt thereof.

In still other embodiments of the present aspect, provided herein is an immunomodulatory oligonucleotide of formula (D″)

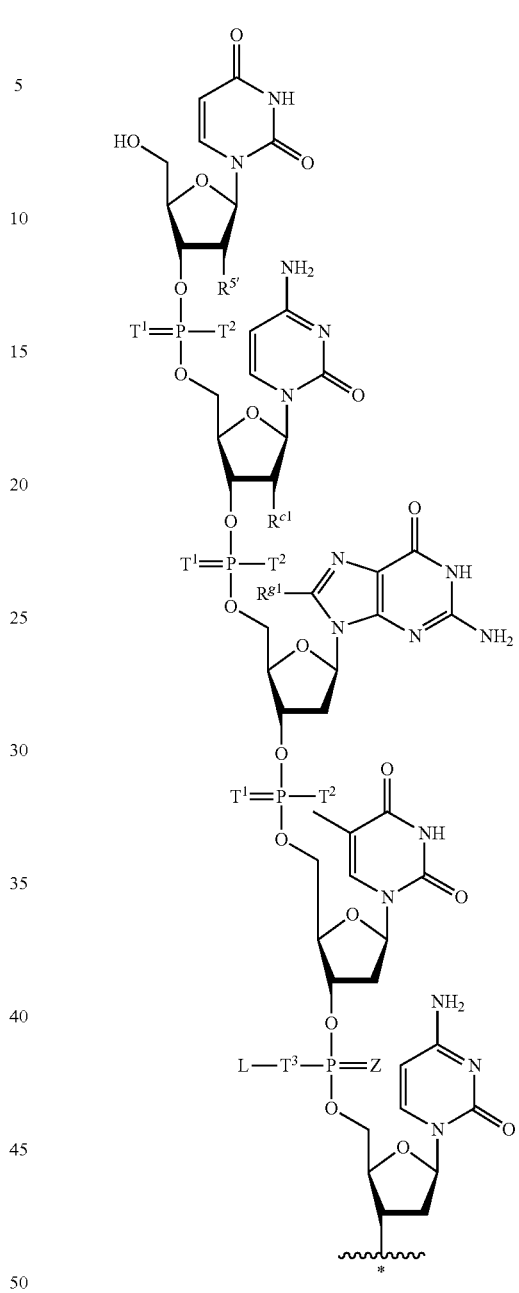

295
-continued
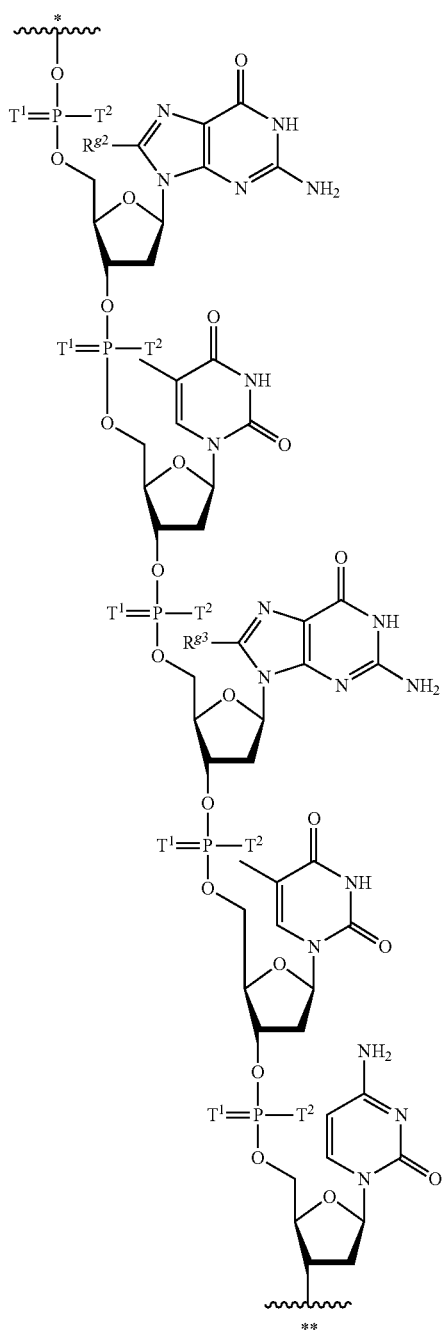
296
-continued
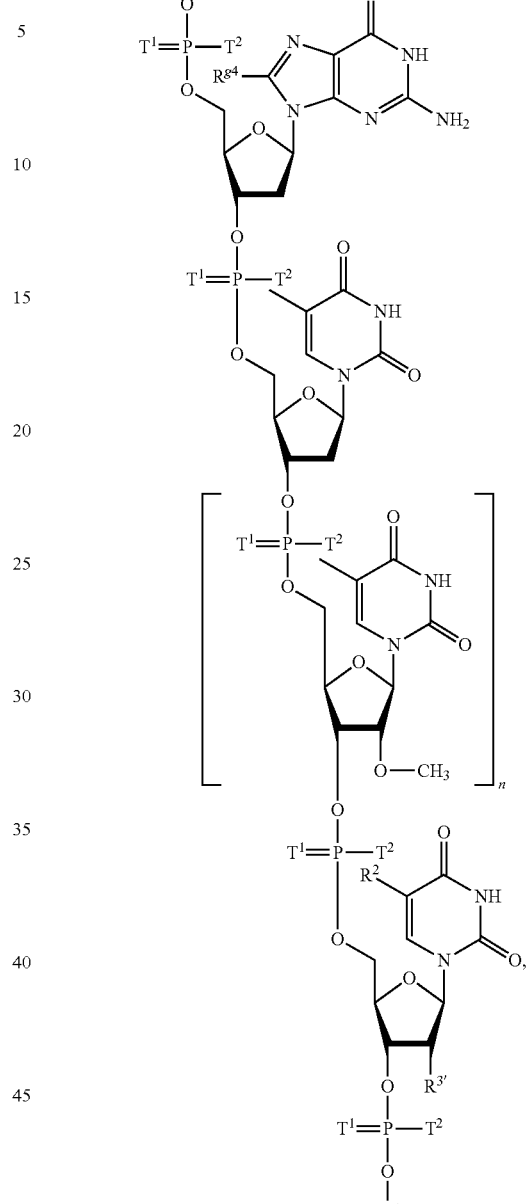
wherein
  ⌇*  and  ⌇** indicate the points of attachment within the oligonucleotide;
  each $T^1$ is independently O or S;
  each $T^2$ is $S^-$;
  $T^3$ is a group
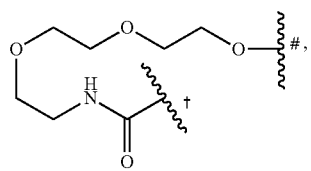 [SMILES: *OCCOCCOCCNC(*)=O]

wherein ⁓† indicates the point of attachment to L and wherein ⁓# indicates the point of attachment to the rest of the oligonucleotide;

L is a group

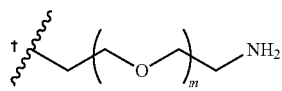

wherein m is an integer from 0 to 50 and wherein ⁓† indicates the point of attachment to the rest of the oligonucleotide via $T^3$;

Z is O or S;

$R^{5'}$ is —H or methoxy;

$R^{c1}$ is —H or methoxy;

$R^{g1}$, $R^{g2}$, $R^{g3}$, and V are H;

$R^{3'}$ is methoxy;

$R^1$ is —$(CH_2)_3$—OH;

$R^2$ is —H or methyl; and n is an integer from 0 to 2, or a pharmaceutically acceptable salt thereof.

In some embodiments of the present aspect, Z is S. In additional embodiments, the oligonucleotide comprises at least one pair of geminal $T^1$ and $T^2$ wherein $T^1$ is S and $T^2$ is $S^-$. In certain embodiments, the oligonucleotide comprises at least two pairs of geminal $T^1$ and $T^2$ wherein $T^1$ is S and $T^2$ is $S^-$.

In still yet another embodiment of the present aspect, provided herein is an oligonucleotide of formula (D)

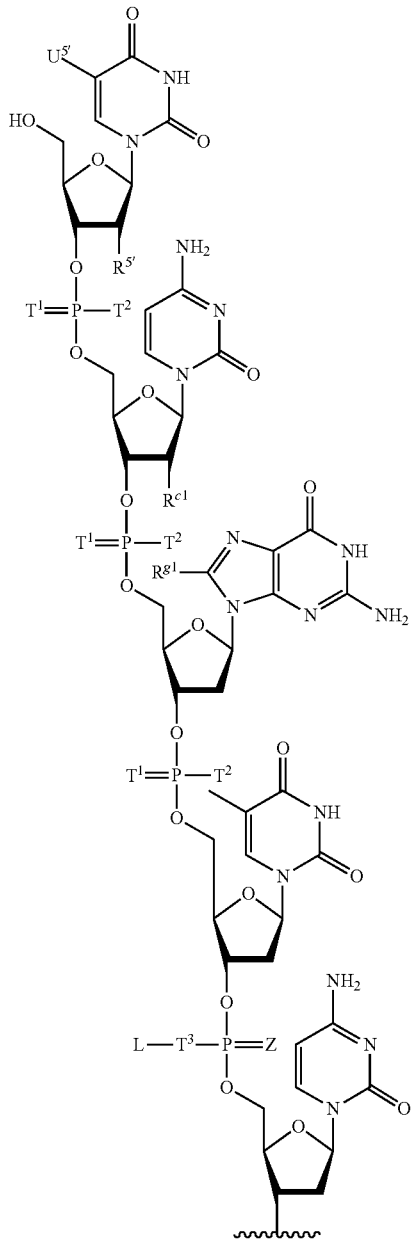

(D')

299
-continued
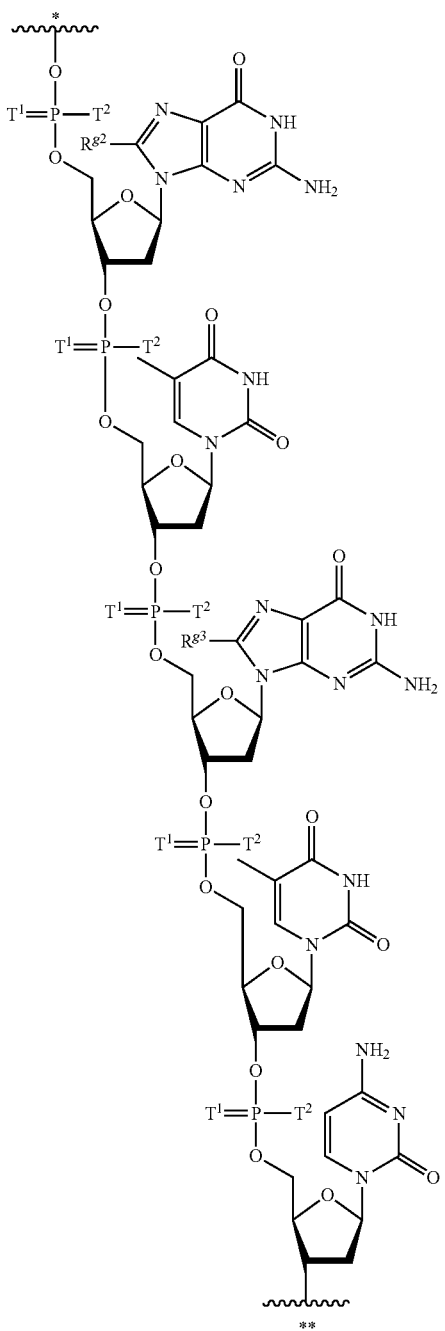
300
-continued
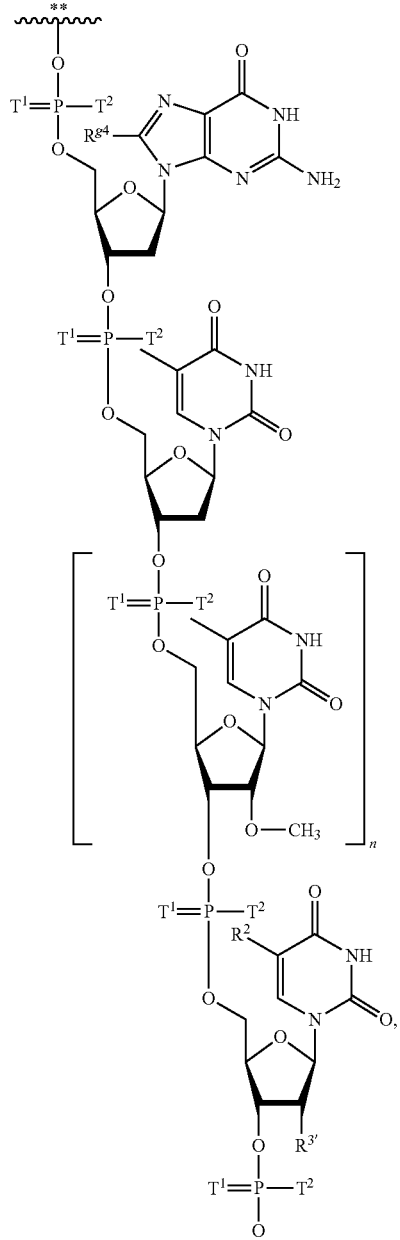
wherein ∼∼* and ∼∼** indicate the points of attachment within the oligonucleotide;
each $T^1$ is independently O or S;
each $T^2$ is $S^-$;
provided that the oligonucleotide comprises at least one pair of geminal $T^1$ and $T^2$ wherein $T^1$ is S and $T^2$ is S, T³ is a group

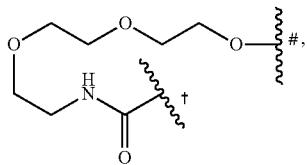 [SMILES: *OCCOCCOCCNC(*)=O]

wherein ⁓† indicates the point of attachment to L and wherein ⁓# indicates the point of attachment to the rest of the oligonucleotide;

L is a group

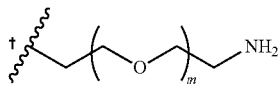

wherein m is an integer from 0 to 50 and wherein ⁓† indicates the point of attachment to the rest of the oligonucleotide via T³;

Z is O or S;
$U^{5'}$ is —H or halogen;
$R^{5'}$ is —H;
$R^{c1}$ is —H;
$R^{g1}$, $R^{g2}$, $R^{g3}$, and V are H;
$R^{3'}$ is methoxy;
$R^1$ is —(CH$_2$)$_3$—OH;
$R^2$ is -methyl; and
n is 1,
or a pharmaceutically acceptable salt thereof.

In some embodiments of any of the foregoing, the at least one pair of geminal T¹ and T² wherein T¹ is S and T² is S is between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11. In still other embodiments of the foregoing, the oligonucleotide comprises at least two pairs of of geminal T¹ and T² wherein T¹ is S and T² is S, and wherein the at least two pairs of of geminal T¹ and T² wherein T¹ is S and T² is S are between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11.

In some embodiments, the oligonucleotide comprises one or two pairs of geminal T¹ and T² wherein T¹ is S and T² is S, and wherein the one or two pairs of geminal T¹ and T² are between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11. In certain embodiments, the oligonucleotide comprises one pair of geminal T¹ and T² wherein T¹ is S and T² is S, and wherein the pair of geminal T¹ and T² is between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11. In certain other embodiments, the oligonucleotide comprises two pairs of geminal T¹ and T² wherein T¹ is S and T² is S, and wherein the two pairs of geminal T¹ and T² wherein T¹ is S and T² is S are between nucleoside residues 2 and 3, between nucleoside residues 3 and 4, between nucleoside residues 5 and 6, between nucleoside residues 6 and 7, between nucleoside residues 7 and 8, between nucleoside residues 8 and 9, between nucleoside residues 9 and 10, or between nucleoside residues 10 and 11.

In some embodiments, $R^{5'}$ is H. In other embodiments, $R^{5'}$ is methoxy. In some embodiments, $R^{c1}$ is H. In yet other embodiments, $R^{c1}$ is methoxy. In still further embodiments, $R^2$ is methyl. In still other embodiments, $R^2$ is H. In yet other additional embodiments, which may be combined with any of the preceding embodiments, T³ is

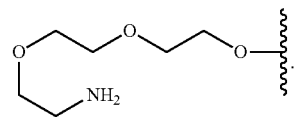

In still other embodiments, T³ is

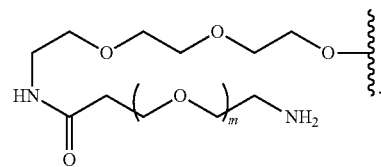

In certain embodiments, m is an integer from 20 to 25.

In another aspect, the immunomodulating oligonucleotide of formula (D) is an oligonucleotide selected from the group consisting of the oligonucleotides of Table 11 and Table 12, or a pharmaceutically acceptable salt thereof. In still further embodiments of the present aspect, the oligonucleotide of formula (D) is selected from the group consisting of the oligonucleotides of Table 12, or a pharmaceutically acceptable salt thereof.

TABLE 11
Modified Oligonucleotide Structures (with -PEG$_3$NHCOPEG$_{24}$NH$_2$)
| Cmpd # | Structure |
|---|---|
| 1.1b | 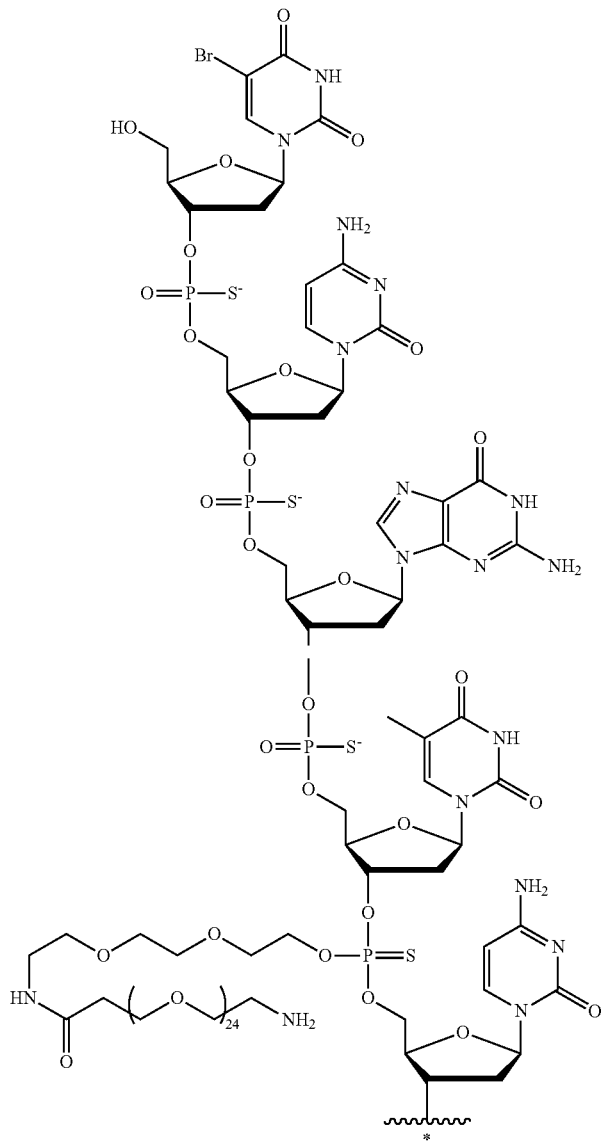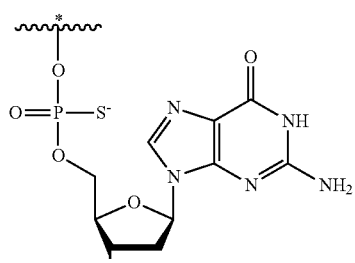 |

TABLE 11-continued
Modified Oligonucleotide Structures (with -PEG$_3$NHCOPEG$_{24}$NH$_2$)
Cmpd # | Structure
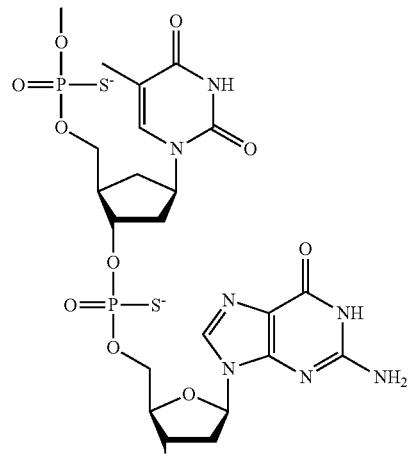
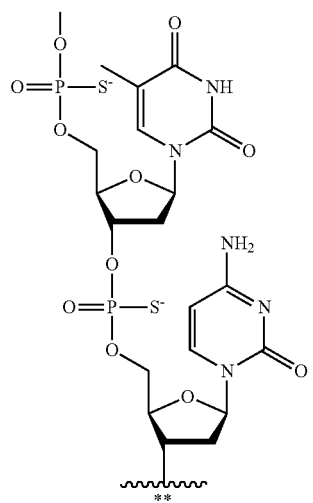

TABLE 11-continued
Modified Oligonucleotide Structures (with -PEG$_3$NHCOPEG$_{24}$NH$_2$)
Cmpd # | Structure
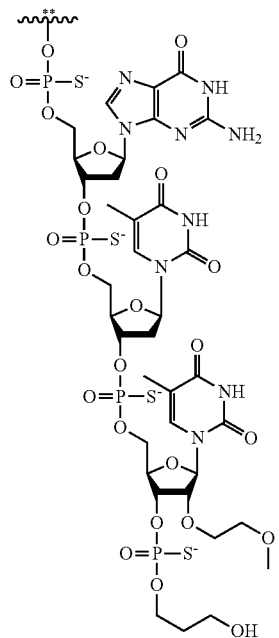
2.1b
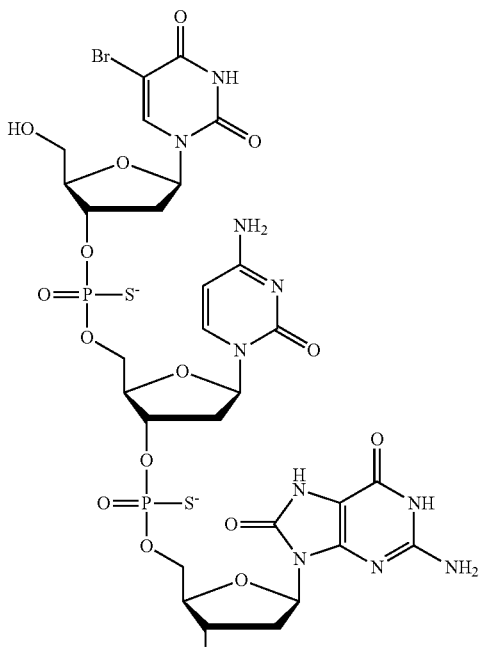

TABLE 11-continued
Modified Oligonucleotide Structures (with -PEG₃NHCOPEG₂₄NH₂)
Cmpd # Structure
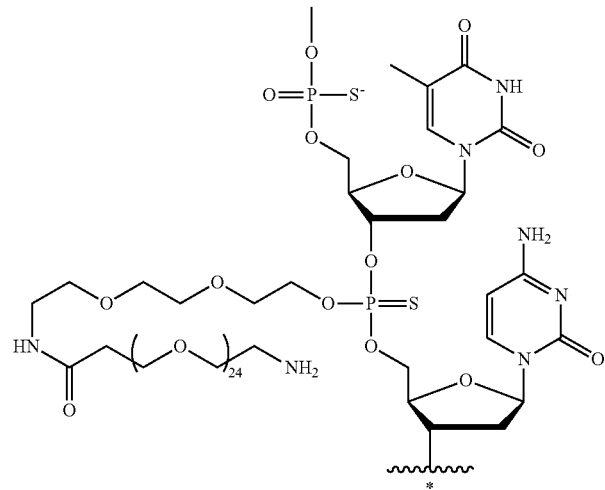
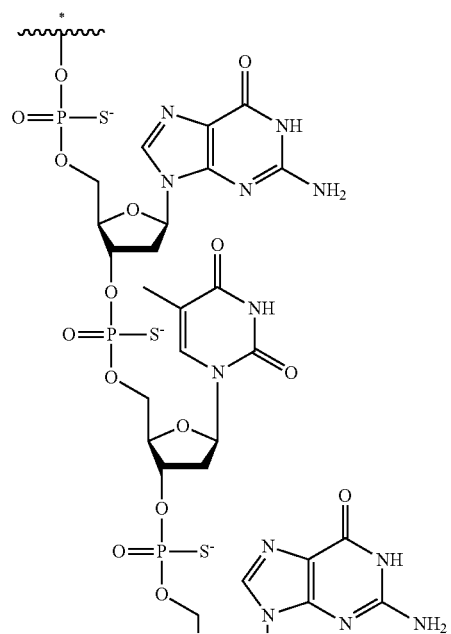

TABLE 11-continued
Modified Oligonucleotide Structures (with -PEG₃NHCOPEG₂₄NH₂)
Cmpd # Structure
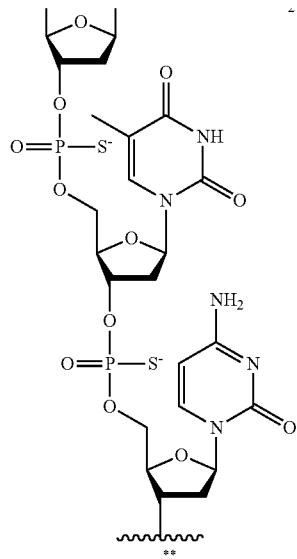
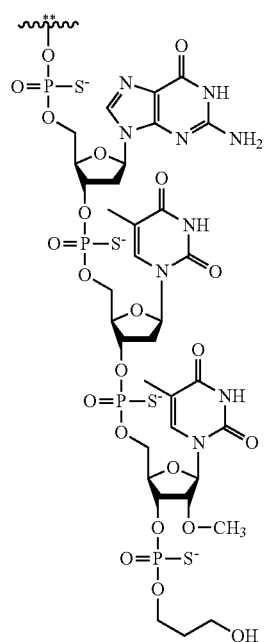

TABLE 11-continued
Modified Oligonucleotide Structures (with -PEG₃NHCOPEG₂₄NH₂)
| Cmpd # | Structure |
|---|---|
| 2.2b | 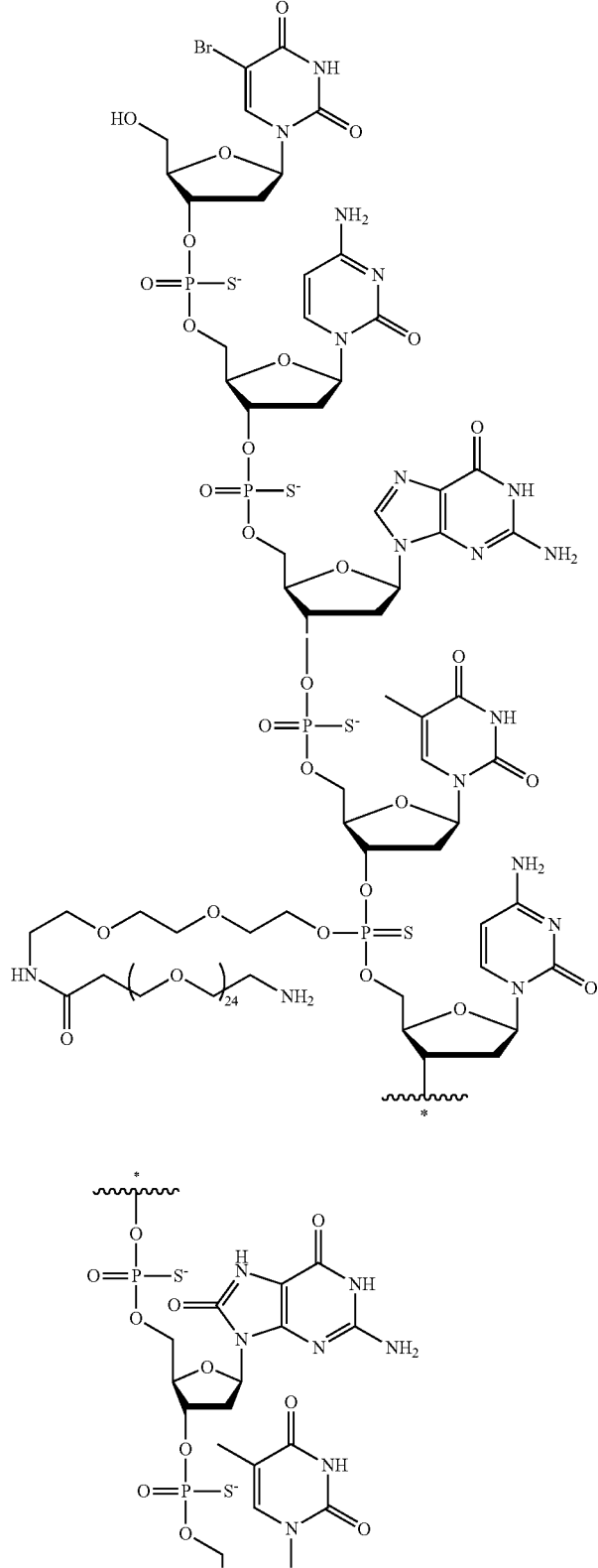 |

TABLE 11-continued
Modified Oligonucleotide Structures (with -PEG₃NHCOPEG₂₄NH₂)
Cmpd # | Structure
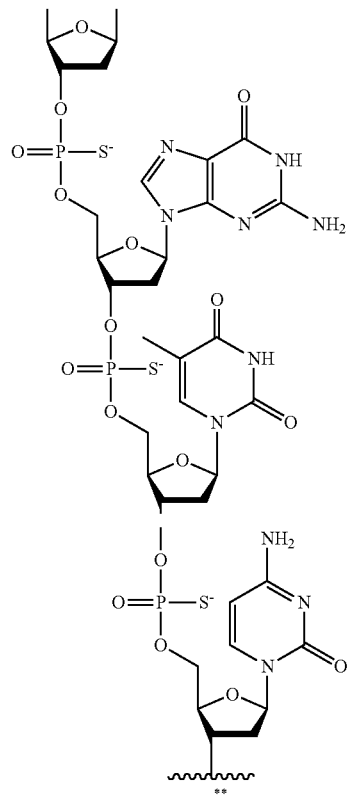
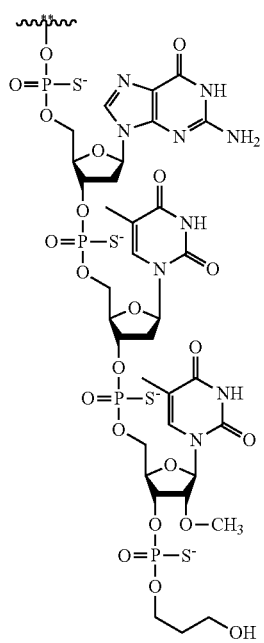

TABLE 11-continued
Modified Oligonucleotide Structures (with -PEG$_3$NHCOPEG$_{24}$NH$_2$)
| Cmpd # | Structure |
|---|---|
| 2.3b | 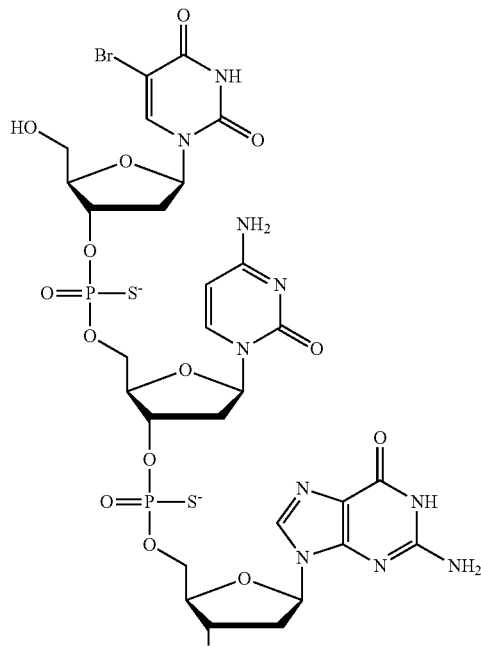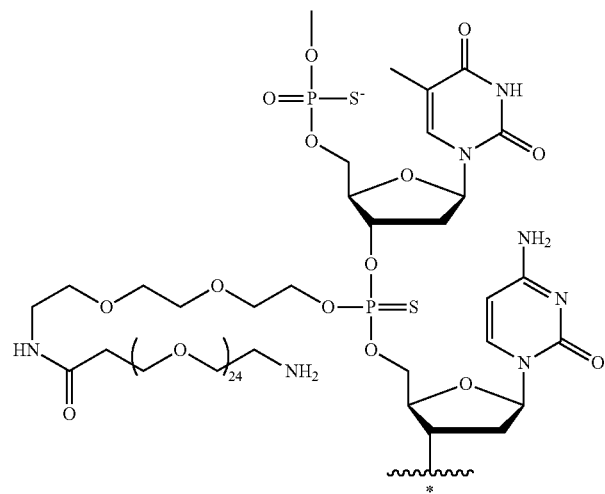 |

TABLE 11-continued
Modified Oligonucleotide Structures (with -PEG₃NHCOPEG₂₄NH₂)
Cmpd # | Structure
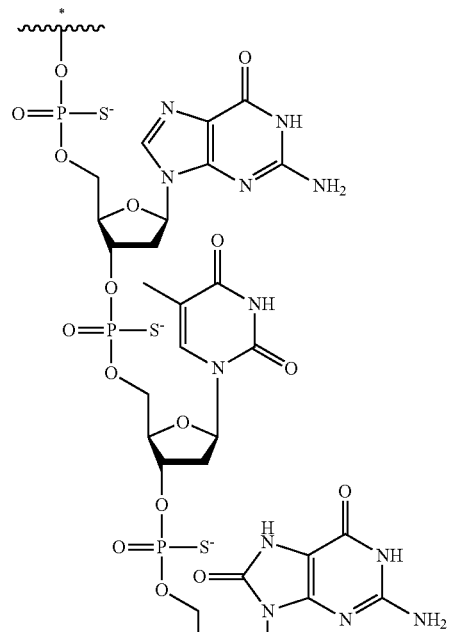
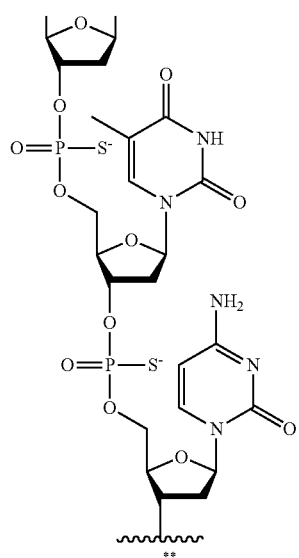

US 11,795,463 B2
321                                                                    322
TABLE 11-continued
Modified Oligonucleotide Structures (with -PEG$_3$NHCOPEG$_{24}$NH$_2$)
Cmpd
Structure
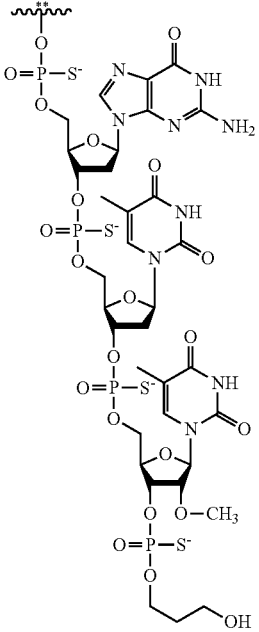
2.4b
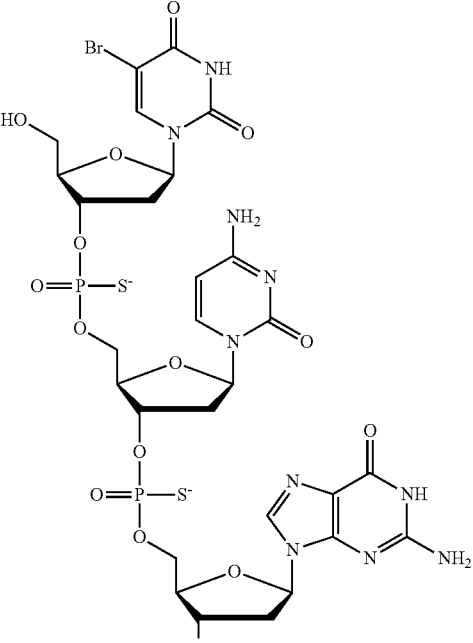

323
TABLE 11-continued
Modified Oligonucleotide Structures (with -PEG$_3$NHCOPEG$_{24}$NH$_2$)
Cmpd #     Structure
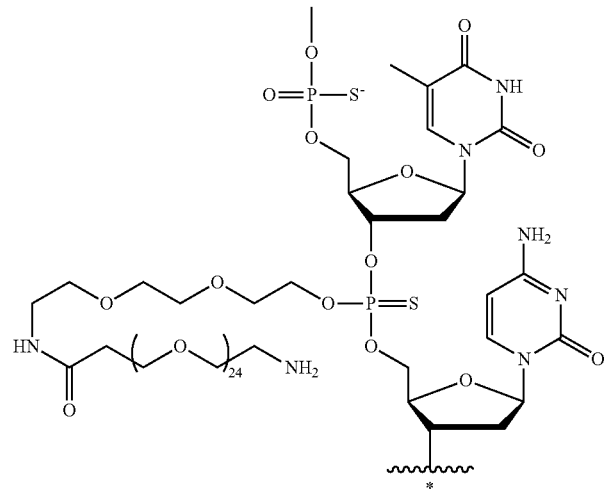
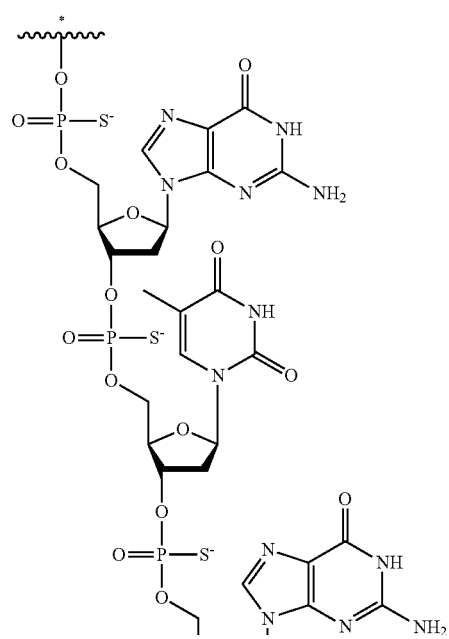

TABLE 11-continued
Modified Oligonucleotide Structures (with -PEG$_3$NHCOPEG$_{24}$NH$_2$)
Cmpd # | Structure
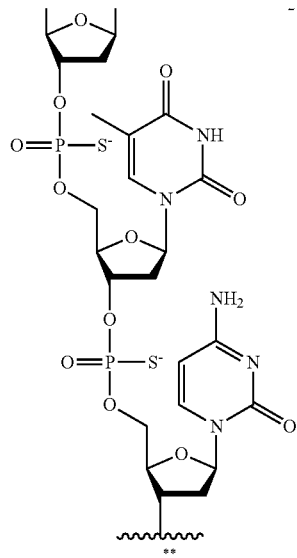
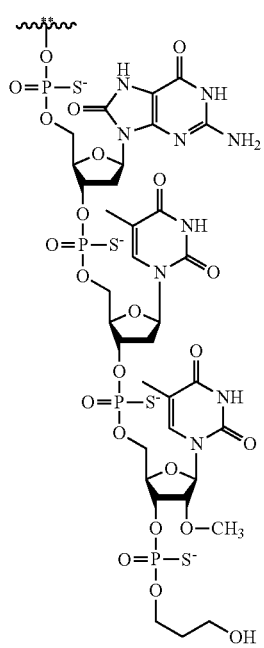

TABLE 12
Modified Oligonucleotide Structures (with -PEG$_3$NHCOPEG$_{24}$NH$_2$)
| Cmpd # | Structure |
|---|---|
| 3.1b | 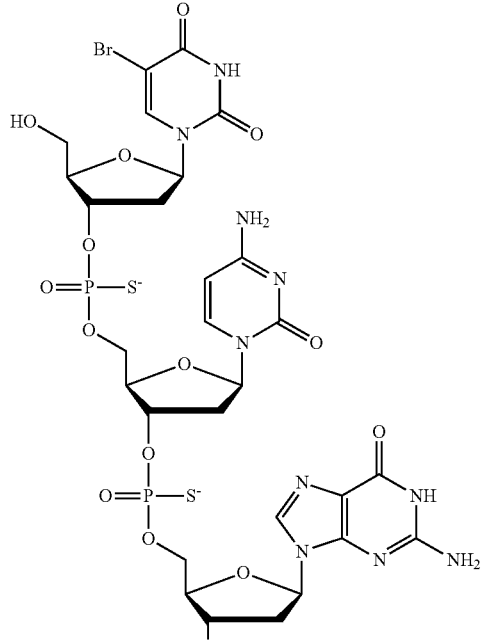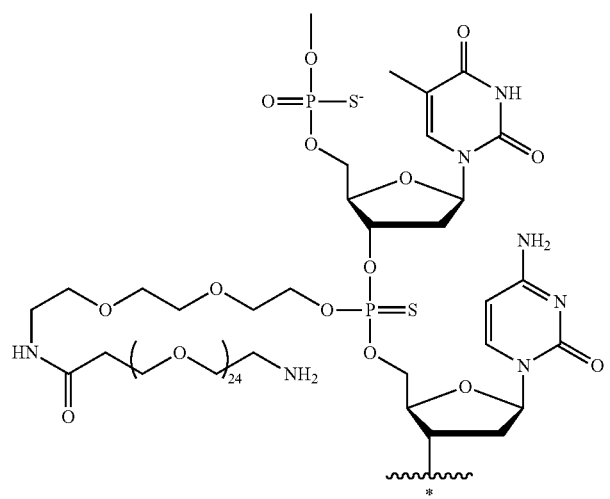 |

TABLE 12-continued
Modified Oligonucleotide Structures (with -PEG₃NHCOPEG₂₄NH₂)
Cmpd # | Structure
---|---
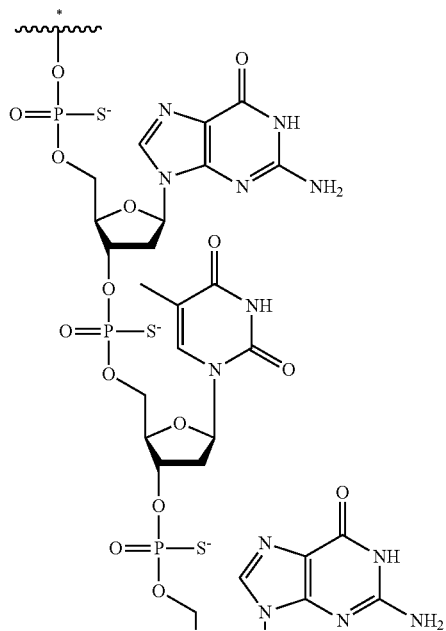
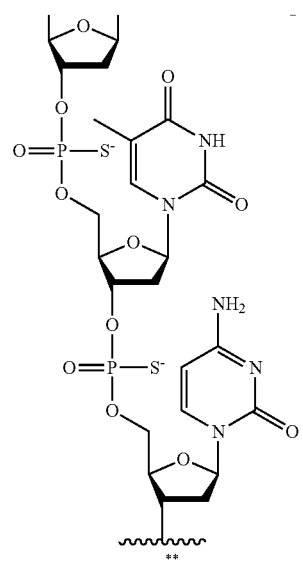

TABLE 12-continued
Modified Oligonucleotide Structures (with -PEG$_3$NHCOPEG$_{24}$NH$_2$)
Cmpd # | Structure
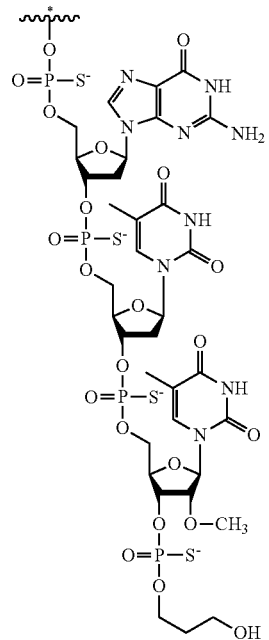
3.2b
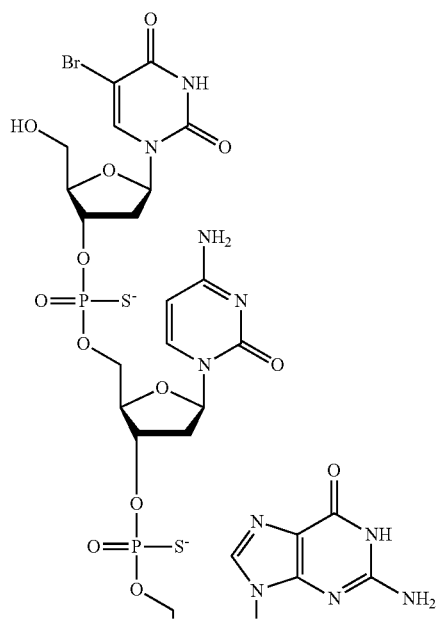

TABLE 12-continued
Modified Oligonucleotide Structures (with -PEG$_3$NHCOPEG$_{24}$NH$_2$)
Cmpd # Structure
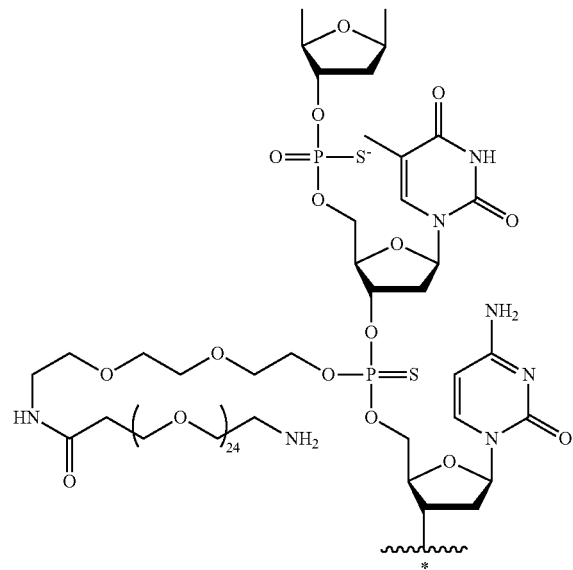
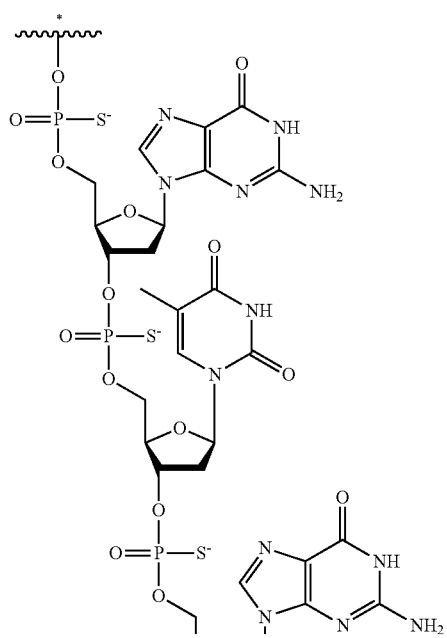

TABLE 12-continued
Modified Oligonucleotide Structures (with -PEG₃NHCOPEG₂₄NH₂)
Cmpd # Structure
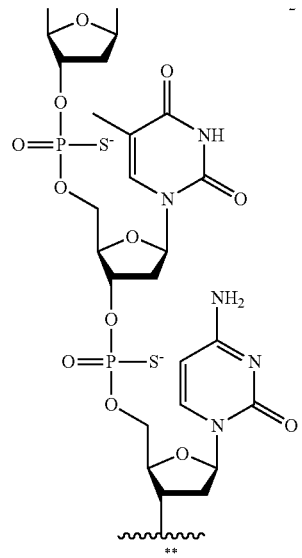
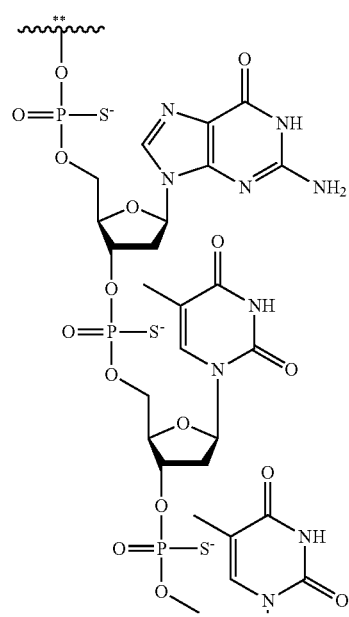

TABLE 12-continued
Modified Oligonucleotide Structures (with -PEG$_3$NHCOPEG$_{24}$NH$_2$)
| Cmpd # | Structure |
|---|---|
| | 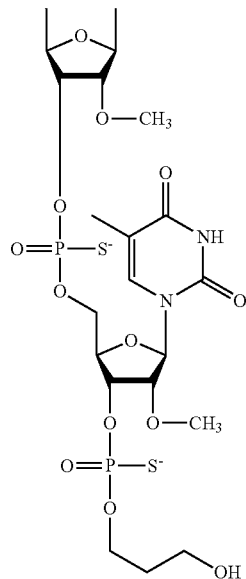 |
| 3.3b | 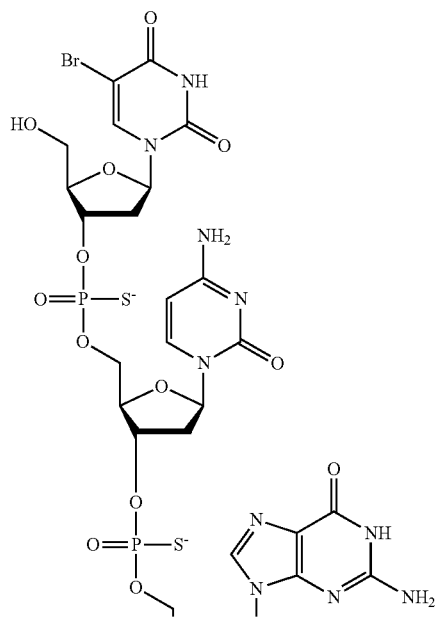 |

TABLE 12-continued
Modified Oligonucleotide Structures (with -PEG$_3$NHCOPEG$_{24}$NH$_2$)
Cmpd # | Structure
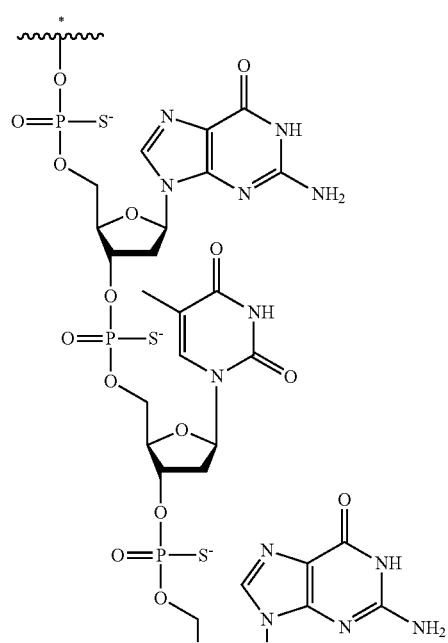

TABLE 12-continued
Modified Oligonucleotide Structures (with -PEG$_3$NHCOPEG$_{24}$NH$_2$)
Cmpd # | Structure
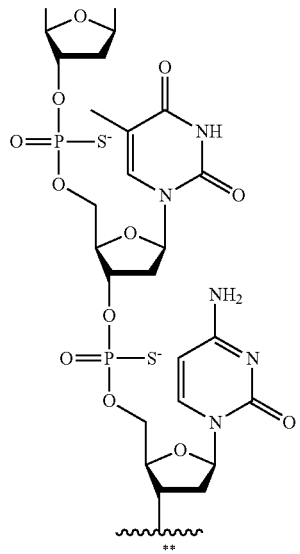
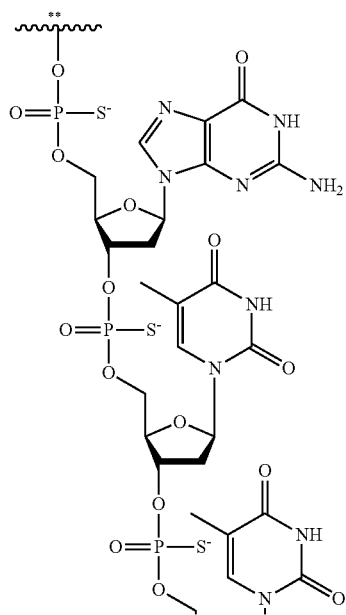

TABLE 12-continued
Modified Oligonucleotide Structures (with -PEG₃NHCOPEG₂₄NH₂)
| Cmpd # | Structure |
|---|---|
| | 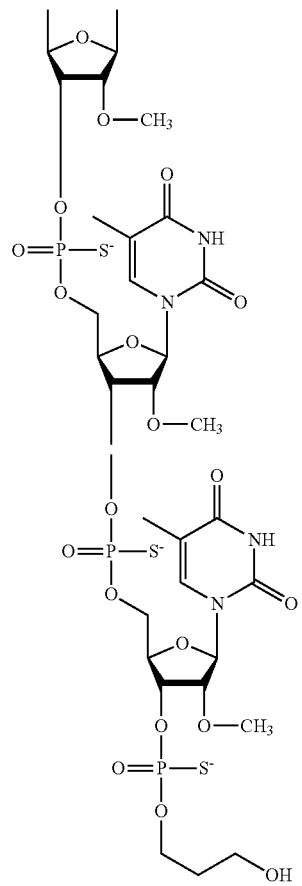 |
| 4.1b | 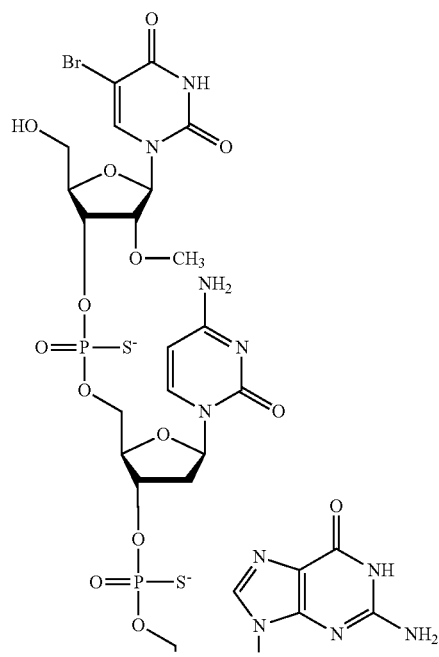 |

TABLE 12-continued
Modified Oligonucleotide Structures (with -PEG$_3$NHCOPEG$_{24}$NH$_2$)
Cmpd # | Structure
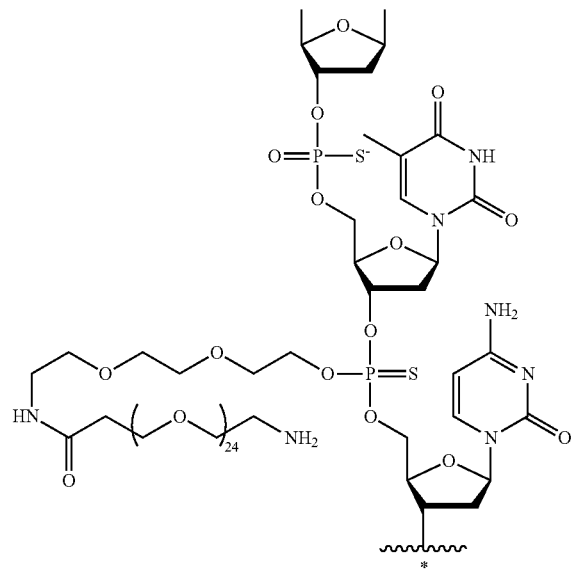
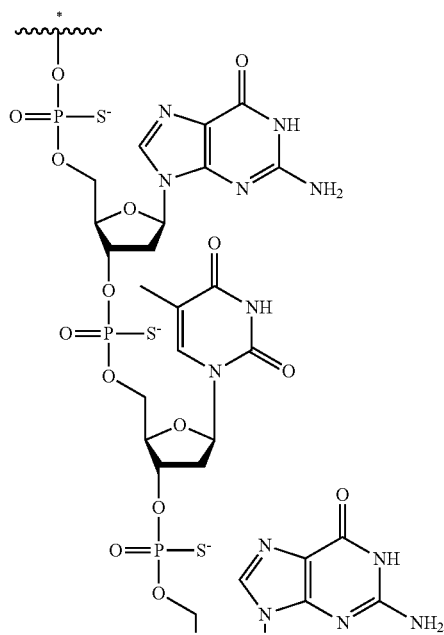

TABLE 12-continued
Modified Oligonucleotide Structures (with -PEG₃NHCOPEG₂₄NH₂)
Cmpd # | Structure
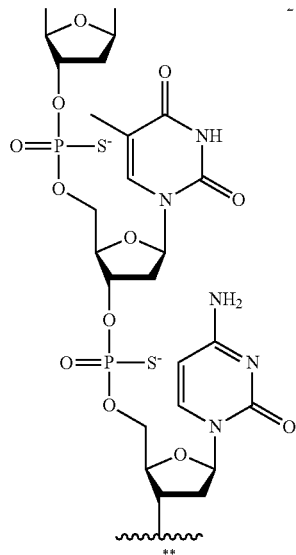
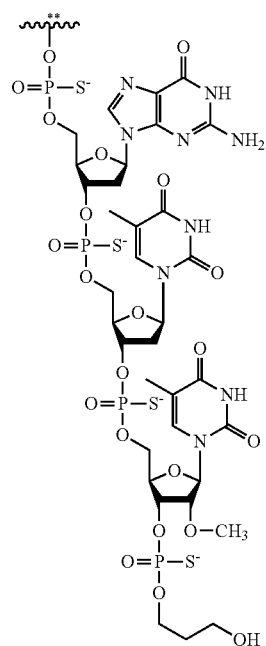

TABLE 12-continued
Modified Oligonucleotide Structures (with -PEG₃NHCOPEG₂₄NH₂)
| Cmpd # | Structure |
|---|---|
| 4.2b | 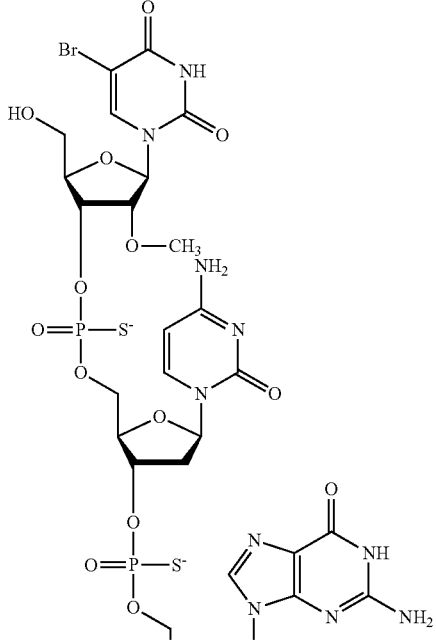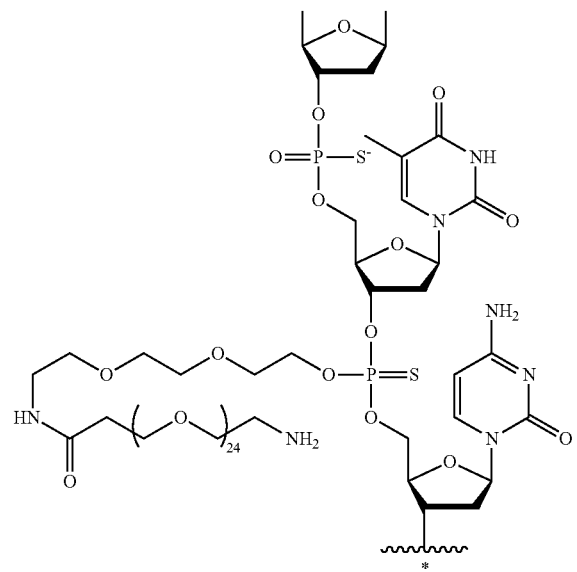 |

TABLE 12-continued
Modified Oligonucleotide Structures (with -PEG$_3$NHCOPEG$_{24}$NH$_2$)
Cmpd # | Structure
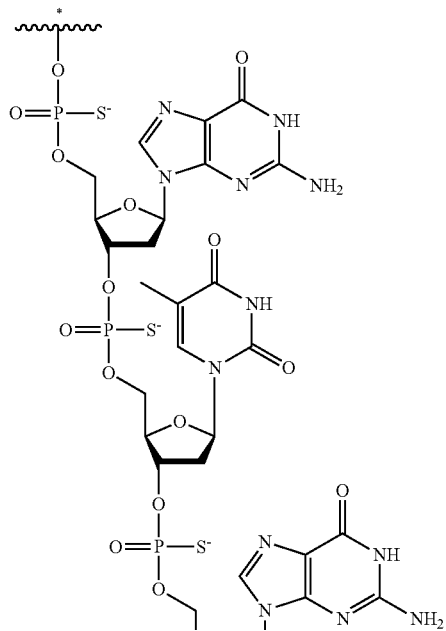
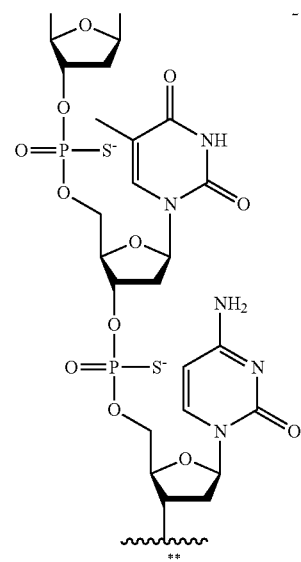

TABLE 12-continued
Modified Oligonucleotide Structures (with -PEG$_3$NHCOPEG$_{24}$NH$_2$)
Cmpd #  Structure
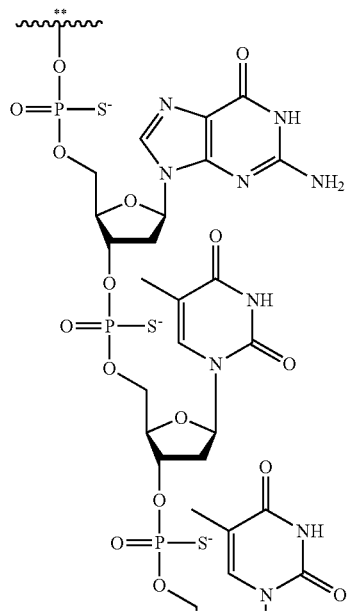
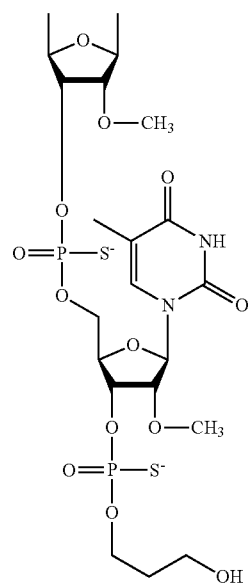

TABLE 12-continued
Modified Oligonucleotide Structures (with -PEG₃NHCOPEG₂₄NH₂)
| Cmpd # | Structure |
|---|---|
| 4.3b | 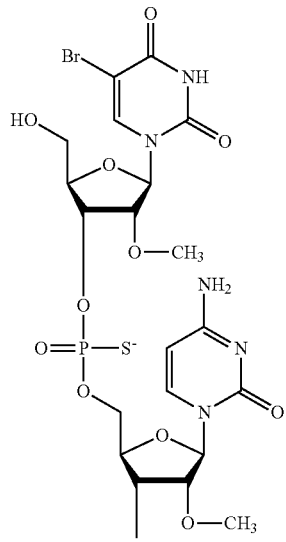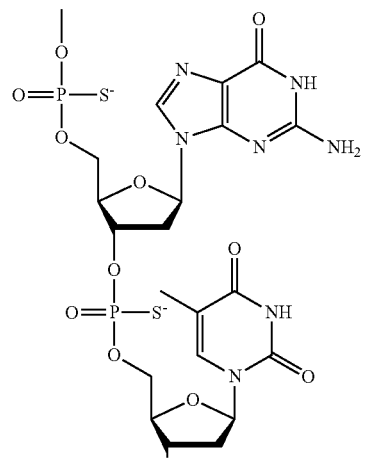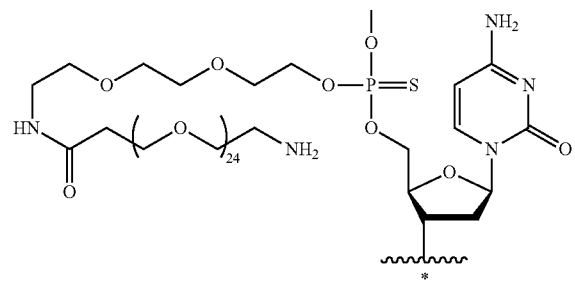 |

TABLE 12-continued
Modified Oligonucleotide Structures (with -PEG$_3$NHCOPEG$_{24}$NH$_2$)
| Cmpd # | Structure |
|---|---|
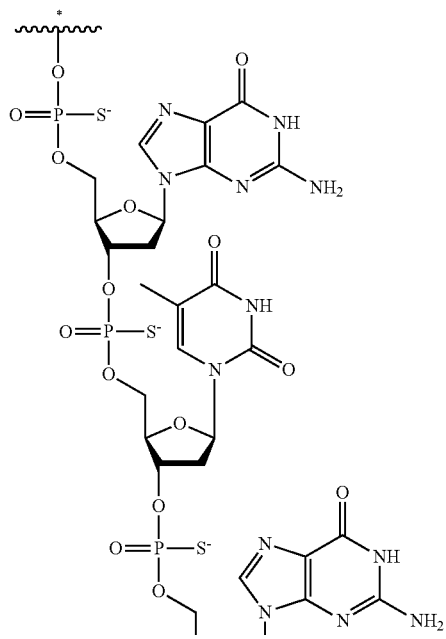
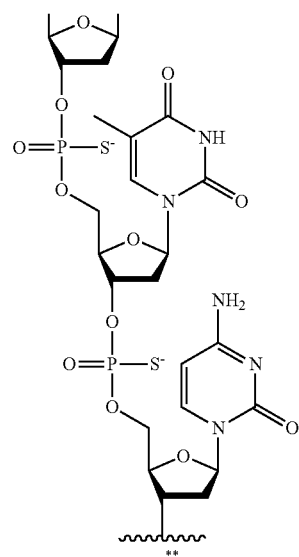

TABLE 12-continued
Modified Oligonucleotide Structures (with -PEG$_3$NHCOPEG$_{24}$NH$_2$)
Cmpd # | Structure
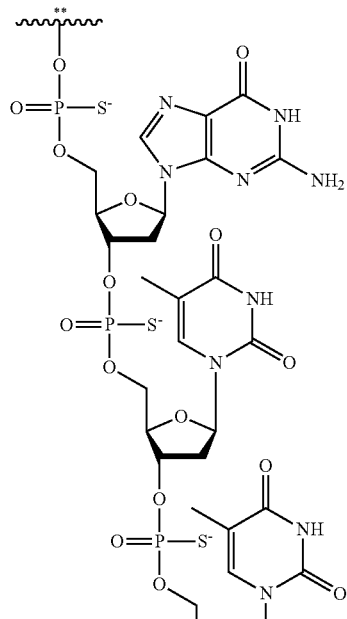
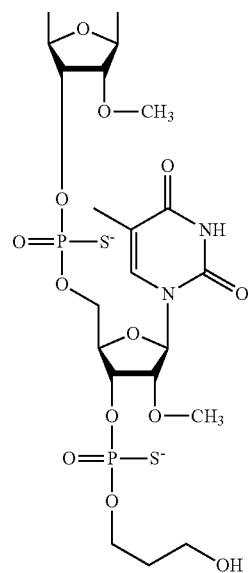

TABLE 12-continued
Modified Oligonucleotide Structures (with -PEG$_3$NHCOPEG$_{24}$NH$_2$)
| Cmpd # | Structure |
|---|---|
| 5.1b | 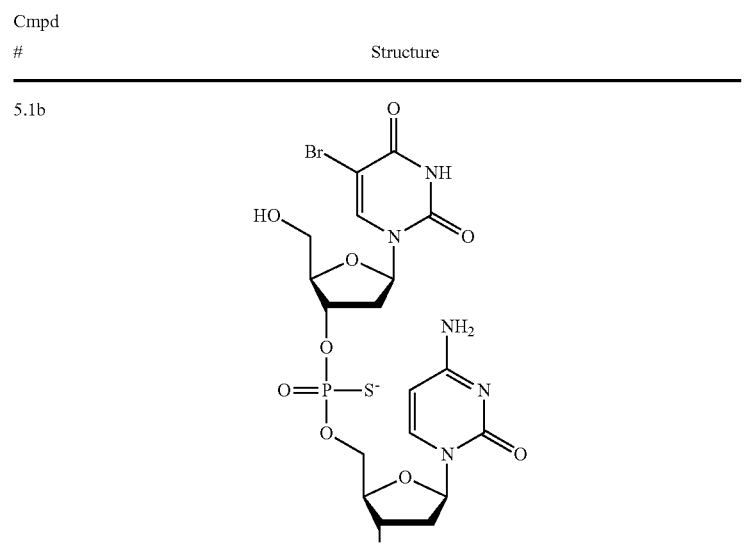<br>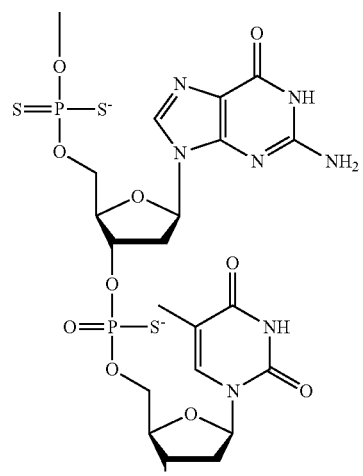<br>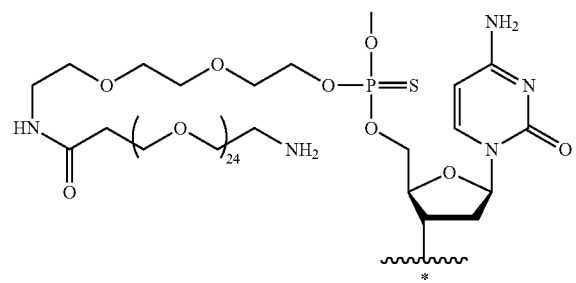 |

TABLE 12-continued
Modified Oligonucleotide Structures (with -PEG$_3$NHCOPEG$_{24}$NH$_2$)
Cmpd # | Structure
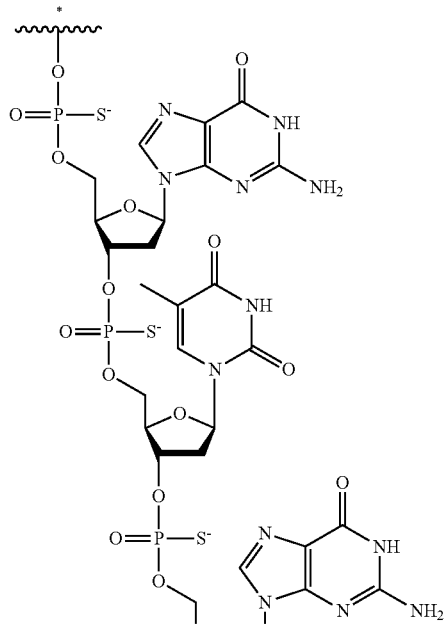
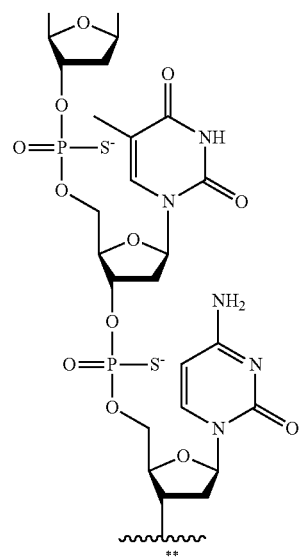

TABLE 12-continued
Modified Oligonucleotide Structures (with -PEG$_3$NHCOPEG$_{24}$NH$_2$)
| Cmpd # | Structure |
|---|---|
| | 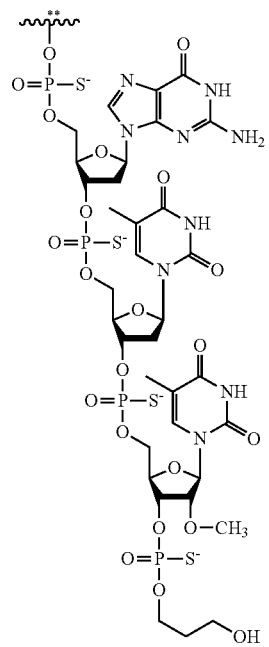 |
| 5.2b | 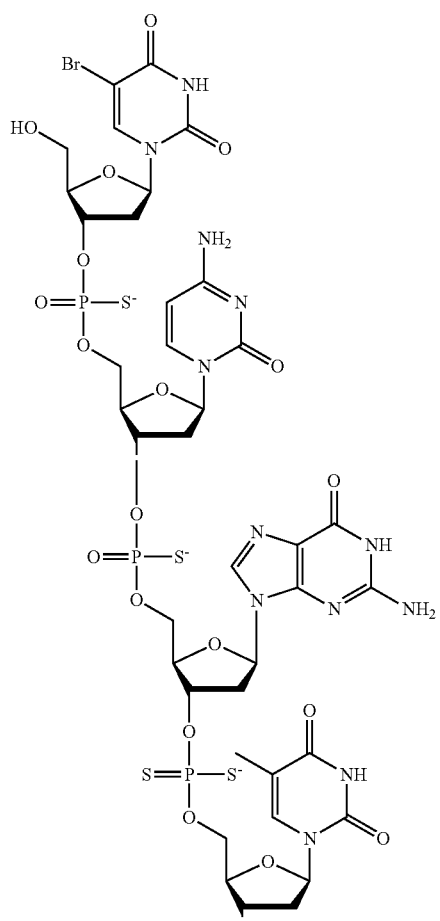 |

TABLE 12-continued
Modified Oligonucleotide Structures (with -PEG$_3$NHCOPEG$_{24}$NH$_2$)
Cmpd # | Structure
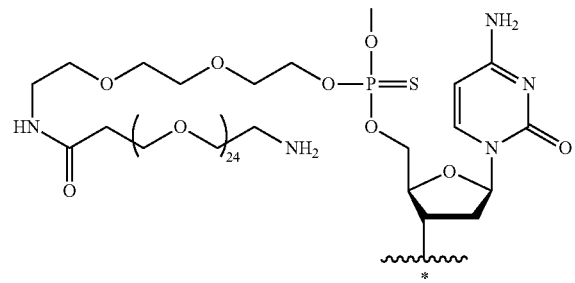
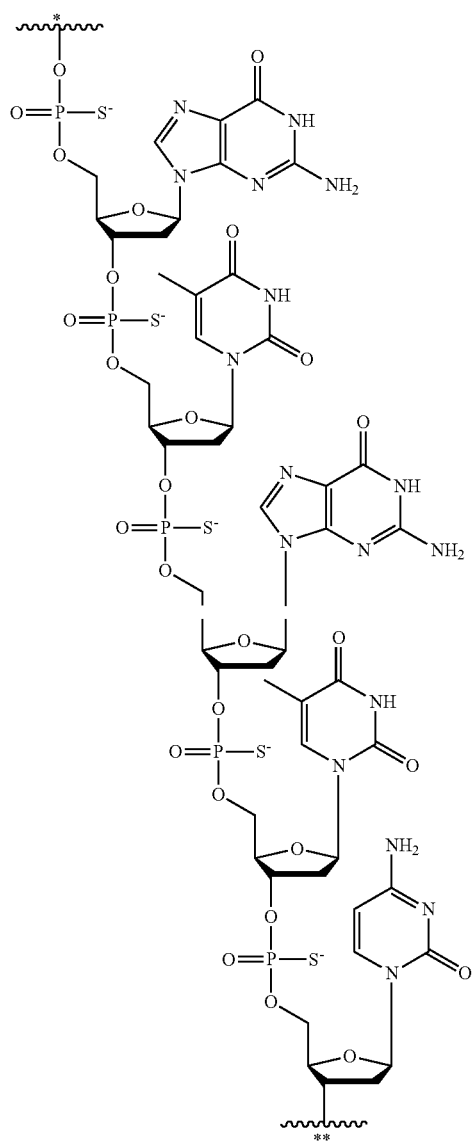

TABLE 12-continued
Modified Oligonucleotide Structures (with -PEG₃NHCOPEG₂₄NH₂)
Cmpd # | Structure
---|---
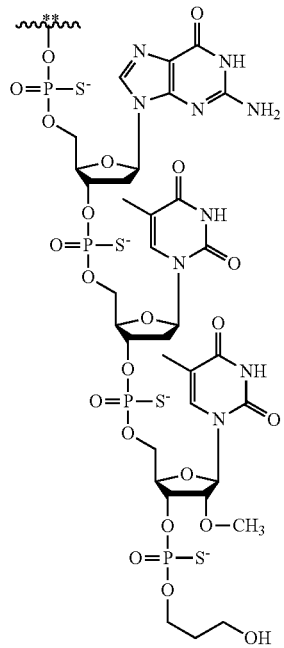
5.3b
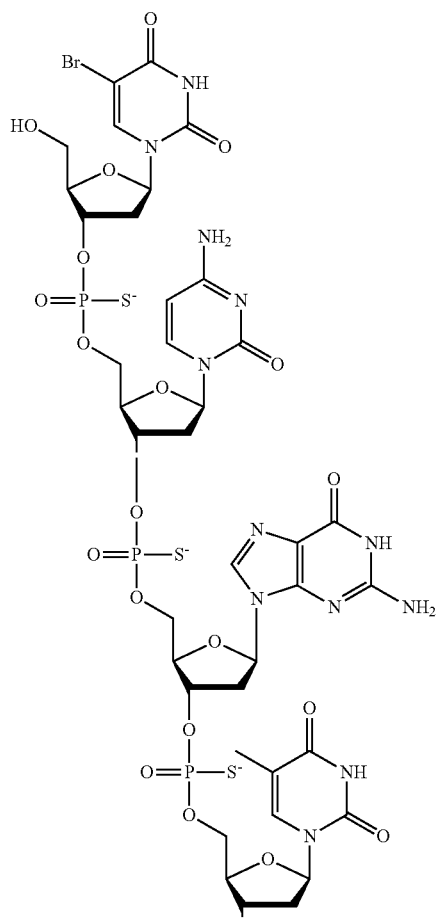

TABLE 12-continued
Modified Oligonucleotide Structures (with -PEG₃NHCOPEG₂₄NH₂)
Cmpd # | Structure
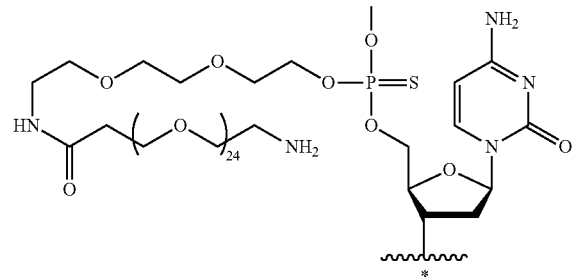
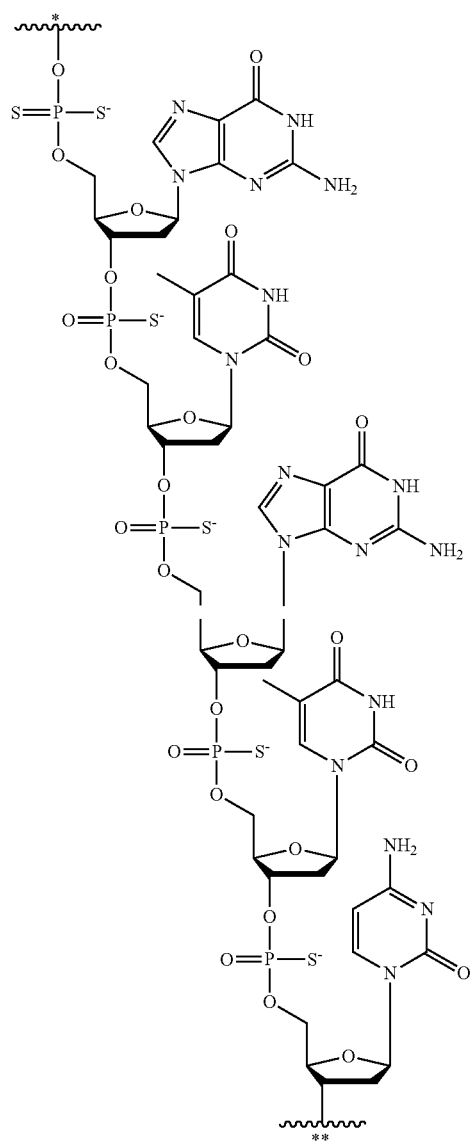

TABLE 12-continued
Modified Oligonucleotide Structures (with -PEG₃NHCOPEG₂₄NH₂)
| Cmpd # | Structure |
|---|---|
| | 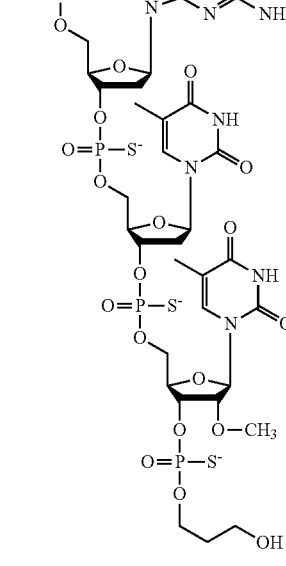 |
| 5.4b | 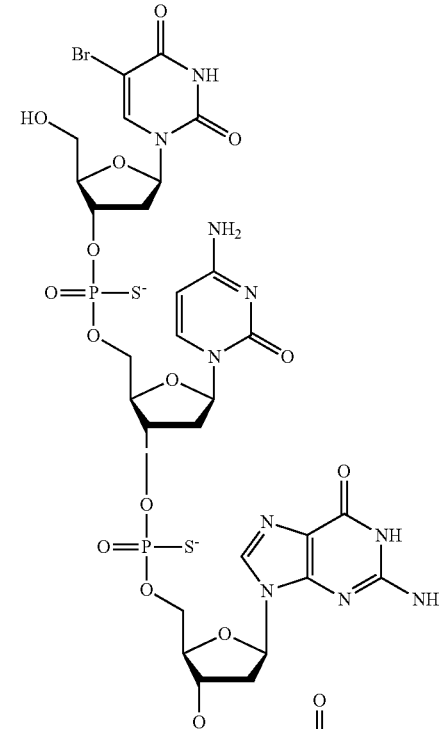 |

TABLE 12-continued
Modified Oligonucleotide Structures (with -PEG$_3$NHCOPEG$_{24}$NH$_2$)
Cmpd # Structure
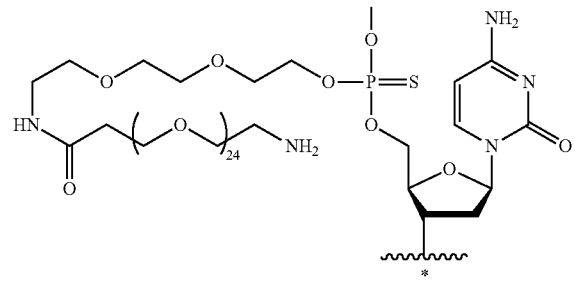
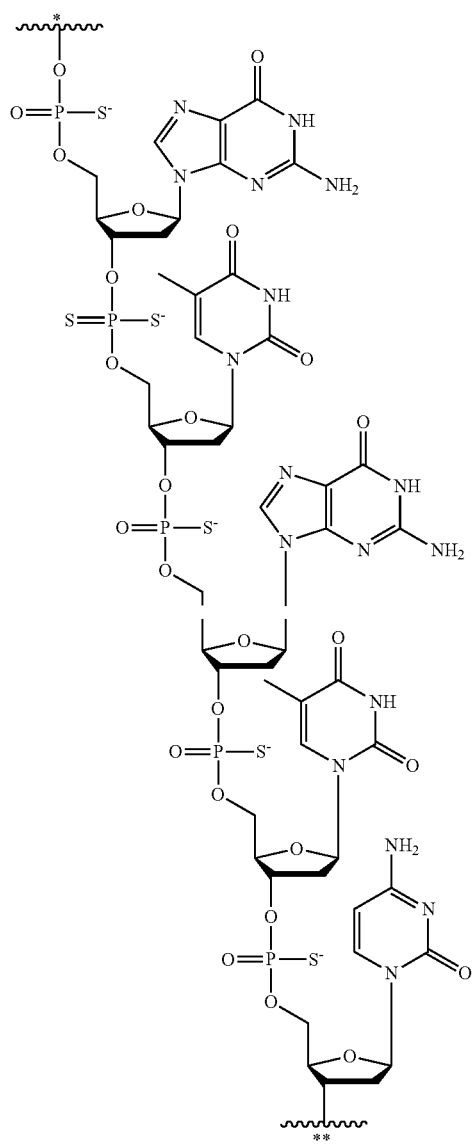

TABLE 12-continued
Modified Oligonucleotide Structures (with -PEG₃NHCOPEG₂₄NH₂)
| Cmpd # | Structure |
|---|---|
| | 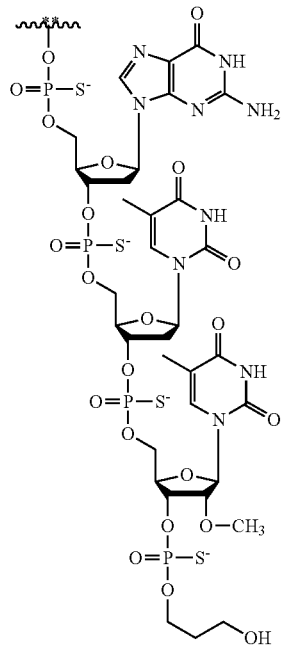 |
| 5.5b | 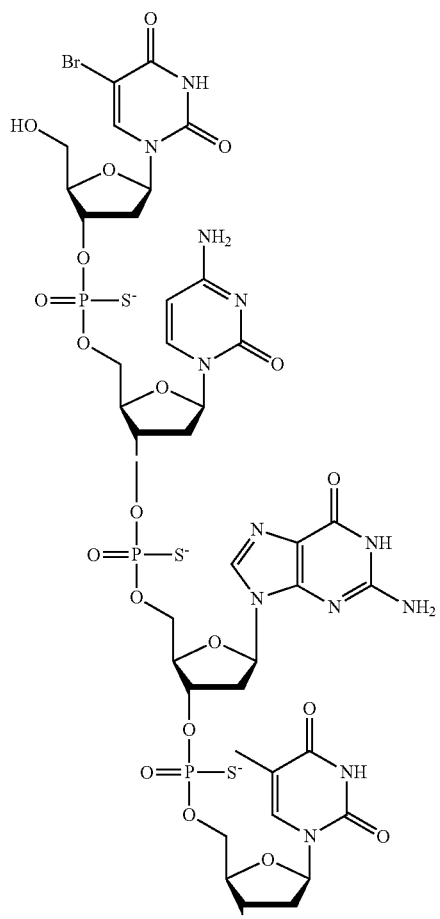 |

TABLE 12-continued
Modified Oligonucleotide Structures (with -PEG$_3$NHCOPEG$_{24}$NH$_2$)
Cmpd # | Structure
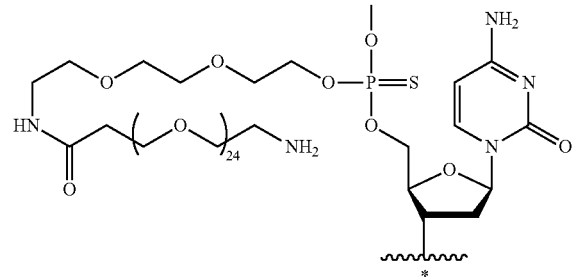
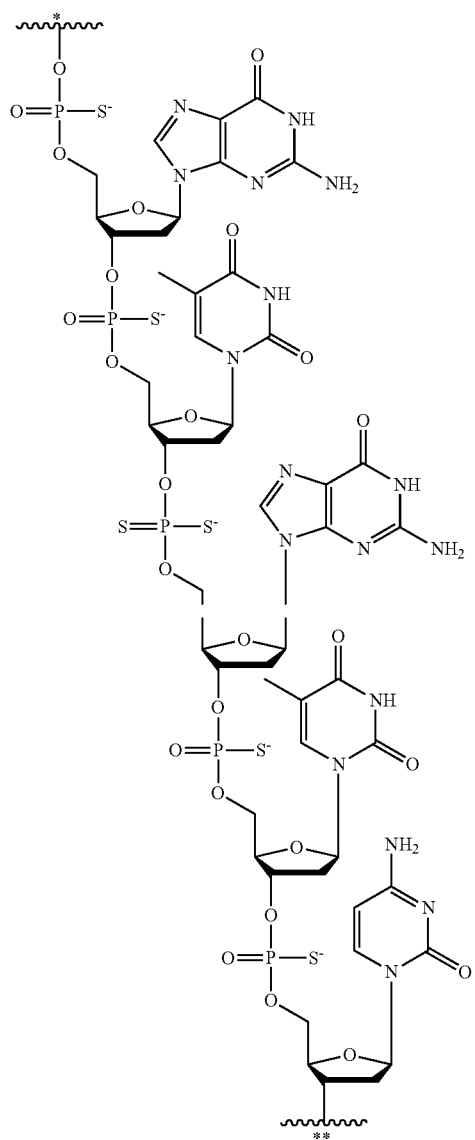

TABLE 12-continued
Modified Oligonucleotide Structures (with -PEG₃NHCOPEG₂₄NH₂)
| Cmpd # | Structure |
|---|---|
| | 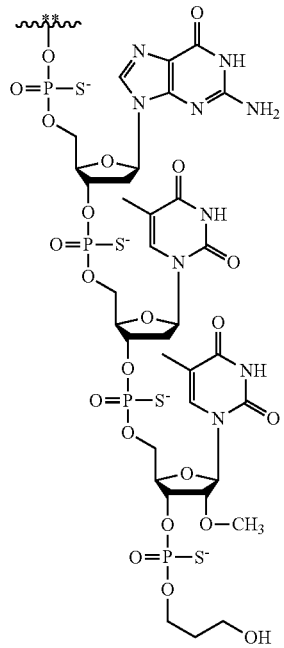 |
| 5.6b | 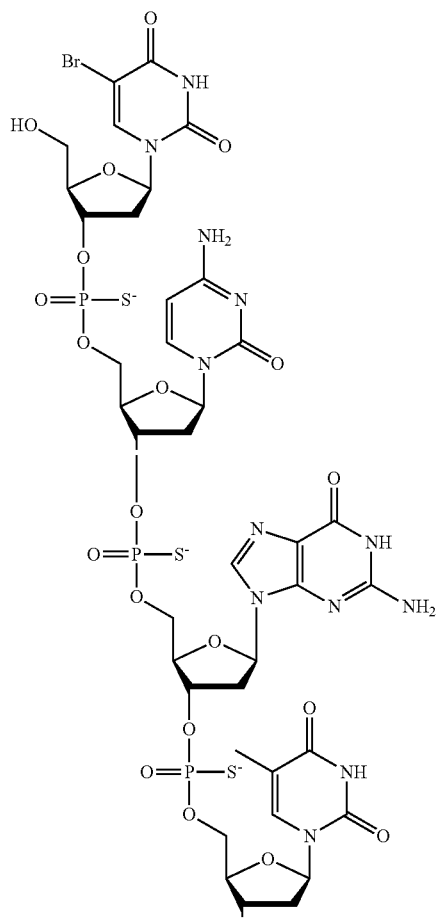 |

TABLE 12-continued
Modified Oligonucleotide Structures (with -PEG$_3$NHCOPEG$_{24}$NH$_2$)
Cmpd # Structure
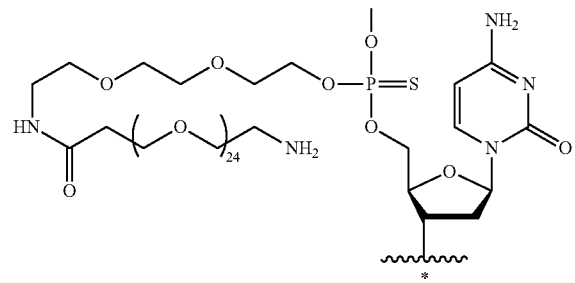
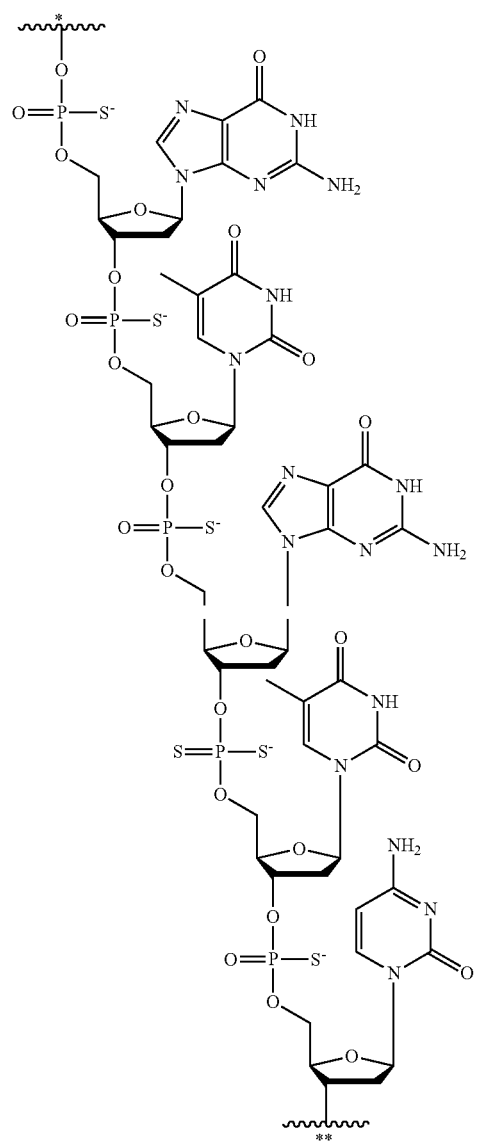

TABLE 12-continued
Modified Oligonucleotide Structures (with -PEG$_3$NHCOPEG$_{24}$NH$_2$)
| Cmpd # | Structure |
|---|---|
| | 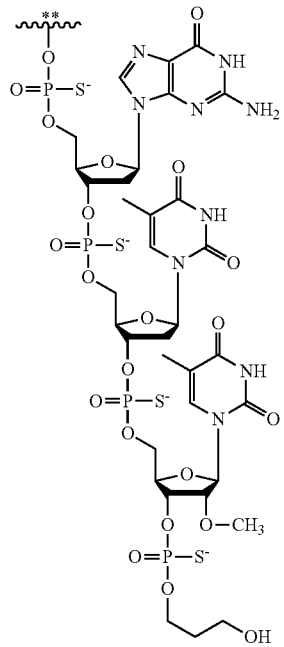 |
| 5.7b | 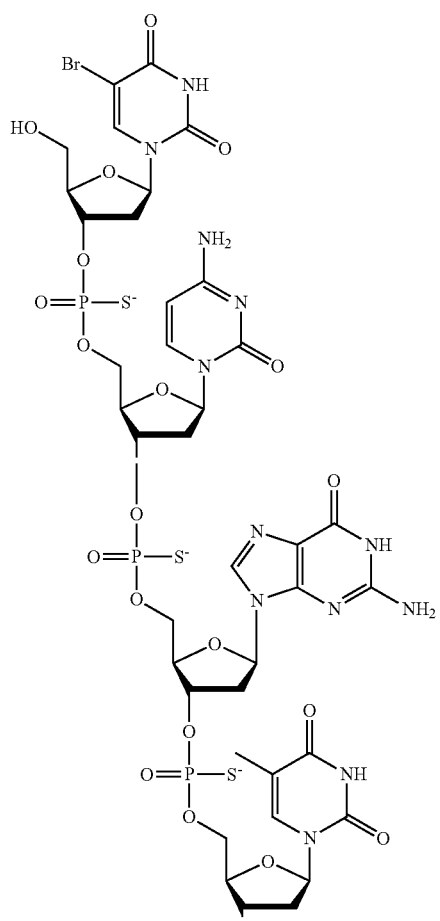 |

TABLE 12-continued
Modified Oligonucleotide Structures (with -PEG$_3$NHCOPEG$_{24}$NH$_2$)
Cmpd # Structure
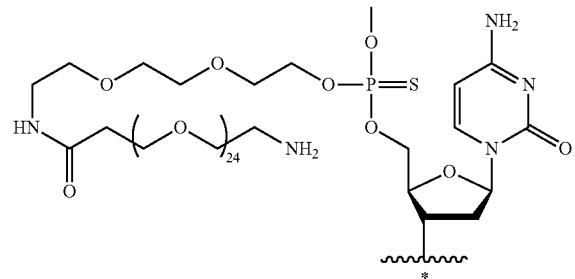
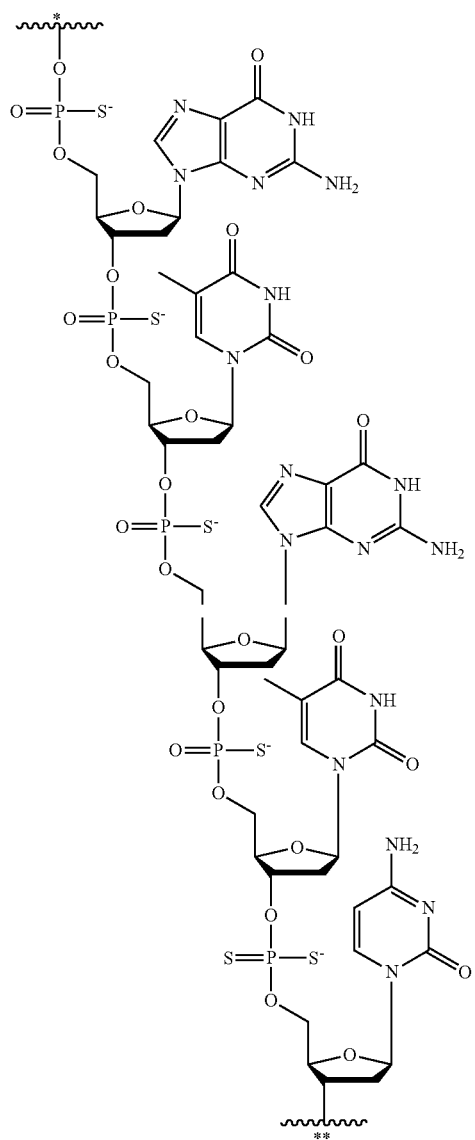

TABLE 12-continued
Modified Oligonucleotide Structures (with -PEG₃NHCOPEG₂₄NH₂)
| Cmpd # | Structure |
|---|---|
| | 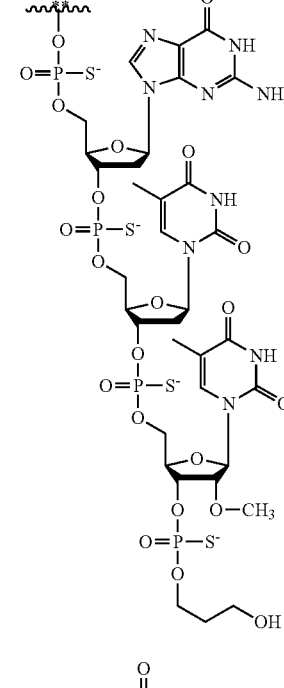 |
| 5.8b | 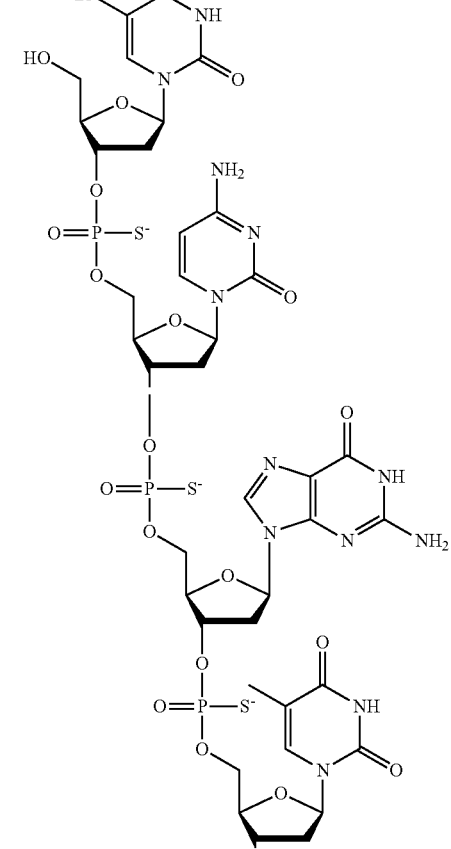 |

TABLE 12-continued
Modified Oligonucleotide Structures (with -PEG₃NHCOPEG₂₄NH₂)
Cmpd # | Structure
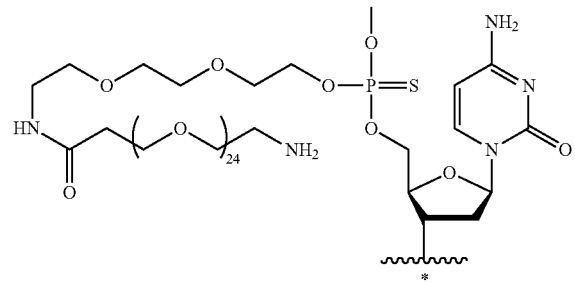
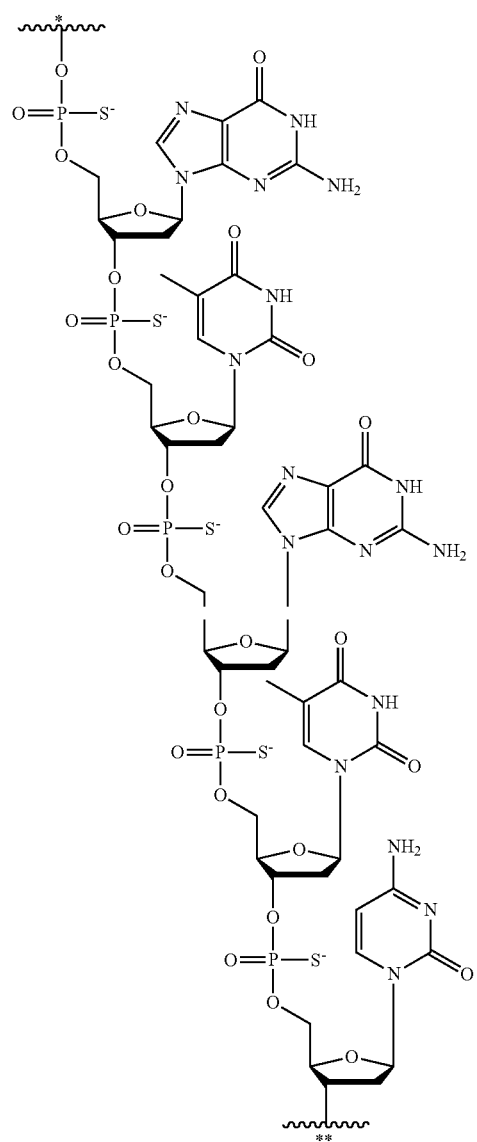

TABLE 12-continued
Modified Oligonucleotide Structures (with -PEG$_3$NHCOPEG$_{24}$NH$_2$)
| Cmpd # | Structure |
|---|---|
| | 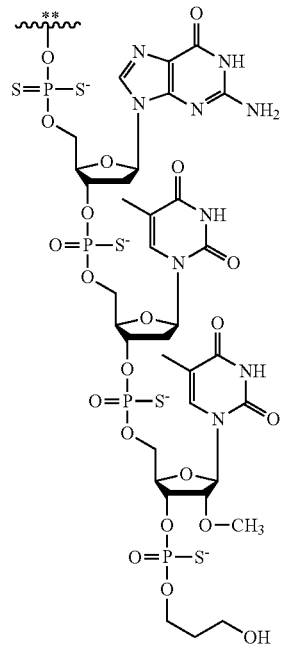 |
| 5.9b | 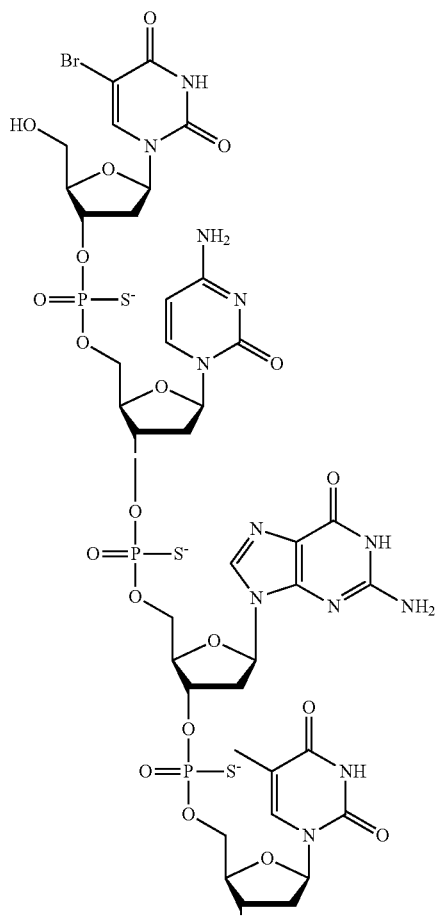 |

TABLE 12-continued
Modified Oligonucleotide Structures (with -PEG$_3$NHCOPEG$_{24}$NH$_2$)
Cmpd # Structure
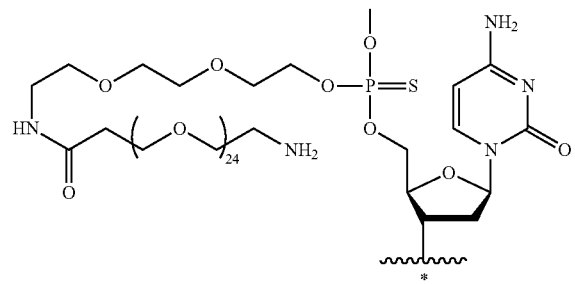
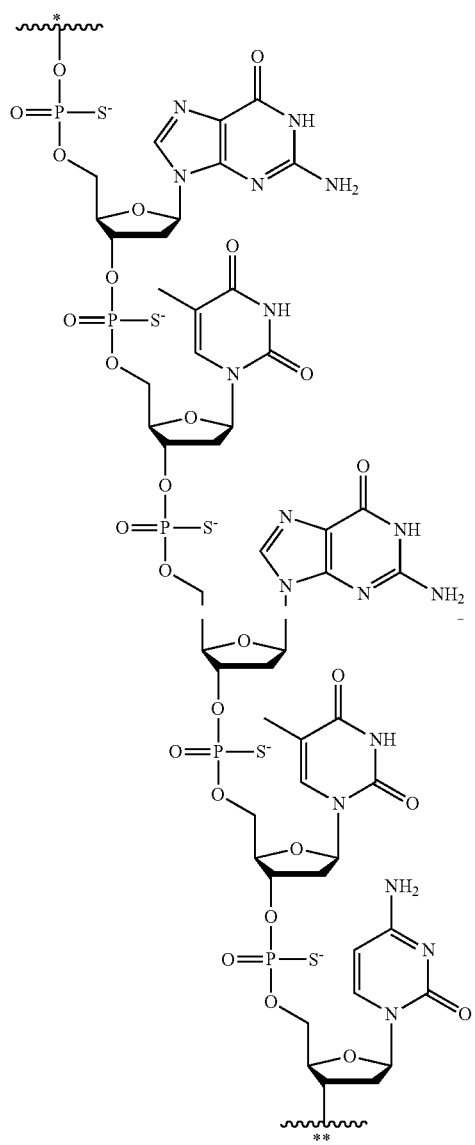

TABLE 12-continued
Modified Oligonucleotide Structures (with -PEG$_3$NHCOPEG$_{24}$NH$_2$)
| Cmpd # | Structure |
|---|---|
| | 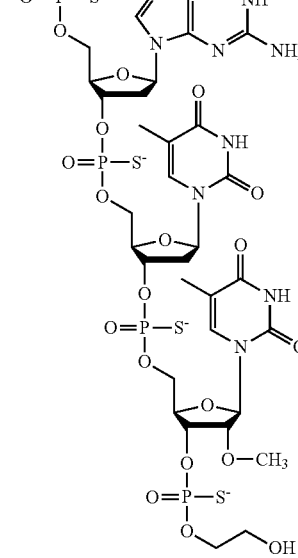 |
| 5.10b | 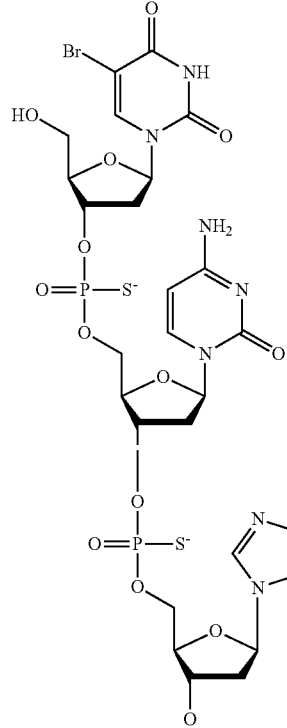 |

TABLE 12-continued
Modified Oligonucleotide Structures (with -PEG$_3$NHCOPEG$_{24}$NH$_2$)
Cmpd # Structure
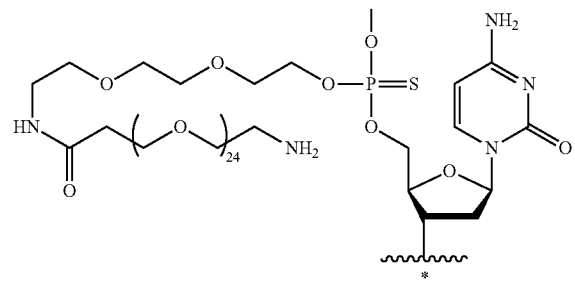
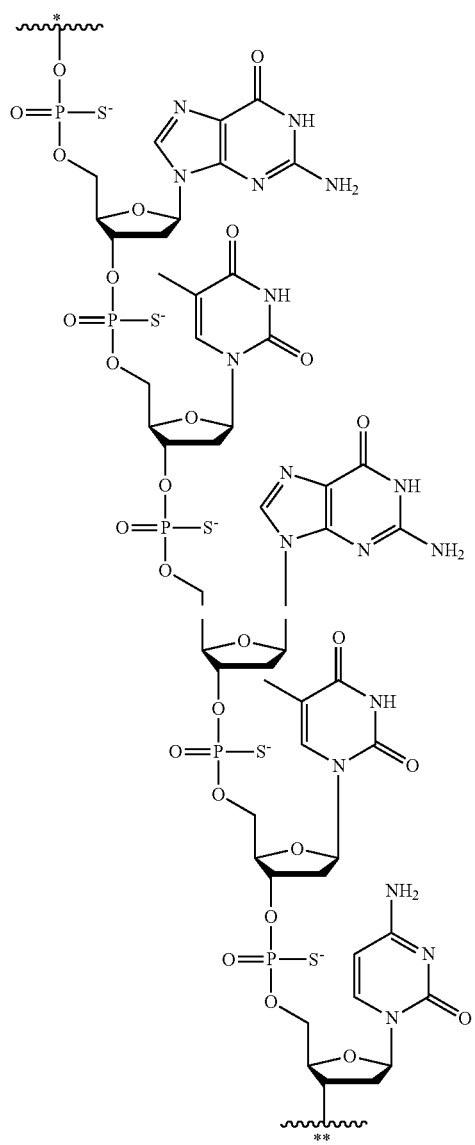

TABLE 12-continued

Modified Oligonucleotide Structures (with -PEG$_3$NHCOPEG$_{24}$NH$_2$)

| Cmpd # | Structure |
|---|---|
| | (structure) |
| 5.11b | (structure) |

TABLE 12-continued
Modified Oligonucleotide Structures (with -PEG₃NHCOPEG₂₄NH₂)
Cmpd # | Structure
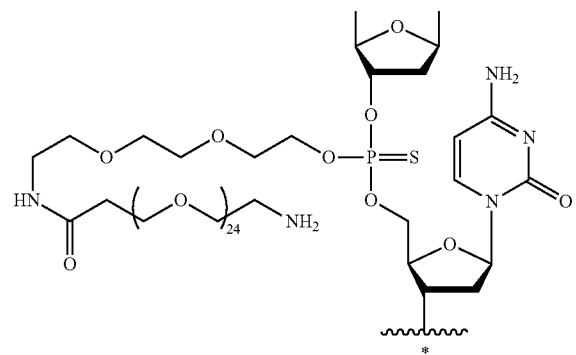
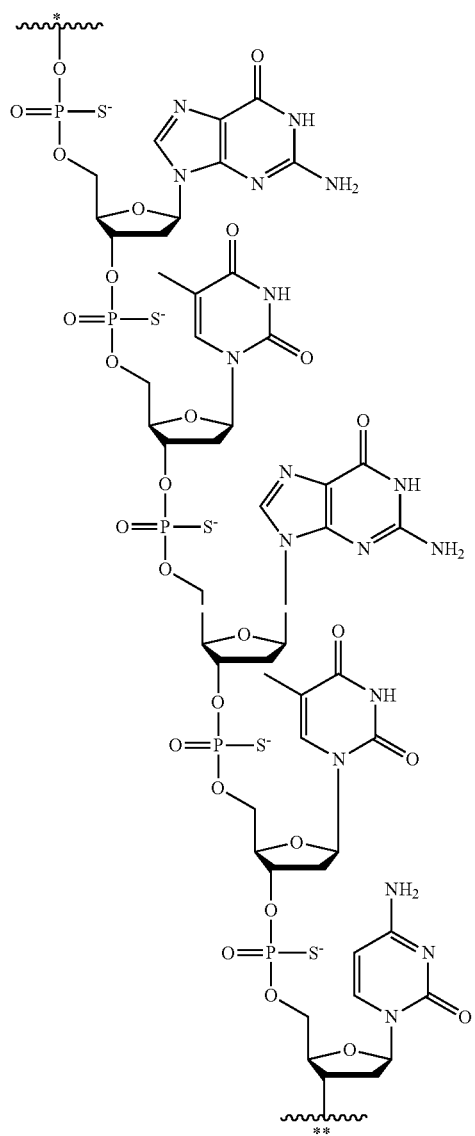

TABLE 12-continued
Modified Oligonucleotide Structures (with -PEG₃NHCOPEG₂₄NH₂)
| Cmpd # | Structure |
|---|---|
| | 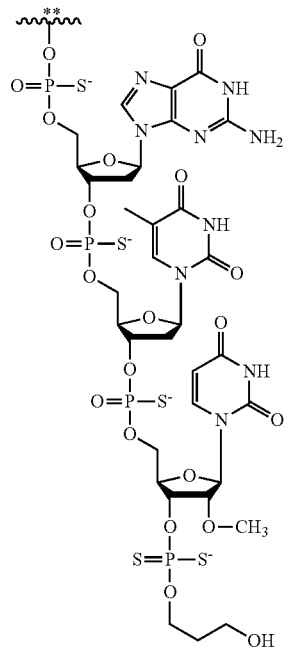 |
| 5.12b | 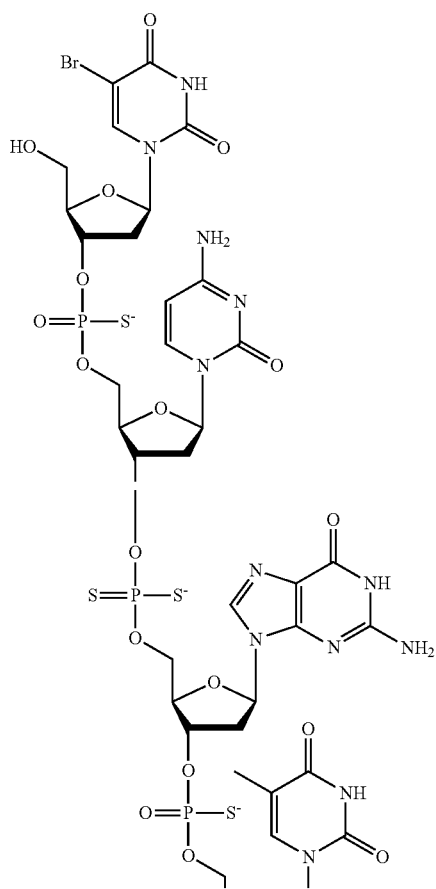 |

TABLE 12-continued
Modified Oligonucleotide Structures (with -PEG₃NHCOPEG₂₄NH₂)
Cmpd # Structure
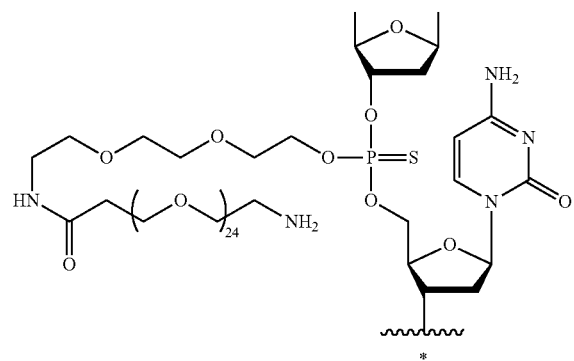
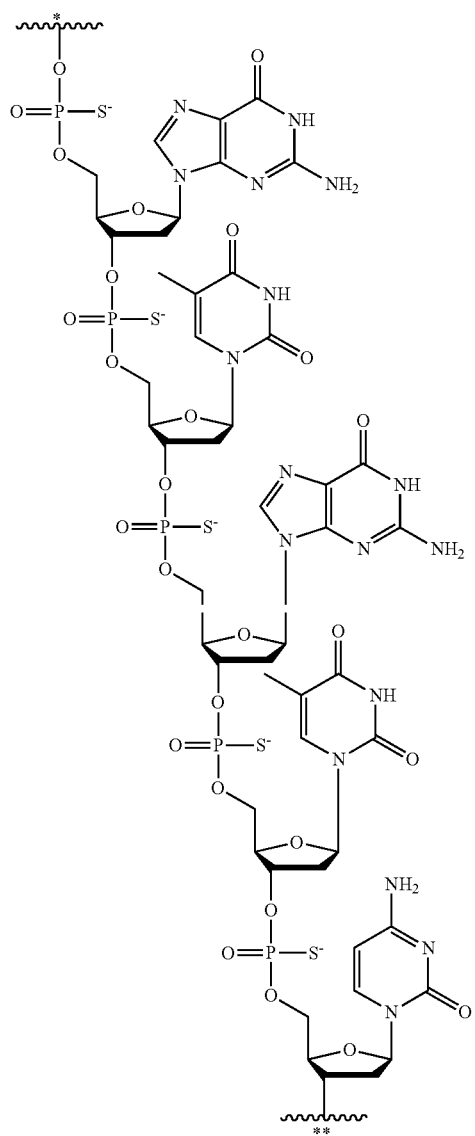

TABLE 12-continued
Modified Oligonucleotide Structures (with -PEG$_3$NHCOPEG$_{24}$NH$_2$)
| Cmpd # | Structure |
|---|---|
|  | 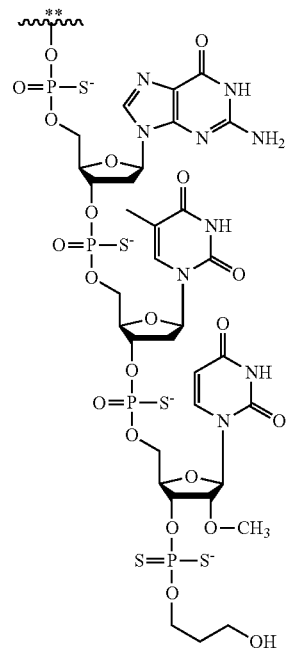 |
| 6.1b | 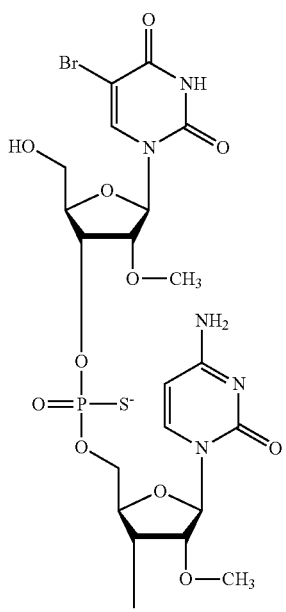 |

TABLE 12-continued
Modified Oligonucleotide Structures (with -PEG$_3$NHCOPEG$_{24}$NH$_2$)
Cmpd
Structure
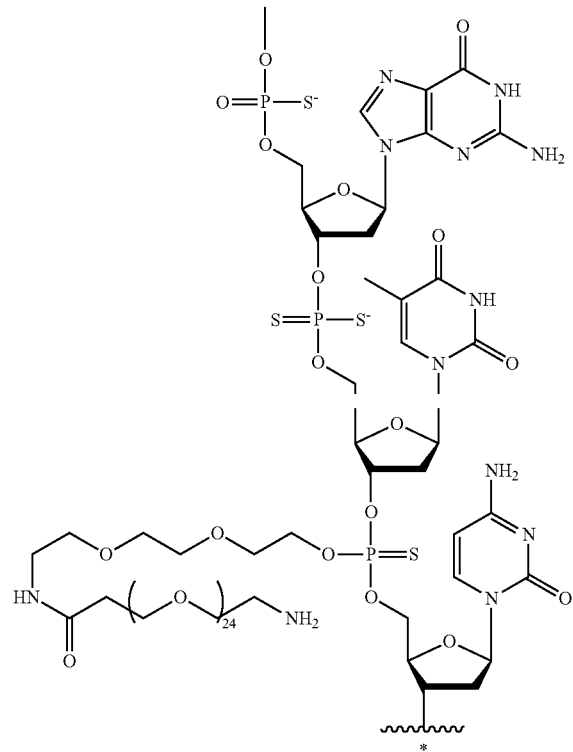
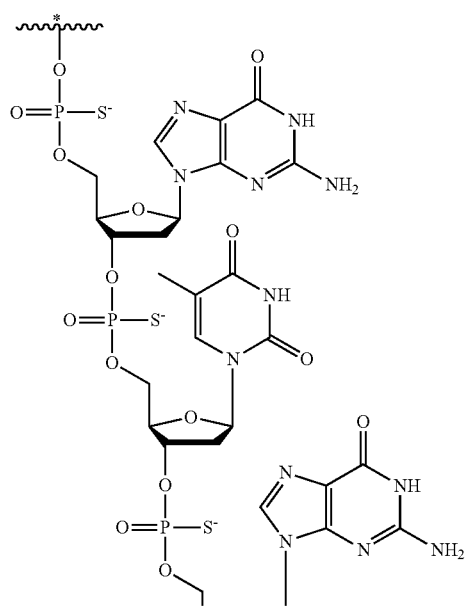

TABLE 12-continued
Modified Oligonucleotide Structures (with -PEG$_3$NHCOPEG$_{24}$NH$_2$)
Cmpd
Structure
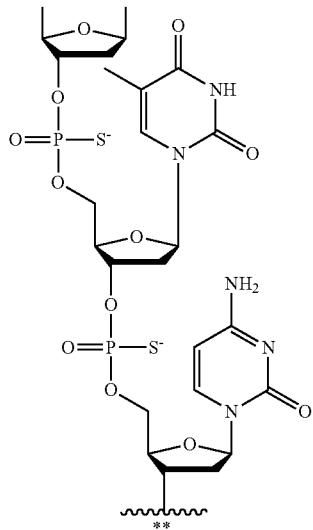
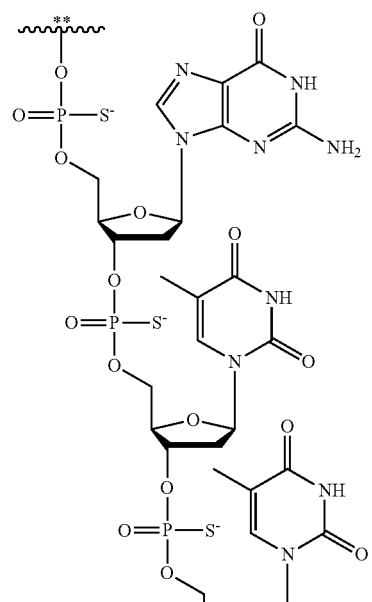

TABLE 12-continued
Modified Oligonucleotide Structures (with -PEG₃NHCOPEG₂₄NH₂)
| Cmpd # | Structure |
|---|---|
| | 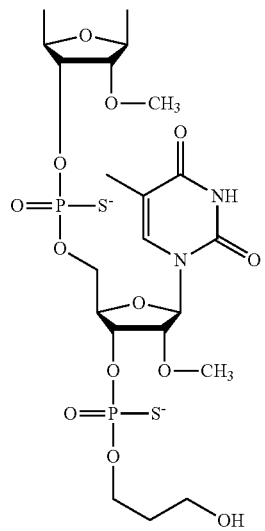 |
| 6.2b | 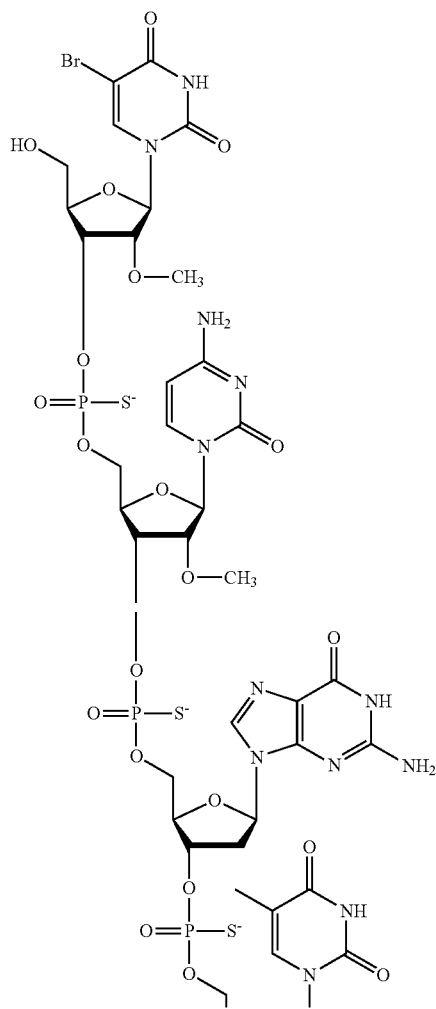 |

TABLE 12-continued
Modified Oligonucleotide Structures (with -PEG$_3$NHCOPEG$_{24}$NH$_2$)
| Cmpd # | Structure |
|---|---|
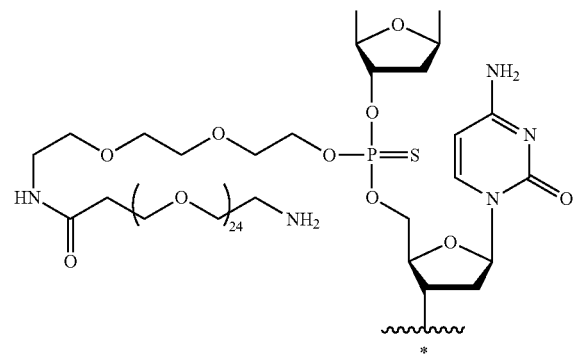
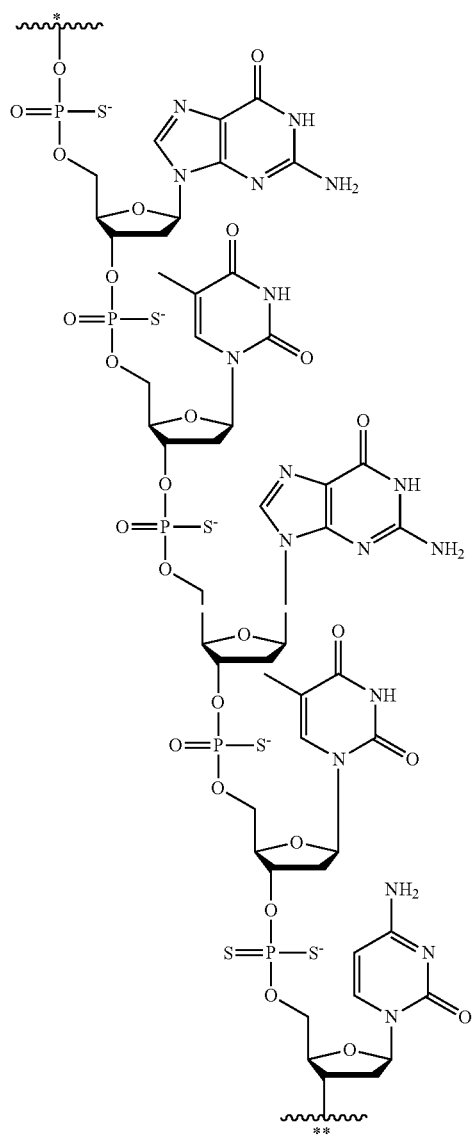

TABLE 12-continued
Modified Oligonucleotide Structures (with -PEG₃NHCOPEG₂₄NH₂)
Cmpd # | Structure
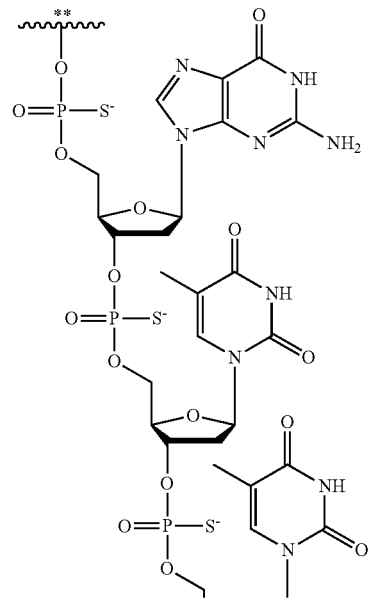
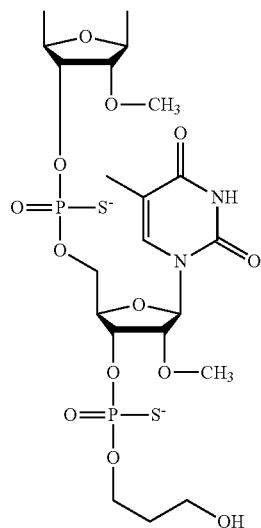

TABLE 12-continued
Modified Oligonucleotide Structures (with -PEG$_3$NHCOPEG$_{24}$NH$_2$)
| Cmpd # | Structure |
|---|---|
| 6.3b | 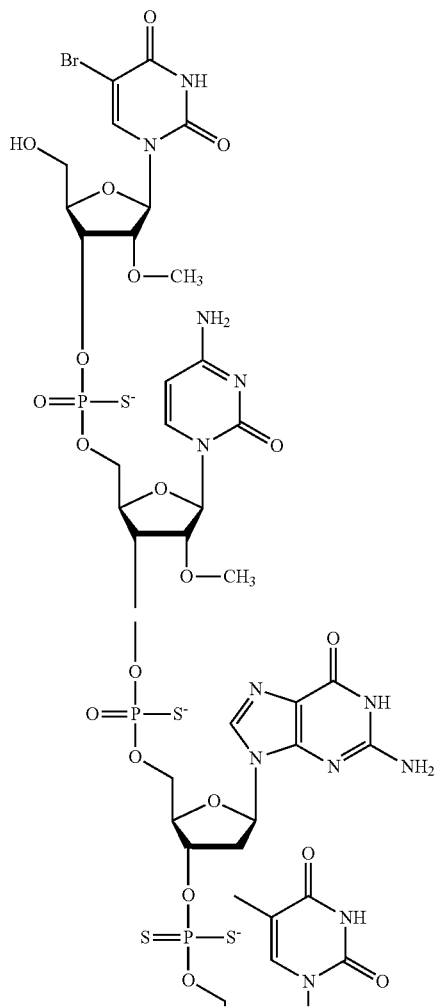 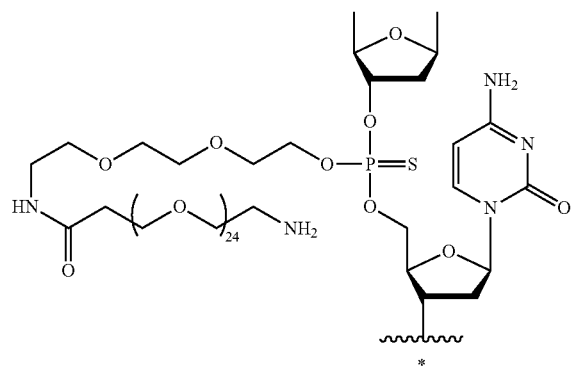 |

TABLE 12-continued
Modified Oligonucleotide Structures (with -PEG$_3$NHCOPEG$_{24}$NH$_2$)
Cmpd # Structure
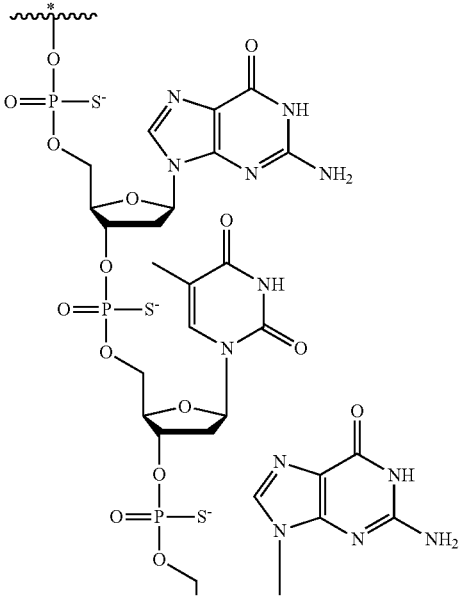
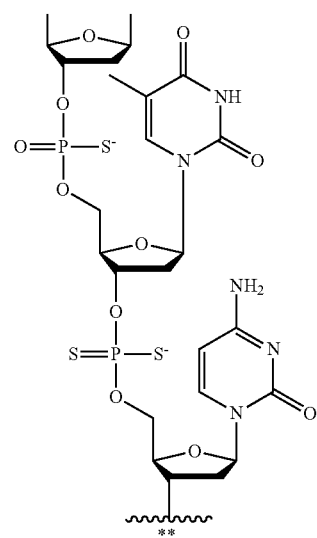

TABLE 12-continued
Modified Oligonucleotide Structures (with -PEG$_3$NHCOPEG$_{24}$NH$_2$)
Cmpd # | Structure
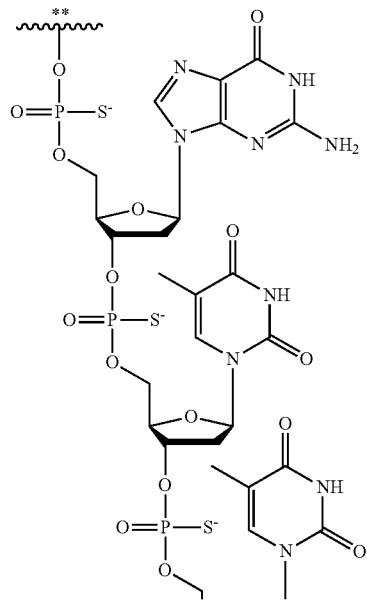
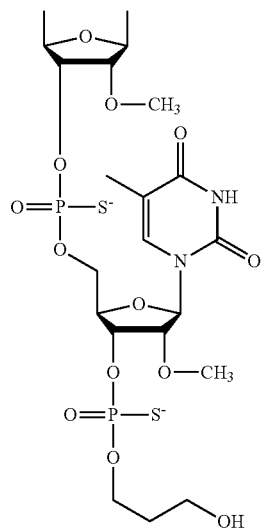

TABLE 12-continued
Modified Oligonucleotide Structures (with -PEG$_3$NHCOPEG$_{24}$NH$_2$)
| Cmpd # | Structure |
|---|---|
| 7.1b | 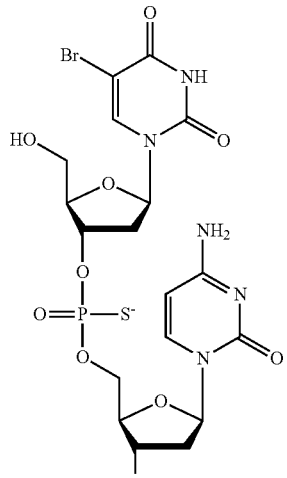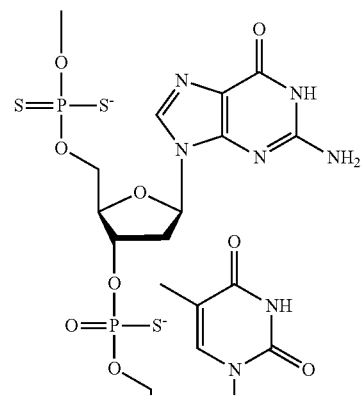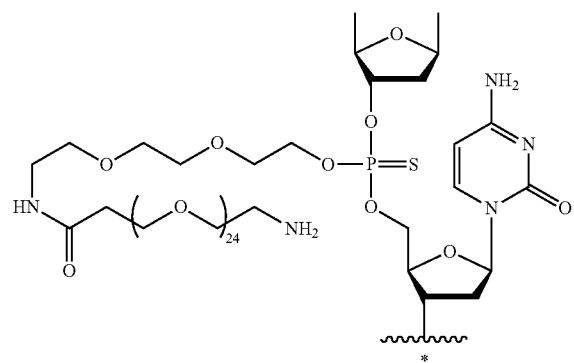 |

TABLE 12-continued
Modified Oligonucleotide Structures (with -PEG$_3$NHCOPEG$_{24}$NH$_2$)
Cmpd # | Structure
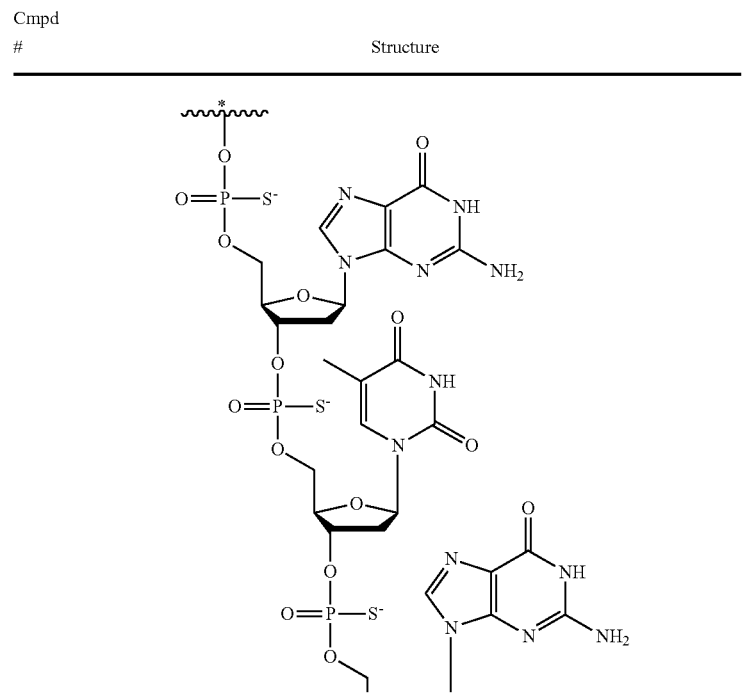
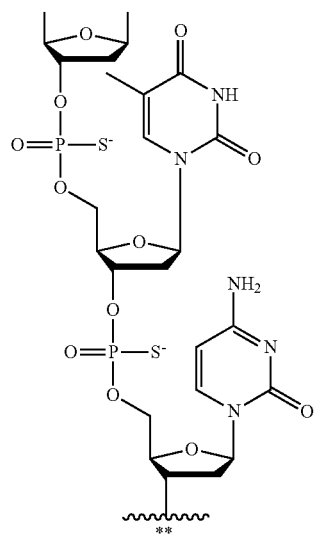

TABLE 12-continued
Modified Oligonucleotide Structures (with -PEG₃NHCOPEG₂₄NH₂)
Cmpd # | Structure
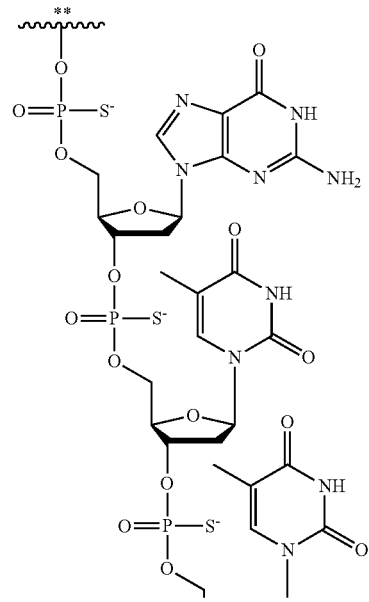
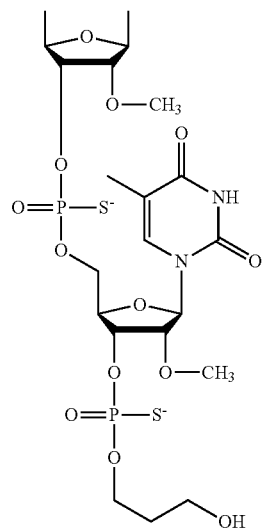

433                                                                      434
TABLE 12-continued
Modified Oligonucleotide Structures (with -PEG$_3$NHCOPEG$_{24}$NH$_2$)
Cmpd # | Structure
7.2b
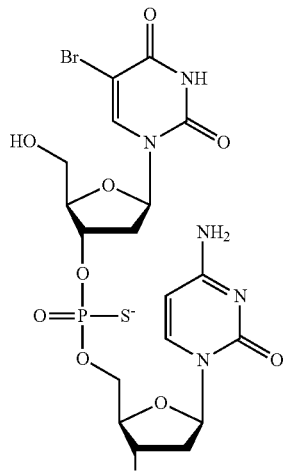
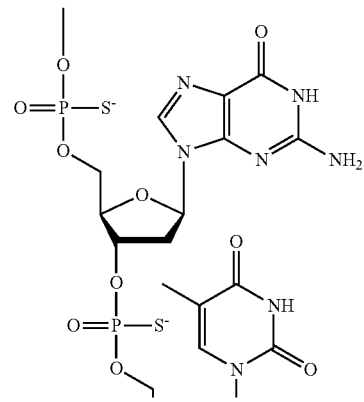
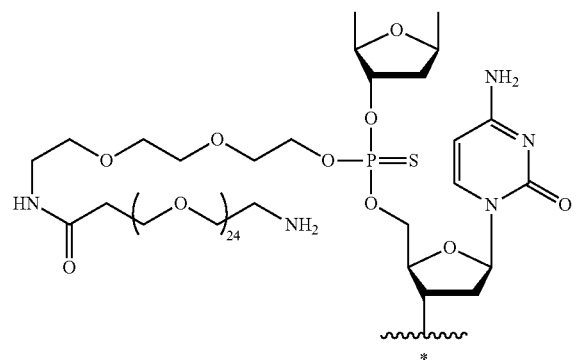

TABLE 12-continued
Modified Oligonucleotide Structures (with -PEG$_3$NHCOPEG$_{24}$NH$_2$)
Cmpd # | Structure
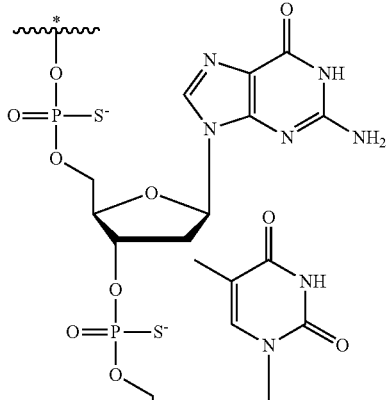
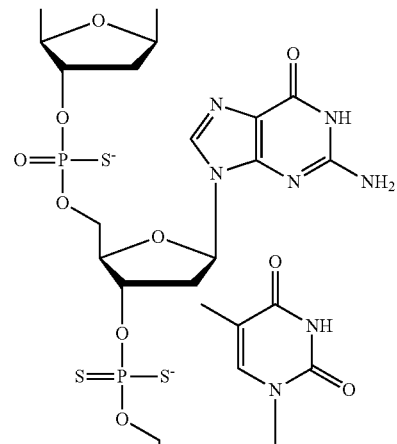
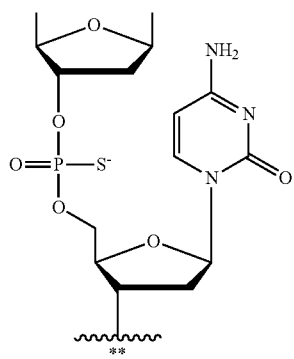

TABLE 12-continued
Modified Oligonucleotide Structures (with -PEG₃NHCOPEG₂₄NH₂)
Cmpd # | Structure
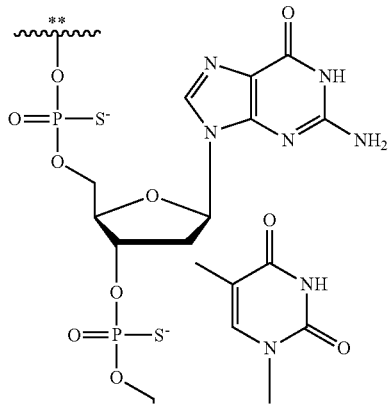
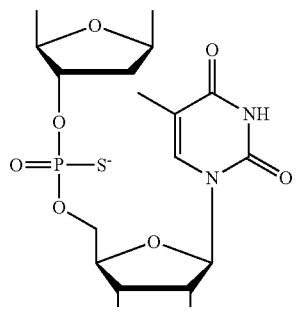
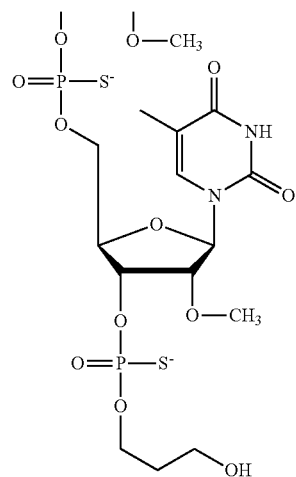

TABLE 12-continued
Modified Oligonucleotide Structures (with -PEG$_3$NHCOPEG$_{24}$NH$_2$)
| Cmpd # | Structure |
|---|---|
| 7.3b | 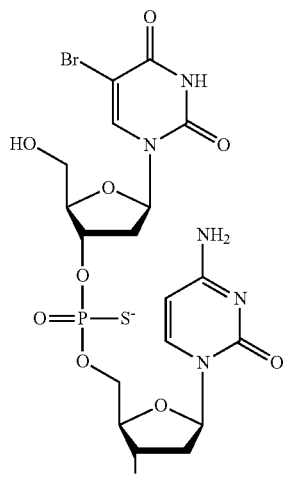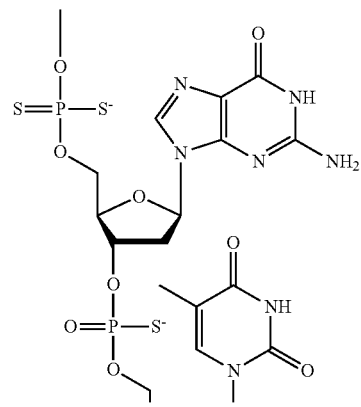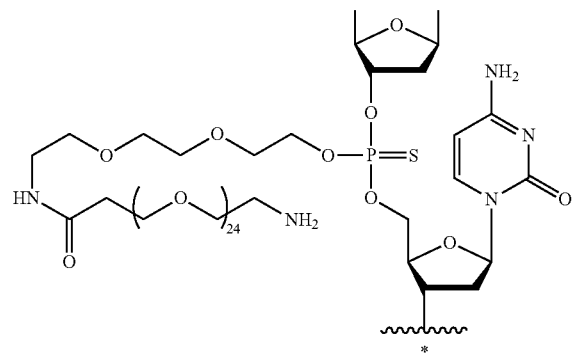 |

441
442
TABLE 12-continued
Modified Oligonucleotide Structures (with -PEG$_3$NHCOPEG$_{24}$NH$_2$)
Cmpd # | Structure
---|---
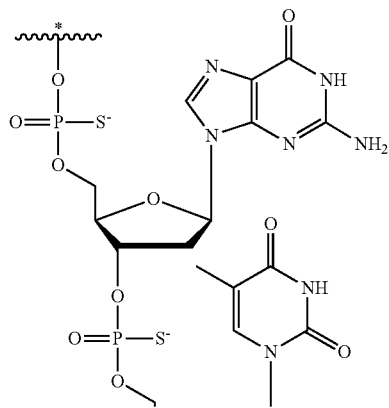
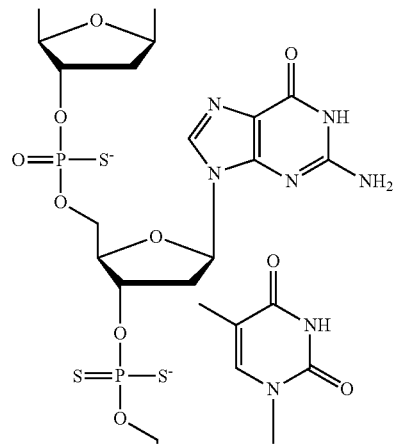
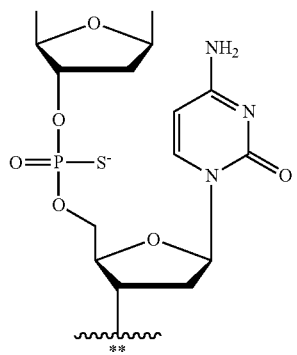

443 444
TABLE 12-continued
Modified Oligonucleotide Structures (with -PEG$_3$NHCOPEG$_{24}$NH$_2$)
| Cmpd # | Structure |
|---|---|
| | 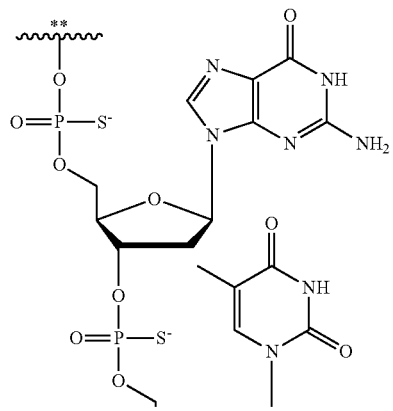 |
| | 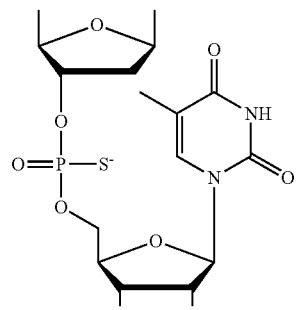 |
| | 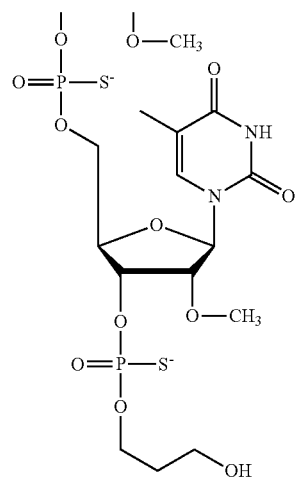 |

TABLE 12-continued
Modified Oligonucleotide Structures (with -PEG$_3$NHCOPEG$_{24}$NH$_2$)
| Cmpd # | Structure |
|---|---|
| 7.4b | 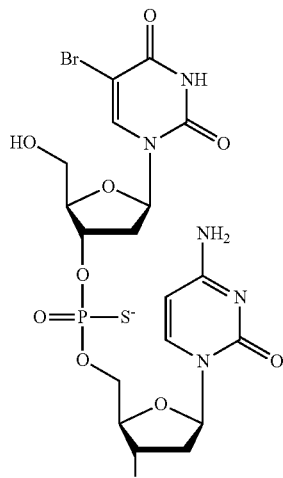 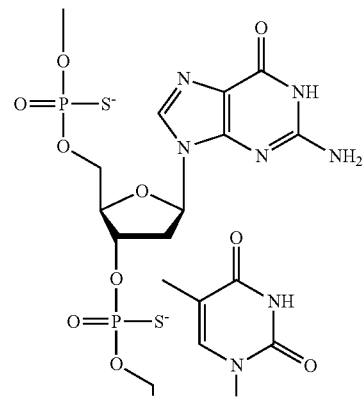 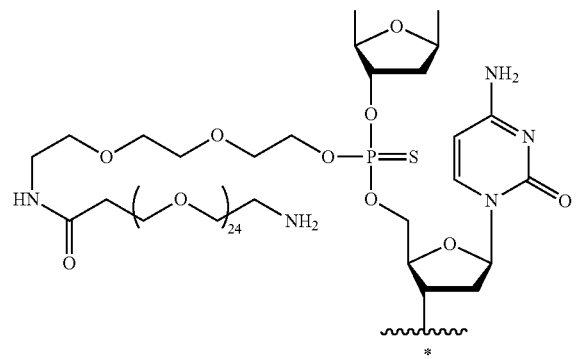 |

TABLE 12-continued
Modified Oligonucleotide Structures (with -PEG₃NHCOPEG₂₄NH₂)
Cmpd # | Structure
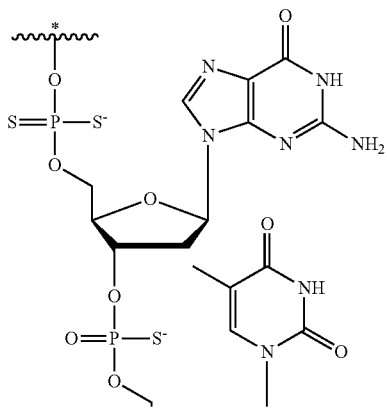
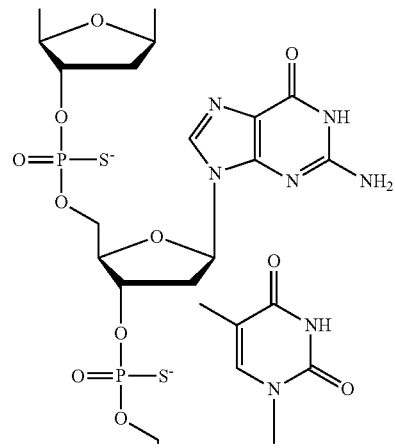
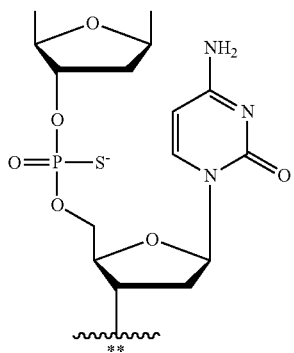

TABLE 12-continued
Modified Oligonucleotide Structures (with -PEG$_3$NHCOPEG$_{24}$NH$_2$)
| Cmpd # | Structure |
|---|---|
| | 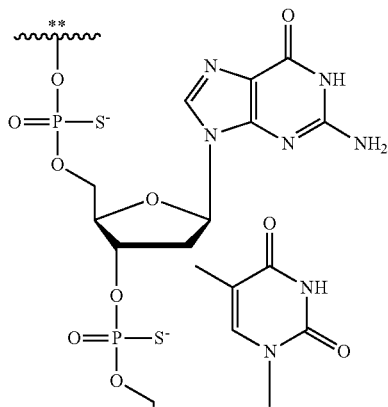 |
| | 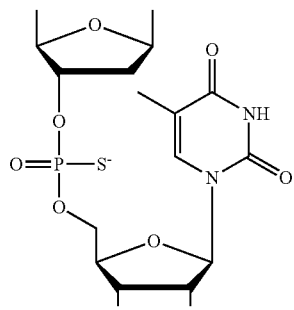 |
| | 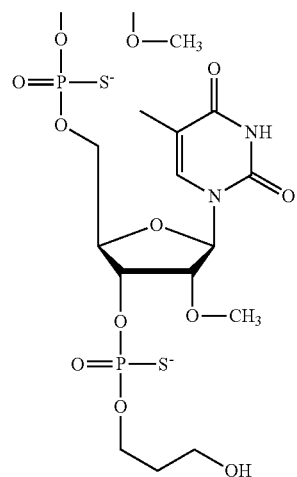 |

TABLE 12-continued
Modified Oligonucleotide Structures (with -PEG$_3$NHCOPEG$_{24}$NH$_2$)
| Cmpd # | Structure |
| --- | --- |
| 7.5b | 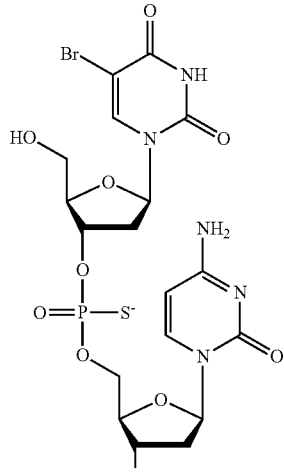 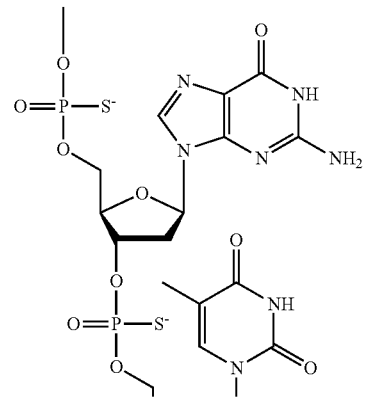 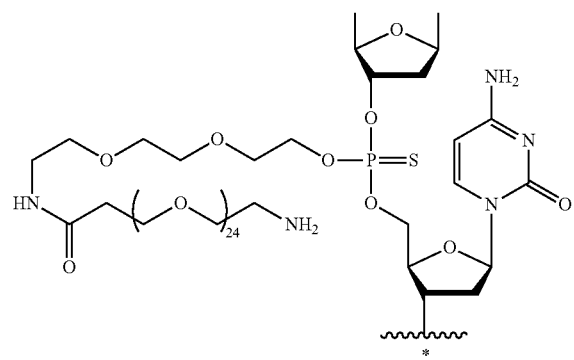 |

TABLE 12-continued
Modified Oligonucleotide Structures (with -PEG₃NHCOPEG₂₄NH₂)
Cmpd # | Structure
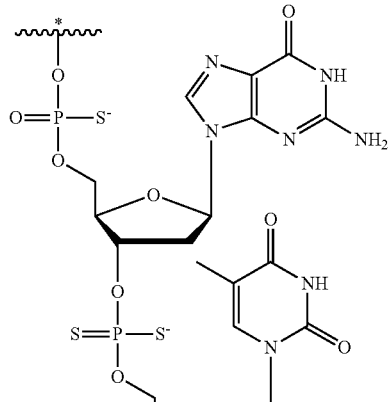
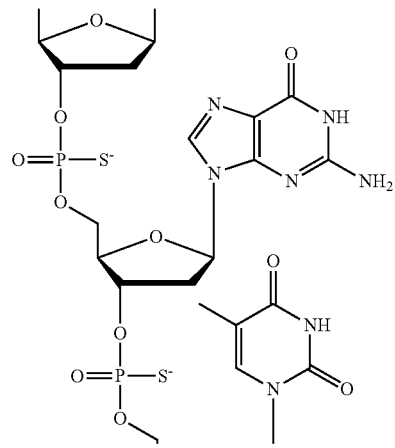
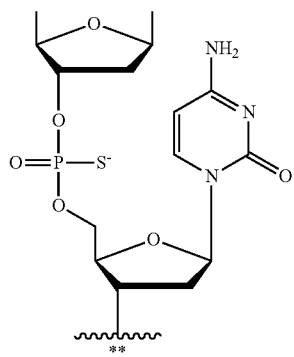

TABLE 12-continued
Modified Oligonucleotide Structures (with -PEG$_3$NHCOPEG$_{24}$NH$_2$)
Cmpd # | Structure
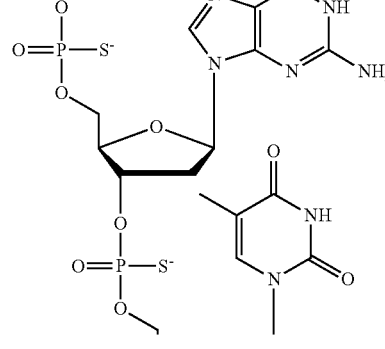
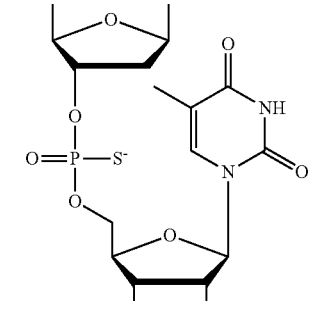
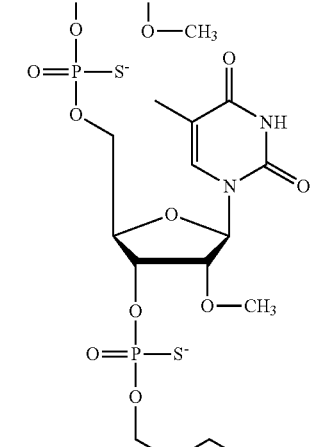

TABLE 12-continued
Modified Oligonucleotide Structures (with -PEG$_3$NHCOPEG$_{24}$NH$_2$)
| Cmpd # | Structure |
|---|---|
| 7.6b | 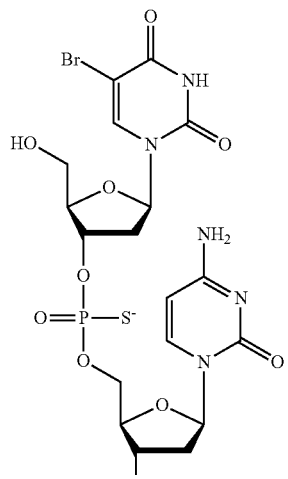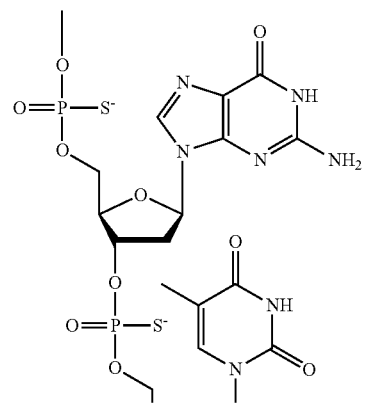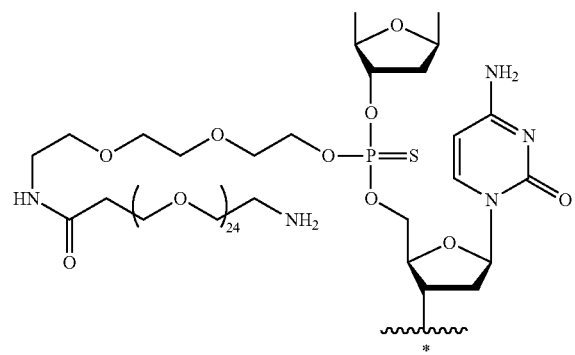 |

TABLE 12-continued
Modified Oligonucleotide Structures (with -PEG₃NHCOPEG₂₄NH₂)
Cmpd # | Structure
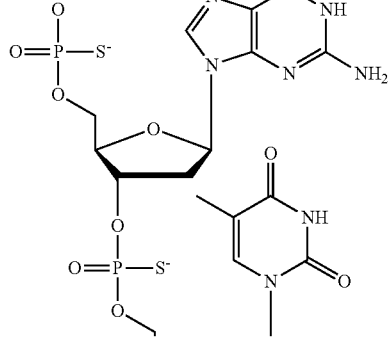
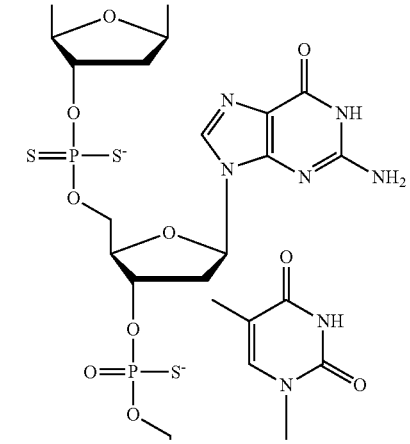
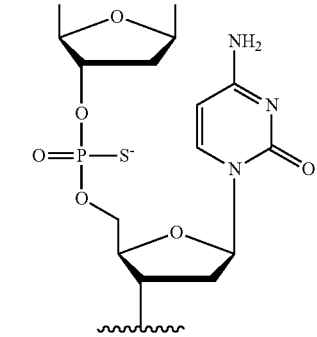

TABLE 12-continued
Modified Oligonucleotide Structures (with -PEG₃NHCOPEG₂₄NH₂)
Cmpd # Structure
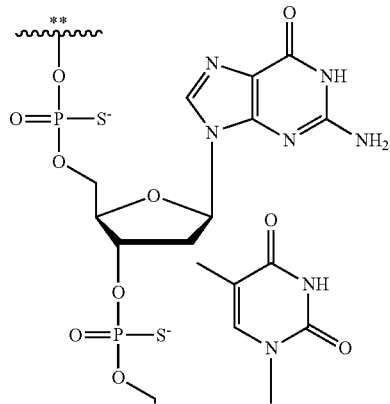
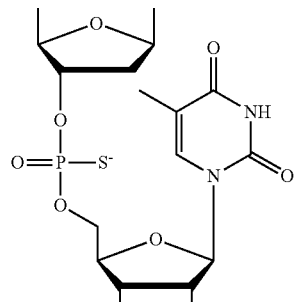
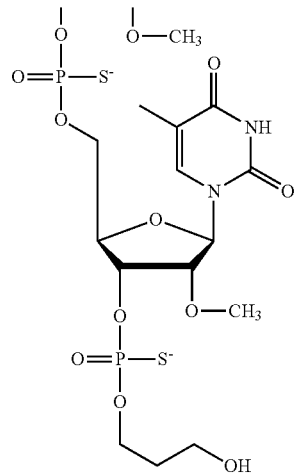

TABLE 12-continued
Modified Oligonucleotide Structures (with -PEG₃NHCOPEG₂₄NH₂)
Cmpd # Structure
7.7b
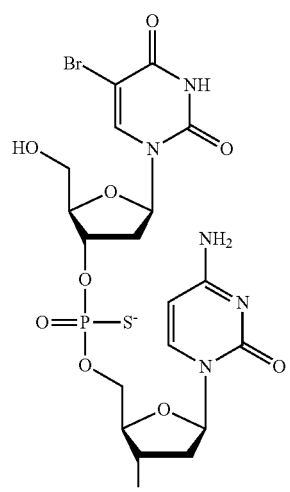
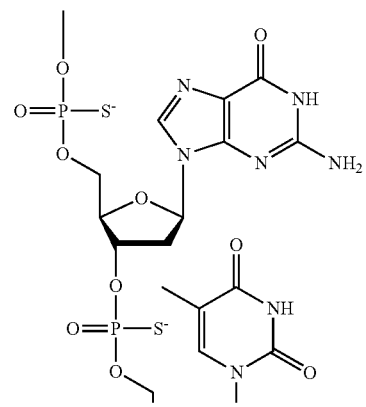
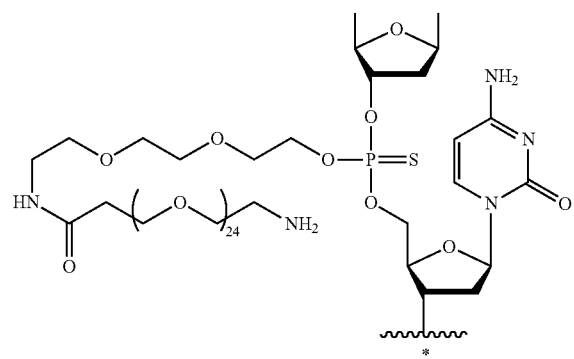

TABLE 12-continued
Modified Oligonucleotide Structures (with -PEG$_3$NHCOPEG$_{24}$NH$_2$)
Cmpd # | Structure
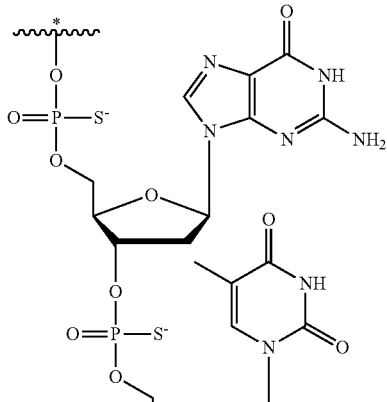
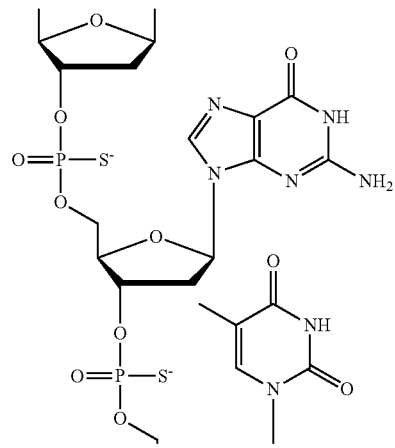
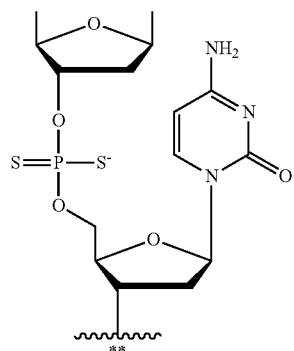

467
TABLE 12-continued
Modified Oligonucleotide Structures (with -PEG$_3$NHCOPEG$_{24}$NH$_2$)
Cmpd #  Structure
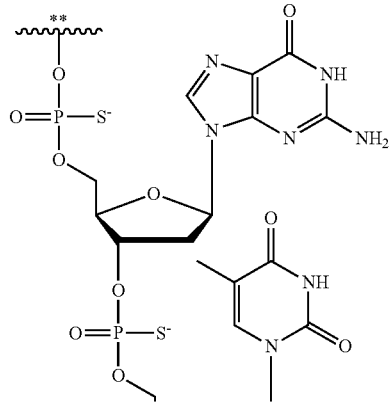
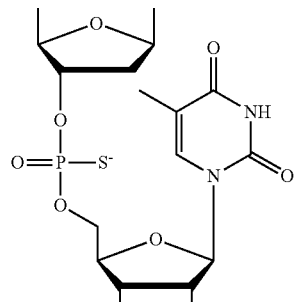
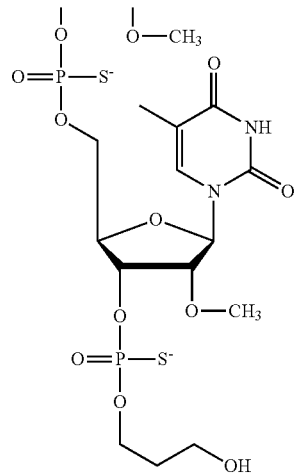

TABLE 12-continued
Modified Oligonucleotide Structures (with -PEG$_3$NHCOPEG$_{24}$NH$_2$)
| Cmpd # | Structure |
|---|---|
| 7.8b | 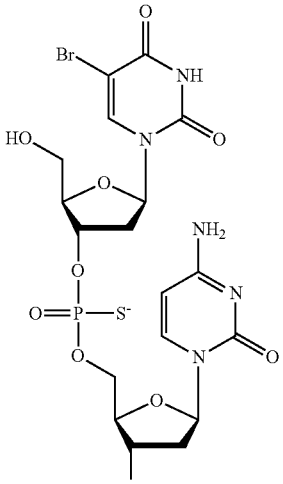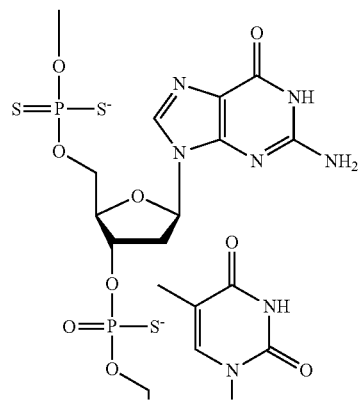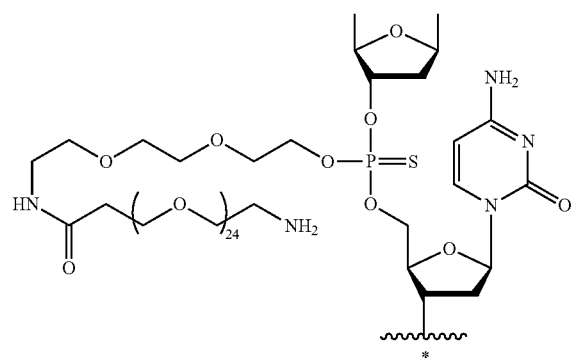 |

TABLE 12-continued
Modified Oligonucleotide Structures (with -PEG$_3$NHCOPEG$_{24}$NH$_2$)
| Cmpd # | Structure |
|---|---|
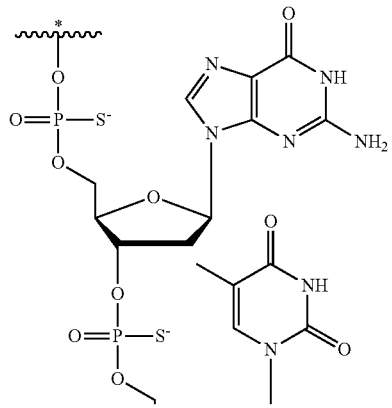
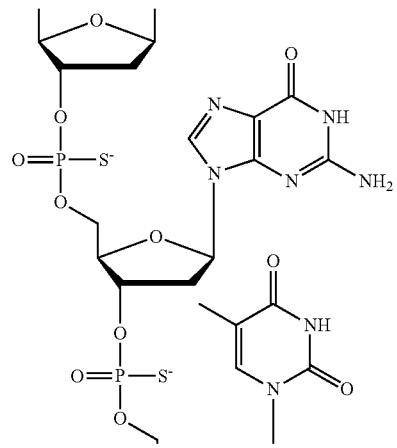
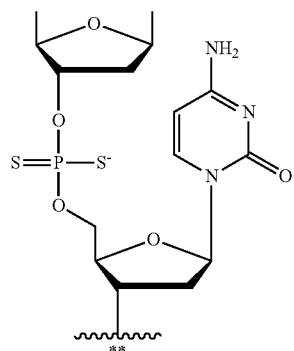

TABLE 12-continued
Modified Oligonucleotide Structures (with -PEG$_3$NHCOPEG$_{24}$NH$_2$)
Cmpd # Structure
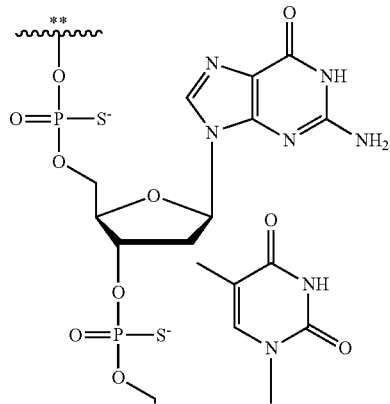
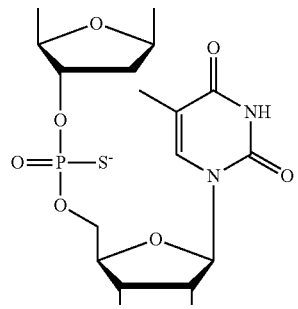
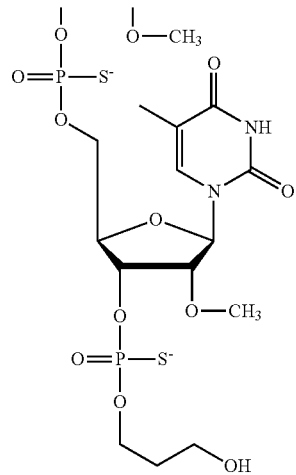

TABLE 12-continued
Modified Oligonucleotide Structures (with -PEG₃NHCOPEG₂₄NH₂)
| Cmpd # | Structure |
|---|---|
| 7.9b | 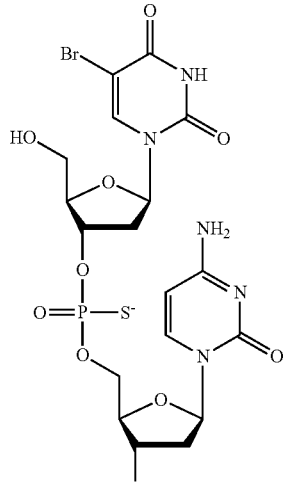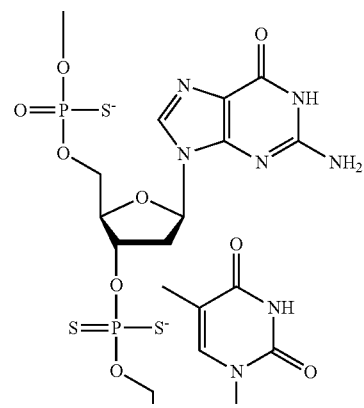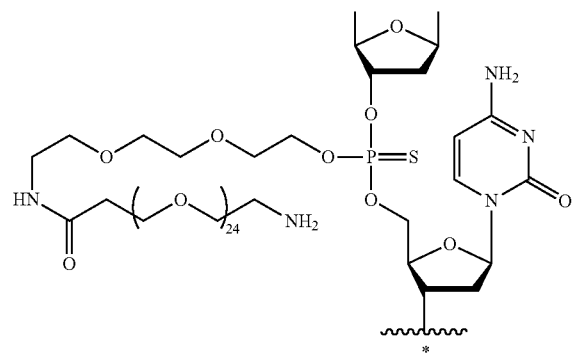 |

TABLE 12-continued
Modified Oligonucleotide Structures (with -PEG₃NHCOPEG₂₄NH₂)
Cmpd # | Structure
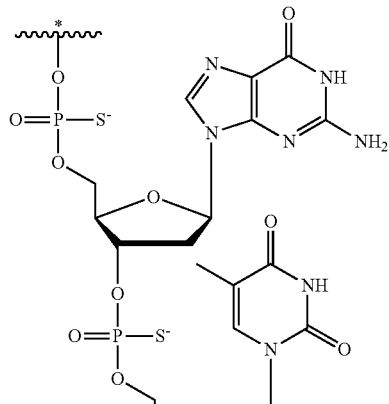
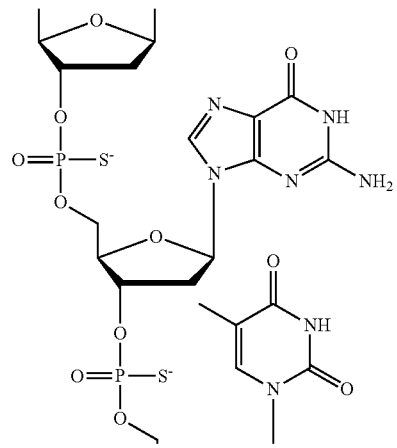
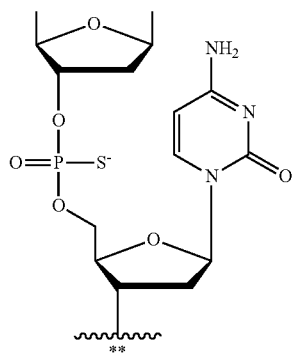

TABLE 12-continued
Modified Oligonucleotide Structures (with -PEG$_3$NHCOPEG$_{24}$NH$_2$)
Cmpd # | Structure
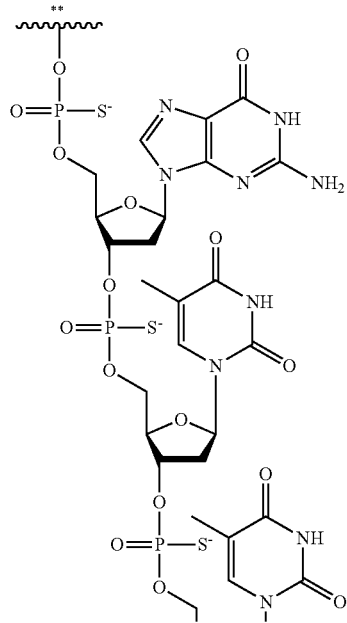
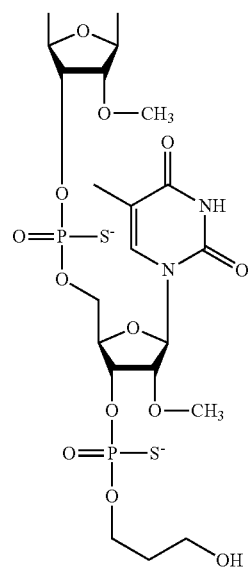

TABLE 12-continued
Modified Oligonucleotide Structures (with -PEG₃NHCOPEG₂₄NH₂)
| Cmpd # | Structure |
|---|---|
| 7.10b | 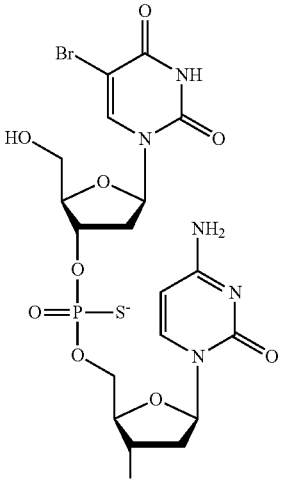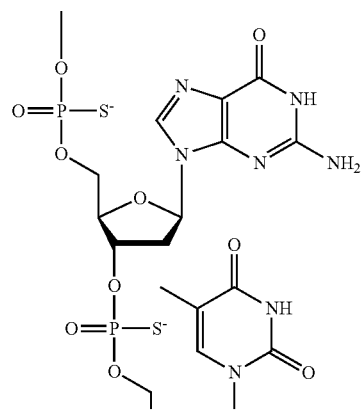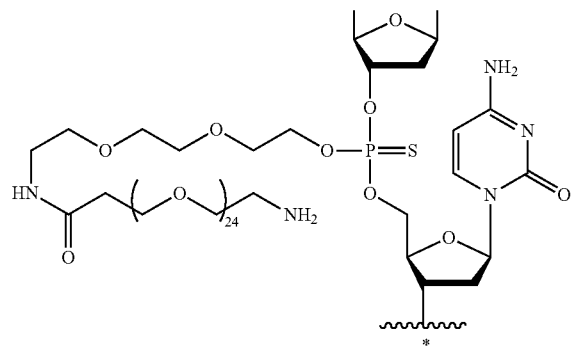 |

TABLE 12-continued
Modified Oligonucleotide Structures (with -PEG$_3$NHCOPEG$_{24}$NH$_2$)
Cmpd # | Structure
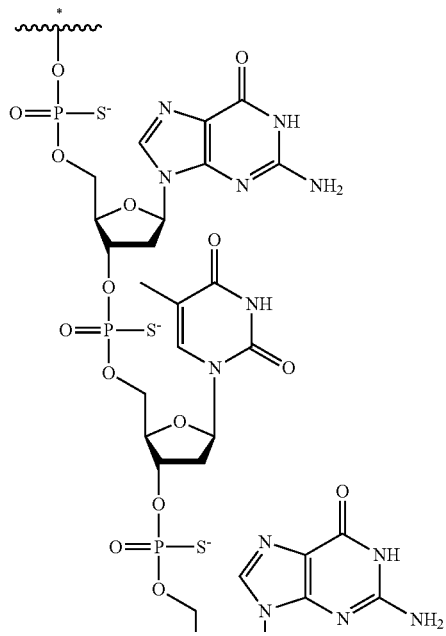
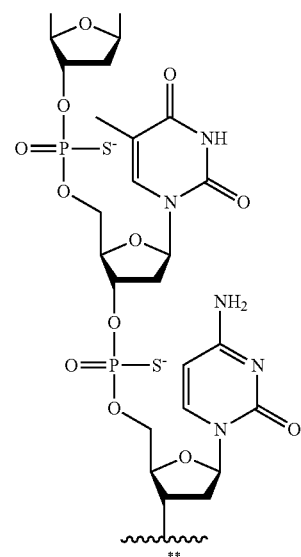

TABLE 12-continued
Modified Oligonucleotide Structures (with -PEG$_3$NHCOPEG$_{24}$NH$_2$)
Cmpd # | Structure
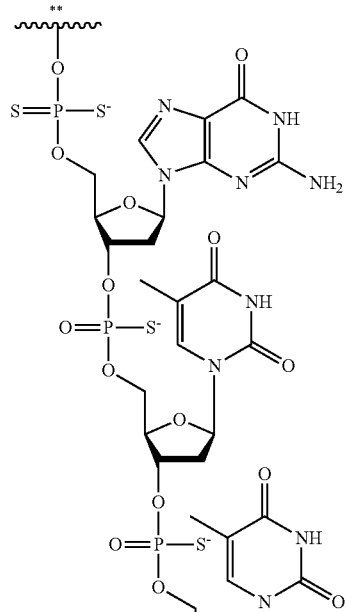
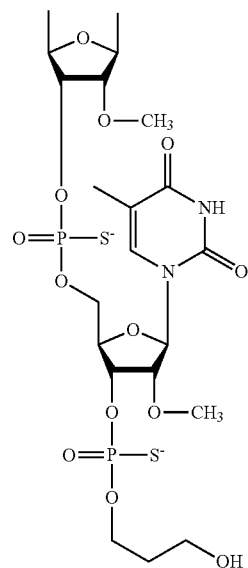

TABLE 12-continued
Modified Oligonucleotide Structures (with -PEG₃NHCOPEG₂₄NH₂)
Cmpd # | Structure
15.7b
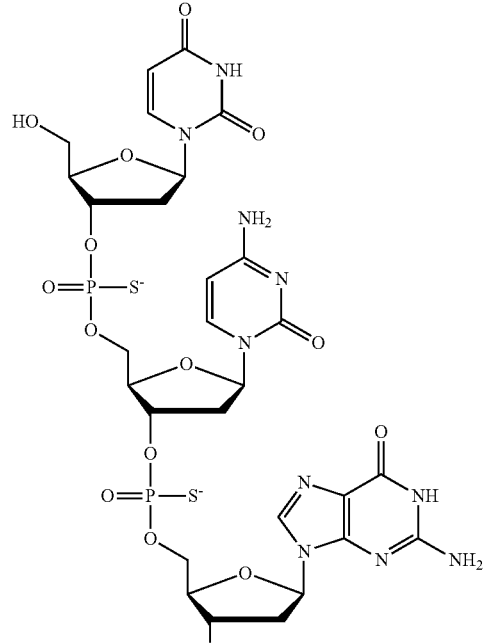
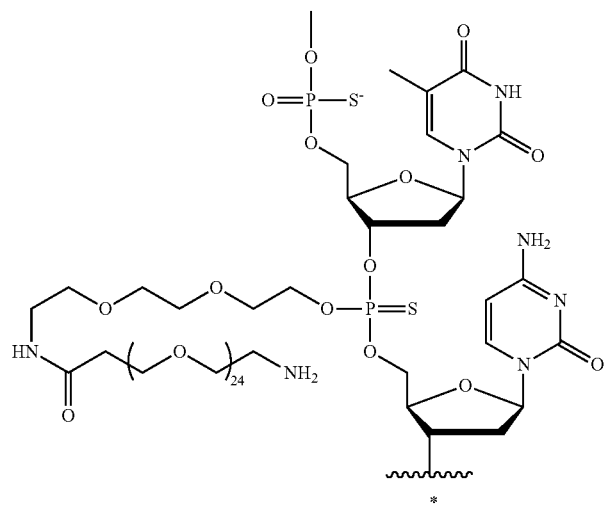

TABLE 12-continued

Modified Oligonucleotide Structures (with -PEG$_3$NHCOPEG$_{24}$NH$_2$)

Cmpd # | Structure

TABLE 12-continued

Modified Oligonucleotide Structures (with -PEG₃NHCOPEG₂₄NH₂)

| Cmpd # | Structure |
|---|---|

As with the oligonucleotides of formula (C), the immunomodulating oligonucleotides of formula (D) may be utilized without conjugation to an antibody or antigen-binding fragment thereof or may be used as precursors to prepare conjugates comprising an antibody or antigen-binding fragment thereof and one or more immunomodulating oligonucleotides of formula (D) linked via Q-tag as shown in the structures of formula (A) as described herein.

In one aspect, provided herein is an immunomodulating oligonucleotide of formula (D), wherein the oligonucleotide is not conjugated to any delivery modality (such as a nanoparticle or protein) or targeting moiety (such as an antibody or antigen-fragment thereof). Such oligonucleotides may be further referred to as "naked" oligonucleotides or "naked" CpGs.

In another aspect, provided herein are immunomodulating oligonucleotides of formula (D), wherein the immunomodulating oligonucleotide is pegylated. In a further aspect, provided herein are immunomodulating oligonucleotides of formula (D), wherein the immunomodulating oligonucleotide is immobilized on a bead. In yet another aspect, provided herein are immunomodulating oligonucleotides of formula (D), wherein the immunomodulating oligonucleotide is formulated in a nanoparticle. In still a further aspect, provided herein are immunomodulating oligonucleotides of formula (D), wherein the immunomodulating oligonucleotide is encapsulated in a liposome. In yet a further aspect, provided herein are immunomodulating oligonucleotides of formula (D), wherein the immunomodulating oligonucleotide is conjugated to a polypeptide.

In still other aspect, provided herein is a method for delivering the immunomodulating oligonucleotide according to any of the embodiments herein, comprising contacting the immunomodulating oligonucleotide with a cell. In some embodiments, the immunomodulating oligonucleotide is pegylated. In other embodiments, the immunomodulating oligonucleotide is immobilized on a bead. In some embodiments, the immunomodulating oligonucleotide is formulated in a nanoparticle. In still other embodiments, the immunomodulating oligonucleotide is encapsulated in a liposome. In some embodiments, the immunomodulating oligonucleotide is conjugated to a polypeptide.

The immunomodulating oligonucleotides of formulae (C) and (D) as described herein may be prepared according to methods known in the art. A general method for the preparation of immunomodulating oligonucleotides, including those provided in the present disclosure, is described below.

General Polynucleotide Synthesis:

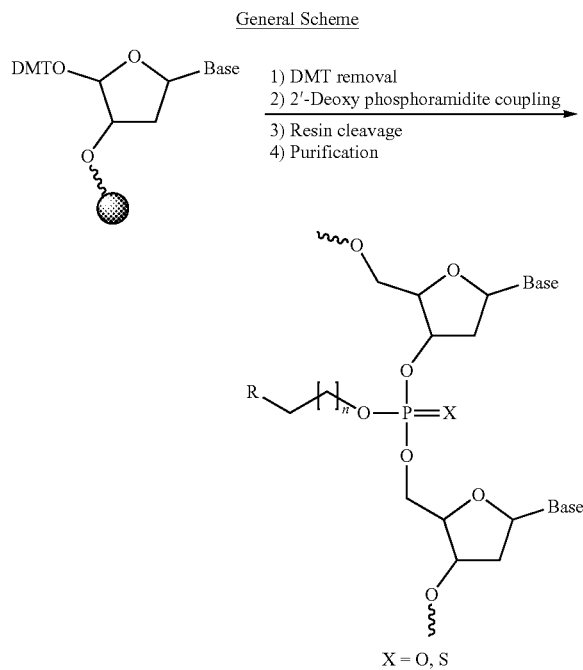

General Scheme

1) DMT removal
2) 2'-Deoxy phosphoramidite coupling
3) Resin cleavage
4) Purification

X = O, S

Experimental Details:

Automated polynucleotide synthesis (1 μmol scale) was carried out on MerMade 6 or 12 with the following reagents and solvents:

Oxidizer—0.02M $I_2$ in THF/pyridine/$H_2O$ (60 s oxidation per cycle),

Sulfurizing Reagent II—dithiazole derivative/pyridine/acetonitrile (0.05 M, in 6:4 pyridine:acetonitrile) (60 s per cycle)

Deblock—3% trichloroacetic acid (2×40 s deblocks per cycle),

Cap Mix A—THF/2,6-lutidine/$Ac_2O$ (60 s capping per cycle), and

Cap Mix B—16% methyl imidazole in THF (60 s capping per cycle)

Exceptions to standard polynucleotide synthesis conditions were as follows:

CPG supports with a non-nucleosidic linker called Unylinker was used.

All 2'-deoxyribose-phosphoramidites were resuspended to 100 mM in 100% anhydrous acetonitrile prior to synthesis, except some of the modified 2'-deoxy-phosphoramidites were dissolved to 100 mM in THF/acetonitrile mixture (1:4) depend on the solubility of the starting material.

Phosphoramidite activation was performed with a 2.5-fold molar excess of 5-benzylthio-1H-tetrazole (BTT). Activated 2'-deoxyribose-phosphoramidites were coupled for 2×1 minute coupling per insertion and modified phosphoramidites were coupled for 2×3 minute coupling per insertion.

Sulfurization of the backbone was performed with 0.05M Sulfurizing Reagent II in pyridine/acetonitrile (6:4) for 1 min.

Polynucleotide Deprotection & Purification Protocol:

Following automated polynucleotide synthesis, solid support and base protecting groups (such as A-Bz, C-Ac, G-iBu, etc.) and methyl esters of phosphotriesters were cleaved and de-protected in 1 mL of AMA (1:1 ratio of 36% aq. ammonia and 40% methylamine in methanol) for 2 h or more at room temperature followed by centrifugal evaporation.

Crude polynucleotide pellets were resuspended in 100 μL of 50% acetonitrile, briefly heated to 65° C. and vortexed thoroughly.

For polynucleotide purification, 100 μL crude polynucleotides were injected onto RP-HPLC with the following buffers/gradient:

Buffer A=50 mM TEAA in Water;
Buffer B=90% Acetontrile; and
Flow Rate=1 mL/min;
Gradient:
0-2 min (100% Buffer A/0% Buffer B),
2-42 min (0% to 60% Buffer B), and
42-55 min (60% to 100% Buffer B).

DBCO Conjugation and Purification Protocol:

DBCO NHS ester was conjugated to the crude 2'-deoxy DMT-polynucleotide as described here. The crude polynucleotide pellet was suspended into 45 μL DMSO, briefly heated to 65° C. and vortexed thoroughly. 5 μL of DIPEA was added followed by DBCO-NHS ester (30 eq), which was pre-dissolved in DMSO (1M). The reaction was allowed to stand for 10 minutes or until product formation was confirmed by MALDI. Total 80 μL of crude polynucleotide samples were injected onto RP-HPLC with the following buffers/gradient:

Buffer A=50 mM TEAA in Water
Buffer B=90% Acetonitrile
Flow Rate=1 mL/min
Gradient:
0-2 min (90% Buffer A/10% Buffer B)
2-42 min (0% to 60% Buffer B)
42-55 min (60% to 100% Buffer B).

Across the dominant RP-HPLC peaks, 0.5 mL fractions were collected and analyzed by MALDI-TOF mass spectrometry to confirm presence of desired mass. Mass-selected, purified fractions were frozen and lyophilized. Once dry, fractions were re-suspended, combined with corresponding fractions, frozen and lyophilized.

DMT Cleavage: lyophilized pellets were suspended in 20 μL of 50% acetonitrile and added 80 μL of acetic acid, samples were kept standing at room temperature for 1 h, frozen and lyophilized. The dried samples were re-dissolved in 20% acetonitrile and desalted through NAP 10 (Sephadex™-G25 DNA Grade) columns. Collected, pure fractions were frozen and lyophilized for final product.

Methods for Attaching Oligonucleotides to Linking Moiety

Cu-catalyzed Click Reaction

Copper-THPTA Complex Preparation

A 5 mM aqueous solution of copper sulfate pentahydrate (CuSO$_4$-5H$_2$O) and a 10 mM aqueous solution of tris(3-hydroxypropyltriazolylmethyl)amine (THPTA) were mixed 1:1 (v/v) (1:2 molar ratio) and allowed to stand at room temperature for 1 hour. This complex can be used to catalyze Huisgen cycloaddition, e.g., as shown in the general conjugation schemes below.

General Procedure (100 nM Scale):

To a solution of 710 μL of water and 100 μL tert-butanol (10% of final volume) in a 1.7 mL Eppendorf tube was added 60 μL of the copper-THPTA complex followed by 50 μL of a 2 mM solution of the oligo, 60 μL of a 20 mM aqueous sodium ascorbate solution and 20 μL of a 10 mM solution of targeting moiety-azide. After thorough mixing the solution was allowed to stand at room temperature for 1 hour. Completion of the reaction was confirmed by gel analysis. The reaction mixture is added to a screw cap vial containing 5-10 fold molar excess of SiliaMetS® TAAcONa (resin bound EDTA sodium salt). The mixture is stirred for 1 hour. This mixture is then eluted through an illustra™Nap™-10 column Sephadex™. The resulting solution is then frozen and lyophilized overnight.

Attachment Through Amide Linkage:

Conjugation through amidation may be performed under the amidation reaction conditions known in the art. See, e.g., Aaronson et al., *Bioconjugate Chem.* 22:1723-1728, 2011.

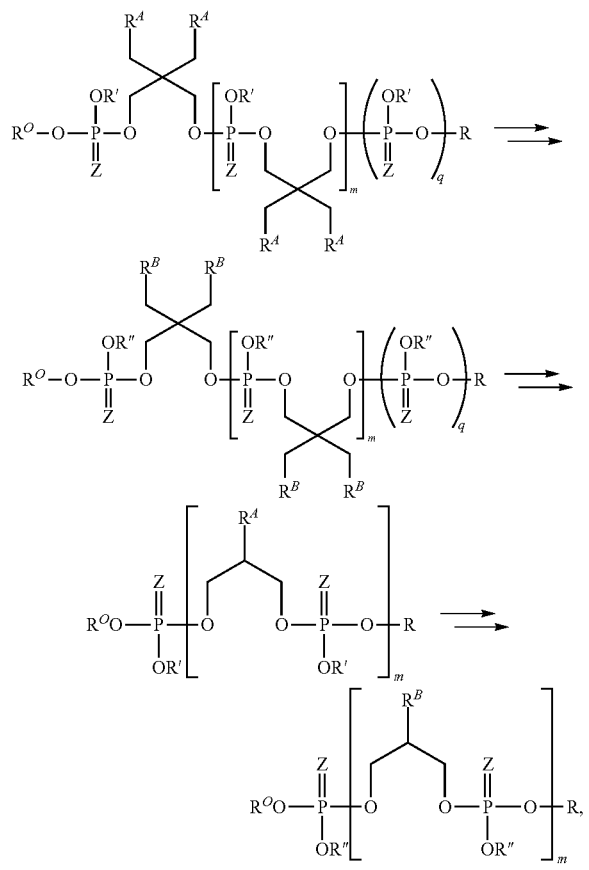

where each q is 0 or 1;

each m is an integer from 0 to 5;

Z is O or S;

$R^O$ is a bond to a nucleoside in a polynucleotide;

R is a bond to H, a nucleoside in a polynucleotide, to solid support, or to a capping group (e.g., —(CH$_2$)$_3$—OH);

each R' is independently H, a bioreversible group, or a non-bioreversible group;

each R" is independently H, -Q$^1$-Q$^4$-Q$^1$-T, a bioreversible group, or a non-bioreversible group;

each $R^A$ is independently H or —OR$^C$, where R$^C$ is -Q$^1$-Q$^{41}$, a bioreversible group, or a non-bioreversible group;

each $R^B$ is independently H or —OR$^D$, where R$^D$ is -Q$^1$-Q$^4$-Q$^2$-T, a bioreversible group, or a non-bioreversible group;

where each Q$^1$ is independently a divalent, trivalent, tetravalent, or pentavalent group, in which one valency is bonded to Q$^4$ or Q$^{41}$, the second valency is open, and each of the remaining valencies, when present, is independently bonded to an auxiliary moiety;

each Q$^2$ is independently a divalent, trivalent, tetravalent, or pentavalent group, in which one valency is bonded to Q$^4$, the second valency is bonded to T, and each of the remaining valencies, when present, is independently bonded to an auxiliary moiety;

Q$^4$ is optionally substituted C$_{2-12}$ heteroalkylene containing —C(O)—N(H)— or —N(H)—C(O)—;

Q$^{41}$ is —NHR$^{N1}$ or —COOR$^{12}$, where R$^{N1}$ is H, N-protecting group, or optionally substituted C$_{1-6}$ alkyl, and R$^{12}$ is H, optionally substituted C$_{1-6}$ alkyl, or O-protecting group; and T is a linking moiety, provided that the starting materials contain at least one -Q$^1$-Q$^{41}$, and products contain -Q$^1$-Q$^4$-Q$^2$-T.

Solution phase attachment:

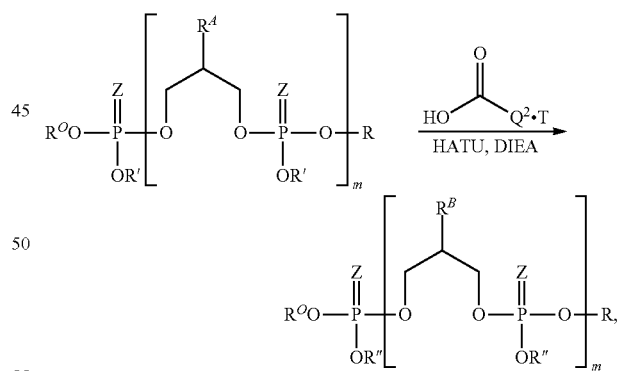

where m is an integer from 0 to 5;

Z is O or S;

$R^O$ is a bond to a nucleoside in a polynucleotide;

R is a bond to H, a nucleoside in a polynucleotide, or to a capping group;

each R' is independently H, -Q$^1$-NH$_2$, a bioreversible group, or a non-bioreversible group;

each R" is independently H, -Q$^1$-NH—CO-Q$^2$-T, a bioreversible group, or a non-bioreversible group;

each $R^A$ is independently H or $-OR^C$, where $R^C$ is -$Q^1$-$NH_2$, a bioreversible group, or a non-bioreversible group;

each $R^B$ is independently H or $-OR^D$, where $R^D$ is -$Q^1$-NH-CO-$Q^2$-T, a bioreversible group, or a non-bioreversible group;

where each $Q^1$ is independently a divalent, trivalent, tetravalent, or pentavalent group, in which one valency is bonded to —NH—CO— or —$NH_2$, the second valency is open, and each of the remaining valencies, when present, is independently bonded to an auxiliary moiety;

each $Q^2$ is independently a divalent, trivalent, tetravalent, or pentavalent group, in which one valency is bonded to —NH—CO—, the second valency is a bond to T, and each of the remaining valencies, when present, is independently bonded to an auxiliary moiety; and T is a linking moiety, provided that the starting material contains -$Q^1$-$NH_2$, and the product contains -$Q^1$-NH—CO-$Q^2$-T.

On-support attachment:

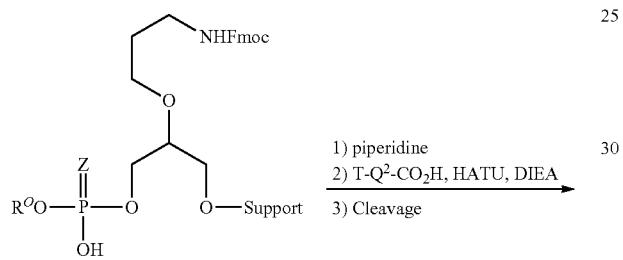

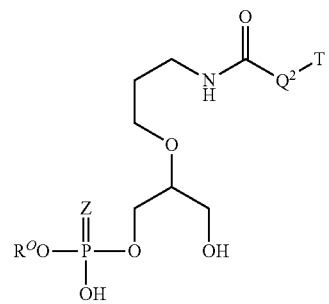

where

Z is O or S;

$R^O$ is a bond to a nucleoside in a polynucleotide;

each $Q^2$ is independently a divalent, trivalent, tetravalent, or pentavalent group, in which one valency is bonded to —NH—CO—, the second valency is a bond to T, and each of the remaining valencies, when present, is independently bonded to an auxiliary moiety; and T is a linking moiety.

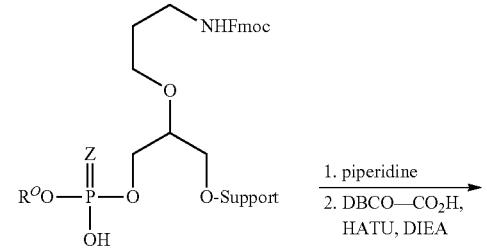

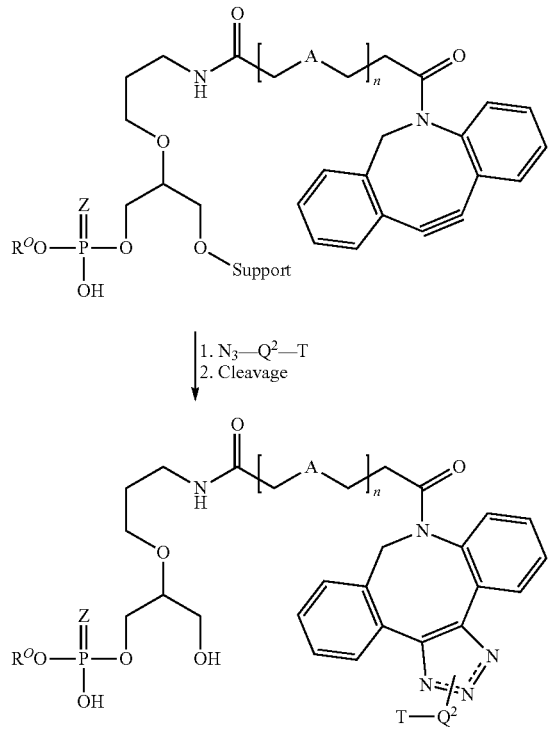

where
n is an integer from 1 to 8;
A is O or —CH$_2$—;
Z is O or S;
R$^O$ is a bond to a nucleoside in a polynucleotide;

each Q$^2$ is independently a divalent, trivalent, tetravalent, or pentavalent group; in which one valency is bonded to the azide or triazole, a second valency is bonded to T, and each of the remaining valencies, when present, is independently bonded to an auxiliary moiety; and
T is a linking moiety.

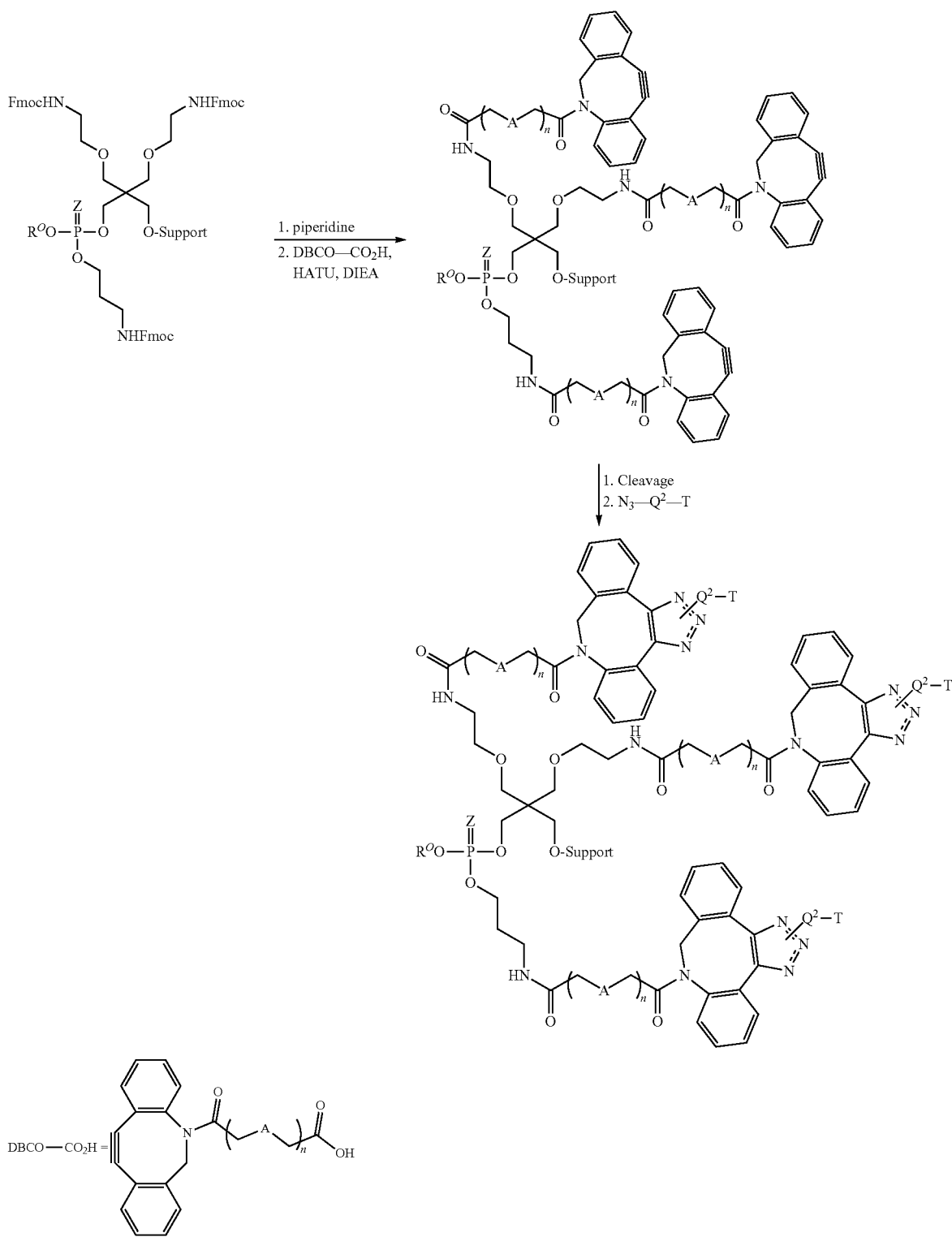

501 where
n is an integer from 1 to 8;
A is O or —CH$_2$—;
Z is O or S;
R$^O$ is a bond to a nucleoside in a polynucleotide;

502 each Q$^2$ is independently a divalent, trivalent, tetravalent, or pentavalent group; in which one valency is bonded to the azide or triazole, a second valency is bonded to T, and each of the remaining valencies, when present, is independently bonded to an auxiliary moiety; and
T is a linking moiety.

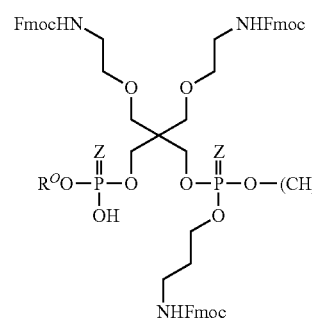

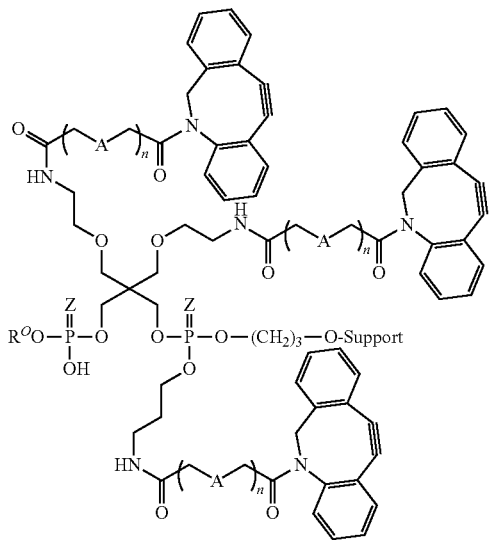

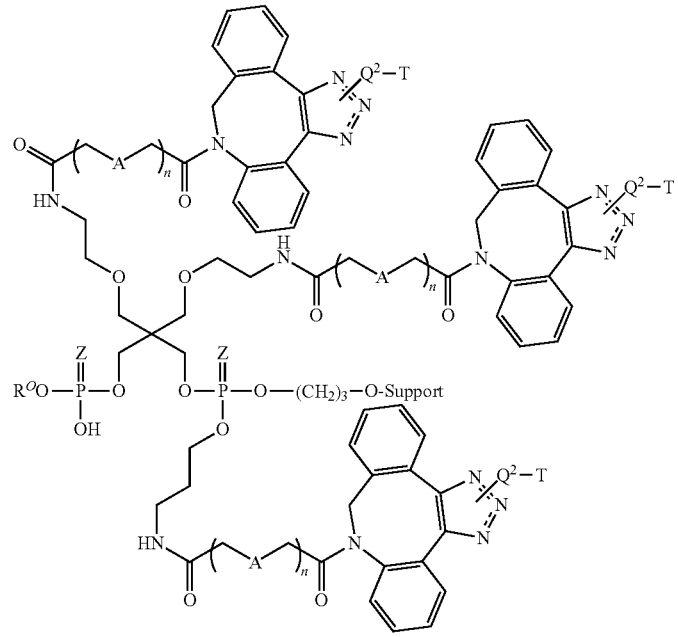

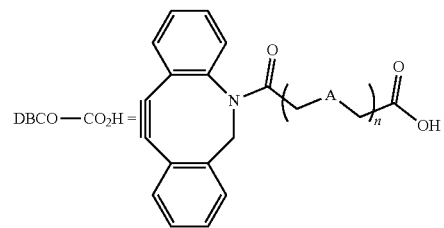

where
n is an integer from 1 to 8;
A is O or —CH$_2$—;
Z is O or S;
R$^O$ is a bond to a nucleoside in a polynucleotide;
each Q$^2$ is independently a divalent, trivalent, tetravalent, or pentavalent group; in which one valency is bonded to the azide or triazole, a second valency is bonded to T, and each of the remaining valencies, when present, is independently bonded to an auxiliary moiety; and
each T is independently a linking moiety.

Representative Example of Fmoc Deprotection of a Phosphotriester:

A polynucleotide including a phosphotriester with Fmoc-protected amine was subjected to deprotection conditions resulting in Fmoc deprotection without observable conversion of the phosphotriester into a phosphodiester.

TCCATGACGTTCCTGACGTT (SEQ ID NO:176)

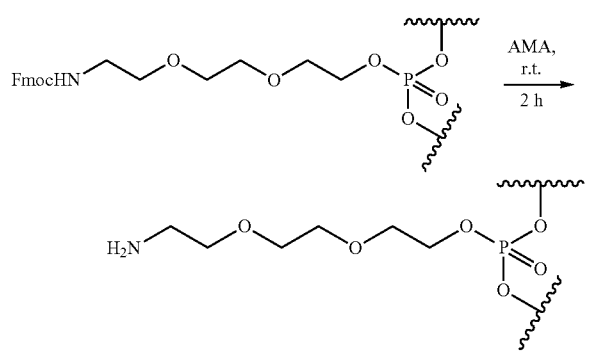

DBCO-NHS Conjugation to TCCATGACGTTCCTGACGTT (SEQ ID NO:176)—Representative Example:

DBCO-NHS conjugation to the amino group in the phosphotriester was complete in 10 min at room temperature, as evidenced by mass spectrometric analysis.

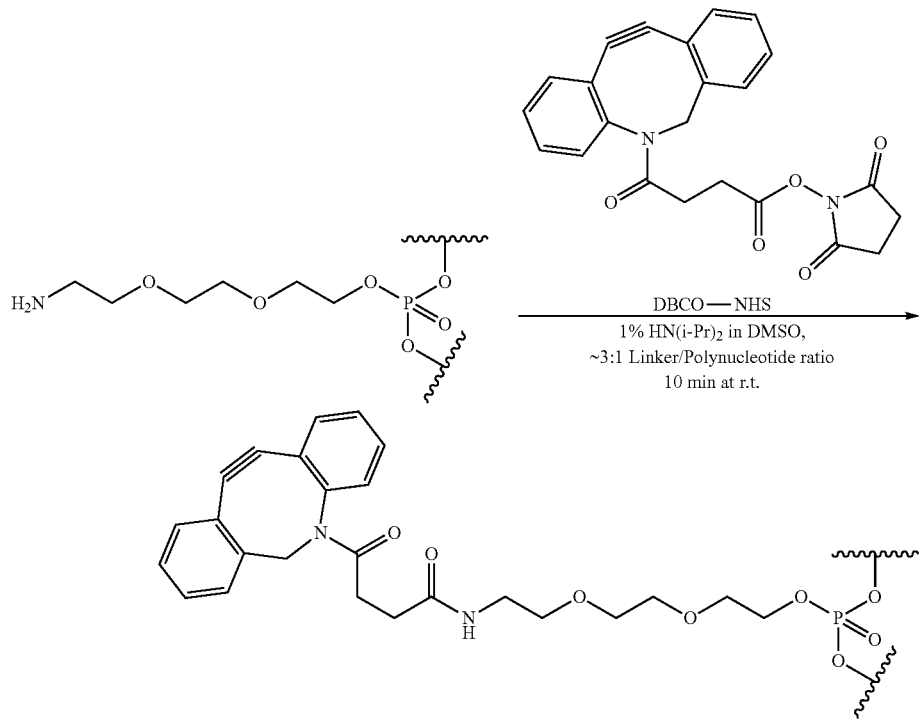

RP-HPLC purification of TCCATGACGTTCCTGACGTT (SEQ ID NO:176) containing a DBCO conjugating group was performed using the following conditions:
Buffer A=50 mM TEAA in Water;
Buffer B=90% Acetontrile; and
Flow Rate=1 mL/min;
Gradient:
  0-2 min (100% Buffer A/0% Buffer B),
  2-22 min (0% to 100% Buffer B), and
  22-25 min (100% Buffer B).

A similar procedure may be used to prepare a polynucleotide using, e.g., 2'-modified nucleoside phosphoramidites, such as those described herein. Such a procedure is provided in International Patent application PCT/US2015/034749; the disclosure of the disulfide phosphotriester oligonucleotide synthesis in PCT/US2015/034749 is hereby incorporated by reference.

V. Methods of Conjugation

Provided herein are methods for preparing a conjugate comprising an antibody or antigen-binding fragment thereof and one or more immunomodulating oligonucleotides linked via one or more Q-tag peptides as shown in the structure of Formula (A). In some embodiments, the methods comprise combining an antibody comprising at least one Q-tag peptide sequence with at least one exposed glutamine residue and an oligonucleotide under conditions sufficient to induce conjugation, i.e., amidation reaction between the CpG and Q tag. In other embodiments, the methods comprise reacting an antibody comprising at least one Q-tag peptide sequence with at least one exposed glutamine residue and an oligonucleotide under chemical conditions sufficient to induce conjugation. In still other embodiments, the methods comprise reacting an antibody comprising at least one Q-tag peptide sequence with at least one exposed glutamine residue and an oligonucleotide under enzymatic conditions, e.g., with transglutaminase, sufficient to induce conjugation.

Transglutaminase-Mediated Conjugation Reaction Conditions

In one aspect, provided herein is a method of preparing a conjugate of formula (A), comprising combining one or more immunomodulating oligonucleotides (P) and an antibody comprising one or more glutamine residues. In one aspect, provided herein is a method of preparing a conjugate comprising an antibody or antigen-binding fragment (Ab) and one or more immunomodulating oligonucleotides (P), wherein the antibody or antigen-binding fragment is linked to one or more Q-tag peptides (Q) comprising the amino acid sequence RPQGF (SEQ ID NO:47), and wherein each immunomodulating oligonucleotide is linked to a Q-tag peptide via an amide bond with the glutamine residue of the Q-tag peptide and a linker (L) as shown in formula (A),

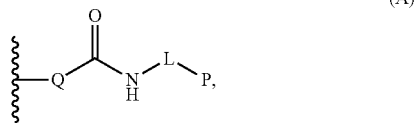

(A)

wherein:
ⵯ indicates the point of attachment of each Q to the antibody or antigen-binding fragment thereof (Ab);
each Q independently comprises a Q-tag peptide sequence RPQGF (SEQ ID NO:47);
each L is independently a bond or a linker moiety connected to Q via an amide bond with the glutamine residue; and
each P is independently an immunomodulating oligonucleotide;

comprising contacting a compound of formula (B)

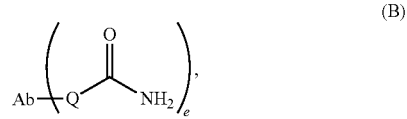

(B)

wherein Ab and Q are as defined for formula (A) above, and e is an integer from 1 to 20, with one or more immunomodulating oligonucleotides P, wherein each P independently has the following formula:

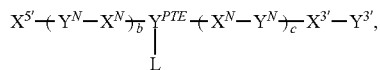

wherein
$X^{5'}$ is a 5' terminal nucleoside;
$X^{3'}$ is a 3' terminal nucleoside;
$Y^{PTE}$ is an internucleoside phosphotriester;

$Y^{3'}$ is a terminal phosphotriester;
each $X^N$ is independently a nucleoside;
each $Y^N$ is independently an internucleoside linker;
b and c are each independently an integer from 1 to 25;
with the proviso that the sum of b and c is at least 5; and
L is a linker moiety having a terminal amine,
in the presence of a transglutaminase.

In another aspect, method for preparing a conjugate comprising an antibody or antigen-binding fragment (Ab) and one or more immunomodulating oligonucleotides (P), wherein the antibody or antigen-binding fragment is linked to one or more Q-tag peptides (Q) comprising at least one glutamine residue, and wherein each immunomodulating oligonucleotide is linked to a Q-tag peptide via an amide bond with the glutamine residue of the Q-tag peptide and a linker (L) as shown in Formula (A),

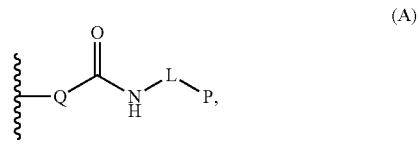

(A)

wherein:
ⵯ indicates the point of attachment of each Q to the antibody or antigen-binding fragment thereof (Ab);
each Q is independently a Q-tag peptide having at least one glutamine residue;
each L is independently a bond or a linker moiety connected to Q via an amide bond with the glutamine residue; and
each P is independently an immunomodulating oligonucleotide;

comprising contacting a compound of formula (B)

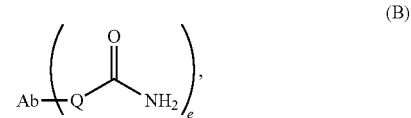

(B)

wherein Ab and Q are as defined for formula (A) above, and e is an integer from 1 to 20, with one or more immunomodulating oligonucleotides P, wherein each oligonucleotide P is independently an immunomodulating oligonucleotide of formula (C) or formula (D), in the presence of a transglutaminase.

In some embodiments, the conjugate comprises one or more, two or more, three or more, four or more, five or more, six or more, seven or more, eight or more, nine or more, ten or more, or twenty or more Q-tag peptides. In some embodiments, the conjugate comprises one, two, three, four, five, six, seven, eight, nine, ten, or twenty Q-tag peptides. In some embodiments, the conjugate has 2 Q-tag peptides. In some embodiments, the conjugate comprises one or more, two or more, three or more, four or more, five or more, six or more, seven or more, eight or more, nine or more, ten or more, or twenty or more immunomodulating oligonucleotides. In some embodiments, the conjugate comprises one, two, three, four, five, six, seven, eight, nine, ten, or twenty immunomodulating oligonucleotides. In some embodiments, the conjugate has one immunomodulating oligonucleotide.

In another aspect, the method comprises combining a compound of Formula (C) and an antibody of formula (B)

comprising one or more glutamine residues in the presence of a transglutaminase. In some embodiments, the method comprises contacting a compound of Formula (D) and an antibody of formula (B) comprising one or more glutamine residues in the presence of a transglutaminase. In some embodiments, the final concentration of the compound of Formula (C) or Formula (D) is in the range of about 1-100 μM. In some embodiments, the final concentration of the Q tag comprising antibody is in the range of about 1-500 μM. In some embodiments, the final concentration of transglutaminase is in the range of about 1-500 μM. In some embodiments, the final concentration of transglutaminase is in the range of about 1-50 μM, about 50-100 μM, about 100-150 μM, about 150-200 μM, about 200-250 μM, about 250-300 μM, about 300-400 μM, about 400-500 μM, about 100-125 μM, about 125-150 μM, about 150-175 μM, about 175-200 μM, about 200-225 μM, about 225-250 μM, about 250-275 μM, about 275-300 μM, about 300-325 μM or about 325-350 μM.

In some embodiments, the ratio of the Q tag comprising antibody and the compound of Formula (C) or Formula (D) is in the range of about 1:1-250:1, about 1:1-5:1, about 5:1-10:1, about 10:1-20:1, about 20:1-30:1, about 30:1-40:1, about 40:1-50:1, about 50:1-75:1, about 75:1-100:1, about 100:1-150:1, about 150:1-200:1, about 200:1-250:1, about 1:1-25:1, about 25:1-50:1, about 50:1-75:1, about 75:1-100:1 or about 100:1-250:1 by weight. In some embodiments, the ratio of the compound of Formula (C) or Formula (D) and the antibody is about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1 or about 20:1 by molarity.

In some embodiments, the ratio of the Q tag comprising antibody and transglutaminase is in the range of about 1:1-500:1, about 1:1-5:1, about 5:1-10:1, about 10:1-20:1, about 20:1-30:1, about 30:1-40:1, about 40:1-50:1, about 50:1-75:1, about 75:1-100:1, about 100:1-150:1, about 150:1-200:1, about 200:1-250:1, about 1:1-25:1, about 25:1-50:1, about 50:1-75:1, about 75:1-100:1, about 100:1-150:1, about 150:1-200:1, about 200:1-250:1, about 250:1-300:1, about 300:1-400:1 or about 400:1-500:1 by weight. In some embodiments, the ratio of the peptide and transglutaminase is about 15:1, about 16:1, about 17:1, about 18:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1 or about 50:1 by molarity.

In some embodiments, the ratio of Q tag:CpG:transglutaminase is about 1:1.3:10. In some embodiments, the ratio of Q tag:CpG:transglutaminase is about 1:1.5:10. In some embodiments, the ratio of Q tag:CpG:transglutaminase is about 1:1.3:15.

In some embodiments, the reaction is incubated at greater than 15° C., greater than 20° C., greater than 25° C., greater than 30° C., greater than 35° C., greater than 40° C., greater than 45° C., or greater than 50° C. In some embodiments, the reaction is incubated at about room temperature. In some embodiments, the reaction is incubated for at least 10 minute, 20 minutes, 30 minutes, 45 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours or 60 hours.

In some embodiments, the method described herein produces the compound of Formula (A) at greater than about 5%, greater than about 10%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 95%, greater than about 97% or greater than about 99% as compared to the peptide.

In some embodiments, the pH of the reaction is in the range of about 4-10. In some embodiments, the pH of the reaction is in the range of about 4-6, about 6-8 or about 8-10. In some embodiments, the pH of the reaction is in the range of about 7-8.

In another aspect, reactions useful for attaching a linking moiety to an oligonucleotide are known in the art, including, but not limited to Hüisgen cycloaddition (metal-catalyzed or metal-free) between an azido and an alkyne-based conjugating group (e.g., optionally substituted C6-16 heterocyclylene containing an endocyclic carbon-carbon triple bond or optionally substituted C8-16 cycloalkynyl) to form a triazole moiety; the Diels-Alder reaction between a dienophile and a diene/hetero-diene; bond formation via pericyclic reactions such as the ene reaction; amide or thioamide bond formation; sulfonamide bond formation (e.g., with azido compounds); alcohol or phenol alkylation (e.g., Williamson alkylation), condensation reactions to form oxime, hydrazone, or semicarbazide group; conjugate addition reactions by nucleophiles (e.g., amines and thiols); disulfide bond formation; and nucleophilic substitution (e.g., by an amine, thiol, or hydroxyl nucleophile) at a carbonyl (e.g., at an activated carboxylic acid ester, such as pentafluorophenyl (PFP) ester or tetrafluorophenyl (TFP) ester) or at an electrophilic arene (e.g., SNAr at an oligofluorinated arene, a fluorobenzonitrile group, or fluoronitrobenzene group).

In certain embodiments, the attachment reaction is a dipolar cycloaddition, and the conjugation moiety includes azido, optionally substituted $C_{6-16}$ heterocyclylene containing an endocyclic carbon-carbon triple bond, or optionally substituted $C_{8-16}$ cycloalkynyl. The complementary reactive group and the conjugating group are selected for their mutual complementarity. For example, an azide is used in one of the conjugating group and the complementary reactive group, while an alkyne is used in the other of the conjugating group and the complementary reactive group.

Attachment of Linking Moiety to the Oligonucleotide

A linking moiety can be attached to an oligonucleotide by forming a bond between a attaching group in the oligonucleotide and a complementary reactive group bonded to the linking moiety. In certain embodiments, the linking moiety, is modified to include a complementary reactive group. Methods of introducing such complementary reactive groups into a linking moiety is known in the art.

In certain embodiments, the complementary reactive group is optionally substituted $C_{2-12}$ alkynyl, optionally substituted N-protected amino, azido, N-maleimido, S-protected thiol,

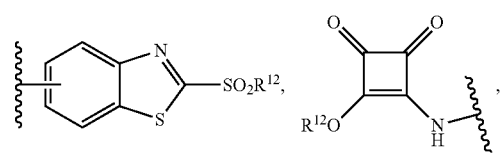

-continued

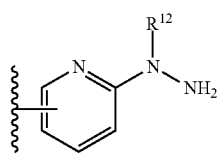

or a N-protected moiety thereof,

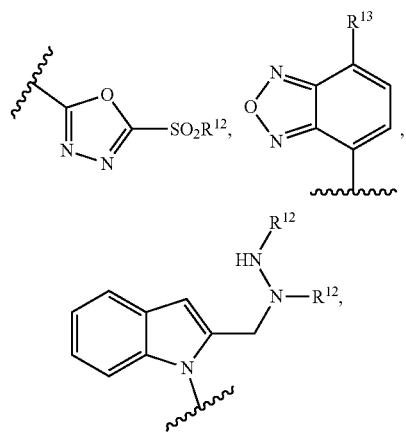

optionally substituted $C_{6-16}$ heterocyclyl containing an endocyclic carbon-carbon triple bond (e.g.,

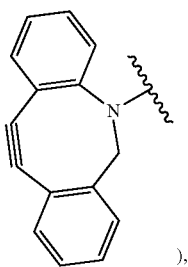 [SMILES: *N1Cc2ccccc2C#Cc2ccccc21]

), 1,2,4,5-tetrazine group (e.g.,

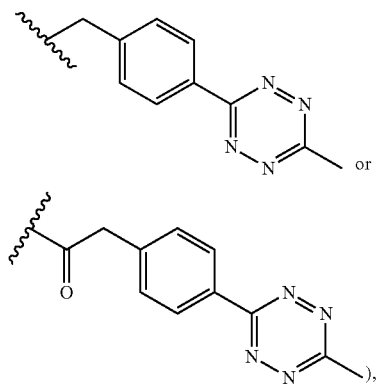

optionally substituted $C_{8-16}$ cycloalkynyl (e.g.,

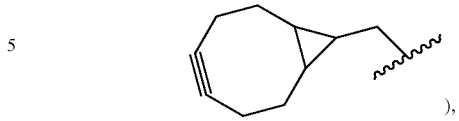

),

—$NHR^{N1}$, optionally substituted $C_{4-8}$ strained cycloalkenyl (e.g., trans-cyclooctenyl or norbornenyl), or optionally substituted $C_{1-16}$ alkyl containing —$COOR^{12}$ or —CHO; wherein:
$R^{N1}$ is H, N-protecting group, or optionally substituted $C_{1-6}$ alkyl;
each $R^{12}$ is independently H, optionally substituted $C_{1-6}$ alkyl, or O-protecting group (e.g., a carboxyl protecting group); and
$R^{c1}$ is halogen (e.g., F).

In certain embodiments, the complementary reactive group is protected until the conjugation reaction. For example, a complementary reactive group that is protected can include —$COOR^{PGO}$ or —$NHR^{PGN}$, where $R^{PGO}$ is an O-protecting group (e.g., a carboxyl protecting group), and $R^{PGN}$ is an N-protecting group.

VI. Pharmaceutical Compositions

The compounds and conjugates of the present invention, such as the conjugates comprising structures of formula (A), antibodies of formula (B), and immunomodulating oligonucleotides of formulae (C), (C'), (C"), (D), (D') and (D"), or a pharmaceutically acceptable salt of any of the foregoing, or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

The pharmaceutical compositions including a conjugate described herein can be delivered to a cell, group of cells, tumor, tissue, or subject using delivery technologies known in the art. In general, any suitable method recognized in the art for delivering a nucleic acid-protein conjugate (in vitro or in vivo) can be adapted for use with a herein described compositions. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the herein described pharmaceutical compositions may comprise one or more pharmaceutically acceptable excipients. In some embodiments, the pharmaceutical compositions described herein can be formulated for administration to a subject.

As used herein, a pharmaceutical composition or medicament includes a pharmacologically effective amount of at least one of the described therapeutic compounds or conjugates and one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert sub stance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The compound or conjugate can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.).

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active compound will be in the range of 25-400 mg per 1-18 weeks or 1-6 months. In some embodiments, an effective amount of an active compound will be in the range of 50-125 mg per 4 weeks or per one month. In some embodiments, an effective amount of an active ingredient will be in the range of from about 0.5 to about 3 mg/kg of body weight per dose. In some embodiments, an effective amount of an active ingredient will be in the range of from about 25-400 mg per dose. In some embodiments, an effective amount of an active ingredient will be in the range of from about 50-125 mg per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

For treatment of disease or for formation of a medicament or composition for treatment of a disease, the pharmaceutical compositions described herein including a compound or conjugate can be combined with an excipient or with a second therapeutic agent or treatment including, but not limited to: a second or other conjugates, a small molecule drug, an antibody, an antibody fragment, and/or a vaccine.

The described compounds or conjugates, when added to pharmaceutically acceptable excipients or adjuvants, can be packaged into kits, containers, packs, or dispensers. The pharmaceutical compositions described herein may be packaged in pre-filled syringes or vials.

VII. Kits

Also provided herein is a kit comprising a conjugate as described above.

In another aspect, the kit further comprises a package insert including, without limitation, appropriate instructions for preparation and administration of the formulation, side effects of the formulation, and any other relevant information. The instructions may be in any suitable format, including, but not limited to, printed matter, videotape, computer readable disk, optical disc or directions to internet-based instructions.

In another aspect, kits for treating an individual who suffers from or is susceptible to the conditions described herein are provided, comprising a first container comprising a dosage amount of a composition or formulation as disclosed herein, and a package insert for use. The container may be any of those known in the art and appropriate for storage and delivery of intravenous formulation. In certain embodiments, the kit further comprises a second container comprising a pharmaceutically acceptable carrier, diluent, adjuvant, etc. for preparation of the formulation to be administered to the individual.

In another aspect, kits may also be provided that contain sufficient dosages of the compositions described herein (including pharmaceutical compositions thereof) to provide effective treatment for an individual for an extended period, such as 1-3 days, 1-5 days, a week, 2 weeks, 3, weeks, 4 weeks, 6 weeks, 8 weeks, 1 cycle, 2 cycles, 3 cycles, 4 cycles, 5 cycles, 6 cycles, 7 cycles, 8 cycles or more.

In some embodiments, the kits may also include multiple doses and may be packaged in quantities sufficient for storage and use in pharmacies, for example, hospital pharmacies and compounding pharmacies. In certain embodiments the kits may include a dosage amount of at least one composition as disclosed herein.

VIII. Methods of Treatment

Also provided herein are methods for treating a disease or disorder in a subject comprising administering an effective amount of a compound or conjugate described herein to the subject in need thereof. Also provided herein are uses of a compound or conjugate described herein in the preparation of a medicament for treating a patient in need of treatment with the oligonucleotide in the conjugate. Also provided are compounds or conjugates as described herein for treating a disease or disorder in a subject in need of the treatment with the oligonucleotide in the compounds or conjugates. Also provided are compounds or conjugates as described herein for treating a patient comprising administering an effective amount of the compound or conjugate to the patient. In some embodiments, the subject has or at the risk of developing cancer. In some embodiments, the disease or disorder is a viral infection. In some embodiments, the disease or disorder is an immunodeficiency, e.g., in which immune activation may be favorable. In some embodiments, the disease or disorder is an autoimmune and/or inflammatory disease or disorder, e.g., in which immune suppression and/or modulation may be favorable.

In some embodiments of the methods of treating cancer as described herein, the cancer being treated with the methods disclosed herein is a solid tumor. In some embodiments, the cancer being treated with the methods disclosed herein is a liquid tumor. In some embodiments, the cancer being treated with the methods disclosed herein is a solid tumor. In particular embodiments, the cancer being treated with the methods disclosed herein is breast cancer, colorectal cancer, lung cancer, head and neck cancer, melanoma, lymphoma, or leukemia. In some embodiments, cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal qammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, sominoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated. In particular embodiments, the cancer being treated with the methods disclosed herein is selected from the list consisting of mantle cell cymphoma (MCL), diffuse large B-cell lymphoma (DLBCL), Burkitts lymphoma, multiple melanoma (MM), chronic lymphocytic leukemia (CLL), acute myeloid leukemia (AML), small lymphocytic lymphoma (SLL), hairy cell leukemia (HCL), lymphoplasmacytic lymphoma (LPL), skeletal muscle lymphoma (SML), splenic marginal zone lymphoma (SMZL), follicle center lymphoma (FCL), colorectal cancer, non-small cell lung cancer (NSCLC), head and neck cancer, breast cancer, pancreatic cancer, glioblastoma (GBM), prostate cancer, esophageal cancer, renal cell carcinoma, hepatic carcinoma, bladder cancer and gastric carcinoma.

In some embodiments, provided herein methods for treating a disease or disorder in a subject comprising administering an effective amount of a CpG-Ab immunoconjugate described herein to the subject in need thereof, wherein the CpG-Ab immunoconjugate binds to CD22, such as a CpG-Ab immunoconjugate comprising an anti-CD22 antibody or antigen binding fragment thereof, and where the disease or disorder treated is a cancer characterized by tumor infiltrating B cells. In some embodiments, such cancers include head and neck squamous cell carcinoma (HNSCC), non-small-cell lung carcinoma (NSCLC), renal cell carcinoma (RCC), gastric cancer, hepatocellular carcinoma (HCC), esophageal cancer, cervical cancer, Merkle cell carcinoma, endometrial cancer, acute lymphoblastic leukemia (ALL), hairy cell leukemia, and diffuse large B cell lymphoma (DLBCL). In some embodiments, such cancers include ovarian cancer, pancreatic cancer, melanoma, cutaneous melanoma, sarcoma, colorectal cancer, breast cancer, cervical squamous cell carcinoma, small cell lung cancer (SCLC), cutaneous squamous cell carcinoma, and urothelial carcinoma. In some embodiments, the CpG-Ab immunoconjugate is listed in one of Tables 2 and 9-12.

In some embodiments, the methods of treatment include administration of a CpG-Ab immunoconjugate that binds to CD22 expressed on the surface of a B cell and the treatment results in one or more of B cell activation, B cell differentiation, increased in T cell effector function, T cell proliferation, secretion of cytokines and chemokines, induction of immunoglobulin secretion and modulation in suppressive myeloid cells within the tumor microenvironment in the treated subject. In some embodiments, the methods of treatment include administration of a CpG-Ab immunoconjugate that binds to CD22 expressed on the surface of a B cell and the treatment results a memory immune response. In some embodiments, such treatment results in anti-tumor activity through both innate and adaptive immune responses.

In some embodiments, the methods of treatment include administration of a CpG-Ab immunoconjugate that binds to HER2 present on a tumor cell and the treatment results in the killing of or impairment of tumor cell(s) such that the volume, size and/or growth of the tumor is reduced or inhibited. In some embodiments, provided herein are methods for treating a disease or disorder in a subject comprising administering an effective amount of a CpG-Ab immunoconjugate described herein to the subject in need thereof, wherein the CpG-Ab immunoconjugate binds to HER2, such as a CpG-Ab immunoconjugate comprising an anti-HER2 antibody or antigen binding fragment thereof, and where the disease or disorder treated is a cancer characterized by HER2-expressing tumor cells. In some embodiments, the disease or disorder treated is a cancer where tumor cells over-express HER2. In some embodiments, the cancer is breast cancer, urothelial cancer or gastric cancer.

In some embodiments, the cancer being treated with the methods disclosed herein is resistant to at least one immunotherapy. In some embodiments, the cancer being treated with the methods disclosed herein is resistant to at least one cancer therapy selected from the group consisting of chemotherapy, radiation, targeted therapy, vaccine therapy, and CAR-T therapy. In some embodiments, the method of treating cancer comprises co-administering to a subject having cancer (i) a therapeutically effective amount of the CpG-containing immunostimulating polynucleotide or the CpG-antibody immunoconjugate; and (ii) the immunotherapeutic agent which the cancer being treated has shown to resist or not to respond, when the cancer is treated with the immunotherapeutic agent alone.

In particular embodiments, the cancer being treated with the methods provided herein has been shown to not to respond to a treatment with an immune checkpoint modulator. In particular embodiments, the immune checkpoint modulator is an inhibitor of PD-1. In particular embodiments, the immune checkpoint modulator is an inhibitor of PD-L1. In some embodiments, the method of treating cancer comprises co-administering to a subject having cancer (i) a therapeutically effective amount of the CpG-containing immunostimulating polynucleotide or the CpG-Ab immunoconjugate; and (ii) a therapeutically effective amount of the inhibitor of PD-1. In some embodiments, the method of treating cancer comprises co-administering to a subject having cancer (i) a therapeutically effective amount of the CpG-containing immunostimulating polynucleotide or the CpG-Ab immunoconjugate; and (ii) a therapeutically effective amount of the inhibitor of PD-L1. In particular, in some embodiments, the inhibitor of PD-1 is an anti-PD-1 antibody or an antigen-binding fragment thereof. In some embodiments, the inhibitor of PD-L1 is an anti-PD-L1 antibody or an antigen-binding fragment thereof. In some embodiments, the treatment is directed to a subject that does not respond to or is resistant to a PD-1 or PD-L1 inhibitor and such subject is treated with a CpG-Ab immunoconjugate that binds CD22, such as a CpG-Ab immunoconjugate comprising an anti-CD22 antibody or antigen binding fragment thereof.

In certain aspects, provided herein are methods of preventing cancer in a subject susceptible of developing cancer, comprising administering to the subject a therapeutically effective amount of a TLR agonist as described herein. In some embodiments, the method comprising administering to the subject a therapeutically effective amount of a CpG-containing immunostimulating polynucleotide or a CpG-Ab immunoconjugate described herein. In particular embodiments, the CpG-Ab immunoconjugate targets an immune cell as described herein. In particular embodiments, the CpG-Ab immunoconjugate targets a TLR-expressing cell as described herein. In particular embodiments, the CpG-Ab immunoconjugate specifically binds to an antigen associated with an immune cell as described herein. In particular embodiments, the CpG-Ab immunoconjugate specifically binds to an antigen associated with an immune cell does not bind to a tumor-associated antigen of the cancer being prevented. In particular embodiments, the CpG-Ab immunoconjugate specifically binds to an antigen associated with a TLR-expressing cell as described herein. In particular embodiments, the CpG-Ab immunoconjugate specifically binds to an antigen associated with a TLR-expressing cell and does not bind to a tumor-associated antigen of the cancer being prevented. In particular embodiments, the CpG-Ab immunoconjugate specifically binds to a tumor-associated antigen of the cancer being prevented as described herein, e.g., an antigen expressed on a tumor cell surface. In particular embodiments, a tumor-associated antigen of the cancer being prevented is also associated with an immune cell or a TLR-expressing cell. In particular embodiments, the CpG-Ab immunoconjugate does not specifically bind to an antigen selected from CD19, CD20, CD22, STAT3, exportin 7, Her2, Src, EGFR, CD52, CXCR-4, and Muc-1.

In some embodiments, the methods of preventing cancer further comprises administering to a subject susceptible to developing cancer (i) a therapeutically effective amount of a CpG-Ab immunoconjugate and (ii) a tumor-associated antigen of the cancer being prevented. In some embodiments, the tumor-associated antigen is not conjugated to the CpG-Ab immunoconjugate. In particular embodiments, the tumor-associated antigen is formulated as a cancer vaccine. In particular embodiments, the CpG-Ab immunoconjugate is formulated as an adjuvant of the cancer vaccine.

In some embodiments, the cancer being prevented or treated using the methods provided herein is an episode of cancer recurrence in a subject who is in partial or complete remission of a prior cancer. In particular embodiments, the prior cancer is a liquid cancer and the recurrent cancer being prevented or treated is a liquid cancer. In particular embodiments, the prior cancer is a solid cancer and the recurrent cancer being prevented or treated is a solid cancer. In particular embodiments, the prior cancer is a liquid cancer and the recurrent cancer being prevented or treated is a solid cancer. In particular embodiments, the prior cancer is a solid cancer and the recurrent cancer being prevented or treated is a liquid cancer.

In some embodiments, the cancer being prevented or treated using the methods provided herein is first episode of cancer recurrence in the subject after the subject showed partial or complete remission. In some embodiments, the cancer being prevented or treated using the methods provided herein is second episode of cancer recurrence in the subject after the subject showed partial or complete remission. In some embodiments, the cancer being prevented or treated using the methods provided herein is third episode of cancer recurrence in the subject after the subject showed partial or complete remission. In some embodiments, the cancer being prevented or treated using the methods provided herein is an episode of cancer recurrence subsequent to the third episode of cancer recurrence in the subject after the subject showed partial or complete remission.

In certain aspects, provided herein are methods of inducing an adaptive immune response in a subject in need thereof, wherein method comprises administering to the subject an therapeutically effective amount of a TLR agonist as described herein. In particular embodiments, the method of inducing an adaptive immune response comprises administering to the subject in need thereof a therapeutically effective amount of a CpG-containing immunostimulating polynucleotide or a CpG-Ab immunoconjugate described herein. In particular embodiments, the CpG-Ab immunoconjugate targets a normal immune cell as described herein. In particular embodiments, the CpG-Ab immunoconjugate targets a TLR-expressing cell as described herein. In particular embodiments, the CpG-Ab immunoconjugate targets a diseased cell selected from a cancer cell or a pathogen infected cell. In particular embodiments, the CpG-Ab immunoconjugate specifically binds to an antigen associated with a normal immune cell as described herein. In particular embodiments, the CpG-Ab immunoconjugate specifically binds to an antigen associated with a normal immune cell does not bind to a disease antigen. In particular embodiments, the CpG-Ab immunoconjugate specifically binds to an antigen associated with a TLR-expressing cell as described herein. In particular embodiments, the CpG-Ab immunoconjugate specifically binds to an antigen associated with a TLR-expressing cell does not bind to a disease antigen. In particular embodiments, the CpG-Ab immunoconjugate specifically binds to a disease antigen as described herein. In particular embodiments, the diseased antigen is also associated with a normal immune cell or a TLR-expressing cell. In particular embodiments, the diseased antigen is a tumor-associated antigen or a pathogenic antigen. In particular embodiments, the CpG-Ab immunoconjugate does not specifically bind to an antigen selected from CD19, CD20, CD22, STATS, exportin 7, Her2, Src, EGFR, CD52, CXCR-4, and Muc-1. In some embodiments, the antibody or conjugate specifically binds an antigen expressed by a cancer or cancer-associated stroma.

In some embodiments of the methods and uses described herein, the CpG-containing immunostimulating polynucleotide is administered to a subject in need thereof at a dosage that is sufficient for activating the TLR9-mediated signaling pathway in the subject. In some embodiments, the CpG-Ab immunoconjugate is administered to a subject in need thereof at a dosage that is sufficient for activating the TLR9 mediated signaling pathway in a cell population targeted by the CpG-Ab immunoconjugate. As described herein, in some embodiments, the cell population targeted by the CpG-Ab immunoconjugate expresses TLR9. In some embodiments, the cell population targeted by the CpG-Ab immunoconjugate can express the TLR9 on the cell surface of the targeted cell, on the endosomal membrane of the targeted cell, or both on the cell surface and on the endosomal membrane of the targeted cell.

Particularly, in some embodiments of the methods and uses described herein, the CpG-containing immunostimulating polynucleotide is administered to a subject in need thereof at a dosage that is effective for inducing one or more of effects selected from (a) specifically binding to a TLR9 receptor by the CpG-containing immunostimulating polynucleotide on a targeted cell; (b) efficient internalization of the CpG-Ab immunoconjugate or the CpG-containing immunostimulating polynucleotide portion thereof by a targeted cell; (c) activating one or more signaling pathways in the targeted cell; (d) inducing secretion of one or more inflammatory cytokines by the targeted cell; (e) suppressing secretion of one or more inflammatory cytokines by the targeted cell; (f) upregulating expression of one or more genes of the targeted cell; (g) suppressing expression of one or more genes of the targeted cell; (h) activating targeted normal immune cells, (i) inducing an immune response that results in the elimination of disease, e.g. cancer cells, (j) inducing apoptosis of a targeted cancer cell, and (k) inducing necrosis of targeted cancer cell.

Particularly, in some embodiments of the methods and uses described herein, wherein upon administration of the CpG-Ab immunoconjugate, the CpG-containing immunostimulating polynucleotide specifically binds to a TLR9 receptor of the targeted cell. Particularly, in some embodiments, binding of CpG-Ab immunoconjugate to an antigen associated with a targeted cell facilitates specific binding of the CpG-containing immunostimulating polynucleotide to a TLR9 receptor. In some embodiments, the target antigen of the CpG-Ab immunoconjugate is located near the TLR9 receptor. In particular embodiments, both the target antigen and the TLR9 receptor locate on the cell membrane of the targeted cell. In particular embodiments, both the target antigen and the TLR9 receptor locate on an intracellular membrane of the targeted cell. In particular embodiments, both the target antigen and the TLR9 receptor locate on the endosomal or phagosomal membrane of the targeted cell. In some embodiments, the target antigen locates on the cell membrane and facilitates internalization of the CpG-Ab immunoconjugate into the cytosol upon binding to the CpG-Ab immunoconjugate.

Particularly, in some embodiments of the methods and uses described herein, the method comprises administering to a subject in need thereof a therapeutically effective amount of a CpG-Ab immunoconjugate targeting a normal immune cell, wherein upon administration of the CpG-Ab immunoconjugate, one or more immunogenic signaling pathways in the targeted cell are activated. In particular embodiments, the activated signaling pathways are one or more selected from the nuclear factor (NF)-κB signaling pathway, the c-Jun N-terminal kinase (JNK) signaling pathway, the AP1 signaling pathway, the IRF3/7 pathway, and the p38 mitogen-activated protein kinase (MAPK) signaling pathway. The activation of a cellular signaling pathway can be detected using methods known in the art, such as but not limited to, detecting the presence of a molecular marker of which the expression is specifically induced upon activation of the signaling pathway of interest.

Particularly, in some embodiments of the methods and uses described herein, the method comprises administering to a subject in need thereof a therapeutically effective amount of a CpG-Ab immunoconjugate targeting a normal immune cell, wherein upon administration of the CpG-Ab immunoconjugate, secretion of one or more inflammatory cytokines is induced. In particular embodiments, the one or more inflammatory cytokines are selected from type I interferon (IFN), interleukin (IL)-6, IL10, IL-12, IL-18, and tumor necrosis factor (TNF).

Particularly, in some embodiments of the methods and uses described herein, the method comprises administering to a subject in need thereof a therapeutically effective amount of a CpG-Ab immunoconjugate targeting a normal immune cell, wherein upon administration of the CpG-Ab immunoconjugate, expression of one or more additional proteins are upregulated. In particular embodiments, the upregulated proteins are one or more selected from antigen presenting molecules (e.g., MHC class I and II), cytokine receptors (e.g., IL-6 receptors, IL-10 receptors, IL-12 receptors, TNF-α receptor, TNF-β receptor, IFN-α receptor, IFN-β receptor, IFN-γ), chemokine receptors (e.g., chemokine receptor 7), costimulatory molecules (e.g., CD3, CD28, CD27, CD30, CD40, CD69, CD80/B7-1, CD86/B7-2, CD134/OX-40, OX-40L, CD137/4-1BB, 4-1BBL, CD278/ICOS, B7-H3, B7h/B7RP-1, LIGHT etc.), HLA-DR and T cell maturation regulatory proteins (e.g., indoleamine 2,3-dioxygenase).

Particularly, in some embodiments of the methods and uses described herein, the method comprises administering to a subject in need thereof a therapeutically effective amount of a CpG-Ab immunoconjugate targeting a normal immune cell, wherein upon administration of the CpG-Ab immunoconjugate, proliferation, differentiation, maturation and/or survival of one or more populations of normal immune cells are increased. In particular embodiments, the one or more increased populations of normal immune cells are selected from CD4+ T cells, CD8+ T cells, natural killer cells, T helper cells, B cells, and myeloid cells (including mDCs and pDCs). in some embodiments of the methods and uses described herein, the method comprises administering to a subject in need thereof a therapeutically effective amount of a CpG-Ab immunoconjugate targeting a normal immune cell, wherein upon administration of the CpG-Ab immunoconjugate, proliferation, differentiation, maturation and/or survival of one or more populations of normal immune cells are reduced. In particular embodiments, the one or more reduced populations of normal immune cells is selected from B-reg cells, T-reg cells, and MDSCs.

In particular embodiments, upon administration of the CpG-Ab immunoconjugate, antigen presentation activities are increased in APCs in the subject. In some embodiments, the APC is selected from B cells, monocytes, dendritic cells, and Langerhans cells, keratinocytes, endothelial cells, astrocytes, fibroblasts, and oligodendrocytes. In particular embodiments, the APC is B cells. In particular embodiments, the APC is dendritic cells. In particular embodiments, the APC is macrophage. In some embodiments, the dendritic cell is pDC. In particular embodiments, the increased antigen presentation activities lead to more efficient presentation of a tumor-associated antigen by the activated APCs.

In particular embodiments, upon administration of the CpG-Ab immunoconjugate, antigen-specific CD4+ T cell mediated immunity against one or more tumor-associated antigen of the cancer being treated or prevented is increased. In particular embodiments, upon administration of the CpG-Ab immunoconjugate, tumor infiltration by CD4+ T cell is increased. In particular embodiments, upon administration of the CpG-Ab immunoconjugate, antigen-specific CD8+ T cell mediated immunity against one or more tumor-associated antigen of the cancer being treated or prevented is increased is increased. In particular embodiments, upon administration of the CpG-Ab immunoconjugate, tumor infiltration by CD8+ T cell is increased. In particular embodiments, upon administration of the CpG-Ab immunoconjugate, B cell secretion of immunoglobulin specifically against one or more tumor-associated antigen of the cancer being treated or prevented is increased is increased.

Particularly, in some embodiments of the methods and uses described herein, the method comprises administering to a subject in need thereof, a therapeutically effective amount of a CpG-Ab immunoconjugate targeting a diseased cell, wherein upon administration of the CpG-Ab immunoconjugate, one or more apoptotic signaling pathways are induced trigger apoptosis of the targeted diseased cell. In some embodiments, the diseased cell is a cancer cell.

In some embodiments of the methods and uses described herein, the CpG-Ab immunoconjugate is administered to a subject in need thereof in an amount that is not effective for activating the complement system in the subject. In some embodiments, the CpG-containing immunostimulating polynucleotide is administered to a subject in need thereof in an amount that is not effective to activate complement C1 in the subject. In some embodiments, the CpG-containing immunostimulating polynucleotide is administered to a subject in need thereof in an amount that is not effective to activate complement C3 in the subject. Complement activation can be detected using methods known in the art. In some embodiments, the CpG-Ab immunoconjugate is administered to a subject in need thereof in an amount that is not effective for the antibody portion of the CpG-Ab immunoconjugate to induce antibody-dependent cell-mediated cytotoxicity in the subject.

As described herein, therapeutic agents, conjugates or compositions comprising the CpG-containing polynucleotides can be used in combination with at least one additional therapeutic agent for preventing or treating cancer. In some embodiments, such combination therapy exhibits a synergistic therapeutic effect that is better than the separate effect of either therapeutic agent alone. In some embodiments, such combination therapies exhibit a synergistic therapeutic effect that is better than the sum of the separate effects of the therapeutic agents alone.

Accordingly, in certain aspects, provided herein are methods for preventing or treating cancer using the CpG-containing immunostimulating polynucleotide in combination with at least one additional cancer therapeutic agent. Such methods comprising administering to a subject in need thereof (i) a therapeutically effective amount of the CpG-containing immunostimulating polynucleotide, and (ii) a therapeutically effective amount of at least one additional cancer therapeutic agents. In particular embodiments, the CpG-containing immunostimulating polynucleotide is administered as a free-standing polynucleotide. In particular embodiments, the CpG-containing immunostimulating polynucleotide is administered as a CpG-Ab immunoconjugate. In particular embodiments, the CpG-containing immunostimulating polynucleotide and the additional therapeutic agents are formulated in the same composition. In other embodiments, CpG-containing immunostimulating polynucleotide and the additional therapeutic agents are formulated in the separate compositions.

In some embodiments, the at least one additional cancer therapeutic agent is selected from T cell agonists, immune checkpoint modulators, STING agonists, RIG-I agonists, other toll-like receptor agonists.

In some embodiments, the additional cancer therapeutic agent is a T cell costimulatory molecule. In some embodiments, the T cell costimulatory molecule is selected from OX40, CD2, CD27, CDS, ICAM-1, LFA-1/CD11a/CD18, ICOS/CD278, 4-1BB/CD137, GITR, CD30, CD40, BAFFR, HVEM, CD7, LIGHT, NKG2C, SLAMF7, NKp80, CD160, B7-H3, and CD83, or a ligand thereof. In some embodiments, a ligand of a costimulatory molecule is an antibody specifically binding to the costimulatory molecule. In particular embodiments, the additional cancer therapeutic agent is selected from an anti-OX40 antibody, an anti-OX40L antibody, an anti-ICOS antibody, an anti-CTLA4 antibody, an anti-CD40L antibody, an anti-CD28 antibody, an anti-LFA1 antibody, an anti-TIM1/TIM3 antibody, anti-LAG3 antibody, anti-Siglec-15 antibody, an anti-PD1 antibody, an anti-PDL1 antibody, an anti-CD27 antibody and an anti-4-1BB antibody.

In some embodiments, the additional cancer therapeutic agent is a tumor-associated antigen produced by the cancer that is being prevented or treated with the method. In some embodiments, the cancer being prevented or treated is leukemia, lymphoma, melanoma, colorectal, breast, prostate, renal, pancreatic, head and neck, skin, and brain cancer, lung cancer, and the tumor-associated antigen is selected from CD19, CD20, CD22, CD38, CD138, CD30, CD52, CD56, CD79, CD123, CD206, CD303, CD304, EGFR, folate receptor alpha, folate receptor beta, mesothelin, Her2, transferrin receptor, and PSMA. In some embodiments, the additional cancer therapeutic agent is an immune checkpoint modulator selected from inhibitors of PD-1, PD-L1, PD-L2, TIM-3, LAG-3, CEACAM-1, CEACAM-5, CLTA-4, VISTA, BTLA, TIGIT, LAIR1, CD47, SIRP-α, CD160, 2B4, CD172a, and TGFR. In particular embodiments, the additional cancer therapeutic agent is a PD-1 inhibitor. In particular embodiments, the additional cancer therapeutic agent is a PD-L1 inhibitor. In particular embodiments, the additional cancer therapeutic agent is a CD47 inhibitor. In some embodiments, the additional cancer therapeutic agent is an antibody specifically binding to the immune checkpoint modulator. In particular embodiments, the additional cancer therapeutic agent is an anti-PD-1 antibody or an antigen-binding fragment thereof. In particular embodiments, the additional cancer therapeutic agent is an anti-PD-L1 antibody or an antigen-binding fragment thereof. In particular embodiments, the additional cancer therapeutic agent is an anti-CD47 antibody or an antigen-binding fragment thereof. In particular embodiments, the additional cancer therapeutic agent is an anti-CD172a antibody or an antigen-binding fragment thereof, In particular embodiments, the additional cancer therapeutic agent is an anti-OX40 antibody or an antigen-binding fragment thereof, In particular embodiments, the additional cancer therapeutic agent is an anti-TIM3 antibody or an antigen-binding fragment thereof, In particular embodiments, the additional cancer therapeutic agent is an anti-LAG3 antibody or an antigen-binding fragment thereof. Anti-PD-1 and anti-PD-L1 antibodies and their uses are described in, for example, US20180030137, U.S. Pat. No. 9,815,898, US20170313776, US20170313774, US20170267762, WO2017019846, WO2018013017, US20180022809, US20180002423, WO2017220990, WO2017218435, WO2017215590, U.S. Pat. No. 9,828,434, and WO2017196867. Anti-CD47 antibodies and their uses are described in, for example U.S. Pat. Nos. 9,663,575, 9,803,016, US20170283498, US20170369572, WO2017215585, WO2017196793, and WO2017049251.

In some embodiments, the additional cancer therapeutic agent is a STING pathway agonist. STING (stimulator of interferon genes, also known as TMEM173, MITA, EMS, and MPYS) is a transmembrane protein localized to the ER that undergoes a conformational change in response to direct binding of cyclic dinucleotides (CDNs), resulting in a downstream signaling cascade involving TBK1 activation, IRF-3 phosphorylation, and production of IFN-β and other cytokines. The STING pathway in tumor-resident host antigen presenting cells is involved in the induction of a spontaneous CD8+ T cell response against tumor-associated antigens. Activation of this pathway and the subsequent production of IFN-β also contributes to the anti-tumor effect. In some embodiments, the STING pathway agonist is ADU-S100. Additional STING agonists and their uses are described in, for example, US20180028553, US20170319680, US20170298139, US20060040887, US20080286296, US20120041057, US20140205653, WO2014179335, WO 2014179760, US20150056224, WO 2016096174, WO 2017011444, WO 2017027645, and WO 2017027646.

In some embodiments, the additional cancer therapeutic agent is a MG-I pathway agonist. MG-I (retinoic acid-inducible gene-I) is a member of pattern-recognition receptors that initiates a host's innate immune system to defend against pathogenic microbes in early phases of infection. There are three members of the (RIG-I)-like receptors family: RIG-I, MDA5 (melanoma differentiation factor 5), and LGP2 (laboratory of genetics and physiology 2), which are expressed in most cell and tissue types. MG-I functions as a cytoplasmic sensor for the recognition of a variety of RNA viruses and subsequent activation of downstream signaling to drive type I IFN production and antiviral gene expressions. Activated MG-I recruits its downstream adaptor molecule MAVS (also known as IPS-1, CARDIF, and VISA) through CARD-CARD-mediated interactions. The oligomeric MG-I CARD assembly and the polymeric formation of MAVS, together serve as a signaling platform for protein complexes that mediate the bifurcation of signaling into two branches. One branch recruits tumor necrosis factor receptor-associated factors (TRAF)-2/6 and the receptor-interacting protein 1 to subsequently activate the IKK complex, resulting in NF-κB activation. The other branch signals through TRAF3 and activates the TANK/IKKγ/IKKε/TBK1 complex, leading to the phosphorylation and dimerization of interferon regulator factors (IRF)-3 and -7. Liu et al., *Front Immunol.* 2017, 7:662. Activation of this pathway contributes to the anti-tumor effect. In some embodiments, the RIG-I pathway agonist is RGT100. RIG-I agonists and their uses are described in, for example, US20170057978, US20170258897, U.S. Pat. Nos. 9,381,208, 9,738,680, 9,650,427, WO2017173427, and WO2017011622.

In some embodiments, the additional cancer therapeutic agent is a toll-like receptor agonist selected from TLR1 agonist, TLR2 agonist, TLR3 agonist, TLR4 agonist, TLR5 agonist, TLR6 agonist, TLR7 agonist, TLR8 agonist, and TLR10 agonist.

In further embodiments, in relation to a method of treating cancer, the CpG-containing immunostimulating polynucleotide is administered (either in the free-standing form or as a CpG-Ab immunoconjugate) in combination with one or more additional therapeutic agents or procedures, for example wherein the additional therapeutic agent or procedure is selected from the group consisting of chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, a cellular immunotherapy, a cell-based therapy (e.g., CAR-T, TILs, TCR-T, CAR-NK, and CAR-macrophage therapies) and an oncolytic virus therapy.

EXAMPLES

The presently disclosed subject matter will be better understood by reference to the following Examples, which are provided as exemplary of the invention, and not by way of limitation.

Materials

Prototype peptides were made in house, but can be purchased at custom peptide suppliers (e.g. CPC Scientific). Oligonucleotides were made in-house or by LGC.

Transglutaminase used in these examples were isolated from various bacterial *Streptoverticillium* strain (e.g., Ajinomoto). The Q-tag mAbs were produced at Sino Biologicals or internally.

Production of Oligonucleotides

Oligonucleotides were generally prepared in accordance with the solid phase synthesis scheme shown below, beginning with an initial deprotection of the solid support for the oligonucleotide synthesis, followed by coupling of the solid support with to the first nucleotide, thiolation to give the phosphothioester and repeated deprotection and coupling to give the entire oligonucleotide sequence.

The general synthesis of oligonucleotides as provided herein is described below.

Deprotection: A dimethoxytrityl-1,3-propanediol glycolate protected controlled pore glass solid support (DMTO-C3-CPG, 1000A, Bulk Density 0.26-0.36 g/cc, Loading 30-40 µmol/g) was reacted with 3% dichloroacetic acid in toluene (v/v) at 25° C., to give the deprotected CPG support. UV absorption of an aliquot of the reaction mixture was measured to identify the reaction endpoint (wavelength 350 nm, target minimum absorbance 0.25 OD, using a fixed watch command setting) and to confirm removal of the dimethoxytrityl protecting group.

Activation/Coupling: The deprotected CPG support was coupled with the first nucleotide phosphoramidite precursor for the 3'-end, for the respective oligonucleotide to be synthesized, by adding and mixing the desired 3' nucleotide (3 equiv.) for 5 minutes at 25° C. to the reactor containing the deprotected CPG support in the presence of an activator 5-Ethylthio-1H-tetrazole (0.5M in ACN) at 60% of the nucleotide concentration.

Thiolation/Sulfurization: Following the coupling step, the linking phosphite triester moiety of the added nucleotide precursor was thiolated (or sulfurized) by adding Polyorg Sulfa (3-phenyl 1,2,4-dithiazoline-5-one), 0.15M in dry ACN, to give the phosphothioester.

Capping: After sulfurization, the CPG support and linked nucleotide were treated with two capping compositions (Capping composition A: 20% N-methylimidazole in ACN; Capping B composition B: 20% Acetic Anhydride, 30% Pyridine, 50% ACN) to block unreacted nucleotide reactants.

Repeat Synthesis: The remaining nucleotides were added in sequence from the 3' end to the 5' end, employing the appropriate phosphoramidite precursors in solution, by repeating the steps of deprotection, activation/coupling, thiolation/sulfurization and capping as described above to obtain the desired oligonucleotide sequence in protected form. All phosphoramidite prescursors were mixed with the CPG support for 5 minutes during the coupling step, except for dT-Thiophosphoramidite, which was mixed for 15 minutes.

Selected phosphoramidite precursors used in the synthesis are shown below. The phosphoramidite precursors were prepared in solutions with the solvents and at the concentrations, respectively shown, to be used in the coupling steps.

| Amidite | Structure | Concentration |
|---|---|---|
| DMT-dC(Ac) Amidite | 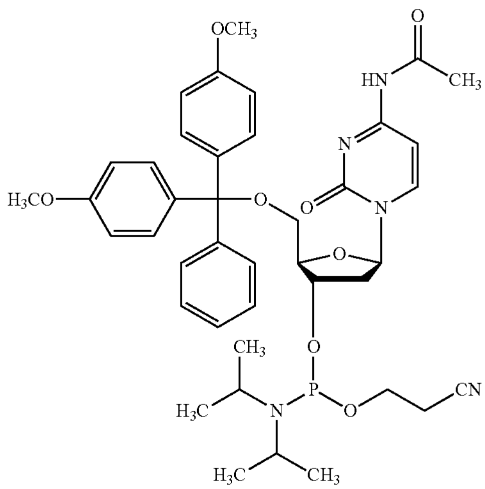 | 0.1M in dry ACN: |
| DMT-dG(dmf) Amidite | 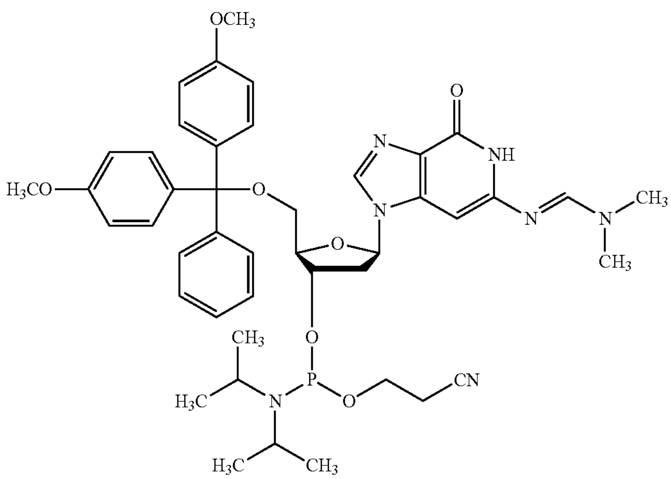 | 0.1M in dry ACN: |
| DMT-dT phosphoramidite | 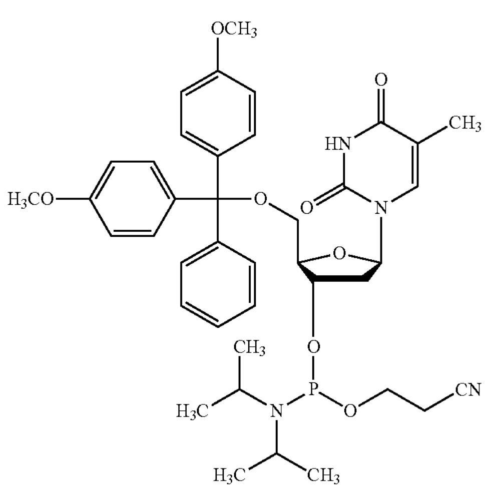 | 0.1M in dry ACN: |

-continued

| Amidite | Structure | Concentration |
|---|---|---|
| Fmoc-protected DMT-dT PEG2 NH2 Amidite | (structure shown) | 0.1M in dry ACN |
| 5-Br-dU-CE Phosphoramidite | (structure shown) | 0.1M in dry ACN |
| dT-Thiophsophoramidite | (structure shown) | 0.15M in dry 10% (v/v) DCM/ACN |
| 2'-O-Methyl 5-Methyl Uridine CED phosphoramidite | | 0.1M in dry ACN |
| dG-Thiophosphoramidite | (structure shown) | 0.1M in dry ACN |

Exemplary Fmoc-protected oligonucleotide compounds 6.1a, 6.2a and 6.3a obtained from the synthesis steps described above are shown below. The deprotection, purification and coupling of compound 6.1a to prepare the compound 6.1b is further described below.
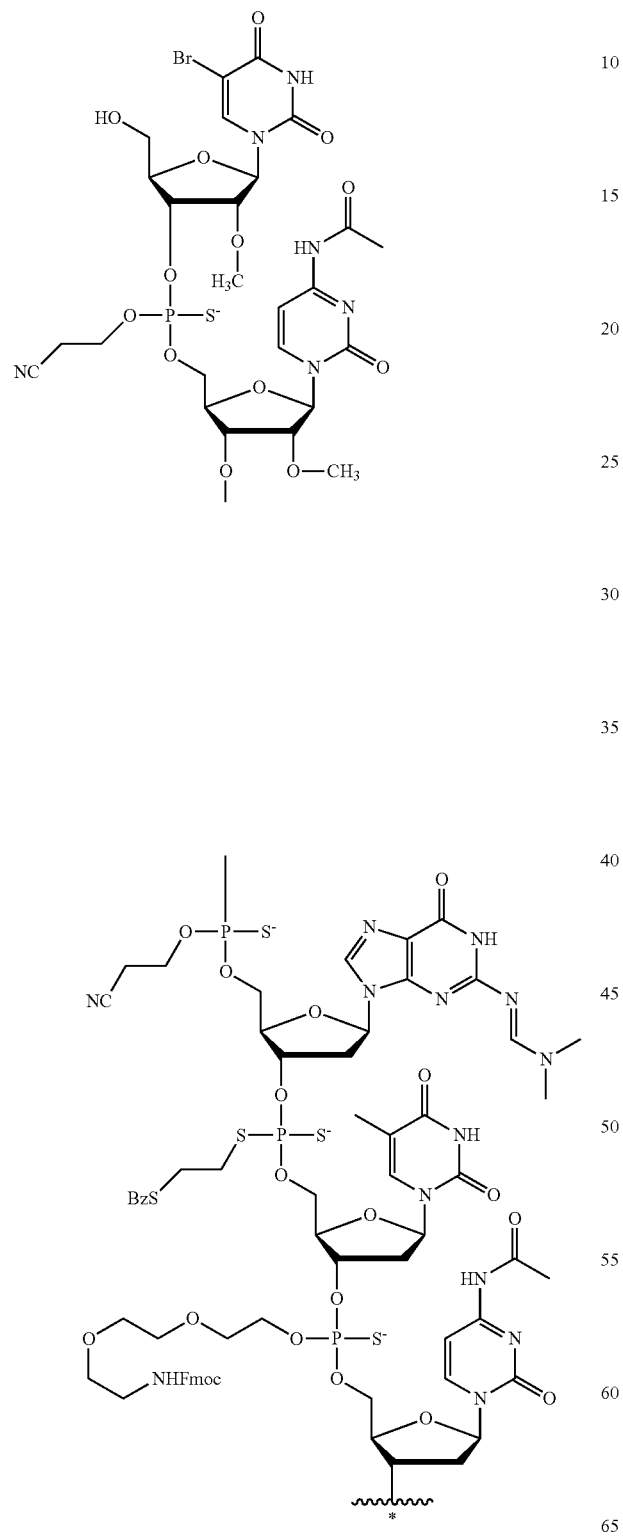
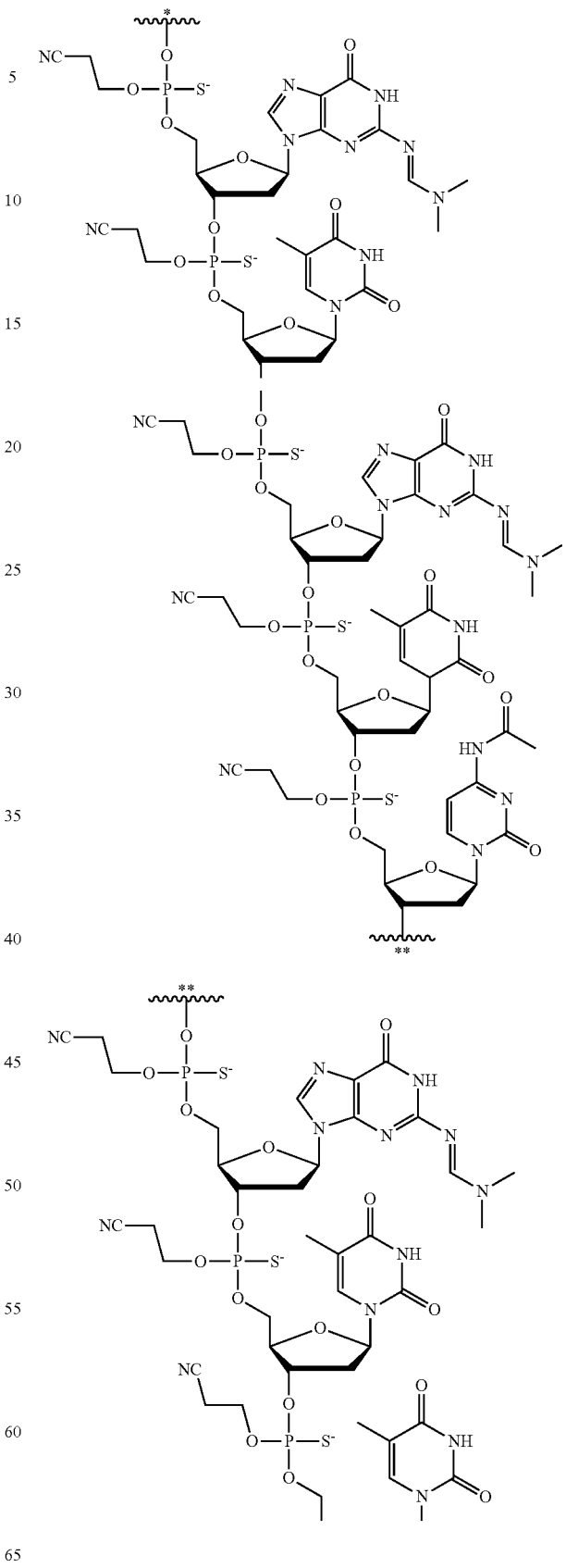

531
-continued
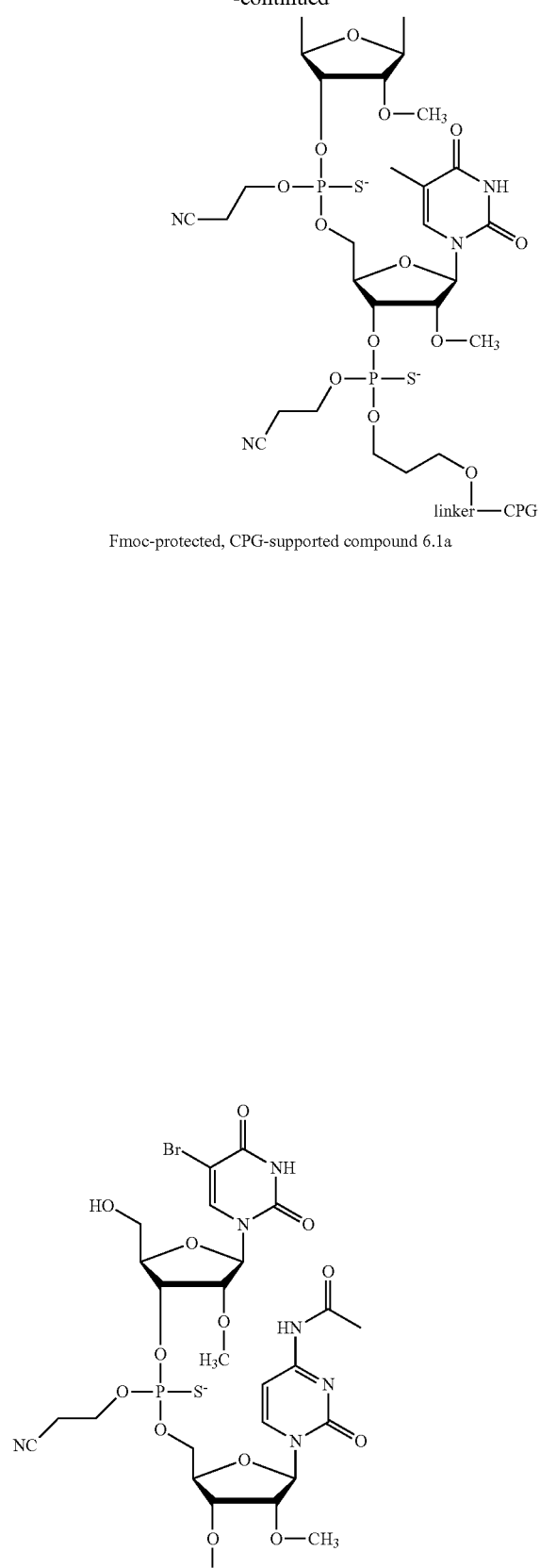
Fmoc-protected, CPG-supported compound 6.1a
532
-continued
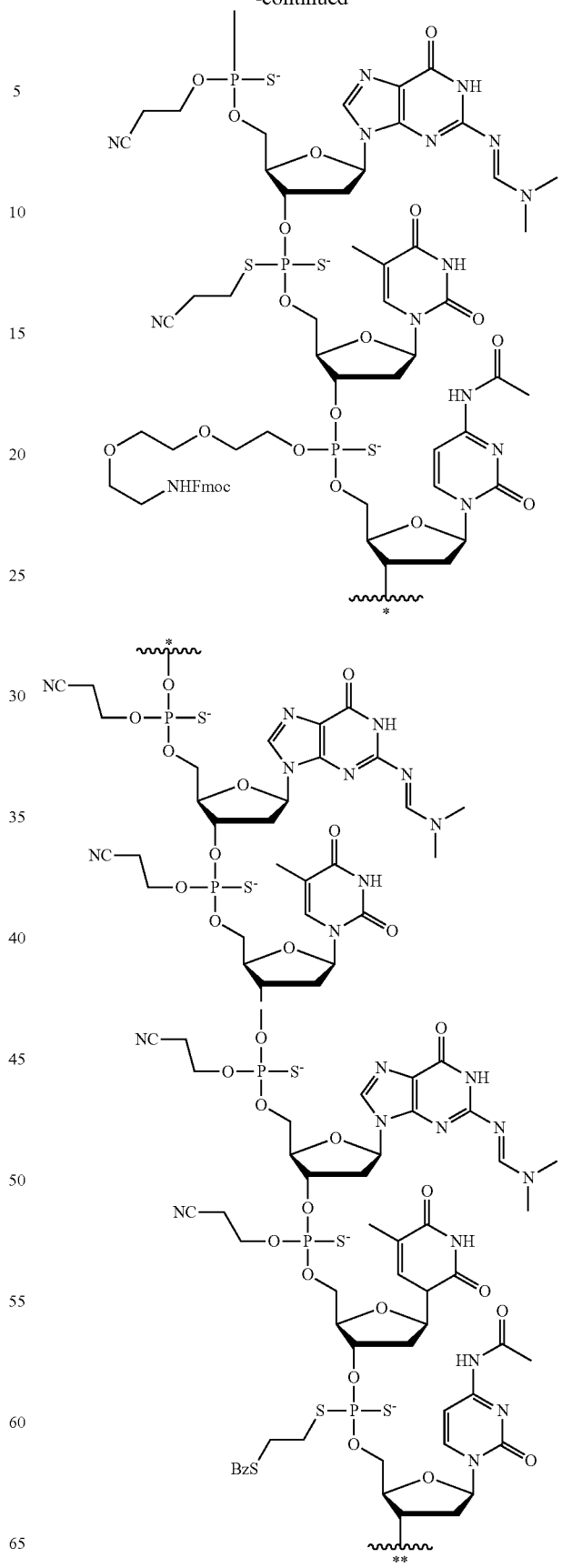

533
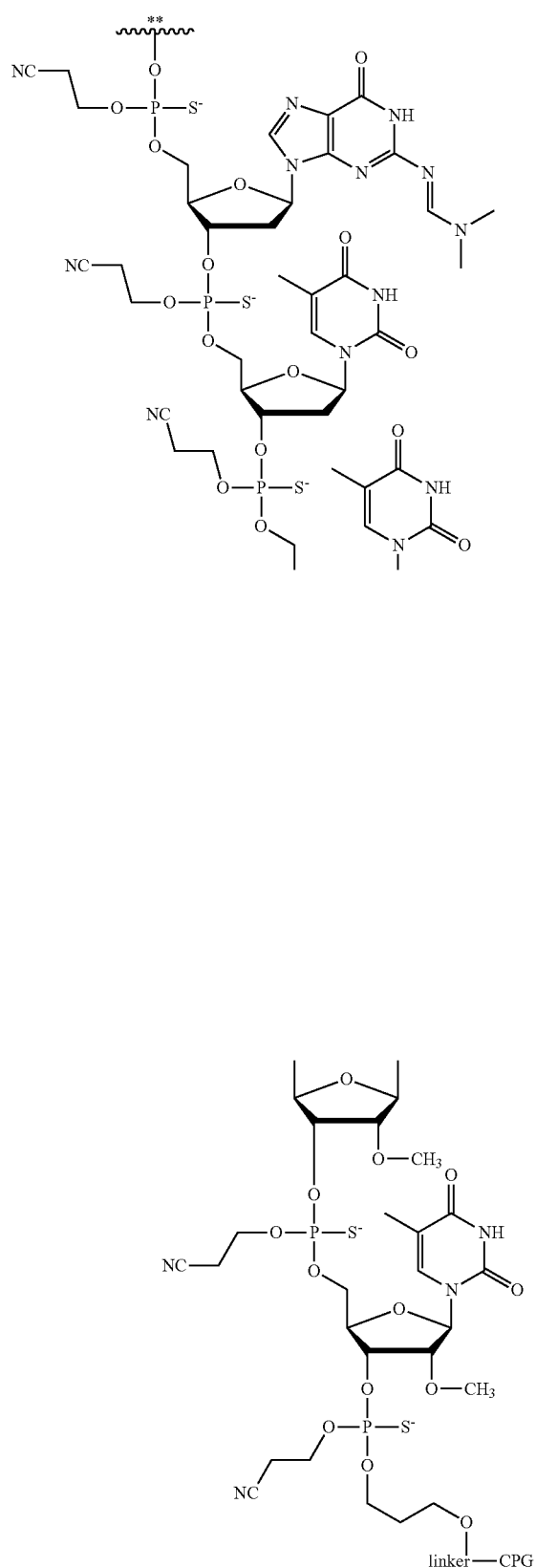
Fmoc-protected, CPG-supported compound 6.2a
534
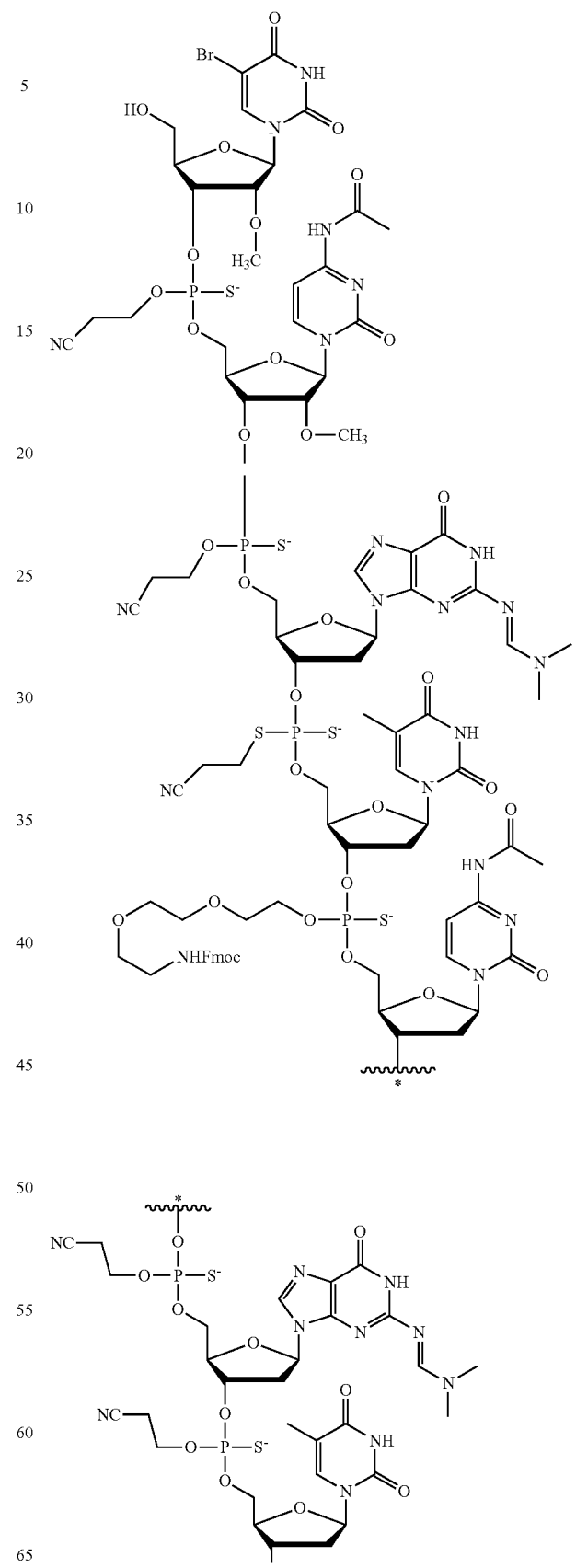

535

-continued

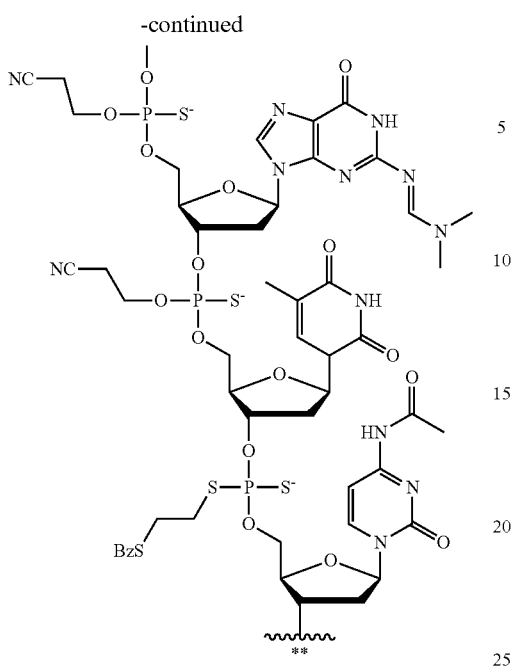

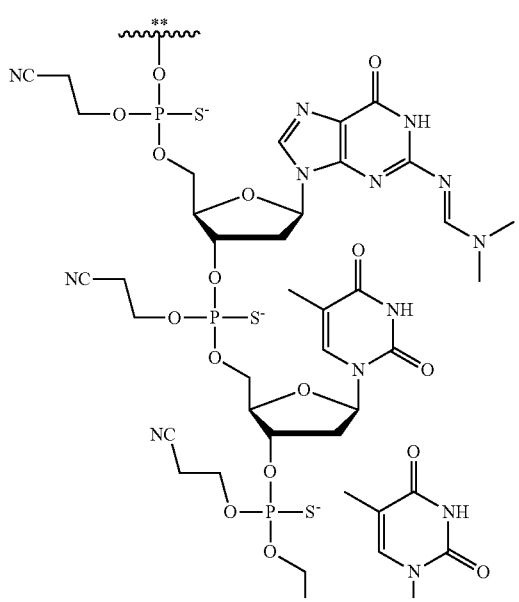

536

-continued

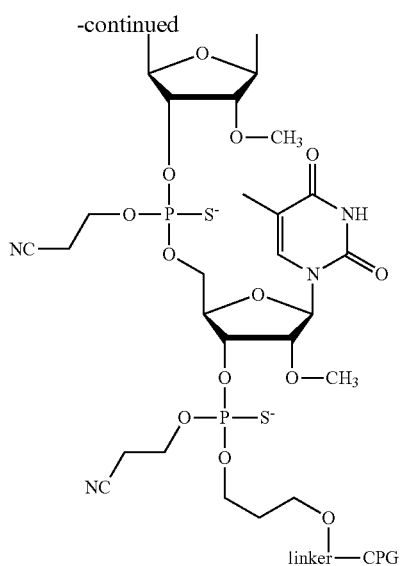

Fmoc-protected, CPG-supported compound 6.3a

The Fmoc-protected, CPG-supported oligonucleotide compound 6.1a obtained from the synthesis above was simultaneously cleaved from the support and deprotected by reacting the CPG support with 20 mM dithiothreitol in ammonium hydroxide:methylamine, 1:1 (v/v) for 2 hours at room temperature to give crude compound 6.1a. The crude product was purified by ion-pair reversed phase HPLC (IP—RP-HPLC) and its identity confirmed by ESI-MS. Crude compound 6.1a was purified by HPLC and desalted.

Compound 6.1a was subsequently reacted with O-[2-(Fmoc-amino)-ethyl]-O'-[3-(N-succinimidyloxy)-3-oxopropyl]polyethylene glycol (Fmoc-N-amido-dPEG24-NHS ester) in sodium bicarbonate buffer to give Fmoc-protected compound 6.1b. Fmoc-protected compound 6.1b was reacted with 20 mM dithiothreitol in ammonium hydroxide:methylamine, 1:1 (v/v) for 2 hours at room temperature to give crude compound 6.1b. The crude product was purified by ion-pair reversed phase HPLC (IP-RP-HPLC) and its identity confirmed by ESI-MS. Crude compound 6.1b was purified by HPLC, desalted, and lyophilized to give the purified oligonucleotide 6.1b.

Production of Antibodies

Antibodies generated in-house are typically expressed in suspension culture of Expi293 system (ThermoFisher) according to the manufacturer's manual. The expressed antibodies are purified via Protein A capture using MabSelectLX chromatography (GE), elution with 0.1M citrate (pH 3.3) and dialyzed in final buffer composition of 1×PBS (Phosphate Buffered Saline, pH 7.4).

One-Step Conjugation Method Via mTG (Microbial Transglutaminase)

Q-tag with the sequence RPQGFGPP (SEQ ID NO: 49) was genetically linked to the C-terminus of the heavy chain of antibody. To perform conjugation, the purified antibody (containing the engineered Q tags at the C-terminal of heavy chain) were first buffer exchanged into 25 mM Tris, 150 mM NaCl pH 8. The Ab-Q-tag containing moiety and CpG were added in molar ratio of 1:1.3 and incubated overnight with a final concentration of 1% mTG (w/v) (Ajinomoto) at room temperature. Final concentration of antibody used for conjugation is generally ~20-25 uM. Mixture was loaded to a Q Sepharose HP (GE) equilibrated in 20% Buffer B (40 mM Tris, 2M NaCl pH8) and 80% Buffer A (40 mM Tris, pH8).

Column was washed with 5 column volumes of 20% Buffer B. Separation was achieved with using a linear gradient from 20% B to 60% B in 30 column volumes. DAR1 peak fractions (Q tag conjugated with one CpG moiety) were pooled and concentrated followed by a gel filtration step using S200 (GE). Monomeric peak fractions were pooled and concentrated.

Biological Evaluation of CpG-Nucleotides and Antibody-CpG Nucleotide Conjugates

Trima residuals were received from Vitalant and diluted 1:4 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface and resuspended in FACS buffer (PBS with 0.5% Bovine Serum Albumin (Gibco)). B cells were purified by negative selection using the B Cell Isolation Kit II, human (Miltenyi Biotec) and LS columns (Miltenyi Biotec) according to manufacturer's protocol.

PBMCs were immediately plated onto a 96-well format (500K/well) in Complete RPMI (RPMI+10% FBS). Five-fold serial dilutions were added to the cells from 100 nM to 6.4 pM of antibody and conjugated antibody and 1 uM to 64 pM of CpG polynucleotides at 37° C. under 5% CO2 for 48 to 96 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR Blocking Reagent (Miltenyi Biotec), anti-CD19, anti-CD20, anti-CD40, anti-HLADR and anti-CD80 for B cell assays and anti-CD14, anti-CD3, anti-CD19, anti-CD14, anti-CD123, anti-CD11c and anti-CD86 for pDC assays. Cells were centrifuged and washed twice in FACS buffer and fixed in 0.5% paraformaldehyde.

CountBright™ Absolute Counting Beads (Thermo Fisher) were added to each well to count the number of cells. Cells were analyzed on Attune NxT Flow Cytometer (Thermo Fisher), with subsequent data analysis by Flowjo 10.7 (Treestar). Dead cells were excluded by gating on the eFluor 780-negative population. Lineage specific cells were first excluded (CD19, CD3, CD14) prior to gating CD123$^+$ CD11c$^-$ cells to identify pDC and gating CD19$^+$, CD20$^+$ or CD19$^+$CD20$^+$ cells to identify B cells.

Figure 1B:
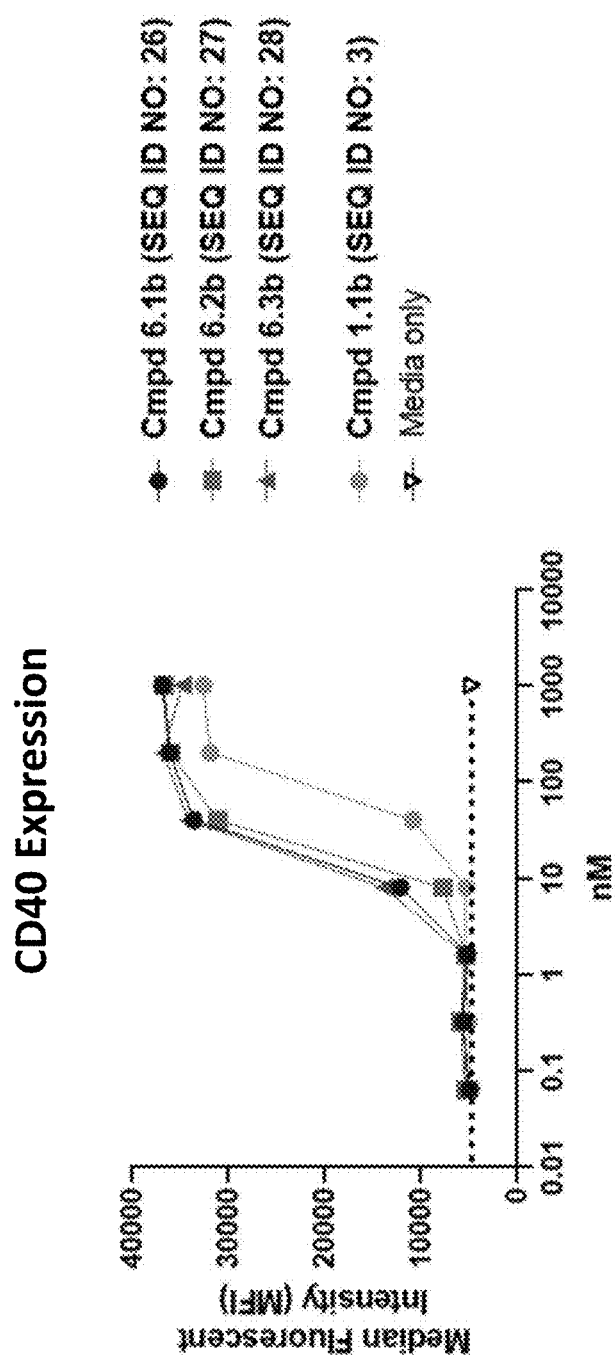

Example 1: Activities of Free Immunomodulating Oligonucleotides (CpGs) in Human PBMCs Human PBMCs were treated with free CpGs (SEQ ID NOs: 3 and 26-28) to evaluate their respective activities as observed by HLADR and CD40 expression on CD19 positive B cells (as shown in FIGS. 1A-1B). CpGs (SEQ ID NO: 26-28) all showed enhanced activities compared with CpG (SEQ ID NO: 3).

Figure 2A:
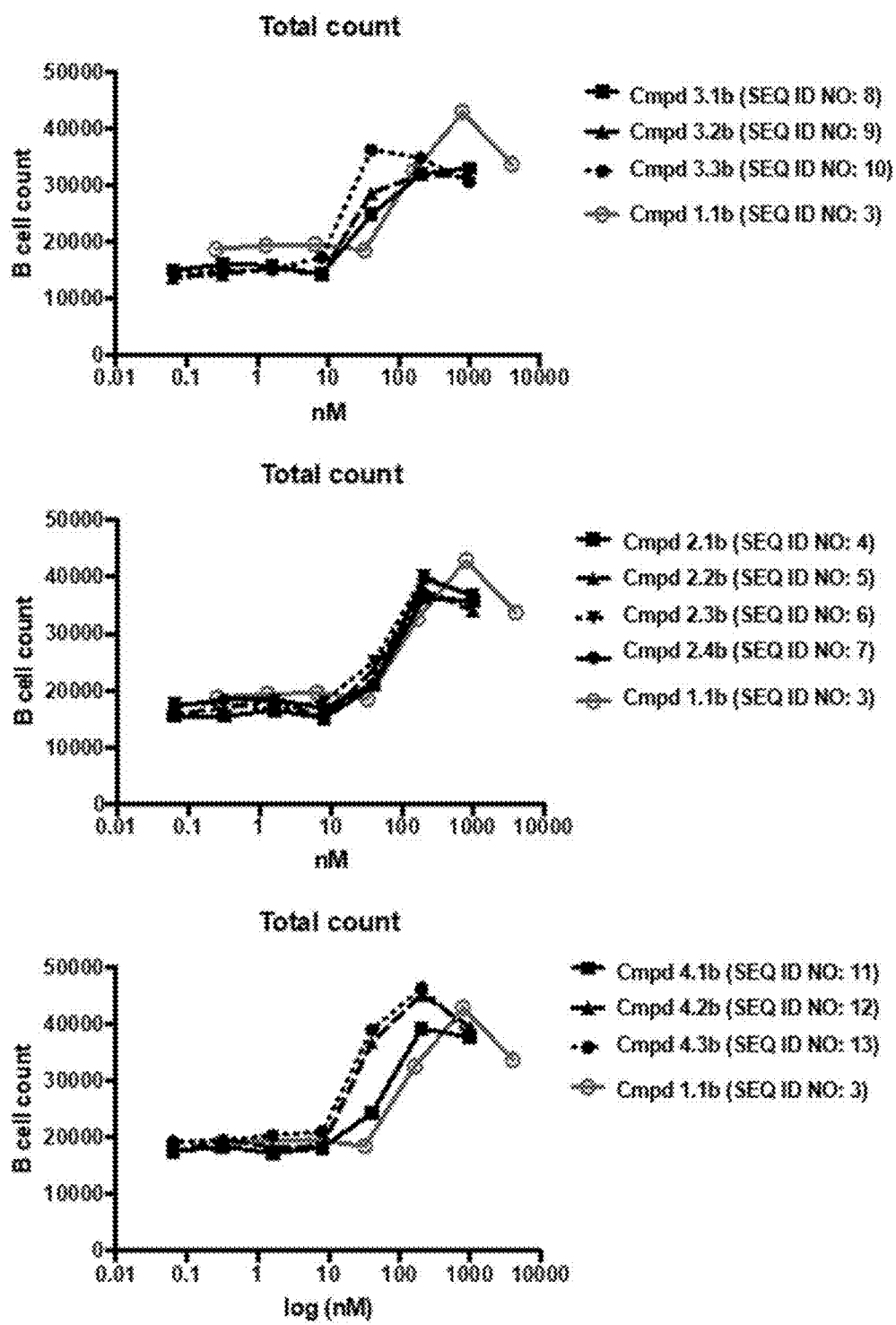
FIGS. 2A-2D show the effect of immunomodulating polynucleotides and their antibody conjugates on increasing B cells numbers and activation.
Figure 2B:
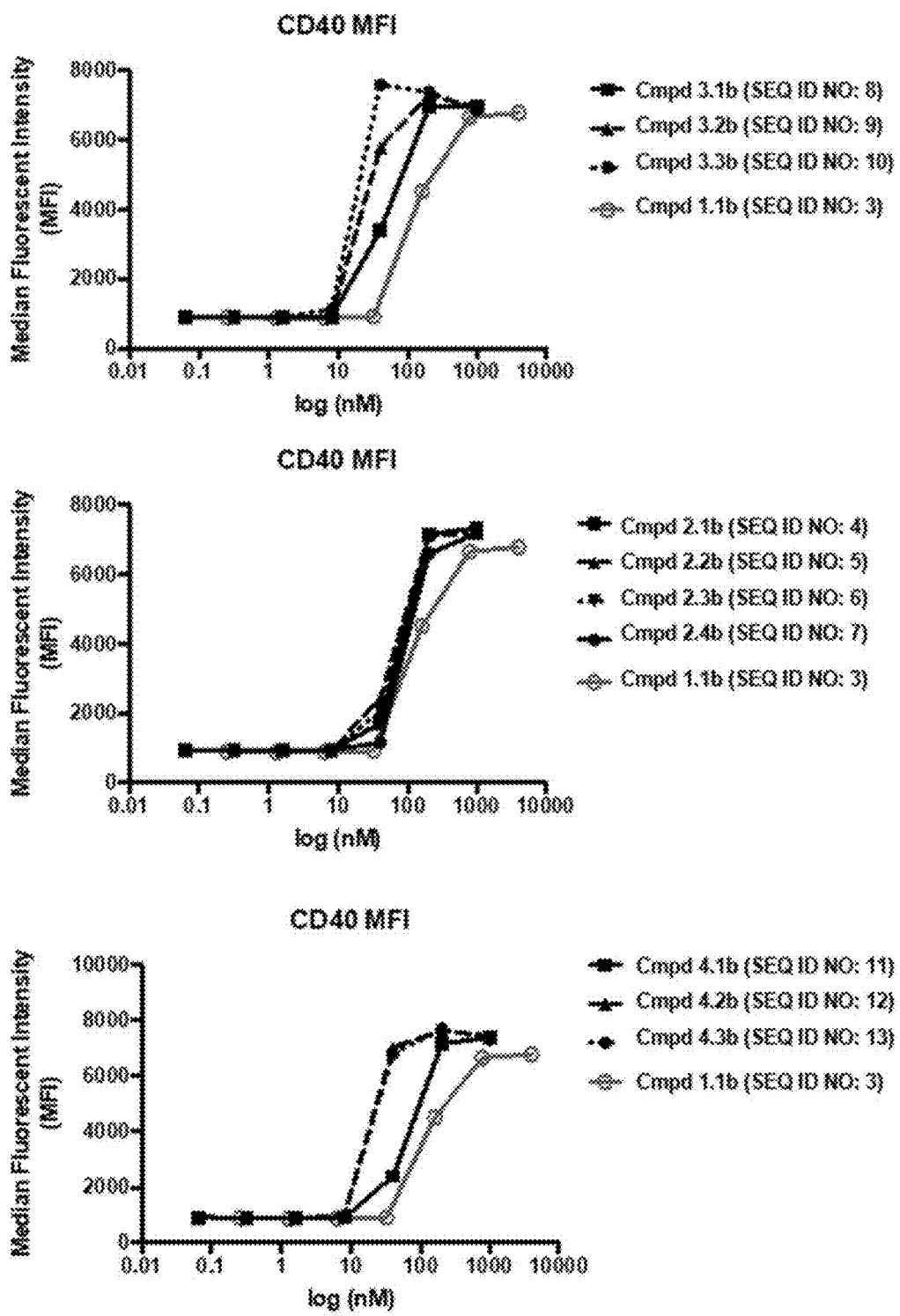
Figure 2C:
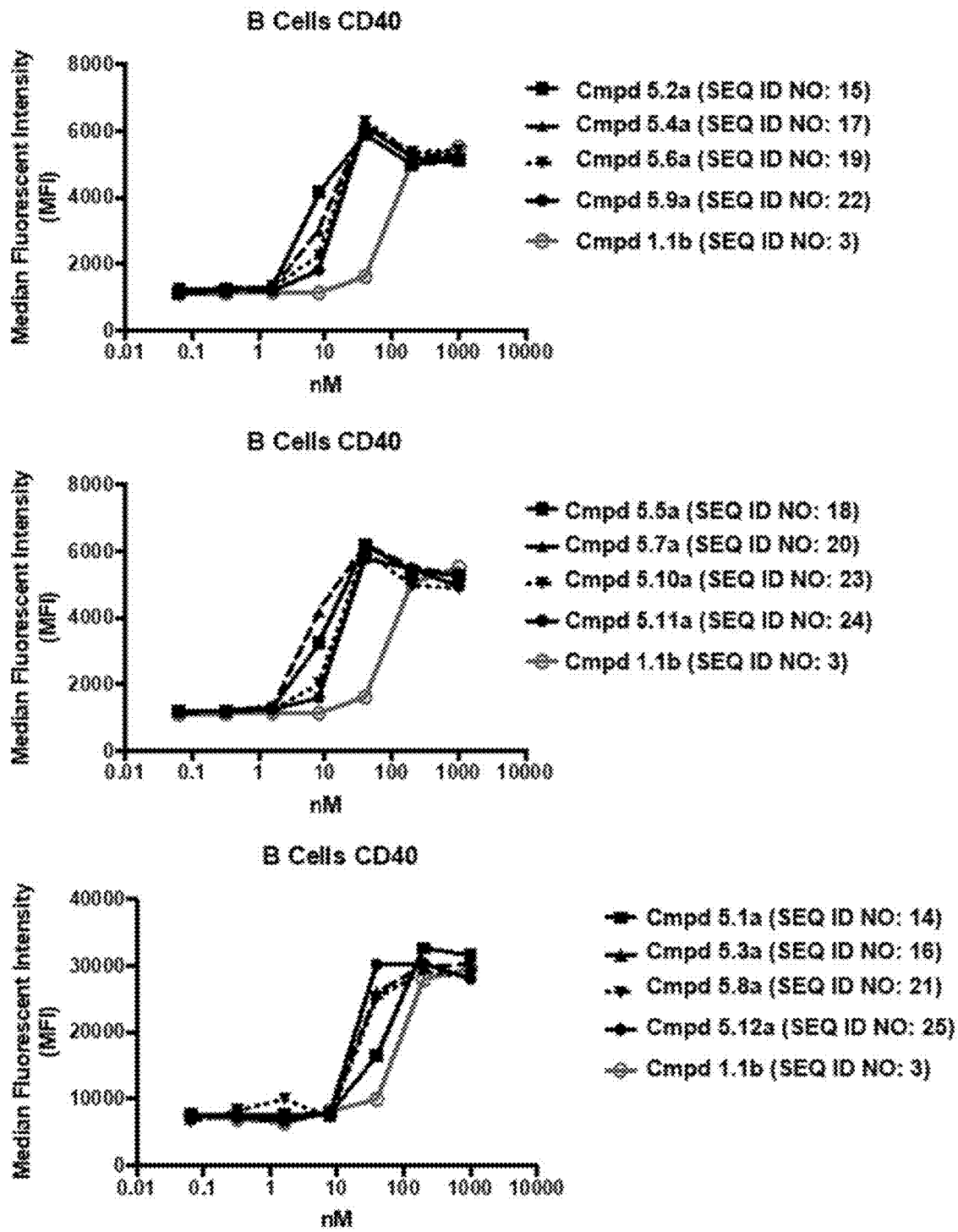

Example 2: Activities of Immunomodulating Polynucleotides and their Respective Antibody Conjugates Various CpG polynucleotides, SEQ ID NO: 3-25, were tested for their effects on proliferation and/or activation of B cells. FIGS. 2A-2C show the respective activities of select CpGs alone. All CpG polynucleotides tested enhanced the activation of B cells after 48 hours of incubation. As determined by counting beads to calculate absolute B cell number and CD40 expression, all CpGs increased the number of B cells and CD40 expression. A select number of CpG polynucleotides tested showed enhanced effects on B-cell proliferation and activation compared with CpG (SEQ ID NO: 3).

Figure 2D:
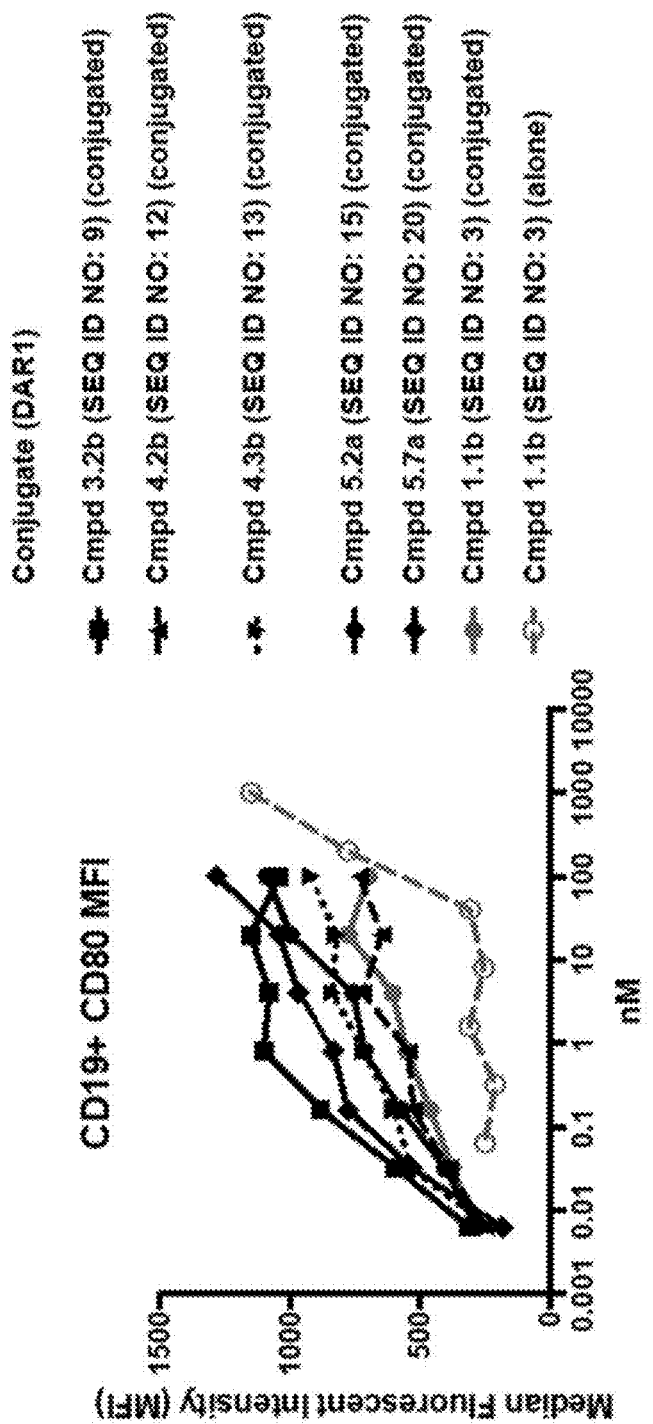

As an antibody-CpG conjugate (FIG. 2D) to anti-CD22 antibody (SEQ ID NO: 56 and SEQ ID NO: 57), all the respective conjugates of modified CpGs (SEQ ID NOS: 9, 12, 13, 15, and 20) have increased B cell activation, compared with the respective conjugate of CpG (SEQ ID: NO 3) and naked CpG (SEQ ID NO: 3), as determined by CD80 expression.

Example 3: Transglutaminase-Mediated Conjugation

The transglutaminase-mediated conjugation was tested using an oligonucleotide A (with the sequence: tucgtcgtgacgtt, SEQ ID NO: 1) coordinated to a PEGylated linker (—NH—C(=O)—PEG$_{23}$-NH$_2$, structure shown below), and Q-tag peptides sequences SEQ ID NOs: 39-47 and 50-52.

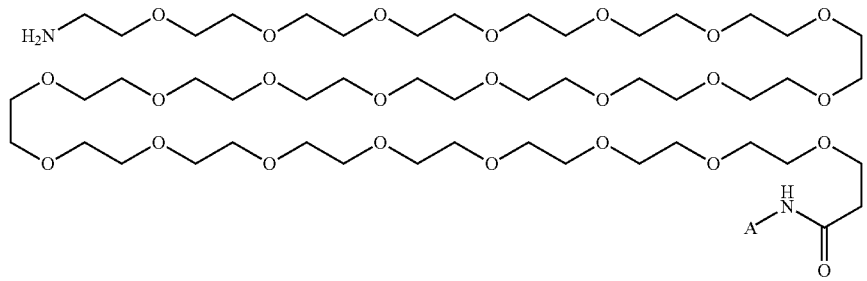

2 nmol of the Q-tag was added to 1 nmol of the linker in the present of 0.04 nmol of transglutaminase in PBS. The final concentration of linker is 50 μM. Reactions were kept at room temperature and quenched with 8 M formamide at 1 hour. The reaction solution was analyzed using reverse-phase HPLC with Xbridge C18 column (4.6×150 mm) using solvent A (50 mM TEAA in water) and solvent B (Acetonitrile) with a gradient of 20% to 60% of solvent B in 10 minutes at 60° C. Alternatively, the reaction solution was analyzed using reverse-phase HPLC with Luna 3μ C18 column (4.6×50 mm) using solvent A (0.1% TFA in water) and solvent B (0.1% TFA in Acetonitrile) with a gradient of 10% to 70% of solvent B in 10 minutes at 50° C.

Figure 3:
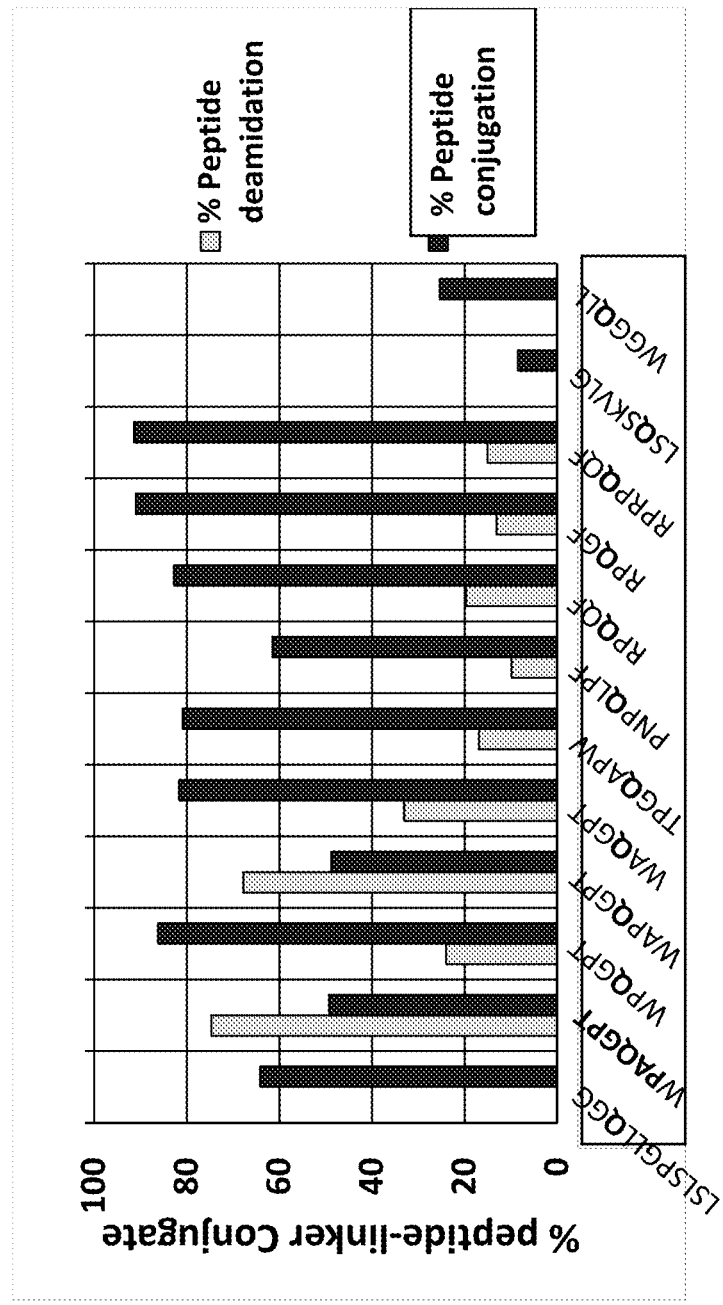
FIG. 3 shows the percentage yields of transglutaminase-mediated conjugations and deconjugations with a polyethylene glycol linker (—NH—C(=O)—PEG$_{23}$-NH$_2$) and various Q-tags. Shown are SEQ ID Nos:39-47 and 49-52.
Figure 4A:
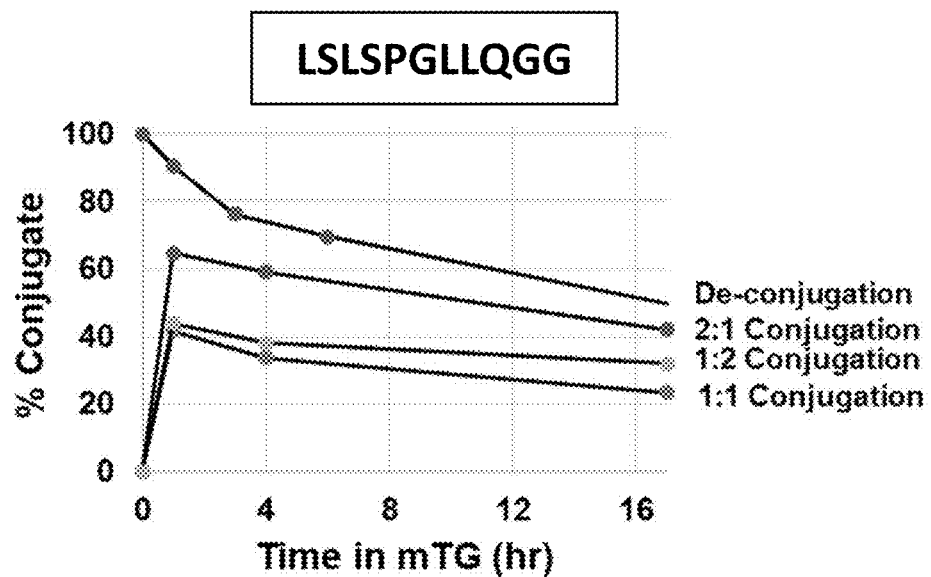
FIGS. 4A and 4B show the percentage change of conjugation and deconjugation over time in transglutaminase conjugation of two Q-tag peptides (LSLSPGLLQGG, SEQ ID NO:39; and RPQGF, SEQ ID NO:47).
Figure 4B:
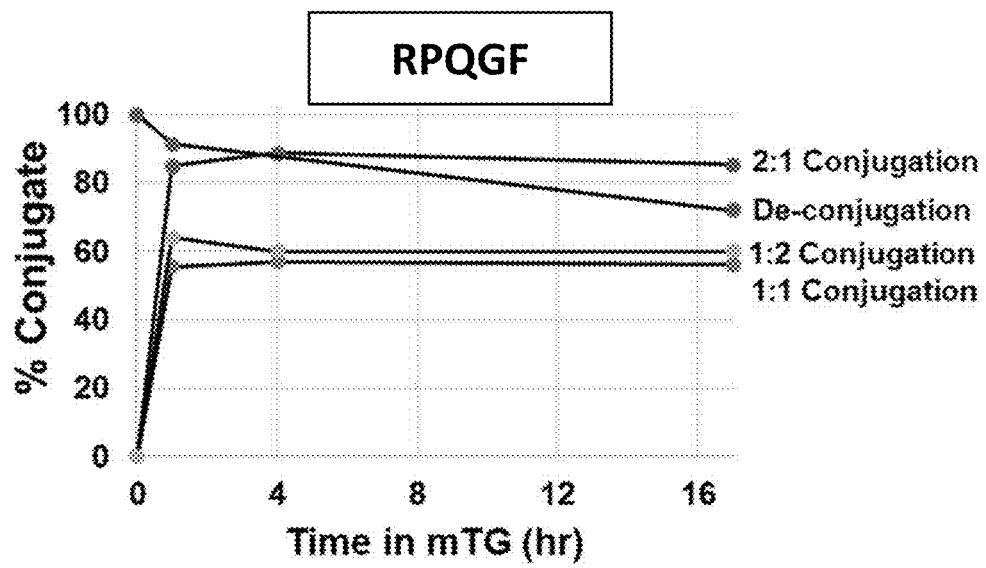
Figure 5A:
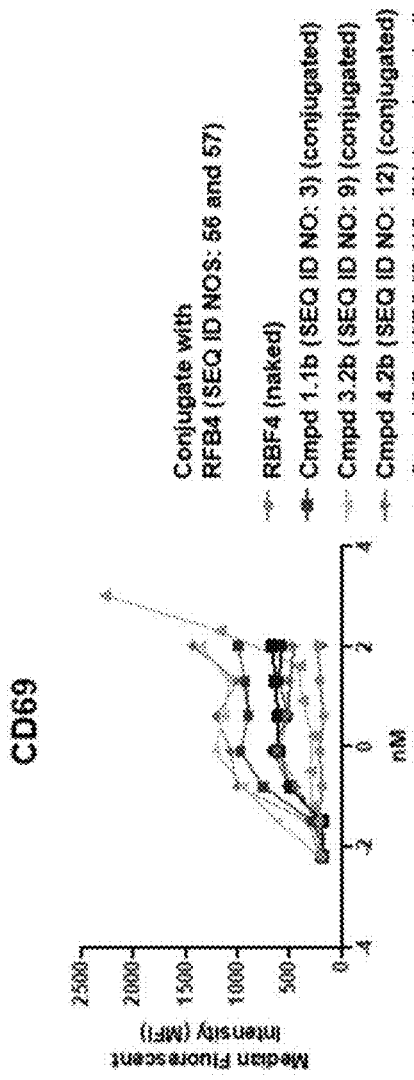
FIGS. 5A-5D depict activity of RBF4 conjugates with various oligonucleotides as shown by their B-cell activation, as assessed by expression of (a) CD40, (b) CD86, (c) HLADR and (d) CD69.
Figure 5B:
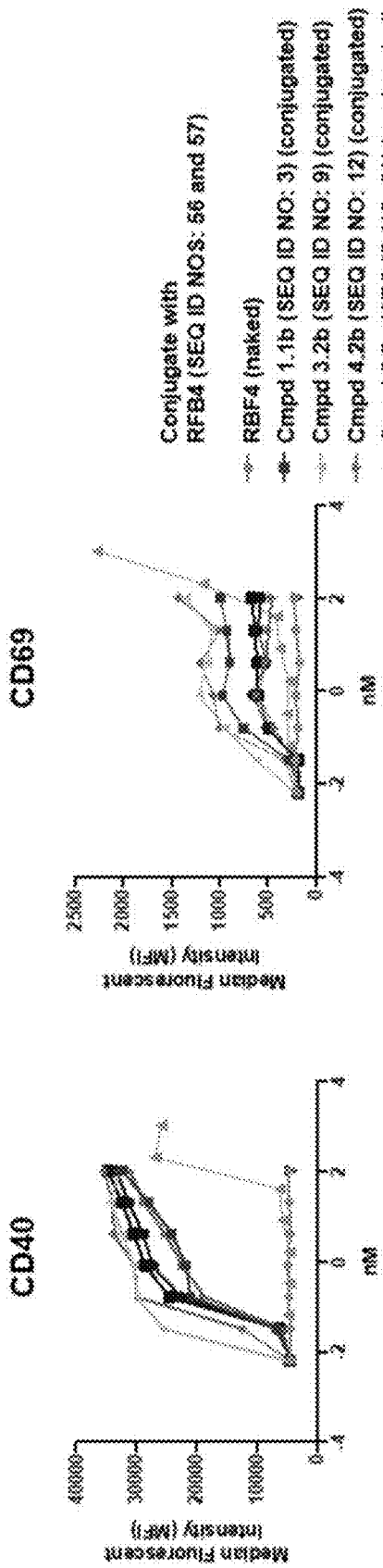
Figure 5C:
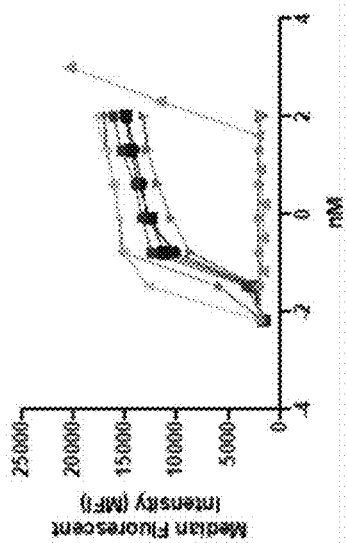
Figure 5D:
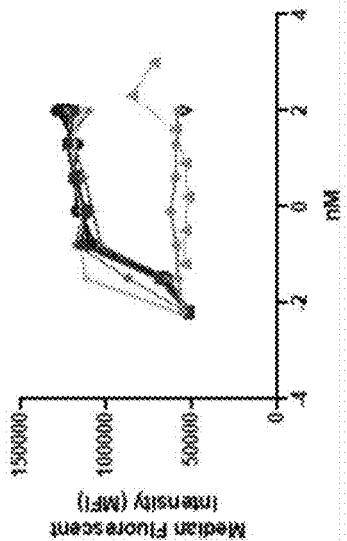

FIG. 3 shows the yields of the transglutaminase-mediated conjugation and peptide deamidation with various Q-tags. RPQGF (SEQ ID NO:47), RPQQF, RPRPQQF showed high conjugate percentage and moderately low deamidation FIGS. 4A-4B show the conjugation and deconjugation of two conjugates prepared from Q-tag with SEQ ID NOs: 39 and 47 over time. RPQGF (SEQ ID NO:47) has higher percentage of conjugation with all Q-tag: linker+CpG ratio tested, over a duration of 16 hrs. Moreover, the deconjugation rate of RPQGF (SEQ ID NO:47) is also slower compared with LSLSPGLLQGG (SEQ ID NO:39).

Example 4: Activities of Anti-CD22 and Anti-BDCA2 Antibody/CpG Conjugates

Q-tag with the sequence RPQGFGPP (SEQ ID NO: 49) was genetically linked to the C-terminus of the heavy chain of antibody. To perform conjugation, the purified antibody (containing the engineered Q tags at the C-terminal of heavy chain) were first buffer exchanged into 25 mM Tris, 150 mM NaCl pH8. The Ab-(Q-tag):CpG containing moiety added in molar ratio of 1:1.3 were mixed and incubated overnight with a final concentration of 1% mTG (w/v) (Ajinomoto) at room temperature. Final concentration of antibody used for conjugation is generally ~20-25 uM. Mixture was loaded to a Q Sepharose HP (GE) equilibrated in 20% Buffer B (40 mM Tris, 2M NaCl pH8) and 80% Buffer A (40 mM Tris, pH8). Column was washed with 5 column volumes of 20% Buffer B. Separation was achieved with using a linear gradient from 20% B to 60% B in 30 column volumes. DAR1 peak fractions (Q-tag conjugated with one CpG moiety) were pooled and concentrated followed by a gel filtration step using 5200 (GE). Monomeric peak fractions were pooled and concentrated.

Trima residuals were received from Vitalant and diluted 1:4 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface and resuspended in FACS buffer (PBS with 0.5% Bovine Serum Albumin (Gibco)).

PBMCs were immediately plated onto a 96-well format (500K/well) in Complete RPMI (RPMI+10% FBS). Five-fold serial dilutions were added to the cells from 100 nM to 6.4 pM of antibody and conjugated antibody and 1 uM to 64 pM of CpG polynucleotides at 37° C. under 5% CO2 for 48 to 96 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR Blocking Reagent (Miltenyi Biotec), anti-CD19, anti-CD20, anti-CD40, anti-HLADR and anti-CD80 for B cell assays and anti-CD14, anti-CD3, anti-CD19, anti-CD14, anti-CD123, antiCD11c and anti-CD86 for pDC assays. Cells were centrifuged and washed twice in FACS buffer and fixed in 0.5% paraformaldehyde. CountBright Absolute Counting Beads (Thermo Fisher) were added to each well to count the number of cells. Cells were analyzed on Attune NxT Flow Cytometer (Thermo Fisher), with subsequent data analysis by Flowjo 10.7 (Treestar). Dead cells were excluded by gating on the eFluor 780-negative population. Lineage specific cells were first excluded (CD19, CD3, CD14) prior to gating CD123+ CD11c− cells to identify pDC and gating CD19+, CD20+ or CD19+CD20+ cells to identify B cells.

Interferon alpha levels were assayed using LegendPlex human inflammation panel 1 (Biolegend). Supernatant from pDC assays were collected after pelleting the cells.

Figure 6D:
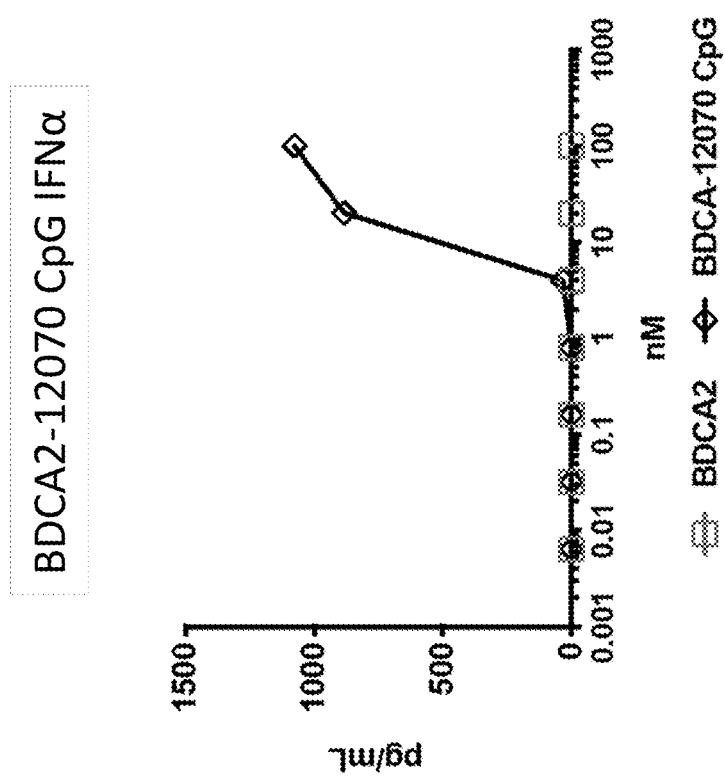

Various B-cell and pDC specific antibodies were conjugated with CpG 12070 (SEQ ID NO: 3), CpG (SEQ ID NOs: 9, 12, 20, 27 and 28), all with the DAR1 configuration, at their C-terminus heavy chain Q-tag (RPQGFGPP) (SEQ ID NO: 49) via transglutaminase reaction. The conjugated antibodies were subsequently tested for their effects on proliferation and/or activation. The anti-CD22 antibodies conjugated with CpG are RFB4 (SEQ ID NOs: 56 and 57). As shown in FIGS. 5A-5D, the anti-CD22-CpG antibodies enhanced the activation of B cells as compared to naked CpG polynucleotide 12070 (SEQ ID NO: 3) and human IgG control antibody after 96 hours. As determined by CD19, CD40, CD69, CD86, and HLADR expression, only anti-CD22-CpG and CpG alone induced B cell activation. Direct delivery of CpG by a targeting antibody results in higher activation as compared to CpG alone. Moreover, anti-CD22 conjugated with CpG (SEQ ID NO: 9 and 20) has enhanced activity compare with anti-CD22 conjugated with CpG (SEQ ID NO: 3).

pDC targeting antibody, anti-BDCA2 (SEQ ID NOs: 111 and 112 for VH and VL sequences, respectively), was similarly conjugated with CpG 12070 (SEQ ID NO: 3), CpG (SEQ ID NO: 9, 12, 20, 27 and 28), all with the DAR1 configuration, and tested for its effects on activation as comparable to unconjugated antibody after 48 hours observed by CD86, CD40 and HLADR expression (FIGS. 6A-6C) and by CD40 expression in monocytes and mDCs as well as CD19, CD40, CD3 and CD69 expression (FIGS. 7A-7D). The CpG 12070:anti-BDCA2 conjugate also induced IFNα expression in human PBMCs (FIG. 6D).

Conjugated anti-pDC-CpG antibodies and CpG alone induced HLADR expression as compared to antibody alone.

BDCA VH sequence:
(SEQ ID NO: 111)
DVQLVESGGGLVKPGGSLRLSCAASGFTFSTYTMSWVRQAPGKGLEWVAT

ISPGDSFGYYYPDSVQGRFTISRDNAKNSLYLQMNSLRAEDTAVYYCTRD

IYYNYGAWFAYWGQGTLVTVSS

BDCA-VL sequence:
(SEQ ID NO: 112)
DIQLTQSPSSLSASVGDRVTITCKASQSVDYDGDSYMNWYQQKPGKAPKL

LIYAASTLESGVPSRFSGSGSGTDFTLTISSLQPEDFATYYCAEDRTFGQ

GTKVEIK

Example 5: Development of Humanized Anti-CD22 Antibodies

This Example describes the generation of humanized anti-CD22 antibodies. The parental antibody was a mouse anti-CD22 antibody (SEQ ID Nos: 56 & 57 for VH and VL sequences, respectively).

Mouse anti-CD22 VH sequence (SEQ ID NO: 56)
EVQLVESGGGLVKPGGSLKLSCAASGFAFSIYDMSWVRQTPEKRLEWVA

YISSGGGTTYYPDTVKGRFTISRDNAKNTLYLQMSSLKSEDTAMYYCAR

HSGYGSSYGVLFAYWGQGTLVTVSS

Mouse anti-CD22 VL sequence (SEQ ID NO: 57)
DIQMTQTTSSLSASLGDRVTISCRASQDISNYLNWYQQKPDGTVKLLIY

YTSILHSGVPSRFSGSGSGTDYSLTISNLEQEDFATYFCQQGNTLPWTF

GGGTKLEIK 4 variants of the VH domain (RH1, RH2, RH3, and RH4; SEQ ID Nos: 64-67, respectively) and 5 variants of the VL domain (RL1, RL2, RL3, RL4, and RL5; SEQ ID Nos:68-72, respectively) were designed. The alignments of the respective VH and VL domains are shown in FIGS. 8A-8B. Framework sequences used for each variant were as follows: RH1—human IGHV1; RH2—human IGHV3 with some mutations; RH3-FW1-3 based on IGHV3-48*03 with FW4 as parental mouse; RH4—human IGHV4; RL1—human IGLV1; RL2—human IGLV1 with some mutations; RL3—FW1-3 based on IGKV1-39*01 with FW4 as parental mouse; RL4—IGKV3; RL5—IGVK2 (FW1 and FW2 flank CDR1; FW2 and FW3 flank CDR2, and FW4 is after CDR3). A total of 20 antibody constructs were generated by combining each VH domain with each VL domain, and using the human IgG1 AAA Fc region with a C-terminal Q-tag (RPQGFGPP) (SEQ ID NO: 49) in the antibody heavy chain constant domain (SEQ ID NO:95), as shown below. IgG1 AAA Fc contains L234A, L235A, and G237A substitutions, amino acid position numbering according to EU index.

| Construct Name | Light chain + Heavy chain |
|---|---|
| TNT69 | RL1_hKappa + RH1_hIgG1_AAA_Qtag |
| TNT70 | RL1_hKappa + RH2_hIgG1_AAA_Qtag |
| TNT71 | RL1_hKappa + RH3_hIgG1_AAA_Qtag |
| TNT72 | RL1_hKappa + RH4_hIgG1_AAA_Qtag |
| TNT73 | RL2_hKappa + RH1_hIgG1_AAA_Qtag |
| TNT74 | RL2_hKappa + RH2_hIgG1_AAA_Qtag |
| TNT75 | RL2_hKappa + RH3_hIgG1_AAA_Qtag |
| TNT76 | RL2_hKappa + RH4_hIgG1_AAA_Qtag |
| TNT77 | RL3_hKappa + RH1_hIgG1_AAA_Qtag |
| TNT78 | RL3_hKappa + RH2_hIgG1_AAA_Qtag |
| TNT79 | RL3_hKappa + RH3_hIgG1_AAA_Qtag |
| TNT80 | RL3_hKappa + RH4_hIgG1_AAA_Qtag |
| TNT81 | RL4_hKappa + RH1_hIgG1_AAA_Qtag |
| TNT82 | RL4_hKappa + RH2_hIgG1_AAA_Qtag |
| TNT83 | RL4_hKappa + RH3_hIgG1_AAA_Qtag |
| TNT84 | RL4_hKappa + RH4_hIgG1_AAA_Qtag |
| TNT85 | RL5_hKappa + RH1_hIgG1_AAA_Qtag |
| TNT86 | RL5_hKappa + RH2_hIgG1_AAA_Qtag |
| TNT87 | RL5_hKappa + RH3_hIgG1_AAA_Qtag |
| TNT88 | RL5_hKappa + RH4_hIgG1_AAA_Qtag |
| TNT89 | Control_hRFB4_LC_hKappa + Control_hRFB4_HC_hIgG1_AAA_Qtag |
| TNT90 | Control_hRFB4 + mutCDRL1_LC_hKappa + Control_hRFB4 + mutCDRH3_HC_hIgG1_AAA_Qtag |
| TNT31 | Mouse RFB4 |

For antibody selection, the following factors were considered: CD22 binding affinity, CD22 biological activity, binding to cynomolgus CD22, expression in CHO or Expi293 cells, conjugation yield, SEC-HPLC profile (e.g., aggregation, peak shape), VH/VL pairing, sequence liabilities, and stability testing (e.g., freeze-thaw and thermostability).

Figure 9:
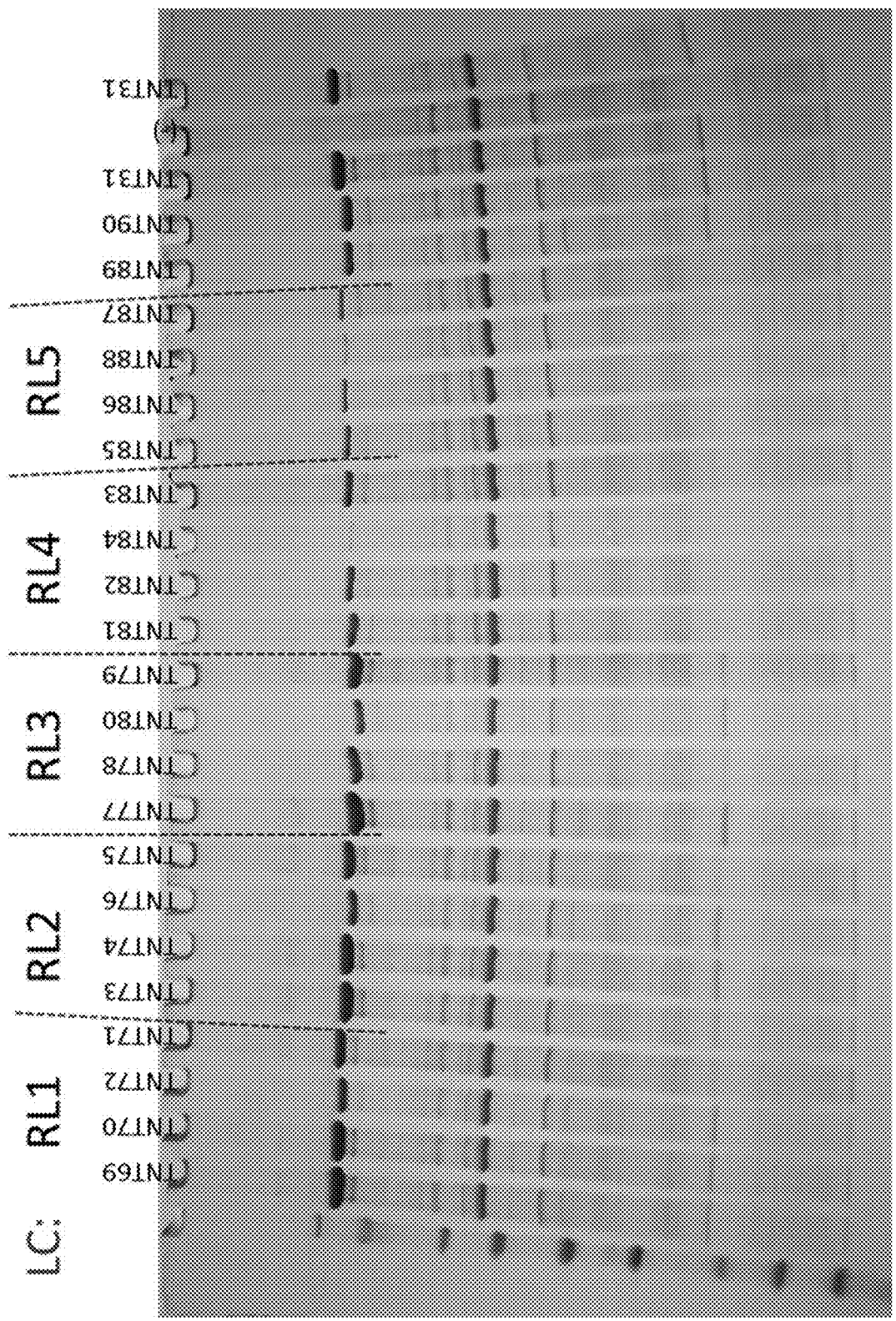
FIG. 9 shows relative expression levels of each combination of humanized anti-CD22 heavy chain and light chain, as indicated.

Each construct was expressed in a 293FS cell line. As shown in FIG. 9, antibodies with RL4 and RL5 had the lowest overall expression levels. RH4 also decreased overall expression level in each light chain pairing.

Binding of humanized anti-CD22 antibodies to human CD22 was measured by surface plasmon resonance (SPR). For assessment of binding by SPR, biotinylated protein A (15 μg/mL) was immobilized to the surface of an NLC chip. 30 μL of mAb supernatant was added to 150 μL of PBS-T and captured over the protein A surface. Serial dilutions of human CD22-gly (300 nM, 3× dilution) were injected over the mAb-coated chips, and binding kinetics were determined. Chips were regenerated using 4:1 v/v of Pierce IgG elution butter/4M NaCl. Binding data are provided below.

| Sample Name | ka 1/Ms | kd 1/s | KD M |
|---|---|---|---|
| TNT69 | 2.01E+05 | 1.26E-04 | 6.24E-10 |
| TNT70 | 2.35E+05 | 1.03E-04 | 4.39E-10 |
| TNT72 | 2.23E+05 | 1.46E-04 | 6.55E-10 |
| TNT71 | 2.81E+05 | 1.46E-03 | 5.20E-09 |
| TNT73 | 1.58E+05 | 2.30E-03 | 1.45E-08 |
| RFB4 | 2.97E+05 | 8.22E-04 | 2.77E-09 |
| TNT74 | 1.86E+05 | 2.89E-03 | 1.56E-08 |
| TNT76 | 1.99E+05 | 6.01E-03 | 3.02E-08 |
| TNT75 | 2.80E+05 | 8.40E-03 | 3.00E-08 |
| TNT77 | 2.03E+05 | 2.07E-03 | 1.02E-08 |
| TNT78 | 1.95E+05 | 4.85E-03 | 2.49E-08 |
| TNT80 | 2.23E+05 | 5.19E-03 | 2.33E-08 |
| TNT79 | 2.70E+05 | 6.29E-03 | 2.33E-08 |
| TNT81 | 1.69E+05 | 1.17E-04 | 6.92E-10 |
| TNT82 | 1.67E+05 | 1.56E-04 | 9.37E-10 |
| TNT84 | 2.71E+05 | 6.67E-04 | 2.46E-09 |
| TNT83 | 2.69E+05 | 1.60E-03 | 5.94E-09 |
| RFB4 | 3.06E+05 | 8.02E-04 | 2.62E-09 |
| TNT85 | 1.35E+05 | 1.69E-04 | 1.25E-09 |
| TNT86 | 1.30E+05 | 1.41E-04 | 1.09E-09 |
| TNT88 | 2.15E+05 | 2.89E-04 | 1.34E-09 |
| TNT87 | 2.50E+05 | 1.71E-03 | 6.85E-09 |
| TNT89 | 3.59E+05 | 1.29E-03 | 3.60E-09 |
| TNT90 | 3.55E+05 | 5.23E-05 | 1.47E-10 |

All of the humanized RFB4 variants bound to human CD22 (d1 to d7 domain according to NP_001762.2) with affinities between ~30 nM and ~0.1 nM. The affinity of the parental RFB4 antibody binding to human CD22 was ~3 nM. TNT71, TNT84, TNT83, TNT85, TNT86, TNT88, TNT89, and TNT90 had affinities equivalent to RFB4. TNT69, TNT70, TNT72, TNT81, TNT82, TNT90 have higher affinity (~0.1 nM) than RFB4.

Binding of humanized anti-CD22 antibodies to human or cynomolgus PBMCs was measured by flow cytometry. Trima residuals were received from Vitalant and cynomolgus monkey whole blood were received from BioIVT. Both were diluted 1:4 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface, washed and resuspended in FACS buffer (PBS with 0.5% Bovine Serum Albumin (Gibco)). 100K PBMCs from human and cynomolgus monkey were plated in 96-well plates and pelleted by centrifugation for five minutes at 400×g and stained at 4° C. in 100 μl Fixable Viability Dye eFluor 780 (Thermo Fisher) diluted 1:4000 in PBS. Cells were centrifuged and stained at 4° C. in 100 μl FACS buffer for 30 minutes containing FcR Blocking Reagent (Miltenyi Biotec), anti-CD20 and Alexa Fluor 647 conjugated CD22 binding antibodies, which were labeled using Molecular Probes Alexa Fluor 647 Protein Labeling kit (Molecular Probes) according to manufacturer's protocol. Cells were centrifuged and washed twice in 200 μl FACS buffer and fixed in 100 μl 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. CD20$^+$ cells were gated to identify B cells and median fluorescent intensity for CD22 was determined.

Humanized RFB4 antibodies were evaluated for binding to B-cells from human and cynomolgus monkey. Table below shows the median fluorescent intensity of CD22 when bound by RFB4 humanized antibodies on CD20$^+$ and CD20$^-$ cells in human and cynomolgus monkey. The fold increase in binding was determined by calculating the ratio of CD22 median fluorescent intensity on $CD20^+$ over $CD20^-$ cells. All humanized antibodies bind CD22 on human B cells similar to parental RFB4 but with variability on cynomolgus monkey B cells. As determined by CD22 median fluorescent intensity on human $CD20^+$ and $CD20^-$ cells, the fold increase in binding for CD22 for the humanized antibodies range from 19-26-fold as compared to 22-fold for parent RFB4. The fold increase in CD22 median fluorescent intensity on cynomolgus monkey $CD20^+$ and $CD20^-$ for the humanized antibodies range from 1-16-fold as compared to 8.3 fold for parent RFB4.

Figure 10A:
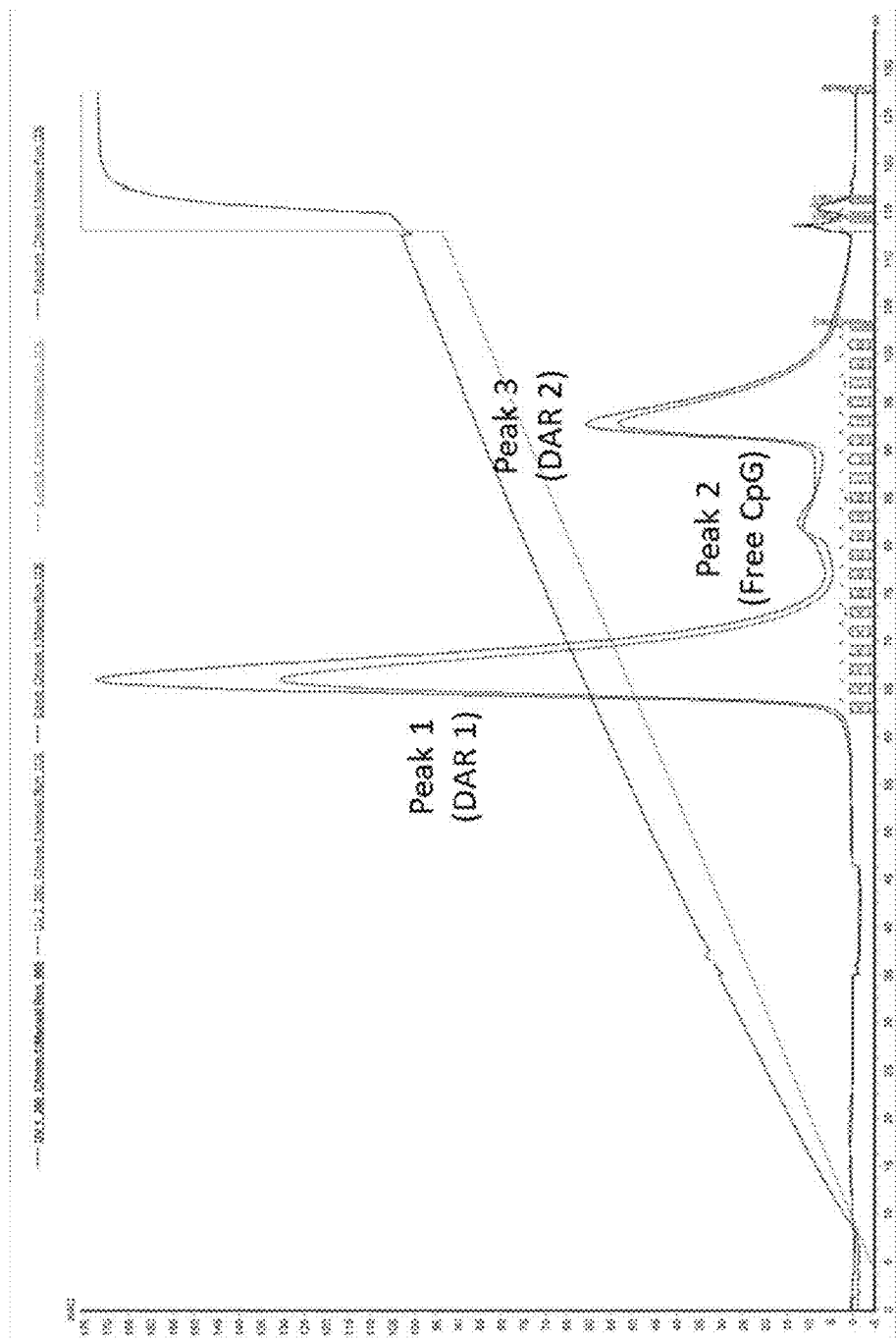
FIGS. 10A-10E show purification of antibody:CpG conjugates. Shown are the purification of conjugates using antibodies TNT70 (FIG. 10A), TNT71 (FIG. 10B), TNT72 (FIG. 10C), and TNT74 (FIG. 10D).
Figure 10B:
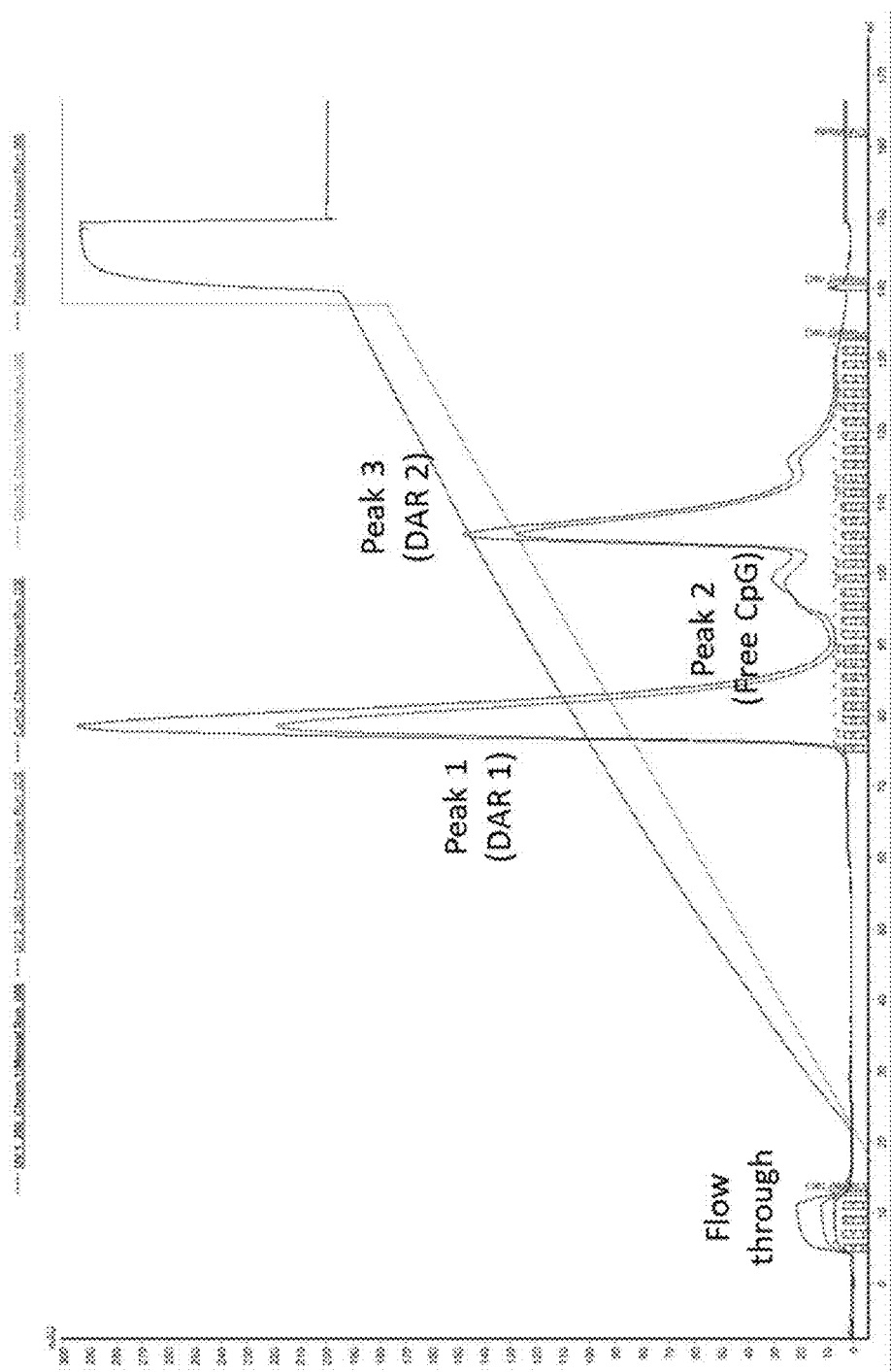
Figure 10C:
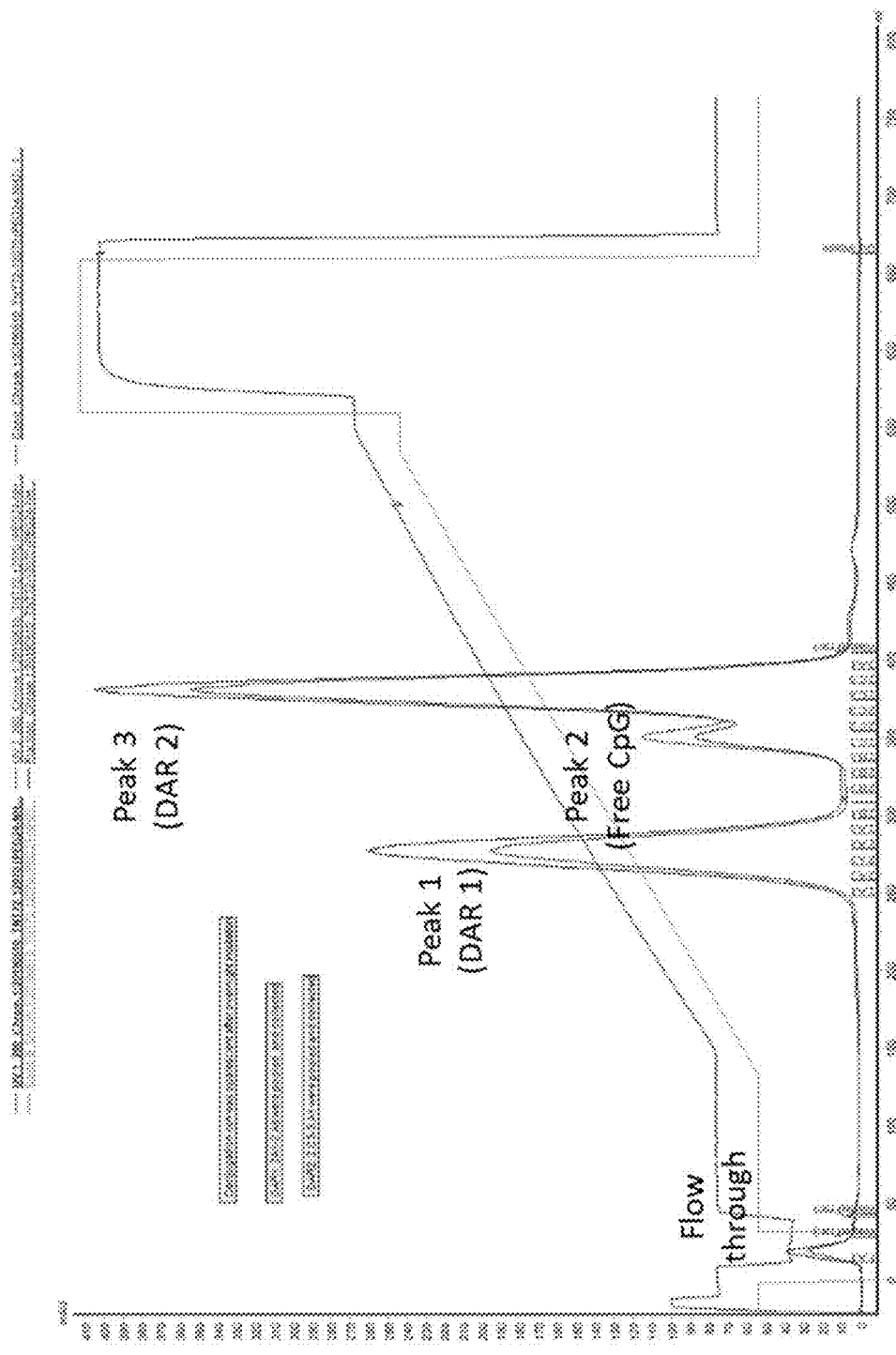
Figure 10D:
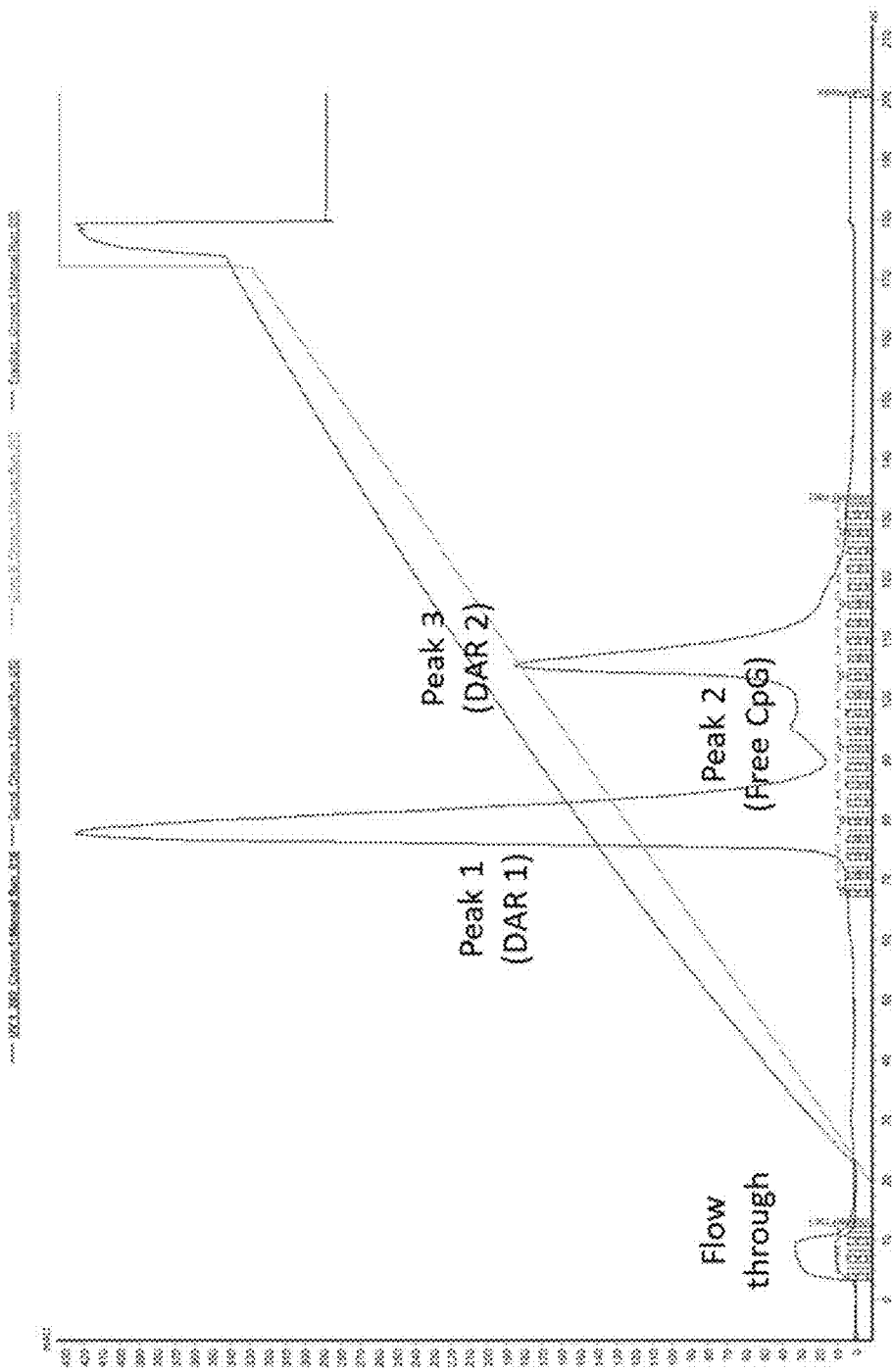
Figure 10E:
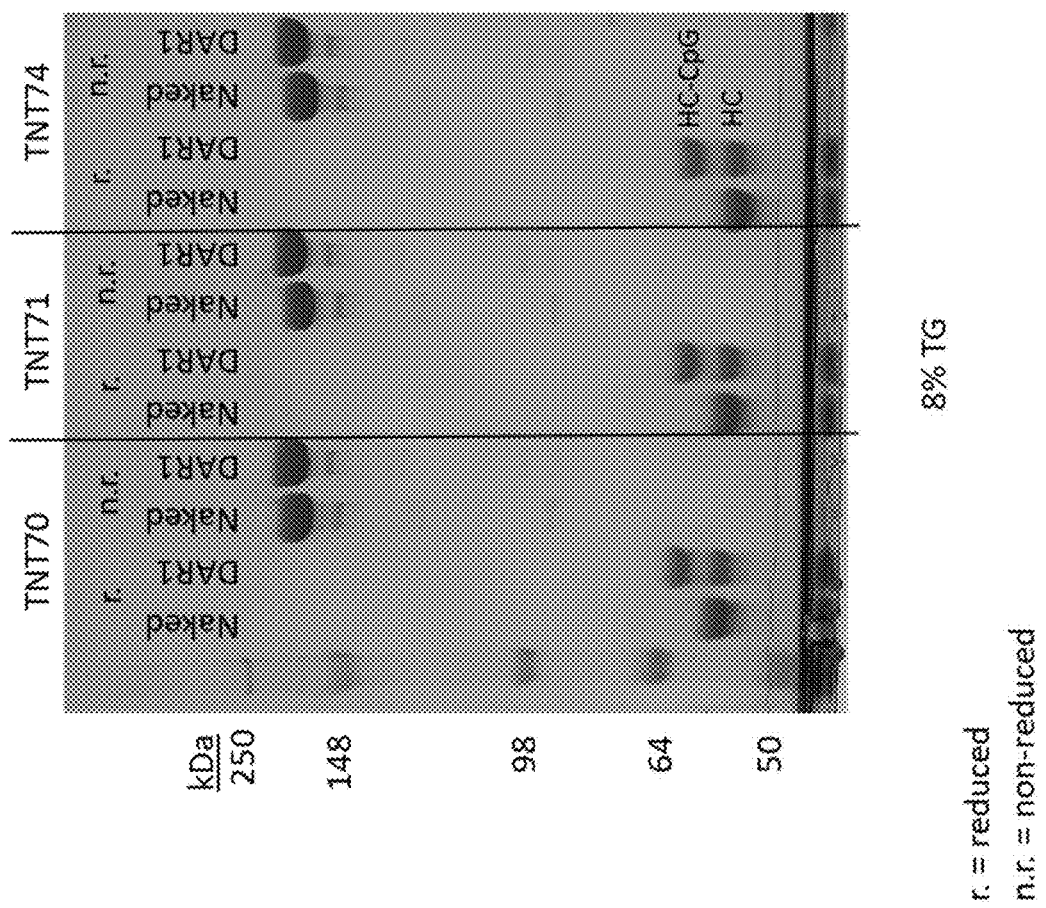

Next, humanized anti-CD22 antibodies were conjugated to CpG 12070, and activity of antibody conjugates (DAR1) was analyzed. Antibody conjugates were purified by chromatography under the following conditions: MonoQ 5/50 GL; buffer A: 50 mM Tris, pH8; buffer B: 50 mM Tris, 2M NaCl, pH8; 2 mL/min, 0-100% B in 200 CV, 1 mL fractions. The results are shown in FIGS. 10A-10D for conjugates to TNT70, TNT71, TNT72, and TNT74, respectively. For purification, only the DAR1 peak was pooled, buffer-exchanged into PBS, and concentrated. Starting material and conjugates were also analyzed in either reduced or non-reduced form by SDS-PAGE (FIG. 10E).

Binding analysis by SPR showed that naked antibodies and CpG conjugates bound to CD22 with similar affinity.

Figure 11:
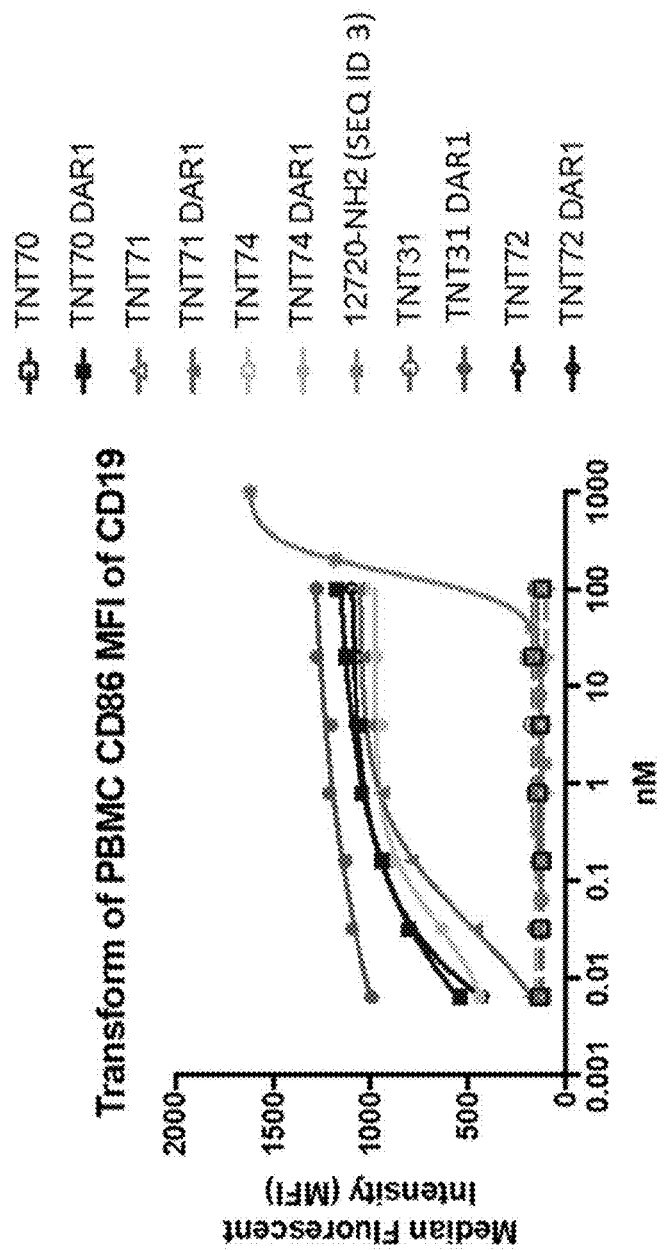
FIG. 11 shows B cell activation by various humanized anti-CD22 antibody:CpG conjugates at different concentrations, as indicated.

As shown in FIG. 11, conjugates to various humanized anti-CD22 antibodies were all able to activate B cells. No relationship between affinity to CD22 and B cell activation was observed.

Figure 12A:
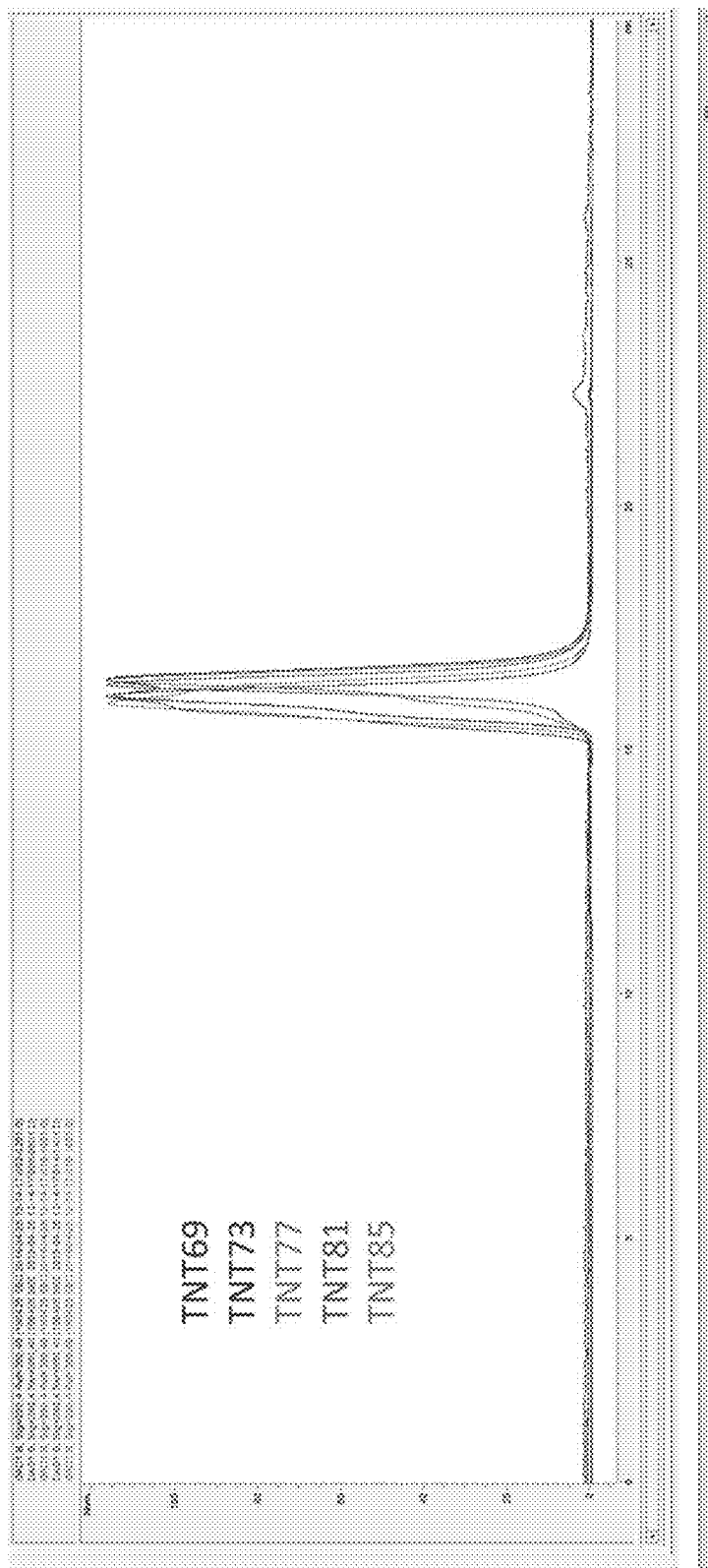
FIGS. 12A-12D show profiles of the indicated CpG:anti-CD22 conjugates, as determined by size exclusion chromatography HPLC (HPLC-SEC). Conjugates using the RH1 (FIG. 12A), RH2 (FIG. 12B), RH3 (FIG. 12C), and RH4 (FIG. 12D) VH domains are grouped.
Figure 12B:
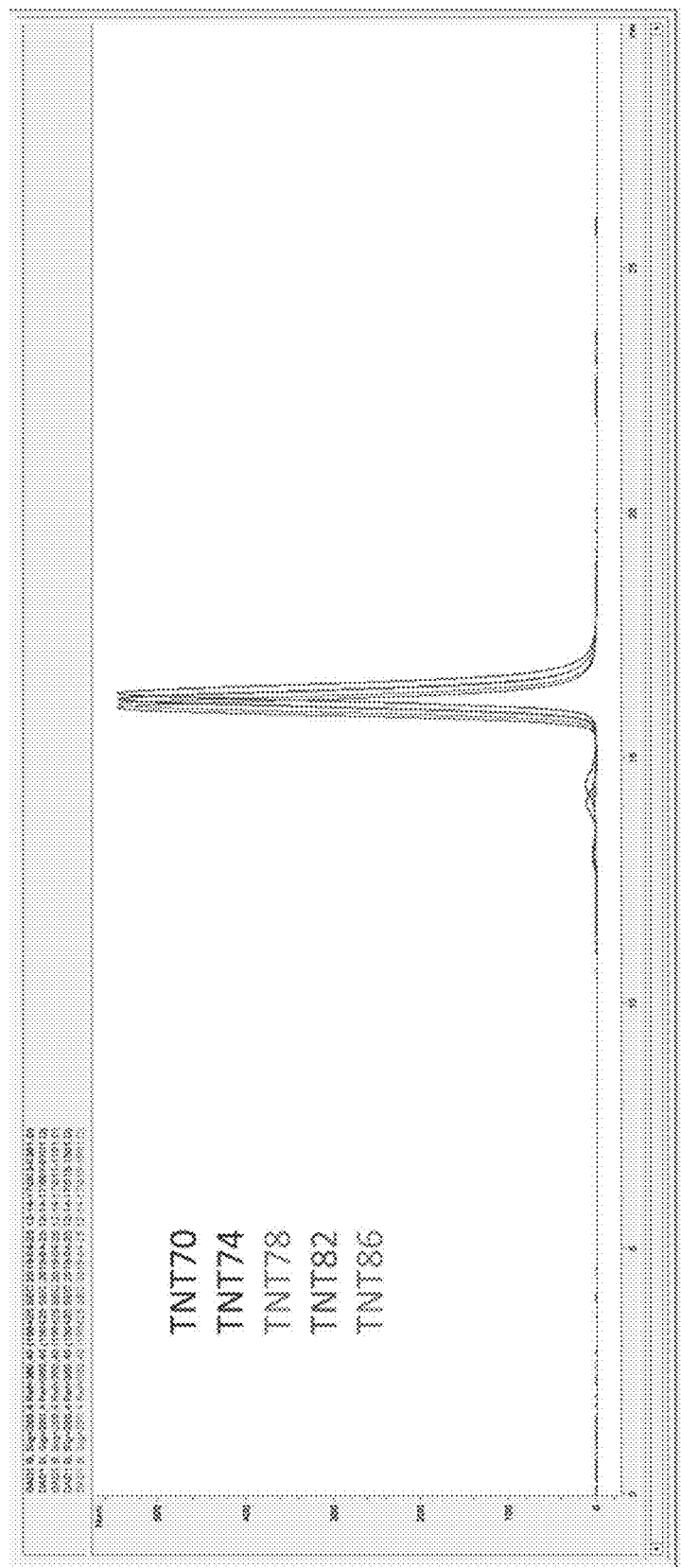
Figure 12C:
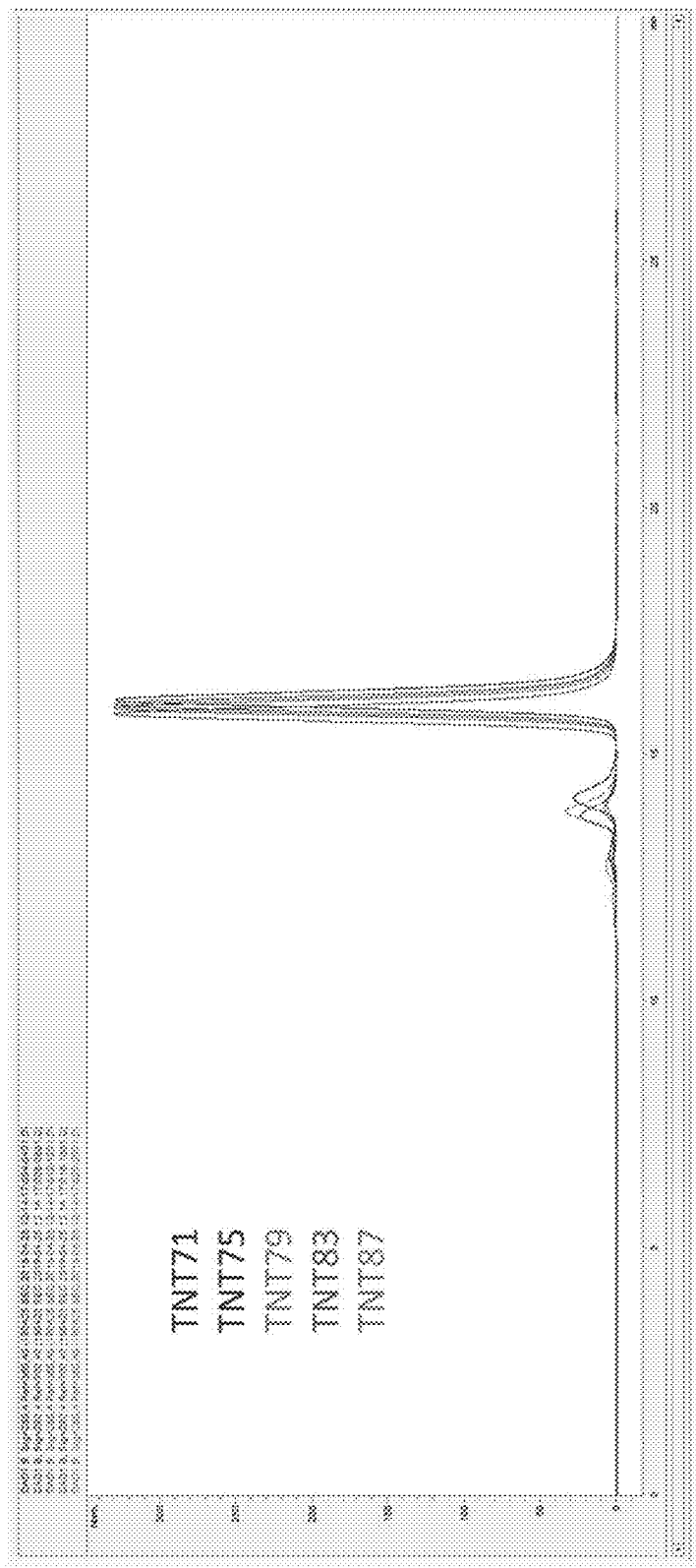
Figure 12D:
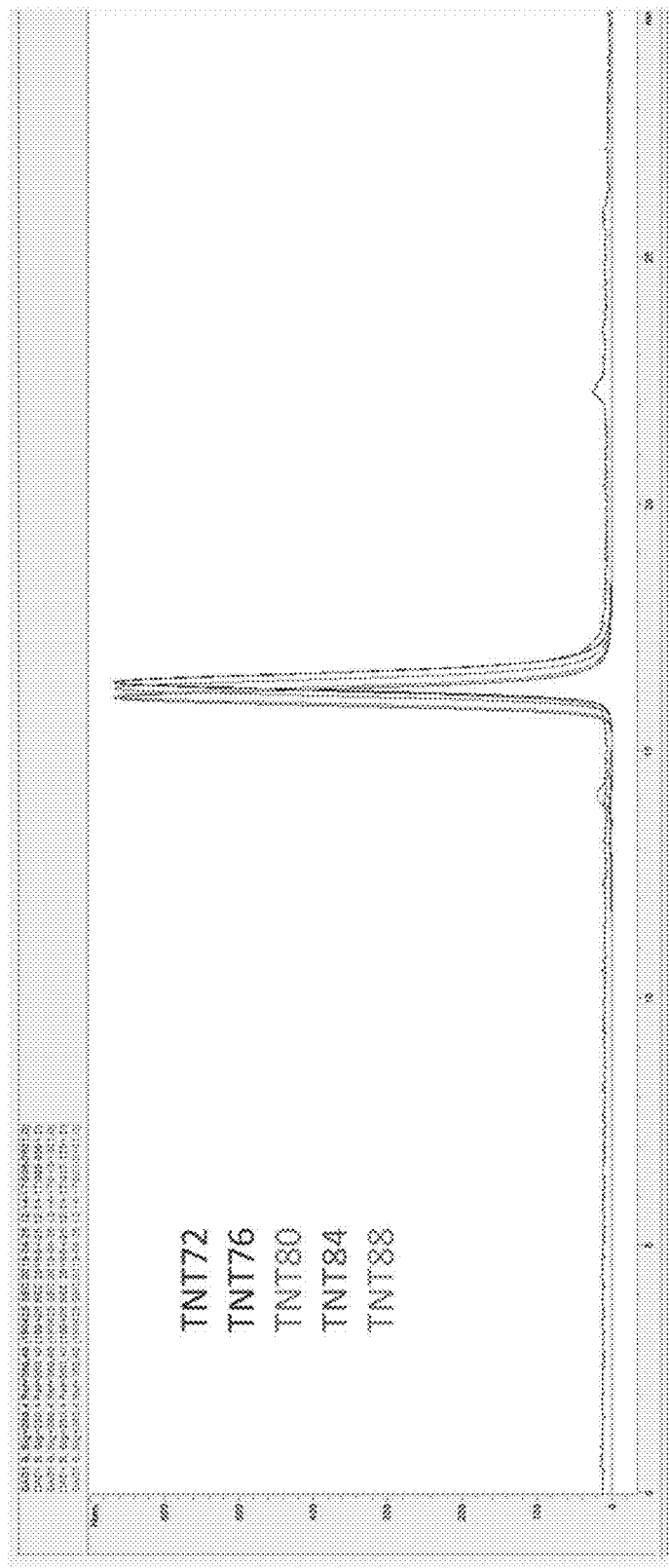

CpG:antibody conjugates were also profiled by size exclusion chromatography (SEC), as shown in FIGS. 12A-12D. Antibody conjugates incorporating the RH1 VH domain showed broad or double SEC peaks (FIG. 12A). Antibody conjugates incorporating the RH2 VH domain were well-behaved based on SEC analysis (FIG. 12B). Antibody conjugates incorporating the RH3 VH domain were prone to aggregation, based on SEC analysis (FIG. 12C). Antibody conjugates incorporating the RH4 VH domain were well-behaved based on SEC analysis but characterized by low overall expression (FIG. 12D).

Pairings of specific VH and VL domains were analyzed. It was known that, generally, IGHV3 pairs frequently with IGKV1 and IGKV3. Preferred pairings included TNT69, TNT70, TNT71, TNT73, TNT74, TNT75, TNT77, TNT78, TNT79, TNT81, TNT82, and TNT83. Potential sequence liabilities, including residues potentially subject to methionine oxidation, deamidation, and isomerization, were also examined.

Selected characteristics of conjugates tested are summarized in FIG. 13A. Antibodies with RH1 behaved abnormally by SEC-HPLC. Antibodies with RH4, RL4, and RL5

| | Human | | | Cyno | | |
|---|---|---|---|---|---|---|
| Sample ID | $CD20^+$ CD22 Median Fluorescent Intensity | $CD20^-$ CD22 Median Fluorescent Intensity | CD22: $CD20^+$/ $CD20^-$ | $CD20^+$ CD22 Median Fluorescent Intensity | $CD20^-$ CD22 Median Fluorescent Intensity | CD22: $CD20^+$/ $CD20^-$ |
| TNT 69 | 1610 | 63.4 | 25.4 | 1412 | 94.9 | 14.9 |
| TNT 70 | 1555 | 65.9 | 23.6 | 1291 | 115 | 11.2 |
| TNT 72 | 1555 | 62.1 | 25.0 | 1368 | 109 | 12.6 |
| TNT 71 | 1457 | 65.9 | 22.1 | 1420 | 101 | 14.1 |
| TNT 73 | 1413 | 70.9 | 19.9 | 216 | 114 | 1.9 |
| TNT 74 | 1313 | 67.1 | 19.6 | 185 | 105 | 1.8 |
| TNT 76 | 1193 | 58.4 | 20.4 | 140 | 85.4 | 1.6 |
| TNT 75 | 1628 | 60.9 | 26.7 | 588 | 88.4 | 6.7 |
| TNT 77 | 1324 | 63.4 | 20.9 | 236 | 90.1 | 2.6 |
| TNT 78 | 1206 | 60.9 | 19.8 | 112 | 90.4 | 1.2 |
| TNT 80 | 1211 | 59.6 | 20.3 | 159 | 86 | 1.8 |
| TNT 79 | 1301 | 60.9 | 21.4 | 349 | 90.1 | 3.9 |
| TNT 82 | 1515 | 63.4 | 23.9 | 1174 | 93.2 | 12.6 |
| TNT 83 | 1489 | 64.6 | 23.0 | 1401 | 130 | 10.8 |
| TNT 85 | 1579 | 68.4 | 23.1 | 1375 | 143 | 9.6 |
| TNT 86 | 1572 | 65.9 | 23.9 | 1428 | 131 | 10.9 |
| TNT 88 | 1531 | 58.4 | 26.2 | 1274 | 86.7 | 14.7 |
| TNT 87 | 1444 | 60.9 | 23.7 | 1368 | 85.4 | 16.0 |
| RFB4 | 1353 | 60.9 | 22.2 | 960 | 115 | 8.3 |

To assess if CpG conjugation affects the binding of respective humanized anti-CD22 to human CD22, SPR assay was carried out. The humanized anti-CD22 antibodies (TNT70, TNT71, TNT72 and TNT74) were conjugated with CpG (SEQ ID NO: 3) with a DAR1 configuration and compared with their respective naked antibodies. Briefly, biotinylated protein A (15 μg/mL) was immobilized to the surface of an NLC chip. 30 nM of purified naked mAb or CpG conjugated mAb solution in PBS-T was used for capture over the protein A surface. Serial dilutions of human CD22 (300 nM, 3×dilution) were injected over the mAb-coated chips, and binding kinetics were determined. Chips were regenerated using 4:1 v/v of Pierce IgG elution butter/4M NaCl. Binding data are provided below.

| Sample Name | ka 1/Ms | kd 1/s | KD M |
|---|---|---|---|
| TNT70 DAR1 | 1.25E+05 | 6.29E−05 | 5.02E−10 |
| TNT71 DAR1 | 8.17E+04 | 3.14E−05 | 3.84E−10 |
| TNT72 DAR1 | 2.01E+05 | 6.59E−05 | 3.28E−10 |
| TNT74 DAR1 | 1.14E+05 | 2.10E−03 | 1.85E−08 |
| TNT71 | 8.84E+04 | 2.33E−05 | 2.63E−10 |
| TNT72 | 3.51E+05 | 3.23E−09 | 9.22E−10 |
| TNT70 | 1.40E+05 | 5.62E−05 | 4.00E−10 |
| TNT74 | 1.10E+05 | 1.99E−03 | 1.82E−08 |

The CpG-conjugated mAbs (TNT70, TNT71, TNT72, and TNT74) bound to human CD22 with similar affinities to the corresponding naked mAb, indicating that CpG conjugation did not alter binding kinetics.

had lower expression levels (FIG. 13B). In particular, antibodies with RL4 (IGKV3) had lower expression in CHO cells, as in Expi293 cells. Antibodies with RH3 had a general tendency towards high aggregation. Pairing RH4 and RL5 was generally non-preferred. Based on all characteristics, including expression level and potential sequence liabilities, pairing the RH2 VH domain with RL1, RL2, or RL3 VL domain was preferred. TNT70, TNT74, TNT78, and TNT82 were selected for further study.

To evaluate melting temperature, differential scanning calorimetry (DSC) was used. DSC was performed using a MicroCal VP Capillary DSC (Malvern). DSC is thought to measure heat capacity as a function of temperature. Melting point (Tm) is thought to be a good indicator of thermal stability and a predictor of long-term stability, with more stable proteins having a higher Tm. Results of DSC testing of selected CpG:antibody conjugates are shown below.

| Sample | $T_{onset}$ | $T_m1$ | $T_m2$ |
|---|---|---|---|
| TNT70 | 61.41 | 71.71 | 79.26 |
| TNT70 DAR1 | 64.23 | 71.71 | 78.09 |
| TNT72 | 62.64 | 71.17 | 86.37 |
| TNT72 DAR1 | 62.54 | 70.80 | 86.00 |

Figure 14:
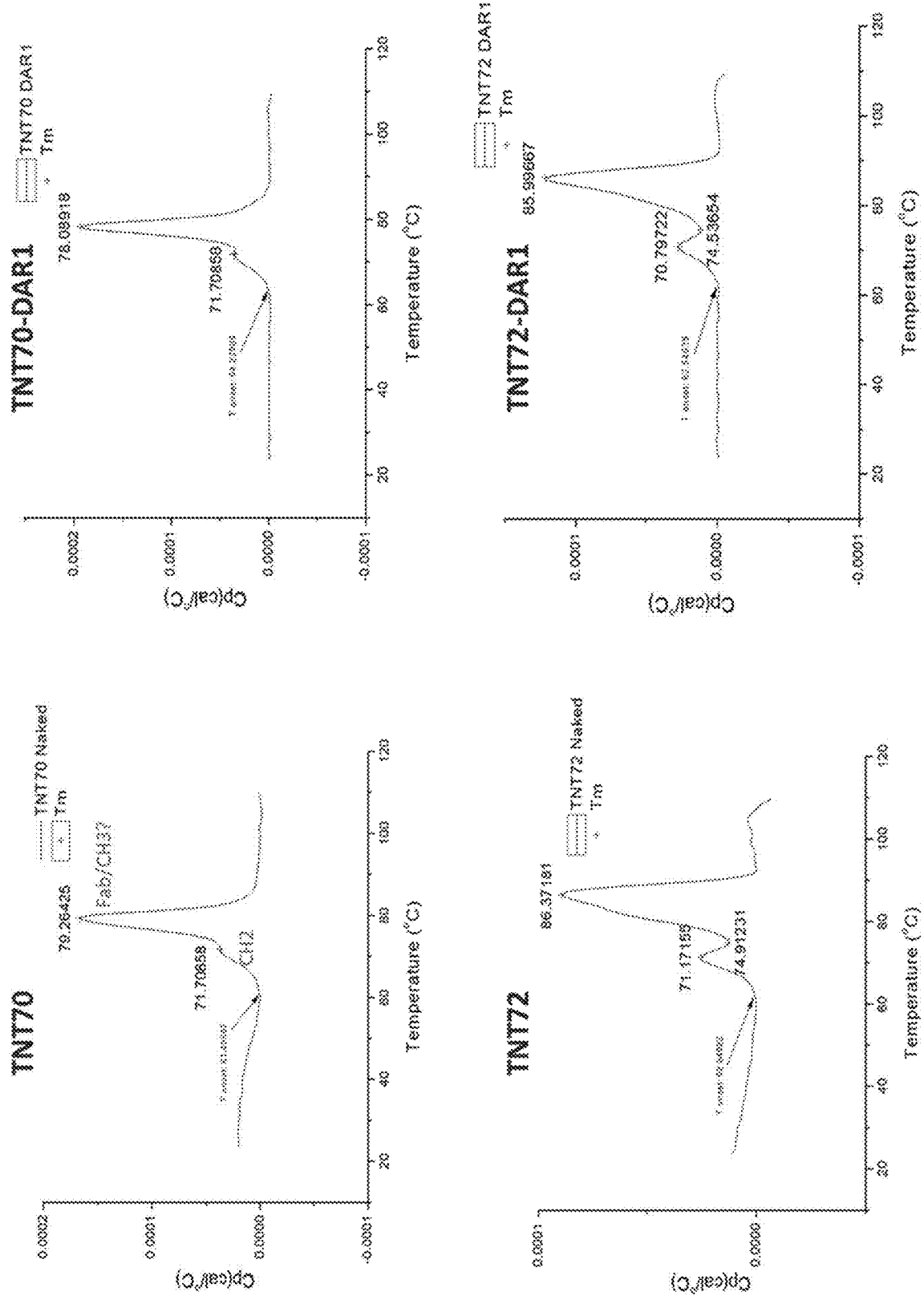
FIG. 14 shows results from analysis of thermal stability of the indicated antibodies and antibody conjugates by differential scanning calorimetry (DSC).

TNT72 had a higher Tm2 than TNT70. This transition is thought to correspond to Fab/CH_3 unfolding. Minor differences in Tm were observed between naked and conjugated antibodies. DSC plots are shown in FIG. 14.

Example 6: Analysis of Humanized Anti-CD22 Variants Mutated to Remove Potential Sequence Liabilities Humanized anti-CD22 antibodies described in Example 5 were next analyzed for potential sequence liabilities. A potential Asn deamination site is present in the CDR-L3 (N92) of all humanized variants (FIG. 8B). This site was mutated in the RL1 VH domain to create antibody variants, which were tested for the impact of mutation on binding affinity to CD22. For engineering variants, N92 was mutated to all possible amino acids. The data for the mutation to A, C, D, E, F, G, H, L, P, S, T, V, or W is shown below.

Figure 15A:
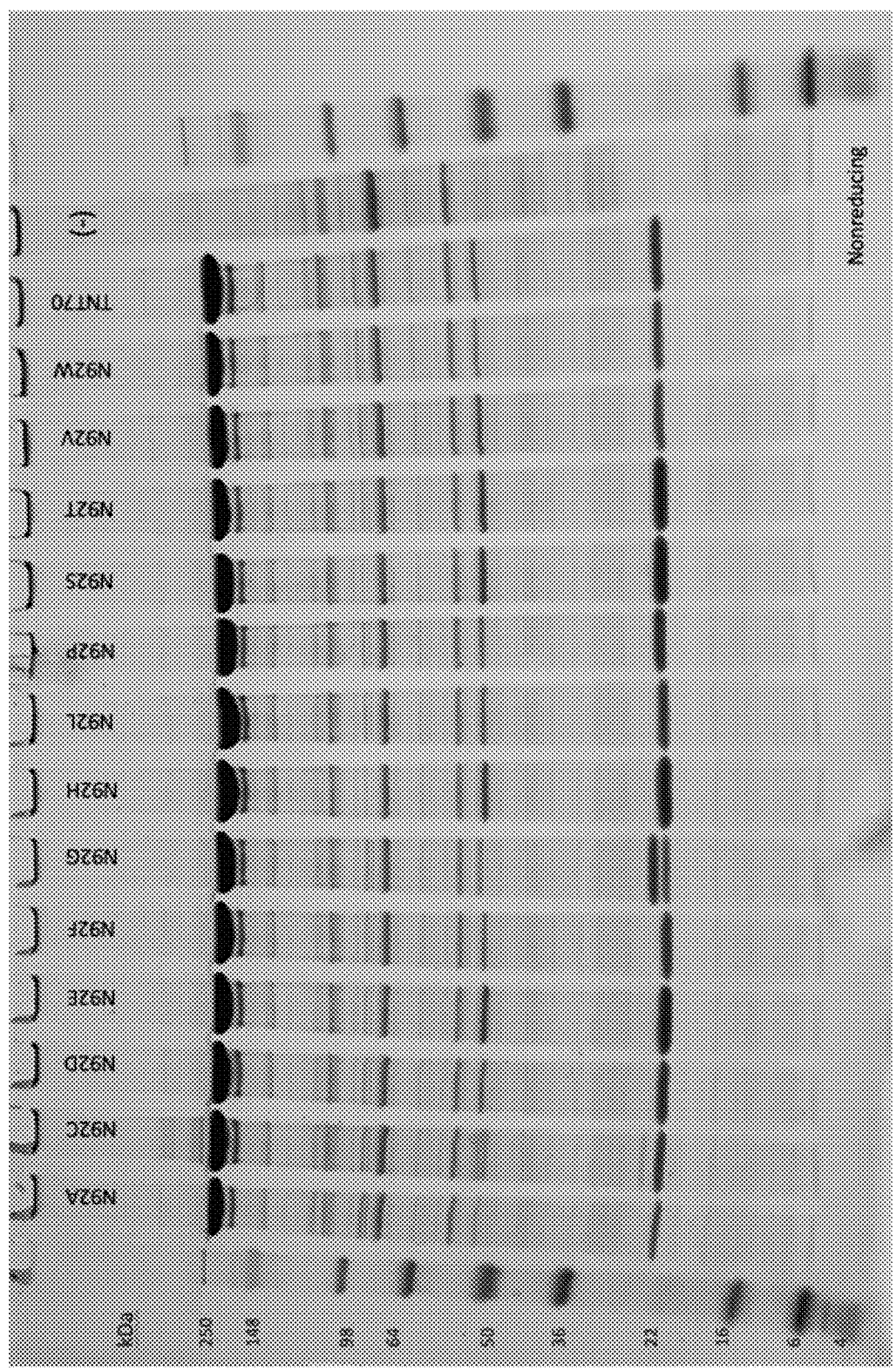
FIGS. 15A and 15B show the expression of N92 substitution variants of the RL1 VL domain under non-reducing (FIG. 15A) or reducing (FIG. 15B) conditions.
Figure 15B:
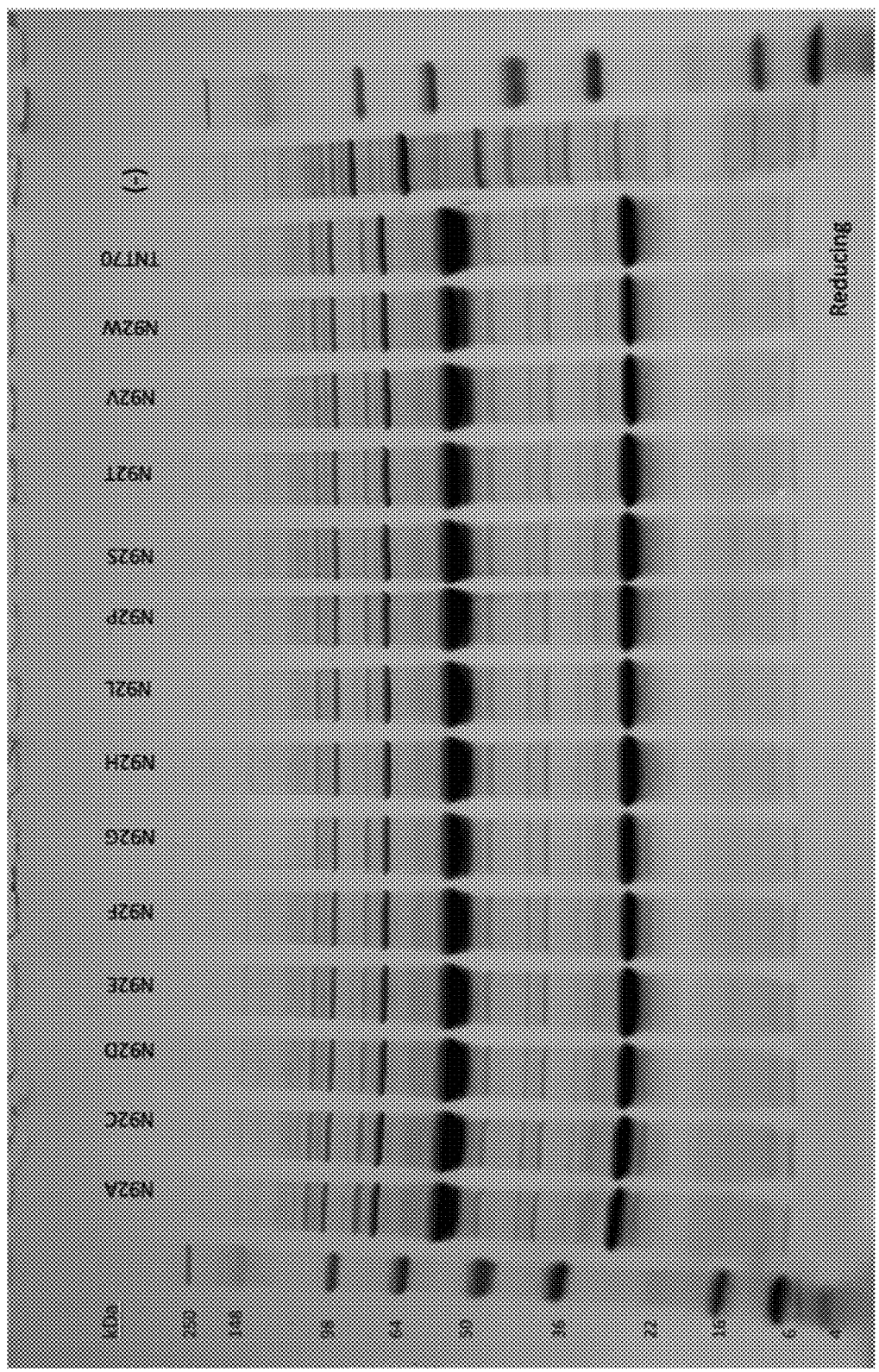
Figure 15C:
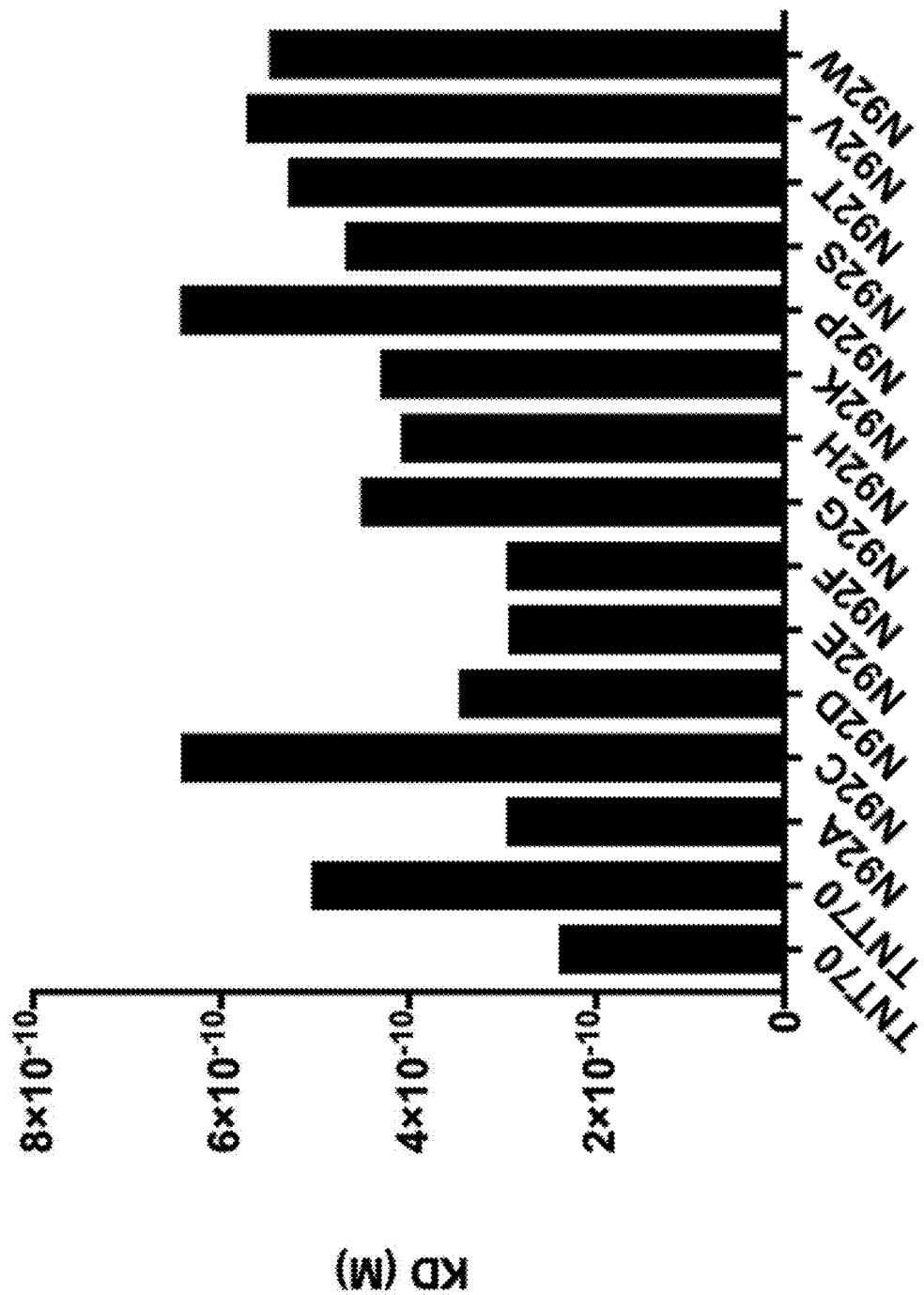
FIGS. 15C-15F show the binding kinetics of antibodies including the N92 substitution variants of the RL1 VL domain to CD22, including KD (FIG. 15C), Ka (FIG. 15D), Kd (FIG. 15E), and capture levels (FIG. 15F), as determined by SPR.
Figure 15D:
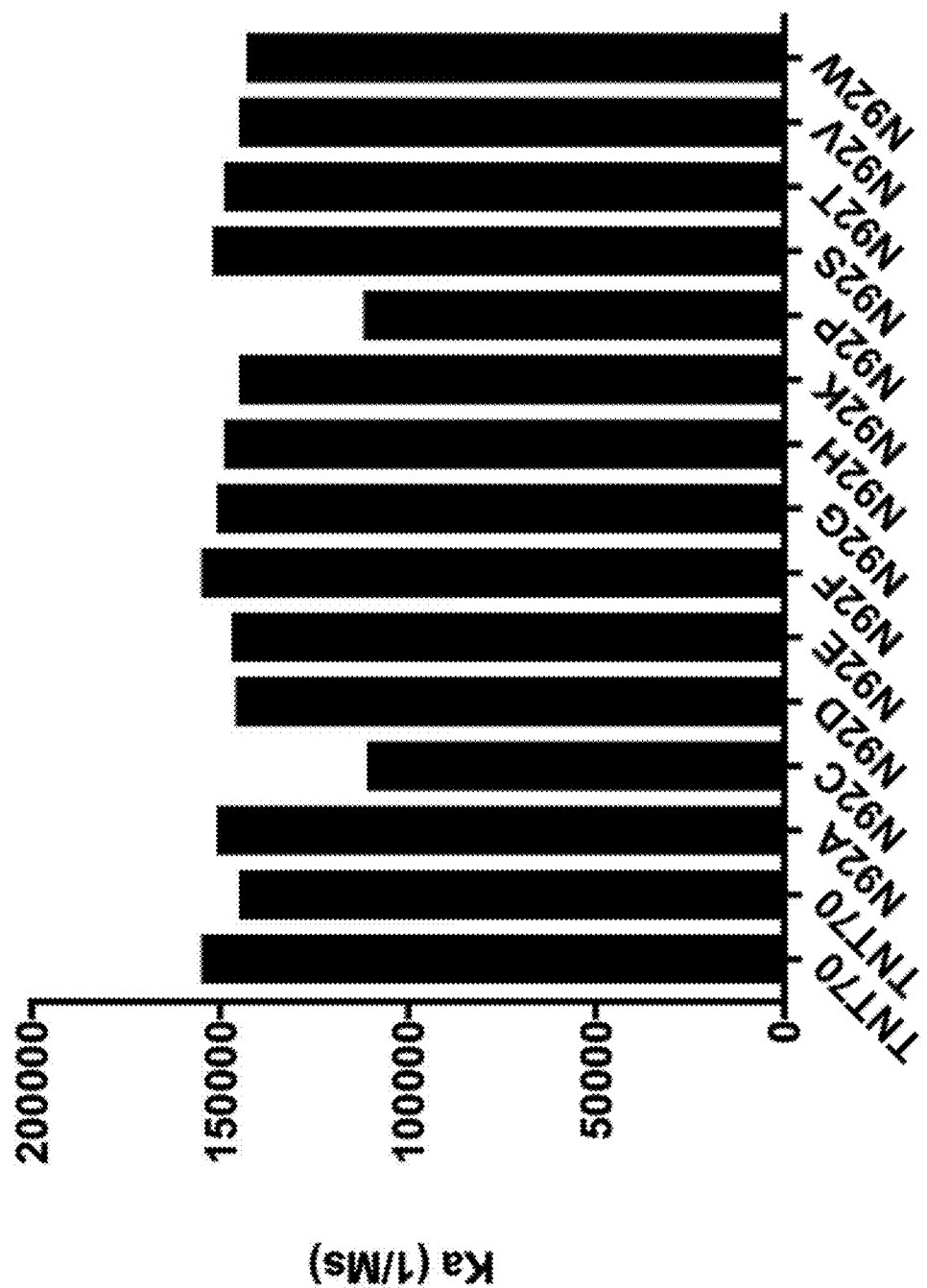
Figure 15E:
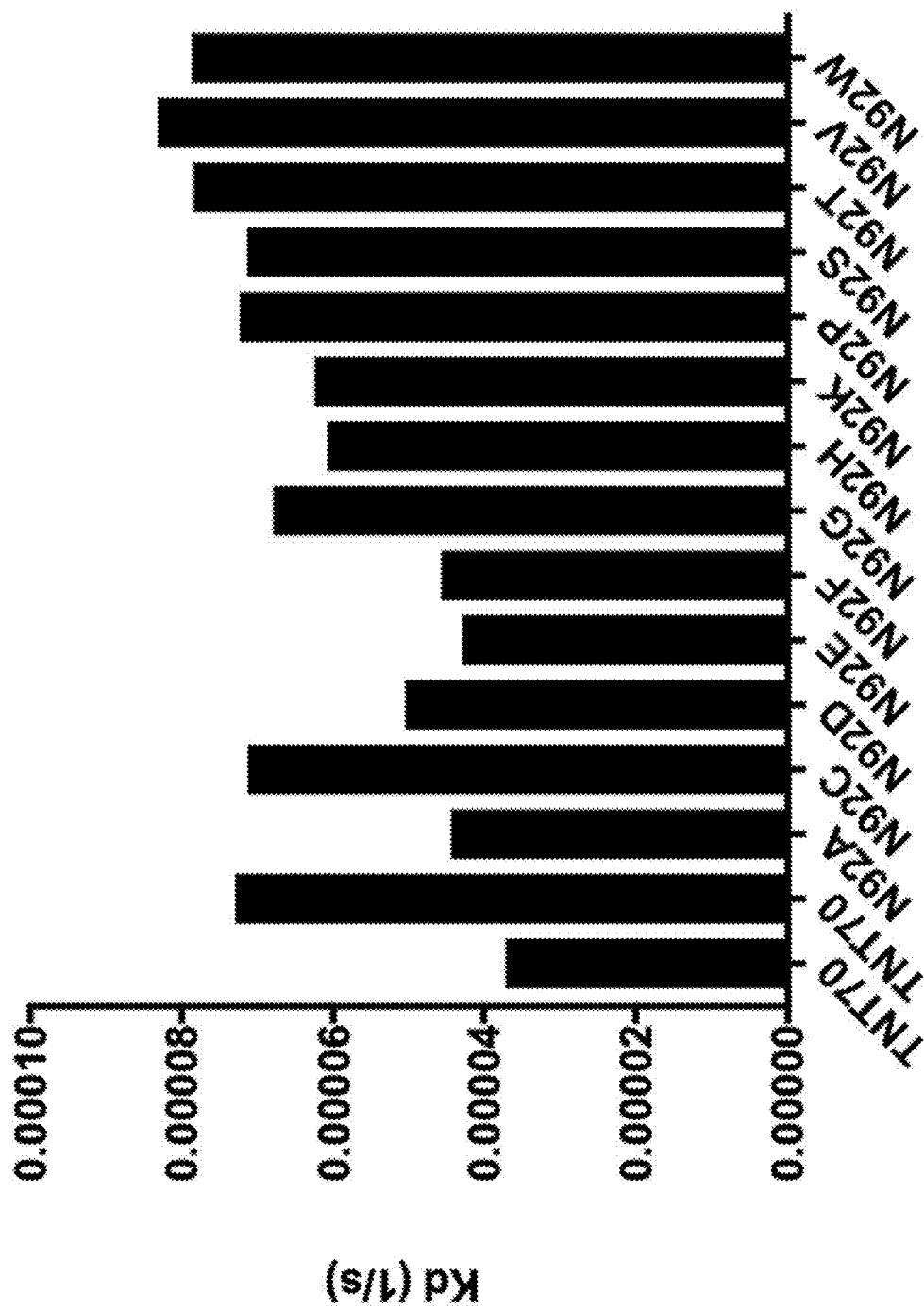
Figure 15F:
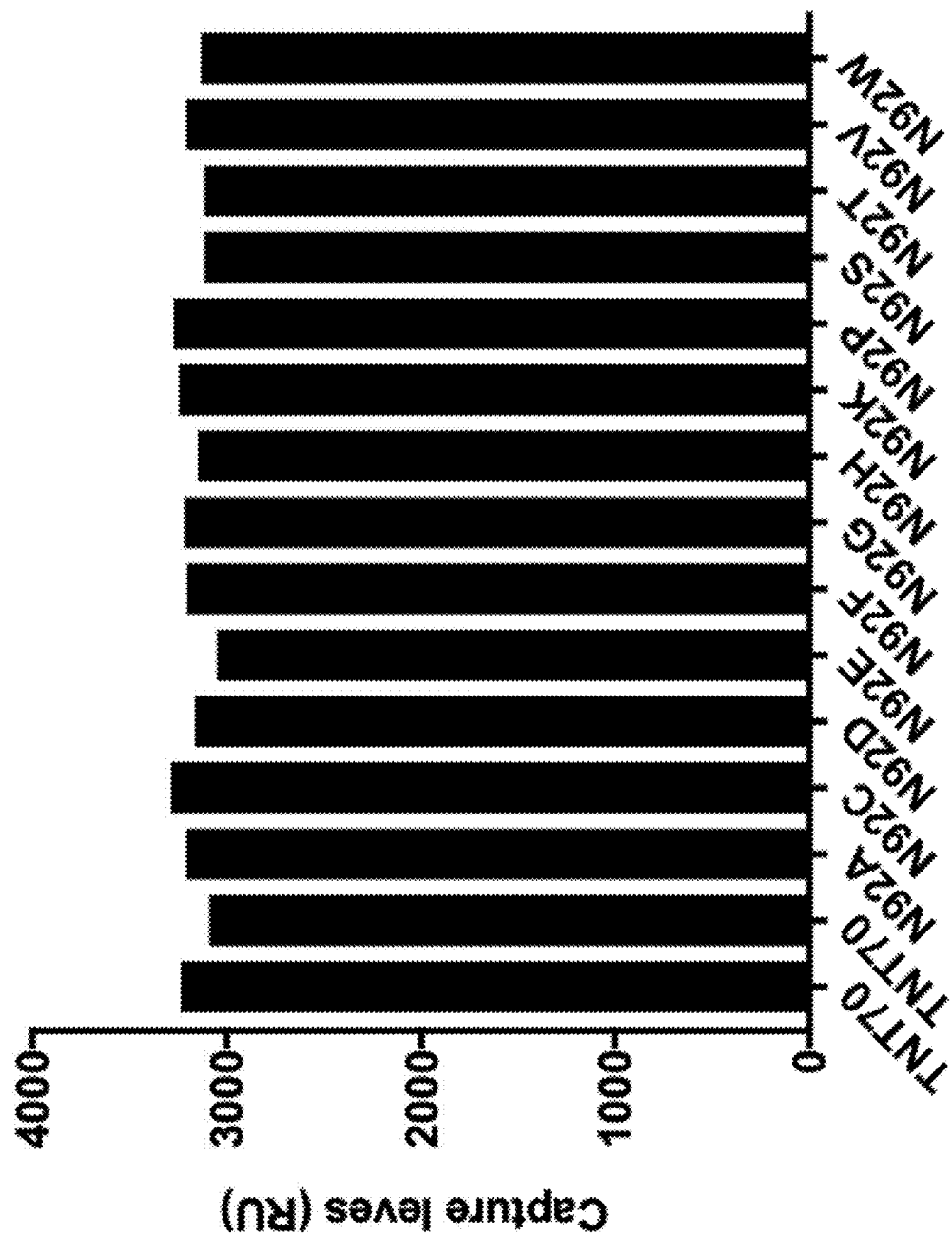
Figure 16E:
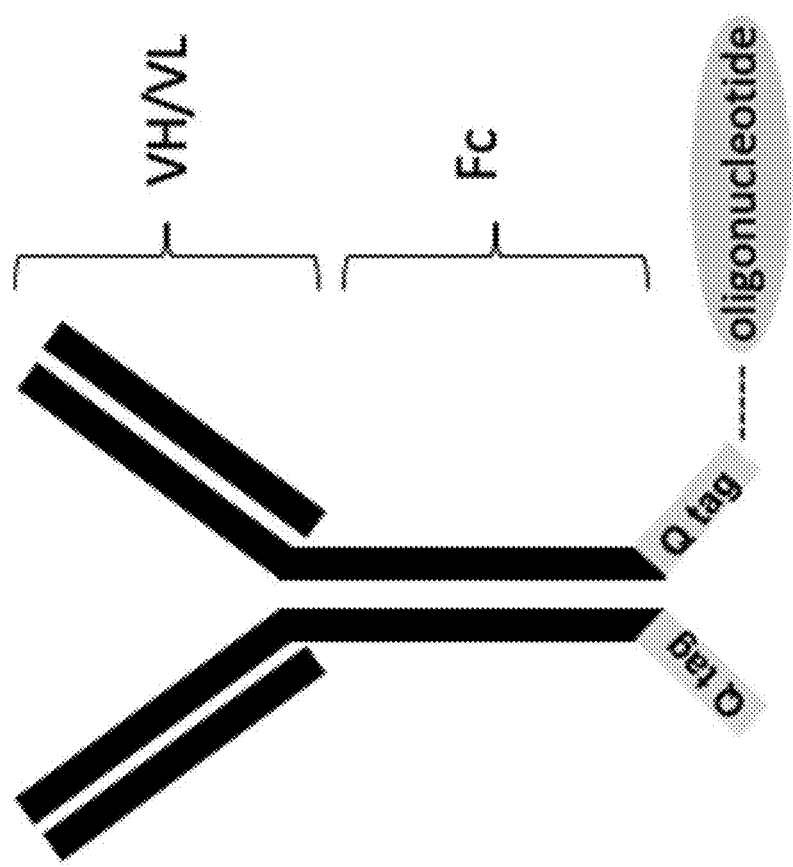

Expression of each variant was compared to TNT70 in reducing (FIG. 15B) or non-reducing (FIG. 15A) conditions. Binding properties of the mutants are summarized below and in FIGS. 15C-15F. All of the N92 substitutions looked to be tolerable with respect to binding affinity to CD22. In particular, N92A, N92D, N92E, and N92F looked to be comparable to the parental antibody, but the KD of all variants looked to be within error of the assay.

| Sample | ka 1/Ms | kd 1/s | KD M |
|---|---|---|---|
| TNT70 | 1.55E+05 | 3.72E−05 | 2.40E−10 |
| TNT70 | 1.45E+05 | 7.30E−05 | 5.04E−10 |
| N92A | 1.51E+05 | 4.45E−05 | 2.95E−10 |
| N92C | 1.11E+05 | 7.13E−05 | 6.43E−10 |
| N92D | 1.46E+05 | 5.05E−05 | 3.46E−10 |
| N92E | 1.47E+05 | 4.29E−05 | 2.93E−10 |
| N92F | 1.55E+05 | 4.58E−05 | 2.95E−10 |
| N92G | 1.51E+05 | 6.80E−05 | 4.52E−10 |
| N92H | 1.49E+05 | 6.08E−05 | 4.09E−10 |
| N92K | 1.45E+05 | 6.25E−05 | 4.31E−10 |
| N92P | 1.12E+05 | 7.24E−05 | 6.44E−10 |
| N92S | 1.52E+05 | 7.14E−05 | 4.68E−10 |
| N92T | 1.49E+05 | 7.85E−05 | 5.29E−10 |
| N92V | 1.45E+05 | 8.32E−05 | 5.73E−10 |
| N92W | 1.43E+05 | 7.87E−05 | 5.49E−10 |

Example 7: Pharmacokinetics of CpG-Antibody Conjugates

Method: Balb/c mice were obtained from Charles River and used for single dose PK study. Each compound conjugate to RFB4 antibody (SEQ ID NO: 56 and SEQ ID NO: 57 for VH and VL domain sequences, respectively) was formulated at a working dose of 2 mg/mL and each mouse was given 200 mg except for Cmpd 4.2b (SEQ ID NO:12) conjugated to RFB4, which was at 170 mg. The RFB4 conjugates were administered intravenously via the mouse tail vein. Three mice were dosed for each RFB4 conjugate. After dosing, mice had blood withdrawn at the following seven time points: 0.5, 6, 24, 48, 72, 144, and 192 hours. Approximately 100 μl of whole blood was collected into microtainer tubes by orbital bleed. Whole blood samples were rested for 30 minutes to allow serum separation. Samples were then centrifuged for 10 minutes at 4 degree at 10000×g. Serum was transferred to a 1.5 ml tube and frozen until analysis. Immulon 96 well ELISA plates (Thermo Fisher Scientific, cat. #3855) were coated overnight with 1 ug/ml, 100 ul/well, sheep anti-human IgG antibody (The Binding Site, cat. #AU003.M) in PBS for anti-human IgG antibody capture or with 2 ug/ml, 100 ul/well, NeutrAvidin Biotin Binding Protein (Thermo Fisher Scientific, cat. #31050) in PBS for anti-BrdU capture. Plates were washed with Tris-Buffered Saline Tween-20 (TBST, 25 mM Tris, 0.15 M NaCl, 0.05% Tween-20, pH 7.5) and blocked for 1 hour with assay buffer (PBS, 1% BSA, 0.05% Tween-20, 0.25% CHAPS, 5 mM EDTA, 0.35 M NaCl) for anti-human IgG antibody capture and with casein blocker (Thermo Fisher Scientific, cat. #37528) for anti-BrdU capture. Plates were washed with TBST. 1 ug/ml, 100 ul/well, of biotinylated anti-BrdU mouse monoclonal antibody (BioLegend, cat. #317904) in assay buffer (PBS, 1% BSA, 0.05% Tween-20, 0.25% CHAPS, 5 mM EDTA, 0.35 M NaCl)+20% casein blocker was added to plates and incubated for 1 hour at room temperature with gentle shaking at 420 rpm on a plate shaker. Plates were washed with TBST. Serum samples were diluted at a minimum of 1:50 in assay buffer+20% casein blocker (Thermo Scientific, cat. #37528) or RFB4 standard curve protein with and without various CpGs attached (two-fold serial dilutions from 100 to 0.2 ng/ml, in 1:50 normal mouse serum diluted in assay buffer+20% casein blocker) were added to blocked plates for 1 hour at room temperature with gentle shaking at 420 rpm on a plate shaker. Plates were washed with TBST. Standard curves and samples were incubated with 0.2 ug/ml goat anti-human IgG-HRP (Bethyl, cat. #A80-319P) for anti-human IgG antibody capture or 0.4 ug/ml goat anti-human IgG-HRP for anti-BrdU, for 1 hour at room temperature with gentle shaking at 420 rpm on a plate shaker. Plates were washed with TBST. All plates were incubated with 1-Step Ultra TMB ELISA solution (Thermo Fisher Scientific, cat. #34028) and the reaction was stopped with 0.16 M sulfuric acid solution (Thermo Fisher Scientific, cat. #N600). Plates were read at an O.D. of 450 nm with a background reference reading at 570 nm on a SpectraMax i3 plate reader (Molecular Devices). Protein concentrations of serum samples were interpolated from the RFB4 antibody standard curves with and without various CpGs attached using a 4 parameter fit curve and Prism software (GraphPad).

Figure 17A:
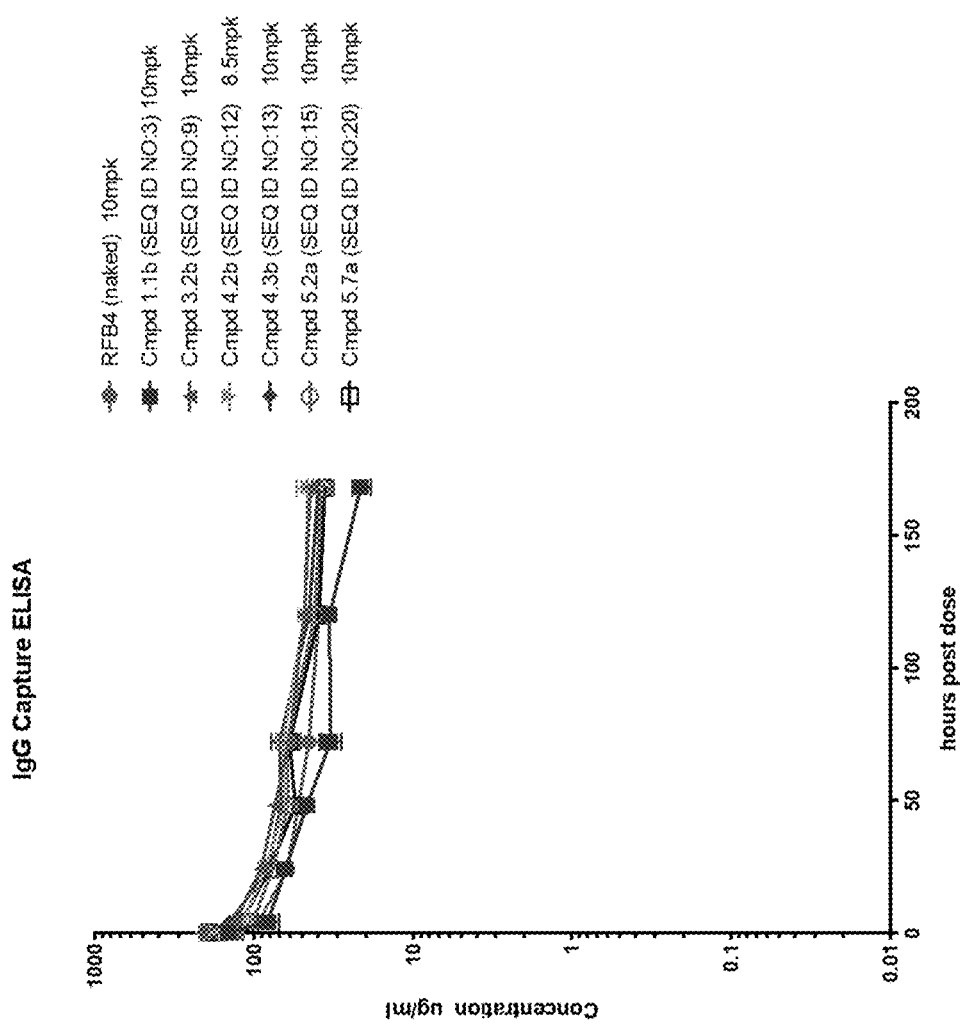
FIGS. 17A-17B depict pharmacokinetic properties of CpG-antibody conjugates.
Figure 17B:
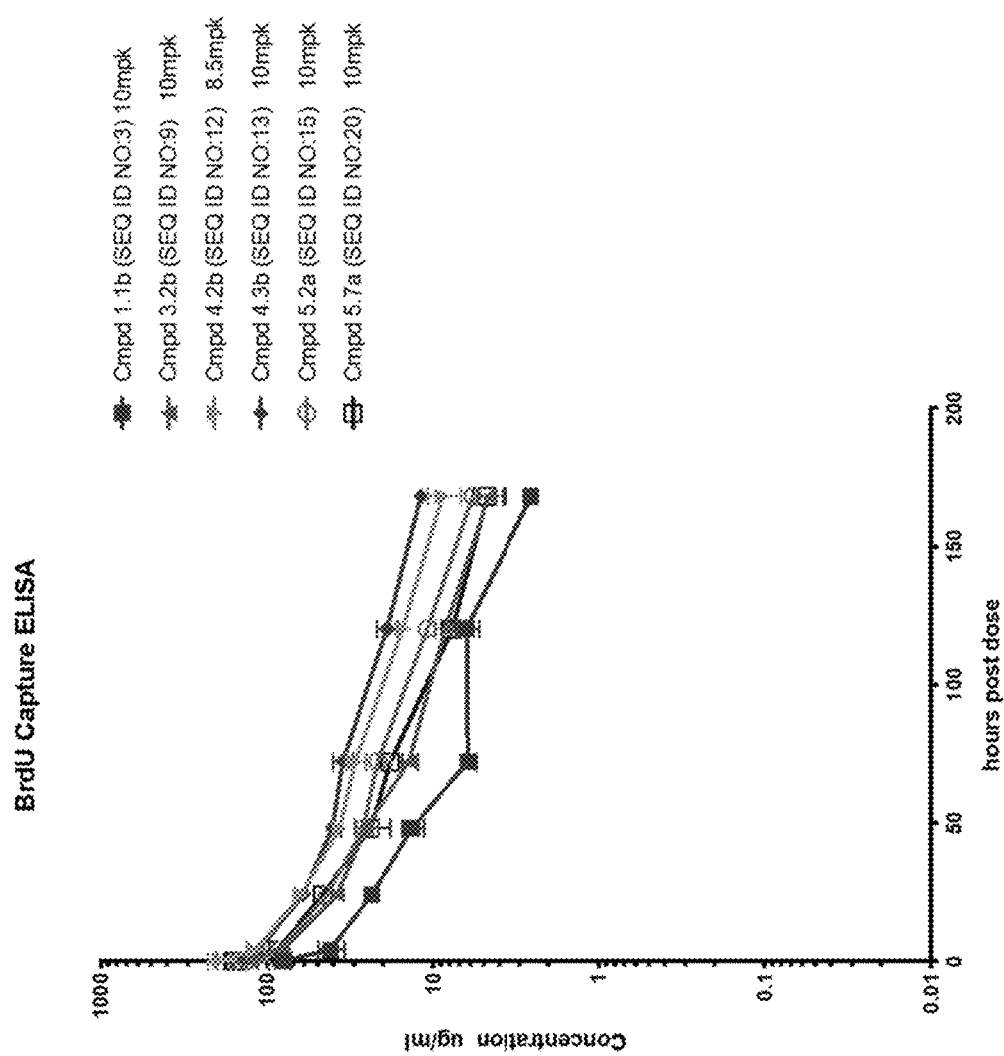

As shown in FIG. 17A, RFB4 conjugated with Cmpd 1.1b (SEQ ID NO:3), Cmpd 3.2b (SEQ ID NO:9), Cmpd 4.2b (SEQ ID NO:12), Cmpd 4.3b (SEQ ID NO:13), Cmpd 5.2a (SEQ ID NO:15) or Cmpd 5.7a (SEQ ID NO:20) have similar half-life compared to naked RFB4 when total antibody was measured. This shows that the conjugation of RFB4 with the respective CpG oligonucleotides does not affect the PK of the antibody. FIG. 17B shows the PK of RFB4 conjugates by capturing the compounds with anti-BrdU antibody. Surprisingly, when the half-life of RFB4 conjugates is evaluated by capturing the 5' region of the CpG using anti-BrdU antibody, Cmpd 3.2b (SEQ ID NO: 9), Cmpd 4.2b (SEQ ID NO:12), Cmpd 4.3b (SEQ ID NO:13, Cmpd 5.2a (SEQ ID NO:15) and Cmpd 5.7a (SEQ ID NO:20) have increased half-life compared to Cmpd 1.1b (SEQ ID NO:3).

Example 8: B Cell Activation in Cynomolgus Monkey PBMCs by CpG Oligonucleotides

Peripheral blood mononuclear cells (PBMCs) were isolated from cynomolgus monkey whole blood by Ficoll (GE) separation. 300,000 PBMC cells were plated in 96 well round bottom plates in RPMI 10% FBS (Life Technologies). Cells were treated with 12070 (compound 1.1b, SEQ ID NO:3), CpG 7-7 (Compound 7.7b; SEQ ID NO:35), or media only at a starting concentration of 1 uM followed by 1:5 titration down. Cells were incubated for 72 hrs prior to staining for flow cytometry. Cells were centrifuged at 400G for 5 min before media removal. Cells were then incubated with fixable live dead dye eFluor780 (eBioscience) for 30 min at 4C. FACS buffer (PBS+2% FBS) was added to the wells before centrifugation at 400G for 5 min. Cells were then incubated in human FcR blocking reagent (Miltenyi Biotec) and stained with flurochrome-labeled antibodies against CD3 (clone SP34, Biolegend), CD14 (clone M5E2, Biolegend), CD16 (clone 3G8, Biolegend), HLADR (clone G46-6, Biolegend), CD1c (clone L161, Biolegend), CD20 (clone 2H7, Biolegend), CD69 (clone FN50, eBioscience), CD8 (clone RPAT8, Biolegend), CD40 (clone 5C3, Biolegend) and CD86 (clone IT2.2 Biolegend) for 1 hr at 4C. Cells were then washed twice in FACS buffer before fixing in 0.5% paraformaldehyde. Cells were acquired on an Attune flow cytometer (Thermofisher) with subsequent analysis using FlowJo Software and tabulated using Prism Software.

Figure 18:
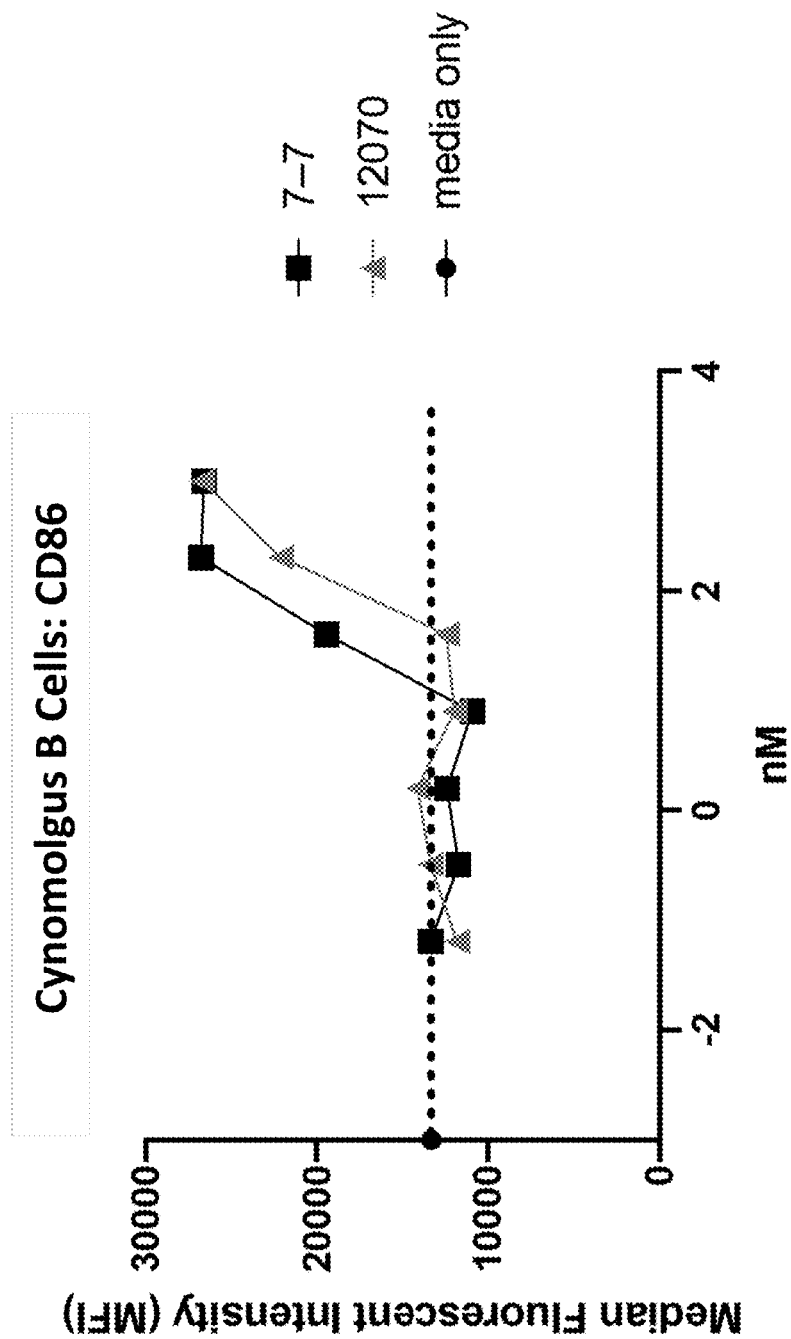
FIG. 18 shows activation of B cells from cynomolgus monkey PBMCs by CpG oligonucleotides, as measured by CD86 expression. Treatment with compound 7.7b (7-7) induced superior CD86 upregulation as compared to that induced by compound 1.1b (12070), demonstrating enhanced B cell activation.

Cynomolgus monkey PBMCs were stimulated for 72 hrs in presence of 7-7 CpG, 12070 CpG or media only at a starting concentration of luM followed by 1:5 titration down. Cells were then stained and analyzed by flow cytometry. Following singlet and dead cell exclusion, CD20+B cells were gated, followed by median fluorescent intensity of CD86 marker. Treatment with 7-7 induced superior CD86 upregulation (FIG. 18), demonstrating enhanced B cell activation compared to 12070.

Example 9: Induction of IL-6 Expression Using Anti-CD22:CpG Oligonucleotide Conjugates Human peripheral blood mononuclear cells (PBMCs) were isolated from Trima residuals (Vitalant) and diluted 1:4 with Phosphate Buffered Saline (PBS, Gibco). Diluted blood was split into tubes and underlayed with 15 mL Ficoll-Paque (GE Healthcare). Tubes were centrifuged for 30 minutes at 400×g. PBMCs were collected from the interface and resuspended in Complete RPMI (RPMI+10% FBS). One million PBMCs were plated in 96 round well plates in Complete RPMI and treated with unconjugated anti-CD22 antibody, or anti-CD22 conjugated to 12070 CpG (compound 1.1b, SEQ ID NO:3) starting at a concentration of 100 nM followed by 1:5 titration down. Cells were incubated for 48 hrs followed by spin at 400×g for 5 min upon which supernatants were collected. IL6 in harvested supernatant were assessed neat using a bead-based immunoassay kit (LegendPlex, Biolegend) per manufacturer's recommendations. Samples were acquired on an Attune flow cytometer (Thermofisher) with subsequent analysis using FlowJo Software and tabulated using Prism Software.

Figure 19:
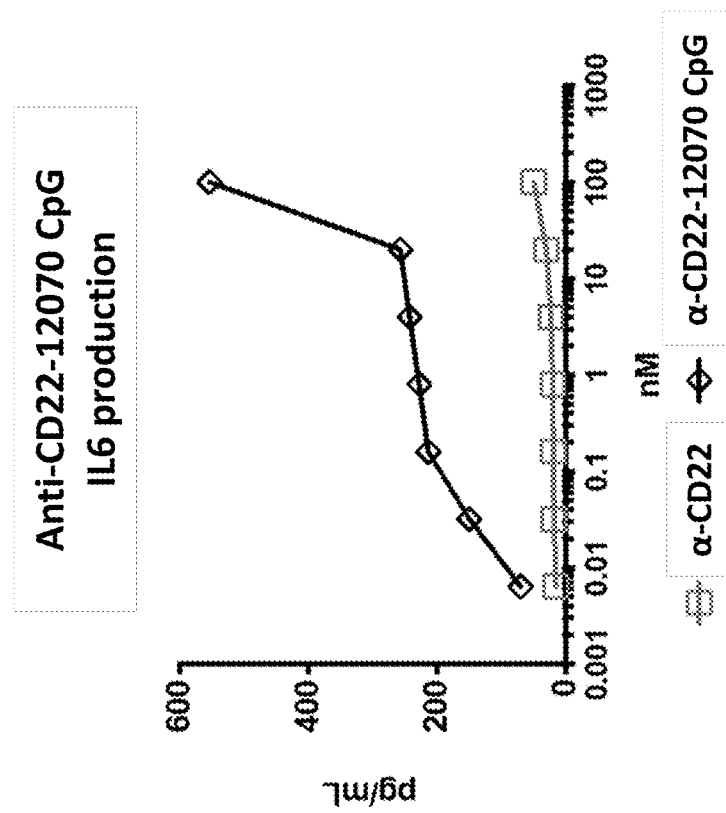
FIG. 19 shows IL-6 induction following treatment with anti-CD22:CpG oligonucleotide conjugate treatment of human PBMCs. Anti-CD22 conjugated to compound 1.1b (12070) CpG induced IL6 expression not achieved by unconjugated anti-CD22 antibody.

Human PBMCs were stimulated for 48 hrs in the presence of unconjugated anti-CD22 antibody or anti-CD22 conjugated to 12070 CpG following which supernatants were harvested and IL6 was assessed by bead-based immunoassay. Anti-CD22 conjugated to 12070 CpG induced robust IL6 expression as compared to that after treatment with unconjugated anti-CD22 antibody (FIG. 19), suggesting that anti-CD22 conjugated to 12070 can robustly induce IL6 expression from the targeted cell type.

Example 10: Activation of Non-Targeted T and B Cells Using Anti-SIRP-α:CpG Oligonucleotide Conjugates Human peripheral blood mononuclear cells (PBMCs) were isolated from Trima residuals (Vitalant) and diluted 1:4 with Phosphate Buffered Saline (PBS, Gibco). Diluted blood was split into tubes and underlayed with 15 mL Ficoll-Paque (GE Healthcare). Tubes were centrifuged for 30 minutes at 400×g. PBMCs were collected from the interface and resuspended in Complete RPMI (RPMI+10% FBS). One million PBMCs were plated in 96 round well plates in Complete RPMI and treated with anti-SIRP-α antibody, or anti-SIRP-α conjugated to 12070 CpG (compound 1.1b, SEQ ID NO:3) starting at a concentration of 100 nM followed by 1:5 titration down. VH and VL domain sequences of the anti-SIRP-α antibody are provided below.

Anti-SIRP-α VH domain:

```
                                         (SEQ ID NO:122)
EVQLVESGGGVVQPGGSLRLSCAASGFTFSSNAMSWVRQAPGKGLEWVA

GISAGGSDTYYPASVKGRFTISRDNSKNTLYLQMNSLRAEDTAVYYCAR

ETWNHLFDYWGQGTLVTVSS
```

Anti-SIRP-α VL domain:

```
                                         (SEQ ID NO:123)
SYELTQPPSVSVSPGQTARITCSGGSYSSYYYAWYQQKPGQAPVTLIYS

DDKRPSNIPERFSGSSSGTTVTLTISGVQAEDEADYYCGGYDQSSYTNP

FGGGTKLTVL
```

Cells were then incubated for 48 hrs prior to flow staining. Cells were centrifuged at 400×g for 5 min before media removal. Cells were then incubated with fixable live dead dye eFluor780 (eBioscience) for 30 min at 4C. FACS buffer (PBS+2% FBS) was added to the wells before centrifugation at 400×g for 5 min. Cells were then incubated in human FcR blocking reagent (Miltenyi Biotec) and stained with flurochrome-labeled antibodies against CD3, CD14, CD16, HLADR, CD11c, CD69, CD40, and CD86 for 1 hr at 4C. Cells were then washed twice in FACS buffer before fixing in 0.5% paraformaldehyde. Cells were acquired on an Attune flow cytometer (Thermofisher) with subsequent analysis using FlowJo Software and tabulated using Prism Software.

Human PBMCs were stimulated for 48 hrs in presence of unconjugated anti-SIRP-α or anti-SIRP-α conjugated to 12070 starting at a concentration of 100 nM followed by 1:5 titration down. Cells were then stained and analyzed by flow cytometry. Following singlet and dead cell exclusion, CD20+B cells (FIG. 20B) or CD3+ T cells (FIG. 20A) were gated, followed by median fluorescent intensity of CD69, an activation marker. Anti-SIRP-α conjugated to 12070 CpG induced robust activation of non-targeted cells such as T cells and B cells, as compared to that after treatment with unconjugated anti-SIRP-α, as evident with the upregulation of CD69 (FIGS. 20A & 20B).

Example 11: Treatment with Antibody:CpG Oligonucleotide Conjugates Elicits Robust Immune Memory Response to Tumors MC38 cells were injected into the right flank of C57BL/6 female mice, at a concentration of $2\times10^6$ cells per mouse in DMEM. Tumors were monitored until the average size of tumors reached 150-155 mm$^3$. Mice were randomized into PBS control, anti-SIRP-α-4523 CpG or anti-mCD22-4523 CpG at 5 mice per cohort. The sequence of the 4523 murine CpG oligonucleotide is tucgtcgtgacgtt-c3, where lower case indicates phosphothioate linkages, bold indicates iodo-uridine, and underlining indicates phosphotriester linker (SEQ ID NO:121). VH and VL domain sequences of the anti-mCD22 antibody are provided below.

Anti-mCD22 VH domain:

(SEQ ID NO:124)
QVQLQQPGAEIVRPGTSVKLSCKASGYTFTDYWMNWVKQRPGQGLEWFG

AIDPSDSYTRYNQEFKGKATLTVDTSSTTAYMQLSSLTSEDSAVYFCAR

SDYTYSFYFDYWGLGTTLTVSS

Anti-mCD22 VL domain:

(SEQ ID NO:125)
DIVMTQAAFSNPVTLGTSASISCRSSKSLLHSNGITYLYWYLQKPGQSP

QLLIYQMSNLASGVPDRFSSSGSGTDFTLRISRVEAEDVGVYYCAQNLE

LPWTFGGGTKLEIK

Anti-SIRP-α-4523 and anti-mCD22-4523 were dosed at 10 mg/kg two times in total, three days apart. Both drugs were administered intraperitoneally. On day 88, mice with eradicated tumors were re-challenged with MC38 (left flank) at $2\times10^6$ cells per mouse in DMEM. Naïve mice that have not been implanted with MC38 mice were included as control for tumor growth. Tumors were measured in two dimensions with calipers, and tumor volume was calculated as: length×width×width×0.5, where length was the larger of the two measurements.

Figure 21C:
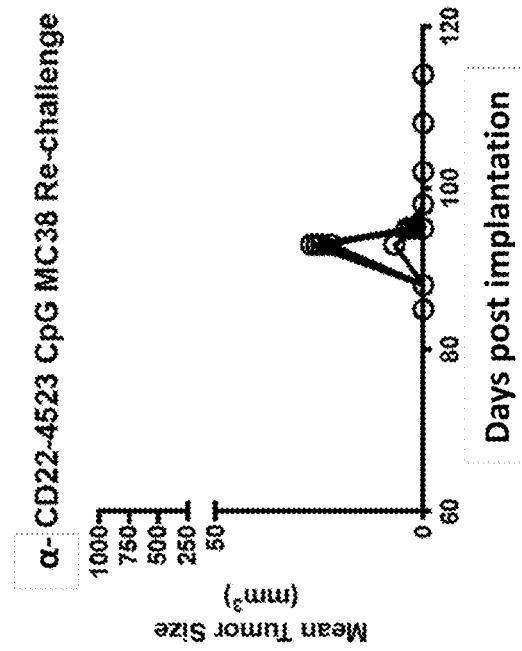
FIGS. 21A-21C show results of tumor immune rechallenge assay in mice. MC38 cells were injected into the right flank of C57BL/6 female mice, at a concentration of 2×10⁶ cells per mouse in DMEM. Tumors were monitored until the average size of tumors reached 150-155 mm³. Mice were randomized into PBS control, anti-SIRP-α-4523 CpG or anti-mCD22-4523 CpG at 5 mice per cohort. Anti-SIRP-α-4523 and anti-mCD22-4523 were dosed at 10 mg/kg two times in total, three days apart. Both drugs were administered intraperitoneally. On day 88, mice with eradicated tumors were re-challenged with MC38 (left flank) at 2×10⁶ cells per mouse in DMEM. Naïve mice that have not been implanted with MC38 mice were included as control for tumor growth. Tumors were measured in two dimensions with calipers, and tumor volume was calculated as: length× width×width×0.5, where length was the larger of the two measurements. Following re-challenge, previously eradicated mice showed efficient tumor rejection as early as three days post-tumor re-implantation suggesting that treatment with both anti-SIRP-α (FIG. 21B) and anti-mCD22 (FIG. 21C) conjugated to 4523 CpG elicited robust immune memory response against the implanted tumor, not seen in naïve mice who are encountering MC3 8 tumor for the first time (FIG. 21A).
Figure 21A:
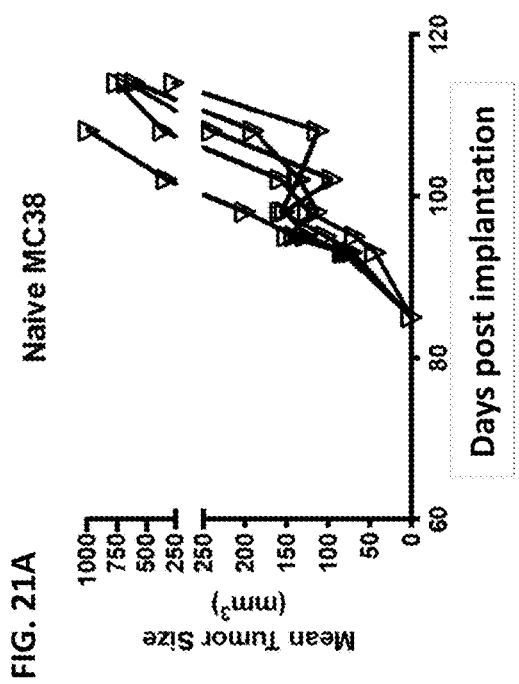
Figure 21B:
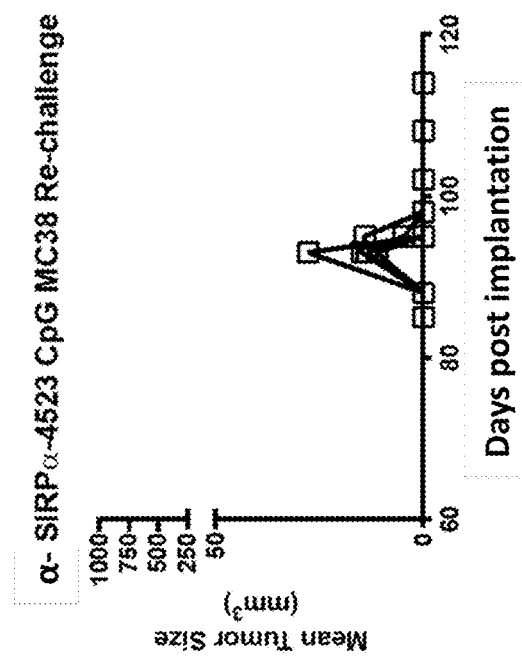

On day 88, there were 5 mice with eradicated tumors for each of the groups treated with either 10 mg/kg anti-SIRP-α 4523 CpG, or anti-mCD22-4523 CpG. Following re-challenge, previously eradicated mice showed efficient tumor rejection as early as three days post-tumor re-implantation suggesting that treatment with both anti-SIRP-α and anti-mCD22 conjugated to 4523 CpG elicit robust immune memory response against the implanted tumor, not seen in naïve mice who are encountering MC38 tumor for the first time (FIGS. 21A-21C).

Example 12: Treatment with Anti-Her2:CpG Oligonucleotide Conjugates Leads to Durable Tumor Eradication The trastuzumab epitope was integrated into the mouse Her2 gene to generate mouse/human (m/h) Her2. m/h Her2 expressing MC38 cells was generated by lentiviral transduction and sorted to obtain cells that express m/h Her2. m/h Her2-MC38 cells were injected into the right flank of C57BL/6 female mice, at a concentration of $2\times10^6$ cells per mouse in DMEM. Tumors were monitored until the average size of tumors reached 70 mm$^3$. Mice were randomized into PBS control, TNT149a (anti-Her2 mIgG2a), and TNT150a (anti-Her2 mIgG1) treatment groups with 5 mice per cohort. Anti-Her2-CpG nucleotide conjugate-treated mice were dosed with 1, 3 and 10 mg/kg three times in total, three days apart. Both drugs were administered intraperitoneally. Heavy and light chain sequences for the anti-Her2 antibodies are provided below.

Anti-Her2 mIgG2a heavy chain:

(SEQ ID NO: 126)
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSAKTTAPSVYPLAPVCGDTTGSSVTLGC

LVKGYFPEPVTLTWNSGSLSSGVHTFPAVLQSDLYTLSSSVTVTSSTWP

SQSITCNVAHPASSTKVDKKIEPRGPTIKPCPPCKCPAPNLLGGPSVFI

FPPKIKDVLMISLSPIVTCVVVDVSEDDPDVQISWFVNNVEVHTAQTQT

HREDYNSTLRVVSALPIQHQDWMSGKEFKCKVNNKDLPAPIERTISKPK

GSVRAPQVYVLPPPEEEMTKKQVTLTCMVTDFMPEDIYVEWTNNGKTEL

NYKNTEPVLDSDGSYFMYSKLRVEKKNWVERNSYSCSVVHEGLHNHHTT

KSFSRTPGLLQGG

Anti-Her2 mIgG1 heavy chain:

(SEQ ID NO:127)
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSAKTTPPSVYPLAPGSAAQTNSMVTLGC

LVKGYFPEPVTVTWNSGSLSSGVHTFPAVLQSDLYTLSSSVTVPSSTWP

SETVTCNVAHPASSTKVDKKIVPRDCGCKPCICTVPEVSSVFIFPPKPK

DVLTITLTPKVTCVVVDISKDDPEVQFSWFVDDVEVHTAQTQPREEQFN

STFRSVSELPIMHQDWLNGKEFKCRVNSAAFPAPIEKTISKTKGRPKAP

QVYTIPPPKEQMAKDKVSLTCMITDFFPEDITVEWQWNGQPAENYKNTQ

PIMDTDGSYFIYSKLNVQKSNWEAGNTFTCSVLHEGLHNHHTEKSLSHS

PGLLQGG

Anti-Her2 light chain:

(SEQ ID NO:128)
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKRADAAPTVSIFPPSSEQLTSGGASVVCFLNNFYPKDINVK

WKIDGSERQNGVLNSWTDQDSKDSTYSMSSTLTLTKDEYERHNSYTCEA

Figure 22A:
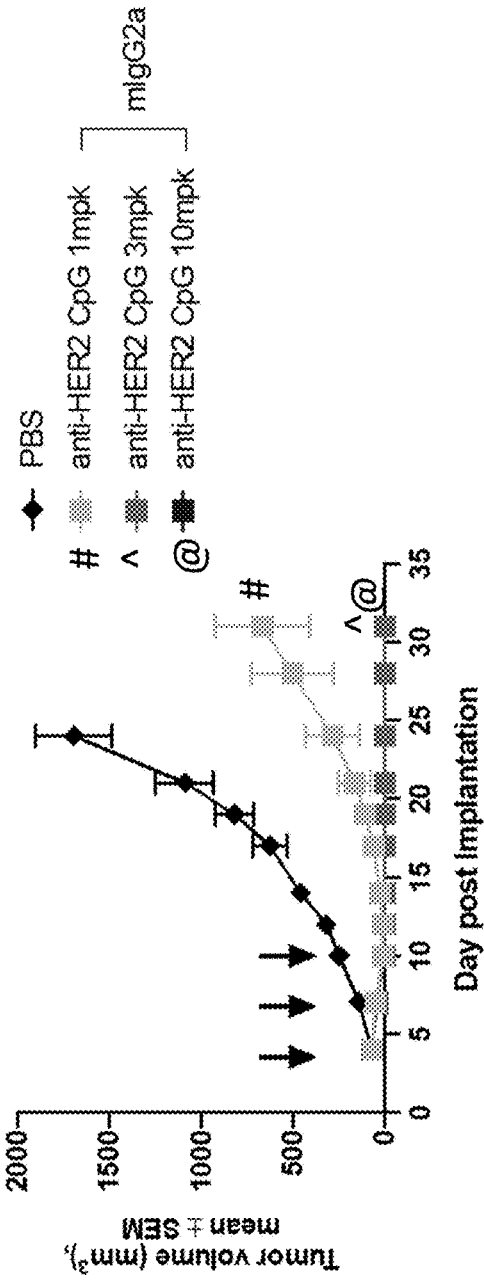
Figure 22B:
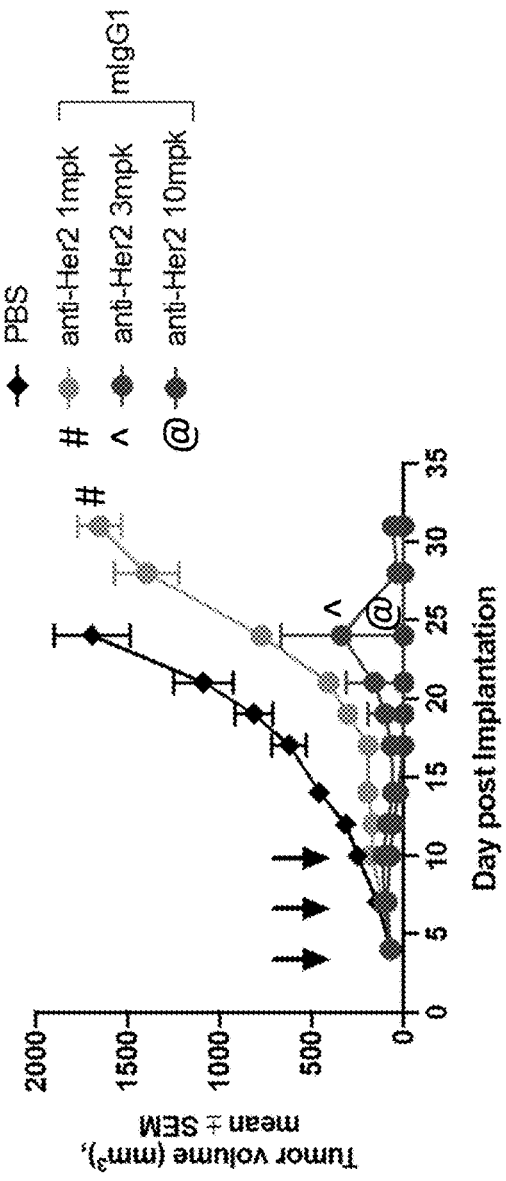

THKTSTSPIVKSFNRNEC m/h Her2 MC38-tumor bearing mice were measured and randomized by tumor volume. On day 4, each cohort of 5 mice had an average tumor size of 70 mm$^3$. Mice were treated PBS or 1, 3, and 10 mg/kg of TNT149a or TNT150a. By day 60, 1, 3 and 10 mg/kg TNT149a treated mice dosed three times, three days apart showed tumor eradication (1/5, 5/5 and 5/5 mice, respectively; FIGS. 22A & 22C) while mice treated with 1, 3 and 10 mg/kg TNT150a showed lower number of mice with eradicated tumors (0/5, 3/5 and 5/5, respectively; FIGS. 22B & 22D). Mice treated with PBS control reached endpoint by day 24 and all groups treated with TNT149a or TNT150a showed delayed tumor growth as compared to PBS control. These data show durability in tumor eradication with both anti-Her2-CpG mIgG1 and mIgG2a and superior activity in mice treated with anti-Her2-CpG nucleotide conjugate containing Fc effector function.

Figure 23A:
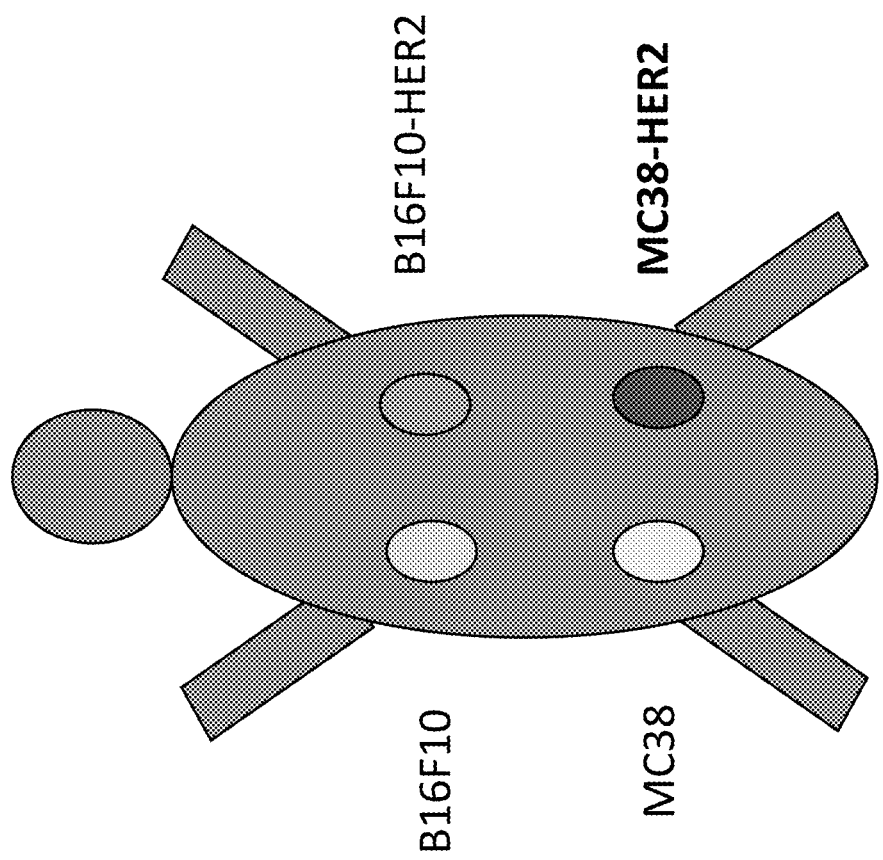
Figure 23B:
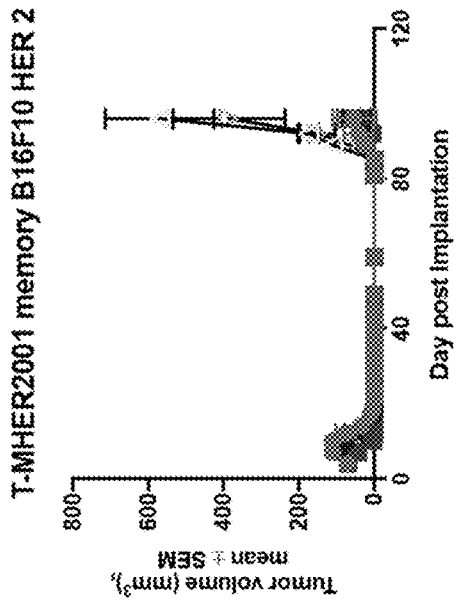
Figure 23C:
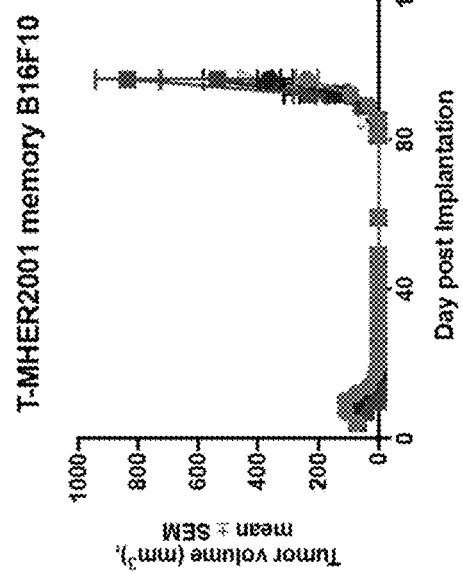
Figure 23D:
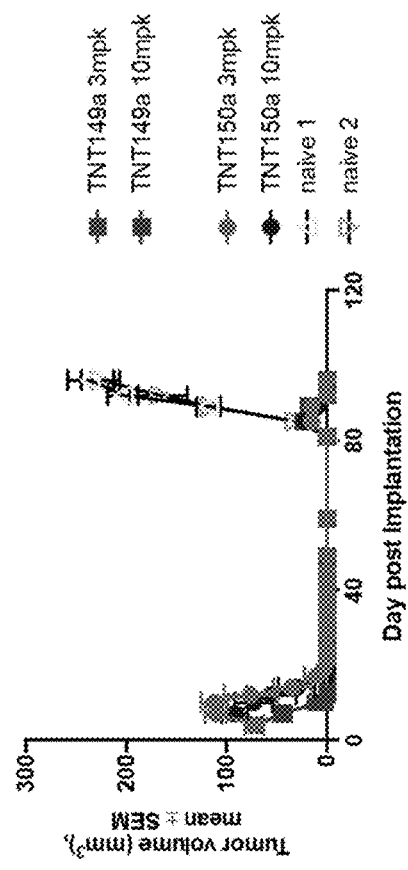
Figure 23E:
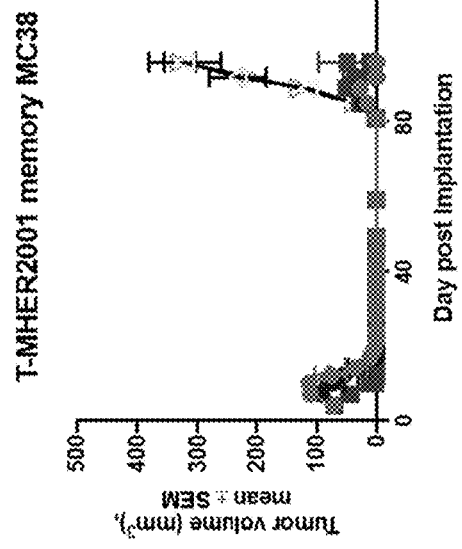
Figure 23F:
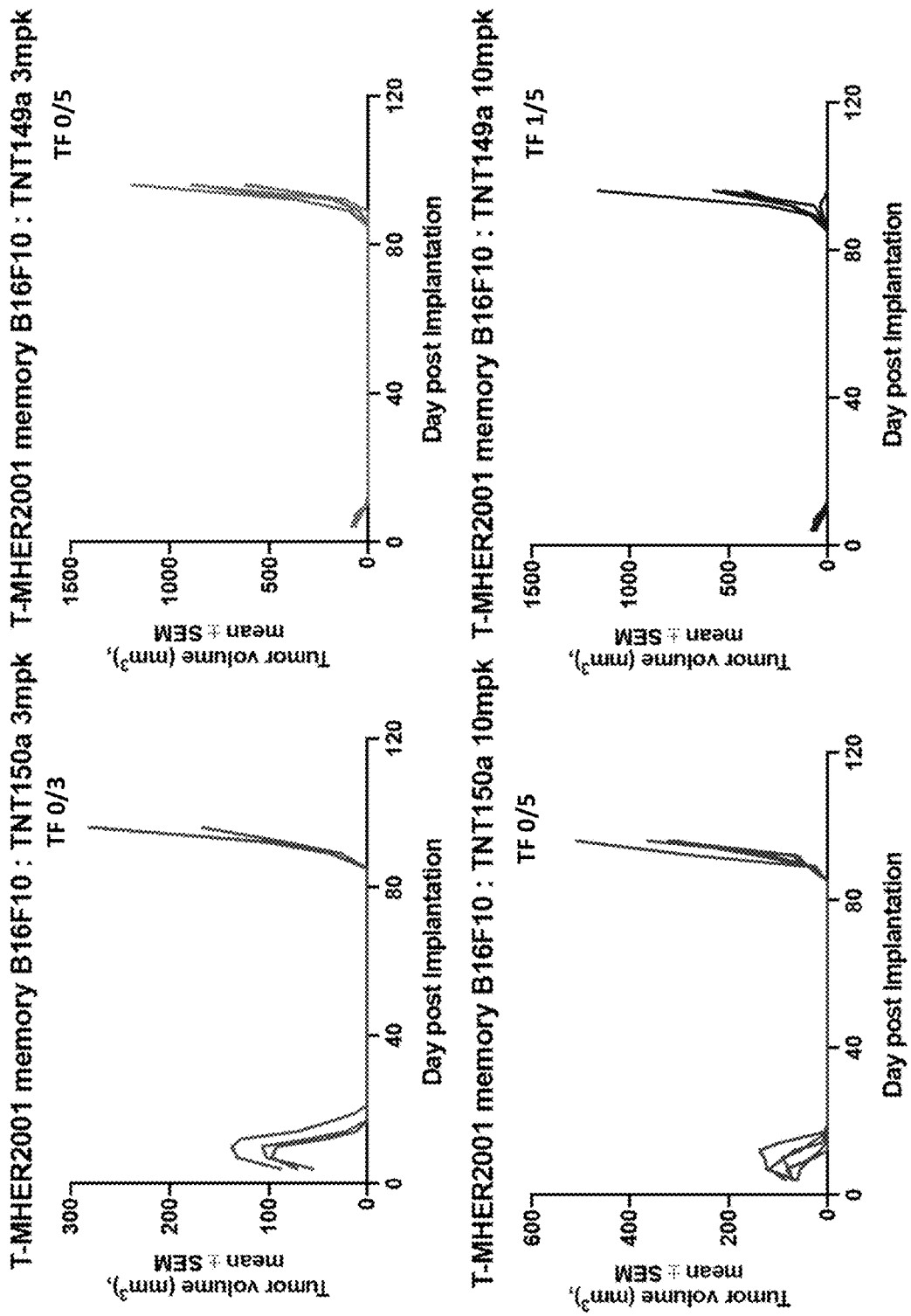
Figure 23G:
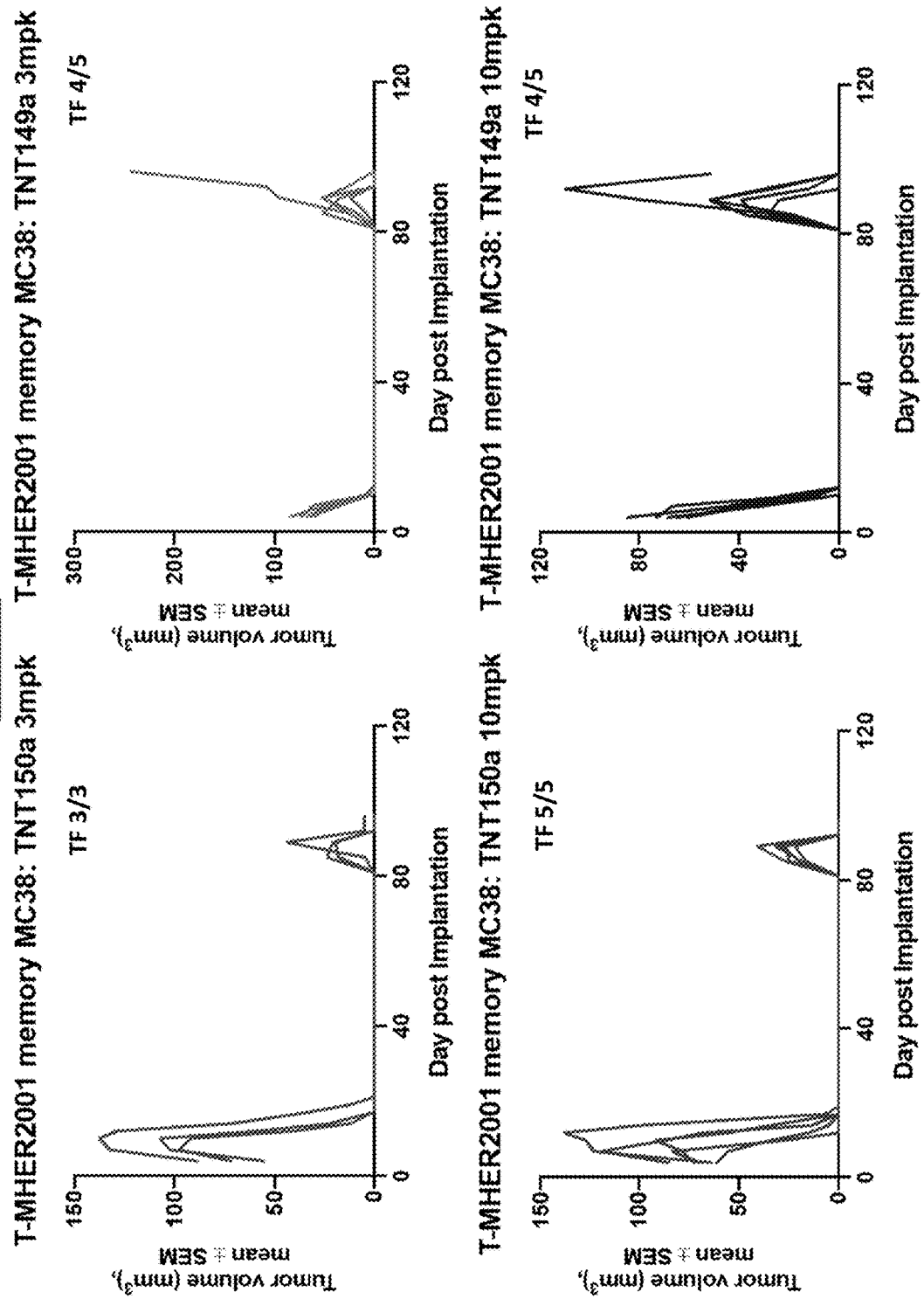
Figure 23I:
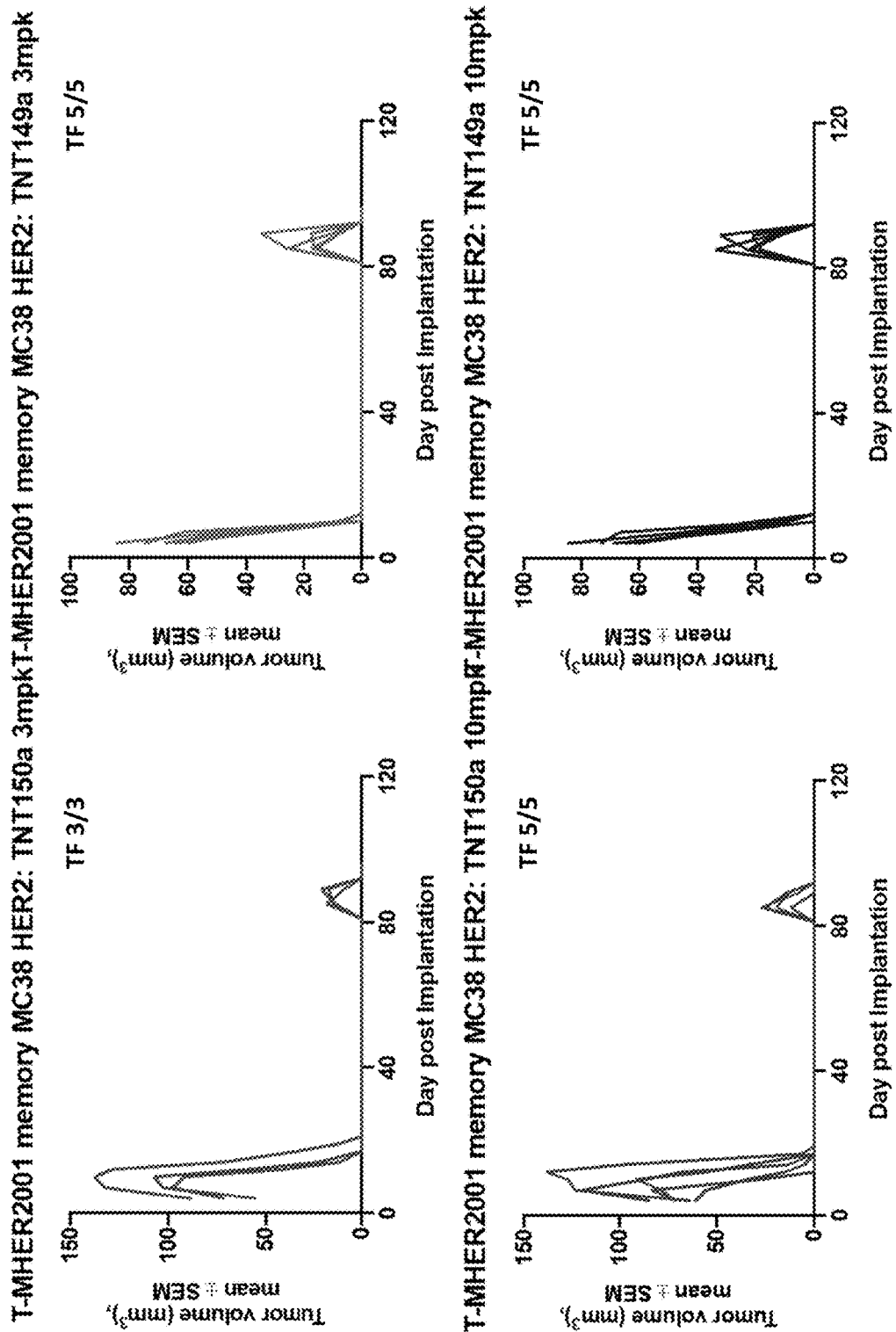

On day 81, there were 5 mice with eradicated tumors for groups treated with 10 mg/kg TNT150a, 3 and 10 mg/kg TNT149a and 3 mice with eradicated tumors for group treated with 3 mg/kg TNT150a. On day 81, mice with eradicated tumors were rechallenged with m/h Her2 MC38 (lower right flank), parent MC38 (lower left flank), m/h Her2 B16F10 (upper right flank) and parent B16F10 (upper left flank) at 2×10$^6$ cells (m/h Her2 MC38 and MC38 cells) and 1×10$^6$ cells (m/h Her2 B16F10 and B16F10 cells) per mouse in DMEM (FIG. 23A). Naïve mice that have not been implanted with m/h Her2 MC38 mice were included. Tumors were measured in two dimensions with calipers, and tumor volume was calculated as: length×width×width×0.5, where length was the larger of the two measurements.

As shown in FIGS. 23B-23I, naïve mice showed growth for all implanted cells. m/h Her2 B16F10, MC38 and m/h Her2 MC38 showed eradicated tumors or significant delayed tumor growth as compared to naïve. In all treatment groups, the parent B16F10 tumors grew except in one case, one of the mouse from the 10 mg/kg Her2 mIgG2a group shows no growth. By day 99, all mice showed complete eradication with m/h Her2 MC38 cells. Both MC38 parent and m/h Her2 B16F10 cells showed tumor eradication with the exception of one mouse for both 3 and 10 mg/kg mice previously treated with TNT149a for MC38 parent cells and 1-3 mice for all previously 3 and 10 mg/kg treated groups. These data show that m/h Her2 MC38 tumor bearing mice with eradicated tumors after treatment with anti-Her2 mIgG1 and mIgG2a have potent and durable anti-tumor response to m/h Her2 MC38, parent MC38 and m/h B16F10 but not parent B16F10 tumors. These results demonstrate epitope spreading to eradicate MC3 8 parental and Her2-expressing B16F10 cells, with slightly better durability seen at higher doses.

Example 13: Treatment with Anti-mCD22:CpG Oligonucleotide Conjugates Leads to Increased Gene Expression Signatures Related to Interferon Signaling, Antigen Presentation, and Cytotoxicity CT26 cells were injected into the right flank of BALB/C female mice, at a concentration of 2×10$^6$ cells per mouse in RPMI. Tumors were monitored until the average size of tumors reached 270-295 mm$^3$. Mice were randomized into PBS control, anti-mCD22 and anti-mCD22-CpG with 4 mice per cohort. Anti-mCD22 and anti-mCD22_CpG were administered intraperitoneally at 10 mg/kg. Tumors were harvested 8 hours post treatment and processed for RNA. All samples were processed and quantified using the Mouse PanCaner IO 360 Panel (NanoString Technologies) per manufacture's protocol by Canopy Biosciences (St. Louis, MO). Normalized expression data were analyzed with nSolver and nCounter Advanced Analysis Software and presented as signature scores. The CpG conjugated to anti-mCD22 is 4523 murine CpG oligonucleotide with the sequence of tucgtcgtgacgtt-c3, where lower case indicates phosphothioate linkages, bold indicates iodo-uridine, and underlining indicates phosphotriester linker (SEQ ID NO:121).

Figure 24B:
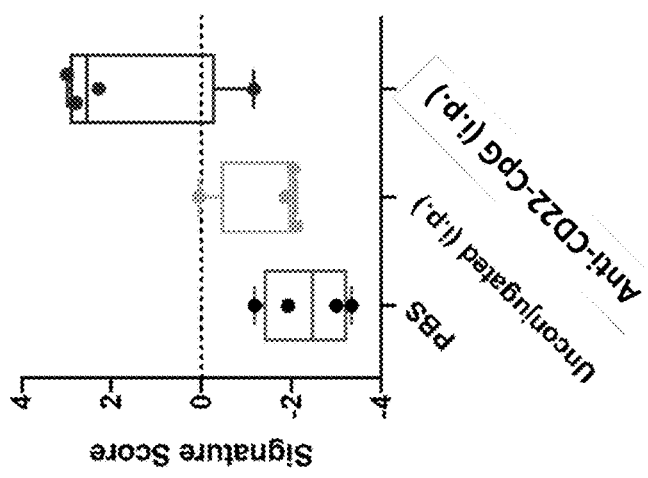
FIGS. 24A-24C show the results of NanoString gene expression analysis in 8 hours after IP administration of anti-mCD22:CpG oligo conjugates. Normalized expression data of the tumors were analyzed with nSolver and nCounter Advanced Analysis Software to obtain gene expression signatures as defined by NanoString. CT26-bearing mice treated with anti-mCD22 CpG showed higher signature scores for interferon signaling (FIG. 24A), antigen presentation (FIG. 24B), and cytotoxicity (FIG. 24C) in the tumor as compared to PBS control and anti-mCD22 alone.
Figure 24C:
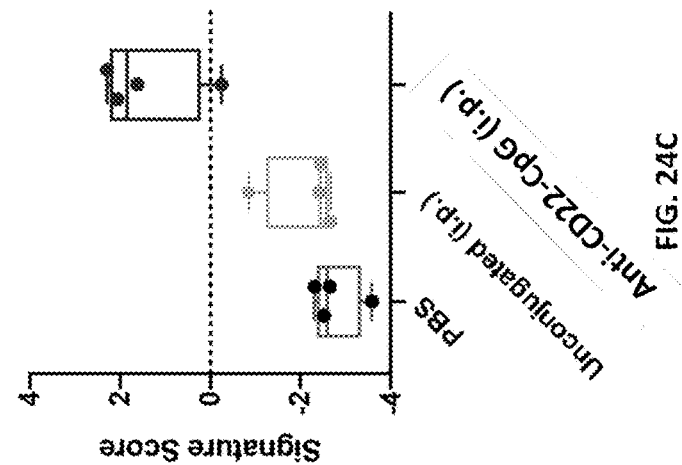
Figure 24A:
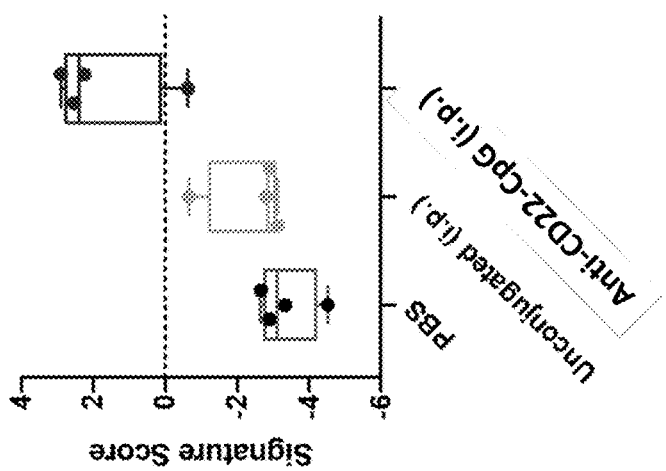

Normalized expression data of the tumors were analyzed with nSolver and nCounter Advanced Analysis Software to obtain gene expression signatures as defined by NanoString. CT26-bearing mice treated with anti-mCD22 CpG showed higher signature scores for interferon signaling (FIG. 24A), antigen presentation (FIG. 24B), and cytotoxicity (FIG. 24C) in the tumor as compared to PBS control and anti-mCD22 alone.

Example 14: Co-Culturing of Murine Bone Marrow-Derived Macrophages and Her2-Positive Tumor Cells in the Presence of Anti-Her2:CpG Conjugates with Active or Inactive Fc Regions CSFE labeled targets cells either Her2 P$^{pos}$ (MC38) or Her2$^{neg}$ (C1498) tumors were co-cultured with mouse-derived macrophages at a 1:2 ratio (target:effector) in the presence of unconjugated Her2, TNT149a, TNT150a or 4523 CpG starting at 100 nM diluted 1:2 (6 pts). Cells were incubated for 24 hrs, spun at 400×g to remove supernatant. Cells were then washed with PBS and transferred PBS with cells to new plate. Remaining cells in original plate were incubated with TrypLE for 10 min, cells were then scraped and transferred to same plate with PBS and cells. Collected cells were then spun and stained with fixable live dead dye, followed by fluorochrome labeled antibodies to mouse WWII and CD11b. Samples were acquired on an Attune flow cytometer (Thermofisher) with subsequent analysis using FlowJo Software and tabulated using Prism Software.

Figure 25:
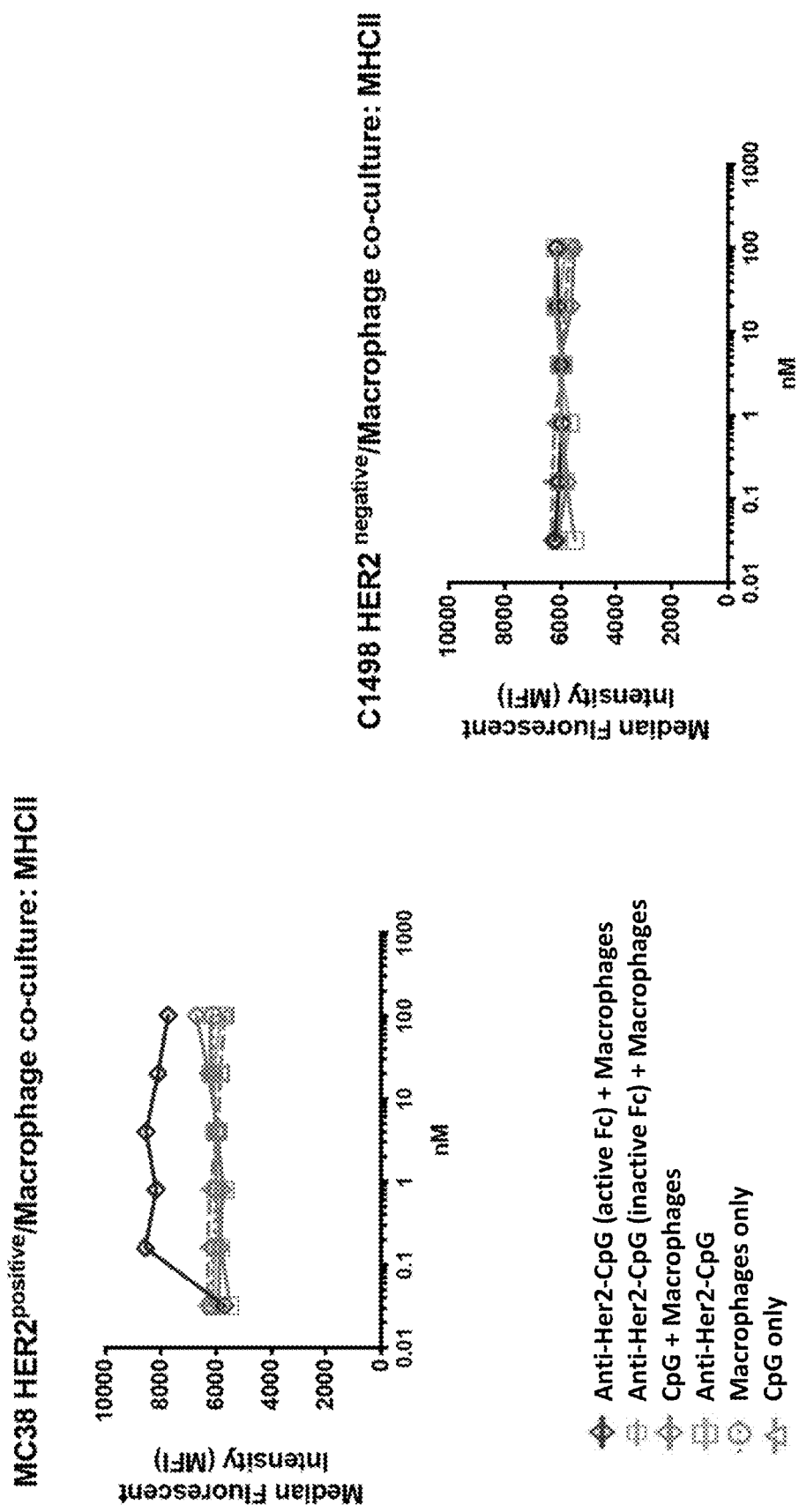
FIG. 25 shows the results of co-culturing murine bone marrow-derived macrophages with Her2-positive or Her2-negative tumor cells in the presence of anti-Her2:CpG conjugates with active or inactive Fc regions.

Bone marrow-derived mouse macrophages were co-cultured in the presence of Her2$^{pos}$ (MC38) or Her2$^{neg}$ (C1498) tumors and treated with anti-Her2, TNT149a, TNT150a or 4523 CpG for 24 hrs. Median WWII was assessed by flow cytometry. Upregulation of WWII activation marker was observed on murine macrophages when co-cultured with Her2$^{pos}$ tumors in the presence of active Her2-CpG conjugate (TNT149a), but not Her2$^{neg}$ tumors, suggesting that presence of Her2 is required for macrophage activation as evidenced by MHCII induction (FIG. 25). Additionally, active Fc (TNT149a) appears to be required for murine macrophage activation in vitro as evidenced by lack of MHCII induction with less active Fc (TNT150a).

Example 15: Induction of B Cell Activation in Human PBMCs by Anti-CD22:CpG Oligonucleotide Conjugates Human peripheral blood mononuclear cells (PBMCs) were isolated from Trima residuals (Vitalant) and diluted 1:4 with Phosphate Buffered Saline (PBS, Gibco). Diluted blood was split into tubes and underlayed with 15 mL Ficoll-Paque (GE Healthcare). Tubes were centrifuged for 30 minutes at 400×g. PBMCs were collected from the interface and resuspended in Complete RPMI (RPMI+10% FBS). One million PBMCs were plated in 96 round well plates in Complete RPMI and treated with anti-CD22 antibody with RH2 VH domain and RL1 N92S VL domain (SEQ ID Nos:65 and 87, respectively) conjugated to 7-7 CpG, TNT52 (RFB4 anti-CD22 conjugated to 12070), 7-7, 12070 or media only starting at a concentration of 100 nM for conjugated antibodies or 1 uM for free CpG followed by 1:5 titration down. Cells were then incubated for 48 hrs prior to flow staining. Cells were centrifuged at 400×g for 5 min before media removal. Cells were then incubated with fixable live dead dye eFluor780 (eBioscience) for 30 min at 4C. FACS buffer (PBS+2% FBS) was added to the wells before centrifugation at 400×g for 5 min. Cells were then incubated in human FcR blocking reagent (Miltenyi Biotec) and stained with fluorochrome-labeled antibodies against CD19, CD40, CD80 and CD86 for 1 hr at 4C. Cells were then washed twice in FACS buffer before fixing in 0.5% paraformaldehyde. Cells were acquired on an Attune NxT cytometer (Thermofisher) with subsequent analysis using FlowJo Software and tabulated using Prism Software.

Human PBMCs were stimulated for 48 hrs in presence of anti-CD22 antibody with RH2 VH domain and RL1 N92S VL domain (SEQ ID Nos:65 and 87, respectively) conjugated to compound 7.7b (7-7) CpG, TNT52a (RFB4 conjugated to 12070), compound 7.7b (7-7) CpG, 12070 CpG, or media only. Cells were then stained and analyzed by flow cytometry. Following singlet and dead cell exclusion, CD20+B cells were gated, followed by median fluorescent intensity of CD40 (FIG. 26A), CD80 (FIG. 26B) and CD86 (FIG. 26C) activation markers. Anti-CD22 antibody with RH2 VH domain and RL1 N92S VL domain conjugated to compound 7.7b (7-7 CpG) displayed higher induction of all activation markers on gated B cells that is superior to RFB4-conjugated to 12070. Additionally, free 7.7b CpG induced superior activation of all interrogated markers compared to 12070 CpG.

Example 16: Evaluation of Free CpG Activity on CD40 Expression by CD19+ B Cells

Materials and Methods

Trima residuals were received from Vitalant and diluted 1:2 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface, resuspended and washed in FACS buffer (PBS with 0.5% Bovine Serum Albumin (Gibco)). After one wash, PBMCs were resuspended in Complete RPMI (RPMI+10% FBS).

PBMCs were immediately plated onto a 96-well format (500K/well) in Complete RPMI. Five-fold serial dilutions were added to the cells from 1 uM to 64 pM of CpG polynucleotides at 37° C. under 5% CO2 for 48 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR Blocking Reagent (Miltenyi Biotec), anti-CD19, anti-CD20, anti-CD40, anti-HLADR and anti-CD80. Cells were centrifuged and washed twice in FACS buffer and fixed in 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. B cells were identified as CD19+CD20+ cells and level of activation marker was assessed by median fluorescent intensity.

For Ramos NFkb Reporter Assay, Ramos-Blue Cells NF-kB/AP-1 Reporter B lymphocytes were purchased from Invivogen. Cells were grown and maintained in complete DMEM supplemented with 2 mM L-glutamine, 10% FBS, 100 ug/mL Normacin, Pen-Strep, 100 ug/mL Zeocin. Stimulation of the Ramos-Blue cells was performed. Briefly, cells were rinsed in growth medium without antibiotics. Cells were counted and resuspended in fresh complete DMEM without selection antibiotics at a density of $2 \times 10^6$ cell/mL. 20 uL of 10 uM CpG 7-7, CpG 12070 and ODN2006 titrated 1:5 were added to a flat-bottom 96-well plate, 180 uL of the cell suspension were added to a final concentration of 1 uM to 64 pM of CpG. Plate was incubated at 37° C. in a 5% CO2 incubator for 24h. On day of assay, QB reagent and QB buffer were thawed before us. Quanti-Blue solution was prepared by adding 1 mL of QB reagent and 1 mL of 1 mL of QB buffer to 98 mL of sterile water in a sterile glass bottle. 180 uL of Quanti-Blue solution was dispensed per well into a new flat-bottom 96-well plate. 20 uL of supernatant from treated Ramos-Blue cells was then added to the 96-well plate. Plate was ten incubated for 6h. Optical density was measured at OD655 using a plate reader (Molecular Devices), and data was tabulated in GraphPad Prism 9.0.

Results

Figure 27:
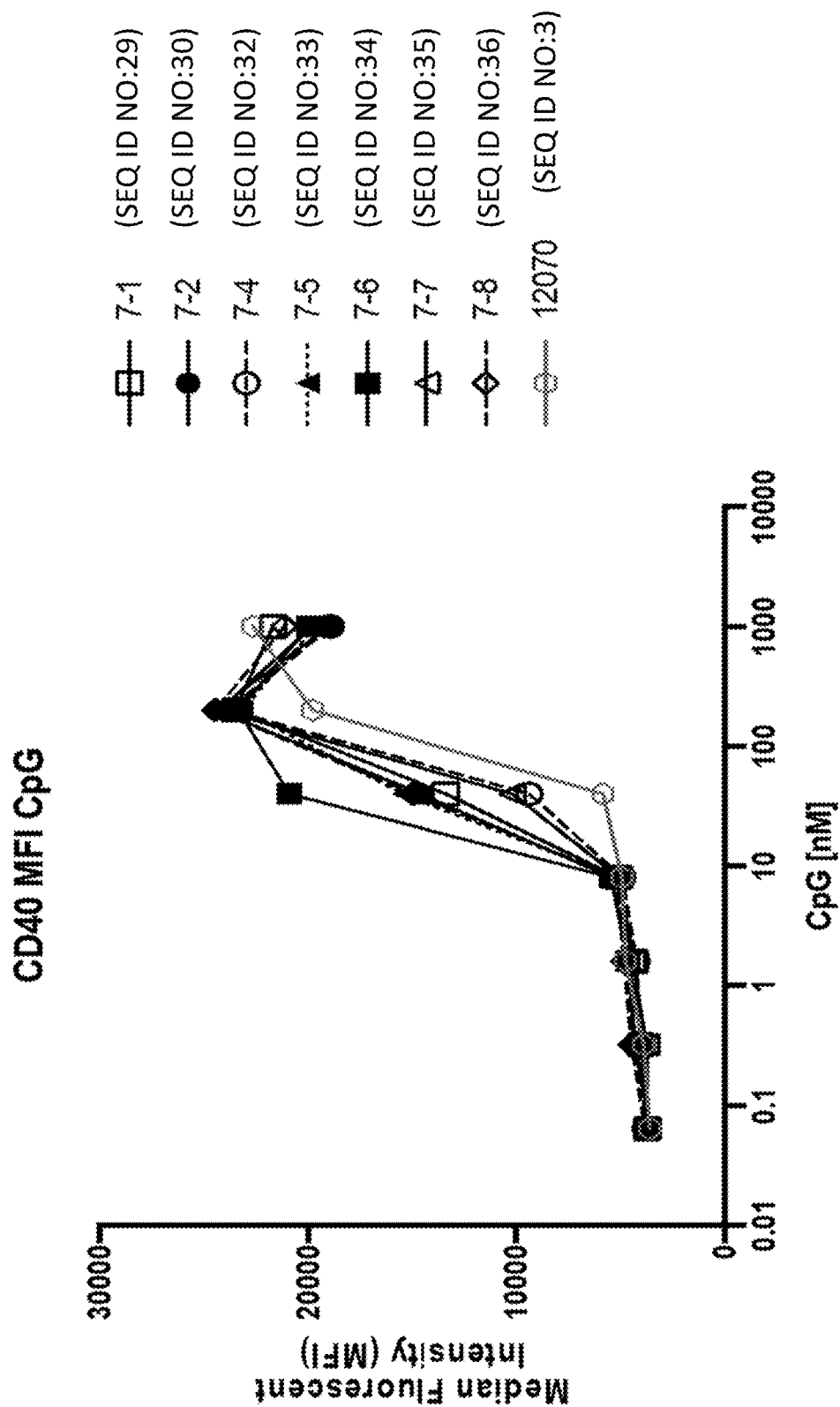
FIG. 27 shows activity of indicated free CpG oligonucleotides on human PBMCs, as assayed by CD40 expression on CD19+ B cells.

Human PBMCs were treated with free CpGs to evaluate their respective activities as observed by CD40 expression on CD19 positive B cells. As shown in FIG. 27, series 7 CpGs (SEQ ID NOS: 29, 30, and 32-36) all showed enhanced activities compared with CpG 12070 (SEQ ID NO: 3).

Figure 28:
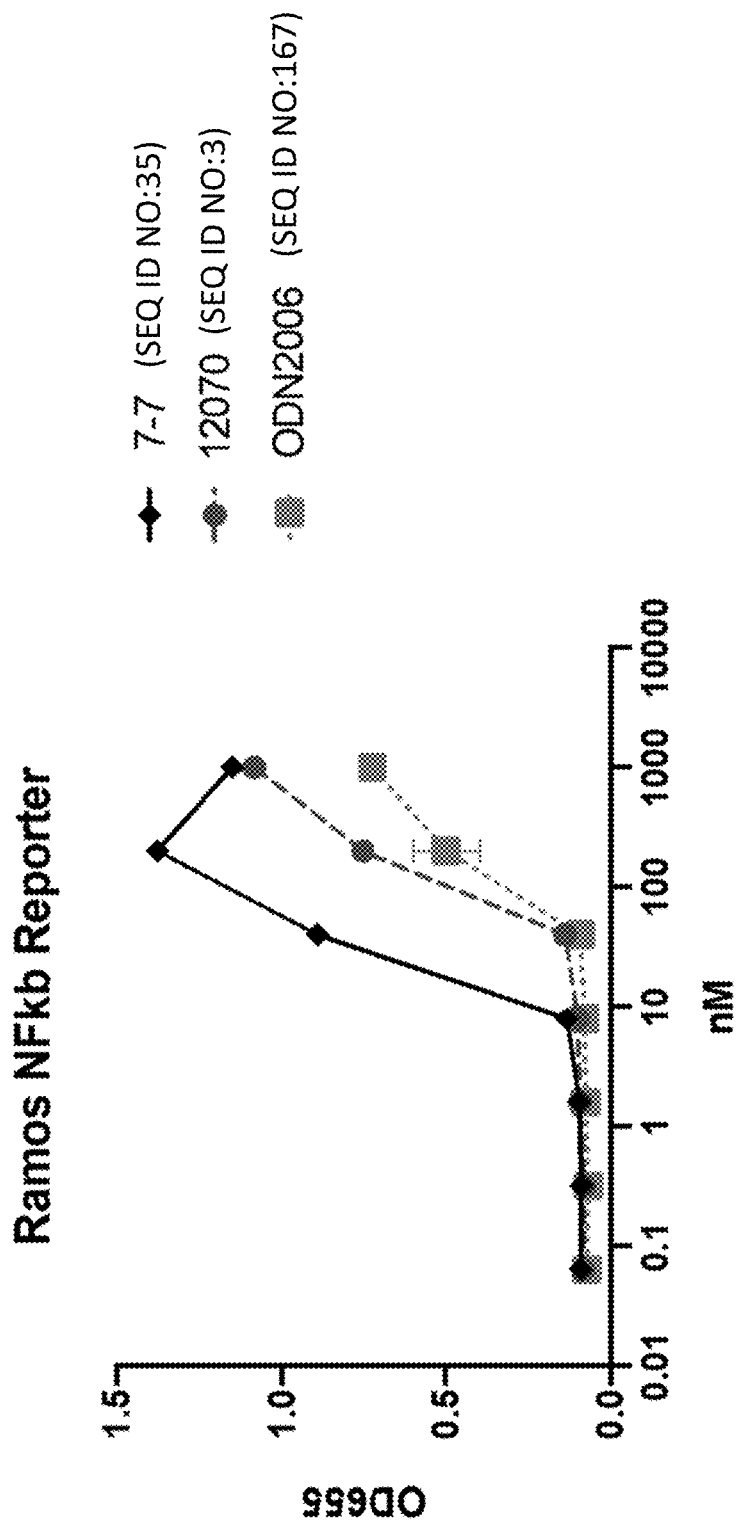
FIG. 28 shows activity of indicated free CpG oligonucleotides on human PBMCs, as assayed by Ramos NFkb Reporter Assay.

CpG oligos 7-7, 12070 and ODN2006 (5'-tcgtcgttttgtcgttttgtcgtt-3'; SEQ ID NO:167) were compared in a NFkb reporter assay. As shown in FIG. 28, CpG 7-7 showed significantly higher activity as compared to 12070 and ODN2006.

Example 17: Evaluation of CpG Activity on PBMCs from Different Donors

The activity of CpG oligos 7-6, 7-7 and 12070 were compared for activity in PBMC cells from three different donor lines (D559, D804 and D643) as observed by CD40 expression. The evaluation of activity of the CpG oligos was performed using the same methods as Example 16 above.

Figure 29A:
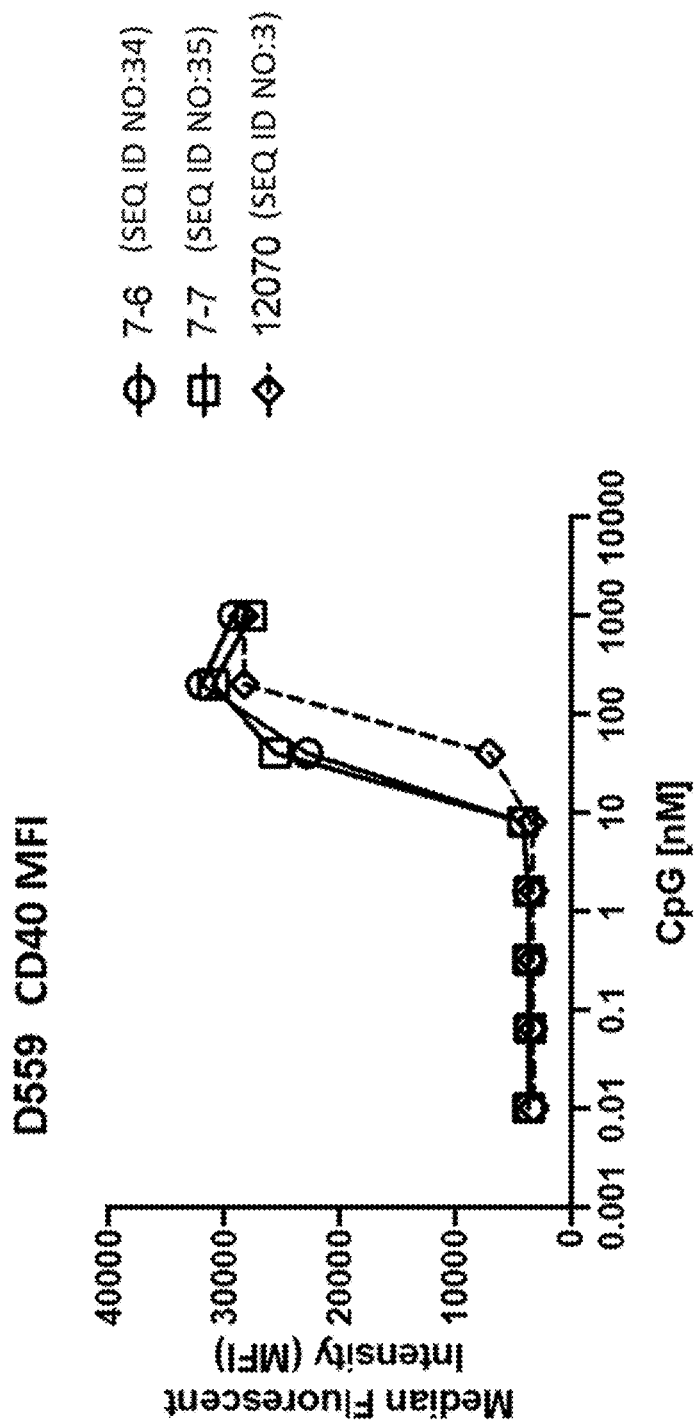
FIGS. 29A-29C show activity of indicated free CpG oligonucleotides on human PBMCs from three different donor lines (D559, D804 and D643), as observed by CD40 expression.
Figure 29B:
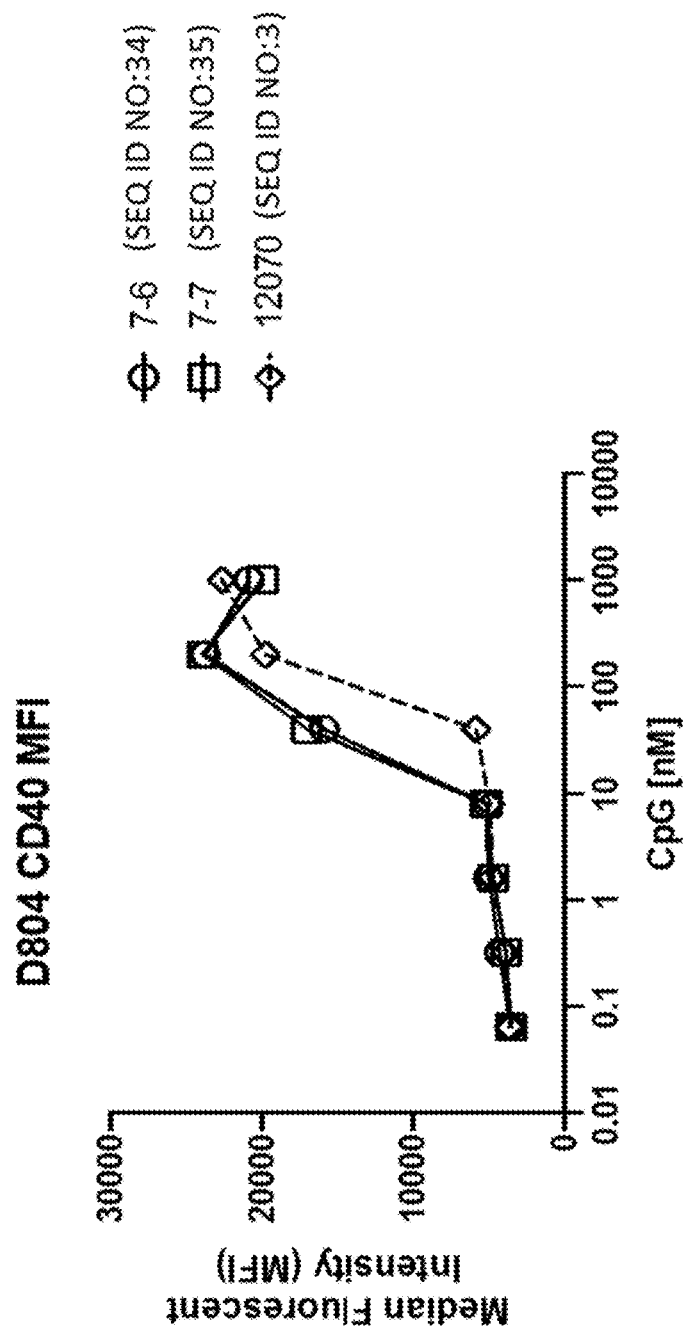
Figure 29C:
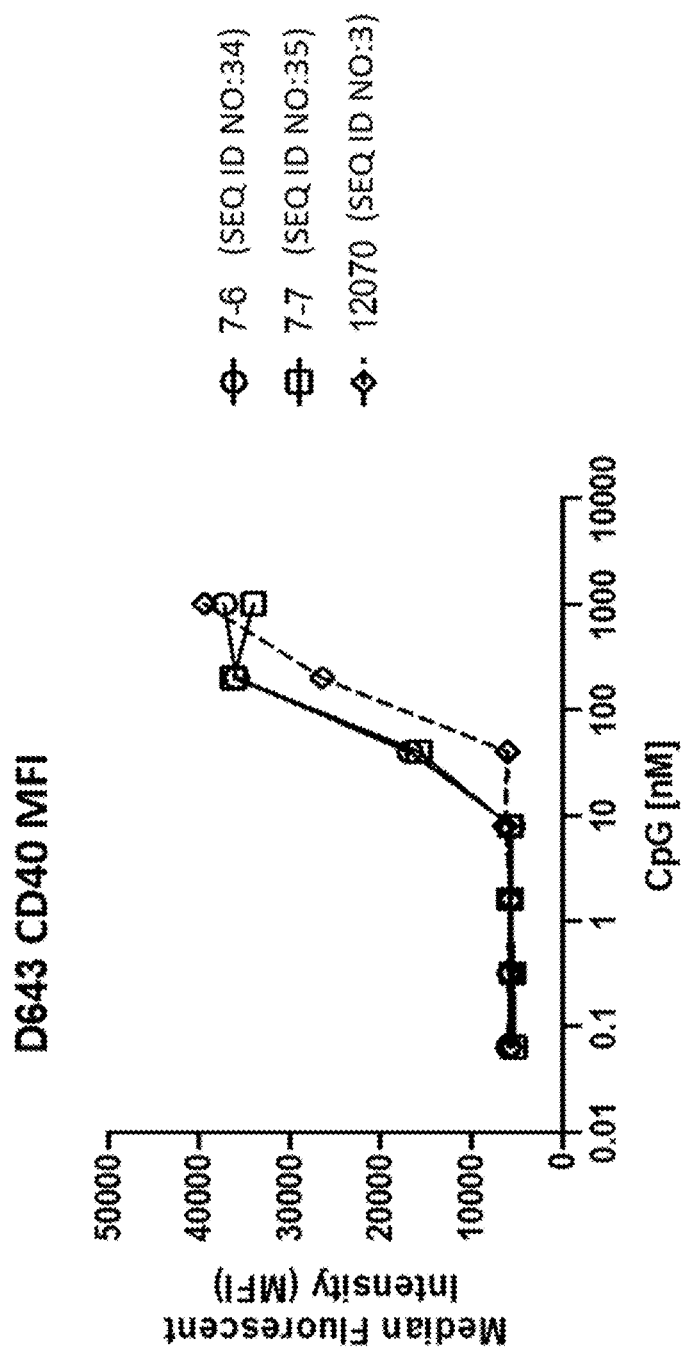

The results showed that the higher activities of 7-6 and 7-7 compared with 12070 were not dependent on the donor (FIGS. 29A-29C).

Example 18: Contributions of 5' Bromo 2'Deoxyuridine and PEG Linkage to CpG Activity For evaluation of CpG oligonucleotides in human PBMCs, Trima residuals were received from Vitalant and diluted 1:4 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface and resuspended in FACS buffer (PBS with 0.5% Bovine Serum Albumin (Gibco)). PBMCs were immediately plated onto a 96-well format (500K/well) in Complete RPMI (RPMI+10% FBS). Five-fold serial dilutions were added to the cells from 1 uM to 64 pM of CpG polynucleotides at 37° C. under 5% CO2 for 48 to 96 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR. Blocking Reagent (Miltenyi Biotec), anti-CD19, anti-CD40, and anti-CD86. Cells were centrifuged and washed twice in FACS buffer and fixed in 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. Gating CD19+, CD20+ or CD19+CD20+ cells to identify B cells. Data was tabulated using GraphPad Prism 9.0.

Figure 30:
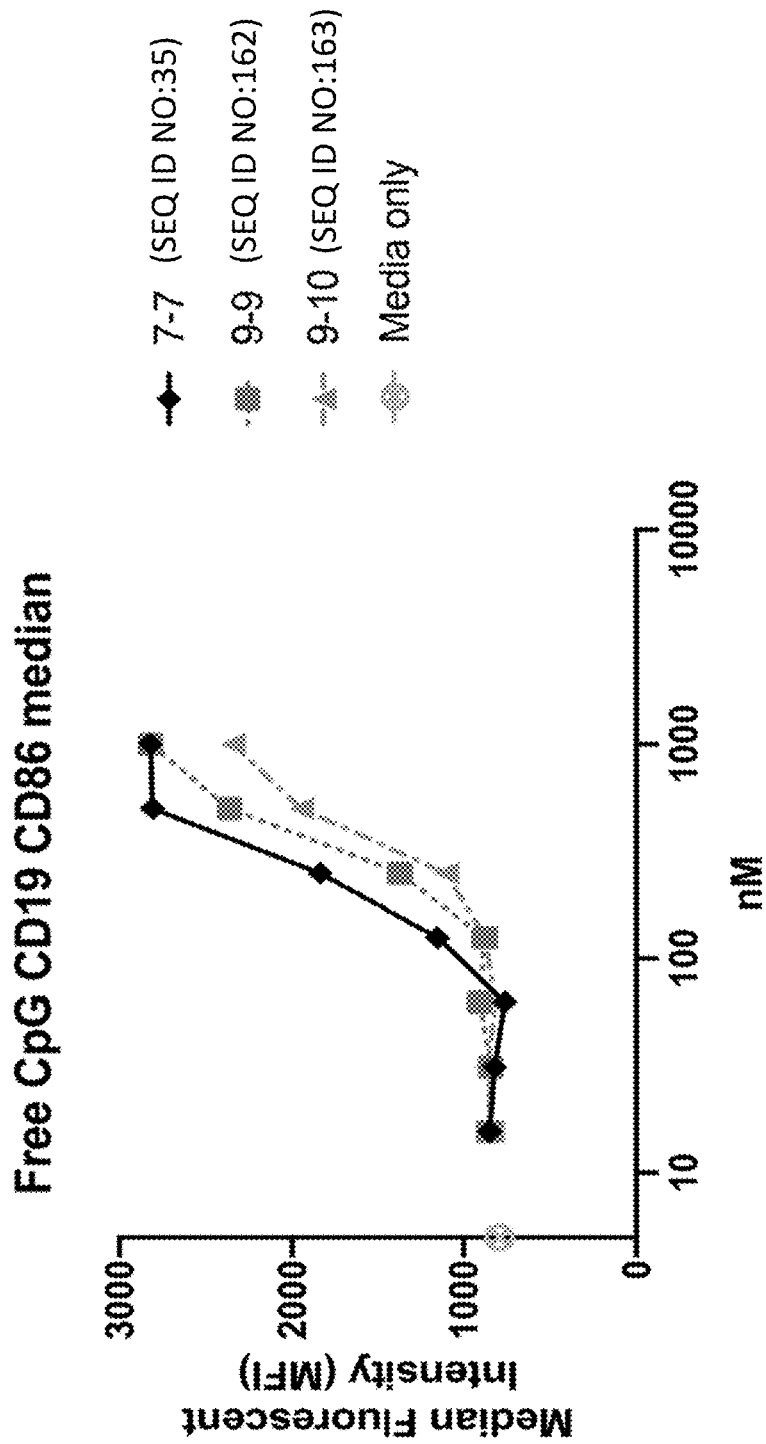
FIG. 30 shows activity of indicated free CpG oligonucleotides on human PBMCs, as assayed by CD40 expression on CD19+ B cells.

As shown in FIG. 30, CpG oligonucleotides 9-9 and 9-10 without the bromo modification at the 5' uridine activated CD86 expression. This implies that the bromo modification is not an essential component of the respective oligonucleotides.

Example 19: Biological Evaluation of CpG-Nucleotides and Antibody-CpG Nucleotide Conjugates Trima residuals were received from Vitalant and diluted 1:2 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface, resuspended and washed in FACS buffer (PBS with 0.5% Bovine Serum Albumin (Gibco)). After one wash, PBMCs were resuspended in Complete RPMI (RPMI+10% FBS). PBMCs were immediately plated onto a 96-well format (500K/well) in Complete RPMI. Five-fold serial dilutions were added to the cells from 100 nM to 6.4 pM conjugated antibody at 37° C. under 5% CO2 for 48 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR Blocking Reagent (Miltenyi Biotec), anti-CD19, anti-CD20, anti-CD40, anti-HLADR and anti-CD80. Cells were centrifuged and washed twice in FACS buffer and fixed in 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. B cells were identified as CD19+ CD20+ cells and level of activation marker was assessed by median fluorescent intensity.

TNT127=RL1_hKappa N92A+RH2_hIgG1_AAA+S-tag (SEQ ID Nos: 73 and 65, respectively)
TNT130a=TNT127 with N92A mutation conjugated to CpG 12070 (DAR1)
TNT133a=TNT127 with N92A mutation conjugated to CpG 7-6 (DAR1)
TNT134a=TNT127 with N92A mutation conjugated to CpG 7-7 (DAR1)

Figure 31:
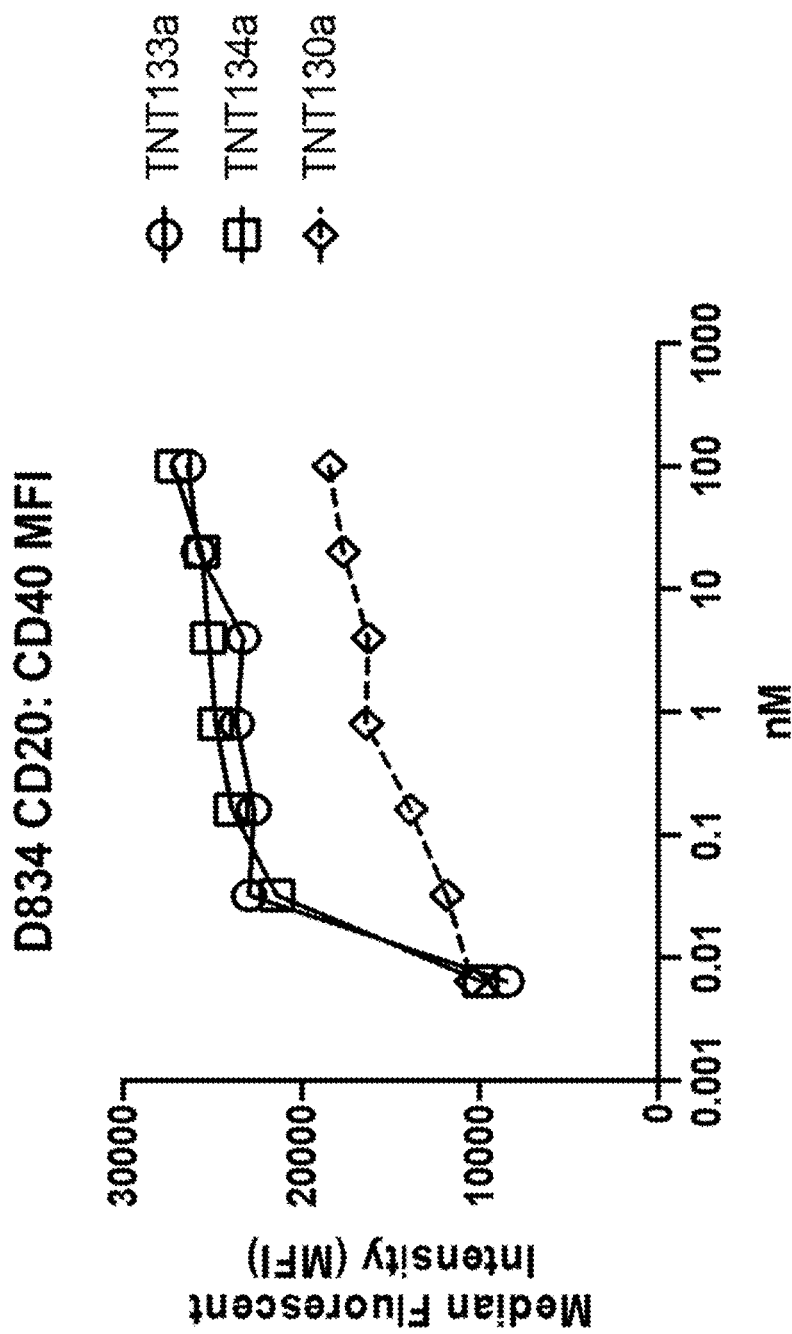
FIG. 31 shows activity of CpG:antibody conjugates on human PBMCs, as assayed by CD40 expression on CD19+ B cells.

The activity of antibody TNT127 was compared when conjugated to CpGs 7-6, 7-7 and 12070. As shown in FIG. 31, antibody conjugates with CpG 7-6 (SEQ ID NO:34) and 7-7 (SEQ ID NO:35) demonstrated substantially better activity as compared to the 12070 (SEQ ID NO:3) conjugate, as observed by CD40 expression.

Example 20: Comparison of Anti-CD22 Antibody:CpG Oligonucleotide Conjugates

Figure 32A:
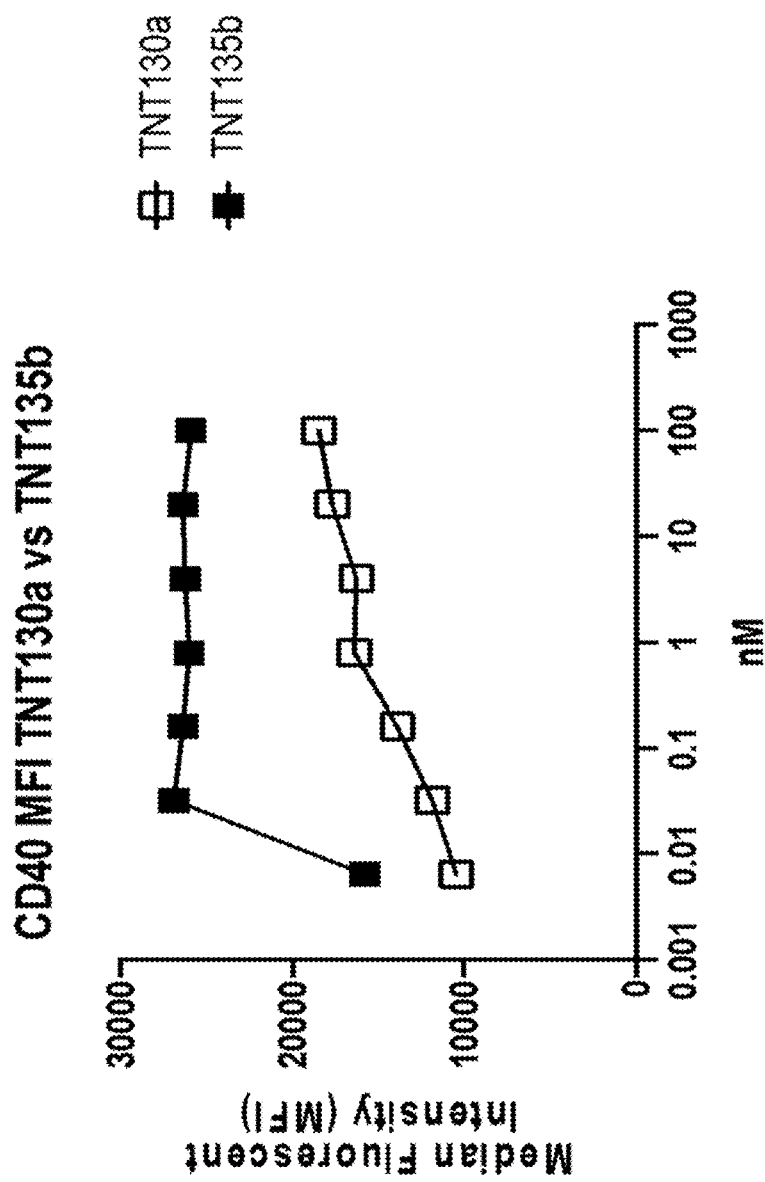
FIGS. 32A-32C show activity of indicated anti-CD22 antibody:CpG oligonucleotide conjugates on human PBMCs, as assayed by CD40 expression on CD19+ B cells.
Figure 32B:
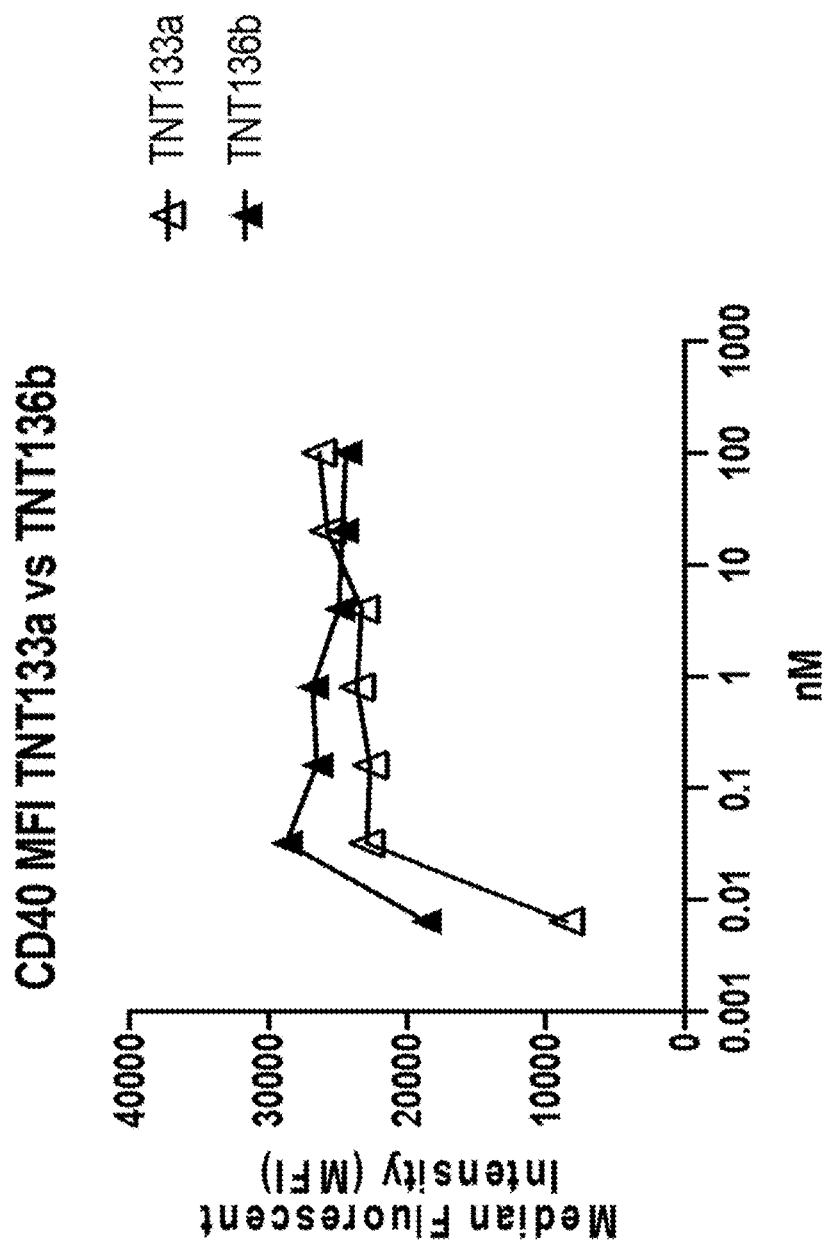
Figure 32C:
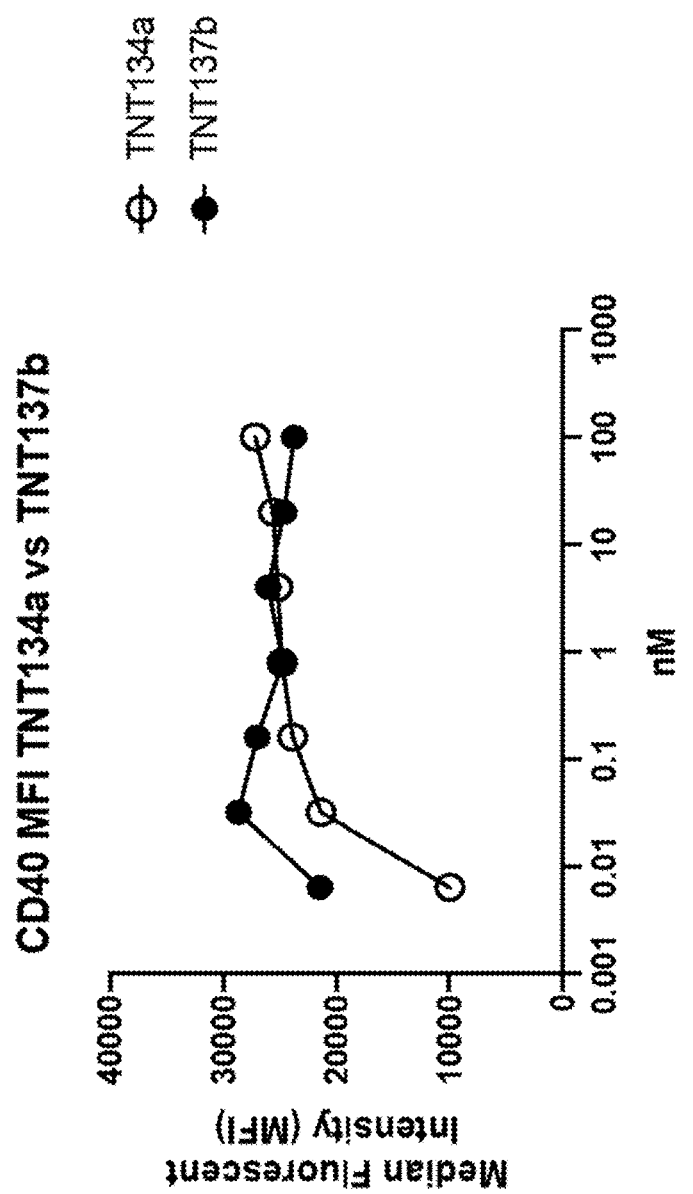

The activity of CD22 antibody-CpG conjugates DAR1 and DAR2 were compared for activity. In all cases tested, at the lower concentration ranges of conjugate, the DAR2 conjugates displayed higher activity as compared to the DAR1 conjugates (FIGS. 32A-32C). However, the DAR1 conjugates with the 7-6 and 7-7 CpGs displayed higher activity that was more comparable to DAR2. Methods were as described in Example 19.

TNT135b=TNT127 with N92A mutation conjugated to CpG 12070 (DAR2)
TNT136b=TNT127 with N92A mutation conjugated to CpG 7-6 (DAR2)
TNT137b=TNT127 with N92A mutation conjugated to CpG 7-7 (DAR2)
TNT130a=TNT127 with N92A mutation conjugated to CpG 12070 (DAR1)
TNT133a=TNT127 with N92A mutation conjugated to CpG 7-6 (DAR1)
TNT134a=TNT127 with N92A mutation conjugated to CpG 7-7 (DAR1)

Example 21: Anti-CD22 Antibody:CpG Oligonucleotide Conjugate Mediates Tumor Killing in the Absence of an Active Fc Domain Immune cell mediated anti-tumor response was tested in a tumor bearing syngeneic model using anti-CD22 CpG oligonucleotide comprising an inactive Fc using the mouse IgG1 N297A Fc. CT26 mouse colon carcinoma cells (ATCC) were cultured in Complete RPMI 1640 (RPMI1640+10% FBS (Gibco)) at 37° C. and 5% CO2. Once cells were 80% confluent, cells were detached with Trypsin 0.25% (Gibco) and washed twice with RPMI 1640 (Gibco). Cells were resuspended at 20E6/mL in RPMI 1640 and kept on ice until use. 100 uL of suspended cells were subcutaneously implanted into the right flank of 6 week old female BALB/c mice (Charles River). Tumor size was measured and recorded twice a week with calipers starting 7 days post implantation until duration of the study, approximately 27 days later. Tumor volume was estimated using the following formula: (length×width×width)/2. Once tumors reached 120 or 250 mm3, approximately 7 days post implantation, mice were randomized by tumor size and treatments were initiated. The conjugates were administered intravenously 1 to 3 doses every 3 days at 10 mg/kg. Mice whose tumors exceeded 2,000 mm$^3$ or exhibited any signs of distress at any time during the study were killed humanely as per IACUC-approved animal protocols.

Figure 33:
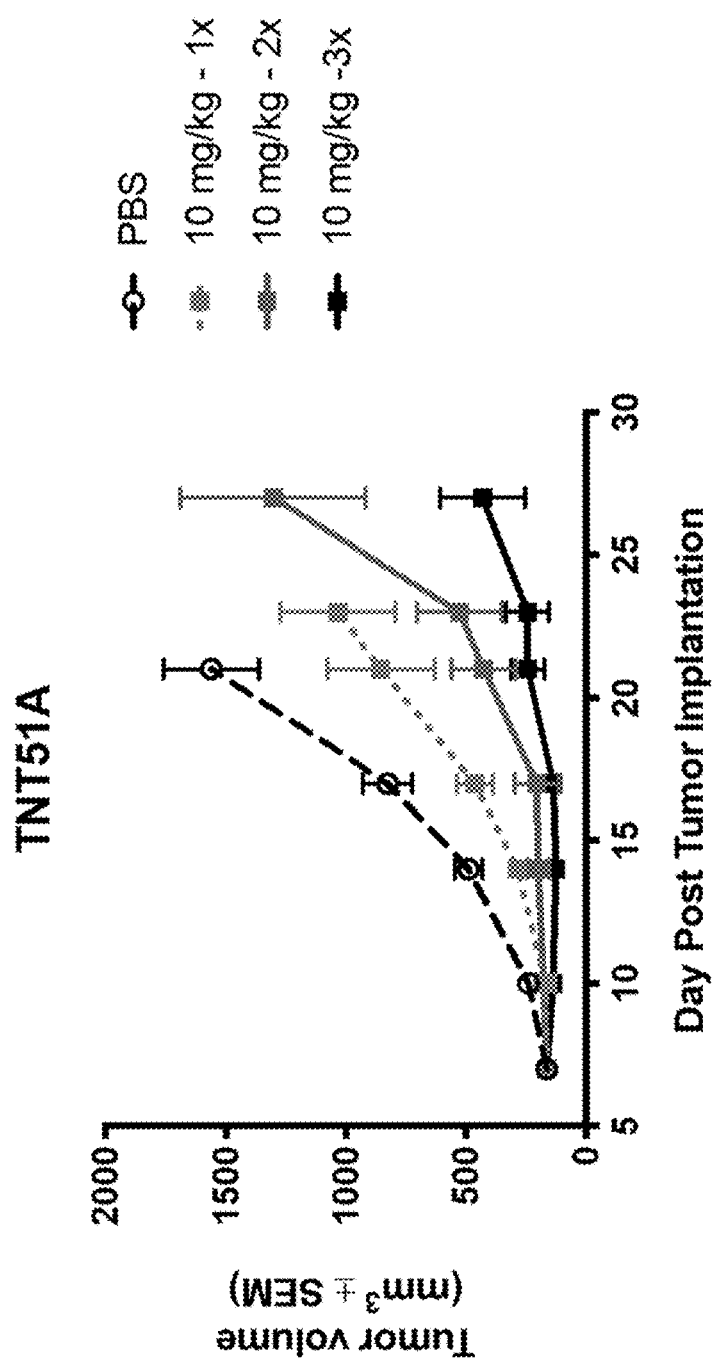
FIG. 33 shows tumor volume over time after treatment with anti-CD22 antibody:CpG oligonucleotide conjugate having a "dead" Fc domain at the indicated number of doses, as compared to PBS. Tumor bearing syngeneic model using CT26 mouse colon carcinoma cells was used. The conjugates were administered intravenously 1 to 3 doses every 3 days at 10 mg/kg.

As shown in FIG. 33, antitumor activity was observed with all dosing schedules with most effective antitumor activity when the anti-CD22-4523 conjugates (inactive Fc) being administered intravenously 1 to 3 doses every 3 days at 10 mg/kg.

Example 22: Activation of TLR9 by Anti-CD22 Antibody:CpG Oligonucleotide Conjugates For biological evaluation of CpG-oligonucleotides and antibody-CpG oligonucleotide conjugates, Trima residuals were received from Vitalant and diluted 1:2 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface, resuspended and washed in FACS buffer (PBS with 0.5% Bovine Serum Albumin (Gibco)). After one wash, PBMCs were resuspended in Complete RPMI (RPMI+10% FBS). PBMCs were immediately plated onto a 96-well format (500K/well) in Complete RPMI. Five-fold serial dilutions were added to the cells from 1 uM to 64 pM of CpG polynucleotides or 100 nM to 6.4 pM conjugated antibody at 37° C. under 5% CO2 for 18 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR Blocking Reagent (Miltenyi Biotec), anti-CD19, anti-CD20, anti-CD40, anti-HLADR, anti-CD80, anti-CD86, anti-CD3, anti-CD14, anti-CD11c, anti-CD69 and anti-CD56. Cells were centrifuged and washed twice in FACS buffer and fixed in 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. B cells were identified as CD19+CD20+ cells, T cells as CD3+CD56−, DC as CD11chiHLADR+, and monocytes as CD14+ and level of activation marker was assessed by median fluorescent intensity.

TNT138a=anti-CD22 antibody having RH2 VH domain and RL1 N92S VL domain (SEQ ID Nos:65 and 87, respectively) conjugated to compound 7.7b (7-7) CpG (SEQ ID NO:35)

Figure 34A:
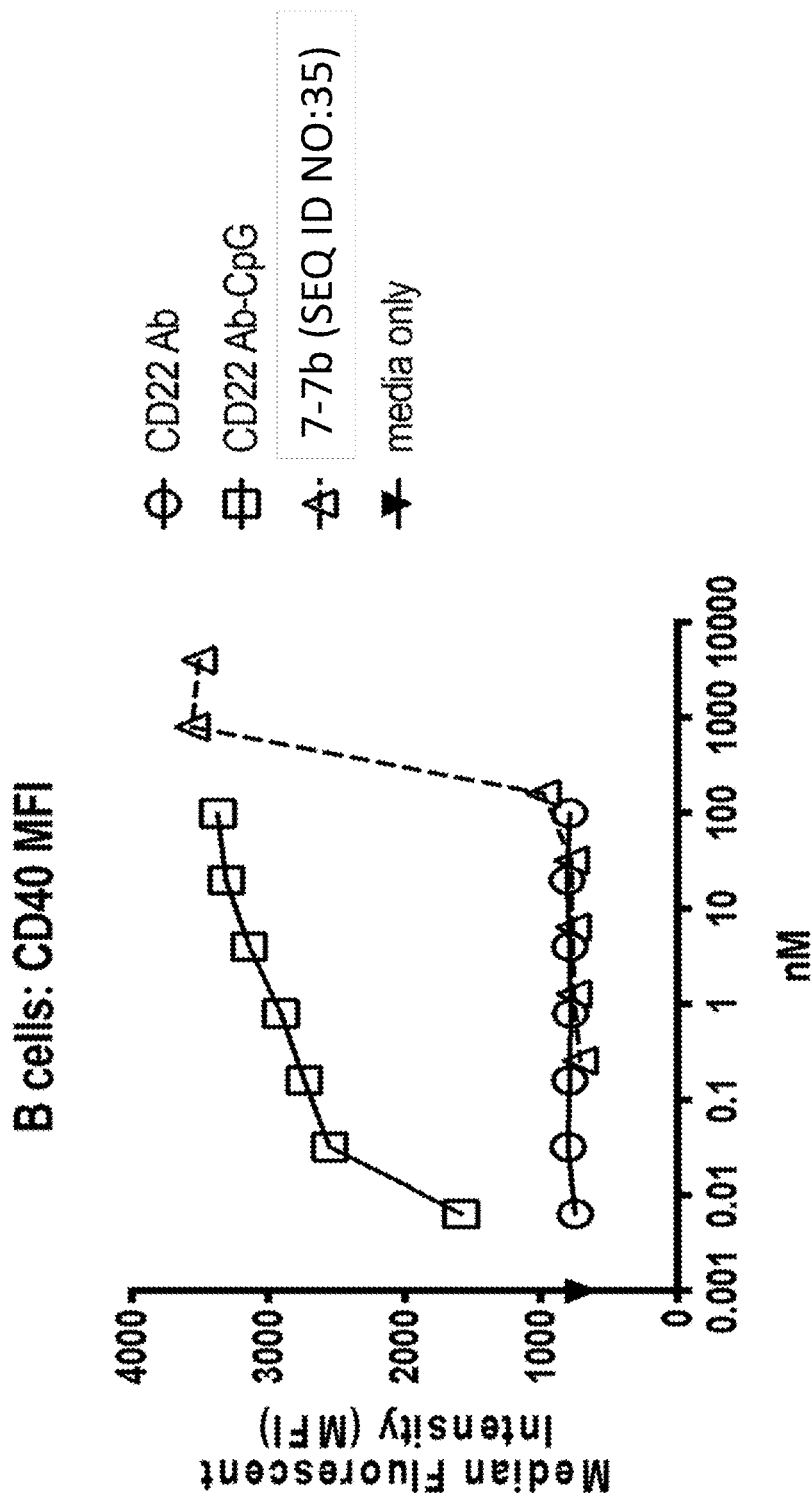
FIGS. 34A-34D show effects of treatment with unconjugated CpG oligonucleotide, unconjugated anti-CD22 antibody, or anti-CD22 antibody:CpG oligonucleotide conjugate on different types of immune cells. Effects on B cells were assayed using the CD40 activation marker (FIG. 34A), effects on dendritic cells were assayed using the CD80 activation marker (FIG. 34B), effects on CD14+ myeloid cells were assayed using the CD86 activation marker (FIG. 34C), and effects on T cells were assayed using the CD69 activation marker (FIG. 34D).
Figure 34B:
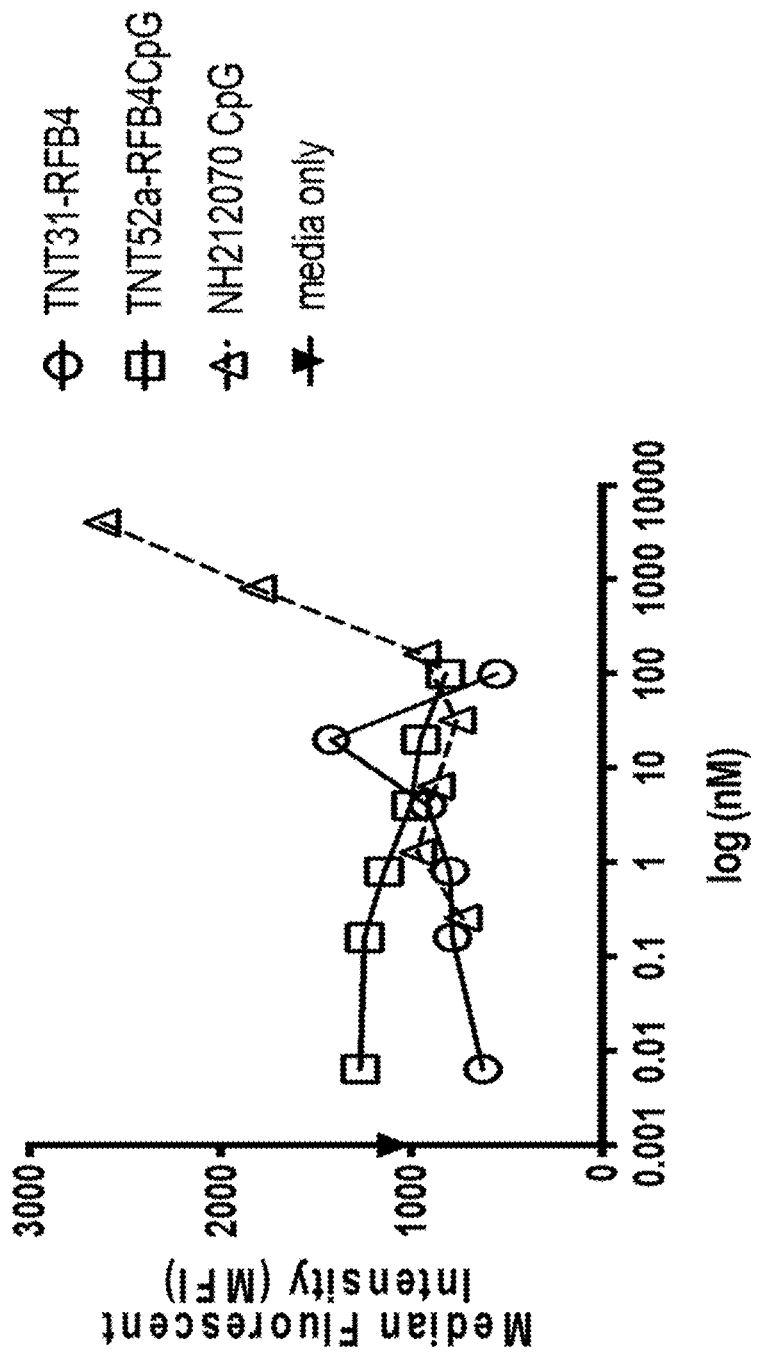
Figure 34C:
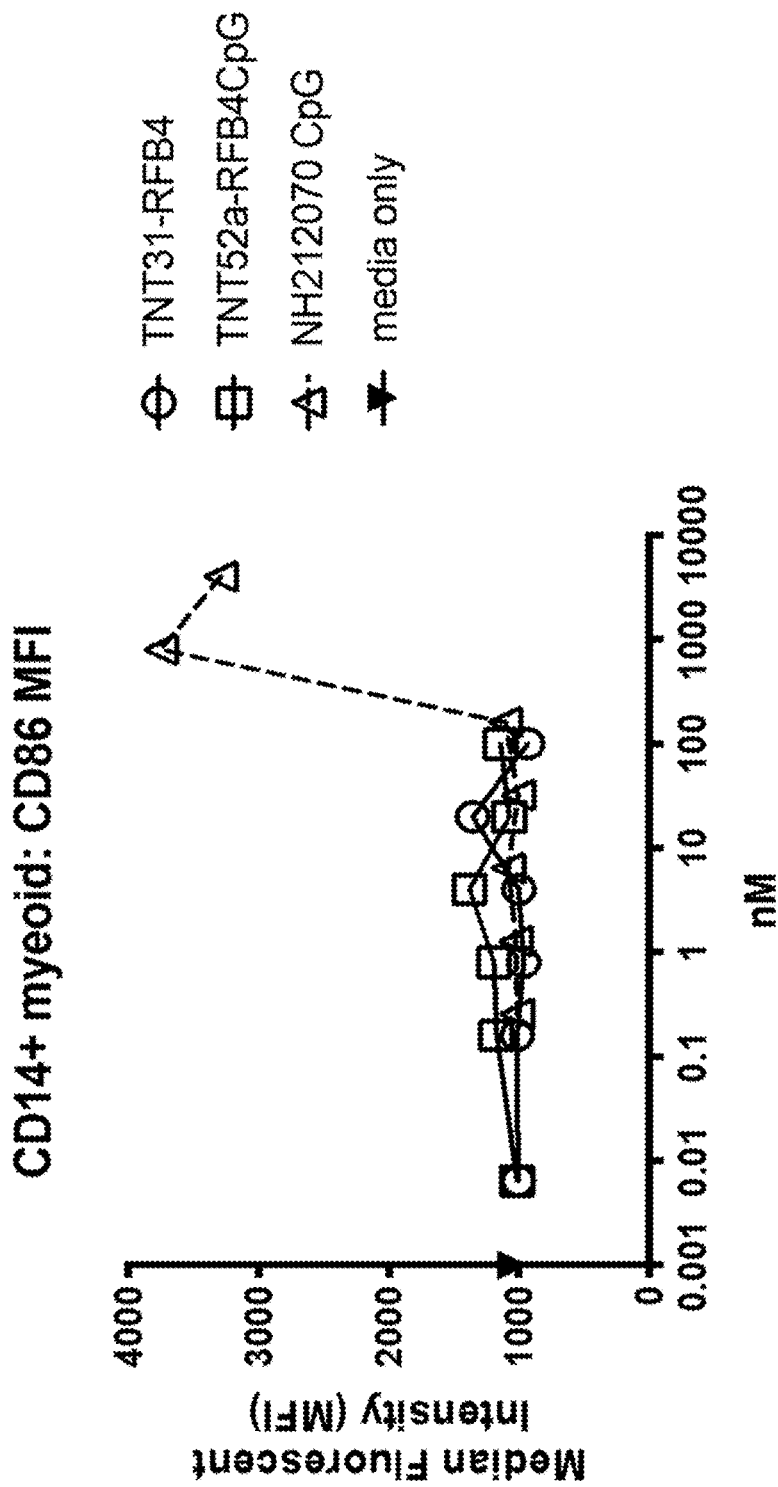
Figure 34D:
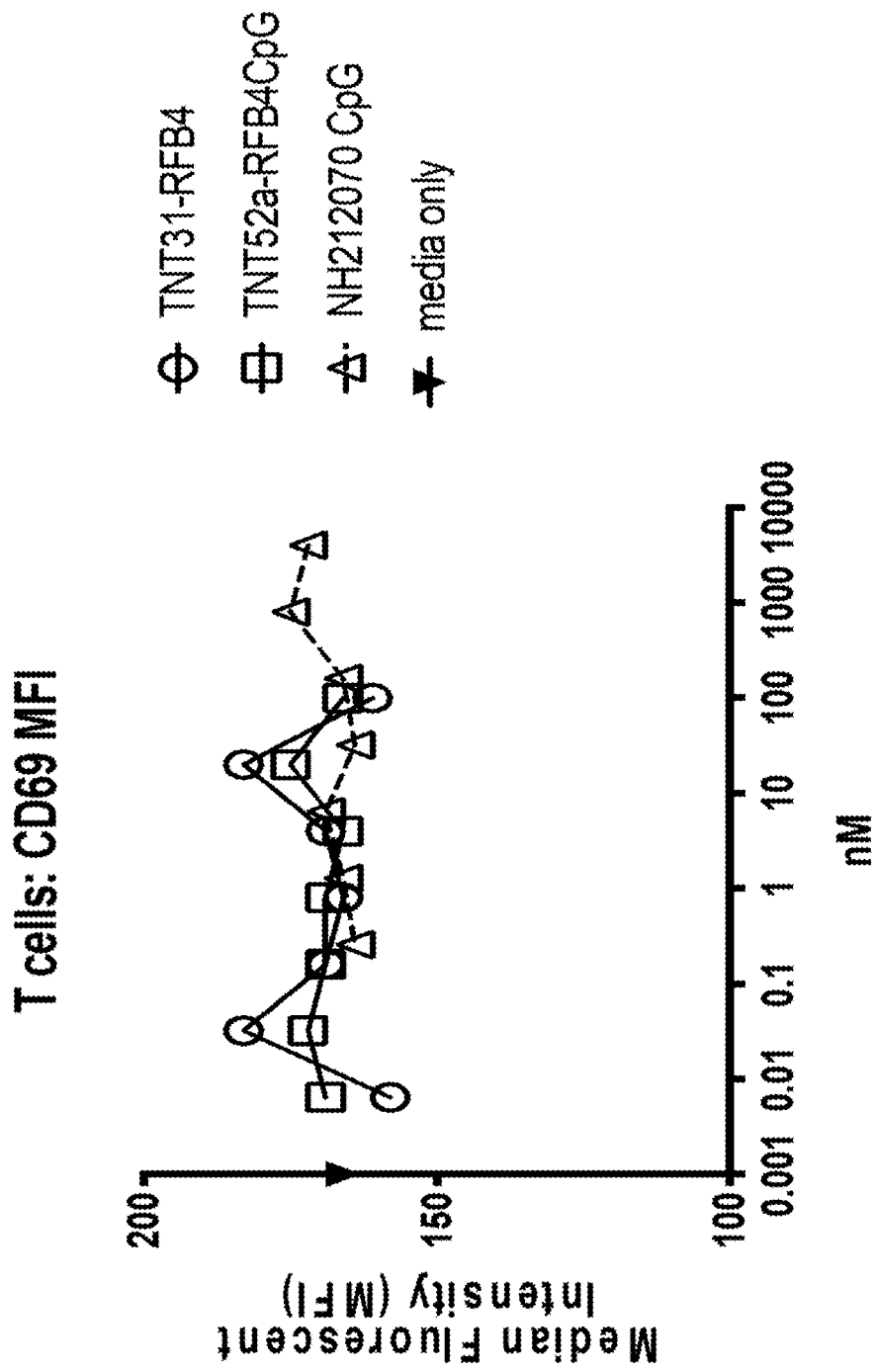

CpG (7-7b; SEQ ID NO:35), CD22 antibody (unconjugated) and CD22 antibody-CpG conjugate (TNT138a, as described above) were compared for TLR9 activation in both TLR9 positive and TLR9 negative immune cells by observing CD40, CD80 and CD69 expression. The CD22-CpG conjugate activated TLR9 positive/CD22 positive B cells, whereas CpG alone was unable to activate these cells except at higher concentrations of oligo (FIG. 34A). The CD22-CpG conjugate did not activate TLR9 positive cells that lacked the CD22 targeted by the conjugate, demonstrating the specificity of delivering the CpG oligo activating function to only cells with the CD22 target using RFB4 antibody and conjugate (FIGS. 34B-34D). Unconjugated CD22 did not exhibit activation in any TLR9 positive immune cells. The CpG, antibody and conjugate did not activate TLR9 negative immune cells as demonstrated by the lack of activation of CD69 in T cells.

Example 23: Biological Evaluation of Anti-Her2 Antibody:CpG Oligonucleotide Conjugates Materials and Methods A mouse spleen coculture was produced using splenocytes derived from the spleens of either a Balbc syngeneic mouse (full immune system) or from a NODSCID immunocompromised mouse (no B, T, dysfunctional DC, NK) (both from (Charles River), each cultured separately in presence of human breast tumor cell line SKBR3 (Her2+++) (ATCC). The cocultures were incubated with CpG conjugates or control. Biological evaluation of CpG-nucleotides and antibody-CpG conjugates in the co-culture assay by observing activation of monocytes, macrophages and dendritic cells was assessed as follows.

SKBR3 were non enzymatically detached with TryplE (Thermo Scientific) and resuspended at 1E6/mL in PBS (Gibco). 300 nM of Carboxyfluorescein Succinimidyl Ester (CF SE (Thermo Scientific)) was added for 20 minutes at 37° C. Excess dye were removed from cells by washing with Complete RPMI (RPMI1640+10% Fetal Bovine Serum (Gibco)). CFSE labeled SKBR3 cells were immediately plated onto a 96-well format (100 k/well) in Complete RPMI.

Fresh spleens were harvested from mice and passed through a 70 um filter (Fisher Scientific) into a 50 mL tube (Falcon) using the rubber end of a 3 mL plunger (Falcon). The dissociated spleen was resuspended in 15 mL of FACs buffer (PBS+0.5% Bovine Serum Albumin (Gibco) and centrifuged for 10 minutes at 400×g. Red blood cells were removed from splenocytes by adding 1 mL of ACK lysis buffer (Gibco) for 2 minutes before neutralizing with 15 mL of FACs buffer. Cells were centrifuged for 10 minutes at 400×g and passaged through a new 70 uM filter. Splenocytes were resuspended in Complete RPMI and were immediately plated (1E6/well) at a 10:1 ratio with the CFSE labeled SKBR3 cells.

Five-fold serial dilutions were added to the cells from 100 nM to 6.4 pM of antibody and conjugated antibody and 1 uM to 64 pM of CpG polynucleotides at 37° C. under 5% CO2 for 48 hours. Cells were pelleted by centrifugation for five minutes at 400×g and stained for 30 minutes at 4° C. in Fixable Viability Dye eFluor 780 (Thermo Fisher) diluted 1:4000 in PBS. Cells were centrifuged and stained at room temperature in FACS buffer for 5 minutes with FcR Blocking Reagent (Biolegend) and then an additional 40 minutes at 4° C. containing anti-CD45, anti-CD49b, anti-CD3, anti-B220, anti-CD11b, anti-MHCII, anti-CD86, anti-CD40, anti-GR1, anti-F480 and anti CD11c. Cells were centrifuged and washed twice in FACS buffer and fixed in 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. Lineage specific cells were first excluded (CD3, B220, CD49b) prior to gating CD11b+GR1midF480+ cells to identify monocyte macrophages and F480-CD11c+MHCII+ cells to identify DC cells.

Anti-huHer2 antibody (SEQ ID Nos:126-128) was tested in context of mIgG1 or mIgG2a Fc domain, either unconjugated or conjugated to 4523 murine CpG oligonucleotide (SEQ ID NO:121).

Results

Figure 35A:
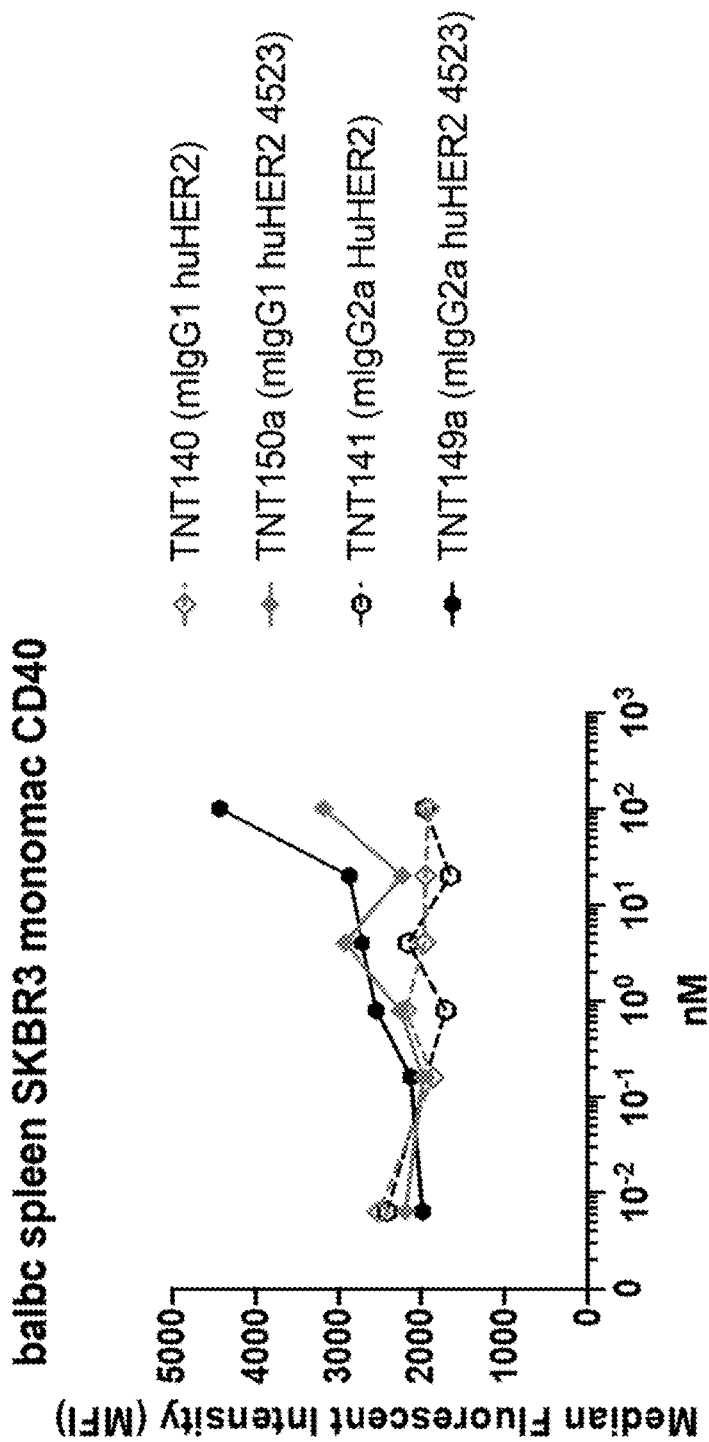
FIGS. 35A & 35B show activation of monocytes, macrophages, and dendritic cells upon treatment with anti-huHer2 antibody having mIgG1 or mIgG2a Fc domain, either unconjugated or conjugated to mouse CpG oligonucleotide.
Figure 35B:
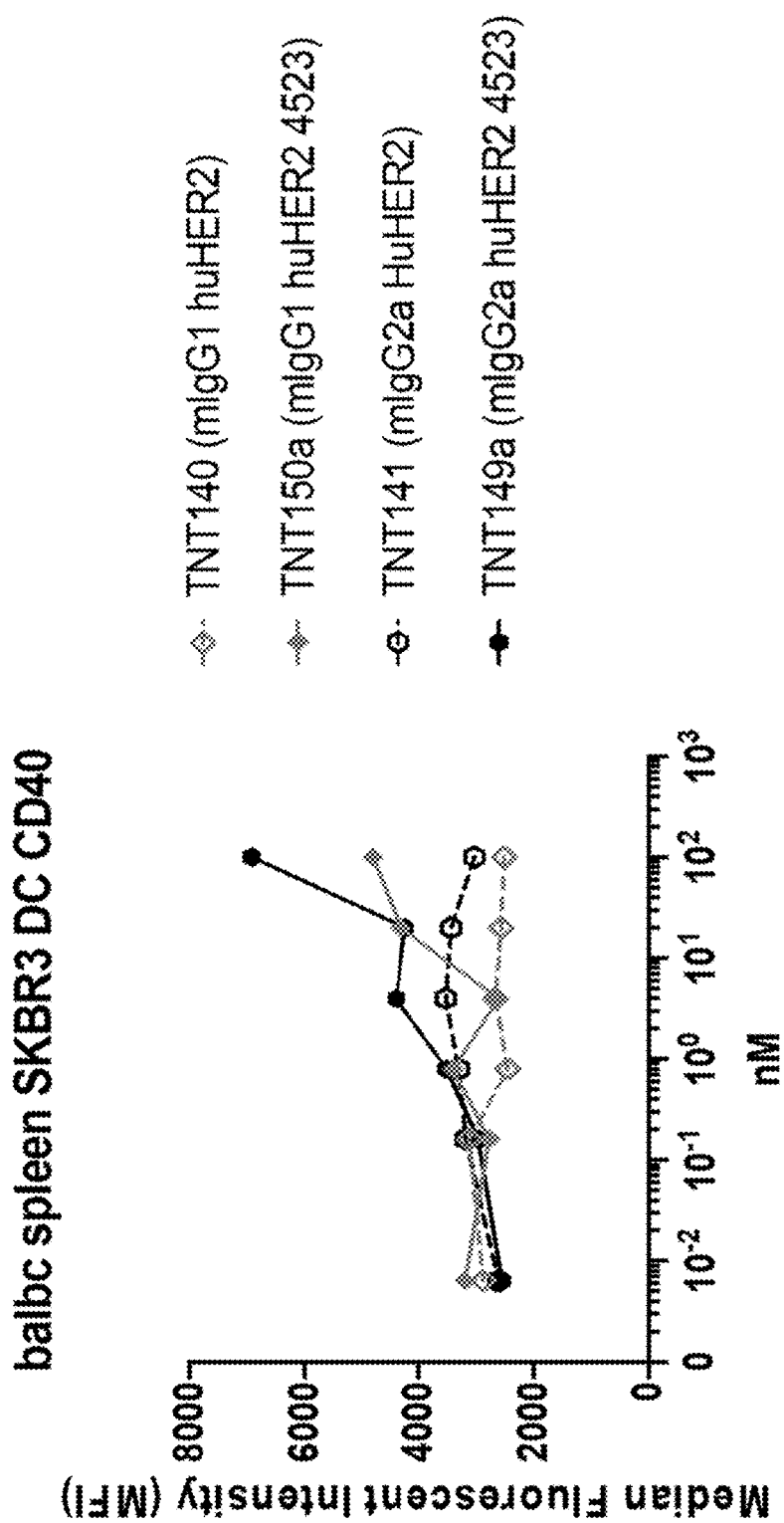

This co-culture model provides an assessment of the activity of the tested CpG conjugates in the presence of a broader immune model system. The results showed that CpG conjugates with mIgG2a Fc domain activated monocytes, macrophages and dendritic cells to a greater extent than the CpG conjugates with mIgG1 Fc domain using spleenocytes from BALBc mice (FIGS. 35A & 35B)

Example 24: Evaluation of CD22 Ab-CpG Conjugate in an Immune Checkpoint Inhibitor Refractory Model EMT6 mouse mammary carcinoma cells (ATCC) were cultured in Complete RPMI 1640 (RPMI1640+10% FBS (Gibco)) at 37° C. and 5% CO2. Cells were detached with Trypsin 0.25% (Gibco) and washed twice with RPMI 1640 (Gibco). Cells were resuspended at 20E6/mL in RPMI 1640 and kept on ice until use. 100 uL of suspended cells were subcutaneously implanted into the right flank of 6 week old female BALB/c mice (Charles River). Tumor size was measured and recorded twice a week with calipers starting 3 days post implantation until duration of the study, approximately 35 days later. Tumor volume was calculated using the following formula: (length×width×width)/2. Once tumors reached on average 75 mm$^3$, approximately 3 days post implantation, mice were randomized by tumor size and treatments were initiated. In this study, the mice were treated with TNT50a, an anti-mouse CD22 antibody (SEQ ID NO: 124 and SEQ ID NO: 125) conjugated to mouse CpG 4523 (SEQ ID NO: 121) of DAR1 configuration. TNT50a conjugates were administered intraperitoneally 2 doses every 3, 5 or 7 days at 10 mg/kg. Mice whose tumors exceeded 2,000 mm³ or exhibited any signs of distress at any time during the study were sacrificed humanely as per IACUC-approved animal protocols.

Figure 36:
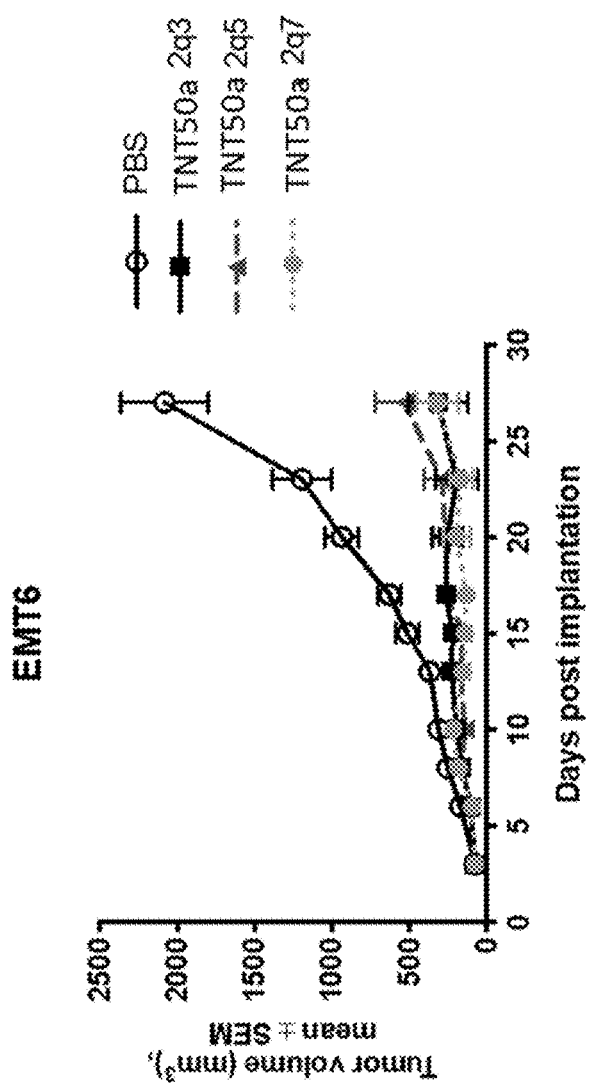
FIG. 36 shows anti-tumor efficacy of anti-CD22 antibody conjugated to CpG oligonucleotide according to 3 dosing regimens in EMT6 breast cancer model that is generally refractory to treatment with anti-PD1/PD-L1.

As shown in FIG. 36, TNT50a showed anti-tumor efficacy in all three dosing regimens. EMT6 breast model is generally refractory to treatment by anti-PD1 and anti-PD-L1 treament. Therefore, the data shows that anti-CD22 Ab-CpG conjugate is superior showing potent single agent activity in checkpoint inhibitor refractory model.

Example 25: Intratumoral Administration

EMT6 mouse mammary carcinoma cells (ATCC) were cultured in Complete RPMI 1640 (RPMI1640+10% FBS (Gibco)) at 37° C. and 5% CO2. Cells were detached with Trypsin 0.25% (Gibco) and washed twice with RPMI 1640 (Gibco). Cells were resuspended at 20E6/mL in RPMI 1640 and kept on ice until use. 100 uL of suspended cells were subcutaneously implanted into the right flank of 6 week old female BALB/c mice (Charles River). Tumor size was measured and recorded twice a week with calipers starting 7 days post implantation until duration of the study, approximately 25 days later. Tumor volume was calculated using the following formula: (length×width×width)/2. Once tumors reached on average 180 mm³, approximately 7 days post implantation, mice were randomized by tumor size and treatments were initiated. In this study, the mice were treated with TNT50a, an anti-mouse CD22 antibody (SEQ ID NO: 124 and SEQ ID NO: 125) conjugated to mouse CpG 4523 (SEQ ID NO: 121) of DAR1 configuration. TNT50a conjugates were administered intratumorally 2 doses every 3 days at 24 uM. Mice whose tumors exceeded 2,000 mm³ or exhibited any signs of distress at any time during the study were sacrificed humanely as per IACUC-approved animal protocols.

Figure 37:
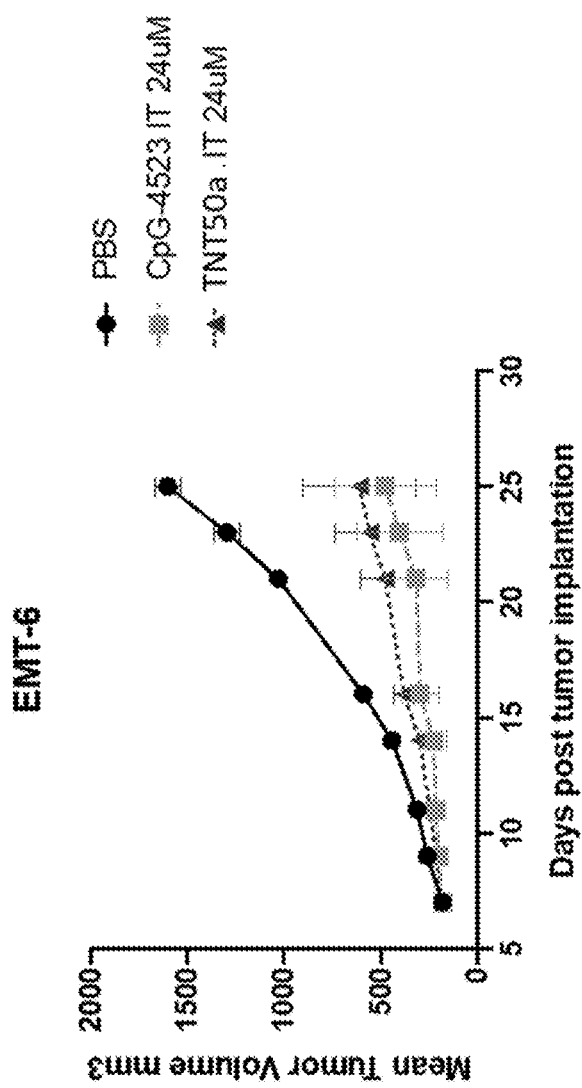
FIG. 37 shows anti-tumor efficacy of anti-CD22 antibody conjugated to CpG oligonucleotide or free CpG oligonucleotide in EMT6 breast cancer model when administered intratumorally.

As shown in FIG. 37, the CD22 Ab-CpG conjugate showed anti-tumor potency as did the free CpG (CpG-4253) when administered intratumorally.

Example 26: Immunophenotyping

Immunophenotyping of multiple syngeneic models administered with TNT50a were conducted. TNT50a, an anti-mouse CD22 antibody (SEQ ID NO: 124 and SEQ ID NO: 125) conjugated to mouse CpG 4523 (SEQ ID NO: 121) of DAR1 configuration. A20 B cell lymphoma, CT26 colon carcinoma, EMT6 mouse mammary carcinoma cells (ATCC) were cultured in Complete RPMI 1640 (RPMI1640+10% FBS (Gibco)) at 37° C. and 5% CO2. Cells were detached with Trypsin 0.25% (Gibco) and washed twice with RPMI 1640 (Gibco). Cells were resuspended at 20E6/mL in RPMI 1640 and kept on ice until use. 100 uL of suspended cells were subcutaneously implanted into the right flank of 6 week old female BALB/c mice (Charles River). Tumor size was measured with calipers. Tumor volume was calculated using the following formula: (length×width×width)/2. Once tumors reached on average 200-300 mm³, mice were randomized by tumor size and treatments were initiated. The conjugates were administered 1 or 2 doses intraperitoneally every 3 days at 10 mg/kg. Mice whose tumors exceeded 2,000 mm³ or exhibited any signs of distress at any time during the study were sacrificed humanely as per IACUC-approved animal protocols.

Spleens and tumors were harvested either two or three days post-last injection for immunophenotyping. Spleens were processed into single-cell suspension in ice-cold PBS, lysed with ACK lysis buffer (Gibco), washed twice and re-suspended in PBS supplemented with 2% FBS. Tumor-derived single-cell suspensions were prepared using a cocktail of Collagenase A (Roche), Collagenase D (Roche) and DNAse (Roche) for 45 min at 37° C. Cell counts were performed using ViCell counter (Beckman Coulter) for spleen and trypan blue exclusion with hemacytometer for tumor. Aliquots of 1-2×10⁶ cells were either used for cell-surface antigen staining or stimulation for cytokine assessment. For surface staining, cells were stained with LIVE/DEAD fixable dye (Thermo Fisher), followed by mouse Fc-block (Bio-legend) and subsequently stained with antibodies according to cell-type specific antibody panels for at least 30 min at 4° C. Following antibodies were used: IgD, CD19, CD95, CD3, CD11b, IL-10, Cd1d, CD5, CD138, CD44, CD4, CD8, CD45, CD62L, IFNg, TNFa, CD25, FOXP3, KI67, CD11c, WICK Ly6C, CD64. All flow antibodies were purchased from either Biolegend or Thermofisher.

Figures 38A, 38B:
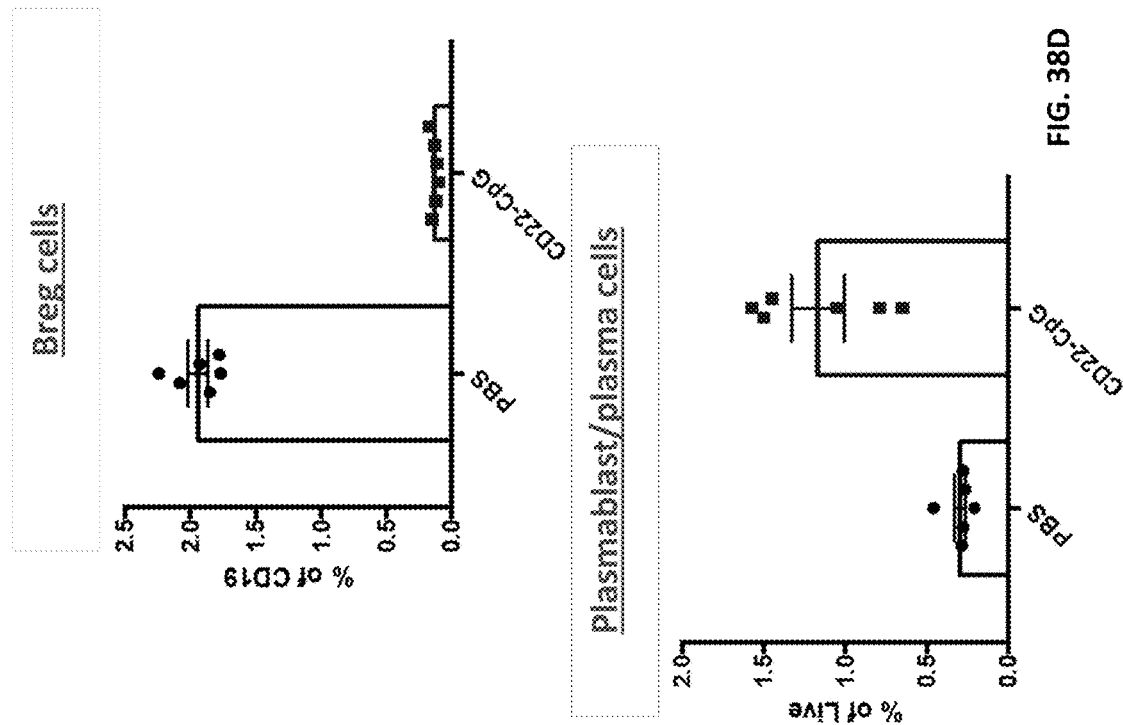
FIGS. 38A-38D show an increase in B cell differentiation and decrease in B regulatory cells in the spleen following administration of anti-CD22 Ab-CpG conjugate.
Figures 38C, 38D:
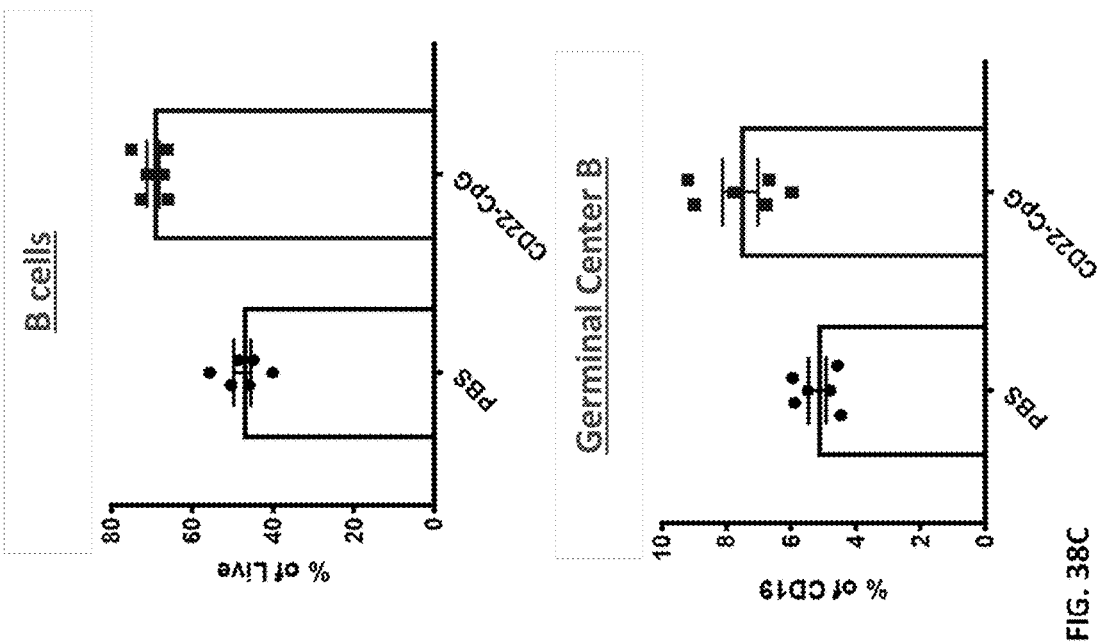
Figure 39A:
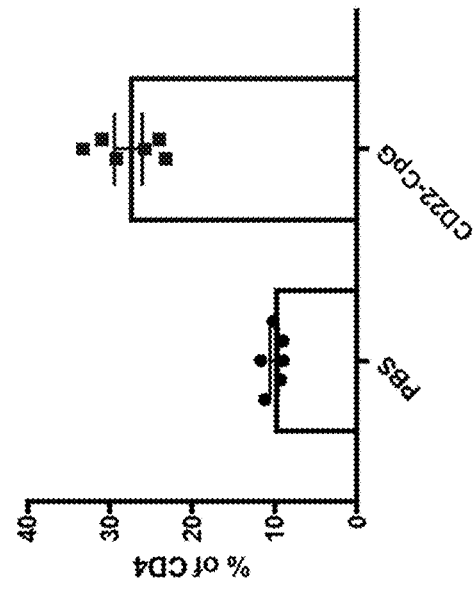
FIGS. 39A-39D show an increase in CD4 and CD8 T effector cells and function in the spleen following administration of anti-CD22 Ab-CpG conjugate.
Figure 39B:
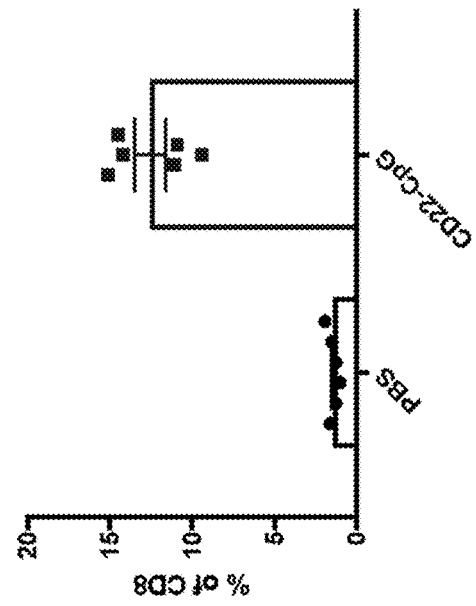
Figure 39C:
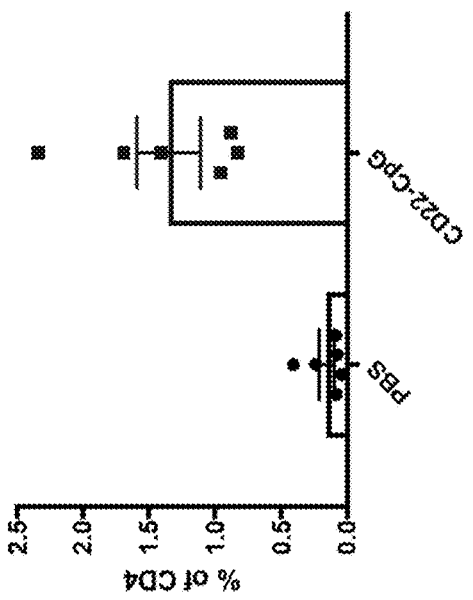
Figure 39D:
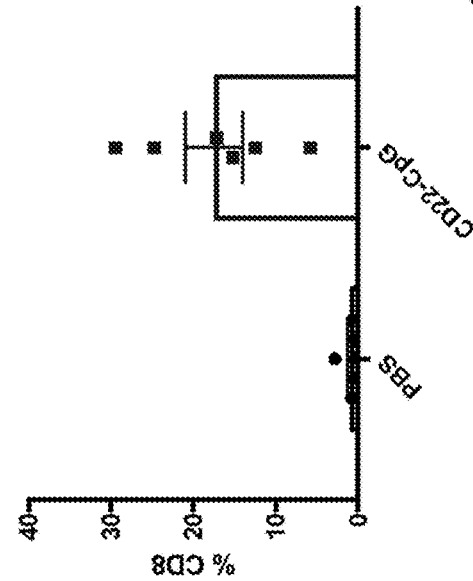
Figure 40B:
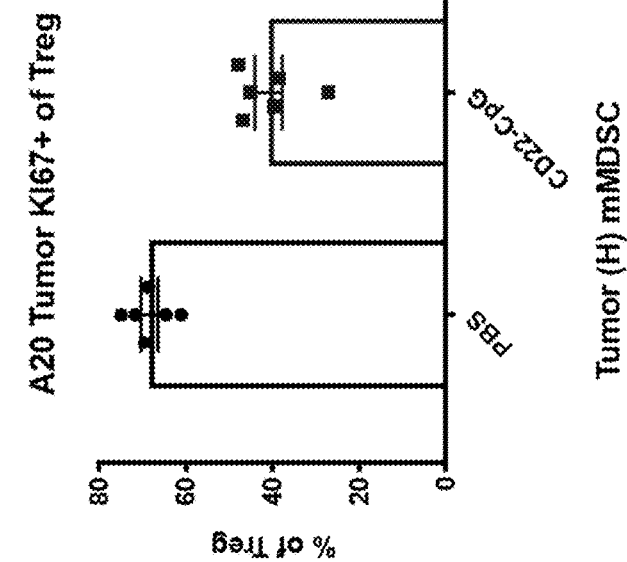
FIGS. 40A-40D show an increase in B cell infiltrates and modulation of suppressive microenvironment in the tumor following administration of anti-CD22 Ab-CpG conjugate.
Figure 40D:
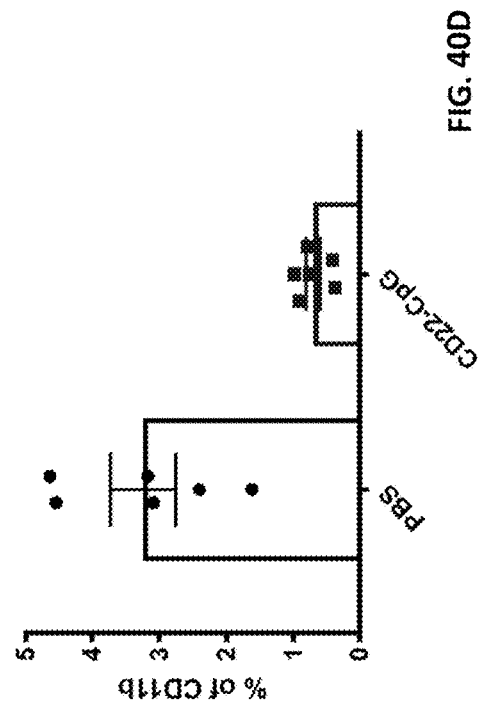
Figure 40A:
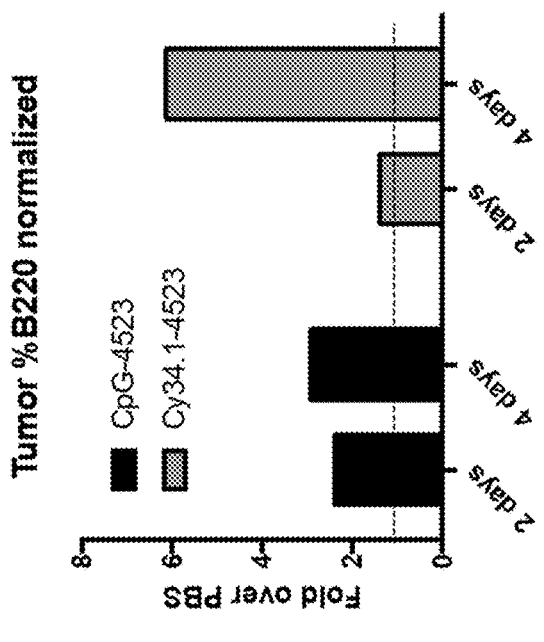
Figure 40C:
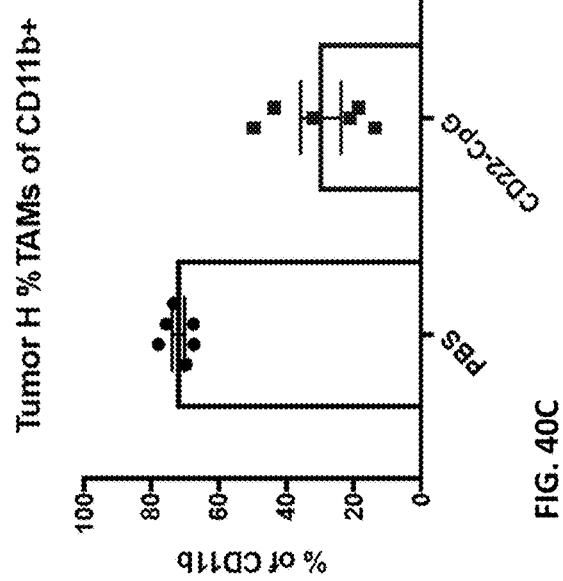

As shown in FIGS. 38-40, the CD22 Ab-CpG conjugate promotes B cell differentiation, decrease in Bregs, increase in T cell effector function and modulation of suppressive myeloid cells. FIGS. 38A-38D show the increase in B cell differentiation and decrease in B regulatory cells in the spleen following administration of the CD22 Ab-CpG conjugate. FIGS. 39A-39D show the increase in CD4 and CD8 T effector cells and function in the spleen following administration of the CD22 Ab-CpG conjugate. FIGS. 40A-40D show the increase in B cell infiltrates and modulation of suppressive microenvironment in the tumor following administration of the CD22 Ab-CpG conjugate.

Example 27: Biological Evaluation of Human B Cell Derived Cytokine Expression

Trima residuals were received from Vitalant and diluted 1:2 with Phosphate Buffered Saline (PBS, Gibco). Diluted blood was split into two tubes and underplayed with 15 mL Ficoll-Paque (GE Healthcare). Tubes were centrifuged for 30 minutes at 400×g. PBMCs were collected from the interface, resuspended and washed in FACS buffer (PBS with 0.5% Bovine Serum Albumin (Gibco)). After one wash, PBMCs were resuspended in Complete RPMI (RPMI+10% FBS). PBMCs were immediately plated onto a 96-well format (1e6/well) in Complete RPMI. Five-fold serial dilutions were added to the cells from 1 uM to 64 pM of CpG polynucleotides at 37° C. under 5% CO2 for 48 hours. Cells were pelleted by centrifugation for five minutes at 400×g and stained at 4° C. in Fixable Viability Dye eFluor 780 (Thermo Fisher) diluted 1:4000 in PBS. Cells were centrifuged and stained at 4° C. in FACS buffer for 30 minutes containing FcR Blocking Reagent (Miltenyi Biotec), anti-CD19, anti-CD40, anti-CD86, anti-CD25. Cells were centrifuged and washed twice in FACS buffer. Cells were then processed for intracellular staining using the Transcription factor fixation/permeabilization concentrate and diluent (eBioscience).

Briefly, cells were incubated in fresh fixation buffer by mixing 1 part of fixation/permeabilization concentrate with 3 parts of fixation permeabilization diluent. Samples were incubated for 30-60 min at 4° C. protected from light. Samples were then centrifuged at 600 g for 5 min at room temperature. Resuspended pellet with 1× permeabilization buffer followed by two rounds of washes and centrifugation at 600 g for 5 min at room temperature. Pellets were resuspended in 100 uL of permeabilization buffer and stained with anti-CCL3, anti-IL2 and anti-IL6 for 60 min at room temperature. Cells were centrifuged and washed twice in FACS buffer and fixed in 0.5% paraformaldehyde. Cells were analyzed on Attune NxT Flow Cytometer (Thermo Fisher), with subsequent data analysis by Flowjo 10.7 (Treestar). Dead cells were excluded by gating on the eFluor 780-negative population. B cells were identified as CD19+ cells, levels of activation marker were assessed by median fluorescent intensity and cytokine/chemokine expression was assessed as a % of CD19+ cells. In these experiments, unconjugated anti-human CD22 antibody (SEQ ID NO: 65 and SEQ ID NO: 87), free CpG (SEQ ID NO: 35, 7-7b) and anti-human CD22 antibody (SEQ ID NO: 65 and SEQ ID NO: 87) conjugated to CpG 7-7 (SEQ ID NO: 35) were tested.

FIGS. 41A-41C show robust induction of B cell cytokines and chemokines upon CD22—mediated TLR9 engagement in human B cells.

Example 28: Biological Evaluation of Murine Serum Cytokine Levels Following Repeat Dosing with Anti-mCD22-CpG Conjugate CT26 colon carcinoma cells (ATCC) were cultured in Complete RPMI 1640 (RPMI1640+10% FBS (Gibco)) at 37° C. and 5% CO2. Cells were detached with Trypsin 0.25% (Gibco) and washed twice with RPMI 1640 (Gibco). Cells were resuspended at 20E6/mL in RPMI 1640 and kept on ice until use. 100 uL of suspended cells were subcutaneously implanted into the right flank of 6 week old female BALB/c mice (Charles River). When tumors reached an average of 300 $mm^3$, mice were randomized into two groups and dosed intraperitoneally with 10 mg/kg of TNT50a, anti-mCD22-CpG or PBS twice, 3 days apart. Forty-eight hours post-each dose mice, and 9 days post-last dose were bled into serum microtainer tubes (BD). Serum was collected following centrifugation and stored at −80C for cytokine evaluation using Isoplexis platform. Briefly, serum samples were thawed at room temperature along with Mouse CodePlex Seretome chip (Isoplexis). Serum samples were loaded neat in duplicates into chip chambers. Following the loading of a calibration chip, the Codeplex Secretome chip was loaded into the Isolight for analysis. Sensitivity range for this assay is 5-5000 pg/mL for 16 evaluated cytokines and chemokines. The anti-mCD22 conjugate used in this study, TNT50a, is an anti-mouse CD22 antibody (SEQ ID NO: 124 and SEQ ID NO: 125) conjugated to mouse CpG 4523 (SEQ ID NO: 121).

Figure 42A:
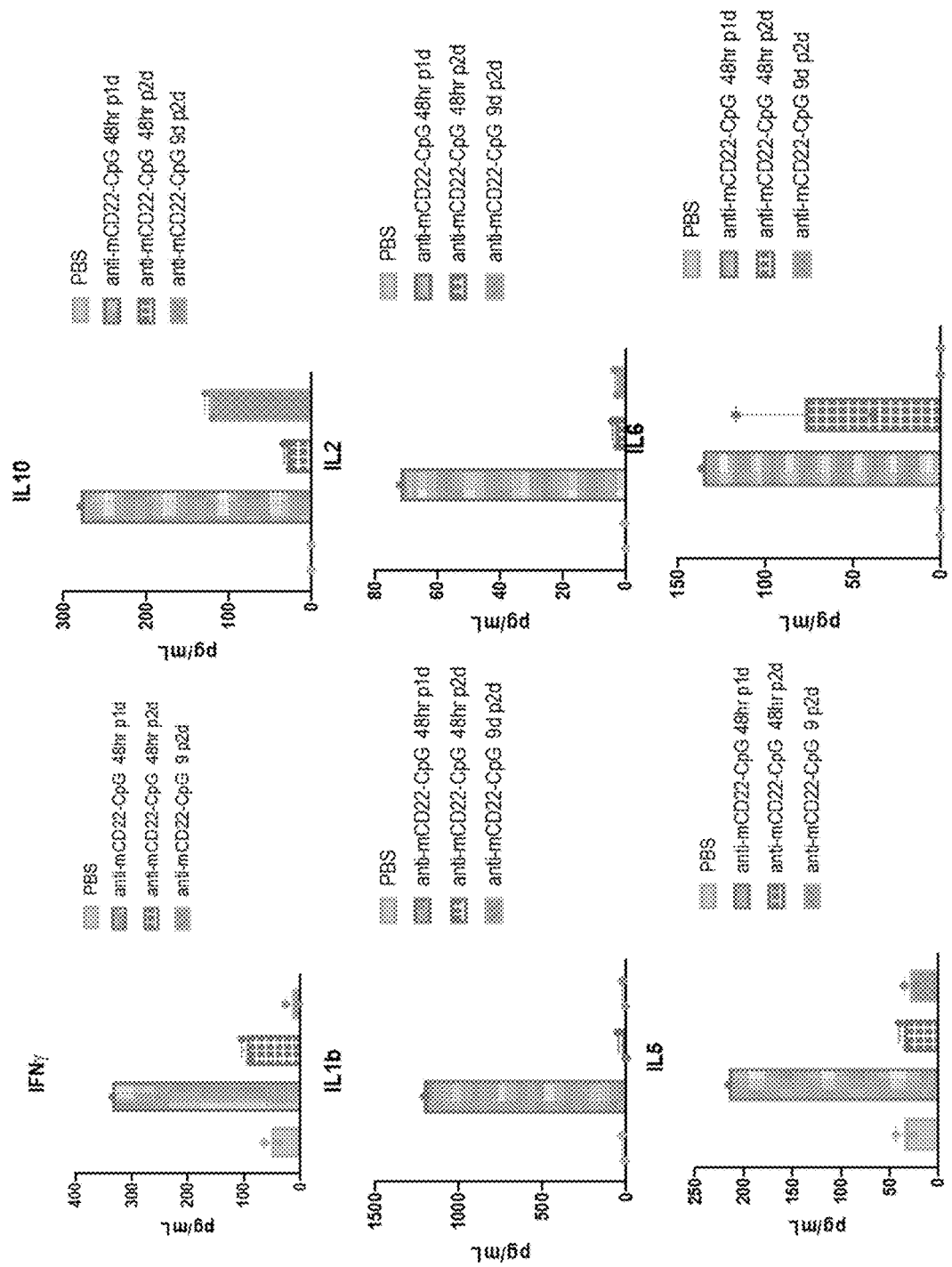
FIGS. 42A & 42B show robust induction of various cytokines and chemokines (as indicated) with anti-mCD22-CpG with no apparent accumulation in the periphery upon repeat dosing in mouse.
Figure 42B:
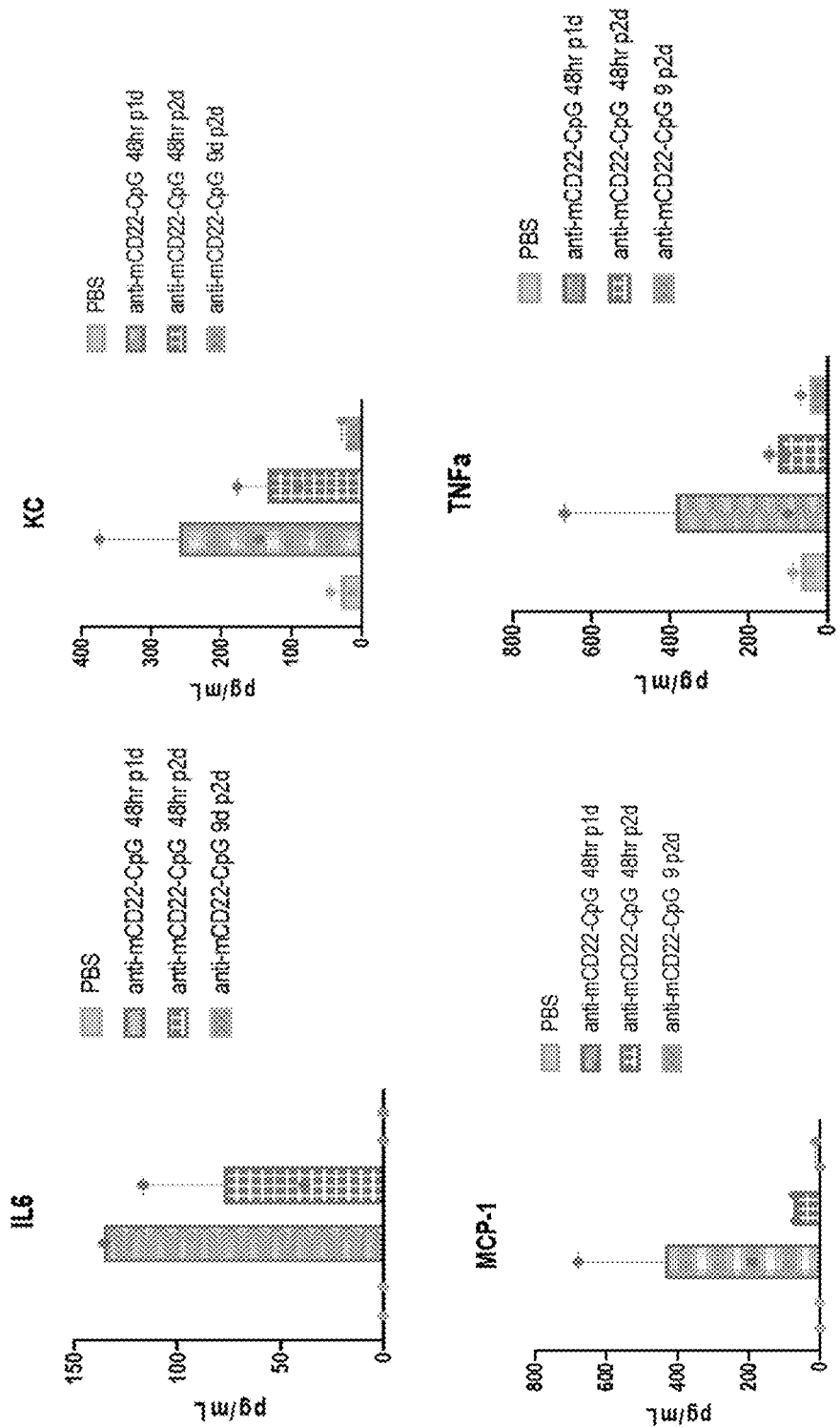

FIGS. 42A & 42B show robust induction of various effector cytokines and chemokines with anti-mCD22-CpG with no apparent accumulation in the periphery upon repeat dosing in mouse.

Example 29: Tumor Killing in PD1 Non-Responders

Figure 43:
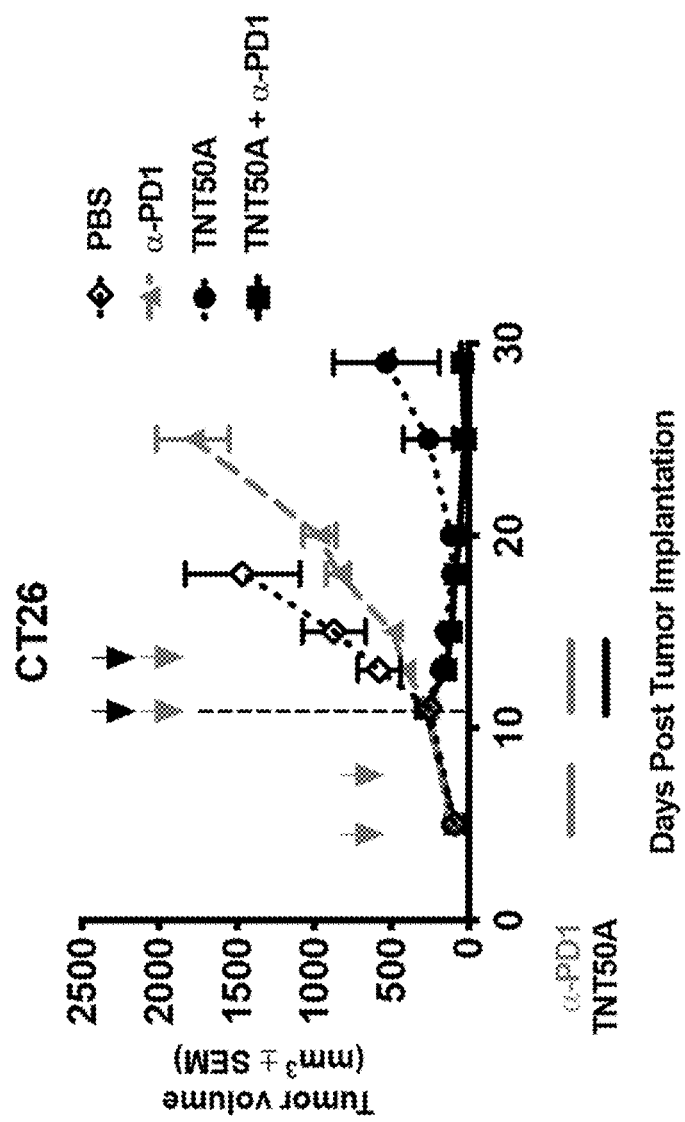
FIG. 43 shows anti-tumor response in groups of CT26 syngeneic mice that are non-responders to anti-PD1 antibody treatment. The treatment is performed using an anti-mouse CD22 antibody (SEQ ID NO: 124 and SEQ ID NO: 125) conjugated to mouse CpG 4523 (SEQ ID NO: 121). Tumor volume was reduced in mice treated with the conjugate or a combination of the conjugate and anti-PD1 antibody, whereas respective mice treated with only anti-PD1 antibody did not experience a significant reduction in tumor volume.

Immune cell mediated anti-tumor response was tested in a tumor bearing syngeneic model using TNT50a, which is an anti-mouse CD22 antibody (SEQ ID NO: 124 and SEQ ID NO: 125) conjugated to mouse CpG 4523 (SEQ ID NO: 121). CT26 mouse colon carcinoma cells (ATCC) were cultured in Complete RPMI 1640 (RPMI1640+10% FBS (Gibco)) at 37° C. and 5% CO2. Once cells were 80% confluent, cells were detached with Trypsin 0.25% (Gibco) and washed twice with RPMI 1640 (Gibco). Cells were resuspended at 20E6/mL in RPMI 1640 and kept on ice until use. 100 uL of suspended cells were subcutaneously implanted into the right flank of 6 week old female BALB/c mice (Charles River). Tumor size was measured and recorded twice a week with calipers starting 5 days post implantation until duration of the study, approximately 30 days later. Tumor volume was estimated using the following formula: (length×width×width)/2. Once tumors reached 50-200 $mm^3$, approximately 5 days post implantation, mice were randomized by tumor size and treatment with anti-PD1 (clone RPMI14 BioXCell) and PBS was initiated. Anti-PD1 and PBS (Gibco) were administered intraperitoneally for 2 doses every 3 days at 10 mg/kg and 3 doses every 3 days respectively. Approximately 11 days post implantation, anti-PD1 treated mice were measured and re-randomized by tumor size. Mice whose tumor progressed from initial size and measured greater than 200 $mm^3$ were considered anti-PD1 non responders. Mice within the anti-PD1 non responder group was re-randomized by tumor size and conjugate treatment was initiated. The conjugates were administered intravenously for 2 doses every 3 days at 10 mg/kg. For combination and single arm control, anti-PD1 treatment continued by intraperitoneal dosing every 3 days at 10 mg/kg for 2 doses. Mice whose tumors exceeded 2,000 $mm^3$ or exhibited any signs of distress at any time during the study were sacrificed humanely as per IACUC-approved animal protocols. FIG. 43 shows that tumor volume was reduced in mice treated with conjugate TNT50a, and mice treated with a combination of conjugate TNT50a and anti-PD1 antibody, whereas mice treated with only anti-PD1 antibody did not experience a significant reduction in tumor volume.

Example 30: Reduction of Lung Metastatic Burden

BALB/C mice were implanted with 4T1 cells, treatment with TNT50a initiated around day 5 when the tumor is around 60 $mm^3$ at 10 mg/kg, 3 doses every 3 days. TNT50a, is an anti-mouse CD22 antibody (SEQ ID NO: 124 and SEQ ID NO: 125) conjugated to mouse CpG 4523 (SEQ ID NO: 121) with a DAR1 configuration. The lungs were harvested 8-9 days post-last injection for metastatic nodule quantification. In brief, lungs were harvested in ice-cold 1×PBS, minced into small pieces then transferred into digestion solution consisting of 2 mg/mL collagenase type V (Worthington) supplemented with 50 ug/mL DNAse (Sigma) and incubated for 2 hrs in a 37C incubator with end-over-end rotation. Suspension was transferred into 70 um strainer, washed once in 1× PBS then transferred into 10 mL selection media consisting of RMPI 1640 supplemented with 10% FBS, penicillin-streptomycin and 10 ug/mL 6-thioguanine. Three to four 1:10 serial dilutions were plated either in 6 well plates or 10 cm dishes and cultured for 10-14 days at 37C, 5% CO2. Metastatic plaques were then fixed in methanol for 5 min at room temperature, re-hydrated in distilled water then stained with 0.03% methylene blue for 5 min at room temperature. Dye was then discarded, plate was rinsed gently with distilled water and allowed to air-dry prior to counting plaques.

Figure 44:
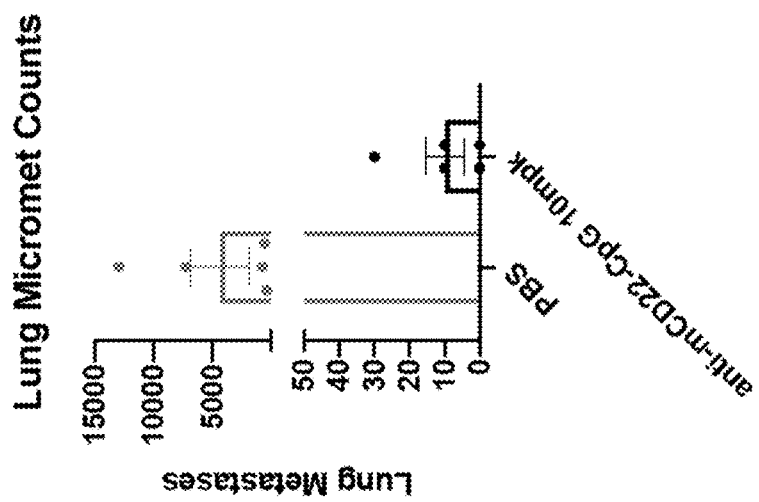
FIG. 44 shows effect of treatment with an anti-mouse CD22 antibody (SEQ ID NO: 124 and SEQ ID NO: 125) conjugated to mouse CpG 4523 (SEQ ID NO: 121) with a DAR1 configuration in BALB/C mice implanted with 4T1 cells. The number of metastatic plaques was significantly reduced in the CD22 Ab-CpG conjugate as compared to the control.

As shown in FIG. 44, the number of metastatic plaques was significantly reduced in the CD22 Ab-CpG conjugate as compared to the control.

What is claimed is:

1. A conjugate comprising an anti-CD22 antibody (Ab) and an immunomodulating oligonucleotide (P), wherein the Ab comprises two antibody light chains, two antibody heavy chains, and two Q-tag peptides (Q) having at least one glutamine residue; wherein one Q-tag peptide is linked to the C-terminus of each of the two antibody heavy chains; wherein one of the two Q-tag peptides is linked to the immunomodulating oligonucleotide via an amide bond with the glutamine residue of the Q-tag peptide and a linker (L) as shown in Formula (A):

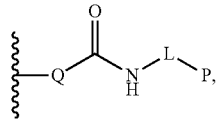

(A)

wherein ∼ indicates the point of attachment of Q to the antibody (Ab);

wherein each heavy chain of the Ab comprises a heavy chain variable (VH) domain comprising the amino acid sequence of SEQ ID NO:65, and each light chain of the Ab comprises a light chain variable (VL) domain comprising an amino acid sequence selected from the group consisting of SEQ ID Nos:68, 73, and 87;

wherein the linker L is

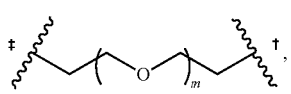

wherein m is 24, and wherein ∼ † indicates the point of attachment to the oligonucleotide P, and ∼ ‡ indicates the point of attachment to the glutamine residue of the Q-tag; and wherein the oligonucleotide P comprises the structure:

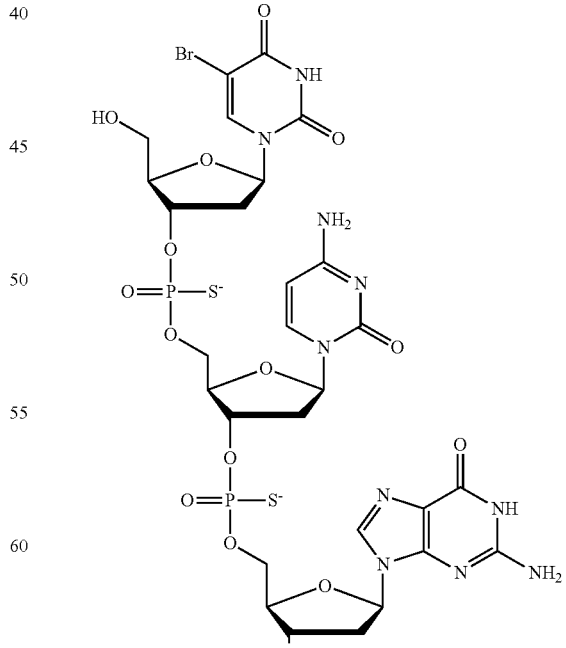

715
-continued
716
-continued
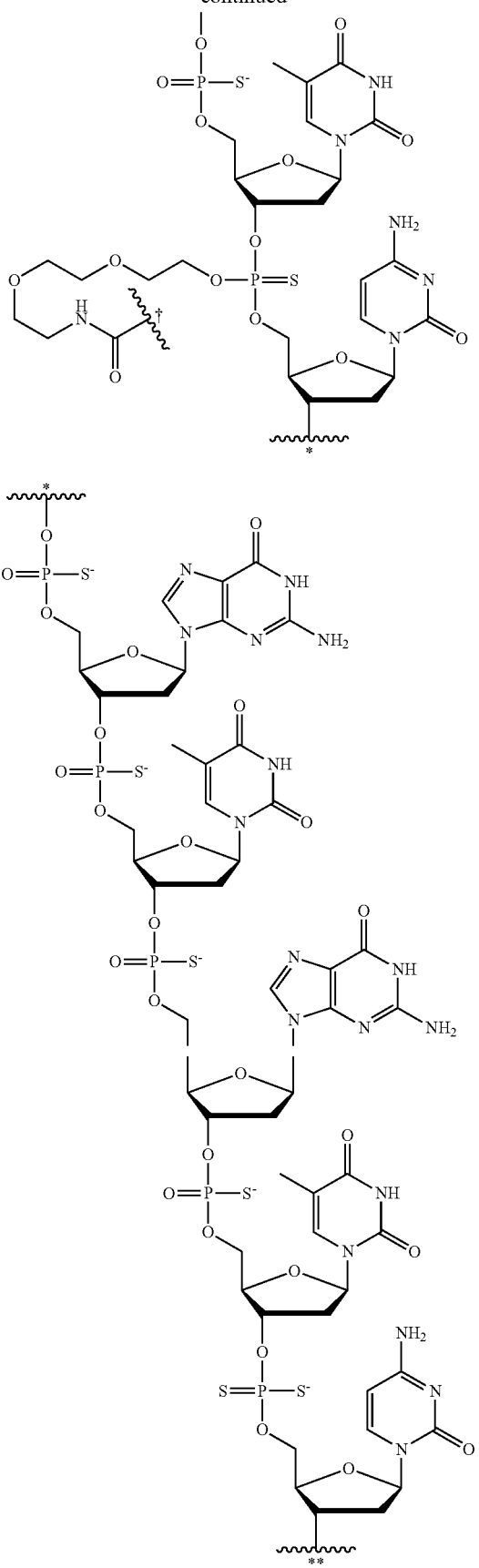
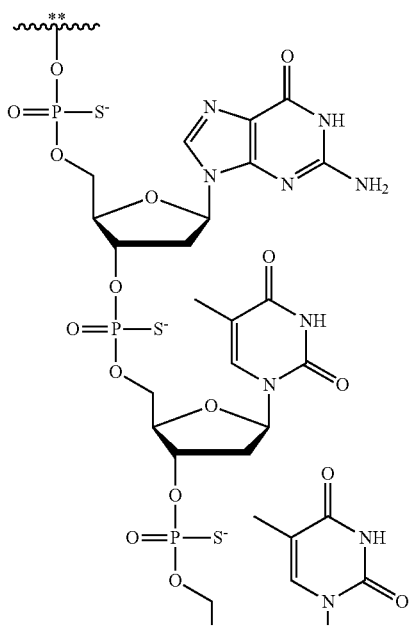
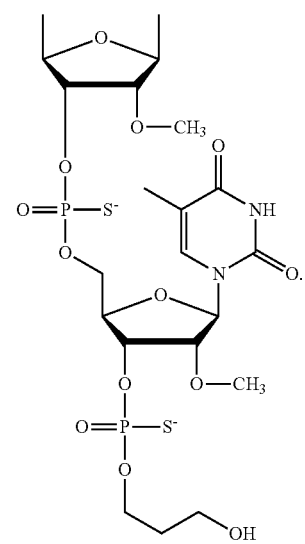
or

717
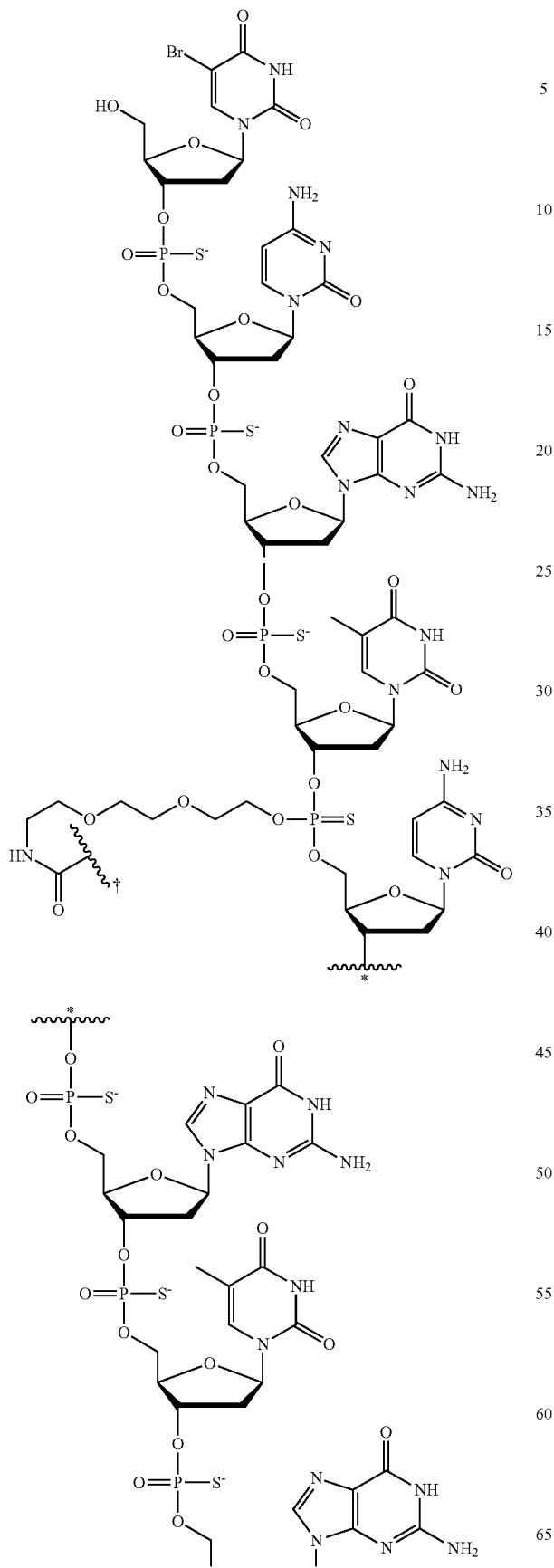
718
-continued
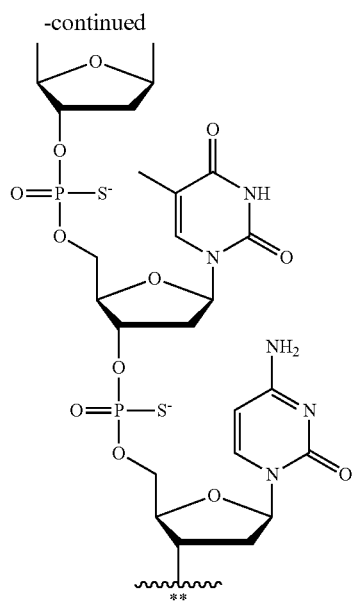
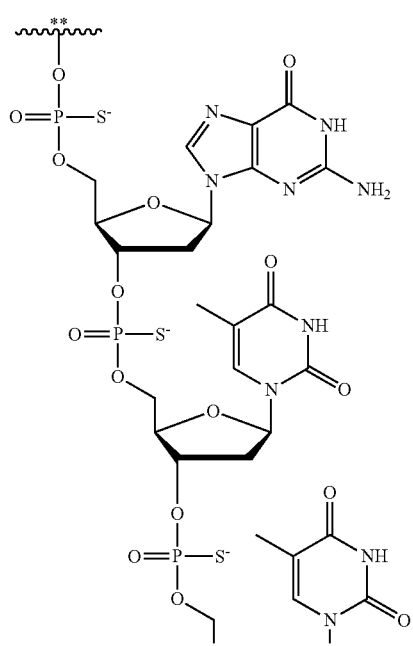

-continued

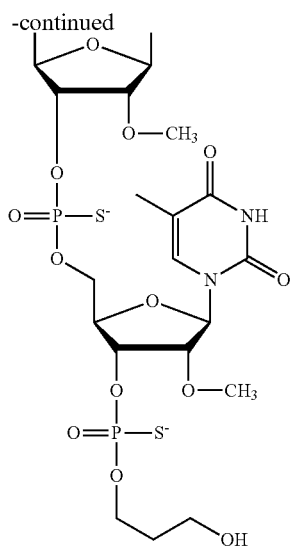

or a pharmaceutically acceptable salt thereof, wherein ⁓* and ⁓** indicate the points of attachment within the oligonucleotide, and wherein ⁓† indicates the point of attachment to the linker L.

2. The conjugate of claim 1, wherein each heavy chain of the Ab comprises a heavy chain variable (VH) domain comprising the amino acid sequence of SEQ ID NO:65, and wherein each light chain of the Ab comprises a light chain variable (VL) domain comprising the amino acid sequence of SEQ ID NO:68.

3. The conjugate of claim 1, wherein each heavy chain of the Ab comprises a heavy chain variable (VH) domain comprising the amino acid sequence of SEQ ID NO:65, and wherein each light chain of the Ab comprises a light chain variable (VL) domain comprising the amino acid sequence of SEQ ID NO:73.

4. The conjugate of claim 1, wherein each heavy chain of the Ab comprises a heavy chain variable (VH) domain comprising the amino acid sequence of SEQ ID NO:65, and wherein each light chain of the Ab comprises a light chain variable (VL) domain comprising the amino acid sequence of SEQ ID NO:87.

5. The conjugate of claim 1, wherein each of the two Q-tag peptides comprises the amino acid sequence RPQGFGPP (SEQ ID NO:49).

6. The conjugate of claim 1, wherein:
(a) each heavy chain of the Ab including Q comprises the amino acid sequence of SEQ ID NO:179, and each light chain of the Ab comprises the amino acid sequence of SEQ ID NO:181;
(b) each heavy chain of the Ab including Q comprises the amino acid sequence of SEQ ID NO:179, and each light chain of the Ab comprises the amino acid sequence of SEQ ID NO:182;
(c) each heavy chain of the Ab including Q comprises the amino acid sequence of SEQ ID NO:180, and each light chain of the Ab comprises the amino acid sequence of SEQ ID NO:181; or
(d) each heavy chain of the Ab including Q comprises the amino acid sequence of SEQ ID NO:180, and each light chain of the Ab comprises the amino acid sequence of SEQ ID NO:182.

7. The conjugate of claim 1, wherein each of the two Q-tag peptides comprises the amino acid sequence RPQGFGPP (SEQ ID NO:49), each heavy chain of the Ab including Q comprises the amino acid sequence of SEQ ID NO:179, each light chain of the Ab comprises the amino acid sequence of SEQ ID NO:182, and the oligonucleotide P comprises the structure:

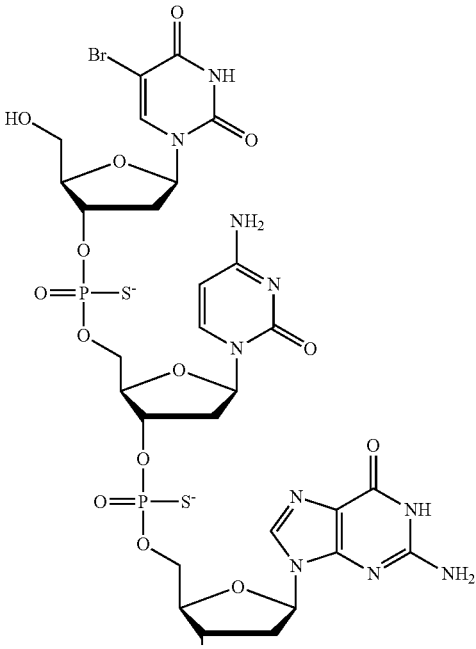

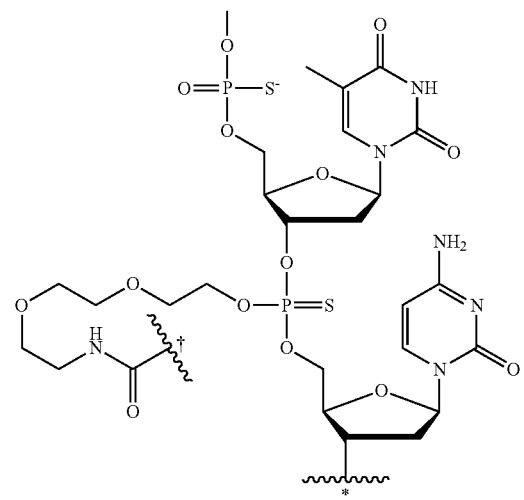

721
-continued
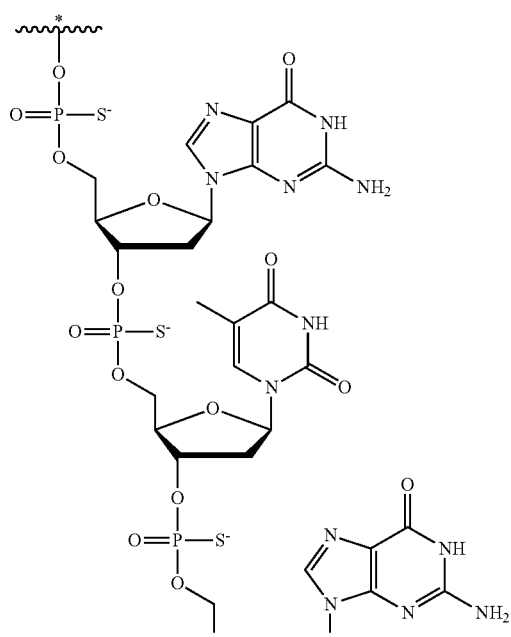
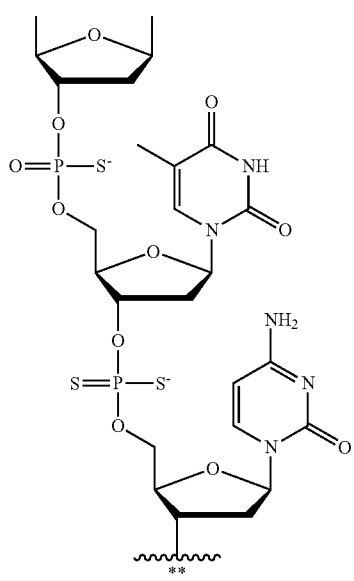
722
-continued
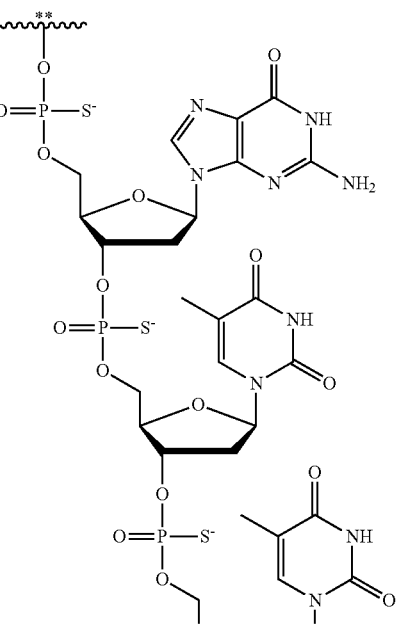
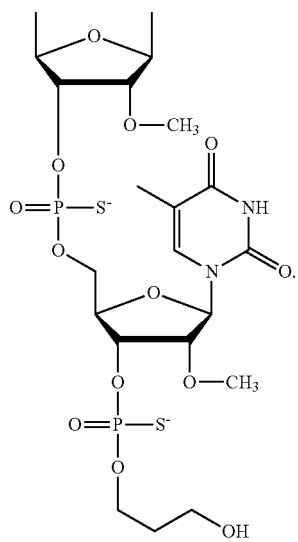
8. The conjugate of claim 1, wherein each of the two Q-tag peptides comprises the amino acid sequence RPQGFGPP (SEQ ID NO:49), each heavy chain of the Ab including Q comprises the amino acid sequence of SEQ ID NO:179, each light chain of the Ab comprises the amino acid sequence of SEQ ID NO:182, and the oligonucleotide P comprises the structure:

723
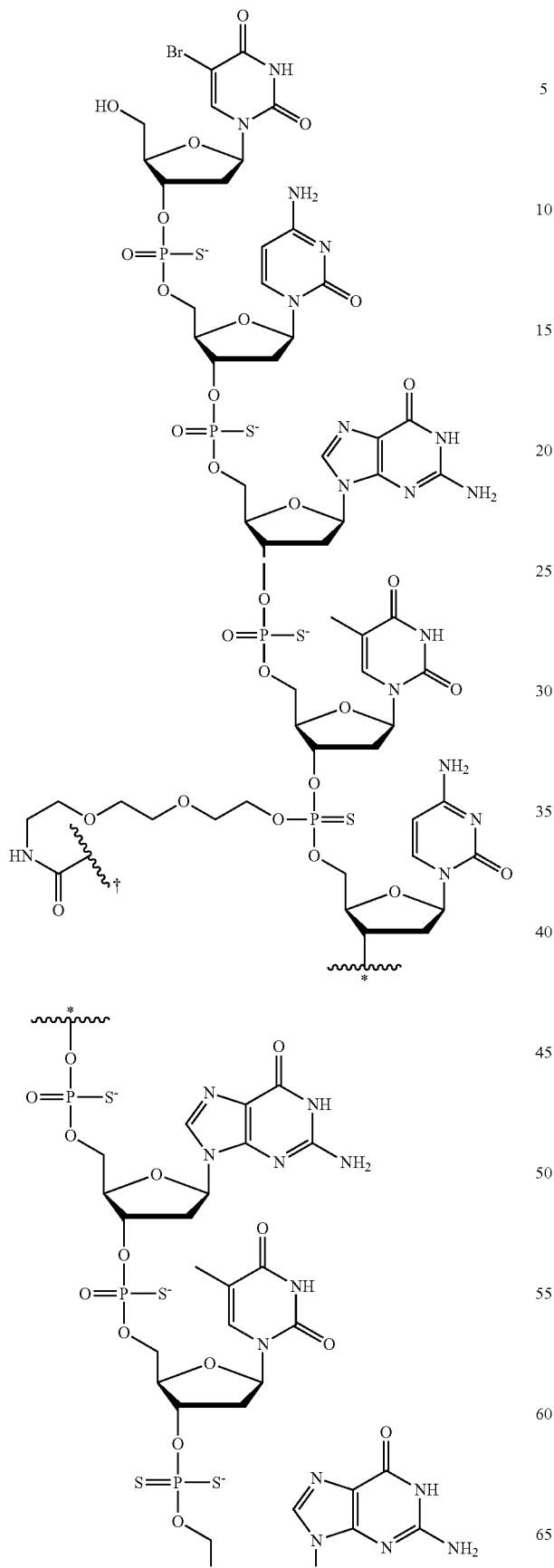
724
-continued
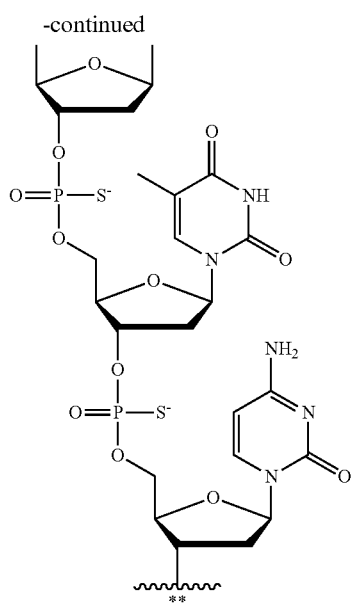
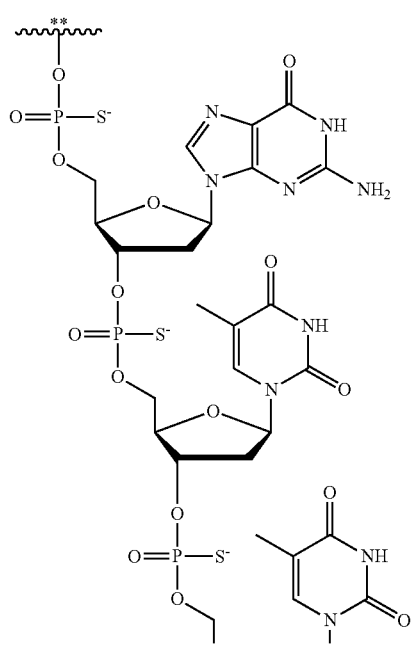

725
-continued
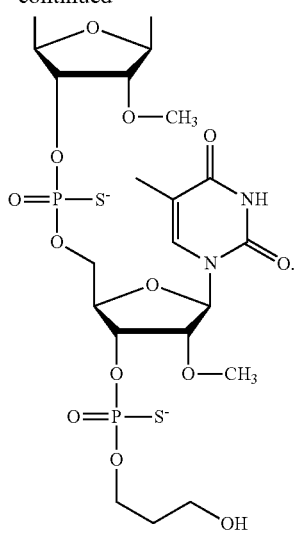
726
-continued
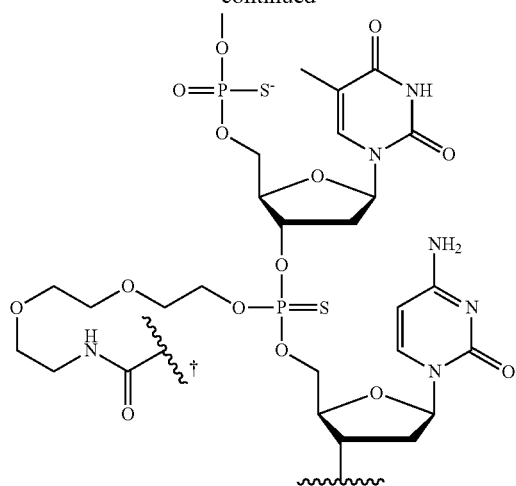
9. The conjugate of claim 1, wherein each of the two Q-tag peptides comprises the amino acid sequence RPQGFGPP (SEQ ID NO:49), each heavy chain of the Ab including Q comprises the amino acid sequence of SEQ ID NO:180, each light chain of the Ab comprises the amino acid sequence of SEQ ID NO:182, and the oligonucleotide P comprises the structure:
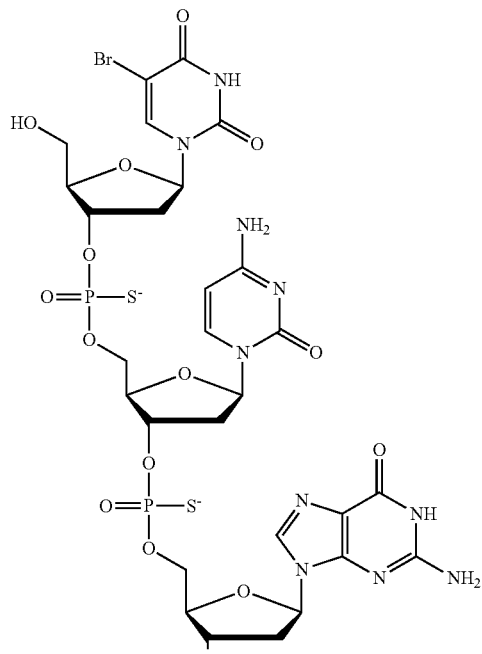
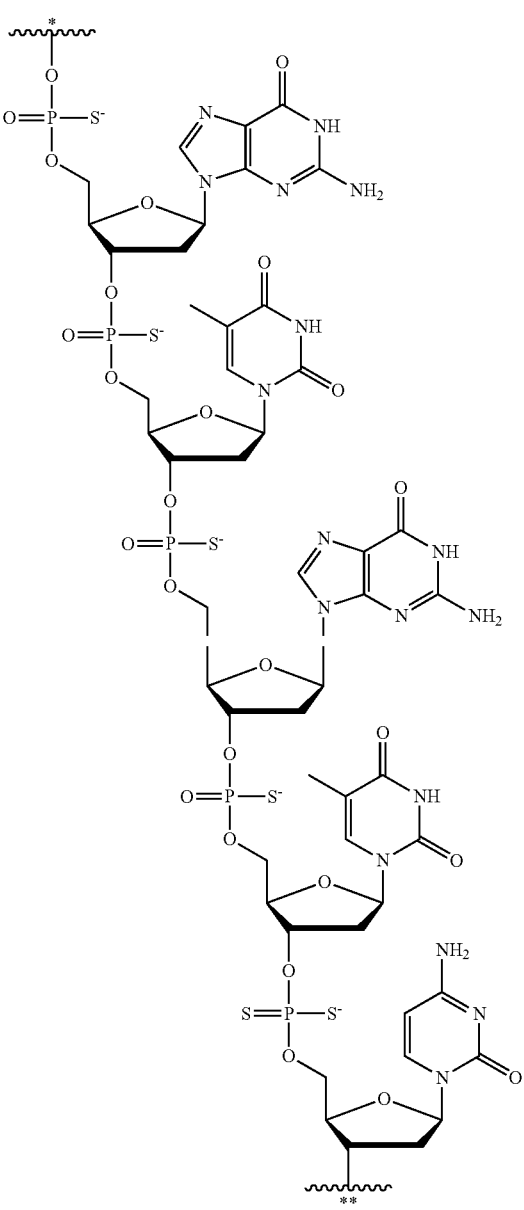 [SMILES: *OP(=O)([S-])OC[C@H]1O[C@@H](n2cnc3c(=O)[nH]c(N)nc32)C[C@H]1OP(=O)([S-])OC[C@H]1O[C@@H](n2cc(C)c(=O)[nH]c2=O)C[C@H]1OP(=O)([S-])OC[C@H]1O[C@@H](n2cnc3c(=O)[nH]c(N)nc32)C[C@H]1OP(=O)([S-])OC[C@H]1O[C@@H](n2cc(C)c(=O)[nH]c2=O)C[C@H]1OP(=S)([S-])OC[C@H]1O[C@@H](n2ccc(N)nc2=O)C[C@H]1*]

727
-continued
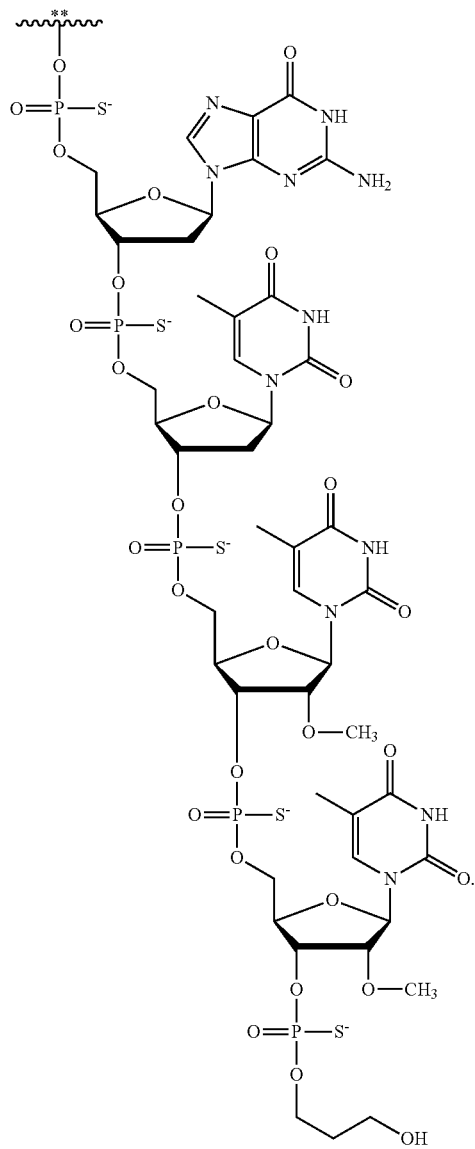
728
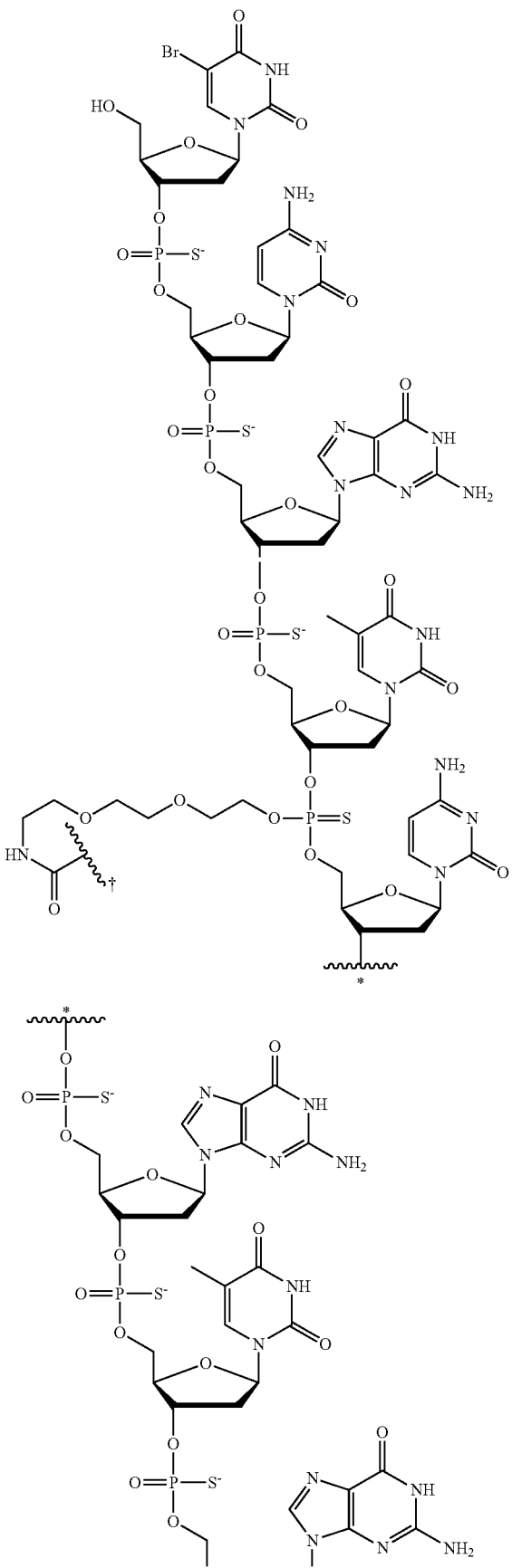
10. The conjugate of claim 1, wherein each of the two Q-tag peptides comprises the amino acid sequence RPQGFGPP (SEQ ID NO:49), each heavy chain of the Ab including Q comprises the amino acid sequence of SEQ ID NO:180, each light chain of the Ab comprises the amino acid sequence of SEQ ID NO:182, and the oligonucleotide P comprises the structure:

729
-continued
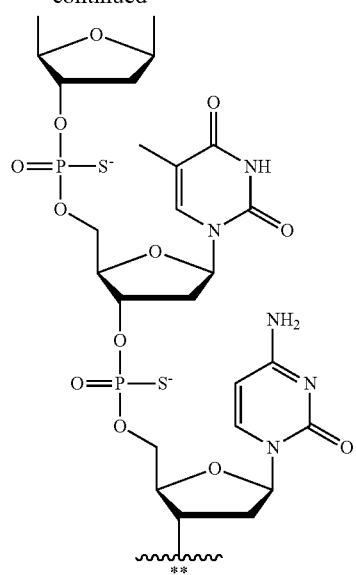
730
-continued
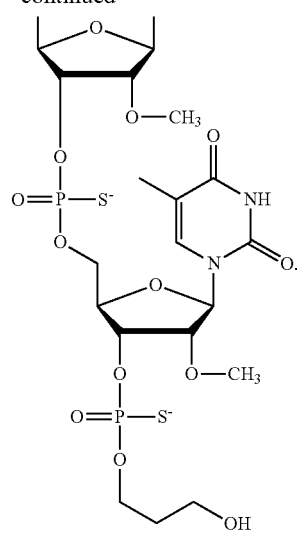
11. The conjugate of claim 1, wherein each of the two Q-tag peptides comprises the amino acid sequence RPQGFGPP (SEQ ID NO:49), each heavy chain of the Ab including Q comprises the amino acid sequence of SEQ ID NO:180, each light chain of the Ab comprises the amino acid sequence of SEQ ID NO:181, and the oligonucleotide P comprises the structure:
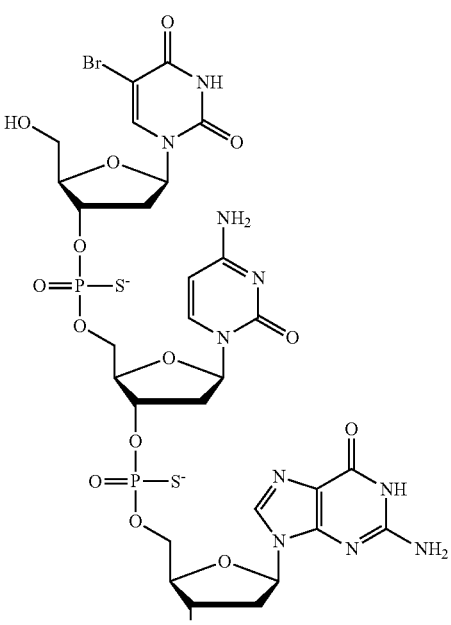

731

-continued

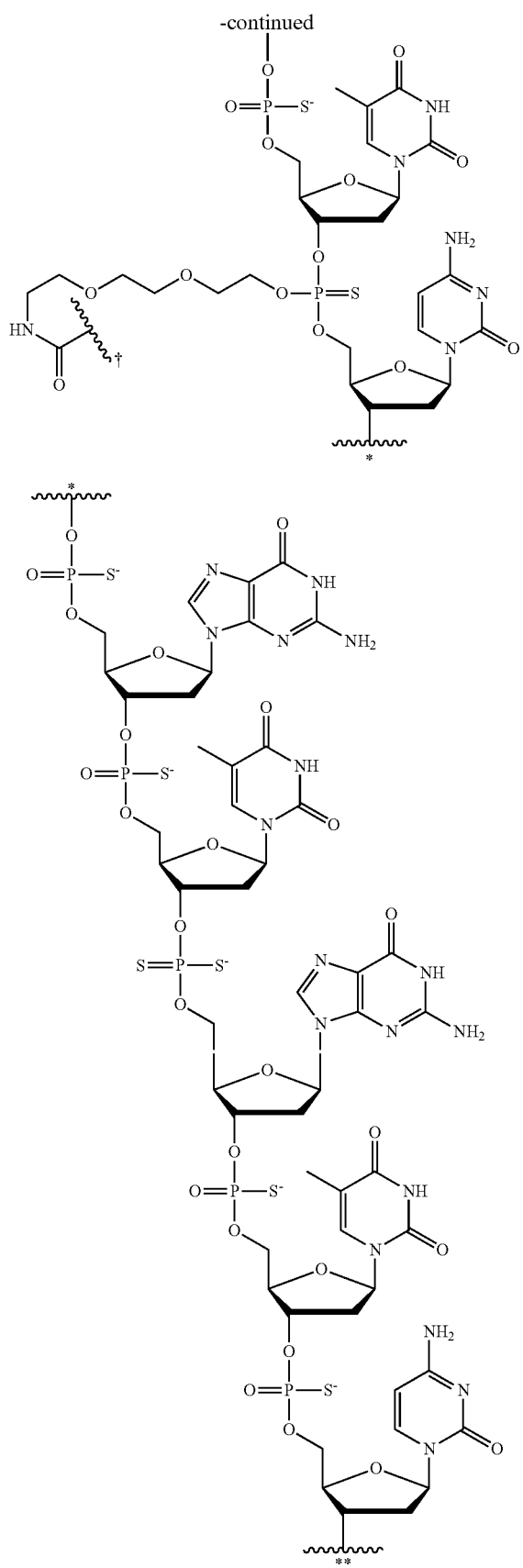

732

-continued

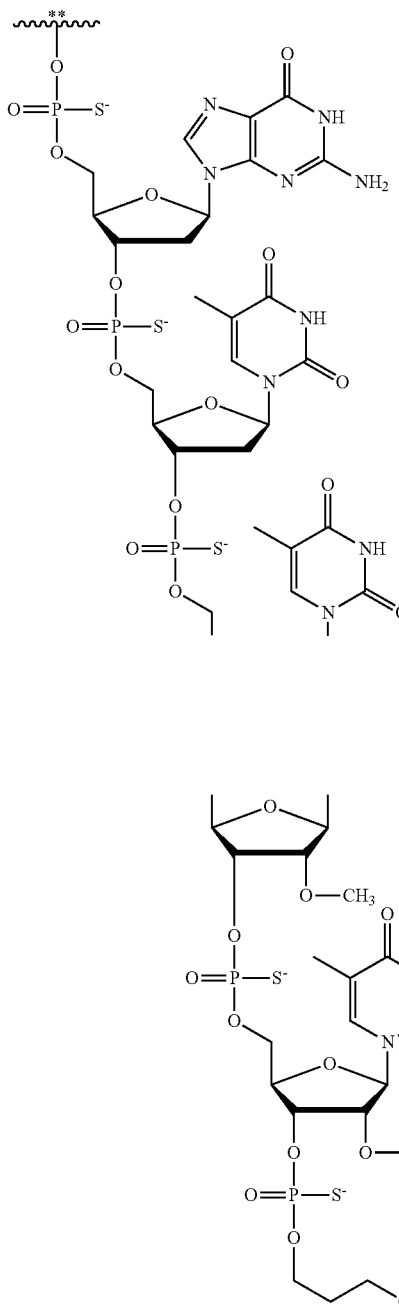

12. A pharmaceutical composition comprising the conjugate of claim 1 and a pharmaceutically acceptable carrier.

13. A pharmaceutical composition comprising the conjugate of claim 7 and a pharmaceutically acceptable carrier.

14. A pharmaceutical composition comprising the conjugate of claim 8 and a pharmaceutically acceptable carrier.

15. A pharmaceutical composition comprising the conjugate of claim 9 and a pharmaceutically acceptable carrier.

16. A pharmaceutical composition comprising the conjugate of claim 10 and a pharmaceutically acceptable carrier.

* * * * *

SEQUENCE LISTING

<160> NUMBER OF SEQ ID NOS: 189

<210> SEQ ID NO 1
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1
tucgtcgtga cgtt                                              14

<210> SEQ ID NO 2
<211> LENGTH: 13
<212> TYPE: DNA
<213> ORGANISM: Artificial Sequence
<220> FEATURE:
<223> OTHER INFORMATION: Synthetic Construct

<400> SEQUENCE: 2
ucgtcgtgtc gtt                                               13

<210> SEQ ID NO 3
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 3
ucgtcgtgtc gtt                                               13

<210> SEQ ID NO 4
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 4
ucgtcgtgtc gtt                                               13

<210> SEQ ID NO 5
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 5
ucgtcgtgtc gtt                                                        13

<210> SEQ ID NO 6
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 6
ucgtcgtgtc gtt                                                        13

<210> SEQ ID NO 7
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 7
ucgtcgtgtc gtt                                                        13

<210> SEQ ID NO 8
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 8
ucgtcgtgtc gtt                                                        13
```

```
<210> SEQ ID NO 9
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 9
ucgtcgtgtc gttt                                                       14

<210> SEQ ID NO 10
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(15)
<223> OTHER INFORMATION: Linkages as shown in Table 2 of the
      specification
<220> FEATURE:
<221> NAME/KEY: misc_feature
<222> LOCATION: (1)..(15)
<223> OTHER INFORMATION: Modified as shown in Table 2 of the
      specification

<400> SEQUENCE: 10
ucgtcgtgtc gtttt                                                      15

<210> SEQ ID NO 11
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 11
ucgtcgtgtc gtt                                                        13

<210> SEQ ID NO 12
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
```

-continued

```
<221> NAME/KEY: misc_feature
<222> LOCATION: (1)..(14)
<223> OTHER INFORMATION: Modified as shown in Table 2 of the
      specification

<400> SEQUENCE: 12
ucgtcgtgtc gttt                                                        14

<210> SEQ ID NO 13
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 13
ucgtcgtgtc gttt                                                        14

<210> SEQ ID NO 14
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 14
ucgtcgtgtc gtt                                                         13

<210> SEQ ID NO 15
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 15
ucgtcgtgtc gtt                                                         13

<210> SEQ ID NO 16
<211> LENGTH: 13
<212> TYPE: DNA
```

```
-continued

<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 16
ucgtcgtgtc gtt                                                          13

<210> SEQ ID NO 17
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 17
ucgtcgtgtc gtt                                                          13

<210> SEQ ID NO 18
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 18
ucgtcgtgtc gtt                                                          13

<210> SEQ ID NO 19
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification
```

-continued

<400> SEQUENCE: 19
ucgtcgtgtc gtt                                                          13

<210> SEQ ID NO 20
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 20
ucgtcgtgtc gtt                                                          13

<210> SEQ ID NO 21
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 21
ucgtcgtgtc gtt                                                          13

<210> SEQ ID NO 22
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 22
ucgtcgtgtc gtt                                                          13

<210> SEQ ID NO 23
<211> LENGTH: 13
<212> TYPE: DNA
<213> ORGANISM: Artificial Sequence
<220> FEATURE:
<223> OTHER INFORMATION: Synthetic Construct
<220> FEATURE:

-continued

```
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 23
ucgtcgtgtc gtt                                                        13

<210> SEQ ID NO 24
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 24
ucgtcgtgtc gtu                                                        13

<210> SEQ ID NO 25
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 25
ucgtcgtgtc gtu                                                        13

<210> SEQ ID NO 26
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 26
ucgtcgtgtc gttt                                                       14
```

```
<210> SEQ ID NO 27
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 27
ucgtcgtgtc gttt                                                        14

<210> SEQ ID NO 28
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 28
ucgtcgtgtc gttt                                                        14

<210> SEQ ID NO 29
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 29
ucgtcgtgtc gttt                                                        14

<210> SEQ ID NO 30
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
```

```
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 30
ucgtcgtgtc gttt                                                      14

<210> SEQ ID NO 31
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 31
ucgtcgtgtc gttt                                                      14

<210> SEQ ID NO 32
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 32
ucgtcgtgtc gttt                                                      14

<210> SEQ ID NO 33
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 33
ucgtcgtgtc gttt                                                      14

<210> SEQ ID NO 34
<211> LENGTH: 14
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 34
ucgtcgtgtc gttt                                                    14

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 35
ucgtcgtgtc gttt                                                    14

<210> SEQ ID NO 36
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 36
ucgtcgtgtc gttt                                                    14

<210> SEQ ID NO 37
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
``` specification

<400> SEQUENCE: 37
ucgtcgtgtc gttt                                                    14

<210> SEQ ID NO 38
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 38
ucgtcgtgtc gttt                                                    14

<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Leu Ser Leu Ser Pro Gly Leu Leu Gln Gly Gly
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Trp Pro Ala Gln Gly Pro Thr
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Trp Pro Gln Gly Pro Thr
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct

<400> SEQUENCE: 42

Trp Ala Pro Gln Gly Pro Thr
1               5

```
<210> SEQ ID NO 43
<211> LENGTH: 6
<212> TYPE: PRT
<213> ORGANISM: Artificial Sequence
<220> FEATURE:
<223> OTHER INFORMATION: Synthetic Construct

<400> SEQUENCE: 43

Trp Ala Gln Gly Pro Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Thr Pro Gly Gln Ala Pro Trp
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Construct

<400> SEQUENCE: 45

Pro Asn Pro Gln Leu Pro Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Construct

<400> SEQUENCE: 46

Arg Pro Gln Gln Phe
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Construct

<400> SEQUENCE: 47

Arg Pro Gln Gly Phe
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Arg Pro Gln Gly Phe Pro Pro
1               5
```

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Arg Pro Gln Gly Phe Gly Pro Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Arg Pro Arg Pro Gln Gln Phe
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Leu Ser Gln Ser Lys Val Leu Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct

<400> SEQUENCE: 52

Trp Gly Gly Gln Leu Leu
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic Construct

<400> SEQUENCE: 53

Trp Ala Leu Gln Arg Pro His Tyr Ser Tyr Pro Asp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Construct

<400> SEQUENCE: 54

Trp Ala Leu Gln Arg Pro Tyr Thr Leu Thr Glu Ser
1               5                   10

```
<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Trp Ala Leu Gln Gly Pro Tyr Thr Leu Thr Glu Ser
1               5                   10

<210> SEQ ID NO 56
<211> LENGTH: 123
<212> TYPE: PRT
<213> ORGANISM: Mus musculus

<400> SEQUENCE: 56

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 57
<211> LENGTH: 107
<212> TYPE: PRT
<213> ORGANISM: Mus musculus

<400> SEQUENCE: 57

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 58
<211> LENGTH: 116
<212> TYPE: PRT
<213> ORGANISM: Artificial Sequence
<220> FEATURE:
```

<223> OTHER INFORMATION: Synthetic Construct

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
            115

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

Asp Ile Gln Leu Thr Gln Ser Pro Ser Ser Leu Ser Ala Ser Val Gly
1               5                   10                  15

Asp Arg Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Leu Glu Ile Lys
            100                 105                 110

<210> SEQ ID NO 60
<211> LENGTH: 124
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala

```
                50                  55                  60
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Glu Val Thr Gly Asp Leu Glu Asp Ala Phe Asp
                100                 105                 110

Ile Trp Gly Gln Gly Thr Met Val Thr Val Ser Ser
            115                 120

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Thr Ile Trp Ser Tyr
                 20                  25                  30

Leu Asn Trp Tyr Gln Gln Arg Pro Gly Lys Ala Pro Asn Leu Leu Ile
             35                  40                  45

Tyr Ala Ala Ser Ser Leu Gln Ser Gly Val Pro Ser Arg Phe Ser Gly
 50                  55                  60

Arg Gly Ser Gly Thr Asp Phe Thr Leu Thr Ile Ser Ser Leu Gln Ala
 65                  70                  75                  80

Glu Asp Phe Ala Thr Tyr Tyr Cys Gln Gln Ser Tyr Ser Ile Pro Gln
                 85                  90                  95

Thr Phe Gly Gln Gly Thr Lys Leu Glu Ile Lys
            100                 105

<210> SEQ ID NO 62
<211> LENGTH: 120
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Glu Phe Ser Arg Ser
                 20                  25                  30

Trp Met Asn Trp Val Arg Gln Ala Pro Gly Lys Gly Leu Glu Trp Val
             35                  40                  45

Gly Arg Ile Tyr Pro Gly Asp Gly Asp Thr Asn Tyr Ser Gly Lys Phe
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Asp Trp Tyr Phe Asp Val Trp Gly Gln
                100                 105                 110

Gly Thr Leu Val Thr Val Ser Ser
            115                 120
```

```
<210> SEQ ID NO 63
<211> LENGTH: 113
<212> TYPE: PRT
<213> ORGANISM: Artificial Sequence
<220> FEATURE:
<223> OTHER INFORMATION: Synthetic Construct

<400> SEQUENCE: 63

Met Asp Ile Gln Met Thr Gln Ser Pro Ser Ser Leu Ser Ala Ser Val
1               5                   10                  15

Gly Asp Arg Val Thr Ile Thr Cys Arg Ser Ser Gln Ser Ile Val His
            20                  25                  30

Ser Val Gly Asn Thr Phe Leu Glu Trp Tyr Gln Gln Lys Pro Gly Lys
        35                  40                  45

Ala Pro Lys Leu Leu Ile Tyr Lys Val Ser Asn Arg Phe Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Phe Gln
                85                  90                  95

Gly Ser Gln Phe Pro Tyr Thr Phe Gly Gln Gly Thr Lys Val Glu Ile
            100                 105                 110

Lys

<210> SEQ ID NO 64
<211> LENGTH: 123
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Gly Thr His Trp Gly Val Leu Phe Ala Tyr
            100                 105                 110

Trp Gly Arg Gly Thr Leu Val Thr Val Ser Ser
        115                 120

<210> SEQ ID NO 65
<211> LENGTH: 123
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Leu Glu Ser Gly Gly Gly Val Val Gln Pro Gly Gly
1               5                   10                  15

Ser Leu Arg Leu Ser Cys Ala Ala Ser Gly Phe Ala Phe Ser Ile Tyr
```

```
                 20                  25                  30

Asp Met Asn Trp Val Arg Gln Ala Pro Gly Lys Gly Leu Glu Trp Val
         35                  40                  45

Ser Ala Ile Ser Ser Gly Gly Thr Thr Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg His Ser Gly Tyr Gly Thr His Trp Gly Val Leu Phe Ala Tyr
                100                 105                 110

Trp Gly Arg Gly Thr Leu Val Thr Val Ser Ser
            115                 120

<210> SEQ ID NO 66
<211> LENGTH: 123
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
                 20                  25                  30

Glu Met Asn Trp Val Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg His Ser Gly Tyr Gly Thr His Trp Gly Val Leu Phe Ala Tyr
                100                 105                 110

Trp Gly Arg Gly Thr Leu Val Thr Val Ser Ser
            115                 120

<210> SEQ ID NO 67
<211> LENGTH: 123
<212> TYPE: PRT
<213> ORGANISM: Homo sapiens

<400> SEQUENCE: 67

Gln Val Gln Leu Gln Glu Ser Gly Pro Gly Leu Val Lys Pro Ser Asp
1               5                  10                  15

Thr Leu Ser Leu Thr Cys Thr Val Ser Gly Phe Ala Phe Ser Ile Tyr
                 20                  25                  30

Asp Met Ser Trp Ile Arg Gln Pro Pro Gly Lys Gly Leu Glu Trp Ile
         35                  40                  45

Ala Tyr Ile Ser Ser Gly Gly Thr Thr Tyr Asn Pro Ser Leu
 50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                 85                  90                  95
```

Ala Arg His Ser Gly Tyr Gly Thr His Trp Gly Val Leu Phe Ala Tyr
            100                 105                 110

Trp Gly Arg Gly Thr Leu Val Thr Val Ser Ser
        115                 120

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Leu Glu Ile Lys
            100                 105

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile His Gly Tyr
            20                  25                  30

Leu Ala Trp Tyr Gln Gln Lys Pro Gly Lys Ala Pro Lys Leu Leu Ile
        35                  40                  45

Tyr Tyr Thr Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: Synthetic Construct

<400> SEQUENCE: 70

Asp Ile Gln Met Thr Gln Ser Pro Ser Ser Leu Ser Ala Ser Val Gly
1               5                   10                  15

-continued

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Leu Glu Ile Lys
                100                 105

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Asp Ile His Gly Tyr
                20                  25                  30

Leu Asn Trp Tyr Gln Gln Lys Pro Gly Gln Ala Pro Arg Leu Leu Ile
            35                  40                  45

Tyr Tyr Thr Ser Ile Leu His Ser Gly Ile Pro Ala Arg Phe Ser Gly
 50                  55                  60

Ser Gly Pro Gly Thr Asp Phe Thr Leu Thr Ile Ser Ser Leu Glu Pro
 65                  70                  75                  80

Glu Asp Phe Ala Val Tyr Tyr Cys Gln Gln Gly Asn Thr Leu Pro Trp
                 85                  90                  95

Thr Phe Gly Gly Gly Thr Lys Leu Glu Ile Lys
                100                 105

<210> SEQ ID NO 72
<211> LENGTH: 107
<212> TYPE: PRT
<213> ORGANISM: Artificial Sequence
<220> FEATURE:
<223> OTHER INFORMATION: Synthetic Construct

<400> SEQUENCE: 72

Asp Ile Val Met Thr Gln Thr Pro Leu Ser Leu Ser Val Thr Pro Gly
 1               5                  10                  15

Gln Pro Ala Ser Ile Ser Cys Arg Ala Ser Gln Asp Ile His Gly Tyr
                20                  25                  30

Leu Asn Trp Tyr Gln Gln Lys Pro Gly Gln Ser Pro Gln Leu Leu Ile
            35                  40                  45

Tyr Tyr Thr Ser Ile Leu His Ser Gly Val Pro Asp Arg Phe Ser Gly
 50                  55                  60

Ser Gly Ser Gly Thr Asp Phe Thr Leu Lys Ile Ser Arg Val Glu Ala
 65                  70                  75                  80

Glu Asp Val Gly Val Tyr Phe Cys Gln Gln Gly Asn Thr Leu Pro Trp
                 85                  90                  95

Thr Phe Gly Gly Gly Thr Lys Leu Glu Ile Lys

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ala Thr Leu Pro Trp
                85                  90                  95

Thr Phe Gly Gln Gly Thr Lys Leu Glu Ile Lys
            100                 105

<210> SEQ ID NO 74
<211> LENGTH: 107
<212> TYPE: PRT
<213> ORGANISM: Artificial Sequence
<220> FEATURE:
<223> OTHER INFORMATION: Synthetic Construct

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Cys Thr Leu Pro Trp
                85                  90                  95

Thr Phe Gly Gln Gly Thr Lys Leu Glu Ile Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

```
Leu Asn Trp Tyr Gln Gln Lys Pro Gly Lys Ala Pro Lys Leu Leu Ile
            35                  40                  45

Tyr Tyr Thr Ser Ile Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Asp Thr Leu Pro Trp
                 85                  90                  95

Thr Phe Gly Gln Gly Thr Lys Leu Glu Ile Lys
            100                 105
```

<210> SEQ ID NO 76
<211> LENGTH: 107
<212> TYPE: PRT
<213> ORGANISM: Artificial Sequence
<220> FEATURE:
<223> OTHER INFORMATION: Synthetic Construct

<400> SEQUENCE: 76

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile His Gly Tyr
             20                  25                  30

Leu Asn Trp Tyr Gln Gln Lys Pro Gly Lys Ala Pro Lys Leu Leu Ile
            35                  40                  45

Tyr Tyr Thr Ser Ile Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Glu Thr Leu Pro Trp
                 85                  90                  95

Thr Phe Gly Gln Gly Thr Lys Leu Glu Ile Lys
            100                 105
```

<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile His Gly Tyr
             20                  25                  30

Leu Asn Trp Tyr Gln Gln Lys Pro Gly Lys Ala Pro Lys Leu Leu Ile
            35                  40                  45

Tyr Tyr Thr Ser Ile Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Phe Thr Leu Pro Trp
                 85                  90                  95

Thr Phe Gly Gln Gly Thr Lys Leu Glu Ile Lys
            100                 105
```

-continued

```
<210> SEQ ID NO 78
<211> LENGTH: 107
<212> TYPE: PRT
<213> ORGANISM: Artificial Sequence
<220> FEATURE:
<223> OTHER INFORMATION: Synthetic Construct

<400> SEQUENCE: 78
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Gly Thr Leu Pro Trp
                85                  90                  95

Thr Phe Gly Gln Gly Thr Lys Leu Glu Ile Lys
            100                 105

```
<210> SEQ ID NO 79
<211> LENGTH: 107
<212> TYPE: PRT
<213> ORGANISM: Artificial Sequence
<220> FEATURE:
<223> OTHER INFORMATION: Synthetic Construct

<400> SEQUENCE: 79
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly His Thr Leu Pro Trp
                85                  90                  95

Thr Phe Gly Gln Gly Thr Lys Leu Glu Ile Lys
            100                 105

```
<210> SEQ ID NO 80
<211> LENGTH: 107
<212> TYPE: PRT
<213> ORGANISM: Artificial Sequence
<220> FEATURE:
<223> OTHER INFORMATION: Synthetic Construct

<400> SEQUENCE: 80
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

```
Tyr Tyr Thr Ser Ile Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Ile Thr Leu Pro Trp
                 85                  90                  95

Thr Phe Gly Gln Gly Thr Lys Leu Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile His Gly Tyr
                 20                  25                  30

Leu Asn Trp Tyr Gln Gln Lys Pro Gly Lys Ala Pro Lys Leu Leu Ile
             35                  40                  45

Tyr Tyr Thr Ser Ile Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Lys Thr Leu Pro Trp
                 85                  90                  95

Thr Phe Gly Gln Gly Thr Lys Leu Glu Ile Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: Synthetic Construct

<400> SEQUENCE: 82

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile His Gly Tyr
                 20                  25                  30

Leu Asn Trp Tyr Gln Gln Lys Pro Gly Lys Ala Pro Lys Leu Leu Ile
             35                  40                  45

Tyr Tyr Thr Ser Ile Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Leu Thr Leu Pro Trp
                 85                  90                  95

Thr Phe Gly Gln Gly Thr Lys Leu Glu Ile Lys
            100                 105

<210> SEQ ID NO 83
<211> LENGTH: 107
<212> TYPE: PRT
```

<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Met Thr Leu Pro Trp
                85                  90                  95

Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: Synthetic Construct

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Pro Thr Leu Pro Trp
                85                  90                  95

Thr Phe Gly Gln Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Gln Thr Leu Pro Trp
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Synthetic Construct

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Arg Thr Leu Pro Trp
                85                  90                  95

Thr Phe Gly Gln Gly Thr Lys Leu Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ser Thr Leu Pro Trp
                85                  90                  95

Thr Phe Gly Gln Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Synthetic Construct

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Thr Thr Leu Pro Trp
                85                  90                  95

Thr Phe Gly Gln Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Val Thr Leu Pro Trp
                85                  90                  95

Thr Phe Gly Gln Gly Thr Lys Leu Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Synthetic Construct

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

-continued

```
Glu Asp Phe Ala Thr Tyr Phe Cys Gln Gln Gly Trp Thr Leu Pro Trp
                85                  90                  95

Thr Phe Gly Gln Gly Thr Lys Leu Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Tyr Thr Leu Pro Trp
                85                  90                  95

Thr Phe Gly Gln Gly Thr Lys Leu Glu Ile Lys
            100                 105

<210> SEQ ID NO 92
<211> LENGTH: 329
<212> TYPE: PRT
<213> ORGANISM: Artificial Sequence
<220> FEATURE:
<223> OTHER INFORMATION: Synthetic Construct

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 93
<211> LENGTH: 329
<212> TYPE: PRT
<213> ORGANISM: Artificial Sequence
<220> FEATURE:
<223> OTHER INFORMATION: Synthetic Construct

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
            195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 94
<211> LENGTH: 329
<212> TYPE: PRT
<213> ORGANISM: Artificial Sequence
<220> FEATURE:
<223> OTHER INFORMATION: Synthetic Construct

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

```
                    225                 230                 235                 240
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 95
<211> LENGTH: 337
<212> TYPE: PRT
<213> ORGANISM: Artificial Sequence
<220> FEATURE:
<223> OTHER INFORMATION: Synthetic Construct

<400> SEQUENCE: 95

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Arg Pro Gln Gly Phe Gly Pro
            325                 330                 335

Pro

<210> SEQ ID NO 96
<211> LENGTH: 329
<212> TYPE: PRT
<213> ORGANISM: Artificial Sequence
<220> FEATURE:
<223> OTHER INFORMATION: Synthetic Construct

<400> SEQUENCE: 96

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 97
<211> LENGTH: 329
<212> TYPE: PRT
<213> ORGANISM: Artificial Sequence
<220> FEATURE:
<223> OTHER INFORMATION: Synthetic Construct

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320
```

Gln Lys Ser Leu Ser Leu Ser Pro Gly
            325

<210> SEQ ID NO 98
<211> LENGTH: 329
<212> TYPE: PRT
<213> ORGANISM: Artificial Sequence
<220> FEATURE:
<223> OTHER INFORMATION: Synthetic Construct

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 99

<211> LENGTH: 325
<212> TYPE: PRT
<213> ORGANISM: Artificial Sequence
<220> FEATURE:
<223> OTHER INFORMATION: Synthetic Construct

<400> SEQUENCE: 99

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | 25 | | | | | 30 | | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | | 35 | | | | 40 | | | | 45 | | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | 55 | | | | 60 | | | | | | |

| Leu | Ser | Ser | Val | Val | Thr | Val | Pro | Ser | Ser | Asn | Phe | Gly | Thr | Gln | Thr |
|---|---|---|---|---|---|---|---|---|---|---|---|---|---|---|---|
| 65 | | | | | 70 | | | | | 75 | | | | | 80 |

| Tyr | Thr | Cys | Asn | Val | Asp | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Thr | Val | Glu | Arg | Lys | Cys | Cys | Val | Glu | Cys | Pro | Pro | Cys | Pro | Ala | Pro |
|---|---|---|---|---|---|---|---|---|---|---|---|---|---|---|---|
| | | | 100 | | | | | 105 | | | | | 110 | | |

| Pro | Val | Ala | Gly | Pro | Ser | Val | Phe | Leu | Phe | Pro | Pro | Lys | Pro | Lys | Asp |
|---|---|---|---|---|---|---|---|---|---|---|---|---|---|---|---|
| | | 115 | | | | | 120 | | | | | 125 | | | |

| Thr | Leu | Met | Ile | Ser | Arg | Thr | Pro | Glu | Val | Thr | Cys | Val | Val | Val | Asp |
|---|---|---|---|---|---|---|---|---|---|---|---|---|---|---|---|
| | 130 | | | | | 135 | | | | | 140 | | | | |

| Val | Ser | His | Glu | Asp | Pro | Glu | Val | Gln | Phe | Asn | Trp | Tyr | Val | Asp | Gly |
|---|---|---|---|---|---|---|---|---|---|---|---|---|---|---|---|
| 145 | | | | | 150 | | | | | 155 | | | | | 160 |

| Val | Glu | Val | His | Asn | Ala | Lys | Thr | Lys | Pro | Arg | Glu | Glu | Gln | Phe | Asn |
|---|---|---|---|---|---|---|---|---|---|---|---|---|---|---|---|
| | | | | 165 | | | | | 170 | | | | | 175 | |

| Ser | Thr | Phe | Arg | Val | Val | Ser | Val | Leu | Thr | Val | Val | His | Gln | Asp | Trp |
|---|---|---|---|---|---|---|---|---|---|---|---|---|---|---|---|
| | | | 180 | | | | | 185 | | | | | 190 | | |

| Leu | Asn | Gly | Lys | Glu | Tyr | Lys | Cys | Lys | Val | Ser | Asn | Lys | Gly | Leu | Pro |
|---|---|---|---|---|---|---|---|---|---|---|---|---|---|---|---|
| | | 195 | | | | | 200 | | | | | 205 | | | |

| Ala | Pro | Ile | Glu | Lys | Thr | Ile | Ser | Lys | Thr | Lys | Gly | Gln | Pro | Arg | Glu |
|---|---|---|---|---|---|---|---|---|---|---|---|---|---|---|---|
| 210 | | | | | 215 | | | | | 220 | | | | | |

| Pro | Gln | Val | Tyr | Thr | Leu | Pro | Pro | Ser | Arg | Glu | Glu | Met | Thr | Lys | Asn |
|---|---|---|---|---|---|---|---|---|---|---|---|---|---|---|---|
| 225 | | | | | 230 | | | | | 235 | | | | | 240 |

| Gln | Val | Ser | Leu | Thr | Cys | Leu | Val | Lys | Gly | Phe | Tyr | Pro | Ser | Asp | Ile |
|---|---|---|---|---|---|---|---|---|---|---|---|---|---|---|---|
| | | | | 245 | | | | | 250 | | | | | 255 | |

| Ala | Val | Glu | Trp | Glu | Ser | Asn | Gly | Gln | Pro | Glu | Asn | Asn | Tyr | Lys | Thr |
|---|---|---|---|---|---|---|---|---|---|---|---|---|---|---|---|
| | | | 260 | | | | | 265 | | | | | 270 | | |

| Thr | Pro | Pro | Met | Leu | Asp | Ser | Asp | Gly | Ser | Phe | Phe | Leu | Tyr | Ser | Lys |
|---|---|---|---|---|---|---|---|---|---|---|---|---|---|---|---|
| | | 275 | | | | | 280 | | | | | 285 | | | |

| Leu | Thr | Val | Asp | Lys | Ser | Arg | Trp | Gln | Gln | Gly | Asn | Val | Phe | Ser | Cys |
|---|---|---|---|---|---|---|---|---|---|---|---|---|---|---|---|
| | 290 | | | | | 295 | | | | | 300 | | | | |

| Ser | Val | Met | His | Glu | Ala | Leu | His | Asn | His | Tyr | Thr | Gln | Lys | Ser | Leu |
|---|---|---|---|---|---|---|---|---|---|---|---|---|---|---|---|
| 305 | | | | | 310 | | | | | 315 | | | | | 320 |

| Ser | Leu | Ser | Pro | Gly |
|---|---|---|---|---|
| | | | | 325 |

<210> SEQ ID NO 100
<211> LENGTH: 325
<212> TYPE: PRT
<213> ORGANISM: Artificial Sequence
<220> FEATURE:
<223> OTHER INFORMATION: Synthetic Construct

<400> SEQUENCE: 100

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | | 35 | | | | | 40 | | | | | 45 | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Asn | Phe | Gly | Thr | Gln | Thr |
|---|---|---|---|---|---|---|---|---|---|---|---|---|---|---|---|
| 65 | | | | | 70 | | | | | 75 | | | | | 80 |

| Tyr | Thr | Cys | Asn | Val | Asp | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Thr | Val | Glu | Arg | Lys | Cys | Cys | Val | Glu | Cys | Pro | Pro | Cys | Pro | Ala | Pro |
|---|---|---|---|---|---|---|---|---|---|---|---|---|---|---|---|
| | | | 100 | | | | | 105 | | | | | 110 | | |

| Pro | Val | Ala | Gly | Pro | Ser | Val | Phe | Leu | Phe | Pro | Pro | Lys | Pro | Lys | Asp |
|---|---|---|---|---|---|---|---|---|---|---|---|---|---|---|---|
| | | | 115 | | | | | 120 | | | | | 125 | | |

| Thr | Leu | Met | Ile | Ser | Arg | Thr | Pro | Glu | Val | Thr | Cys | Val | Val | Val | Asp |
|---|---|---|---|---|---|---|---|---|---|---|---|---|---|---|---|
| | 130 | | | | | 135 | | | | | 140 | | | | |

| Val | Ser | His | Glu | Asp | Pro | Glu | Val | Gln | Phe | Asn | Trp | Tyr | Val | Asp | Gly |
|---|---|---|---|---|---|---|---|---|---|---|---|---|---|---|---|
| 145 | | | | | 150 | | | | | 155 | | | | | 160 |

| Val | Glu | Val | His | Asn | Ala | Lys | Thr | Lys | Pro | Arg | Glu | Glu | Gln | Phe | Asn |
|---|---|---|---|---|---|---|---|---|---|---|---|---|---|---|---|
| | | | | 165 | | | | | 170 | | | | | 175 | |

| Ser | Thr | Phe | Arg | Val | Val | Ser | Val | Leu | Thr | Val | Val | His | Gln | Asp | Trp |
|---|---|---|---|---|---|---|---|---|---|---|---|---|---|---|---|
| | | | 180 | | | | | 185 | | | | | 190 | | |

| Leu | Asn | Gly | Lys | Glu | Tyr | Lys | Cys | Lys | Val | Ser | Asn | Lys | Gly | Leu | Pro |
|---|---|---|---|---|---|---|---|---|---|---|---|---|---|---|---|
| | | | 195 | | | | | 200 | | | | | 205 | | |

| Ser | Ser | Ile | Glu | Lys | Thr | Ile | Ser | Lys | Thr | Lys | Gly | Gln | Pro | Arg | Glu |
|---|---|---|---|---|---|---|---|---|---|---|---|---|---|---|---|
| | 210 | | | | | 215 | | | | | 220 | | | | |

| Pro | Gln | Val | Tyr | Thr | Leu | Pro | Pro | Ser | Arg | Glu | Glu | Met | Thr | Lys | Asn |
|---|---|---|---|---|---|---|---|---|---|---|---|---|---|---|---|
| 225 | | | | | 230 | | | | | 235 | | | | | 240 |

| Gln | Val | Ser | Leu | Thr | Cys | Leu | Val | Lys | Gly | Phe | Tyr | Pro | Ser | Asp | Ile |
|---|---|---|---|---|---|---|---|---|---|---|---|---|---|---|---|
| | | | | 245 | | | | | 250 | | | | | 255 | |

| Ala | Val | Glu | Trp | Glu | Ser | Asn | Gly | Gln | Pro | Glu | Asn | Asn | Tyr | Lys | Thr |
|---|---|---|---|---|---|---|---|---|---|---|---|---|---|---|---|
| | | | 260 | | | | | 265 | | | | | 270 | | |

| Thr | Pro | Pro | Met | Leu | Asp | Ser | Asp | Gly | Ser | Phe | Phe | Leu | Tyr | Ser | Lys |
|---|---|---|---|---|---|---|---|---|---|---|---|---|---|---|---|
| | | 275 | | | | | 280 | | | | | 285 | | | |

| Leu | Thr | Val | Asp | Lys | Ser | Arg | Trp | Gln | Gln | Gly | Asn | Val | Phe | Ser | Cys |
|---|---|---|---|---|---|---|---|---|---|---|---|---|---|---|---|
| | 290 | | | | | 295 | | | | | 300 | | | | |

| Ser | Val | Met | His | Glu | Ala | Leu | His | Asn | His | Tyr | Thr | Gln | Lys | Ser | Leu |
|---|---|---|---|---|---|---|---|---|---|---|---|---|---|---|---|
| 305 | | | | | 310 | | | | | 315 | | | | | 320 |

| Ser | Leu | Ser | Pro | Gly |
|---|---|---|---|---|
| | | | | 325 |

<210> SEQ ID NO 101
<211> LENGTH: 325
<212> TYPE: PRT
<213> ORGANISM: Artificial Sequence
<220> FEATURE:
<223> OTHER INFORMATION: Synthetic Construct

<400> SEQUENCE: 101

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
|---|---|---|---|---|---|---|---|---|---|---|---|---|---|---|---|

-continued

```
                20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 102
<211> LENGTH: 325
<212> TYPE: PRT
<213> ORGANISM: Artificial Sequence
<220> FEATURE:
<223> OTHER INFORMATION: Synthetic Construct

<400> SEQUENCE: 102

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                  50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
                130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 103
<211> LENGTH: 325
<212> TYPE: PRT
<213> ORGANISM: Artificial Sequence
<220> FEATURE:
<223> OTHER INFORMATION: Synthetic Construct

<400> SEQUENCE: 103

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                85                  90                  95
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 104
<211> LENGTH: 326
<212> TYPE: PRT
<213> ORGANISM: Artificial Sequence
<220> FEATURE:
<223> OTHER INFORMATION: Synthetic Construct

<400> SEQUENCE: 104

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
```

```
                115                 120                 125
Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Gln Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 105
<211> LENGTH: 326
<212> TYPE: PRT
<213> ORGANISM: Artificial Sequence
<220> FEATURE:
<223> OTHER INFORMATION: Synthetic Construct

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Ala Val Ser Gln Glu Asp Pro Glu Val Gln Phe Asn Trp Tyr Val Asp
```

```
                145                 150                 155                 160
        Gly Val Glu Val His Asn Ala Lys Thr Lys Pro Arg Glu Glu Gln Phe
                        165                 170                 175

Asn Ser Thr Tyr Arg Val Val Ser Val Leu Thr Val Leu His Gln Asp
                        180                 185                 190

Trp Leu Asn Gly Lys Glu Tyr Lys Cys Lys Val Ser Asn Lys Gly Leu
                        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
        225                 230                 235                 240

Asn Gln Val Ser Leu Thr Cys Leu Val Lys Gly Phe Tyr Pro Ser Asp
                        245                 250                 255

Ile Ala Val Glu Trp Glu Ser Asn Gly Gln Pro Glu Asn Asn Tyr Lys
                        260                 265                 270

Thr Thr Pro Pro Val Leu Asp Ser Asp Gly Ser Phe Phe Leu Tyr Ser
                        275                 280                 285

Arg Leu Thr Val Asp Lys Ser Arg Trp Gln Glu Gly Asn Val Phe Ser
                        290                 295                 300

Cys Ser Val Met His Glu Ala Leu His Asn His Tyr Thr Gln Lys Ser
        305                 310                 315                 320

Leu Ser Leu Ser Leu Gly
                        325

<210> SEQ ID NO 106
<211> LENGTH: 326
<212> TYPE: PRT
<213> ORGANISM: Artificial Sequence
<220> FEATURE:
<223> OTHER INFORMATION: Synthetic Construct

<400> SEQUENCE: 106

Ala Ser Thr Lys Gly Pro Ser Val Phe Pro Leu Ala Pro Cys Ser Arg
        1               5                   10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Ser Leu Gly Thr Lys Thr
        65                  70                  75                  80

Tyr Thr Cys Asn Val Asp His Lys Pro Ser Asn Thr Lys Val Asp Lys
                        85                  90                  95

Arg Val Glu Ser Lys Tyr Gly Pro Pro Cys Pro Pro Cys Pro Ala Pro
                        100                 105                 110

Glu Phe Glu Gly Gly Pro Ser Val Phe Leu Phe Pro Pro Lys Pro Lys
                        115                 120                 125

Asp Thr Leu Met Ile Ser Arg Thr Pro Glu Val Thr Cys Val Val Val
                        130                 135                 140

Asp Val Ser Gln Glu Asp Pro Glu Val Gln Phe Asn Trp Tyr Val Asp
        145                 150                 155                 160

Gly Val Glu Val His Asn Ala Lys Thr Lys Pro Arg Glu Glu Gln Phe
                        165                 170                 175

Asn Ser Thr Tyr Arg Val Val Ser Val Leu Thr Val Leu His Gln Asp
```

```
                    180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
        210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly
                325

<210> SEQ ID NO 107
<211> LENGTH: 326
<212> TYPE: PRT
<213> ORGANISM: Artificial Sequence
<220> FEATURE:
<223> OTHER INFORMATION: Synthetic Construct

<400> SEQUENCE: 107

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Ala Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
```

```
                210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 108
<211> LENGTH: 107
<212> TYPE: PRT
<213> ORGANISM: Homo sapiens

<400> SEQUENCE: 108

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 109
<211> LENGTH: 106
<212> TYPE: PRT
<213> ORGANISM: Homo sapiens

<400> SEQUENCE: 109

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
```

-continued

```
                100                 105

<210> SEQ ID NO 110
<211> LENGTH: 106
<212> TYPE: PRT
<213> ORGANISM: Homo sapiens

<400> SEQUENCE: 110

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 111
<211> LENGTH: 122
<212> TYPE: PRT
<213> ORGANISM: Artificial Sequence
<220> FEATURE:
<223> OTHER INFORMATION: Synthetic Construct

<400> SEQUENCE: 111

Asp Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Ala Pro Gly Lys Gly Leu Glu Trp Val
        35                  40                  45

Ala Thr Ile Ser Pro Gly Asp Ser Phe Gly Tyr Tyr Tyr Pro Asp Ser
    50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Thr Arg Asp Ile Tyr Tyr Asn Tyr Gly Ala Trp Phe Ala Tyr Trp
            100                 105                 110

Gly Gln Gly Thr Leu Val Thr Val Ser Ser
        115                 120

<210> SEQ ID NO 112
<211> LENGTH: 107
<212> TYPE: PRT
<213> ORGANISM: Artificial Sequence
<220> FEATURE:
<223> OTHER INFORMATION: Synthetic Construct

<400> SEQUENCE: 112

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
```

```
                    20                  25                  30
Gly Asp Ser Tyr Met Asn Trp Tyr Gln Gln Lys Pro Gly Lys Ala Pro
                35                  40                  45

Lys Leu Leu Ile Tyr Ala Ala Ser Thr Leu Glu Ser Gly Val Pro Ser
         50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Ala Glu Asp Arg
                 85                  90                  95

Thr Phe Gly Gln Gly Thr Lys Val Glu Ile Lys
                100                 105
```

<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113

```
Gly Phe Ala Phe Ser Ile Tyr Asp
 1               5
```

<210> SEQ ID NO 114
<211> LENGTH: 8
<212> TYPE: PRT
<213> ORGANISM: Artificial Sequence
<220> FEATURE:
<223> OTHER INFORMATION: Synthetic Construct

<400> SEQUENCE: 114

```
Gly Phe Thr Phe Ser Ser Tyr Glu
 1               5
```

<210> SEQ ID NO 115
<211> LENGTH: 8
<212> TYPE: PRT
<213> ORGANISM: Artificial Sequence
<220> FEATURE:
<223> OTHER INFORMATION: Synthetic Construct

<400> SEQUENCE: 115

```
Ile Ser Ser Gly Gly Gly Thr Thr
 1               5
```

<210> SEQ ID NO 116
<211> LENGTH: 16
<212> TYPE: PRT
<213> ORGANISM: Artificial Sequence
<220> FEATURE:
<223> OTHER INFORMATION: Synthetic Construct

<400> SEQUENCE: 116

```
Ala Arg His Ser Gly Tyr Gly Thr His Trp Gly Val Leu Phe Ala Tyr
 1               5                  10                  15
```

<210> SEQ ID NO 117
<211> LENGTH: 6
<212> TYPE: PRT
<213> ORGANISM: Artificial Sequence
<220> FEATURE:
<223> OTHER INFORMATION: Synthetic Construct

<400> SEQUENCE: 117

Gln Asp Ile His Gly Tyr
1               5

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Gln Ser Ile Ser Ser Tyr
1               5

<210> SEQ ID NO 119
<211> LENGTH: 3
<212> TYPE: PRT
<213> ORGANISM: Artificial Sequence
<220> FEATURE:
<223> OTHER INFORMATION: Synthetic Construct

<400> SEQUENCE: 119

Tyr Thr Ser
1

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct

<400> SEQUENCE: 120

Gln Gln Gly Asn Thr Leu Pro Trp Thr
1               5

<210> SEQ ID NO 121
<211> LENGTH: 14
<212> TYPE: DNA
<213> ORGANISM: Mus musculus

<400> SEQUENCE: 121
tucgtcgtga cgtt                                                       14

<210> SEQ ID NO 122
<211> LENGTH: 118
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
                20                  25                  30

Ala Met Ser Trp Val Arg Gln Ala Pro Gly Lys Gly Leu Glu Trp Val
            35                  40                  45

Ala Gly Ile Ser Ala Gly Gly Ser Asp Thr Tyr Tyr Pro Ala Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
                100                 105                 110

Leu Val Thr Val Ser Ser
        115

<210> SEQ ID NO 123
<211> LENGTH: 108
<212> TYPE: PRT
<213> ORGANISM: Artificial Sequence
<220> FEATURE:
<223> OTHER INFORMATION: Synthetic Construct

<400> SEQUENCE: 123

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu
            100                 105

<210> SEQ ID NO 124
<211> LENGTH: 120
<212> TYPE: PRT
<213> ORGANISM: Artificial Sequence
<220> FEATURE:
<223> OTHER INFORMATION: Synthetic Construct

<400> SEQUENCE: 124

Gln Val Gln Leu Gln Gln Pro Gly Ala Glu Ile Val Arg Pro Gly Thr
1               5                   10                  15

Ser Val Lys Leu Ser Cys Lys Ala Ser Gly Tyr Thr Phe Thr Asp Tyr
            20                  25                  30

Trp Met Asn Trp Val Lys Gln Arg Pro Gly Gln Gly Leu Glu Trp Phe
        35                  40                  45

Gly Ala Ile Asp Pro Ser Asp Ser Tyr Thr Arg Tyr Asn Gln Glu Phe
    50                  55                  60

Lys Gly Lys Ala Thr Leu Thr Val Asp Thr Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Asp Tyr Thr Tyr Ser Phe Tyr Phe Asp Tyr Trp Gly Leu
            100                 105                 110

Gly Thr Thr Leu Thr Val Ser Ser
        115                 120

<210> SEQ ID NO 125
<211> LENGTH: 112
<212> TYPE: PRT
<213> ORGANISM: Artificial Sequence
<220> FEATURE:
<223> OTHER INFORMATION: Synthetic Construct

<400> SEQUENCE: 125

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110
```

<210> SEQ ID NO 126
<211> LENGTH: 454
<212> TYPE: PRT
<213> ORGANISM: Artificial Sequence
<220> FEATURE:
<223> OTHER INFORMATION: Synthetic Construct

<400> SEQUENCE: 126

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240
```

```
Pro Ser Val Phe Ile Phe Pro Pro Lys Ile Lys Asp Val Leu Met Ile
            245                 250                 255

Ser Leu Ser Pro Ile Val Thr Cys Val Val Asp Val Ser Glu Asp
        260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Leu Leu Gln Gly Gly
    450

<210> SEQ ID NO 127
<211> LENGTH: 448
<212> TYPE: PRT
<213> ORGANISM: Artificial Sequence
<220> FEATURE:
<223> OTHER INFORMATION: Synthetic Construct

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140
```

```
Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Val Thr Val Pro Ser Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
            210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
            325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Ile Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
            420                 425                 430

His Thr Glu Lys Ser Leu Ser His Ser Pro Gly Leu Leu Gln Gly Gly
            435                 440                 445

<210> SEQ ID NO 128
<211> LENGTH: 214
<212> TYPE: PRT
<213> ORGANISM: Artificial Sequence
<220> FEATURE:
<223> OTHER INFORMATION: Synthetic Construct

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 129
<211> LENGTH: 24
<212> TYPE: DNA
<213> ORGANISM: Artificial Sequence
<220> FEATURE:
<223> OTHER INFORMATION: Synthetic Construct

<400> SEQUENCE: 129
tcgtcgtttt gtcgttttgt cgtt                                          24

<210> SEQ ID NO 130
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 130
ucgtcgtgtc gtt                                                      13

<210> SEQ ID NO 131
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
```

<223> OTHER INFORMATION: Modified as shown in Table 2 of the
      specification

<400> SEQUENCE: 131
ucgtcgtgtc gtt                                                            13

<210> SEQ ID NO 132
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 132
ucgtcgtgtc gtt                                                            13

<210> SEQ ID NO 133
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 133
ucgtcgtgtc gtt                                                            13

<210> SEQ ID NO 134
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 134
ucgtcgtgtc gtt                                                            13

<210> SEQ ID NO 135
<211> LENGTH: 13
<212> TYPE: DNA
<213> ORGANISM: Artificial Sequence
<220> FEATURE:

```
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 135
ucgtcgtgtc gtt                                                          13

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 136
ucgtcgtgtc gttt                                                         14

<210> SEQ ID NO 137
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(15)
<223> OTHER INFORMATION: Linkages as shown in Table 2 of the
      specification
<220> FEATURE:
<221> NAME/KEY: misc_feature
<222> LOCATION: (1)..(15)
<223> OTHER INFORMATION: Modified as shown in Table 2 of the
      specification

<400> SEQUENCE: 137
ucgtcgtgtc gtttt                                                        15

<210> SEQ ID NO 138
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 138
```

```
ucgtcgtgtc gtt                                                             13

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 139
ucgtcgtgtc gttt                                                            14

<210> SEQ ID NO 140
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 140
ucgtcgtgtc gttt                                                            14

<210> SEQ ID NO 141
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 141
ucgtcgtgtc gtt                                                             13

<210> SEQ ID NO 142
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
```

```
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 142
ucgtcgtgtc gtt                                                          13

<210> SEQ ID NO 143
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 143
ucgtcgtgtc gtt                                                          13

<210> SEQ ID NO 144
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 144
ucgtcgtgtc gtt                                                          13

<210> SEQ ID NO 145
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 145
ucgtcgtgtc gtt                                                          13
```

-continued

```
<210> SEQ ID NO 146
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 146
ucgtcgtgtc gtt                                                          13

<210> SEQ ID NO 147
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 147
ucgtcgtgtc gtt                                                          13

<210> SEQ ID NO 148
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 148
ucgtcgtgtc gtt                                                          13

<210> SEQ ID NO 149
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
```

```
<222> LOCATION: (1)..(13)
<223> OTHER INFORMATION: Modified as shown in Table 2 of the
      specification

<400> SEQUENCE: 149
ucgtcgtgtc gtt                                                         13

<210> SEQ ID NO 150
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 150
ucgtcgtgtc gtt                                                         13

<210> SEQ ID NO 151
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 151
ucgtcgtgtc gtu                                                         13

<210> SEQ ID NO 152
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(13)
<223> OTHER INFORMATION: Linkages as shown in Table 2 of the
      specification
<220> FEATURE:
<221> NAME/KEY: misc_feature
<222> LOCATION: (1)..(13)
<223> OTHER INFORMATION: Modified as shown in Table 2 of the
      specification

<400> SEQUENCE: 152
ucgtcgtgtc gtu                                                         13

<210> SEQ ID NO 153
<211> LENGTH: 14
<212> TYPE: DNA
<213> ORGANISM: Artificial Sequence
```

-continued

```
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 153
ucgtcgtgtc gttt                                                    14

<210> SEQ ID NO 154
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 154
ucgtcgtgtc gttt                                                    14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 155
ucgtcgtgtc gttt                                                    14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification
```

```
<400> SEQUENCE: 156
ucgtcgtgtc gttt                                                          14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 157
ucgtcgtgtc gttt                                                          14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 158
ucgtcgtgtc gttt                                                          14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 159
ucgtcgtgtc gttt                                                          14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
-continued

<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 160
ucgtcgtgtc gttt                                                      14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 161
ucgtcgtgtc gttt                                                      14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 162
ucgtcgtgtc gttt                                                      14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 163
ucgtcgtgtc gttt                                                      14
```

```
<210> SEQ ID NO 164
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 164
ucgtcgtgtc gttt                                                      14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 165
ucgtcgtgtc gttt                                                      14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(14)
<223> OTHER INFORMATION: Linkages as shown in Table 2 of the
      specification
<220> FEATURE:
<221> NAME/KEY: misc_feature
<222> LOCATION: (1)..(14)
<223> OTHER INFORMATION: Modified as shown in Table 2 of the
      specification

<400> SEQUENCE: 166
ucgtcgtgtc gttt                                                      14

<210> SEQ ID NO 167
<211> LENGTH: 24
<212> TYPE: DNA
<213> ORGANISM: Artificial Sequence
<220> FEATURE:
<223> OTHER INFORMATION: Synthetic Construct

<400> SEQUENCE: 167
tcgtcgtttt gtcgttttgt cgtt                                           24
```

-continued

<210> SEQ ID NO 168
<211> LENGTH: 120
<212> TYPE: PRT
<213> ORGANISM: Artificial Sequence
<220> FEATURE:
<223> OTHER INFORMATION: Synthetic Construct

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 170
<211> LENGTH: 119
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

```
Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 171
<211> LENGTH: 107
<212> TYPE: PRT
<213> ORGANISM: Artificial Sequence
<220> FEATURE:
<223> OTHER INFORMATION: Synthetic Construct

<400> SEQUENCE: 171

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys
            100                 105

<210> SEQ ID NO 172
<211> LENGTH: 5
<212> TYPE: PRT
<213> ORGANISM: Artificial Sequence
<220> FEATURE:
<223> OTHER INFORMATION: Synthetic Construct

<400> SEQUENCE: 172

Leu Leu Gln Gly Gly
 1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic Construct

<400> SEQUENCE: 173

Gly Gly Gly Leu Leu Gln Gly Gly
 1               5

<210> SEQ ID NO 174
<211> LENGTH: 14
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = absent or 2'-deoxythymidine or as defined
      in the specification
<220> FEATURE:
<221> NAME/KEY: misc_feature
<222> LOCATION: 2
<223> OTHER INFORMATION: n = 2'-deoxyribonucleotide with a modified
      nucleobase or as defined in the specification
<220> FEATURE:
<221> NAME/KEY: misc_feature
<222> LOCATION: 5
<223> OTHER INFORMATION: n = 2'-deoxyadenosine or 2'-deoxythymidine,
      each optionally comprising a 3'-phosphotriester, or as defined in
      the specification
<220> FEATURE:
<221> NAME/KEY: misc_feature
<222> LOCATION: 8
<223> OTHER INFORMATION: Can be present in repeats of any integer
      ranging from about one to about four
<220> FEATURE:
<221> NAME/KEY: misc_feature
<222> LOCATION: 10
<223> OTHER INFORMATION: n = 2'-deoxyadenosine or 2'-deoxythymidine or
      as defined in the specification
<220> FEATURE:
<221> NAME/KEY: misc_feature
<222> LOCATION: 13
<223> OTHER INFORMATION: n = 2'-deoxythymidine optionally comprising a
      3'-phosphotriester or as defined in the specification
<220> FEATURE:
<221> NAME/KEY: misc_feature
<222> LOCATION: 3, 6, 11
<223> OTHER INFORMATION: 2'-deoxycytidine
<220> FEATURE:
<221> NAME/KEY: misc_feature
<222> LOCATION: 4, 7, 9, 12
<223> OTHER INFORMATION: 2'-deoxyguanosine

<400> SEQUENCE: 174
nncgncgtgn cgnt                                                        14

<210> SEQ ID NO 175
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = any amino acid except Pro
<220> FEATURE:
<221> NAME/KEY: VARIANT
<222> LOCATION: 3
<223> OTHER INFORMATION: Xaa = Thr, Ser, or Cys
<220> FEATURE:
<221> NAME/KEY: VARIANT
<222> LOCATION: 4
<223> OTHER INFORMATION: Xaa = any amino acid except Pro

<400> SEQUENCE: 175

Asn Xaa Xaa Xaa
1

<210> SEQ ID NO 176
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 176
tccatgacgt tcctgacgtt                                                                                      20

<210> SEQ ID NO 177
<211> LENGTH: 3
<212> TYPE: PRT
<213> ORGANISM: Artificial Sequence
<220> FEATURE:
<223> OTHER INFORMATION: Synthetic Construct

<400> SEQUENCE: 177

Ala Ala Ser
1

<210> SEQ ID NO 178
<211> LENGTH: 337
<212> TYPE: PRT
<213> ORGANISM: Artificial Sequence
<220> FEATURE:
<223> OTHER INFORMATION: Synthetic Construct

<400> SEQUENCE: 178

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Arg Pro Gln Gly Phe Gly Pro
                325                 330                 335

Pro

<210> SEQ ID NO 179
<211> LENGTH: 460
<212> TYPE: PRT
<213> ORGANISM: Artificial Sequence
<220> FEATURE:
<223> OTHER INFORMATION: Synthetic Construct

<400> SEQUENCE: 179

Gln Val Gln Leu Leu Glu Ser Gly Gly Gly Val Val Gln Pro Gly Gly
1               5                   10                  15

Ser Leu Arg Leu Ser Cys Ala Ala Ser Gly Phe Ala Phe Ser Ile Tyr
            20                  25                  30

Asp Met Asn Trp Val Arg Gln Ala Pro Gly Lys Gly Leu Glu Trp Val
        35                  40                  45

Ser Ala Ile Ser Ser Gly Gly Thr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Gly Thr His Trp Gly Val Leu Phe Ala Tyr
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Arg Pro Gln Gly Phe Gly Pro Pro
450                 455                 460

<210> SEQ ID NO 180
<211> LENGTH: 460
<212> TYPE: PRT
<213> ORGANISM: Artificial Sequence
<220> FEATURE:
<223> OTHER INFORMATION: Synthetic Construct

<400> SEQUENCE: 180

Gln Val Gln Leu Leu Glu Ser Gly Gly Gly Val Val Gln Pro Gly Gly
1               5                   10                  15

Ser Leu Arg Leu Ser Cys Ala Ala Ser Gly Phe Ala Phe Ser Ile Tyr
            20                  25                  30

Asp Met Asn Trp Val Arg Gln Ala Pro Gly Lys Gly Leu Glu Trp Val
        35                  40                  45

Ser Ala Ile Ser Ser Gly Gly Gly Thr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Gly Thr His Trp Gly Val Leu Phe Ala Tyr
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Arg Pro Gln Gly Phe Gly Pro Pro
    450                 455                 460

<210> SEQ ID NO 181
<211> LENGTH: 214
<212> TYPE: PRT
<213> ORGANISM: Artificial Sequence
<220> FEATURE:
<223> OTHER INFORMATION: Synthetic Construct

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ala Thr Leu Pro Trp
                85                  90                  95
```

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 182
<211> LENGTH: 214
<212> TYPE: PRT
<213> ORGANISM: Artificial Sequence
<220> FEATURE:
<223> OTHER INFORMATION: Synthetic Construct

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Gly Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ser Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 183
<211> LENGTH: 454

<212> TYPE: PRT
<213> ORGANISM: Artificial Sequence
<220> FEATURE:
<223> OTHER INFORMATION: Synthetic Construct

<400> SEQUENCE: 183

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Arg Pro
        435                 440                 445

Gln Gly Phe Gly Pro Pro
    450
```

<210> SEQ ID NO 184
<211> LENGTH: 457
<212> TYPE: PRT
<213> ORGANISM: Artificial Sequence
<220> FEATURE:
<223> OTHER INFORMATION: Synthetic Construct

<400> SEQUENCE: 184

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Arg Pro Gln Gly Phe Gly Pro Pro
450                 455

<210> SEQ ID NO 185
<211> LENGTH: 214
<212> TYPE: PRT
<213> ORGANISM: Artificial Sequence
<220> FEATURE:
<223> OTHER INFORMATION: Synthetic Construct

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

-continued

Ala Cys Glu Val Thr His Gln Gly Leu Ser Ser Pro Val Thr Lys Ser
            195                 200                 205

Phe Asn Arg Gly Glu Cys
            210

<210> SEQ ID NO 186
<211> LENGTH: 453
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

```
Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Arg Pro Gln
        435                 440                 445

Gly Phe Gly Pro Pro
    450

<210> SEQ ID NO 187
<211> LENGTH: 456
<212> TYPE: PRT
<213> ORGANISM: Artificial Sequence
<220> FEATURE:
<223> OTHER INFORMATION: Synthetic Construct

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Arg Pro Gln Gly Phe Gly Pro Pro
    450                 455

<210> SEQ ID NO 188
<211> LENGTH: 214
<212> TYPE: PRT
<213> ORGANISM: Artificial Sequence
<220> FEATURE:
<223> OTHER INFORMATION: Synthetic Construct

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 189
<211> LENGTH: 8
<212> TYPE: PRT
<213> ORGANISM: Artificial Sequence
<220> FEATURE:
<223> OTHER INFORMATION: Synthetic Construct

<400> SEQUENCE: 189

Ile Ser Ser Ser Gly Ser Thr Ile
1               5
```